(12) United States Patent
Ahrens et al.

(10) Patent No.: US 8,962,529 B2
(45) Date of Patent: Feb. 24, 2015

(54) SUBSTITUTED PICOLINIC ACIDS, SALTS AND ACID DERIVATIVES THEREOF, AND USE THEREOF AS HERBICIDES

(75) Inventors: Harmut Ahrens, Egelsbach (DE); Marco Brünjes, Hofheim (DE); Hansjörg Dietrich, Liederbach am Taunus (DE); Elmar Gatzweiler, Büdingen (DE); Isolde Häuser-Hahn, Leverkusen (DE); Stefan Lehr, Liederbach (DE); Dirk Schmutzler, Hattersheim (DE)

(73) Assignee: Bayer Cropscience AG, Monheim (DE)

( * ) Notice: Subject to any disclaimer, the term of this patent is extended or adjusted under 35 U.S.C. 154(b) by 59 days.

(21) Appl. No.: 13/278,261

(22) Filed: Oct. 21, 2011

(65) Prior Publication Data

US 2012/0157314 A1   Jun. 21, 2012

Related U.S. Application Data

(60) Provisional application No. 61/405,847, filed on Oct. 22, 2010.

(30) Foreign Application Priority Data

Oct. 22, 2010  (EP) ..................................... 10188566

(51) Int. Cl.
*A01N 43/82*   (2006.01)
*C07D 409/10*  (2006.01)
*C07D 413/10*  (2006.01)
*A01N 43/40*   (2006.01)
*A01N 43/56*   (2006.01)
*C07D 401/10*  (2006.01)

(52) U.S. Cl.
CPC .............. *C07D 413/10* (2013.01); *A01N 43/40* (2013.01); *A01N 43/56* (2013.01); *A01N 43/82* (2013.01); *C07D 401/10* (2013.01); *C07D 409/10* (2013.01)
USPC ........ 504/260; 504/255; 546/255; 546/269.1; 546/271.4; 546/272; 546/7; 546/272.4; 546/282.4; 546/283.7

(58) Field of Classification Search
USPC ................................ 546/269.1; 504/255, 260
See application file for complete search history.

(56) References Cited

PUBLICATIONS

Internatonal Search Report of PCT/EP2011/068125 Dated Dec. 27, 2011.

*Primary Examiner* — Patricia L Morris
(74) *Attorney, Agent, or Firm* — Miles and Stockbridge

(57) ABSTRACT

The present invention relates to novel, herbicidally active picolinic acid derivatives of the formula (I) and to processes for preparation thereof. The present invention further provides for the use thereof as a herbicide, especially as a herbicide for selective control of weed plants in useful plant crops, and as a plant growth regulator alone or in combination with safeners and/or in a mixture with other herbicides.

8 Claims, No Drawings

SUBSTITUTED PICOLINIC ACIDS, SALTS AND ACID DERIVATIVES THEREOF, AND USE THEREOF AS HERBICIDES

CROSS REFERENCE TO RELATED APPLICATIONS

This application claims priority to EP 10188663 filed Oct. 22, 2010 and U.S. Provisional Application No. 61/405,847 filed Oct. 22, 2010, the content of which are both incorporated herein by reference in their entireties.

BACKGROUND

1. Field of the Invention

The present invention relates to novel, herbicidally active picolinic acid derivatives and to processes for preparation thereof and the intermediates used therein. The present invention further provides for the use thereof as a herbicide, especially as a herbicide for selective control of weed plants in useful plant crops, and as a plant growth regulator alone or in combination with safeners and/or in a mixture with other herbicides.

2. Description of Related Art

WO 01/51468 describes herbicidally active picolinic acids. In contrast to the present invention, the picolinic acids described therein, however, do not have any aryl or hetaryl substituents in the 6 position of the picolinic acid.

WO 03/011853 describes herbicidally active picolinic acids which may bear, in the 6 position, aryl or heteroaryl groups which in turn may have further substituents. In contrast to the present invention, the prior art, however, does not teach picolinic acids which have, in the 6 position, aryl or hetaryl substituents which are themselves in turn substituted by heterocyclyl groups.

WO 2007/092184 discloses, inter alia, picolinic acids which may be substituted in the 6 position by aryl or heteroaryl groups. However, the prior art does not disclose that the aryl or heteroaryl groups in the 6 position of the picolinic acid may themselves be substituted by heterocyclic groups.

Applications WO 2007/082098, US 2008/0045734, US 2008/0051596 and US 2009/0088322 disclose herbicidally active picolinic acids which bear aryl groups in the 6 position. These may in turn bear further substituents, but not heterocycles.

The herbicidally active picolinic acids disclosed in US 2004/0198608 do not have any aryl or heteroaryl radicals in the 6 position.

WO 2009/081112 discloses herbicidal pyrimidines which bear substituted amines in the 6 position. However, the active herbicidal ingredients known in the prior art have disadvantages on use thereof, for example that they have (a) only inadequate, if any, herbicidal action against weed plants, (b) too small a range of weed plants controlled, or (c) too low a selectivity in useful plant crops.

It is therefore desirable to provide chemical active ingredients which do not have the disadvantages of the prior art and can be used as herbicides or plant growth regulators.

SUMMARY

It has now been found that, surprisingly, certain substituted picolinic acids and the agrochemical derivatives thereof have good herbicidal action and simultaneously high compatibility with useful plants. The present invention therefore provides compounds of the formula (I), N-oxides thereof, and agrochemically suitable derivatives, preferably the methyl and ethyl esters, and salts thereof, preferably the sodium, potassium or ammonium salts thereof,

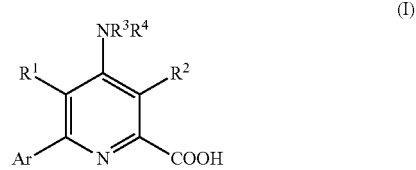

in which the radicals are each defined as follows:
$R^1$ is selected from hydrogen, halogen, cyano and $(C_1\text{-}C_4)$ haloalkyl;
$R^2$ is halogen, cyano, $(C_1\text{-}C_4)$alkyl, $(C_1\text{-}C_4)$haloalkyl, $(C_2\text{-}C_4)$alkoxyalkyl, $(C_2\text{-}C_4)$alkylthioalkyl, $(C_2\text{-}C_4)$alkenyl, oxiranyl, $(C_1\text{-}C_4)$alkyloxiranyl, oxiranyl-$(C_1\text{-}C_4)$alkyl, $(C_2\text{-}C_4)$haloalkenyl, 2-halooxiranyl, 3-halooxiranyl, 2,3-dihalooxiranyl, $(C_3\text{-}C_6)$alkoxyalkenyl, $(C_3\text{-}C_6)$alkylthioalkenyl, $(C_2\text{-}C_4)$alkynyl, $(C_2\text{-}C_4)$haloalkynyl, formyl, $(C_2\text{-}C_4)$alkylcarbonyl, $(C_2\text{-}C_4)$haloalkylcarbonyl, $(C_1\text{-}C_4)$alkoxy, $(C_1\text{-}C_4)$haloalkoxy, $(C_1\text{-}C_4)$alkylthio, $(C_1\text{-}C_4)$haloalkylthio;
$R^3$ is H, $(C_1\text{-}C_4)$alkyl optionally substituted by 1-2 $R^5$ radicals, $(C_2\text{-}C_4)$alkenyl optionally substituted by 1-2 $R^6$ radicals, or $(C_2\text{-}C_4)$alkynyl optionally substituted by 1-2 $R^7$ radicals; or $R^3$ is $C(=O)R^8$, $NO_2$, $OR^9$, $S(O)_2R^{10}$, $N(R^{11})R^{12}$ or $N=C(R^{13})R^{14}$;
$R^4$ is H, $(C_1\text{-}C_4)$alkyl optionally substituted by 1-2 $R^5$ radicals, or $C(=O)R^8$;
or
$R^3$ and $R^4$ together form a $-(CH_2)_4-$, $-(CH_2)_5-$, $-CH_2CH=CHCH_2-$ or $-(CH_2)_2O(CH_2)_2-$ group, where each of these groups may optionally be substituted by 1-2 $R^{15}$ radicals;
or
$R^3$ and $R^4$ together form a $=C(R^{16})N(R^{17})R^{18}$ or $=C(R^{19})OR^{20}$ group;
Ar is an aryl group selected from a group consisting of phenyl, indanyl or naphthyl; or a heteroaryl group selected from 3-, 4-, 5- and 6-membered heteroaromatic rings which contain one or more heteroatoms selected from N, O, S and P as ring members and may optionally be fused to other aromatic systems; where the aryl group or the heteroaryl group may optionally be substituted by 1-3 $R^{21}$ radicals, or two adjacent $R^{21}$ radicals together form a $-OCH_2O-$, $-CH_2CH_2O-$, $-OCH_2CH_2O-$, $-OCH(CH_3)O-$, $-OC(CH_3)_2O-$, $-OCF_2O-$, $-CF_2CF_2O-$, $-OCF_2CF_2O-$ or $-CH=CH-CH=CH-$ group;
and where the aryl group or the heteroaryl group bears, as substituents, at least one heterocyclyl radical (Het) selected from 3-, 4-, 5- and 6-membered aromatic and nonaromatic rings which may have 1, 2, 3 or 4 heteroatoms selected from N, O, S and P, and to which one or two aromatic or nonaromatic 5- or 6-membered hetero- or carbocycles may optionally be fused, where the ring or the fused ring may be substituted by in each case 1 to 3 $R^{26}$ radicals;
$R^5$, $R^6$ and $R^7$ are each independently selected from halogen, $(C_1\text{-}C_3)$alkoxy, $(C_1\text{-}C_3)$haloalkoxy, $(C_1\text{-}C_3)$alkylthio, $(C_1\text{-}C_3)$haloalkylthio, amino, $(C_1\text{-}C_3)$alkylamino, $(C_2\text{-}C_4)$dialkylamino and $(C_2\text{-}C_4)$alkoxycarbonyl;
$R^8$ is selected from hydrogen, $(C_1\text{-}C_4)$alkyl, $(C_1\text{-}C_3)$haloalkyl, $(C_1\text{-}C_4)$alkoxy, phenyl, phenoxy and benzyloxy;
$R^9$ is selected from hydrogen, $(C_1\text{-}C_4)$alkyl, $(C_1\text{-}C_3)$haloalkyl and $CHR^{23}C(O)OR^{24}$;

$R^{10}$ is selected from $(C_1-C_4)$alkyl and $(C_1-C_3)$haloalkyl;

$R^{11}$ is selected from hydrogen, $(C_1-C_4)$alkyl and $C(=O)R^{25}$;

$R^{12}$ is selected from hydrogen and $(C_1-C_4)$alkyl;

$R^{13}$ is selected from hydrogen, $(C_1-C_4)$alkyl and phenyl optionally substituted by 1-3 radicals which are each independently $CH_3$, Cl or $OCH_3$;

$R^{14}$ is selected from hydrogen and $(C_1-C_4)$alkyl; or $R^{13}$ and $R^{14}$ together form a —$(CH_2)_4$— or —$(CH_2)_5$— group;

$R^{15}$ is selected from halogen, $(C_1-C_3)$alkyl, $(C_1-C_3)$alkoxy, $(C_1-C_3)$haloalkoxy, $(C_1-C_3)$alkylthio, $(C_1-C_3)$haloalkylthio, amino, $(C_1-C_3)$alkylamino, $(C_2-C_4)$dialkylamino and $(C_2-C_4)$alkoxycarbonyl;

$R^{16}$ is selected from hydrogen and $(C_1-C_4)$alkyl;

$R^{17}$ and $R^{18}$ are each independently selected from hydrogen and $(C_1-C_4)$alkyl; or $R^{17}$ and $R^{18}$ together form a —$(CH_2)_4$—, —$(CH_2)_5$—, —$CH_2CH=CHCH_2$— or —$(CH_2)_2O(CH_2)_2$— group;

$R^{19}$ is selected from hydrogen and $(C_1-C_4)$alkyl;

$R^{20}$ is $(C_1-C_4)$alkyl;

$R^{21}$ is selected from halogen, cyano, nitro, $(C_1-C_6)$alkyl, $(C_1-C_6)$haloalkyl, $(C_3-C_6)$cycloalkyl, $(C_3-C_6)$halocycloalkyl, $(C_1-C_4)$hydroxyalkyl, $(C_2-C_4)$-alkoxyalkyl, $(C_2-C_4)$haloalkoxyalkyl, $(C_2-C_4)$alkenyl, $(C_2-C_4)$haloalkenyl, $(C_2-C_4)$alkynyl, $(C_3-C_4)$haloalkynyl, hydroxyl, $(C_1-C_4)$alkoxy, $(C_1-C_4)$-haloalkoxy, $(C_2-C_4)$alkenyloxy, $(C_2-C_4)$haloalkenyloxy, $(C_2-C_4)$-alkynyloxy, $(C_3-C_4)$haloalkynyloxy, $(C_1-C_4)$alkylthio, $(C_1-C_4)$haloalkylthio, $(C_1-C_4)$alkylsulfinyl, $(C_1-C_4)$haloalkylsulfinyl, $(C_1-C_4)$alkylsulfonyl, $(C_1-C_4)$haloalkylsulfonyl, $(C_2-C_4)$alkenylthio, $(C_2-C_4)$haloalkenylthio, $(C_2-C_4)$alkenylsulfinyl, $(C_2-C_4)$haloalkenylsulfinyl, $(C_2-C_4)$alkenylsulfonyl, $(C_2-C_4)$haloalkenylsulfonyl, $(C_2-C_4)$alkynylthio, $(C_3-C_4)$haloalkynylthio, $(C_2-C_4)$alkynylsulfinyl, $(C_3-C_4)$haloalkynylsulfinyl, $(C_2-C_4)$alkynylsulfonyl, $(C_3-C_4)$haloalkynylsulfonyl, amino, $(C_1-C_6)$alkylamino, $(C_2-C_8)$-dialkylamino, formyl, $(C_2-C_6)$alkylcarbonyl, $(C_2-C_6)$alkoxycarbonyl, $(C_2-C_6)$alkylaminocarbonyl, $(C_3-C_8)$dialkylaminocarbonyl, $(C_3-C_6)$-trialkylsilyl, phenyl and phenoxy, each phenyl ring or phenoxy ring optionally substituted by 1-3 substituents each independently selected from $R^{22}$;

$R^{22}$ is selected from halogen, cyano, nitro, $(C_1-C_6)$alkyl, $(C_1-C_6)$haloalkyl, $(C_3-C_6)$cycloalkyl, $(C_3-C_6)$halocycloalkyl, $(C_2-C_4)$-haloalkenyl, $(C_2-C_4)$alkynyl, $(C_3-C_4)$haloalkynyl, $(C_1-C_4)$alkoxy, $(C_1-C_4)$-haloalkoxy, $(C_1-C_4)$alkylthio, $(C_1-C_4)$haloalkylthio, $(C_1-C_4)$alkylsulfinyl, $(C_1-C_4)$alkylsulfonyl, $(C_1-C_4)$alkylamino, $(C_2-C_8)$dialkylamino, $(C_3-C_6)$-cycloalkylamino, $(C_4-C_6)$(alkyl)cycloalkylamino, $(C_2-C_4)$alkylcarbonyl, $(C_2-C_6)$alkoxycarbonyl, $(C_2-C_6)$alkylaminocarbonyl, $(C_3-C_8)$dialkylaminocarbonyl and $(C_3-C_6)$trialkylsilyl;

$R^{23}$ is selected from hydrogen, $(C_1-C_4)$alkyl, $(C_1-C_3)$haloalkyl, $(C_1-C_4)$alkoxy, phenyl, phenoxy and benzyloxy;

$R^{24}$ is selected from hydrogen and $(C_1-C_4)$alkyl;

$R^{25}$ is selected from hydrogen, $(C_1-C_4)$alkyl and benzyl;

$R^{26}$ is selected from halogen, cyano, nitro, $(C_1-C_6)$alkyl, $(C_1-C_6)$haloalkyl, $(C_1-C_6)$cycloalkyl, $(C_1-C_6)$halocycloalkyl, $(C_1-C_4)$hydroxyalkyl, $(C_2-C_4)$-alkoxyalkyl, $(C_2-C_4)$haloalkoxyalkyl, $(C_2-C_4)$alkenyl, $(C_2-C_4)$haloalkenyl, $(C_2-C_4)$alkynyl, $(C_3-C_4)$haloalkynyl, hydroxyl, $(C_1-C_4)$alkoxy, $(C_1-C_4)$haloalkoxy, $(C_2-C_4)$alkenyloxy, $(C_2-C_4)$haloalkenyloxy, $(C_2-C_4)$alkynyloxy, $(C_3-C_4)$haloalkynyloxy, $(C_1-C_4)$alkylthio, $(C_1-C_4)$haloalkylthio, $(C_1-C_4)$alkylsulfinyl, $(C_1-C_4)$haloalkylsulfinyl, $(C_1-C_4)$alkylsulfonyl, $(C_1-C_4)$haloalkylsulfonyl, $(C_2-C_4)$alkenylthio, $(C_2-C_4)$haloalkenylthio, $(C_2-C_4)$alkenylsulfinyl, $(C_2-C_4)$haloalkenylsulfinyl, $(C_2-C_4)$alkenylsulfonyl, $(C_2-C_4)$haloalkenylsulfonyl, $(C_2-C_4)$alkynylthio, $(C_3-C_4)$haloalkynylthio, $(C_3-C_4)$alkynylsulfinyl, $(C_3-C_4)$haloalkynylsulfinyl, $(C_3-C_4)$alkynylsulfonyl, $(C_3-C_4)$haloalkynylsulfonyl, amino, $(C_1-C_6)$alkylamino, $(C_2-C_8)$-dialkylamino, formyl, $(C_2-C_6)$alkylcarbonyl, $(C_2-C_6)$alkoxycarbonyl, $(C_2-C_6)$alkylaminocarbonyl, $(C_3-C_8)$dialkylaminocarbonyl, $(C_3-C_6)$trialkylsilyl, phenyl, phenoxy and a 5- or 6-membered heterocyclic ring.

DETAILED DESCRIPTION OF A PREFERRED EMBODIMENT

Preference is given to compounds of the formula (I) and the N-oxides, agrochemically suitable derivatives, esters and salts thereof, preferably the sodium, potassium or ammonium salts thereof, in which the radicals are each defined as follows:

$R^1$ is selected from hydrogen, fluorine, chlorine, bromine and iodine;

$R^2$ is selected from fluorine, chlorine, bromine and iodine, cyano, methyl, ethyl, n-propyl, i-propyl, n-butyl, s-butyl, i-butyl, tert-butyl, trifluoromethyl and difluoromethyl;

$R^3$ is selected from hydrogen, methyl, ethyl, n-propyl, i-propyl, n-butyl, s-butyl, i-butyl, tert-butyl, trifluoromethyl and difluoromethyl;

$R^4$ is selected from hydrogen, methyl, ethyl, n-propyl, i-propyl, n-butyl, s-butyl, i-butyl, tert-butyl, trifluoromethyl and difluoromethyl;

or $R^3$ and $R^4$ together form a —$(CH_2)_4$—, —$(CH_2)_5$—, —$CH_2CH=CHCH_2$— or —$(CH_2)_2O(CH_2)_2$— group, where each of these groups may optionally be substituted by 1-2 $R^{15}$ radicals;

or $R^3$ and $R^4$ together form a $=C(R^{16})N(R^{17})R^{18}$ or $=C(R^{19})OR^{20}$ group;

Ar is an aryl group selected from a group consisting of phenyl, indanyl and naphthyl; or a heteroaryl group selected from 3-, 4-, 5- and 6-membered heteroaromatic rings which contain one or more heteroatoms selected from N, O, S and P as ring members and may optionally be fused to other aromatic systems;

where the aryl group or the heteroaryl group may optionally be substituted by 1-3 $R^{21}$ radicals, or two adjacent $R^{21}$ radicals together form a —$OCH_2O$—, —$CH_2CH_2O$—, —$OCH_2CH_2O$—, —$OCH(CH_3)O$—, —$OC(CH_3)_2O$—, —$OCF_2O$—, —$CF_2CF_2O$—, —$OCF_2CF_2O$— or —$CH=CH—CH=CH$— group;

and where the phenyl, indanyl or naphthyl or the heteroaryl group bears, as substituents, at least one heterocyclyl radical selected from pyridyl, pyrimidinyl, pyridazinyl, pyrazinyl, 1,2,3-triazinyl, 1,2,4-triazinyl, 1,3,5-triazinyl, thienyl, thiazolyl, isothiazolyl, oxazolyl, isoxazolyl, furyl, pyrrolyl, pyrazolyl and imidazolyl, oxiranyl, $(C_1-C_4)$alkyloxiranyl, di$(C_1-C_4)$alkyl oxiranyl and tri$(C_1-C_4)$alkyloxiranyl, 2-oxetanyl, 3-oxetanyl, 3-$(C_1-C_4)$alkyloxetan-2-yl, 2-$(C_1-C_4)$alkyloxetan-3-yl, pyrrolidyl, piperidyl, piperazinyl, dioxolanyl, morpholinyl, tetrahydrofuryl, 1,2,4-triazolyl, 1,2,3-triazolyl, 1,2,3-thiadiazolyl, 1,3,4-thiyadiazolyl, 1,3,5-thiadiazolyl, 1,2,3-oxadiazolyl, 1,3,4-oxadiazolyl, 1,3,5-oxadiazolyl, where the ring or the fused ring may each be substituted by 1 to 3 $R^{26}$ radicals;

$R^{15}$ is selected from fluorine, chlorine, bromine, methyl, ethyl, n-propyl, i-propyl, n-butyl, s-butyl, i-butyl, tert-butyl, trifluoromethyl and difluoromethyl;

$R^{16}$ is selected from hydrogen, methyl, ethyl, n-propyl, i-propyl, n-butyl, s-butyl, i-butyl and tert-butyl;

$R^{17}$ and $R^{18}$ are each independently selected from hydrogen, methyl, ethyl, n-propyl, i-propyl, n-butyl, s-butyl, i-butyl and tert-butyl;
or
$R^{17}$ and $R^{18}$ together form a —(CH$_2$)$_4$—, —(CH$_2$)$_5$—, —CH$_2$CH=CHCH$_2$— or —(CH$_2$)$_2$O(CH$_2$)$_2$— group;
$R^{19}$ is selected from hydrogen, methyl, ethyl, n-propyl, i-propyl, n-butyl, s-butyl, i-butyl and tert-butyl;
$R^{20}$ is selected from methyl, ethyl, n-propyl, i-propyl, n-butyl, s-butyl, i-butyl and tert-butyl;
$R^{21}$ is selected from methyl, ethyl, n-propyl, i-propyl, n-butyl, s-butyl, i-butyl, tert-butyl, cyano, nitro, fluorine, chlorine, bromine, iodine, trifluoromethyl, difluoromethyl, methoxy, ethoxy, i-propoxy and n-propoxy;
$R^{26}$ is selected from methyl, ethyl, n-propyl, i-propyl, n-butyl, s-butyl, i-butyl, tert-butyl, cyano, nitro, fluorine, chlorine, bromine, iodine, trifluoromethyl, difluoromethyl, methoxy, ethoxy, i-propoxy and n-propoxy.

Particular preference is given to compounds of the formula (I) and the N-oxides, agrochemically suitable derivatives, esters and salts thereof, preferably the sodium, potassium or ammonium salts thereof, in which the radicals are each defined as follows:
$R^1$ is selected from hydrogen, fluorine and chlorine;
$R^2$ is selected from fluorine, chlorine, bromine, iodine;
$R^3$ is hydrogen;
$R^4$ is hydrogen;
Ar is a phenyl or pyridyl group,
where the phenyl or pyridyl group is optionally substituted by 1-3 $R^{21}$ radicals,
and where the phenyl or pyridyl group bears, as substituents, at least one heterocyclyl radical selected from 1,2,4-oxadiazol-5-yl, thien-2-yl, pyrrol-1-yl, pyrazol-1-yl, pyridin-2-yl, pyridin-3-yl, pyridin-4-yl, 1,3-oxazol-2-yl, isoxazol-3-yl, oxiranyl, 1-methyloxiran-1-yl, 2-methyloxiran-1-yl, 1,2-dimethyloxiran-1-yl, 2,2-dimethyloxiran-1-yl and trimethyloxiran-1-yl; where the heterocyclyl radical may be substituted by 1 to 3 $R^{26}$ radicals;
$R^{21}$ is selected from fluorine, chlorine, trifluoromethyl, methyl and methoxy,
$R^{26}$ is selected from methyl, tert-butyl, fluorine, chlorine, trifluoromethyl and methoxy.

In a further preferred embodiment of the invention, Ar is a phenyl radical substituted in the 4 position by a heterocyclyl group, preferably by 1,2,4-oxadiazol-5-yl, thien-2-yl, pyrrol-1-yl, pyrazol-1-yl or pyridin-3-yl, which may in turn be substituted by 1, 2 or 3 radicals selected from methyl, tert-butyl, fluorine, chlorine, trifluoromethyl and methoxy.

In a preferred embodiment of the invention, the phenyl radical is additionally substituted in the 2 position by a halogen atom, preferably by fluorine, and in the 3 position by an alkoxy group, preferably methoxy.

In a further preferred embodiment of the invention, Ar is a phenyl radical substituted in the 3 position by a heterocyclyl group, preferably by 1,2,4-oxadiazol-5-yl, thien-2-yl, pyrrol-1-yl, pyrazol-1-yl or pyridin-3-yl, and which may in turn be substituted by 1, 2 or 3 radicals selected from methyl, tert-butyl, fluorine, chlorine, trifluoromethyl and methoxy.

In a preferred embodiment of the invention, the phenyl radical is additionally substituted in the 2 position by a halogen atom, preferably by fluorine, and in the 4 position likewise by a halogen atom, preferably by chlorine.

In a further preferred embodiment of the invention, Ar is a 3-pyridyl radical substituted in the 6 position by a heterocyclyl group, preferably by 1,2,4-oxadiazol-5-yl, thien-2-yl, pyrrol-1-yl, pyrazol-1-yl or by pyridin-3-yl, and the heterocyclyl group may in turn be substituted by 1, 2 or 3 radicals selected from methyl, tert-butyl, fluorine, chlorine, trifluoromethyl and methoxy.

In a preferred embodiment of the invention, the 3-pyridyl radical is additionally substituted in the 2 position by a halogen atom, preferably by fluorine or chlorine.

A further particularly preferred embodiment of the invention relates to the compounds of the following formulae (I-i) to (I-x)

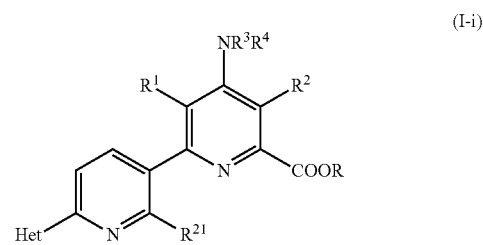
(I-i)

where
R is selected from hydrogen, methyl and ethyl,
$R^{21}$ is selected from hydrogen, chlorine and fluorine,
$R^1$ to $R^4$ and Het are each as defined above;

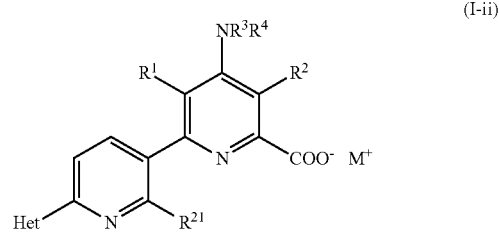
(I-ii)

where
M$^+$ is selected from sodium, potassium and ammonium, and
$R^1$ to $R^4$,
$R^{21}$ is selected from hydrogen, fluorine or chlorine
and Het are each as defined above;

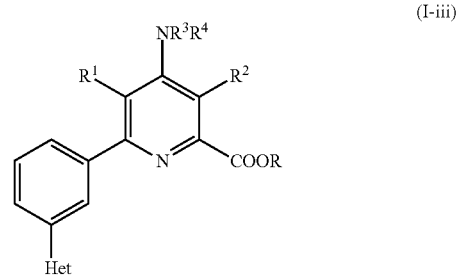
(I-iii)

where
R is selected from hydrogen, methyl and ethyl, and
$R^1$ to $R^4$ and Het are each as defined above;

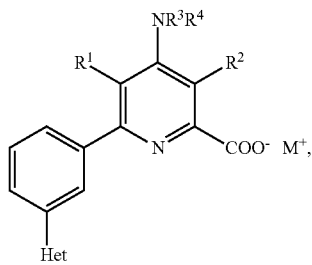
(I-iv)

where
M⁺ is selected from sodium, potassium and ammonium, and R$^1$ to R$^4$ and Het are each as defined above;

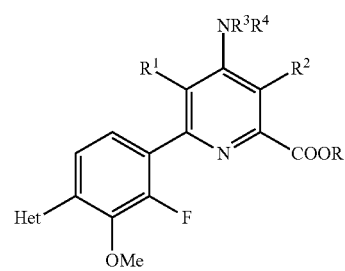
(I-v)

where R is selected from hydrogen, methyl and ethyl, and R$^1$ to R$^4$ and Het are each as defined above;

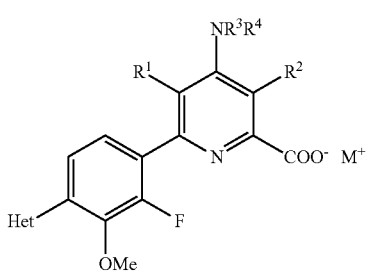
(I-vi)

where
M⁺ is selected from sodium, potassium and ammonium, and R$^1$ to R$^4$ and Het are each as defined above;

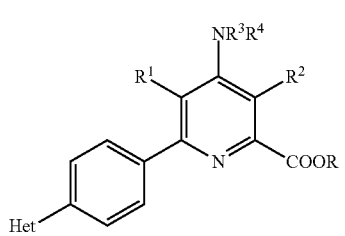
(I-vii)

where
R is selected from hydrogen, methyl and ethyl, and R$^1$ to R$^4$ and Het are each as defined above;

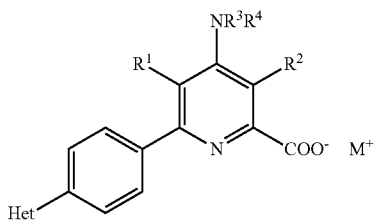
(I-viii)

where
M⁺ is selected from sodium, potassium and ammonium, and R$^1$ to R$^4$ and Het are each as defined above;

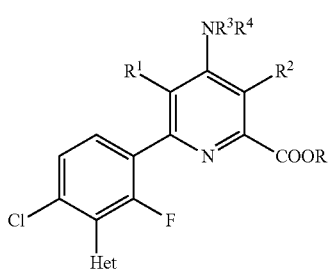
(I-ix)

where
R is selected from hydrogen, methyl and ethyl, and R$^1$ to R$^4$ and Het are each as defined above;

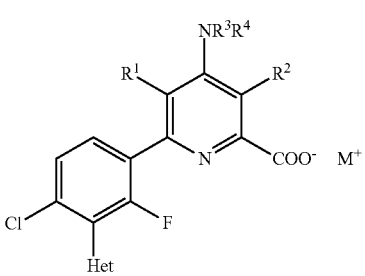
(I-x)

where
M⁺ is selected from sodium, potassium and ammonium, and R$^1$ to R$^4$ and Het are each as defined above.

According to the type and bonding of the substituents, the compounds of the formulae (I) may be present as stereoisomers. The possible stereoisomers defined by the specific three-dimensional form thereof, such as enantiomers, diastereomers, Z and E isomers, geometric isomers and atropisomers, and mixtures thereof, are all encompassed by formula (I).

If, for example, one or more alkenyl groups are present, diastereomers (Z and E isomers) may occur. If, for example, one or more asymmetrically substituted carbon atoms are present and/or asymmetrically substituted sulfur atoms, for example in the form of sulfoxides, it is possible for enantiomers and diastereomers to occur. Stereoisomers can be isolated from the mixtures obtained in the preparation by customary separation methods, for example by chromatographic separation processes. It is likewise possible to selectively prepare stereoisomers by use of stereoselective reactions using optically active starting materials and/or auxiliaries.

The invention thus also relates to all stereoisomers encompassed by the formula (I), even if they are not shown with their specific stereomeric form, and mixtures thereof.

The compounds of the formula (I) may form salts as a result of addition of a suitable inorganic or organic acid, for example mineral acids, for example HCl, HBr, H$_2$SO$_4$, H$_3$PO$_4$ or HNO$_3$, or organic acids, for example carboxylic acids such as formic acid, acetic acid, propionic acid, oxalic acid, lactic acid or salicylic acid, or sulfonic acids, for example p-toluenesulfonic acid, onto a basic group such as amino, alkylamino, dialkylamino, piperidino, morpholino or pyridino. These salts then contain the conjugate base of the acid as an anion. Suitable substituents present in deprotonated form, for example sulfonic acids or carboxylic acids, can also form internal salts with groups which are themselves protonatable, such as amino groups. The compounds of the formula (I) can form N-oxides. The N-oxides can be formed in a known manner, for example by oxidation of the particular pyridines with peroxycarboxylic acids or hydrogen peroxide in solvents such as acetonitrile, dichloromethane, chloroform, acetone, acetic acid, for example at temperatures between 0° and 100° C. (see: D. Spitzner, Science of Synthesis 2005, 15, 218-219 and the literature cited therein in each case).

In addition to the carboxylic acids of the formula (I), essentially the same inventive herbicidal properties may also be possessed by those compounds of the formula (I) in which the carboxylic acid group of the picolinic acid has been converted to a derivative from which the acid can be formed again in the plant or in the surroundings thereof.

The term "agrochemically suitable derivative", which is used to describe the inventive variations in the carboxylic acid function in the 2 position of the formula (I), refers to any esters, acyl hydrazides, imidates, thioimidates, amidines, amides, orthoesters, acyl cyanides, acyl halides, thioesters, thionoesters, dithiol esters, nitriles or other carboxylic acid derivatives known in the prior art which (a) do not significantly impair the herbicidal activity of the active ingredients, for example 6-aryl- or 6-heteroaryl-4-aminopicolinic acids, and (b) can be hydrolyzed, oxidized or metabolized in the plant, the surroundings thereof or the soil to the picolinic acids of the formula (I), which are present in dissociated or undissociated form depending on the pH.

Preferred agrochemically suitable derivatives of the picolinic acids of the formula (I) are especially salts, esters and amides.

Equally, the term "agrochemically suitable derivatives", with regard to the amino group in the 4 position, also describes any salts, silylamines; phosphorylamines, phosphine imines, phosphoramidates, sulfonamides, sulfilimides, sulfoximines, aminals, hemiaminals, amides, thioamides, carbamates, thiocarbamates, amidines, ureas, imines, nitro, nitroso, azido or other nitrogen-containing derivatives which are described in the prior art and (a) do not significantly impair the herbicidal activity of the active ingredients, for example 6-aryl- or 6-heteroaryl-4-aminopicolinic acids, and (b) can be hydrolyzed, oxidized or metabolized in the plant, the surroundings thereof or the soil to the free amines of the formula (I), which are present in dissociated or undissociated form depending on the pH.

Agrochemically suitable derivatives, esters and salts preferred in the context of the present invention are represented by the formulae (I-a) to (I-c).

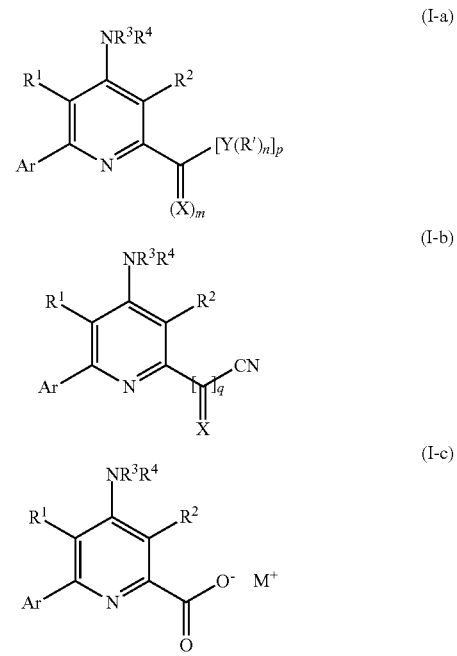

in formula (I-a) the radicals are each defined as follows:
X is selected from O, S, NH and NR" where R" is a (C$_1$-C$_4$)alkyl group;
m is 0 or 1;
Y is selected from halogen, O, S and N;
n is 0, 1 or 2;
p is 1, 2 or 3
R' is selected from hydrogen, halogen, (C$_1$-C$_4$)alkyl, (C$_1$-C$_4$)haloalkyl, (C$_2$-C$_4$)alkoxyalkyl, (C$_2$-C$_4$)alkylthioalkyl, (C$_2$-C$_4$)alkenyl, oxiranyl, (C$_1$-C$_4$)alkyloxiranyl, oxiranyl-(C$_1$-C$_4$)alkyl, (C$_2$-C$_4$)haloalkenyl, 2-halooxiranyl, 3-halooxiranyl, 2,3-dihalooxiranyl, (C$_3$-C$_6$)alkoxyalkenyl, (C$_3$-C$_6$)alkylthioalkenyl, (C$_2$-C$_4$)alkynyl, (C$_2$-C$_4$)haloalkynyl, formyl, (C$_2$-C$_4$)alkylcarbonyl, (C$_2$-C$_4$)haloalkylcarbonyl, (C$_1$-C$_4$)alkoxy, (C$_1$-C$_4$)haloalkoxy, (C$_1$-C$_4$)alkylthio, (C$_1$-C$_4$)haloalkylthio, hydroxyl and NH$_2$;
where the other radicals are each as defined below;
in formula (I-b) the radicals are each defined as follows:
X is selected from O and S;
q is 0 or 1;
where the other radicals are each as defined below;
in formula (I-c) M$^+$ is defined as a cation, particular preference being given to the sodium, potassium and ammonium salts of the inventive compounds of the formula (I).
The other radicals are each as defined below.
For instance, formula (I-a)
where X=O, m=1, Y=O, R'=(C$_1$-C$_4$)alkyl, n=1, p=1 represents the corresponding esters of the inventive compounds of the formula (I);
where X=O, m=1, Y=NH, R'=NH$_2$, n=1, p=1 represents the corresponding acyl hydrazides of the inventive compounds of the formula (I);
where X=NH or NR", m=1, Y=O, R'=H or (C$_1$-C$_4$)alkyl, n=1, p=1 represents the corresponding imidates of the inventive compounds of the formula (I);
where X=NH or NR", m=1, Y=S, R'=H or (C$_1$-C$_4$)Alkyl, n=1, p=1 represents the corresponding thioimidates of the inventive compounds of the formula (I);

where X=NH or NR", m=1, Y=N, R'=H or $(C_1$-$C_4)$alkyl, n=2, p=1 represents the corresponding amidines of the inventive compounds of the formula (I);

where X=O, m=1, Y=N, R'=H or $(C_1$-$C_4)$alkyl, n=2, p=1 represents the corresponding amides of the inventive compounds of the formula (I), where m=0, Y=O, R'=$(C_1$-$C_4)$alkyl, n=1, p=3 represents the corresponding orthoesters of the inventive compounds of the formula (I);

where X=O, m=1, Y=S, R'=H or $(C_1$-$C_4)$alkyl, n=1, p=1 represents the corresponding thioesters of the inventive compounds of the formula (I);

where X=S, m=1, Y=O, R'=H or $(C_1$-$C_4)$alkyl, n=1, p=1 represents the corresponding thionoesters of the inventive compounds of the formula (I);

where X=S, m=1, Y=S, R'=H or $(C_1$-$C_4)$alkyl, n=1, p=1 represents the corresponding dithiolesters of the inventive compounds of the formula (I);

where X=O, m=1, Y=halogen, n=0, p=1 represents acyl halides of the inventive compounds of the formula (I);

where X=O, m=1, Y=N, R'=OH and H or $(C_1$-$C_4)$alkoxy, n=2, p=1 represents hydroxamic acids or alkoxy amides of the inventive compounds of the formula (I).

In addition, formula (I-b)

where X=O and q=1 represents the corresponding acyl cyanides, where q=0 represents the corresponding nitriles.

Formula (I-c) represents derivatives in salt form of the inventive compounds of the formula (I).

Salts can be formed in a known manner, for example by the action of a base on compounds of the formula (I). Suitable bases are, for example, organic amines such as trialkylamines, morpholine, piperidine or pyridine, and also ammonia, ammonium hydroxides, carbonates and hydrogencarbonates, alkali metal hydroxides, carbonates and hydrogencarbonates or alkaline earth metal hydroxides, carbonates and hydrogencarbonates, especially sodium hydroxide and potassium hydroxide, sodium carbonate and potassium carbonate and sodium hydrogencarbonate and potassium hydrogencarbonate. These salts are compounds in which the acidic hydrogen is replaced by a cation suitable for agriculture, for example metal salts, especially alkali metal salts or alkaline earth metal salts, especially sodium and potassium salts, or else salts with organic amines or ammonium salts, for example with ammonium ions of the formula [NRR'R"R'"]$^+$ in which R, R', R" and R'" are each independently H or an organic radical, especially $(C_1$-$C_6)$alkyl, $(C_6$-$C_{10})$aryl, $(C_7$-$C_{20})$aralkyl or $(C_7$-$C_{20})$alkylaryl. Examples are [NH$_4$]$^+$, [NH$_3$CH$_3$]$^+$, [NH$_2$(CH$_3$)$_2$]$^+$, [NH(CH$_3$)$_3$]$^+$, [N(CH$_3$)$_4$]$^+$, [NH$_2$CH$_3$C$_2$H$_5$]$^+$ or [NH$_2$CH$_3$C$_6$H$_5$]$^+$. Also useful are alkylsulfonium and alkylsulfoxonium salts, such as $(C_1$-$C_4)$-trialkylsulfonium and $(C_1$-$C_4)$-trialkylsulfoxonium salts.

Particular preference is given to the sodium, potassium and ammonium salts of the inventive compounds of the formula (I).

The compounds of the formula (I) and the N-oxides and agrochemically suitable derivatives and salts thereof are also referred to as compounds used in accordance with the invention or inventive compounds for short. The terms used above and below are familiar to those skilled in the art and, more particularly, unless defined differently, have the meanings elucidated hereinafter:

An inorganic radical is a radical lacking carbon atoms, preferably halogen, OH and the inorganic salts thereof in which the H is replaced by a cation, for example alkali metal and alkaline earth metal salts, —NH$_2$ and the ammonium salts thereof with (inorganic) acids, for example mineral acids, —N$_3$ (azide), —N$_2$$^+$A$^-$ (diazonium group, where A$^-$ is an anion), —NO, —NHOH, —NHNH$_2$, —NO$_2$, —ONO, —ONO$_2$, —SH, —SOH (sulfenic acid group), —S(O)OH (sulfinic acid group), —S(O)$_2$OH (or else SO$_3$H for short, sulfonic acid group), —O—SO$_2$H (sulfite group), —O—SO$_3$H (sulfate group), —SO$_2$NH$_2$ (sulfamoyl group), —SO$_2$NHOH (hydroxysulfamoyl group), —NHS(O)OH (sulfinoamino group), —NHS(O)$_2$OH (sulfoamino group), —P(O)(OH)$_2$ (phosphonic acid group), —O—P(OH)$_3$ (phosphate group), —P(O)(NH$_2$)$_2$, —PO(OH)(NH$_2$), —PS(OH)$_2$, —PS(NH$_2$)$_2$ or —PS(OH)(NH$_2$), —B(OH)$_2$ (boronic acid group) and the hydrated or dehydrated forms of the acid groups and the (inorganic) salts thereof;

the term "inorganic radical" also includes the hydrogen radical (the hydrogen atom), the latter in these definitions often already being part of the unsubstituted base structure of an organic radical (example: "unsubstituted phenyl");

the term "inorganic radical" here preferably does not include pseudohalogen groups such as CN, SCN, organic metal complexes, carbonate or COOH, which are assigned to the organic radicals due to the content of carbon atoms.

The term "halogen" or "halogen atom" means, for example, fluorine, chlorine, bromine or iodine.

If the term is used for a radical, "halogen" or "halogen atom" means, for example, a fluorine, chlorine, bromine or iodine atom.

Alkyl is a straight-chain, branched or cyclic hydrocarbyl radical. The expression "$(C_1$-$C_4)$alkyl" is, for example, a brief notation for alkyl having one to 4 carbon atoms corresponding to the range stated for carbon atoms and includes, for example, the methyl, ethyl, 1-propyl, 2-propyl, 1-butyl, 2-butyl, 2-methylpropyl, tert-butyl, cyclopropyl and cyclobutyl radicals. General alkyl radicals with a greater specified range of carbon atoms, e.g. "$(C_1$-$C_6)$alkyl", correspondingly also include straight-chain, branched or cyclic alkyl radicals with a greater number of carbon atoms, i.e. according to the example also the alkyl radicals having 5 and 6 carbon atoms. Unless stated specifically, in the case of the hydrocarbyl radicals such as alkyl, alkenyl and alkynyl radicals, including in composite radicals, preference is given to the lower carbon skeletons, for example having 1 to 6 carbon atoms, or in the case of unsaturated groups having 2 to 6 carbon atoms. Alkyl radicals, including in the composite radicals such as alkoxy, haloalkyl etc., are, for example, methyl, ethyl, cyclo-, n- or i-propyl, cyclo-, n-, i-, t- or 2-butyl, pentyls, hexyls such as cyclohexyl, n-hexyl, i-hexyl and 1,3-dimethylbutyl, heptyls such as cycloheptyl, n-heptyl, 1-methylhexyl and 1,4-dimethylpentyl.

Preferred cyclic alkyl radicals have preferably 3-8 ring carbon atoms, e.g. cyclopropyl, cyclobutyl, cyclopentyl or cyclohexyl. In the case of optionally substituted cyclic alkyl radicals, cyclic systems with substituents are included, also including substituents with a double bond on the cyclic alkyl radical, for example an alkylidene group such as methylidene.

In the case of optionally substituted cyclic alkyl radicals, polycyclic aliphatic systems are also included, such as bicyclo[1.1.0]butan-1-yl, bicyclo[1.1.0]butan-2-yl, bicyclo[2.1.0]pentan-1-yl, bicyclo[2.1.0]pentan-2-yl, bicyclo[2.1.0]pentan-5-yl, bicyclo[2.2.1]hept-2-yl (norbornyl), adamantan-1-yl and adamantan-2-yl.

In the case of optionally substituted cyclic alkyl radicals, spirocyclic aliphatic systems are also included, for example spiro[2.2]pent-1-yl, spiro[2.3]hex-1-yl, spiro[2.3]hex-4-yl, 3-spiro[2.3]hex-5-yl.

Alkenyl and alkynyl radicals are defined as the possible unsaturated straight-chain, branched or cyclic radicals corresponding to the alkyl radicals, where at least one double bond or triple bond is present. Preference is given to radicals having one double bond or having one triple bond.

Alkenyl also includes straight-chain, branched or cyclic hydrocarbyl radicals having more than one double bond, such as 1,3-butadienyl, 1,4-pentadienyl or cyclohexadienyl, but also allenyl or cumulenyl radicals having one or more cumulated double bonds, for example allenyl (1,2-propadienyl), 1,2-butadienyl and 1,2,3-pentatrienyl.

Alkynyl also includes straight-chain, branched or cyclic hydrocarbyl radicals having more than one triple bond or else having one or more triple bonds and one or more double bonds, for example 1,3-butatrienyl or 3-penten-1-yn-1-yl.

Alkenyl is, for example, vinyl which may be optionally substituted by further alkyl radicals, e.g. prop-1-en-1-yl, but-1-en-1-yl; allyl, 1-methylprop-2-en-1-yl, 2-methylprop-2-en-1-yl, but-2-en-1-yl, 1-methylbut-3-en-1-yl and 1-methylbut-2-en-1-yl, 2-methylprop-1-en-1-yl, 1-methylprop-1-en-1-yl, 1-methylprop-2-en-1-yl, 2-methylprop-2-en-1-yl, but-2-en-1-yl, but-3-en-1-yl, 1-methylbut-3-en-1-yl or 1-methylbut-2-en-1-yl, pentenyl, 2-methylpentenyl or hexenyl.

$(C_2$-$C_6)$-Alkynyl is, for example, ethynyl, propargyl, 1-methylprop-2-yn-1-yl, 2-butynyl, 2-pentynyl or 2-hexynyl, preferably propargyl, but-2-yn-1-yl, but-3-yn-1-yl or 1-methylbut-3-yn-1-yl.

Cyclic alkenyl radicals are a carbocyclic, nonaromatic, partially unsaturated ring system having preferably 4-8 carbon atoms, e.g. 1-cyclobutenyl, 2-cyclobutenyl, 1-cyclopentenyl, 2-cyclopentenyl, 3-cyclopentenyl, or 1-cyclohexenyl, 2-cyclohexenyl, 3-cyclohexenyl, 1,3-cyclohexadienyl or 1,4-cyclohexadienyl, also including substituents with a double bond on the cycloalkenyl radical, for example an alkylidene group such as methylidene. In the case of optionally substituted cycloalkenyl, the elucidations for substituted cyclic alkyl radicals apply correspondingly.

Alkylidene, for example also in the form of $(C_1$-$C_{10})$alkylidene, is the radical of a straight-chain, branched or cyclic hydrocarbyl radical bonded via a double bond. Possible bonding sites for alkylidene are naturally only positions on the base structure where two hydrogen atoms can be replaced by the double bond; radicals are, for example, $=CH_2$, $=CH-CH_3$, $=C(CH_3)-CH_3$, $=C(CH_3)-C_2H_5$ or $=C(C_2H_5)-C_2H_5$.

Aryl is a mono-, bi- or polycyclic aromatic system having preferably 6 to 14, especially 6 to 10, ring carbon atoms, for example phenyl, indanyl, naphthyl, anthryl, phenanthrenyl, and the like, preferably phenyl.

In the case of optionally substituted aryls, polycyclic systems such as tetrahydronaphthyl, indenyl, indanyl, fluorenyl, biphenylyl, are also included, where the bonding site is on the aromatic system. In systematic terms, aryl is generally also encompassed by the term "optionally substituted phenyl".

Heteroaryl is a mono-, bi- or polycyclic aromatic system comprising at least one 3-, 4-, 5- or 6-membered aromatic ring having 1, 2, 3 or 4 heteroatoms selected from N, O, S and P as ring members.

Heterocyclyl (Het) is a mono-, bi- or polycyclic aromatic or nonaromatic system comprising at least one 3-, 4-, 5- or 6-membered aromatic or nonaromatic ring having 1, 2, 3 or 4 heteroatoms selected from N, O, S and P as ring members.

The definition "substituted by one or more radicals", unless defined differently, independently means one or more identical or different radicals, where two or more radicals on one cycle as the base structure may form one or more rings. Substituted radicals, such as a substituted alkyl, alkenyl, alkynyl, aryl, phenyl, benzyl, heterocyclyl and heteroaryl radical, are, for example, a substituted radical derived from the unsubstituted base structure, where the substituents are, for example, one or more, preferably 1, 2 or 3, radicals from the group of halogen, alkoxy, alkylthio, hydroxyl, amino, nitro, carboxyl or a carboxyl group equivalent, cyano, isocyano, azido, alkoxycarbonyl, alkylcarbonyl, formyl, carbamoyl, mono- and dialkylaminocarbonyl, substituted amino such as acylamino, mono- and dialkylamino, trialkylsilyl and optionally substituted cyclic alkyl, optionally substituted aryl, optionally substituted heterocyclyl, where each of the latter cyclic groups may also be bonded via heteroatoms or divalent functional groups as is the case for the alkyl radicals mentioned, and alkylsulfinyl, including both enantiomers of the alkylsulfinyl group, alkylsulfonyl, alkylphosphinyl, alkylphosphonyl and, in the case of cyclic radicals (="cyclic base structure"), also alkyl, haloalkyl, alkylthioalkyl, alkoxyalkyl, optionally substituted mono- and dialkylaminoalkyl and hydroxylalkyl; the term "substituted radicals" such as substituted alkyl (e.g. straight-chain, branched or cyclic alkyl) etc. includes, as substituents in addition to the saturated hydrocarbon-containing radicals mentioned, corresponding unsaturated aliphatic and aromatic radicals, such as optionally substituted alkenyl, alkynyl, alkenyloxy, alkynyloxy, alkenylthio, alkynylthio, alkenyloxycarbonyl, alkynyloxycarbonyl, alkenylcarbonyl, alkynylcarbonyl, mono- and dialkenylaminocarbonyl, mono- and dialkynylaminocarbonyl, mono- and dialkenylamino, mono- and dialkynylamino, trialkenylsilyl, trialkynylsilyl, phenyl, phenoxy etc. The case of substituted cyclic radicals with aliphatic moieties in the ring also includes cyclic systems with those substituents bonded to the ring by a double bond, for example by an alkylidene group such as methylidene or ethylidene, or an oxo group, imino group or substituted imino group.

If two or more radicals form one or more rings, they may be carbocyclic, heterocyclic, saturated, partly saturated, unsaturated, for example also aromatic and optionally further substituted. The fused rings are preferably 5- or 6-membered rings, particular preference being given to benzofused cycles.

The substituents mentioned by way of example ("first substituent level") may, to the extent that they contain hydrocarbon-containing moieties, optionally be further substituted therein ("second substituent level"), for example by one of the substituents as defined for the first substituent level. Corresponding further substituent levels are possible. Preferably, the term "substituted radical" includes only one or two possible substituent levels.

Preferred substituents for the substituent levels are, for example, amino, hydroxyl, halogen, nitro, cyano, isocyano, mercapto, isothiocyanato, carboxyl, carbonamide, $SF_5$, aminosulfonyl, alkyl, alkenyl, alkynyl, monoalkylamino, dialkylamino, N-alkanoylamino, alkoxy, alkenyloxy, alkynyloxy, alkoxycarbonyl, alkenyloxycarbonyl, alkynyloxycarbonyl, aryloxycarbonyl, alkanoyl, alkenylcarbonyl, alkynylcarbonyl, arylcarbonyl, alkylthio, alkenylthio, alkynylthio, alkylsulfenyl, alkylsulfinyl, including both enantiomers of the alkylsulfinyl group, alkylsulfonyl, monoalkyl-aminosulfonyl, dialkylaminosulfonyl, alkylphosphinyl, alkylphosphonyl, including both enantiomers for alkylphosphinyl and alkylphosphonyl, N-alkylaminocarbonyl, N,N-dialkylaminocarbonyl, N-alkanoylaminocarbonyl, N-alkanoyl-N-alkylaminocarbonyl, aryl, aryloxy, benzyl, benzyloxy, benzylthio, arylthio, arylamino, benzylamino, heterocyclyl and trialkylsilyl.

Substituents composed of several substituent levels are preferably, for example, alkoxyalkyl such as monoalkoxyalkyl or dialkoxyalkyl, alkylthioalkyl, alkylthioalkoxy, alkoxyalkoxy such as monoalkoxyalkoxy or dialkoxyalkoxy, benzyl, phenethyl, benzyloxy, haloalkyl, haloalkoxy, haloalkylthio, haloalkanoyl, haloalkylcarbonyl, haloalkoxycarbonyl, haloalkoxyalkoxy, haloalkoxyalkylthio, haloalkoxyalkanoyl, haloalkoxyalkyl, alkanoylalkyl, haloalkanoylalkyl, alkanoyloxyalkyl.

In the case of radicals comprising carbon atoms, preference is given to those having 1 to 6 carbon atoms, preferably 1 to 4 carbon atoms, especially 1 or 2 carbon atoms. Preference is generally given to substituents from the group of halogen, e.g. fluorine and chlorine, ($C_1$-$C_4$)alkyl, preferably methyl or ethyl, ($C_1$-$C_4$)haloalkyl, preferably trifluoromethyl, ($C_1$-$C_4$) alkoxy, preferably methoxy or ethoxy, ($C_1$-$C_4$)haloalkoxy, nitro and cyano. Particular preference is given to the substituents methyl, methoxy, fluorine and chlorine.

Substituted amino such as mono- or disubstituted amino is a radical from the group of the substituted amino radicals N-substituted, for example, by one or two identical or different radicals from the group of alkyl, hydroxyl, amino, alkoxy, acyl and aryl; preferably mono- and dialkylamino, mono- and diarylamino, such as optionally substituted anilines, acylamino, N,N-diacylamino, N-alkyl-N-arylamino, N-alkyl-N-acylamino and saturated N-heterocycles; preference is given to alkyl radicals having 1 to 4 carbon atoms; aryl is preferably phenyl or substituted phenyl; the definition below applies to acyl, which is preferably ($C_1$-$C_4$)alkanoyl. The same applies to substituted hydroxylamino or hydrazino.

Substituted amino also includes quaternary ammonium compounds (salts) with four organic substituents on the nitrogen atom.

A carboxyl group equivalent is, for example, an alkyl ester, aryl ester, O-alkyl thioester, S-alkyl dithioester, S-alkyl thioester, carboximide ester, carboximide thioester; 5,6-dihydro-1,2,4-dioxazin-3-yl; 5,6-dihydro-1,2,4-oxathiazin-3-yl, trialkyl orthoester, dialkoxyalkylamino ester, dialkylaminoalkoxy ester, trialkylamino ester, amidine, dialkoxyketene acetal or dialkyldithioketene acetal.

Optionally substituted phenyl is preferably phenyl which is unsubstituted or mono- or polysubstituted, preferably up to trisubstituted, by identical or different radicals from the group of halogen, ($C_1$-$C_4$)alkyl, ($C_1$-$C_4$)alkoxy, ($C_1$-$C_4$)alkoxy-($C_1$-$C_4$)alkoxy, ($C_1$-$C_4$)alkoxy-($C_1$-$C_4$)alkyl, ($C_1$-$C_4$)haloalkyl, ($C_1$-$C_4$)haloalkoxy, ($C_1$-$C_4$)alkylthio, ($C_1$-$C_4$)haloalkylthio, cyano, isocyano and nitro, e.g. o-, m- and p-tolyl, dimethylphenyls, 2-, 3- and 4-chlorophenyl, 2-, 3- and 4-fluorophenyl, 2-, 3- and 4-trifluoromethyl- and -trichloromethylphenyl, 2,4-, 3,5-, 2,5- and 2,3-dichlorophenyl, o-, m- and p-methoxyphenyl.

Optionally substituted heterocyclyl is preferably heterocyclyl which is unsubstituted or mono- or polysubstituted, preferably up to trisubstituted, by identical or different radicals from the group of halogen, cyano, ($C_1$-$C_4$)alkyl, ($C_1$-$C_4$) alkoxy, ($C_1$-$C_4$)alkoxy-($C_1$-$C_4$)alkoxy, ($C_1$-$C_4$)alkoxy-($C_1$-$C_4$)alkyl, ($C_1$-$C_4$)haloalkyl, ($C_1$-$C_4$)haloalkoxy, nitro and oxo, especially mono- or polysubstituted by radicals from the group of halogen, ($C_1$-$C_4$)alkyl, ($C_1$-$C_4$)alkoxy, ($C_1$-$C_4$)haloalkyl and oxo, very particularly by one or two ($C_1$-$C_4$)alkyl radicals.

Haloalkyl, -alkenyl and -alkynyl are, respectively, alkyl, alkenyl and alkynyl substituted partly or fully by identical or different halogen atoms, e.g. monohaloalkyl such as $CH_2CH_2Cl$, $CH_2CH_2F$, $CHClCH_3$, $CHFCH_3$, $CH_2Cl$, $CH_2F$; perhaloalkyl such as $CCl_3$ or $CF_3$ or $CF_2CF_3$; polyhaloalkyl such as $CHF_2$, $CH_2F$, $CH_2CHFCl$, $CHCl_2$, $CF_2CF_2H$, $CH_2CF_3$; haloalkoxy is, for example, $OCF_3$, $OCHF_2$, $OCH_2F$, $OCF_2CF_3$, $OCH_2CF_3$ and $OCH_2CH_2Cl$; the same applies to haloalkenyl and other halogen-substituted radicals.

An organic acid radical is a radical of an oxo acid or thio acid of the formula

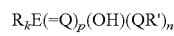

where
R is an organic radical,
E is an atom from the group of C, S, P,
Q is independently an atom or a molecule fragment from the group of O, S, NR' and
R' is independently a hydrogen atom, alkyl, haloalkyl, alkoxyalkyl or optionally aryl; k, p are natural numbers, k=1, 2; p=0-2;
n is a natural number or zero.

The organic acid radical arises in a formal sense through removal of a hydroxyl group on the acid function, where the organic R radical in the acid may also be bonded to the acid function via one or more heteroatoms:

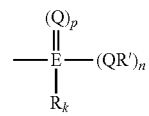

For oxo acids of carbon, this is described in IUPAC Compendium of Chemical Terminology (1997).

Examples of organic acids derived from the oxo acids or thio acids of sulfur (E=S) are S(O)OCH$_3$, SO$_2$OH, SO$_2$OCH$_3$ or SO$_2$NHR(N-substituted sulfonamide acids). In the case that k=1, alkylsulfonyl and alkylsulfinyl radicals are also included, for example (H$_3$C)S(O)$_2$, (F$_3$C)S(O)$_2$, p-tolylS(O)$_2$, (H$_3$C)S(O)(NH-n-C$_4$H$_9$), (C$_6$H$_5$)S(S)(O) or (C$_6$H$_5$)S(O).

Examples of organic acids derived from the oxo acids or thio acids of phosphorus (E=P) are radicals derived from phosphinic acid and phosphonic acid, where these radicals may be further esterified, for example —PO(OCH$_3$)$_2$, (C$_2$H$_5$O)P(O)OH, (C$_2$H$_5$O)P(O)(SC$_6$H$_5$), (H$_3$CO)P(O)NH (C$_6$H$_5$) or —PO(NMe$_2$)$_2$.

In the case that k=1, alkylphosphinyl and alkylphosphonyl radicals are also included, for example (H$_3$C)$_2$P(O), (C$_6$H$_5$)$_2$P(O), (H$_3$C)(C$_6$H$_5$)P(O); (H$_3$C)P(O)OCH$_3$, (H$_5$C$_2$)P (O)(OC$_2$H$_5$), (C$_6$H$_5$)P(O)(OC$_2$H$_5$), (C$_2$H$_5$)P(O)(SC$_6$H$_5$), (H$_3$C)P(O)NH(C$_6$H$_5$), (H$_3$C)P(S)(NH-i-C$_3$H$_7$), (C$_6$H$_5$)P(S) (OC$_2$H$_5$) or (C$_6$H$_5$)P(S)(SC$_2$H$_5$).

Organic acid radicals derived from the oxo acids of carbon (E=C, Q=O) are also referred to in the narrower sense by the term "acyl".

Examples of acyl are the —CO—R radical of a carboxylic acid HO—CO—R and radicals of acids derived therefrom, or the radical of carbonic monoesters or N-substituted carbamic acids, and also carbonates and the esters thereof.

Acyl is, for example, formyl, oxalyl (ester), alkylcarbonyl such as [(C$_1$-C$_4$)alkyl]-carbonyl, haloalkylcarbonyl, phenylcarbonyl, alkyloxycarbonyl, especially tert-butyloxycarbonyl, phenyloxycarbonyl, benzyloxycarbonyl, fluorenyloxycarbonyl, N-alkyl-1-iminoalkyl, N-alkyl- and N,N-dialkylcarbamoyl. The radicals may each have further substitution in the alkyl or phenyl moiety, for example in the alkyl moiety by one or more radicals from the group of halogen, cyano, alkoxy, phenyl and phenoxy; examples of substituents in the phenyl moiety are the substituents already mentioned above in general terms for substituted phenyl.

Acyl is preferably an acyl radical in the narrower sense, i.e. a radical of an organic acid in which the acid group is bonded directly to the carbon atom of an organic radical, for example alkanoyl such as formyl and acetyl, aroyl such as phenylcarbonyl, and other radicals of saturated or unsaturated organic acids.

"Aroyl" is an aryl radical as defined above which is bonded via a carbonyl group, for example the benzoyl group.

If a general radical is defined by "hydrogen", this means a hydrogen atom.

The "yl position" of a radical refers to the bonding site thereof.

The present invention also provides methods for preparing the inventive compounds. The inventive compounds can alternatively be prepared by different processes.

In the processes which follow, solvents are used in some cases. In this context, "inert solvents" refer in each case to solvents which are inert under the particular reaction conditions, but need not be inert under all reaction conditions.

In the synthesis routes described hereinafter, the $R^1$, $R^2$, $R^3$, $R^4$ and Ar radicals—unless explicitly stated otherwise—are each as defined in the main claim.

Products of the formula (I) can be synthesized by reacting picolinic acids, or derivatives (II) thereof which have a substitution pattern suitable for this reaction and which bear a leaving group in the form of the "L" group, with an organometallic reagent (III). According to the reactant (II) used and according to the reaction conditions, the product (I) forms as an acid derivative or as a free acid or salt thereof (scheme 1). It may be necessary in a subsequent step to convert the acid derivative to the free acid or salt thereof. If the free acid is the desired product, it is necessary to hydrolyze, for example, a picolinic ester (I) to the free acid, or else, for example, the free picolinic acid or one of the salts thereof is used as the reactant (II).

Scheme 1:

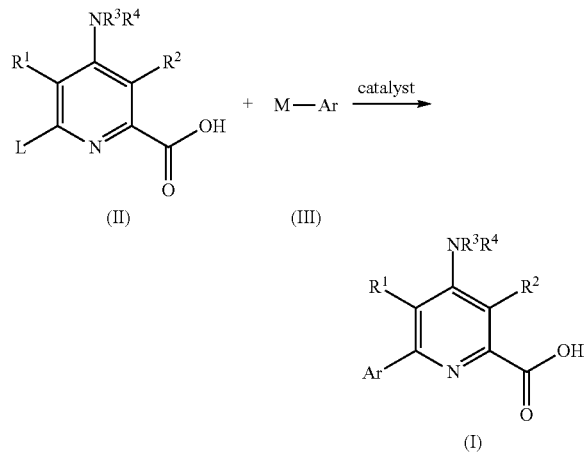

In scheme 1, the "L" group represents radicals such as chlorine, bromine, iodine or trifluoromethanesulfonate, for example. In addition, in scheme 1, the "M" radical represents, for example, Mg-Hal, Zn-Hal, Sn(($C_1$-$C_4$)alkyl)$_3$, lithium, copper or B(OR$^{27}$)(OR$^{28}$) where the $R^{27}$ and $R^{28}$ radicals are each independently, for example, hydrogen, ($C_1$-$C_4$)-alkyl, or, when the $R^{27}$ and $R^{28}$ radicals are joined to one another, together are ethylene or propylene. The catalyst is, for example, a transition metal catalyst, especially palladium catalysts such as palladium diacetate or bis(triphenylphosphine)palladium(II) dichloride, or nickel catalysts such as nickel(II) acetylacetonate or bis(triphenylphosphine)nickel (II) chloride. The Hal radical represents halide.

An alternative route consists in the reaction of a picolinic acid derivative (IV) which has a substitution pattern suitable for this reaction and which bears a metal- or semimetal-containing radical in the form of the "M" group with a reaction partner (V) in which the "L" radical is a leaving group (scheme 2).

Scheme 2:

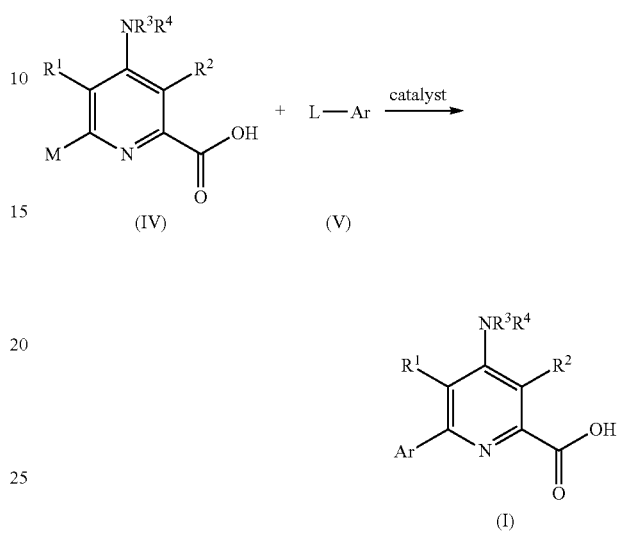

In scheme 2, the "L" group represents radicals such as chlorine, bromine, iodine or trifluoromethanesulfonate, for example. In addition, in scheme 2, the "M" radical represents, for example, Mg-Hal, Zn-Hal, Sn(($C_1$-$C_4$)alkyl)$_3$, lithium, copper or B(OR$^{27}$)(OR$^{28}$) where the $R^{27}$ and $R^{28}$ radicals are each independently, for example, hydrogen, ($C_1$-$C_4$)-alkyl, or, when the $R^{27}$ and $R^{28}$ radicals are joined to one another, together are ethylene or propylene. The catalyst is, for example, a transition metal catalyst, especially palladium catalysts such as palladium diacetate or bis(triphenylphosphine)palladium(II) dichloride, or nickel catalysts such as nickel(II) acetylacetonate or bis(triphenylphosphine)nickel (II) chloride. The Hal radical represents halide.

Reactions as in schemes 1 and 2 are well known in the literature and have been described specifically for picolinic acid derivatives, for example, in WO 03/011853 and WO 2009/046090.

A heterocyclyl group as a substituent on the "Ar" group can be introduced in a similar manner via a cross-coupling reaction as described in schemes 1 and 2, if this heterocyclyl group is suitable for such synthesis methods with regard to the physicochemical character thereof (scheme 3).

Scheme 3:

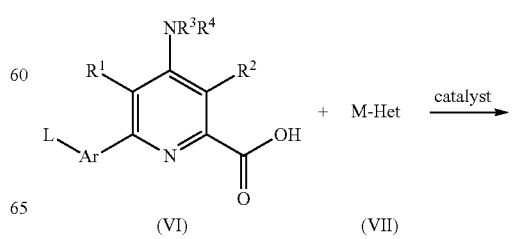

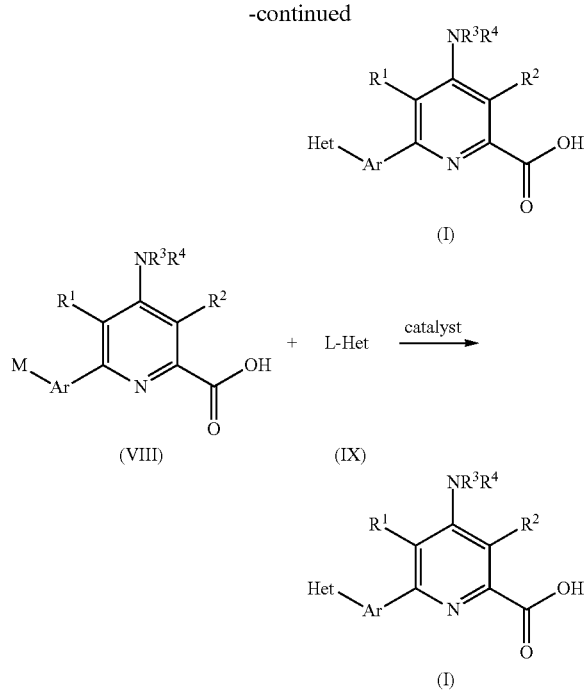

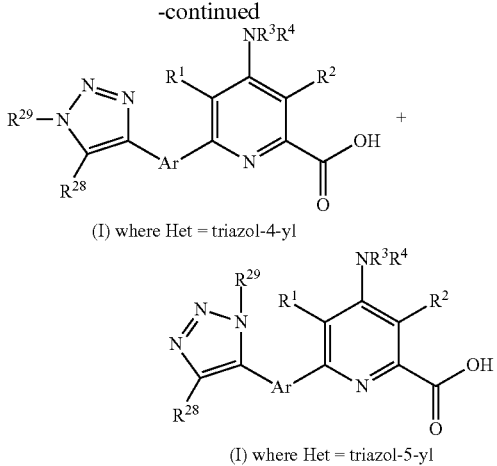

The definitions of the variables are the same as in schemes 1 and 2; the variable "Het" represents "heterocyclyl". Since the synthesis methods correspond to those in schemes 1 and 2, catalysts of the same type are used. Such cross-couplings are well known in the literature and are described, for example, by Kotha, S. et al. (Tetrahedron 58 (2002) 48, 9633-9695), R. J. Hooley and C. Lee (Chemtracts—Organic Chemistry 16: 518-526 (2003)) or R. Rossi (Synthesis 2004, 15, 2419-2440).

Another option is the formation of a heterocycle. A multitude of methods are known in the literature for this purpose. One example is the formation of triazoles from alkynes, which themselves are obtainable via a Sonogashira coupling (V. V. Fokin and K. B. Sharpless et al., Angew. Chem. Int. Ed. 2002, 41, 14, 2596; K. Sonogashira, Y. Tohda, N. Hagihara, Tetrahedron Lett. 1975, 4467; H. Doucet and J.-C. Hierso, Angew. Chem. 2007, 119, 850).

Scheme 4:

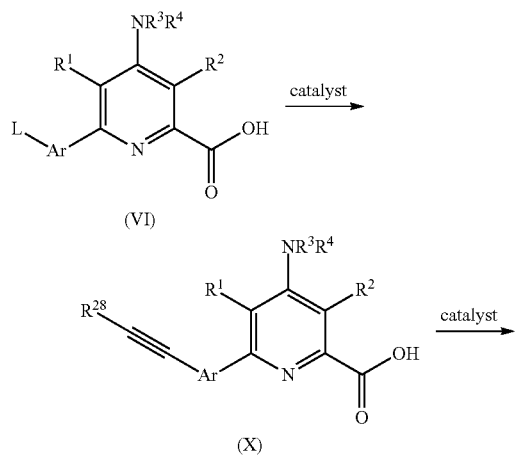

The $R^{28}$ radical is generally hydrogen. A further development, which also includes the conversion of alkynes where $R^{28} \neq H$, is described by J. E. Moses in Angew. Chem. 2010, 122, 33-36.

The route to the picolinic acid derivatives (II) and (IV), and also to the aryl derivatives (III), is described in the prior art, for example in WO 01/51468, WO 03/011853 and WO 2009/046090.

It may be appropriate for the synthesis steps detailed above to be preceded or followed by further reactions for derivatization, introduction or removal of functional groups. For example, it may be advantageous in the reactions in schemes 1 to 4 to use protected carboxylic acid derivatives instead of free carboxylic acids. In many cases, esters such as methyl or ethyl esters are suitable. tert-Butyl esters often screen the carboxyl group in a sterically effective manner against nucleophilic reagents and can be detached easily in an acidic medium (T. W. Greene, P. G. M. Wuts, Protective Groups in Organic Synthesis, 2nd Edition, John Wiley & Sons, Inc. 1991, p. 227 ff.). Further suitable radicals are those which are much more stable than carboxyl groups but are obtainable in a simple manner from carboxylic acids and can also be converted easily back to the free carboxylic acids. Examples of these include oxazolines (T. W. Greene, P. G. M. Wuts, Protective Groups in Organic Synthesis, 2nd Edition, John Wiley & Sons, Inc. 1991, p. 265 ff.; Z. Hell et al., Tetrahedron Letters 43 (2002), 3985-3987).

It may in some cases be advantageous to switch the sequence of the reaction steps described in the above schemes, or else to combine them with one another.

The particular reaction mixtures are generally worked up by known processes, for example by crystallization, aqueous extractive workup, by chromatographic methods, or by combination of these methods.

Libraries of inventive compounds which can be synthesized by the abovementioned reactions can also be prepared in a parallelized manner, which can be done in a manual, semiautomated or fully automated manner. It is possible, for example, to automate the performance of the reaction, the workup or the purification of the products or intermediates. This is understood overall to mean a procedure as described, for example, by D. Tiebes in Combinatorial Chemistry—Synthesis, Analysis, Screening (editor: Günther Jung), Wiley publishers 1999, on pages 1 to 34.

For parallelized reaction performance and workup, it is possible to use a range of commercially available equipment, for example Calypso reaction blocks from Barnstead International, Dubuque, Iowa 52004-0797, USA or reaction stations from Radleys, Shire Hill, Saffron Walden, Essex, CB11 3AZ, England, or MultiPROBE Automated Workstations from Perkin Elmer, Waltham, Mass. 02451, USA. For the parallelized purification of inventive compounds or of intermediates obtained in the preparation, apparatus available includes chromatography apparatus, for example from ISCO, Inc., 4700 Superior Street, Lincoln, Nebr. 68504, USA.

The apparatus detailed leads to a modular procedure, in which the individual steps are automated, but manual operations have to be conducted between the steps. This can be avoided by the use of partly or fully integrated automation systems, in which the particular automation modules are operated, for example, by robots. Such automation systems can be purchased, for example, from Caliper, Hopkinton, Mass. 01748, USA.

The performance of individual or several synthesis steps can be supported by the use of polymer-supported reagents/scavenger resins. The specialist literature describes a multitude of experimental protocols, for example in ChemFiles, Vol. 4, No. 1, Polymer-Supported Scavengers and Reagents for Solution-Phase Synthesis (Sigma-Aldrich).

In addition to the methods described here, inventive compounds can be prepared completely or partially by solid phase-supported methods. For this purpose, individual intermediates or all intermediates of the synthesis or of a synthesis matched to the appropriate procedure are bound to a synthesis resin. Solid phase-supported synthesis methods have been described sufficiently in the specialist literature, for example Barry A. Bunin in "The Combinatorial Index", Academic Press publishers, 1998 and Combinatorial Chemistry—Synthesis, Analysis, Screening (editor: Günther Jung), Wiley publishers, 1999. The use of solid phase-supported synthesis methods allows a range of protocols known from the literature, which can in turn be executed in a manual or automated manner. The reactions can be performed, for example, by means of IRORI technology in microreactors from Nexus Biosystems, 12140 Community Road, Poway, Calif. 92064, USA.

Both on the solid phase and in the liquid phase, the performance of individual or several synthesis steps can be supported by the use of microwave technology. The specialist literature describes a range of experimental protocols, for example Microwaves in Organic and Medicinal Chemistry (editors: C. O. Kappe and A. Stadler), Wiley publishers, 2005.

The preparation by the process described herein affords inventive compounds in the form of substance libraries. The present invention also provides libraries containing at least two inventive compounds.

The inventive compounds have excellent herbicidal efficacy against a broad spectrum of economically important mono- and dicotyledonous annual weed plants. The active ingredients also have good control over perennial weed plants which are difficult to control, which produce shoots from rhizomes, rootstocks or other permanent organs.

The present invention therefore also provides a method for controlling unwanted plants or for regulating the growth of plants, preferably in crops of plants, in which one or more inventive compound(s) is/are applied to the plants (for example weed plants such as monocotyledonous or dicotyledonous weeds or unwanted crop plants), to the seeds (for example grains, seeds or vegetative propagules such as tubers or shoot parts with buds) or to the area on which the plants grow (for example the area under cultivation). In this context, the inventive compounds can be applied for example pre-sowing (if appropriate also by incorporation into the soil), pre-emergence or post-emergence. Examples of individual representatives of the monocotyledonous and dicotyledonous weed flora which can be controlled by the inventive compounds will be mentioned, though there is no intention to impose a restriction to particular species mentioned.

Monocotyledonous weed plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous weed plants of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

If the inventive compounds are applied to the soil surface before germination, either the emergence of the weed seedlings is prevented completely or the weeds grow until they have reached the cotyledon stage, but then stop growing and, ultimately, die completely after three to four weeks have passed.

When the active ingredients are applied post-emergence to the green plant parts, growth stops after the treatment, and the weed plants remain in the growth stage of the time of application or die fully after a certain period of time, so that competition by weeds, which is harmful to the crop plants, is thus eliminated at a very early stage and in a sustained manner.

Although the inventive compounds display an outstanding herbicidal activity against monocotyledonous and dicotyledonous weed plants, crop plants of economically important crops such as dicotyledonous crops, for example of the genera *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia*, or monocotyledonous crops, for example of the genera *Allium, Ananas, Asparagus, Avena, Hordeum, Oryza, Panicum, Saccharum, Secale, Sorghum, Triticale, Triticum, Zea*, especially *Zea* and *Triticum*, are damaged only to an insignificant extent, if at all, depending on the structure of the particular inventive compound and its application rate. For these reasons, the inventive compounds are highly suitable for the selective control of unwanted vegetation in plant crops such as agriculturally useful plants or ornamentals.

Moreover, the inventive compounds (depending on their particular structure and the application rate applied) have outstanding growth-regulating properties in crop plants. They engage in the plant's own metabolism in a regulatory manner and can therefore be used for controlled influence of plant constituents and to facilitate harvesting, for example by triggering desiccation and stunted growth. In addition, they are also suitable for general control and inhibition of unwanted vegetative growth without destroying the plants in the process. Inhibition of vegetative growth plays an important role in many monocotyledonous and dicotyledonous crops since, for example, this can reduce or completely prevent lodging.

Owing to their herbicidal and plant growth-regulating properties, the inventive compounds can also be used to control weed plants in crops of known genetically modified plants or genetically modified plants which are yet to be developed. The transgenic plants generally feature special advantageous properties, for example resistances to certain pesticides, mainly certain herbicides, resistances to plant diseases or causative organisms of plant diseases, such as certain insects or microorganisms such as fungi, bacteria or viruses. Other special properties relate, for example, to the harvested material with regard to quantity, quality, storability, composition and specific constituents. Thus, transgenic plants with an increased starch content or a modified starch quality or those with a different fatty acid composition of the harvested material are known. Further special properties may be tolerance or resistance to abiotic stressors, for example heat, cold, drought, salt and ultraviolet radiation.

Preference is given to employing the inventive compounds in economically important transgenic crops of useful plants and ornamentals, for example of cereals such as wheat, barley, rye, oats, sorghum and millet, rice, cassava and maize or else crops of sugar beet, cotton, soybean, oilseed rape, potato, tomato, peas and other vegetables.

The inventive compounds can preferably be used as herbicides in crops of useful plants which are resistant, or have been made resistant by recombinant means, to the phytotoxic effects of the herbicides.

Conventional ways of generating novel plants which have modified properties compared to existing plants are, for example, traditional breeding methods and the generation of mutants. Alternatively, novel plants with modified properties can be generated with the aid of recombinant methods (see, for example, EP 0221044, EP 0131624). For example, the following have been described in several cases:

recombinant modifications of crop plants for the purpose of modifying the starch synthesized in the plants (for example WO 92/011376 A, WO 92/014827 A, WO 91/019806 A), transgenic crop plants which are resistant to certain herbicides of the glufosinate type (cf., for example, EP 0 242 236 A, EP 0 242 246 A) or of the glyphosate type (WO 92/000377 A) or of the sulfonylurea type (EP 0 257 993 A, U.S. Pat. No. 5,013,659), or are resistant to combinations or mixtures of these herbicides by virtue of "gene stacking", such as transgenic crop plants, for example maize or soya with the trade name or the designation Optimum™ GAT™ (Glyphosate ALS Tolerant), transgenic crop plants, for example cotton which is capable of producing *Bacillus thuringiensis* toxins (Bt toxins), which make the plants resistant to certain pests (EP 0 142 924 A, EP 0 193 259 A), transgenic crop plants with a modified fatty acid composition (WO 91/013972 A), genetically modified crop plants with novel constituents or secondary metabolites, for example novel phytoalexins, which bring about an increased disease resistance (EP 0 309 862 A, EP 0 464 461 A), genetically modified plants with reduced photorespiration which feature higher yields and higher stress tolerance (EP 0 305 398 A), transgenic crop plants which produce pharmaceutically or diagnostically important proteins ("molecular pharming"), transgenic crop plants which are distinguished by higher yields or better quality, transgenic crop plants which are distinguished by a combination, for example of the abovementioned novel properties ("gene stacking").

A large number of molecular biology techniques by means of which novel transgenic plants with modified properties can be produced are known in principle; see, for example, I. Potrykus and G. Spangenberg (eds.) Gene Transfer to Plants, Springer Lab Manual (1995), Springer Verlag Berlin, Heidelberg, or Christou, "Trends in Plant Science" 1 (1996) 423-431).

For such recombinant manipulations, it is possible to introduce nucleic acid molecules into plasmids, which permit a mutagenesis or sequence modification by recombination of DNA sequences. For example, base substitutions can be carried out, part-sequences can be removed, or natural or synthetic sequences may be added with the aid of standard methods. For the bonding of the DNA fragments to one another, it is possible to add adapters or linkers to the fragments; see, for example, Sambrook et al., 1989, Molecular Cloning, A Laboratory Manual, 2nd ed., Cold Spring Harbor Laboratory Press, Cold Spring Harbor, N.Y.; or Winnacker "Gene and Klone" [Genes and Clones], VCH Weinheim 2nd ed., 1996.

The production of plant cells with a reduced activity for a gene product can be achieved for example by the expression of at least one corresponding antisense RNA, or of a sense RNA for achieving a cosuppression effect, or by the expression of at least one correspondingly constructed ribozyme which specifically cleaves transcripts of the abovementioned gene product.

To this end, it is possible firstly to use DNA molecules which comprise all of the coding sequence of a gene product, including any flanking sequences which may be present, or else DNA molecules which only comprise parts of the coding sequence, it being necessary for these parts to be long enough to bring about an antisense effect in the cells. It is also possible to use DNA sequences which have a high degree of homology with the coding sequences of a gene product, but which are not entirely identical.

When expressing nucleic acid molecules in plants, the protein synthesized may be localized in any compartment of the plant cell. In order to achieve localization in a particular compartment, however, it is possible for example to link the coding region to DNA sequences which ensure localization in a specific compartment. Such sequences are known to the skilled worker (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give intact plants. In principle, the transgenic plants may be plants of any plant species, that is to say both monocotyledonous and dicotyledonous plants.

Thus, it is possible to obtain transgenic plants which feature modified properties as the result of overexpression, suppression or inhibition of homologous (=natural) genes or gene sequences or expression of heterologous (=foreign) genes or gene sequences.

The inventive compounds can preferably be used in transgenic crops which are resistant to growth regulators, for example 2, 4 D, dicamba, or to herbicides which inhibit essential plant enzymes, for example acetolactate synthases (ALS), EPSP synthases, glutamine synthases (GS) or hydroxyphenylpyruvate dioxygenases (HPPD), or to herbicides from the group of the sulfonylureas, glyphosates, glufosinates or benzoylisoxazoles and analogous active ingredients, or to any combinations of these active ingredients.

The inventive compounds can more preferably be used in transgenic crop plants which are resistant to a combination of glyphosates and glufosinates, glyphosates and sulfonylureas or imidazolinones. It is very particularly preferred to employ the inventive compounds in transgenic crop plants, for example maize or soya, with the trade name or the designation Optimum™ GAT™ (Glyphosate ALS Tolerant).

When the inventive compounds are employed in transgenic crops, effects are frequently observed—in addition to the effects on weed plants which can be observed in other crops—which are specific for the application in the transgenic crop in question, for example a modified or specifically widened spectrum of weeds which can be controlled, modified application rates which may be employed for application, preferably good combinability with the herbicides to which the transgenic crop is resistant, and an effect on growth and yield of the transgenic crop plants.

The invention therefore also provides for the use of the inventive compounds as herbicides for controlling weed plants in transgenic crop plants.

The inventive compounds can be used, for example, in the form of wettable powders, emulsifiable concentrates, sprayable solutions, dusting products or granules in the customary formulations. The invention therefore also provides herbicidal and plant growth-regulating compositions which comprise the inventive compounds.

The inventive compounds can be formulated in various ways according to which biological and/or physicochemical parameters are required. Possible formulations include, for example: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), oil- or water-based dispersions, oil-miscible solutions, capsule suspensions (CS), dusting products (DP), seed-dressing products, granules for scattering and soil application, granules (GR) in the form of microgranules, spray granules, coated granules and adsorption granules, water-dispersible granules (WG), water-soluble granules (SG), ULV formulations, microcapsules and waxes.

These individual formulation types are known in principle and are described, for example, in: Winnacker-Küchler, "Chemische Technologie" [Chemical Technology], Volume 7, C. Hanser Verlag Munich, 4th Ed. 1986; Wade van Valkenburg, "Pesticide Formulations", Marcel Dekker, N.Y., 1973; K. Martens, "Spray Drying" Handbook, 3rd Ed. 1979, G. Goodwin Ltd. London.

The necessary formulation assistants, such as inert materials, surfactants, solvents and further additives, are likewise known and are described, for example, in: Watkins, "Handbook of Insecticide Dust Diluents and Carriers", 2nd Ed., Darland Books, Caldwell N.J., H. v. Olphen, "Introduction to Clay Colloid Chemistry"; 2nd Ed., J. Wiley & Sons, N.Y; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Interface-Active Ethylene Oxide Adducts], Wiss. Verlagsgesell., Stuttgart 1976; Winnacker-Küchler, "Chemische Technologie", Volume 7, C. Hanser Verlag Munich, 4th Ed. 1986.

Based on these formulations, it is also possible to prepare combinations with other pesticidally active substances, for example, insecticides, acaricides, herbicides, fungicides, and also with safeners, fertilizers and/or growth regulators, for example in the form of a finished formulation or as a tankmix.

Wettable powders are preparations which can be dispersed uniformly in water and, as well as the active ingredient, apart from a diluent or inert substance, also comprise surfactants of the ionic and/or nonionic type (wetting agents, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleylmethyltauride. To prepare the wettable powders, the active herbicidal ingredients are ground finely, for example in customary apparatus such as hammer mills, blower mills and air-jet mills, and simultaneously or subsequently mixed with the formulation assistants.

Emulsifiable concentrates are prepared by dissolving the active ingredient in an organic solvent, for example butanol, cyclohexanone, dimethylformamide, xylene or else relatively high-boiling aromatics or hydrocarbons or mixtures of the organic solvents with addition of one or more surfactants of the ionic and/or nonionic type (emulsifiers). The emulsifiers used may, for example, be: calcium alkylarylsulfonates such as calcium dodecylbenzenesulfonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters, or polyoxyethylene sorbitan esters, for example polyoxyethylene sorbitan fatty acid esters.

Dusting products are obtained by grinding the active ingredient with finely divided solid substances, for example talc, natural clays such as kaolin, bentonite and pyrophyllite, or diatomaceous earth.

Suspension concentrates may be water- or oil-based. They may be prepared, for example, by wet grinding by means of commercial bead mills and optional addition of surfactants as have, for example, already been listed above for the other formulation types.

Emulsions, for example oil-in-water emulsions (EW), can be prepared, for example, by means of stirrers, colloid mills and/or static mixers using aqueous organic solvents and optionally surfactants, as have, for example, already been listed above for the other formulation types.

Granules can be produced either by spraying the active ingredient onto adsorptive granulated inert material or by applying active ingredient concentrates by means of adhesives, for example polyvinyl alcohol, sodium polyacrylate or else mineral oils, onto the surface of carriers such as sand, kaolinites or of granulated inert material. It is also possible to granulate suitable active ingredients in the manner customary for the production of fertilizer granules—if desired in a mixture with fertilizers.

Water-dispersible granules are prepared generally by the customary processes such as spray-drying, fluidized bed granulation, pan granulation, mixing with high-speed mixers and extrusion without solid inert material.

For the production of pan, fluidized bed, extruder and spray granules, see, for example, processes in "Spray-Drying Handbook" 3rd ed. 1979, G. Goodwin Ltd., London; J. E. Browning, "Agglomeration", Chemical and Engineering 1967, pages 147 ff; "Perry's Chemical Engineer's Handbook", 5th Ed., McGraw-Hill, New York 1973, pp. 8-57.

For further details regarding the formulation of crop protection compositions, see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical formulations contain generally 0.1 to 99% by weight, especially 0.1 to 95% by weight, of inventive compounds.

In wettable powders, the active ingredient concentration is, for example, about 10 to 90% by weight; the remainder to 100% by weight consists of customary formulation constituents. In the case of emulsifiable concentrates, the active ingredient concentration may be about 1 to 90% by weight, preferably 5 to 80% by weight. Dust-type formulations contain 1 to 30% by weight of active ingredient, preferably usually 5 to 20% by weight of active ingredient; sprayable solutions contain about 0.05 to 80% by weight, preferably 2 to 50% by weight of active ingredient. In water-dispersible granules, the active ingredient content depends partly on whether the active compound is present in solid or liquid form and which granulation assistants, fillers, etc. are used. In the granules dispersible in water, the content of active ingredient is, for example, between 1 and 95% by weight, preferably between 10 and 80% by weight.

In addition, the active ingredient formulations mentioned optionally comprise the respective customary adhesives, wetting agents, dispersants, emulsifiers, penetrants, preservatives, antifreezes and solvents, fillers, carriers and dyes, defoamers, evaporation inhibitors and agents which influence the pH and the viscosity.

Suitable combination partners for the inventive compounds in mixture formulations or in tankmixes are, for example, known active ingredients, which are based on inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoene desaturase, photosystem I, photosystem II, protoporphyrinogen oxidase, as described, for example, in Weed Research 26 (1986) 441-445 or "The Pesticide Manual", 15th edition, The British Crop Protection Council and the Royal Soc. of Chemistry, 2006 and literature cited therein. Known herbicides or plant growth regulators which can be combined with the inventive compounds include, for example, the following active ingredients (the compounds are referred to by the common name according to the International Organization for Standardization (ISO) or by the chemical name or by the code number) and always include all use forms, such as acids, salts, esters and isomers such as stereoisomers and optical isomers. In this list, one or else, in some cases, more than one application form is mentioned by way of example:

acetochlor, acibenzolar, acibenzolar-S-methyl, acifluorfen, acifluorfen-sodium, aclonifen, alachlor, allidochlor, alloxydim, alloxydim-sodium, ametryne, amicarbazone, amidochlor, amidosulfuron, aminocyclopyrachlor, aminocyclopyrachlor-potassium, aminocyclopyrachlor-methyl, aminopyralid, amitrole, ammonium sulfamate, ancymidol, anilofos, asulam, atrazine, azafenidin, azimsulfuron, aziprotryne, beflubutamid, benazolin, benazolin-ethyl, bencarbazone, benfluralin, benfuresate, bensulide, bensulfuron, bensulfuron-methyl, bentazone, benzfendizone, benzobicyclon, benzofenap, benzofluor, benzoylprop, bicyclopyrone, bifenox, bilanafos, bilanafos-sodium, bispyribac, bispyribac-sodium, bromacil, bromobutide, bromofenoxim, bromoxynil, bromuron, buminafos, busoxinone, butachlor, butafenacil, butamifos, butenachlor, butralin, butroxydim, butylate, cafenstrole, carbetamide, carfentrazone, carfentrazone-ethyl, chlomethoxyfen, chloramben, chlorazifop, chlorazifop-butyl, chlorbromuron, chlorbufam, chlorfenac, chlorfenac-sodium, chlorfenprop, chlorflurenol, chlorflurenol-methyl, chloridazon, chlorimuron, chlorimuron-ethyl, chlormequat-chloride, chlornitrofen, chlorophthalim, chlorthal-dimethyl, chlortoluron, chlorsulfuron, cinidon, cinidon-ethyl, cinmethylin, cinosulfuron, clethodim, clodinafop, clodinafop-propargyl, clofencet, clomazone, clomeprop, cloprop, clopyralid, cloransulam, cloransulam-methyl, cumyluron, cyanamide, cyanazine, cyclanilide, cycloate, cyclosulfamuron, cycloxydim, cycluron, cyhalofop, cyhalofop-butyl, cyperquat, cyprazine, cyprazole, 2,4-D, 2,4-DB, daimuron/dymron, dalapon, daminozide, dazomet, n-decanol, desmedipham, desmetryn, detosyl-pyrazolate (DTP), diallate, dicamba, dichlobenil, dichlorprop, dichlorprop-P, diclofop, diclofop-methyl, diclofop-P-methyl, diclosulam, diethatyl, diethatyl-ethyl, difenoxuron, difenzoquat, diflufenican, diflufenzopyr, diflufenzopyr-sodium, dikegulac-sodium, dimefuron, dimepiperate, dimethachlor, dimethametryn, dimethenamid, dimethenamid-P, dimethipin, dimetrasulfuron, dinitramine, dinoseb, dinoterb, diphenamid, dipropetryn, diquat, diquat-dibromide, dithiopyr, diuron, DNOC, eglinazine-ethyl, endothal, EPTC, esprocarb, ethalfluralin, ethametsulfuron, ethametsulfuron-methyl, ethephon, ethidimuron, ethiozin, ethofumesate, ethoxyfen, ethoxyfen-ethyl, ethoxysulfuron, etobenzanid, F-5331, i.e. N-[2-chloro-4-fluoro-5-[4-(3-fluoropropyl)-4,5-dihydro-5-oxo-1H-tetrazol-1-yl]phenyl]ethanesulfonamide, F-7967, i.e. 3-[7-chloro-5-fluoro-2-(trifluoromethyl)-1H-benzimidazol-4-yl]-1-methyl-6-(trifluoromethyl)pyrimidine-2,4(1H,3H)-dione, fenoprop, fenoxaprop, fenoxaprop-P, fenoxaprop-ethyl, fenoxaprop-P-ethyl, fenoxasulfone, fentrazamide, fenuron, flamprop, flamprop-M-isopropyl, flamprop-M-methyl, flazasulfuron, florasulam, fluazifop, fluazifop-P, fluazifop-butyl, fluazifop-P-butyl, fluazolate, flucarbazone, flucarbazone-sodium, flucetosulfuron, fluchloralin, flufenacet (thiafluamide), flufenpyr, flufenpyr-ethyl, flumetralin, flumetsulam, flumiclorac, flumiclorac-pentyl, flumioxazin, flumipropyn, fluometuron, fluorodifen, fluoroglycofen, fluoroglycofen-ethyl, flupoxam, flupropacil, flupropanate, flupyrsulfuron, flupyrsulfuron-methyl-sodium, flurenol, flurenol-butyl, fluridone, fluorochloridone, fluoroxypyr, fluoroxypyr-meptyl, flurprimidol, flurtamone, fluthiacet, fluthiacet-methyl, fluthiamide, fomesafen, foramsulfuron, forchlorfenuron, fosamine, furyloxyfen, gibberellic acid, glufosinate, glufosinate-ammonium, glufosinate-P, glufosinate-P-ammonium, glufosinate-P-sodium, glyphosate, glyphosate-isopropylammonium, H-9201, i.e. O-(2,4-dimethyl-6-nitrophenyl) O-ethyl isopropylphosphoramidothioate, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HW-02, i.e. 1-(dimethoxyphosphoryl)ethyl (2,4-dichlorophenoxy)acetate, imazamethabenz, imazamethabenz-methyl, imazamox, imazamox-ammonium, imazapic, imazapyr, imazapyr-isopropylammonium, imazaquin, imazaquin-ammonium, imazethapyr, imazethapyr-ammonium, imazosulfuron, inabenfide, indanofan, indaziflam, indoleacetic acid (IAA), 4-indol-3-ylbutyric acid (IBA), iodosulfuron, iodosulfuron-methyl-sodium, iofensulfuron, iofensulfuron-sodium, ioxynil, ipfencarbazone, isocarbamid, isopropalin, isoproturon, isouron, isoxaben, isoxachlortole, isoxaflutole, isoxapyrifop, KUH-043, i.e. 3-({[5-(difluoromethyl)-1-methyl-3-(trifluoromethyl)-1H-pyrazol-4-yl]methyl}sulfonyl)-5,5-dimethyl-4,5-dihydro-1,2-oxazole, karbutilate, ketospiradox, lactofen, lenacil, linuron, maleic hydrazide, MCPA, MCPB, MCPB-methyl, -ethyl and -sodium, mecoprop, mecoprop-sodium, mecoprop-butotyl, mecoprop-P-butotyl, mecoprop-P-dimethylammonium, mecoprop-P-2-ethylhexyl, mecoprop-P-potassium, mefenacet, mefluidide, mepiquat-chloride, mesosulfuron, mesosulfuron-methyl, mesotrione, methabenzthiazuron, metam, metamifop, metamitron, metazachlor, metazasulfuron, methazole, methiopyrsulfuron, methiozolin, methoxyphenone, methyldymron, 1-methylcyclopropene, methyl isothiocyanate, metobenzuron, metobromuron, metolachlor, S-metolachlor, metosulam, metoxuron, metribuzin, metsulfuron, metsulfuron-methyl, molinate, monalide, monocarbamide, monocarbamide dihydrogensulfate, monolinuron, monosulfuron, monosulfuron ester, monuron, MT-128, i.e. 6-chloro-N-[(2E)-3-chloroprop-2-en-1-yl]-5-methyl-N-phenylpyridazine-3-amine, MT-5950, i.e. N-[3-chloro-4-(1-methylethyl)phenyl]-2-methylpentanamide, NGGC-011, naproanilide, napropamide, naptalam, NC-310, i.e. 4-(2,4-dichlorobenzoyl)-1-methyl-5-benzyloxypyrazole, neburon, nicosulfuron, nipyraclofen, nitralin, nitrofen, nitrophenolate-sodium (isomer mixture), nitrofluorfen, nonanoic acid, norflurazon, orbencarb, orthosulfamuron, oryzalin, oxadiargyl, oxadiazon, oxasulfuron, oxaziclomefone, oxyfluorfen, paclobutrazole, paraquat, paraquat dichloride, pelargonic acid (nonanoic acid), pendimethalin, pendralin, penoxsulam, pentanochlor, pentoxazone, perfluidone, pethoxamid, phenisopham, phenmedipham, phenmedipham-ethyl, picloram, picolinafen, pinoxaden, piperophos, pirifenop, pirifenop-butyl, pretilachlor, primisulfuron, primisulfuron-methyl, probenazole, profluazole, procyazine, prodiamine, prifluraline, profoxydim, prohexadione, prohexadione-calcium, prohydrojasmone, prometon, prometryn, propachlor, propanil, propaquizafop, propazine, propham, propisochlor, propoxycarbazone, propoxycarbazone-sodium, propyrisulfuron, propyzamide, prosulfalin, prosulfocarb, prosulfuron, prynachlor, pyraclonil, pyraflufen, pyraflufen-ethyl, pyrasulfotole, pyrazolynate (pyrazolate), pyrazosulfuron, pyrazosulfuron-ethyl, pyrazoxyfen, pyribambenz, pyribambenz-isopropyl, pyribambenz-propyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, saflufenacil, secbumeton, sethoxydim, siduron, simazine, simetryn, SN-106279, i.e. methyl (2R)-2-({7-[2-chloro-4-(trifluoromethyl)phenoxy]-2-naphthyl}oxy)propanoate, sulcotrione, sulfallate (CDEC), sulfentrazone, sulfometuron, sulfometuron-methyl, sulfosate (glyphosate-trimesium), sulfosulfuron, SW-065, SYN-523, SYP-249, i.e. 1-ethoxy-3-methyl-1-oxobut-3-en-2-yl 5-[2-chloro-4-(trifluoromethyl)phenoxy]-2-nitrobenzoate, SYP-300, i.e. 1-[7-fluoro-3-oxo-4-(prop-2-yn-1-yl)-3,4-dihydro-2H-1,4-benzoxazin-6-yl]-3-propyl-2-thioxoimidazolidine-4,5-dione, tebutam, tebuthiuron, tecnazene, tefuryltrione, tembotrione, tepraloxydim, terbacil, terbucarb, terbuchlor, terbumeton, terbuthylazine, terbutryne, thenylchlor, thiafluamide, thiazafluoron, thiazopyr, thidiazimin, thidiazuron, thiencarbazone, thiencarbazone-methyl, thifensulfuron, thifensulfuron-methyl, thiobencarb, tiocarbazil, topramezone, tralkoxydim, triafamone, triallate, triasulfuron, triaziflam, triazofenamide, tribenuron, tribenuron-methyl, trichloroacetic acid (TCA), triclopyr, tridiphane, trietazine, trifloxysulfuron, trifloxysulfuron-sodium, trifluralin, triflusulfuron, triflusulfuron-methyl, trimeturon, trinexapac, trinexapac-ethyl, tritosulfuron, tsitodef, uniconazole, uniconazole-P, vernolate, ZJ-0862, i.e. 3,4-dichloro-N-{2-[(4,6-dimethoxypyrimidin-2-yl)oxy]benzyl}-aniline, and the following compounds:

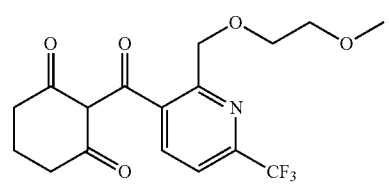

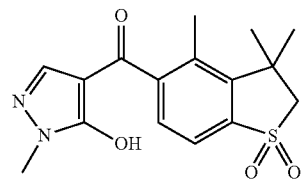

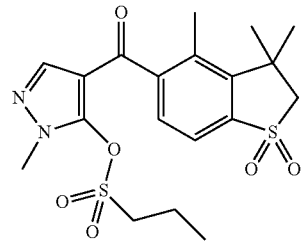

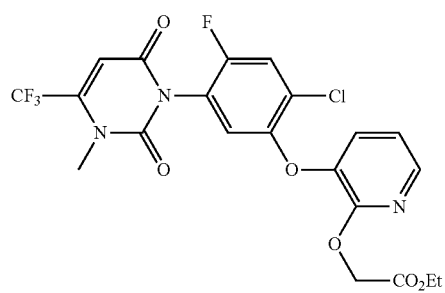

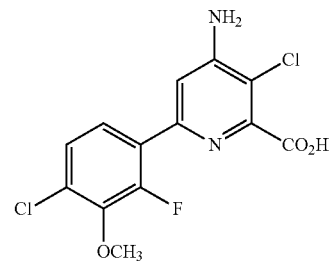

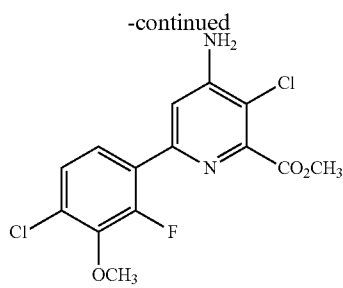

Of particular interest is the selective control of weed plants in crops of useful and ornamental plants. Even though the inventive compounds already have very good to adequate selectivity in many crops, it is possible in principle for phytotoxicity to occur in the plants of some crops and in particular also in mixtures with other herbicides which are less selective. In this regard, combinations of particular interest are those which comprise the inventive compounds in combination with safeners, and optionally further pesticides such as herbicides. The safeners, which are used in an antidotally effective content, reduce the phytotoxic side effects of the pesticides used, for example in economically important crops such as cereals (for example wheat, barley, rye, corn, rice, millet/sorghum), sugar beet, sugar cane, oilseed rape, cotton and soybeans, preferably cereals.

The following groups of compounds are examples of possible safeners:

S1) compounds from the group of heterocyclic carboxylic acid derivatives:

S1$^a$) compounds of the dichlorophenylpyrazoline-3-carboxylic acid type (S1$^a$), preferably compounds such as 1-(2,4-dichlorophenyl)-5-(ethoxycarbonyl)-5-methyl-2-pyrazoline-3-carboxylic acid, ethyl 1-(2,4-dichlorophenyl)-5-(ethoxycarbonyl)-5-methyl-2-pyrazoline-3-carboxylate (S1-1) ("mefenpyr-diethyl"), and related compounds as described in WO-A-91/07874;

S1$^b$) derivatives of dichlorophenylpyrazolecarboxylic acid (S1$^b$), preferably compounds such as ethyl 1-(2,4-dichlorophenyl)-5-methylpyrazole-3-carboxylate (S1-2), ethyl 1-(2,4-dichlorophenyl)-5-isopropylpyrazole-3-carboxylate (S1-3), ethyl 1-(2,4-dichlorophenyl)-5-(1,1-dimethylethyl)-pyrazole-3-carboxylate (S1-4) and related compounds as described in EP-A-333 131 and EP-A-269 806;

S1$^c$) derivatives of 1,5-diphenylpyrazole-3-carboxylic acid (S1$^c$), preferably compounds such as ethyl 1-(2,4-dichlorophenyl)-5-phenylpyrazole-3-carboxylate (S1-5), methyl 1-(2-chlorophenyl)-5-phenylpyrazole-3-carboxylate (S1-6) and related compounds as described, for example, in EP-A-268554;

S1$^d$) compounds of the triazolecarboxylic acid type (S1$^d$), preferably compounds such as fenchlorazole(-ethyl), i.e. ethyl 1-(2,4-dichlorophenyl)-5-trichloro-methyl-(1H)-1,2,4-triazole-3-carboxylate (S1-7), and related compounds as described in EP-A-174 562 and EP-A-346 620;

S1$^e$) compounds of the 5-benzyl- or 5-phenyl-2-isoxazoline-3-carboxylic acid type, or of the 5,5-diphenyl-2-isoxazoline-3-carboxylic acid type (S1$^e$), preferably compounds such as ethyl 5-(2,4-dichlorobenzyl)-2-isoxazoline-3-carboxylate (S1-8) or ethyl 5-phenyl-2-isoxazoline-3-carboxylate (S1-9) and related compounds as described in WO-A-91/08202, or 5,5-diphenyl-2-isoxazoline-carboxylic acid (S1-10) or ethyl 5,5-diphenyl-2-isoxazoline-3-carboxylate (S1-11) ("isoxadifen-ethyl") or n-propyl 5,5-diphenyl-2-isoxazoline-3-carboxylate (S1-12) or the ethyl 5-(4-fluorophenyl)-5-phenyl-2-isoxazoline-3-carboxylate type (S1-13), as described in patent application WO-A-95/07897.

S2) Compounds from the group of 8-quinolinyloxy derivatives (S2):

S2$^a$) compounds of the 8-quinolinoxyacetic acid type (S2$^a$), preferably 1-methylhexyl (5-chloro-8-quinolinoxy)acetate ("cloquintocet-mexyl") (S2-1), 1,3-dimethylbut-1-yl (5-chloro-8-quinolinoxy)acetate (S2-2), 4-allyloxybutyl (5-chloro-8-quinolinoxy)acetate (S2-3), 1-allyloxyprop-2-yl (5-chloro-8-quinolinoxy)acetate (S2-4), ethyl (5-chloro-8-quinolinoxy)acetate (S2-5), methyl (5-chloro-8-quinolinoxy)acetate (S2-6), allyl (5-chloro-8-quinolinoxy)-acetate (S2-7), 2-(2-propylideneiminoxy)-1-ethyl (5-chloro-8-quinolinoxy)-acetate (S2-8), 2-oxoprop-1-yl (5-chloro-8-quinolinoxy)acetate (S2-9) and related compounds as described in EP-A-86 750, EP-A-94 349 and EP-A-191 736 or EP-A-0 492 366, and also (5-chloro-8-quinolinoxy)acetic acid (S2-10), hydrates and salts thereof, for example the lithium, sodium, potassium, calcium, magnesium, aluminum, iron, ammonium, quaternary ammonium, sulfonium or phosphonium salts thereof, as described in WO-A-2002/34048;

S2$^b$) compounds of the (5-chloro-8-quinolinoxy)malonic acid type (S2$^b$), preferably compounds such as diethyl (5-chloro-8-quinolinoxy)malonate, diallyl (5-chloro-8-quinolinoxy)malonate, methyl ethyl (5-chloro-8-quinolinoxy)-malonate and related compounds as described in EP-A-0 582 198.

S3) Active ingredients of the dichloroacetamide type (S3), which are often used as pre-emergence safeners (soil-acting safeners), for example "dichlormid" (N,N-diallyl-2,2-dichloroacetamide) (S3-1), "R-29148" (3-dichloroacetyl-2,2,5-trimethyl-1,3-oxazolidine) from Stauffer (S3-2), "R-28725" (3-dichloroacetyl-2,2-dimethyl-1,3-oxazolidine) from Stauffer (S3-3), "benoxacor" (4-dichloroacetyl-3,4-dihydro-3-methyl-2H-1,4-benzoxazine) (S3-4), "PPG-1292" (N-allyl-N-[(1,3-dioxolan-2-yl)methyl]-dichloroacetamide) from PPG Industries (S3-5), "DKA-24" (N-allyl-N-[(allylaminocarbonyl)methyl] dichloroacetamide) from Sagro-Chem (S3-6), "AD-67" or "MON 4660" (3-dichloroacetyl-1-oxa-3-azaspiro[4,5]decane) from Nitrokemia or Monsanto (S3-7), "TI-35" (1-dichloroacetylazepane) from TRI-Chemical RT (S3-8), "diclonon" (dicyclonone) or "BAS145138" or "LAB145138" (S3-9) ((RS)-1-dichloroacetyl-3,3,8a-trimethylperhydropyrrolo[1,2-a]pyrimidin-6-one) from BASF, "furilazole" or "MON 13900" ((RS)-3-dichloroacetyl-5-(2-furyl)-2,2-dimethyloxazolidine) (S3-10), and the (R)-isomer thereof (S3-11).

S4) Compounds from the class of the acylsulfonamides (S4):

S4$^a$) N-acylsulfonamides of the formula (S4$^a$) and their salts, as described in WO-A-97/45016.

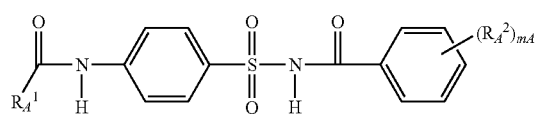

(S4$^a$)

in which $R_A^1$ is $(C_1\text{-}C_6)$alkyl, $(C_3\text{-}C_6)$cycloalkyl, where the 2 last-mentioned radicals are substituted by $v_A$ substituents from the group consisting of halogen, $(C_1\text{-}C_4)$alkoxy, ($C_1$-$C_6$)haloalkoxy and ($C_1$-$C_4$)alkylthio and, in the case of cyclic radicals, also by ($C_1$-$C_4$)alkyl and ($C_1$-$C_4$)haloalkyl;

$R_A^2$ is halogen, ($C_1$-$C_4$)alkyl, ($C_1$-$C_4$)alkoxy, $CF_3$;

$m_A$ is 1 or 2;

$v_A$ is 0, 1, 2 or 3;

S4$^b$) compounds of the 4-(benzoylsulfamoyl)benzamide type of the formula (S4$^b$) and salts thereof, as described in WO-A-99/16744,

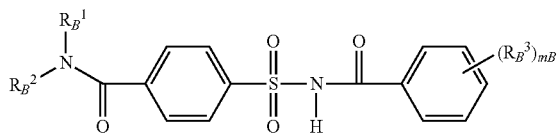

(S4$^b$)

in which $R_B^1$, $R_B^2$ are each independently hydrogen, ($C_1$-$C_6$)alkyl, ($C_3$-$C_6$)cycloalkyl, ($C_3$-$C_6$)alkenyl, ($C_3$-$C_6$)alkynyl, $R_B^3$ is halogen, ($C_1$-$C_4$)alkyl, ($C_1$-$C_4$)haloalkyl or ($C_1$-$C_4$)alkoxy and $m_B$ is 1 or 2, for example those in which $R_B^1$=cyclopropyl, $R_B^2$=hydrogen and ($R_B^3$)=2-OMe (S4-1, "cyprosulfamide"), $R_B^1$=cyclopropyl, $R_B^2$=hydrogen and ($R_B^3$)=5-Cl-2-OMe (S4-2), $R_B^1$=ethyl, $R_B^2$=hydrogen and ($R_B^3$)=2-OMe (S4-3), $R_B^1$=isopropyl, $R_B^2$=hydrogen and ($R_B^3$)=5-$C_{1-2}$-OMe (S4-4) and $R_B^1$=isopropyl, $R_B^2$=hydrogen and ($R_B^3$)=2-OMe (S4-5).

S4$^c$) Compounds from the class of the benzoylsulfamoylphenylureas of the formula (S4$^c$), as described in EP-A-365484

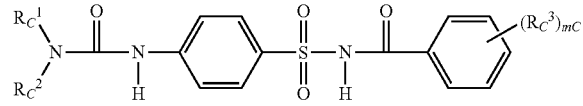

(S4$^c$)

in which $R_C^1$, $R_C^2$ are each independently hydrogen, ($C_1$-$C_8$)alkyl, ($C_3$-$C_8$)cycloalkyl, ($C_3$-$C_6$)alkenyl, ($C_3$-$C_6$)alkynyl, $R_C^3$ is halogen, ($C_1$-$C_4$)alkyl, ($C_1$-$C_4$)alkoxy, $CF_3$ $m_C$ is 1 or 2;

for example

1-[4-(N-2-methoxybenzoylsulfamoyl)phenyl]-3-methylurea,

1-[4-(N-2-methoxybenzoylsulfamoyl)phenyl]-3,3-dimethylurea,

1-[4-(N-4,5-dimethylbenzoylsulfamoyl)phenyl]-3-methylurea.

S5) Active ingredients from the class of hydroxyaromatics and aromatic-aliphatic carboxylic acid derivatives (S5), for example ethyl 3,4,5-triacetoxybenzoate, 3,5-dimethoxy-4-hydroxybenzoic acid, 3,5-dihydroxybenzoic acid, 4-hydroxy-salicylic acid, 4-fluorosalicylic acid, 2-hydroxycinnamic acid, 2,4-dichloro-cinnamic acid, as described in WO-A-2004/084631, WO-A-2005/015994, WO-A-2005/016001.

S6) Active ingredients from the class of the 1,2-dihydroquinoxalin-2-ones (S6), for example 1-methyl-3-(2-thienyl)-1,2-dihydroquinoxalin-2-one, 1-methyl-3-(2-thienyl)-1,2-dihydroquinoxaline-2-thione, 1-(2-aminoethyl)-3-(2-thienyl)-1,2-dihydro-quinoxalin-2-one hydrochloride, 1-(2-methylsulfonylaminoethyl)-3-(2-thienyl)-1,2-dihydroquinoxalin-2-one, as described in WO-A-2005/112630.

S7) Compounds from the class of the diphenylmethoxyacetic acid derivatives (S7), for example methyl diphenylmethoxyacetate (CAS Reg. No. 41858-19-9) (S7-1), ethyl diphenylmethoxyacetate or diphenylmethoxyacetic acid, as described in WO-A-98/38856.

S8) Compounds of the formula (S8), as described in WO-A-98/27049

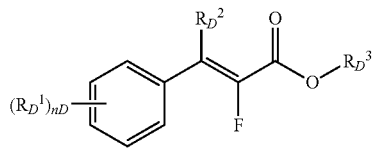

(S8)

in which the symbols and the indices are each defined as follows:

$R_D^1$ is halogen, ($C_1$-$C_4$)alkyl, ($C_1$-$C_4$)haloalkyl, ($C_1$-$C_4$)alkoxy, ($C_1$-$C_4$)haloalkoxy, $R_D^2$ is hydrogen or ($C_1$-$C_4$)alkyl $R_D^3$ is hydrogen, ($C_1$-$C_8$)alkyl, ($C_2$-$C_4$)alkenyl, ($C_2$-$C_4$)alkynyl, or aryl, where each of the aforementioned C-containing radicals is unsubstituted or substituted by one or more, preferably up to three, identical or different radicals from the group consisting of halogen and alkoxy; or salts thereof $n_D$ is an integer from 0 to 2.

S9) Active ingredients from the class of the 3-(5-tetrazolylcarbonyl)-2-quinolones (S9), for example 1,2-dihydro-4-hydroxy-1-ethyl-3-(5-tetrazolylcarbonyl)-2-quinolone (CAS Reg No.: 219479-18-2), 1,2-dihydro-4-hydroxy-1-methyl-3-(5-tetrazolyl-carbonyl)-2-quinolone (CAS Reg. No. 95855-00-8), as described in WO-A-1999/000020.

S10) Compounds of the formulae (S10$^a$) or (S10$^b$) as described in WO-A-2007/023719 and WO-A-2007/023764

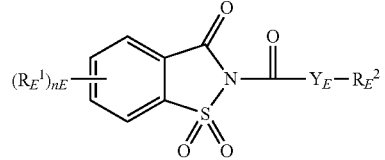

(S10$^a$)

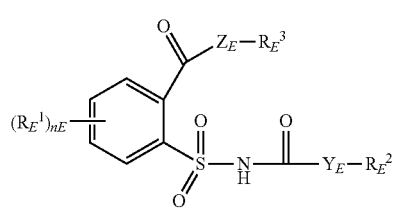

(S10$^b$)

in which $R_E^1$ is halogen, ($C_1$-$C_4$)alkyl, methoxy, nitro, cyano, $CF_3$, $OCF_3$ $Y_E$, $Z_E$ are each independently O or S, $n_E$ is an integer from 0 to 4,
$R_E^2$ is $(C_1-C_{16})$alkyl, $(C_2-C_6)$alkenyl, $(C_3-C_6)$cycloalkyl, aryl; benzyl, halobenzyl,
$R_E^3$ is hydrogen or $(C_1-C_6)$alkyl.

S11) Active ingredients of the oxyimino compound type (S11), which are known as seed dressings, for example
"oxabetrinil" ((Z)-1,3-dioxolan-2-ylmethoxyimino(phenyl)acetonitrile) (S11-1), which is known as seed dressing safener for millet against metolachlor damage,
"fluxofenim" (1-(4-chlorophenyl)-2,2,2-trifluoro-1-ethanone O-(1,3-dioxolan-2-ylmethyl)oxime) (S11-2), which is known as seed dressing safener for millet against metolachlor damage, and
"cyometrinil" or "CGA-43089" ((Z)-cyanomethoxyimino (phenyl)acetonitrile) (S11-3), which is known as seed dressing safener for millet against metolachlor damage.

S12) Active ingredients from the class of the isothiochromanones (S12), for example methyl [(3-oxo-1H-2-benzothiopyran-4(3H)-ylidene)methoxy]acetate (CAS Reg. No. 205121-04-6) (S12-1) and related compounds from WO-A-1998/13361.

S13) One or more compounds from group (S13):
"naphthalic anhydride" (1,8-naphthalenedicarboxylic anhydride) (S13-1), which is known as seed dressing safener for corn against thiocarbamate herbicide damage,
"fenclorim" (4,6-dichloro-2-phenylpyrimidine) (S13-2), which is known as safener for pretilachlor in sown rice,
"flurazole" (benzyl 2-chloro-4-trifluoromethyl-1,3-thiazole-5-carboxylate) (S13-3), which is known as seed dressing safener for millet against alachlor and metolachlor damage,
"CL 304415" (CAS Reg. No. 31541-57-8) (4-carboxy-3,4-dihydro-2H-1-benzopyran-4-acetic acid) (S13-4) from American Cyanamid, which is known as safener for corn against imidazolinone damage,
"MG 191" (CAS Reg. No. 96420-72-3) (2-dichloromethyl-2-methyl-1,3-dioxolane) (S13-5) from Nitrokemia, which is known as safener for corn,
"MG-838" (CAS Reg. No. 133993-74-5) (2-propenyl 1-oxa-4-azaspiro[4.5]-decane-4-carbodithioate) (S13-6) from Nitrokemia
"disulfoton" (O,O-diethyl S-2-ethylthioethyl phosphorodithioate) (S13-7),
"dietholate" (O,O-diethyl O-phenylphosphorothioate) (S13-8),
"mephenate" (4-chlorophenyl methylcarbamate) (S13-9).

S14) Active ingredients which, in addition to a herbicidal effect against harmful plants, also have a safener effect on crop plants such as rice, for example "dimepiperate" or "MY-93" (S-1-methyl-1-phenylethyl piperidine-1-carbothioate), which is known as safener for rice against molinate herbicide damage,
"daimuron" or "SK 23" (1-(1-methyl-1-phenylethyl)-3-p-tolylurea), which is known as safener for rice against imazosulfuron herbicide damage,
"cumyluron"="JC-940" (3-(2-chlorophenylmethyl)-1-(1-methyl-1-phenylethyl)-urea, see JP-A-60087254) which is known as safener for rice against damage by some herbicides,
"methoxyphenone" or "NK 049" (3,3'-dimethyl-4-methoxybenzophenone), which is known as safener for rice against damage by some herbicides,
"CSB" (1-bromo-4-(chloromethylsulfonyl)benzene) from Kumiai (CAS Reg. No. 54091-06-4), which is known as safener against damage by some herbicides in rice.

S15) Compounds of the formula (S15) or tautomers thereof as described in WO-A-2008/131861 and WO-A-2008/131860

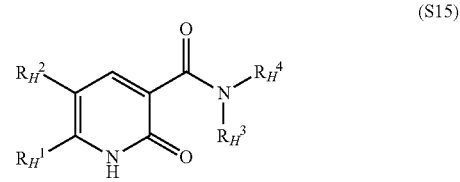

(S15)

in which
$R_H^1$ is a $(C_1-C_6)$haloalkyl radical and
$R_H^2$ is hydrogen or halogen and
$R_H^3$, $R_H^4$ are each independently hydrogen, $(C_1-C_{16})$alkyl, $(C_2-C_{16})$alkenyl or $(C_2-C_{16})$alkynyl,
where each of the latter 3 radicals is unsubstituted or substituted by one or more radicals from the group of halogen, hydroxyl, cyano, $(C_1-C_4)$alkoxy, $(C_1-C_4)$haloalkoxy, $(C_1-C_4)$alkylthio, $(C_1-C_4)$alkylamino, di[$(C_1-C_4)$alkyl]amino, [$(C_1-C_4)$alkoxy]carbonyl, [$(C_1-C_4)$haloalkoxy]-carbonyl, $(C_3-C_6)$cycloalkyl which is unsubstituted or substituted, phenyl which is unsubstituted or substituted, and heterocyclyl which is unsubstituted or substituted,
or $(C_3-C_6)$cycloalkyl, $(C_4-C_6)$cycloalkenyl, $(C_3-C_6)$cycloalkyl which is fused on one side of the ring to a 4 to 6-membered saturated or unsaturated carbocyclic ring, or $(C_4-C_6)$cycloalkenyl which is fused on one side of the ring to a 4 to 6-membered saturated or unsaturated carbocyclic ring,
where each of the latter 4 radicals are unsubstituted or substituted by one or more radicals from the group of halogen, hydroxyl, cyano, $(C_1-C_4)$alkyl, $(C_1-C_4)$haloalkyl, $(C_1-C_4)$alkoxy, $(C_1-C_4)$haloalkoxy, $(C_1-C_4)$alkylthio, $(C_1-C_4)$alkylamino, di[$(C_1-C_4)$alkyl]amino, [$(C_1-C_4)$alkoxy]carbonyl, [$(C_1-C_4)$haloalkoxy]carbonyl, $(C_3-C_6)$cycloalkyl which is unsubstituted or substituted, phenyl which is unsubstituted or substituted, and heterocyclyl which is unsubstituted or substituted,
or
$R_H^3$ is $(C_1-C_4)$alkoxy, $(C_2-C_4)$alkenyloxy, $(C_2-C_6)$alkynyloxy or $(C_2-C_4)$haloalkoxy and
$R_H^4$ is hydrogen or $(C_1-C_4)$-alkyl or
$R_H^3$ and $R_H^4$ together with the directly bonded nitrogen atom are a four- to eight-membered, heterocyclic ring which, as well as the nitrogen atom, may also contain further ring heteroatoms, preferably up to two further ring heteroatoms from the group of N, O and S, and which is unsubstituted or substituted by one or more radicals from the group of halogen, cyano, nitro, $(C_1-C_4)$alkyl, $(C_1-C_4)$haloalkyl, $(C_1-C_4)$alkoxy, $(C_1-C_4)$haloalkoxy and $(C_1-C_4)$alkylthio.

S16) Active ingredients which are used primarily as herbicides but also have safener action on crop plants, for example
(2,4-dichlorophenoxy)acetic acid (2,4-D), (4-chlorophenoxy)acetic acid, (R,S)-2-(4-chloro-o-tolyloxy)propionic acid (mecoprop), 4-(2,4-dichlorophenoxy)-butyric acid (2,4-DB), (4-chloro-o-tolyloxy)acetic acid (MCPA), 4-(4-chloro-o-tolyloxy)butyric acid, 4-(4-chlorophenoxy)butyric acid, 3,6-dichloro-2-methoxybenzoic acid (dicamba), 1-(ethoxycarbonyl)ethyl 3,6-dichloro-2-methoxy-benzoate (lactidichlor-ethyl).

Some of the safeners are also known as herbicides and thus display, in addition to herbicidal action for weed plants, simultaneously also protective action for the crop plants.

The weight ratios of herbicide (mixture) to safener depend generally on the application rate of herbicide and the efficacy of the particular safener and can vary within wide limits, for example in the range from 200:1 to 1:200, preferably 100:1 to 1:100, especially 20:1 to 1:20. Analogously to the inventive compounds or mixtures thereof, the safeners can be formulated with further pesticides and be provided and applied as a finished formulation or tankmix with the inventive compounds.

For use, the formulations present in commercially available form are optionally diluted in a customary manner, for example in the case of wettable powders, emulsifiable concentrates, dispersions and water-dispersible granules by means of water. Dust formulations, soil granules and granules for broadcasting, and also sprayable solutions, are typically not diluted with any further inert substances before use.

The required application rate of the inventive compounds varies with the outside conditions, such as temperature, humidity, the type of herbicide used, among other factors. It can vary within wide limits, for example between 0.001 and 10.0 kg/ha or more of active substance, but is preferably between 0.005 and 5 g/ha.

EXAMPLES

A. Synthesis Examples

Syntheses of inventive compounds are described by way of example hereinafter, though these examples do not have limiting character.

(1) Methyl 4-amino-3-chloro-6-(4'-(thiophen-2"-yl)phenyl)pyridine-2-carboxylate (Example No. 1-170)

Step 1: Synthesis of 6-bromo-3-chloropyridine-2-carboxylic acid 20.0 g (104.2 mmol) of 3,6-dichloropyridine-2-carboxylic acid are admixed with 50 ml of acetic acid. Then 5 ml (33% by weight; 28.96 mmol) of a solution of hydrogen bromide in acetic acid are added. The mixture is heated to 110° C., and a further 22 ml (33% by weight; 127.4 mmol) of a solution of hydrogen bromide in acetic acid are added dropwise at this temperature. The reaction mixture is stirred at 110° C. until monitoring of the reaction by HPLC indicates virtually complete conversion. To accelerate the conversion, a further 40 ml in total (33% by weight; 231.7 mmol) of a solution of hydrogen bromide in acetic acid are added dropwise on three occasions during the reaction. For workup, the reaction mixture is poured onto ice-water. The contents are filtered and the residue is washed with water. The residue obtained is 20.5 g of the product with a purity of approx. 95% by weight. The filtrate is freed of the solvents on a rotary evaporator and the residue is stirred with water. The mixture is filtered; the residue obtained is 2.78 g of the product with a purity of approx. 89% by weight.

Step 2: Synthesis of methyl 6-bromo-3-chloropyridine-2-carboxylate 8.12 g (34.3 mmol) of 6-bromo-3-chloropyridine-2-carboxylic acid are admixed with 50 ml (1.25M; 62.5 mmol) of a solution of hydrogen chloride in methanol. The mixture is heated under reflux for 2 h, in the course of which 20 ml each time (1.25M; 25 mmol) of a solution of hydrogen chloride in methanol are added every 30 min. For workup, the reaction mixture is freed of the solvent on a rotary evaporator and the residue is admixed with diethyl ether and an aqueous sodium hydrogencarbonate solution. After the phase separation, the organic phase is dried; after the filtration, the filtrate is freed of the solvent on a rotary evaporator. The residue obtained is 7.78 g of the product with a purity of approx. 90% by weight.

Step 3: Synthesis of methyl 6-bromo-3-chloropyridine-2-carboxylate N-oxide

Is performed analogously to the methods from WO 01/51468, pages 25-26.

Step 4: Synthesis of methyl 6-bromo-3-chloro-4-nitropyridine-2-carboxylate N-oxide Is performed analogously to the methods from WO 01/51468, pages 25-26.

Step 5: Synthesis of methyl 4-amino-6-bromo-3-chloropyridine-2-carboxylate

Is performed analogously to the methods from WO 01/51468, pages 25-26.

Step 6: Synthesis of methyl 4-amino-3-chloro-6-(4'-(thiophen-2"-yl)phenyl)pyridine-2-carboxylate (Example No. 1-170)

A mixture of 280 mg (95% by weight; 1.00 mmol) of methyl 4-amino-6-bromo-3-chloropyridine-2-carboxylate, 245 mg (1.20 mmol) of 4-(thiophen-2"-yl)phenylboronic acid and 205 mg (1.35 mmol) of cesium fluoride is initially charged in a mixture of 20 ml of 1,2-dimethoxyethane and water (1:1). After this mixture has been degassed, 95 mg (0.14 mmol) of bis(triphenylphosphine)palladium(II) dichloride are added under nitrogen. The contents are stirred at a temperature of 80° C. for 50 h. For workup, the reaction mixture is admixed with dichloromethane and water. After the phase separation, the organic phase is freed of the solvents on a rotary evaporator. The residue is purified by chromatography to obtain 28.6 mg of the product with a purity of approx. 80% by weight.

The compounds described in tables 1-10 below are obtained analogously to the synthesis examples described above.

The abbreviations in tables 1-10 mean:
Me=methyl
Et=ethyl
cBu=cyclobutyl
cPr=cyclopropyl
iPr=isopropyl
cHex=cyclohexyl
tBu=tert-butyl
Ph=phenyl
Vin=vinyl
Ac=acetyl
Hal=halogen

TABLE 1

Hetarylpyridines:

(I-vii)

Structure: Pyridine with $NR^3R^4$ at position 4, $R^1$ at position 5, $R^2$ at position 3, COOR at position 2, and a 4-Het-phenyl group at position 6.

| No. | Het | $R^1$ | $R^2$ | $R^3$ | $R^4$ | R | Physical data: $^1$H NMR: δ [CDCl$_3$] |
|---|---|---|---|---|---|---|---|
| 1-1 | 3-tert-butyl-1,2,4-oxadiazol-5-yl | H | Cl | H | H | H | 8.21 (d, 2H), 8.13 (d, 2H), 7.38 (s, 1H), 1.39 (s, 9H) [measured in d$^6$-DMSO] |
| 1-2 | 3-tert-butyl-1,2,4-oxadiazol-5-yl | H | Cl | H | H | Me | 8.20 (d, 2H), 8.07 (d, 2H), 7.18 (s, 1H), 4.85 (br. s, 2H), 4.02 (s, 3H), 1.45 (s, 9H) |
| 1-3 | 3-tert-butyl-1,2,4-oxadiazol-5-yl | H | Cl | H | H | Et | |
| 1-4 | 3-tert-butyl-1,2,4-oxadiazol-5-yl | H | Br | H | H | H | |
| 1-5 | 3-tert-butyl-1,2,4-oxadiazol-5-yl | H | Br | H | H | Me | |
| 1-6 | 3-tert-butyl-1,2,4-oxadiazol-5-yl | H | Br | H | H | Et | |
| 1-7 | 3-tert-butyl-1,2,4-oxadiazol-5-yl | H | F | H | H | H | |
| 1-8 | 3-tert-butyl-1,2,4-oxadiazol-5-yl | H | F | H | H | Me | |
| 1-9 | 3-tert-butyl-1,2,4-oxadiazol-5-yl | H | I | H | H | H | |
| 1-10 | 3-tert-butyl-1,2,4-oxadiazol-5-yl | H | I | H | H | Me | |
| 1-11 | 3-tert-butyl-1,2,4-oxadiazol-5-yl | H | CN | H | H | H | |
| 1-12 | 3-tert-butyl-1,2,4-oxadiazol-5-yl | H | CN | H | H | Me | |
| 1-13 | 3-tert-butyl-1,2,4-oxadiazol-5-yl | H | CF$_3$ | H | H | H | |
| 1-14 | 3-tert-butyl-1,2,4-oxadiazol-5-yl | H | CF$_3$ | H | H | Me | |
| 1-15 | 3-tert-butyl-1,2,4-oxadiazol-5-yl | F | Cl | H | H | H | |
| 1-16 | 3-tert-butyl-1,2,4-oxadiazol-5-yl | F | Cl | H | H | Me | |
| 1-17 | 3-tert-butyl-1,2,4-oxadiazol-5-yl | F | Cl | H | H | Et | |
| 1-18 | 3-tert-butyl-1,2,4-oxadiazol-5-yl | F | Br | H | H | H | |
| 1-19 | 3-tert-butyl-1,2,4-oxadiazol-5-yl | F | Br | H | H | Me | |
| 1-20 | 3-tert-butyl-1,2,4-oxadiazol-5-yl | F | Br | H | H | Et | |
| 1-21 | 3-tert-butyl-1,2,4-oxadiazol-5-yl | F | F | H | H | H | |
| 1-22 | 3-tert-butyl-1,2,4-oxadiazol-5-yl | F | F | H | H | Me | |
| 1-23 | 3-tert-butyl-1,2,4-oxadiazol-5-yl | F | I | H | H | H | |
| 1-24 | 3-tert-butyl-1,2,4-oxadiazol-5-yl | F | I | H | H | Me | |
| 1-25 | 3-tert-butyl-1,2,4-oxadiazol-5-yl | F | CN | H | H | H | |
| 1-26 | 3-tert-butyl-1,2,4-oxadiazol-5-yl | F | CN | H | H | Me | |
| 1-27 | 3-tert-butyl-1,2,4-oxadiazol-5-yl | F | CF$_3$ | H | H | H | |
| 1-28 | 3-tert-butyl-1,2,4-oxadiazol-5-yl | F | CF$_3$ | H | H | Me | |
| 1-29 | 3-tert-butyl-1,2,4-oxadiazol-5-yl | Cl | Cl | H | H | H | 8.27 (d, 2H), 7.80 (d, 2H), 5.63 (bs, 2H), 1.46 (s, 9H) |
| 1-30 | 3-tert-butyl-1,2,4-oxadiazol-5-yl | Cl | Cl | H | H | Me | 8.21 (d, 2H), 7.81 (d, 2H), 5.37 (bs, 2H), 3.99 (s, 3H), 1.45 (s, 9H) |
| 1-31 | 3-tert-butyl-1,2,4-oxadiazol-5-yl | Cl | Cl | H | H | Et | |
| 1-32 | 3-tert-butyl-1,2,4-oxadiazol-5-yl | Cl | Br | H | H | H | |
| 1-33 | 3-tert-butyl-1,2,4-oxadiazol-5-yl | Cl | Br | H | H | Me | |
| 1-34 | 3-tert-butyl-1,2,4-oxadiazol-5-yl | Cl | Br | H | H | Et | |
| 1-35 | 3-tert-butyl-1,2,4-oxadiaozl-5-yl | Cl | F | H | H | H | |
| 1-36 | 3-tert-butyl-1,2,4-oxadiazol-5-yl | Cl | F | H | H | Me | |
| 1-37 | 3-tert-butyl-1,2,4-oxadiazol-5-yl | Cl | I | H | H | H | |
| 1-38 | 3-tert-butyl-1,2,4-oxadiaozl-5-yl | Cl | I | H | H | Me | |
| 1-39 | 3-tert-butyl-1,2,4-oxadiazol-5-yl | Cl | CN | H | H | H | |
| 1-40 | 3-tert-butyl-1,2,4-oxadiazol-5-yl | Cl | CN | H | H | Me | |
| 1-41 | 3-tert-butyl-1,2,4-oxadiazol-5-yl | Cl | CF$_3$ | H | H | H | |
| 1-42 | 3-tert-butyl-1,2,4-oxadiazol-5-yl | Cl | CF$_3$ | H | H | Me | |
| 1-43 | 3-tert-butyl-1,2,4-oxadiazol-5-yl | H | Cl | Me | H | | |
| 1-44 | 3-tert-butyl-1,2,4-oxadiazol-5-yl | H | Cl | H | Me | Me | |
| 1-45 | 3-tert-butyl-1,2,4-oxadiazol-5-yl | H | Cl | H | Me | Et | |
| 1-46 | 3-tert-butyl-1,2,4-oxadiazol-5-yl | H | Br | H | Me | H | |
| 1-47 | 3-tert-butyl-1,2,4-oxadiazol-5-yl | H | Br | H | Me | Me | |
| 1-48 | 3-tert-butyl-1,2,4-oxadiazol-5-yl | H | Br | H | Me | Et | |
| 1-49 | 3-tert-butyl-1,2,4-oxadiazol-5-yl | H | F | H | Me | H | |
| 1-50 | 3-tert-butyl-1,2,4-oxadiazol-5-yl | H | F | H | Me | Me | |
| 1-51 | 3-tert-butyl-1,2,4-oxadiazol-5-yl | H | I | H | Me | H | |
| 1-52 | 3-tert-butyl-1,2,4-oxadiazol-5-yl | H | I | H | Me | Me | |
| 1-53 | 3-tert-butyl-1,2,4-oxadiazol-5-yl | H | CN | H | Me | H | |
| 1-54 | 3-tert-butyl-1,2,4-oxadiazol-5-yl | H | CN | H | Me | Me | |
| 1-55 | 3-tert-butyl-1,2,4-oxadiazol-5-yl | H | CF$_3$ | H | Me | H | |
| 1-56 | 3-tert-butyl-1,2,4-oxadiazol-5-yl | H | CF$_3$ | H | Me | Me | |

TABLE 1-continued

Hetarylpyridines:

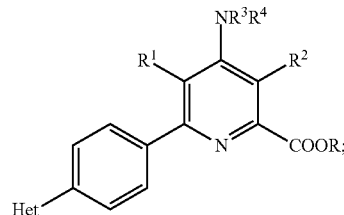

(I-vii)

| No. | Het | R¹ | R² | R³ | R⁴ | R | Physical data: ¹H NMR: δ [CDCl₃] |
|---|---|---|---|---|---|---|---|
| 1-57 | 3-tert-butyl-1,2,4-oxadiazol-5-yl | H | Cl | H | Me | H | |
| 1-58 | 3-tert-butyl-1,2,4-oxadiazol-5-yl | F | Cl | H | Me | Me | |
| 1-59 | 3-tert-butyl-1,2,4-oxadiazol-5-yl | F | Cl | H | Me | Et | |
| 1-60 | 3-tert-butyl-1,2,4-oxadiazol-5-yl | F | Br | H | Me | H | |
| 1-61 | 3-tert-butyl-1,2,4-oxadiazol-5-yl | F | Br | H | Me | Me | |
| 1-62 | 3-tert-butyl-1,2,4-oxadiazol-5-yl | F | Br | H | Me | Et | |
| 1-63 | 3-tert-butyl-1,2,4-oxadiazol-5-yl | F | F | H | Me | H | |
| 1-64 | 3-tert-butyl-1,2,4-oxadiazol-5-yl | F | F | H | Me | Me | |
| 1-65 | 3-tert-butyl-1,2,4-oxadiazol-5-yl | F | I | H | Me | H | |
| 1-66 | 3-tert-butyl-1,2,4-oxadiazol-5-yl | F | I | H | Me | Me | |
| 1-67 | 3-tert-butyl-1,2,4-oxadiazol-5-yl | F | CN | H | Me | H | |
| 1-68 | 3-tert-butyl-1,2,4-oxadiazol-5-yl | F | CN | H | Me | Me | |
| 1-69 | 3-tert-butyl-1,2,4-oxadiazol-5-yl | F | CF₃ | H | Me | H | |
| 1-70 | 3-tert-butyl-1,2,4-oxadiazol-5-yl | F | CF₃ | H | Me | Me | |
| 1-71 | 3-tert-butyl-1,2,4-oxadiazol-5-yl | Cl | Cl | H | Me | H | |
| 1-72 | 3-tert-butyl-1,2,4-oxadiazol-5-yl | Cl | Cl | H | Me | Me | |
| 1-73 | 3-tert-butyl-1,2,4-oxadiazol-5-yl | Cl | Cl | H | Me | Et | |
| 1-74 | 3-tert-butyl-1,2,4-oxadiazol-5-yl | Cl | Br | H | Me | H | |
| 1-75 | 3-tert-butyl-1,2,4-oxadiazol-5-yl | Cl | Br | H | Me | Me | |
| 1-76 | 3-tert-butyl-1,2,4-oxadiazol-5-yl | Cl | Br | H | Me | Et | |
| 1-77 | 3-tert-butyl-1,,24-oxadiazol-5-yl | Cl | F | H | Me | H | |
| 1-78 | 3-tert-butyl-1,2,4-oxadiazol-5-yl | Cl | F | H | Me | Me | |
| 1-79 | 3-tert-butyl-1,2,4-oxadiazol-5-yl | Cl | I | H | Me | H | |
| 1-80 | 3-tert-butyl-1,2,4-oxadiazol-5-yl | Cl | I | H | Me | Me | |
| 1-81 | 3-tert-butyl-1,2,4-oxadiazol-5-yl | Cl | CN | H | Me | H | |
| 1-82 | 3-tert-butyl-1,2,4-oxadiazol-5-yl | Cl | CN | H | Me | Me | |
| 1-83 | 3-tert-butyl-1,2,4-oxadiazol-5-yl | Cl | CF₃ | H | Me | H | |
| 1-84 | 3-tert-butyl-1,2,4-oxadiazol-5-yl | Cl | CF₃ | H | Me | Me | |
| 1-85 | 3-tert-butyl-1,2,4-oxadiazol-5-yl | H | Cl | Me | Me | H | |
| 1-86 | 3-tert-butyl-1,2,4-oxadiazol-5-yl | H | Cl | Me | Me | Me | |
| 1-87 | 3-tert-butyl-1,2,4-oxadiazol-5-yl | H | Cl | Me | Me | Et | |
| 1-88 | 3-tert-butyl-1,2,4-oxadiazol-5-yl | H | Br | Me | Me | H | |
| 1-89 | 3-tert-butyl-1,2,4-oxadiazol-5-yl | H | Br | Me | Me | Me | |
| 1-90 | 3-tert-butyl-1,2,4-oxadiazol-5-yl | H | Br | Me | Me | Et | |
| 1-91 | 3-tert-butyl-1,2,4-oxadiazol-5-yl | H | F | Me | Me | H | |
| 1-92 | 3-tert-butyl-1,2,4-oxadiazol-5-yl | H | F | Me | Me | Me | |
| 1-93 | 3-tert-butyl-1,2,4-oxadiazol-5-yl | H | I | Me | Me | H | |
| 1-94 | 3-tert-butyl-1,2,4-oxadiazol-5-yl | H | I | Me | Me | Me | |
| 1-95 | 3-tert-butyl-1,2,4-oxadiazol-5-yl | H | CN | Me | Me | H | |
| 1-96 | 3-tert-butyl-1,2,4-oxadiazol-5-yl | H | CN | Me | Me | Me | |
| 1-97 | 3-tert-butyl-1,2,4-oxadiazol-5-yl | H | CF₃ | Me | Me | H | |
| 1-98 | 3-tert-butyl-1,2,4-oxadiazol-5-yl | H | CF₃ | Me | Me | Me | |
| 1-99 | 3-tert-butyl-1,2,4-oxadiazol-5-yl | F | Cl | Me | Me | H | |
| 1-100 | 3-tert-butyl-1,2,4-oxadiazol-5-yl | F | Cl | Me | Me | Me | |
| 1-101 | 3-tert-butyl-1,2,4-oxadiazol-5-yl | F | Cl | Me | Me | Et | |
| 1-102 | 3-tert-butyl-1,2,4-oxadiazol-5-yl | F | Br | Me | Me | H | |
| 1-103 | 3-tert-butyl-1,2,4-oxadiazol-5-yl | F | Br | Me | Me | Me | |
| 1-104 | 3-tert-butyl-1,2,4-oxadiazol-5-yl | F | Br | Me | Me | Et | |
| 1-105 | 3-tert-butyl-1,2,4-oxadiazol-5-yl | F | F | Me | Me | H | |
| 1-106 | 3-tert-butyl-1,2,4-oxadiazol-5-yl | F | F | Me | Me | Me | |
| 1-107 | 3-tert-butyl-1,2,4-oxadiazol-5-yl | F | I | Me | Me | H | |
| 1-108 | 3-tert-butyl-1,2,4-oxadiazol-5-yl | F | I | Me | Me | Me | |
| 1-109 | 3-tert-butyl-1,2,4-oxadiazol-5-yl | F | CN | Me | Me | H | |
| 1-110 | 3-tert-butyl-1,2,4-oxadiazol-5-yl | F | CN | Me | Me | Me | |
| 1-111 | 3-tert-butyl-1,2,4-oxadiazol-5-yl | F | CF₃ | Me | Me | H | |
| 1-112 | 3-tert-butyl-1,2,4-oxadiazol-5-yl | F | CF₃ | Me | Me | Me | |
| 1-113 | 3-tert-butyl-1,2,4-oxadiazol-5-yl | Cl | Cl | Me | Me | H | |
| 1-114 | 3-tert-butyl-1,2,4-oxadiazol-5-yl | Cl | Cl | Me | Me | Me | |
| 1-115 | 3-tert-butyl-1,2,4-oxadiazol-5-yl | Cl | Cl | Me | Me | Et | |
| 1-116 | 3-tert-butyl-1,2,4-oxadiazol-5-yl | Cl | Br | Me | Me | H | |
| 1-117 | 3-tert-butyl-1,2,4-oxadiazol-5-yl | Cl | Br | Me | Me | Me | |
| 1-118 | 3-tert-butyl-1,2,4-oxadiazol-5-yl | Cl | F | Me | Me | Et | |
| 1-119 | 3-tert-butyl-1,2,4-oxadiazol-5-yl | Cl | F | Me | Me | H | |

TABLE 1-continued

Hetarylpyridines:

(I-vii)

| No. | Het | R¹ | R² | R³ | R⁴ | R | Physical data: $^1$H NMR: δ [CDCl$_3$] |
|---|---|---|---|---|---|---|---|
| 1-120 | 3-tert-butyl-1,2,4-oxadiazol-5-yl | Cl | F | Me | Me | Me | |
| 1-121 | 3-tert-butyl-1,2,4-oxadiazol-5-yl | Cl | I | Me | Me | H | |
| 1-122 | 3-tert-butyl-1,2,4-oxadiazol-5-yl | Cl | I | Me | Me | Me | |
| 1-123 | 3-tert-butyl-1,2,4-oxadiazol-5-yl | Cl | CN | Me | Me | H | |
| 1-124 | 3-tert-butyl-1,2,4-oxadiazol-5-yl | Cl | CN | Me | Me | Me | |
| 1-125 | 3-tert-butyl-1,2,4-oxadiazol-5-yl | Cl | CF$_3$ | Me | Me | H | |
| 1-126 | 3-tert-butyl-1,2,4-oxadiazol-5-yl | Cl | CF$_3$ | Me | Me | Me | |
| 1-127 | 3-tert-butyl-1,2,4-oxadiazol-5-yl | H | Cl | =CHNMe$_2$ | | H | |
| 1-128 | 3-tert-butyl-1,2,4-oxadiazol-5-yl | H | Cl | =CHNMe$_2$ | | Me | |
| 1-129 | 3-tert-butyl-1,2,4-oxadiazol-5-yl | H | Cl | =CHNMe$_2$ | | Et | |
| 1-130 | 3-tert-butyl-1,2,4-oxadiazol-5-yl | H | Br | =CHNMe$_2$ | | H | |
| 1-131 | 3-tert-butyl-1,2,4-oxadiazol-5-yl | H | Br | =CHNMe$_2$ | | Me | |
| 1-132 | 3-tert-butyl-1,2,4-oxadiazol-5-yl | H | Br | =CHNMe$_2$ | | Et | |
| 1-133 | 3-tert-butyl-1,2,4-oxadiazol-5-yl | H | F | =CHNMe$_2$ | | H | |
| 1-134 | 3-tert-butyl-1,2,4-oxadiazol-5-yl | H | F | =CHNMe$_2$ | | Me | |
| 1-135 | 3-tert-butyl-1,2,4-oxadiazol-5-yl | H | I | =CHNMe$_2$ | | H | |
| 1-136 | 3-tert-butyl-1,2,4-oxadiazol-5-yl | H | I | =CHNMe$_2$ | | Me | |
| 1-137 | 3-tert-butyl-1,2,4-oxadiazol-5-yl | H | CN | =CHNMe$_2$ | | H | |
| 1-138 | 3-tert-butyl-1,2,4-oxadiazol-5-yl | H | CN | =CHNMe$_2$ | | Me | |
| 1-139 | 3-tert-butyl-1,2,4-oxadiazol-5-yl | H | CF$_3$ | =CHNMe$_2$ | | H | |
| 1-140 | 3-tert-butyl-1,2,4-oxadiazol-5-yl | H | CF$_3$ | =CHNMe$_2$ | | Me | |
| 1-141 | 3-tert-butyl-1,2,4-oxadiazol-5-yl | F | Cl | =CHNMe$_2$ | | H | |
| 1-142 | 3-tert-butyl-1,2,4-oxadiazol-5-yl | F | Cl | =CHNMe$_2$ | | Me | |
| 1-143 | 3-tert-butyl-1,2,4-oxadiazol-5-yl | F | Cl | =CHNMe$_2$ | | Et | |
| 1-144 | 3-tert-butyl-1,2,4-oxadiazol-5-yl | F | Br | =CHNMe$_2$ | | H | |
| 1-145 | 3-tert-butyl-1,2,4-oxadiazol-5-yl | F | Br | =CHNMe$_2$ | | Me | |
| 1-146 | 3-tert-butyl-1,2,4-oxadiazol-5-yl | F | Br | =CHNMe$_2$ | | Et | |
| 1-147 | 3-tert-butyl-1,2,4-oxadiazol-5-yl | F | F | =CHNMe$_2$ | | H | |
| 1-148 | 3-tert-butyl-1,2,4-oxadiazol-5-yl | F | F | =CHNMe$_2$ | | Me | |
| 1-149 | 3-tert-butyl-1,2,4-oxadiazol-5-yl | F | I | =CHNMe$_2$ | | H | |
| 1-150 | 3-tert-butyl-1,2,4-oxadiazol-5-yl | F | I | =CHNMe$_2$ | | Me | |
| 1-151 | 3-tert-butyl-1,2,4-oxadiazol-5-yl | F | CN | =CHNMe$_2$ | | H | |
| 1-152 | 3-tert-butyl-1,2,4-oxadiazol-5-yl | F | CN | =CHNMe$_2$ | | Me | |
| 1-153 | 3-tert-butyl-1,2,4-oxadiazol-5-yl | F | CF$_3$ | =CHNMe$_2$ | | H | |
| 1-154 | 3-tert-butyl-1,2,4-oxadiazol-5-yl | F | CF$_3$ | =CHNMe$_2$ | | Me | |
| 1-155 | 3-tert-butyl-1,2,4-oxadiazol-5-yl | Cl | Cl | =CHNMe$_2$ | | H | |
| 1-156 | 3-tert-butyl-1,2,4-oxadiazol-5-yl | Cl | Cl | =CHNMe$_2$ | | Me | |
| 1-157 | 3-tert-butyl-1,2,4-oxadiazol-5-yl | Cl | Cl | =CHNMe$_2$ | | Et | |
| 1-158 | 3-tert-butyl-1,2,4-oxadiazol-5-yl | Cl | Br | =CHNMe$_2$ | | H | |
| 1-159 | 3-tert-butyl-1,2,4-oxadiazol-5-yl | Cl | Br | =CHNMe$_2$ | | Me | |
| 1-160 | 3-tert-butyl-1,2,4-oxadiazol-5-yl | Cl | Br | =CHNMe$_2$ | | Et | |
| 1-161 | 3-tert-butyl-1,2,4-oxadiazol-5-yl | Cl | F | =CHNMe$_2$ | | H | |
| 1-162 | 3-tert-butyl-1,2,4-oxadiazol-5-yl | Cl | F | =CHNMe$_2$ | | Me | |
| 1-163 | 3-tert-butyl-1,2,4-oxadiazol-5-yl | Cl | I | =CHNMe$_2$ | | H | |
| 1-164 | 3-tert-butyl-1,2,4-oxadiazol-5-yl | Cl | I | =CHNMe$_2$ | | Me | |
| 1-165 | 3-tert-butyl-1,2,4-oxadiazol-5-yl | Cl | CN | =CHNMe$_2$ | | H | |
| 1-166 | 3-tert-butyl-1,2,4-oxadiazol-5-yl | Cl | CN | =CHNMe$_2$ | | Me | |
| 1-167 | 3-tert-butyl-1,2,4-oxadiazol-5-yl | Cl | CF$_3$ | =CHNMe$_2$ | | H | |
| 1-168 | 3-tert-butyl-1,2,4-oxadiazol-5-yl | Cl | CF$_3$ | =CHNMe$_2$ | | Me | |
| 1-169-1 | thien-2-yl | H | Cl | H | H | H | |
| 1-169-2 | thien-2-yl | H | Cl | H | H | Me | 7.93 (d, 2H), 7.68 (d, 2H), 7.37 (m, 1H), 7.31 (d, 1H), 7.13 (s, 1H), 7.11 (m, 1H), 4.78 (br. s, 2H), 4.01 (s, 3H) |
| 1-170 | thien-2-yl | H | Cl | H | H | Et | |
| 1-171 | thien-2-yl | H | Br | H | H | H | |
| 1-172 | thien-2-yl | H | Br | H | H | Me | |
| 1-173 | thien-2-yl | H | Br | H | H | Et | |
| 1-174 | thien-2-yl | H | F | H | H | H | |
| 1-175 | thien-2-yl | H | F | H | H | Me | |
| 1-176 | thien-2-yl | H | I | H | H | H | |
| 1-177 | thien-2-yl | H | I | H | H | Me | |
| 1-178 | thien-2-yl | H | CN | H | H | H | |

TABLE 1-continued

Hetarylpyridines:

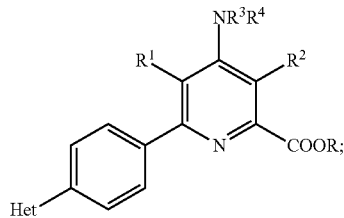

(I-vii)

| No. | Het | R¹ | R² | R³ | R⁴ | R | Physical data: $^1$H NMR: δ [CDCl$_3$] |
|---|---|---|---|---|---|---|---|
| 1-179 | thien-2-yl | H | CN | H | H | Me | |
| 1-180 | thien-2-yl | H | CF$_3$ | H | H | H | |
| 1-181 | thien-2-yl | H | CF$_3$ | H | H | Me | |
| 1-182 | thien-2-yl | F | Cl | H | H | H | |
| 1-183 | thien-2-yl | F | Cl | H | H | Me | |
| 1-184 | thien-2-yl | F | Cl | H | H | Et | |
| 1-185 | thien-2-yl | F | Br | H | H | H | |
| 1-186 | thien-2-yl | F | Br | H | H | Me | |
| 1-187 | thien-2-yl | F | Br | H | H | Et | |
| 1-188 | thien-2-yl | F | F | H | H | H | |
| 1-189 | thien-2-yl | F | F | H | H | Me | |
| 1-190 | thien-2-yl | F | I | H | H | H | |
| 1-191 | thien-2-yl | F | I | H | H | Me | |
| 1-192 | thien-2-yl | F | CN | H | H | H | |
| 1-193 | thien-2-yl | F | CN | H | H | Me | |
| 1-194 | thien-2-yl | F | CF$_3$ | H | H | H | |
| 1-195 | thien-2-yl | F | CF$_3$ | H | H | Me | |
| 1-196 | thien-2-yl | H | Cl | H | Me | H | |
| 1-197 | thein-2-yl | H | Cl | H | Me | Me | |
| 1-198 | thien-2-yl | H | Cl | H | Me | Et | |
| 1-199 | thien-2-yl | H | Br | H | Me | H | |
| 1-200 | thien-2-yl | H | Br | H | Me | Me | |
| 1-201 | thien-2-yl | H | Br | H | Me | Et | |
| 1-202 | thien-2-yl | H | F | H | Me | H | |
| 1-203 | thien-2-yl | H | F | H | Me | Me | |
| 1-204 | thien-2-yl | H | I | H | Me | H | |
| 1-205 | thien-2-yl | H | I | H | Me | Me | |
| 1-206 | thien-2-yl | H | CN | H | Me | H | |
| 1-207 | thien-2-yl | H | CN | H | Me | Me | |
| 1-208 | thien-2-yl | H | CF$_3$ | H | Me | H | |
| 1-209 | thien-2-yl | H | CF$_3$ | H | Me | Me | |
| 1-210 | thien-2-yl | F | Cl | H | Me | H | |
| 1-211 | thien-2-yl | F | Cl | H | Me | Me | |
| 1-212 | thien-2-yl | F | Cl | H | Me | Et | |
| 1-213 | thien-2-yl | F | Br | H | Me | H | |
| 1-214 | thien-2-yl | F | Br | H | Me | Me | |
| 1-215 | thien-2-yl | F | Br | H | Me | Et | |
| 1-216 | thien-2-yl | F | F | H | Me | H | |
| 1-217 | thien-2-yl | F | F | H | Me | Me | |
| 1-218 | thien-2-yl | F | I | H | Me | H | |
| 1-219 | thien-2-yl | F | I | H | Me | Me | |
| 1-220 | thien-2-yl | F | CN | H | Me | H | |
| 1-221 | thien-2-yl | F | CN | H | Me | Me | |
| 1-222 | thien-2-yl | F | CF$_3$ | H | Me | H | |
| 1-223 | thien-2-yl | F | CF$_3$ | H | Me | Me | |
| 1-224 | thien-2-yl | H | Cl | Me | Me | H | |
| 1-225 | thien-2-yl | H | Cl | Me | Me | Me | |
| 1-226 | thien-2-yl | H | Cl | Me | Me | Et | |
| 1-227 | thien-2-yl | H | Br | Me | Me | H | |
| 1-228 | thien-2-yl | H | Br | Me | Me | Me | |
| 1-229 | thien-2-yl | H | Br | Me | Me | Et | |
| 1-230 | thien-2-yl | H | F | Me | Me | H | |
| 1-231 | thien-2-yl | H | F | Me | Me | Me | |
| 1-232 | thien-2-yl | H | I | Me | Me | H | |
| 1-233 | thien-2-yl | H | I | Me | Me | Me | |
| 1-234 | thien-2-yl | H | CN | Me | Me | H | |
| 1-235 | thien-2-yl | H | CN | Me | Me | Me | |
| 1-236 | thien-2-yl | H | CF$_3$ | Me | Me | H | |
| 1-237 | thien-2-yl | H | CF$_3$ | Me | Me | Me | |
| 1-238 | thien-2-yl | F | Cl | Me | Me | H | |
| 1-239 | thien-2-yl | F | Cl | Me | Me | Me | |
| 1-240 | thien-2-yl | F | Cl | Me | Me | Et | |
| 1-241 | thien-2-yl | F | Br | Me | Me | H | |

TABLE 1-continued

Hetarylpyridines:

(I-vii)

| No. | Het | R¹ | R² | R³ | R⁴ | R | Physical data: $^1$H NMR: δ [CDCl$_3$] |
|---|---|---|---|---|---|---|---|
| 1-242 | thien-2-yl | F | Br | Me | Me | Me | |
| 1-243 | thien-2-yl | F | Br | Me | Me | Et | |
| 1-244 | thien-2-yl | F | F | Me | Me | H | |
| 1-245 | thien-2-yl | F | F | Me | Me | Me | |
| 1-246 | thien-2-yl | F | I | Me | Me | H | |
| 1-247 | thien-2-yl | F | I | Me | Me | Me | |
| 1-248 | thien-2-yl | F | CN | Me | Me | H | |
| 1-249 | thien-2-yl | F | CN | Me | Me | Me | |
| 1-250 | thien-2-yl | F | CF$_3$ | Me | Me | H | |
| 1-251 | thien-2-yl | F | CF$_3$ | Me | Me | Me | |
| 1-252 | thien-2-yl | H | Cl | =CHNMe$_2$ | | H | |
| 1-253 | thein-2-yl | H | Cl | =CHNMe$_2$ | | Me | |
| 1-254 | thien-2-yl | H | Cl | =CHNMe$_2$ | | Et | |
| 1-255 | thien-2-yl | H | Br | =CHNMe$_2$ | | H | |
| 1-256 | thien-2-yl | H | Br | =CHNMe$_2$ | | Me | |
| 1-257 | thien-2-yl | H | Br | =CHNMe$_2$ | | Et | |
| 1-258 | thien-2-yl | H | F | =CHNMe$_2$ | | H | |
| 1-259 | thien-2-yl | H | F | =CHNMe$_2$ | | Me | |
| 1-260 | thien-2-yl | H | I | =CHNMe$_2$ | | H | |
| 1-261 | thien-2-yl | H | I | =CHNMe$_2$ | | Me | |
| 1-262 | thien-2-yl | H | CN | =CHNMe$_2$ | | H | |
| 1-263 | thien-2-yl | H | CN | =CHNMe$_2$ | | Me | |
| 1-264 | thien-2-yl | H | CF$_3$ | =CHNMe$_2$ | | H | |
| 1-265 | thien-2-yl | H | CF$_3$ | =CHNMe$_2$ | | Me | |
| 1-266 | thien-2-yl | F | Cl | =CHNMe$_2$ | | H | |
| 1-267 | thien-2-yl | F | Cl | =CHNMe$_2$ | | Me | |
| 1-268 | thien-2-yl | F | Cl | =CHNMe$_2$ | | Et | |
| 1-269 | thien-2-yl | F | Br | =CHNMe$_2$ | | H | |
| 1-270 | thien-2-yl | F | Br | =CHNMe$_2$ | | Me | |
| 1-271 | thien-2-yl | F | Br | =CHNMe$_2$ | | Et | |
| 1-272 | thien-2-yl | F | F | =CHNMe$_2$ | | H | |
| 1-273 | thien-2-yl | F | F | =CHNMe$_2$ | | Me | |
| 1-274 | thien-2-yl | F | I | =CHNMe$_2$ | | H | |
| 1-275 | thien-2-yl | F | I | =CHNMe$_2$ | | Me | |
| 1-276 | thien-2-yl | F | CN | =CHNMe$_2$ | | H | |
| 1-277 | thien-2-yl | F | CN | =CHNMe$_2$ | | Me | |
| 1-278 | thien-2-yl | F | CF$_3$ | =CHNMe$_2$ | | H | |
| 1-279 | thien-2-yl | F | CF$_3$ | =CHNMe$_2$ | | Me | |
| 1-280 | pyrrol-1-yl | H | Cl | H | H | H | |
| 1-281 | pyrrol-1-yl | H | Cl | H | H | Me | 7.98 (d, 2H), 7.46 (d, 2H), 7.13 (d, 2H), 7.11 (s, 1H), 6.37 (d, 2H), 4.82 (br. s, 2H), 4.02 (s, 3H) |
| 1-282 | pyrrol-1-yl | H | Cl | H | H | Et | |
| 1-283 | pyrrol-1-yl | H | Br | H | H | H | |
| 1-284 | pyrrol-1-yl | H | Br | H | H | Me | |
| 1-285 | pyrrol-1-yl | H | Br | H | H | Et | |
| 1-286 | pyrrol-1-yl | H | F | H | H | H | |
| 1-287 | pyrrol-1-yl | H | F | H | H | Me | |
| 1-288 | pyrrol-1-yl | H | I | H | H | H | |
| 1-289 | pyrrol-1-yl | H | I | H | H | Me | |
| 1-290 | pyrrol-1-yl | H | CN | H | H | H | |
| 1-291 | pyrrol-1-yl | H | CN | H | H | Me | |
| 1-292 | pyrrol-1-yl | H | CF$_3$ | H | H | H | |
| 1-293 | pyrrol-1-yl | H | CF$_3$ | H | H | Me | |
| 1-294 | pyrrol-1-yl | F | Cl | H | H | H | |
| 1-295 | pyrrol-1-yl | F | Cl | H | H | Me | |
| 1-296 | pyrrol-1-yl | F | Cl | H | H | Et | |
| 1-297 | pyrrol-1-yl | F | Br | H | H | H | |
| 1-298 | pyrrol-1-yl | F | Br | H | H | Me | |
| 1-299 | pyrrol-1-yl | F | Br | H | H | Et | |
| 1-300 | pyrrol-1-yl | F | F | H | H | H | |
| 1-301 | pyrrol-1-yl | F | F | H | H | Me | |

TABLE 1-continued

Hetarylpyridines:

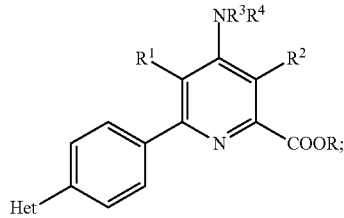

(I-vii)

| No. | Het | R¹ | R² | R³ | R⁴ | R | Physical data: ¹H NMR: δ [CDCl₃] |
|---|---|---|---|---|---|---|---|
| 1-302 | pyrrol-1-yl | F | I | H | H | H | |
| 1-303 | pyrrol-1-yl | F | I | H | H | Me | |
| 1-304 | pyrrol-1-yl | F | CN | H | H | H | |
| 1-305 | pyrrol-1-yl | F | CN | H | H | Me | |
| 1-306 | pyrrol-1-yl | F | CF₃ | H | H | H | |
| 1-307 | pyrrol-1-yl | F | CF₃ | H | H | Me | |
| 1-308 | pyrrol-1-yl | H | Cl | H | Me | H | |
| 1-309 | pyrrol-1-yl | H | Cl | H | Me | Me | |
| 1-310 | pyrrol-1-yl | H | Cl | H | Me | Et | |
| 1-311 | pyrrol-1-yl | H | Br | H | Me | H | |
| 1-312 | pyrrol-1-yl | H | Br | H | Me | Me | |
| 1-313 | pyrrol-1-yl | H | Br | H | Me | Et | |
| 1-314 | pyrrol-1-yl | H | F | H | Me | H | |
| 1-315 | pyrrol-1-yl | H | F | H | Me | Me | |
| 1-316 | pyrrol-1-yl | H | I | H | Me | H | |
| 1-317 | pyrrol-1-yl | H | I | H | Me | Me | |
| 1-318 | pyrrol-1-yl | H | CN | H | Me | H | |
| 1-319 | pyrrol-1-yl | H | CN | H | Me | Me | |
| 1-320 | pyrrol-1-yl | H | CF₃ | H | Me | H | |
| 1-321 | pyrrol-1-yl | H | CF₃ | H | Me | Me | |
| 1-322 | pyrrol-1-yl | F | Cl | H | Me | H | |
| 1-323 | pyrrol-1-yl | F | Cl | H | Me | Me | |
| 1-324 | pyrrol-1-yl | F | Cl | H | Me | Et | |
| 1-325 | pyrrol-1-yl | F | Br | H | Me | H | |
| 1-326 | pyrrol-1-yl | F | Br | H | Me | Me | |
| 1-327 | pyrrol-1-yl | F | Br | H | Me | Et | |
| 1-328 | pyrrol-1-yl | F | F | H | Me | H | |
| 1-329 | pyrrol-1-yl | F | F | H | Me | Me | |
| 1-330 | pyrrol-1-yl | F | I | H | Me | H | |
| 1-331 | pyrrol-1-yl | F | I | H | Me | Me | |
| 1-332 | pyrrol-1-yl | F | CN | H | Me | H | |
| 1-333 | pyrrol-1-yl | F | CN | H | Me | Me | |
| 1-334 | pyrrol-1-yl | F | CF₃ | H | Me | H | |
| 1-335 | pyrrol-1-yl | F | CF₃ | H | Me | Me | |
| 1-336 | pyrrol-1-yl | H | Cl | Me | Me | H | |
| 1-337 | pyrrol-1-yl | H | Cl | Me | Me | Me | |
| 1-338 | pyrrol-1-yl | H | Cl | Me | Me | Et | |
| 1-339 | pyrrol-1-yl | H | Br | Me | Me | H | |
| 1-340 | pyrrol-1-yl | H | Br | Me | Me | Me | |
| 1-341 | pyrrol-1-yl | H | Br | Me | Me | Et | |
| 1-342 | pyrrol-1-yl | H | F | Me | Me | H | |
| 1-343 | pyrrol-1-yl | H | F | Me | Me | Me | |
| 1-344 | pyrrol-1-yl | H | I | Me | Me | H | |
| 1-345 | pyrrol-1-yl | H | I | Me | Me | Me | |
| 1-346 | pyrrol-1-yl | H | CN | Me | Me | H | |
| 1-347 | pyrrol-1-yl | H | CN | Me | Me | Me | |
| 1-348 | pyrrol-1-yl | H | CF₃ | Me | Me | H | |
| 1-349 | pyrrol-1-yl | H | CF₃ | Me | Me | Me | |
| 1-350 | pyrrol-1-yl | F | Cl | Me | Me | H | |
| 1-351 | pyrrol-1-yl | F | Cl | Me | Me | Me | |
| 1-352 | pyrrol-1-yl | F | Cl | Me | Me | Et | |
| 1-353 | pyrrol-1-yl | F | Br | Me | Me | H | |
| 1-354 | pyrrol-1-yl | F | Br | Me | Me | Me | |
| 1-355 | pyrrol-1-yl | F | Br | Me | Me | Et | |
| 1-356 | pyrrol-1-yl | F | F | Me | Me | H | |
| 1-357 | pyrrol-1-yl | F | F | Me | Me | Me | |
| 1-358 | pyrrol-1-yl | F | I | Me | Me | H | |
| 1-359 | pyrrol-1-yl | F | I | Me | Me | Me | |
| 1-360 | pyrrol-1-yl | F | CN | Me | Me | H | |
| 1-361 | pyrrol-1-yl | F | CN | Me | Me | Me | |
| 1-362 | pyrrol-1-yl | F | CF₃ | Me | Me | H | |
| 1-363 | pyrrol-1-yl | F | CF₃ | Me | Me | Me | |
| 1-364 | pyrrol-1-yl | H | Cl | =CHNMe₂ | | H | |

TABLE 1-continued

Hetarylpyridines:

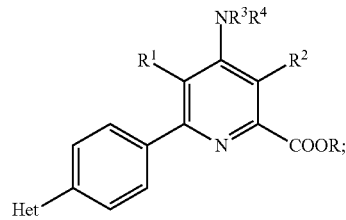

(I-vii)

| No. | Het | R¹ | R² | R³ | R⁴ | R | Physical data: $^1$H NMR: δ [CDCl$_3$] |
|---|---|---|---|---|---|---|---|
| 1-365 | pyrrol-1-yl | H | Cl | =CHNMe₂ | | Me | |
| 1-366 | pyrrol-1-yl | H | Cl | =CHNMe₂ | | Et | |
| 1-367 | pyrrol-1-yl | H | Br | =CHNMe₂ | | H | |
| 1-368 | pyrrol-1-yl | H | Br | =CHNMe₂ | | Me | |
| 1-369 | pyrrol-1-yl | H | Br | =CHNMe₂ | | Et | |
| 1-370 | pyrrol-1-yl | H | F | =CHNMe₂ | | H | |
| 1-371 | pyrrol-1-yl | H | F | =CHNMe₂ | | Me | |
| 1-372 | pyrrol-1-yl | H | I | =CHNMe₂ | | H | |
| 1-373 | pyrrol-1-yl | H | I | =CHNMe₂ | | Me | |
| 1-374 | pyrrol-1-yl | H | CN | =CHNMe₂ | | H | |
| 1-375 | pyrrol-1-yl | H | CN | =CHNMe₂ | | Me | |
| 1-376 | pyrrol-1-yl | H | CF₃ | =CHNMe₂ | | H | |
| 1-377 | pyrrol-1-yl | H | CF₃ | =CHNMe₂ | | Me | |
| 1-378 | pyrrol-1-yl | F | Cl | =CHNMe₂ | | H | |
| 1-379 | pyrrol-1-yl | F | Cl | =CHNMe₂ | | Me | |
| 1-380 | pyrrol-1-yl | F | Cl | =CHNMe₂ | | Et | |
| 1-381 | pyrrol-1-yl | F | Br | =CHNMe₂ | | H | |
| 1-382 | pyrrol-1-yl | F | Br | =CHNMe₂ | | Me | |
| 1-383 | pyrrol-1-yl | F | Br | =CHNMe₂ | | Et | |
| 1-384 | pyrrol-1-yl | F | F | =CHNMe₂ | | H | |
| 1-385 | pyrrol-1-yl | F | F | =CHNMe₂ | | Me | |
| 1-386 | pyrrol-1-yl | F | I | =CHNMe₂ | | H | |
| 1-387 | pyrrol-1-yl | F | I | =CHNMe₂ | | Me | |
| 1-388 | pyrrol-1-yl | F | CN | =CHNMe₂ | | H | |
| 1-389 | pyrrol-1-yl | F | CN | =CHNMe₂ | | Me | |
| 1-390 | pyrrol-1-yl | F | CF₃ | =CHNMe₂ | | H | |
| 1-391 | pyrrol-1-yl | F | CF₃ | =CHNMe₂ | | Me | |
| 1-392 | pyrazol-1-yl | H | Cl | H | H | H | |
| 1-393 | pyrazol-1-yl | H | Cl | H | H | Me | |
| 1-394 | pyrazol-1-yl | H | Cl | H | H | Et | |
| 1-395 | pyrazol-1-yl | H | Br | H | H | H | |
| 1-396 | pyrazol-1-yl | H | Br | H | H | Me | |
| 1-397 | pyrazol-1-yl | H | Br | H | H | Et | |
| 1-398 | pyrazol-1-yl | H | F | H | H | H | |
| 1-399 | pyrazol-1-yl | H | F | H | H | Me | |
| 1-400 | pyrazol-1-yl | H | I | H | H | H | |
| 1-401 | pyrazol-1-yl | H | I | H | H | Me | |
| 1-402 | pyrazol-1-yl | H | CN | H | H | H | |
| 1-403 | pyrazol-1-yl | H | CN | H | H | Me | |
| 1-404 | pyrazol-1-yl | H | CF₃ | H | H | H | |
| 1-405 | pyrazol-1-yl | H | CF₃ | H | H | Me | |
| 1-406 | pyrazol-1-yl | F | Cl | H | H | H | |
| 1-407 | pyrazol-1-yl | F | Cl | H | H | Me | |
| 1-408 | pyrazol-1-yl | F | Cl | H | H | Et | |
| 1-409 | pyrazol-1-yl | F | Br | H | H | H | |
| 1-410 | pyrazol-1-yl | F | Br | H | H | Me | |
| 1-411 | pyrazol-1-yl | F | Br | H | H | Et | |
| 1-412 | pyrazol-1-yl | F | F | H | H | H | |
| 1-413 | pyrazol-1-yl | F | F | H | H | Me | |
| 1-414 | pyrazol-1-yl | F | I | H | H | H | |
| 1-415 | pyrazol-1-yl | F | I | H | H | Me | |
| 1-416 | pyrazol-1-yl | F | CN | H | H | H | |
| 1-417 | pyrazol-1-yl | F | CN | H | H | Me | |
| 1-418 | pyrazol-1-yl | F | CF₃ | H | H | H | |
| 1-419 | pyrazol-1-yl | F | CF₃ | H | H | Me | |
| 1-420 | pyrazol-1-yl | H | Cl | H | Me | H | |
| 1-421 | pyrazol-1-yl | H | Cl | H | Me | Me | |
| 1-422 | pyrazol-1-yl | H | Cl | H | Me | Et | |
| 1-423 | pyrazol-1-yl | H | Br | H | Me | H | |
| 1-424 | pyrazol-1-yl | H | Br | H | Me | Me | |
| 1-425 | pyrazol-1-yl | H | Br | H | Me | Et | |
| 1-426 | pyrazol-1-yl | H | F | H | Me | H | |
| 1-427 | pyrazol-1-yl | H | F | H | Me | Me | |

TABLE 1-continued

Hetarylpyridines:

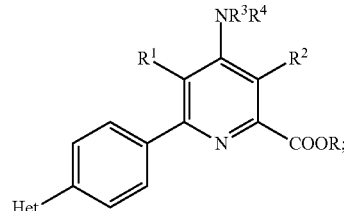

(I-vii)

| No. | Het | R¹ | R² | R³ | R⁴ | R | Physical data: ¹H NMR: δ [CDCl₃] |
|---|---|---|---|---|---|---|---|
| 1-428 | pyrazol-1-yl | H | I | H | Me | H | |
| 1-429 | pyrazol-1-yl | H | I | H | Me | Me | |
| 1-430 | pyrazol-1-yl | H | CN | H | Me | H | |
| 1-431 | pyrazol-1-yl | H | CN | H | Me | Me | |
| 1-432 | pyrazol-1-yl | H | CF₃ | H | Me | H | |
| 1-433 | pyrazol-1-yl | H | CF₃ | H | Me | Me | |
| 1-434 | pyrazol-1-yl | F | Cl | H | Me | H | |
| 1-435 | pyrazol-1-yl | F | Cl | H | Me | Me | |
| 1-436 | pyrazol-1-yl | F | Cl | H | Me | Et | |
| 1-437 | pyrazol-1-yl | F | Br | H | Me | H | |
| 1-438 | pyrazol-1-yl | F | Br | H | Me | Me | |
| 1-439 | pyrazol-1-yl | F | Br | H | Me | Et | |
| 1-440 | pyrazol-1-yl | F | F | H | Me | H | |
| 1-441 | pyrazol-1-yl | F | F | H | Me | Me | |
| 1-442 | pyrazol-1-yl | F | I | H | Me | H | |
| 1-443 | pyrazol-1-yl | F | I | H | Me | Me | |
| 1-444 | pyrazol-1-yl | F | CN | H | Me | H | |
| 1-445 | pyrazol-1-yl | F | CN | H | Me | Me | |
| 1-446 | pyrazol-1-yl | F | CF₃ | H | Me | H | |
| 1-447 | pyrazol-1-yl | F | CF₃ | H | Me | Me | |
| 1-448 | pyrazol-1-yl | H | Cl | Me | Me | H | |
| 1-449 | pyrazol-1-yl | H | Cl | Me | Me | Me | |
| 1-450 | pyrazol-1-yl | H | Cl | Me | Me | Et | |
| 1-451 | pyrazol-1-yl | H | Br | Me | Me | H | |
| 1-452 | pyrazol-1-yl | H | Br | Me | Me | Me | |
| 1-453 | pyrazol-1-yl | H | Br | Me | Me | Et | |
| 1-454 | pyrazol-1-yl | H | F | Me | Me | H | |
| 1-455 | pyrazol-1-yl | H | F | Me | Me | Me | |
| 1-456 | pyrazol-1-yl | H | I | Me | Me | H | |
| 1-457 | pyrazol-1-yl | H | I | Me | Me | Me | |
| 1-458 | pyrazol-1-yl | H | CN | Me | Me | H | |
| 1-459 | pyrazol-1-yl | H | CN | Me | Me | Me | |
| 1-460 | pyrazol-1-yl | H | CF₃ | Me | Me | H | |
| 1-461 | pyrazol-1-yl | H | CF₃ | Me | Me | Me | |
| 1-462 | pyrazol-1-yl | F | Cl | Me | Me | H | |
| 1-463 | pyrazol-1-yl | F | Cl | Me | Me | Me | |
| 1-464 | pyrazol-1-yl | F | Cl | Me | Me | Et | |
| 1-465 | pyrazol-1-yl | F | Br | Me | Me | H | |
| 1-466 | pyrazol-1-yl | F | Br | Me | Me | Me | |
| 1-467 | pyrazol-1-yl | F | Br | Me | Me | Et | |
| 1-468 | pyrazol-1-yl | F | F | Me | Me | H | |
| 1-469 | pyrazol-1-yl | F | F | Me | Me | Me | |
| 1-470 | pyrazol-1-yl | F | I | Me | Me | H | |
| 1-471 | pyrazol-1-yl | F | I | Me | Me | Me | |
| 1-472 | pyrazol-1-yl | F | CN | Me | Me | H | |
| 1-473 | pyrazol-1-yl | F | CN | Me | Me | Me | |
| 1-474 | pyrazol-1-yl | F | CF₃ | Me | Me | H | |
| 1-475 | pyrazol-1-yl | F | CF₃ | Me | Me | Me | |
| 1-476 | pyrazol-1-yl | H | Cl | =CHNMe₂ | | H | |
| 1-477 | pyrazol-1-yl | H | Cl | =CHNMe₂ | | Me | |
| 1-478 | pyrazol-1-yl | H | Cl | =CHNMe₂ | | Et | |
| 1-479 | pyrazol-1-yl | H | Br | =CHNMe₂ | | H | |
| 1-480 | pyrazol-1-yl | H | Br | =CHNMe₂ | | Me | |
| 1-481 | pyrazol-1-yl | H | Br | =CHNMe₂ | | Et | |
| 1-482 | pyrazol-1-yl | H | F | =CHNMe₂ | | H | |
| 1-483 | pyrazol-1-yl | H | F | =CHNMe₂ | | Me | |
| 1-484 | pyrazol-1-yl | H | I | =CHNMe₂ | | H | |
| 1-485 | pyrazol-1-yl | H | I | =CHNMe₂ | | Me | |
| 1-486 | pyrazol-1-yl | H | CN | =CHNMe₂ | | H | |
| 1-487 | pyrazol-1-yl | H | CN | =CHNMe₂ | | Me | |
| 1-488 | pyrazol-1-yl | H | CF₃ | =CHNMe₂ | | H | |
| 1-489 | pyrazol-1-yl | H | CF₃ | =CHNMe₂ | | Me | |
| 1-490 | pyrazol-1-yl | F | Cl | =CHNMe₂ | | H | |

TABLE 1-continued

Hetarylpyridines:

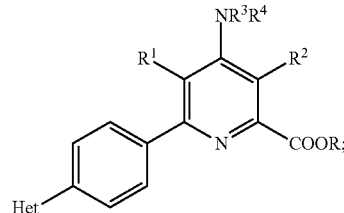

(I-vii)

| No. | Het | R¹ | R² | R³ | R⁴ | R | Physical data: ¹H NMR: δ [CDCl₃] |
|---|---|---|---|---|---|---|---|
| 1-491 | pyrazol-1-yl | F | Cl | =CHNMe₂ | | Me | |
| 1-492 | pyrazol-1-yl | F | Cl | =CHNMe₂ | | Et | |
| 1-493 | pyrazol-1-yl | F | Br | =CHNMe₂ | | H | |
| 1-494 | pyrazol-1-yl | F | Br | =CHNMe₂ | | Me | |
| 1-495 | pyrazol-1-yl | F | Br | =CHNMe₂ | | Et | |
| 1-496 | pyrazol-1-yl | F | F | =CHNMe₂ | | H | |
| 1-497 | pyrazol-1-yl | F | F | =CHNMe₂ | | Me | |
| 1-498 | pyrazol-1-yl | F | I | =CHNMe₂ | | H | |
| 1-499 | pyrazol-1-yl | F | I | =CHNMe₂ | | Me | |
| 1-500 | pyrazol-1-yl | F | CN | =CHNMe₂ | | H | |
| 1-501 | pyrazol-1-yl | F | CN | =CHNMe₂ | | Me | |
| 1-502 | pyrazol-1-yl | F | CF₃ | =CHNMe₂ | | H | |
| 1-503 | pyrazol-1-yl | F | CF₃ | =CHNMe₂ | | Me | |
| 1-504 | pyridin-3-yl | H | Cl | H | H | H | |
| 1-505 | pyridin-3-yl | H | Cl | H | H | Me | |
| 1-506 | pyridin-3-yl | H | Cl | H | H | Et | |
| 1-507 | pyridin-3-yl | H | Br | H | H | H | |
| 1-508 | pyridin-3-yl | H | Br | H | H | Me | |
| 1-509 | pyridin-3-yl | H | Br | H | H | Et | |
| 1-510 | pyridin-3-yl | H | F | H | H | H | |
| 1-511 | pyridin-3-yl | H | F | H | H | Me | |
| 1-512 | pyridin-3-yl | H | I | H | H | H | |
| 1-513 | pyridin-3-yl | H | I | H | H | Me | |
| 1-514 | pyridin-3-yl | H | CN | H | H | H | |
| 1-515 | pyridin-3-yl | H | CN | H | H | Me | |
| 1-516 | pyridin-3-yl | H | CF₃ | H | H | H | |
| 1-517 | pyridin-3-yl | H | CF₃ | H | H | Me | |
| 1-518 | pyridin-3-yl | F | Cl | H | H | H | |
| 1-519 | pyridin-3-yl | F | Cl | H | H | Me | |
| 1-520 | pyridin-3-yl | F | Cl | H | H | Et | |
| 1-521 | pyridin-3-yl | F | Br | H | H | H | |
| 1-522 | pyridin-3-yl | F | Br | H | H | Me | |
| 1-523 | pyridin-3-yl | F | Br | H | H | Et | |
| 1-524 | pyridin-3-yl | F | F | H | H | H | |
| 1-525 | pyridin-3-yl | F | F | H | H | Me | |
| 1-526 | pyridin-3-yl | F | I | H | H | H | |
| 1-527 | pyridin-3-yl | F | I | H | H | Me | |
| 1-528 | pyridin-3-yl | F | CN | H | H | H | |
| 1-529 | pyridin-3-yl | F | CN | H | H | Me | |
| 1-530 | pyridin-3-yl | F | CF₃ | H | H | H | |
| 1-531 | pyridin-3-yl | F | CF₃ | H | H | Me | |
| 1-532 | pyridin-3-yl | H | Cl | H | Me | H | |
| 1-533 | pyridin-3-yl | H | Cl | H | Me | Me | |
| 1-534 | pyridin-3-yl | H | Cl | H | Me | Et | |
| 1-535 | pyridin-3-yl | H | Br | H | Me | H | |
| 1-536 | pyridin-3-yl | H | Br | H | Me | Me | |
| 1-537 | pyridin-3-yl | H | Br | H | Me | Et | |
| 1-538 | pyridin-3-yl | H | F | H | Me | H | |
| 1-539 | pyridin-3-yl | H | F | H | Me | Me | |
| 1-540 | pyridin-3-yl | H | I | H | Me | H | |
| 1-541 | pyridin-3-yl | H | I | H | Me | Me | |
| 1-542 | pyridin-3-yl | H | CN | H | Me | H | |
| 1-543 | pyridin-3-yl | H | CN | H | Me | Me | |
| 1-544 | pyridin-3-yl | H | CF₃ | H | Me | H | |
| 1-545 | pyridin-3-yl | H | CF₃ | H | Me | Me | |
| 1-546 | pyridin-3-yl | F | Cl | H | Me | H | |
| 1-547 | pyridin-3-yl | F | Cl | H | Me | Me | |
| 1-548 | pyridin-3-yl | F | Cl | H | Me | Et | |
| 1-549 | pyridin-3-yl | F | Br | H | Me | H | |
| 1-550 | pyridin-3-yl | F | Br | H | Me | Me | |
| 1-551 | pyridin-3-yl | F | Br | H | Me | Et | |
| 1-552 | pyridin-3-yl | F | F | H | Me | H | |
| 1-553 | pyridin-3-yl | F | F | H | Me | Me | |

TABLE 1-continued

Hetarylpyridines:

(I-vii)

| No. | Het | R¹ | R² | R³ | R⁴ | R | Physical data: $^1$H NMR: δ [CDCl$_3$] |
|---|---|---|---|---|---|---|---|
| 1-554 | pyridin-3-yl | F | I | H | Me | H | |
| 1-555 | pyridin-3-yl | F | I | H | Me | Me | |
| 1-556 | pyridin-3-yl | F | CN | H | Me | H | |
| 1-557 | pyridin-3-yl | F | CN | H | Me | Me | |
| 1-558 | pyridin-3-yl | F | CF$_3$ | H | Me | H | |
| 1-559 | pyridin-3-yl | F | CF$_3$ | H | Me | Me | |
| 1-560 | pyridin-3-yl | H | Cl | Me | Me | H | |
| 1-561 | pyridin-3-yl | H | Cl | Me | Me | Me | |
| 1-562 | pyridin-3-yl | H | Cl | Me | Me | Et | |
| 1-563 | pyridin-3-yl | H | Br | Me | Me | H | |
| 1-564 | pyridin-3-yl | H | Br | Me | Me | Me | |
| 1-565 | pyridin-3-yl | H | Br | Me | Me | Et | |
| 1-566 | pyridin-3-yl | H | F | Me | Me | H | |
| 1-567 | pyridin-3-yl | H | F | Me | Me | Me | |
| 1-568 | pyridin-3-yl | H | I | Me | Me | H | |
| 1-569 | pyridin-3-yl | H | I | Me | Me | Me | |
| 1-570 | pyridin-3-yl | H | CN | Me | Me | H | |
| 1-571 | pyridin-3-yl | H | CN | Me | Me | Me | |
| 1-572 | pyridin-3-yl | H | CF$_3$ | Me | Me | H | |
| 1-573 | pyridin-3-yl | H | CF$_3$ | Me | Me | Me | |
| 1-574 | pyridin-3-yl | F | Cl | Me | Me | H | |
| 1-575 | pyridin-3-yl | F | Cl | Me | Me | Me | |
| 1-576 | pyridin-3-yl | F | Cl | Me | Me | Et | |
| 1-577 | pyridin-3-yl | F | Br | Me | Me | H | |
| 1-578 | pyridin-3-yl | F | Br | Me | Me | Me | |
| 1-579 | pyridin-3-yl | F | Br | Me | Me | Et | |
| 1-580 | pyridin-3-yl | F | F | Me | Me | H | |
| 1-581 | pyridin-3-yl | F | F | Me | Me | Me | |
| 1-582 | pyridin-3-yl | F | I | Me | Me | H | |
| 1-583 | pyridin-3-yl | F | I | Me | Me | Me | |
| 1-584 | pyridin-3-yl | F | CN | Me | Me | H | |
| 1-585 | pyridin-3-yl | F | CN | Me | Me | Me | |
| 1-586 | pyridin-3-yl | F | CF$_3$ | Me | Me | H | |
| 1-587 | pyridin-3-yl | F | CF$_3$ | Me | Me | Me | |
| 1-588 | pyridin-3-yl | H | Cl | =CHNMe$_2$ | | H | |
| 1-589 | pyridin-3-yl | H | Cl | =CHNMe$_2$ | | Me | |
| 1-590 | pyridin-3-yl | H | Cl | =CHNMe$_2$ | | Et | |
| 1-591 | pyridin-3-yl | H | Br | =CHNMe$_2$ | | H | |
| 1-592 | pyridin-3-yl | H | Br | =CHNMe$_2$ | | Me | |
| 1-593 | pyridin-3-yl | H | Br | =CHNMe$_2$ | | Et | |
| 1-594 | pyridin-3-yl | H | F | =CHNMe$_2$ | | H | |
| 1-595 | pyridin-3-yl | H | F | =CHNMe$_2$ | | Me | |
| 1-596 | pyridin-3-yl | H | I | =CHNMe$_2$ | | H | |
| 1-597 | pyridin-3-yl | H | I | =CHNMe$_2$ | | Me | |
| 1-598 | pyridin-3-yl | H | CN | =CHNMe$_2$ | | H | |
| 1-599 | pyridin-3-yl | H | CN | =CHNMe$_2$ | | Me | |
| 1-600 | pyridin-3-yl | H | CF$_3$ | =CHNMe$_2$ | | H | |
| 1-601 | pyridin-3-yl | H | CF$_3$ | =CHNMe$_2$ | | Me | |
| 1-602 | pyridin-3-yl | F | Cl | =CHNMe$_2$ | | H | |
| 1-603 | pyridin-3-yl | F | Cl | =CHNMe$_2$ | | Me | |
| 1-604 | pyridin-3-yl | F | Cl | =CHNMe$_2$ | | Et | |
| 1-605 | pyridin-3-yl | F | Br | =CHNMe$_2$ | | H | |
| 1-606 | pyridin-3-yl | F | Br | =CHNMe$_2$ | | Me | |
| 1-607 | pyridin-3-yl | F | Br | =CHNMe$_2$ | | Et | |
| 1-608 | pyridin-3-yl | F | F | =CHNMe$_2$ | | H | |
| 1-609 | pyridin-3-yl | F | F | =CHNMe$_2$ | | Me | |
| 1-610 | pyridin-3-yl | F | I | =CHNMe$_2$ | | H | |
| 1-611 | pyridin-3-yl | F | I | =CHNMe$_2$ | | Me | |
| 1-612 | pyridin-3-yl | F | CN | =CHNMe$_2$ | | H | |
| 1-613 | pyridin-3-yl | F | CN | =CHNMe$_2$ | | Me | |
| 1-614 | pyridin-3-yl | F | CF$_3$ | =CHNMe$_2$ | | H | |
| 1-615 | pyridin-3-yl | F | CF$_3$ | =CHNMe$_2$ | | Me | |
| 1-616 | oxiranyl | H | Cl | H | H | H | |

TABLE 1-continued

Hetarylpyridines:

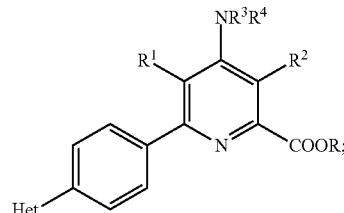

(I-vii)

| No. | Het | R¹ | R² | R³ | R⁴ | R | Physical data: ¹H NMR: δ [CDCl₃] |
|---|---|---|---|---|---|---|---|
| 1-617 | oxiranyl | H | Cl | H | H | Me | |
| 1-618 | oxiranyl | H | Cl | H | H | Et | |
| 1-619 | oxiranyl | H | Br | H | H | H | |
| 1-620 | oxiranyl | H | Br | H | H | Me | |
| 1-621 | oxiranyl | H | Br | H | H | Et | |
| 1-622 | oxiranyl | H | F | H | H | H | |
| 1-623 | oxiranyl | H | F | H | H | Me | |
| 1-624 | oxiranyl | H | I | H | H | H | |
| 1-625 | oxiranyl | H | I | H | H | Me | |
| 1-626 | oxiranyl | H | CN | H | H | H | |
| 1-627 | oxiranyl | H | CN | H | H | Me | |
| 1-628 | oxiranyl | H | CF₃ | H | H | H | |
| 1-629 | oxiranyl | H | CF₃ | H | H | Me | |
| 1-630 | oxiranyl | F | Cl | H | H | H | |
| 1-631 | oxiranyl | F | Cl | H | H | Me | |
| 1-632 | oxiranyl | F | Cl | H | H | Et | |
| 1-633 | oxiranyl | F | Br | H | H | H | |
| 1-634 | oxiranyl | F | Br | H | H | Me | |
| 1-635 | oxiranyl | F | Br | H | H | Et | |
| 1-636 | oxiranyl | F | F | H | H | H | |
| 1-637 | oxiranyl | F | F | H | H | Me | |
| 1-638 | oxiranyl | F | I | H | H | H | |
| 1-639 | oxiranyl | F | I | H | H | Me | |
| 1-640 | oxiranyl | F | CN | H | H | H | |
| 1-641 | oxiranyl | F | CN | H | H | Me | |
| 1-642 | oxiranyl | F | CF₃ | H | H | H | |
| 1-643 | oxiranyl | F | CF₃ | H | H | Me | |
| 1-644 | oxiranyl | H | Cl | H | Me | H | |
| 1-645 | oxiranyl | H | Cl | H | Me | Me | |
| 1-646 | oxiranyl | H | Cl | H | Me | Et | |
| 1-647 | oxiranyl | H | Br | H | Me | H | |
| 1-648 | oxiranyl | H | Br | H | Me | Me | |
| 1-649 | oxiranyl | H | Br | H | Me | Et | |
| 1-650 | oxiranyl | H | F | H | Me | H | |
| 1-651 | oxiranyl | H | F | H | Me | Me | |
| 1-652 | oxiranyl | H | I | H | Me | H | |
| 1-653 | oxiranyl | H | I | H | Me | Me | |
| 1-654 | oxiranyl | H | CN | H | Me | H | |
| 1-655 | oxiranyl | H | CN | H | Me | Me | |
| 1-656 | oxiranyl | H | CF₃ | H | Me | H | |
| 1-657 | oxiranyl | H | CF₃ | H | Me | Me | |
| 1-658 | oxiranyl | F | Cl | H | Me | H | |
| 1-659 | oxiranyl | F | Cl | H | Me | Me | |
| 1-660 | oxiranyl | F | Cl | H | Me | Et | |
| 1-661 | oxiranyl | F | Br | H | Me | H | |
| 1-662 | oxiranyl | F | Br | H | Me | Me | |
| 1-663 | oxiranyl | F | Br | H | Me | Et | |
| 1-664 | oxiranyl | F | F | H | Me | H | |
| 1-665 | oxiranyl | F | F | H | Me | Me | |
| 1-666 | oxiranyl | F | I | H | Me | H | |
| 1-667 | oxiranyl | F | I | H | Me | Me | |
| 1-668 | oxiranyl | F | CN | H | Me | H | |
| 1-669 | oxiranyl | F | CN | H | Me | Me | |
| 1-670 | oxiranyl | F | CF₃ | H | Me | H | |
| 1-671 | oxiranyl | F | CF₃ | H | Me | Me | |
| 1-672 | oxiranyl | H | Cl | Me | Me | H | |
| 1-673 | oxiranyl | H | Cl | Me | Me | Me | |
| 1-674 | oxiranyl | H | Cl | Me | Me | Et | |
| 1-675 | oxiranyl | H | Br | Me | Me | H | |
| 1-676 | oxiranyl | H | Br | Me | Me | Me | |
| 1-677 | oxiranyl | H | Br | Me | Me | Et | |
| 1-678 | oxiranyl | H | F | Me | Me | H | |
| 1-679 | oxiranyl | H | F | Me | Me | Me | |

TABLE 1-continued

Hetarylpyridines:

(I-vii)

| No. | Het | R¹ | R² | R³ | R⁴ | R | Physical data: $^1$H NMR: δ [CDCl$_3$] |
|---|---|---|---|---|---|---|---|
| 1-680 | oxiranyl | H | I | Me | Me | H | |
| 1-681 | oxiranyl | H | I | Me | Me | Me | |
| 1-682 | oxiranyl | H | CN | Me | Me | H | |
| 1-683 | oxiranyl | H | CN | Me | Me | Me | |
| 1-684 | oxiranyl | H | CF$_3$ | Me | Me | H | |
| 1-685 | oxiranyl | H | CF$_3$ | Me | Me | Me | |
| 1-686 | oxiranyl | F | Cl | Me | Me | H | |
| 1-687 | oxiranyl | F | Cl | Me | Me | Me | |
| 1-688 | oxiranyl | F | Cl | Me | Me | Et | |
| 1-689 | oxiranyl | F | Br | Me | Me | H | |
| 1-690 | oxiranyl | F | Br | Me | Me | Me | |
| 1-691 | oxiranyl | F | Br | Me | Me | Et | |
| 1-692 | oxiranyl | F | F | Me | Me | H | |
| 1-693 | oxiranyl | F | F | Me | Me | Me | |
| 1-694 | oxiranyl | F | I | Me | Me | H | |
| 1-695 | oxiranyl | F | I | Me | Me | Me | |
| 1-696 | oxiranyl | F | CN | Me | Me | H | |
| 1-697 | oxiranyl | F | CN | Me | Me | Me | |
| 1-698 | oxiranyl | F | CF$_3$ | Me | Me | H | |
| 1-699 | oxiranyl | F | CF$_3$ | Me | Me | Me | |
| 1-700 | oxiranyl | H | Cl | =CHNMe$_2$ | | H | |
| 1-701 | oxiranyl | H | Cl | =CHNMe$_2$ | | Me | |
| 1-702 | oxiranyl | H | Cl | =CHNMe$_2$ | | Et | |
| 1-703 | oxiranyl | H | Br | =CHNMe$_2$ | | H | |
| 1-704 | oxiranyl | H | Br | =CHNMe$_2$ | | Me | |
| 1-705 | oxiranyl | H | Br | =CHNMe$_2$ | | Et | |
| 1-706 | oxiranyl | H | F | =CHNMe$_2$ | | H | |
| 1-707 | oxiranyl | H | F | =CHNMe$_2$ | | Me | |
| 1-708 | oxiranyl | H | I | =CHNMe$_2$ | | H | |
| 1-709 | oxiranyl | H | I | =CHNMe$_2$ | | Me | |
| 1-710 | oxiranyl | H | CN | =CHNMe$_2$ | | H | |
| 1-711 | oxiranyl | H | CN | =CHNMe$_2$ | | Me | |
| 1-712 | oxiranyl | H | CF$_3$ | =CHNMe$_2$ | | H | |
| 1-713 | oxiranyl | H | CF$_3$ | =CHNMe$_2$ | | Me | |
| 1-714 | oxiranyl | F | Cl | =CHNMe$_2$ | | H | |
| 1-715 | oxiranyl | F | Cl | =CHNMe$_2$ | | Me | |
| 1-716 | oxiranyl | F | Cl | =CHNMe$_2$ | | Et | |
| 1-717 | oxiranyl | F | Br | =CHNMe$_2$ | | H | |
| 1-718 | oxiranyl | F | Br | =CHNMe$_2$ | | Me | |
| 1-719 | oxiranyl | F | Br | =CHNMe$_2$ | | Et | |
| 1-720 | oxiranyl | F | F | =CHNMe$_2$ | | H | |
| 1-721 | oxiranyl | F | F | =CHNMe$_2$ | | Me | |
| 1-722 | oxiranyl | F | I | =CHNMe$_2$ | | H | |
| 1-723 | oxiranyl | F | I | =CHNMe$_2$ | | Me | |
| 1-724 | oxiranyl | F | CN | =CHNMe$_2$ | | H | |
| 1-725 | oxiranyl | F | CN | =CHNMe$_2$ | | Me | |
| 1-726 | oxiranyl | F | CF$_3$ | =CHNMe$_2$ | | H | |
| 1-727 | oxiranyl | F | CF$_3$ | =CHNMe$_2$ | | Me | |
| 1-728 | 3,3-dimethyl-oxetan-2-yl | H | Cl | H | H | H | |
| 1-729 | 3,3-dimethyl-oxetan-2-yl | H | Cl | H | H | Me | |
| 1-730 | 3,3-dimethyl-oxetan-2-yl | H | Cl | H | H | Et | |
| 1-731 | 3,3-dimethyl-oxetan-2-yl | H | Br | H | H | H | |
| 1-732 | 3,3-dimethyl-oxetan-2-yl | H | Br | H | H | Me | |
| 1-733 | 3,3-dimethyl-oxetan-2-yl | H | Br | H | H | Et | |
| 1-734 | 3,3-dimethyl-oxetan-2-yl | H | F | H | H | H | |
| 1-735 | 3,3-dimethyl-oxetan-2-yl | H | F | H | H | Me | |
| 1-736 | 3,3-dimethyl-oxetan-2-yl | H | I | H | H | H | |
| 1-737 | 3,3-dimethyl-oxetan-2-yl | H | I | H | H | Me | |
| 1-738 | 3,3-dimethyl-oxetan-2-yl | H | CN | H | H | H | |
| 1-739 | 3,3-dimethyl-oxetan-2-yl | H | CN | H | H | Me | |
| 1-740 | 3,3-dimethyl-oxetan-2-yl | H | CF$_3$ | H | H | H | |
| 1-741 | 3,3-dimethyl-oxetan-2-yl | H | CF$_3$ | H | H | Me | |
| 1-742 | 3,3-dimethyl-oxetan-2-yl | F | Cl | H | H | H | |

TABLE 1-continued

Hetarylpyridines:

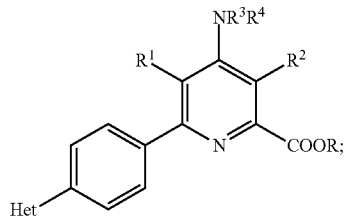

(I-vii)

| No. | Het | R¹ | R² | R³ | R⁴ | R | Physical data: $^1$H NMR: δ [CDCl$_3$] |
|---|---|---|---|---|---|---|---|
| 1-743 | 3,3-dimethyl-oxetan-2-yl | F | Cl | H | H | Me | |
| 1-744 | 3,3-dimethyl-oxetan-2-yl | F | Cl | H | H | Et | |
| 1-745 | 3,3-dimethyl-oxetan-2-yl | F | Br | H | H | H | |
| 1-746 | 3,3-dimethyl-oxetan-2-yl | F | Br | H | H | Me | |
| 1-747 | 3,3-dimethyl-oxetan-2-yl | F | Br | H | H | Et | |
| 1-748 | 3,3-dimethyl-oxetan-2-yl | F | F | H | H | H | |
| 1-749 | 3,3-dimethyl-oxetan-2-yl | F | F | H | H | Me | |
| 1-750 | 3,3-dimethyl-oxetan-2-yl | F | I | H | H | H | |
| 1-751 | 3,3-dimethyl-oxetan-2-yl | F | I | H | H | Me | |
| 1-752 | 3,3-dimethyl-oxetan-2-yl | F | CN | H | H | H | |
| 1-753 | 3,3-dimethyl-oxetan-2-yl | F | CN | H | H | Me | |
| 1-754 | 3,3-dimethyl-oxetan-2-yl | F | CF$_3$ | H | H | H | |
| 1-755 | 3,3-dimethyl-oxetan-2-yl | F | CF$_3$ | H | H | Me | |
| 1-756 | 3,3-dimethyl-oxetan-2-yl | H | Cl | H | Me | H | |
| 1-757 | 3,3-dimethyl-oxetan-2-yl | H | Cl | H | Me | Me | |
| 1-758 | 3,3-dimethyl-oxetan-2-yl | H | Cl | H | Me | Et | |
| 1-759 | 3,3-dimethyl-oxetan-2-yl | H | Br | H | Me | H | |
| 1-760 | 3,3-dimethyl-oxetan-2-yl | H | Br | H | Me | Me | |
| 1-761 | 3,3-dimethyl-oxetan-2-yl | H | Br | H | Me | Et | |
| 1-762 | 3,3-dimethyl-oxetan-2-yl | H | F | H | Me | H | |
| 1-763 | 3,3-dimethyl-oxetan-2-yl | H | F | H | Me | Me | |
| 1-764 | 3,3-dimethyl-oxetan-2-yl | H | I | H | Me | H | |
| 1-765 | 3,3-dimethyl-oxetan-2-yl | H | I | H | Me | Me | |
| 1-766 | 3,3-dimethyl-oxetan-2-yl | H | CN | H | Me | H | |
| 1-767 | 3,3-dimethyl-oxetan-2-yl | H | CN | H | Me | Me | |
| 1-768 | 3,3-dimethyl-oxetan-2-yl | H | CF$_3$ | H | Me | H | |
| 1-769 | 3,3-dimethyl-oxetan-2-yl | H | CF$_3$ | H | Me | Me | |
| 1-770 | 3,3-dimethyl-oxetan-2-yl | F | Cl | H | Me | H | |
| 1-771 | 3,3-dimethyl-oxetan-2-yl | F | Cl | H | Me | Me | |
| 1-772 | 3,3-dimethyl-oxetan-2-yl | F | Cl | H | Me | Et | |
| 1-773 | 3,3-dimethyl-oxetan-2-yl | F | Br | H | Me | H | |
| 1-774 | 3,3-dimethyl-oxetan-2-yl | F | Br | H | Me | Me | |
| 1-775 | 3,3-dimethyl-oxetan-2-yl | F | Br | H | Me | Et | |
| 1-776 | 3,3-dimethyl-oxetan-2-yl | F | F | H | Me | H | |
| 1-777 | 3,3-dimethyl-oxetan-2-yl | F | F | H | Me | Me | |
| 1-778 | 3,3-dimethyl-oxetan-2-yl | F | I | H | Me | H | |
| 1-779 | 3,3-dimethyl-oxetan-2-yl | F | I | H | Me | Me | |
| 1-780 | 3,3-dimethyl-oxetan-2-yl | F | CN | H | Me | H | |
| 1-781 | 3,3-dimethyl-oxetan-2-yl | F | CN | H | Me | Me | |
| 1-782 | 3,3-dimethyl-oxetan-2-yl | F | CF$_3$ | H | Me | H | |
| 1-783 | 3,3-dimethyl-oxetan-2-yl | F | CF$_3$ | H | Me | Me | |
| 1-784 | 3,3-dimethyl-oxetan-2-yl | H | Cl | Me | Me | H | |
| 1-785 | 3,3-dimethyl-oxetan-2-yl | H | Cl | Me | Me | Me | |
| 1-786 | 3,3-dimethyl-oxetan-2-yl | H | Cl | Me | Me | Et | |
| 1-787 | 3,3-dimethyl-oxetan-2-yl | H | Br | Me | Me | H | |
| 1-788 | 3,3-dimethyl-oxetan-2-yl | H | Br | Me | Me | Me | |
| 1-789 | 3,3-dimethyl-oxetan-2-yl | H | Br | Me | Me | Et | |
| 1-790 | 3,3-dimethyl-oxetan-2-yl | H | F | Me | Me | H | |
| 1-791 | 3,3-dimethyl-oxetan-2-yl | H | F | Me | Me | Me | |
| 1-792 | 3,3-dimethyl-oxetan-2-yl | H | I | Me | Me | H | |
| 1-793 | 3,3-dimethyl-oxetan-2-yl | H | I | Me | Me | Me | |
| 1-794 | 3,3-dimethyl-oxetan-2-yl | H | CN | Me | Me | H | |
| 1-795 | 3,3-dimethyl-oxetan-2-yl | H | CN | Me | Me | Me | |
| 1-796 | 3,3-dimethyl-oxetan-2-yl | H | CF$_3$ | Me | Me | H | |
| 1-797 | 3,3-dimethyl-oxetan-2-yl | H | CF$_3$ | Me | Me | Me | |
| 1-798 | 3,3-dimethyl-oxetan-2-yl | F | Cl | Me | Me | H | |
| 1-799 | 3,3-dimethyl-oxetan-2-yl | F | Cl | Me | Me | Me | |
| 1-800 | 3,3-dimethyl-oxetan-2-yl | F | Cl | Me | Me | Et | |
| 1-801 | 3,3-dimethyl-oxetan-2-yl | F | Br | Me | Me | H | |
| 1-802 | 3,3-dimethyl-oxetan-2-yl | F | Br | Me | Me | Me | |
| 1-803 | 3,3-dimethyl-oxetan-2-yl | F | Br | Me | Me | Et | |
| 1-804 | 3,3-dimethyl-oxetan-2-yl | F | F | Me | Me | H | |
| 1-805 | 3,3-dimethyl-oxetan-2-yl | F | F | Me | Me | Me | |

TABLE 1-continued

Hetarylpyridines:

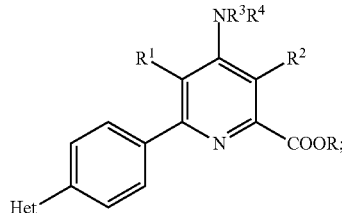

(I-vii)

| No. | Het | R¹ | R² | R³ | R⁴ | R | Physical data: ¹H NMR: δ [CDCl₃] |
|---|---|---|---|---|---|---|---|
| 1-806 | 3,3-dimethyl-oxetan-2-yl | F | I | Me | Me | H | |
| 1-807 | 3,3-dimethyl-oxetan-2-yl | F | I | Me | Me | Me | |
| 1-808 | 3,3-dimethyl-oxetan-2-yl | F | CN | Me | Me | H | |
| 1-809 | 3,3-dimethyl-oxetan-2-yl | F | CN | Me | Me | Me | |
| 1-810 | 3,3-dimethyl-oxetan-2-yl | F | CF₃ | Me | Me | H | |
| 1-811 | 3,3-dimethyl-oxetan-2-yl | F | CF₃ | Me | Me | Me | |
| 1-812 | 3,3-dimethyl-oxetan-2-yl | H | Cl | =CHNMe₂ | | H | |
| 1-813 | 3,3-dimethyl-oxetan-2-yl | H | Cl | =CHNMe₂ | | Me | |
| 1-814 | 3,3-dimethyl-oxetan-2-yl | H | Cl | =CHNMe₂ | | Et | |
| 1-815 | 3,3-dimethyl-oxetan-2-yl | H | Br | =CHNMe₂ | | H | |
| 1-816 | 3,3-dimethyl-oxetan-2-yl | H | Br | =CHNMe₂ | | Me | |
| 1-817 | 3,3-dimethyl-oxetan-2-yl | H | Br | =CHNMe₂ | | Et | |
| 1-818 | 3,3-dimethyl-oxetan-2-yl | H | F | =CHNMe₂ | | H | |
| 1-819 | 3,3-dimethyl-oxetan-2-yl | H | F | =CHNMe₂ | | Me | |
| 1-820 | 3,3-dimethyl-oxetan-2-yl | H | I | =CHNMe₂ | | H | |
| 1-821 | 3,3-dimethyl-oxetan-2-yl | H | I | =CHNMe₂ | | Me | |
| 1-822 | 3,3-dimethyl-oxetan-2-yl | H | CN | =CHNMe₂ | | H | |
| 1-823 | 3,3-dimethyl-oxetan-2-yl | H | CN | =CHNMe₂ | | Me | |
| 1-824 | 3,3-dimethyl-oxetan-2-yl | H | CF₃ | =CHNMe₂ | | H | |
| 1-825 | 3,3-dimethyl-oxetan-2-yl | H | CF₃ | =CHNMe₂ | | Me | |
| 1-826 | 3,3-dimethyl-oxetan-2-yl | F | Cl | =CHNMe₂ | | H | |
| 1-827 | 3,3-dimethyl-oxetan-2-yl | F | Cl | =CHNMe₂ | | Me | |
| 1-828 | 3,3-dimethyl-oxetan-2-yl | F | Cl | =CHNMe₂ | | Et | |
| 1-829 | 3,3-dimethyl-oxetan-2-yl | F | Br | =CHNMe₂ | | H | |
| 1-830 | 3,3-dimethyl-oxetan-2-yl | F | Br | =CHNMe₂ | | Me | |
| 1-831 | 3,3-dimethyl-oxetan-2-yl | F | Br | =CHNMe₂ | | Et | |
| 1-832 | 3,3-dimethyl-oxetan-2-yl | F | F | =CHNMe₂ | | H | |
| 1-833 | 3,3-dimethyl-oxetan-2-yl | F | F | =CHNMe₂ | | Me | |
| 1-834 | 3,3-dimethyl-oxetan-2-yl | F | I | =CHNMe₂ | | H | |
| 1-835 | 3,3-dimethyl-oxetan-2-yl | F | I | =CHNMe₂ | | Me | |
| 1-836 | 3,3-dimethyl-oxetan-2-yl | F | CN | =CHNMe₂ | | H | |
| 1-837 | 3,3-dimethyl-oxetan-2-yl | F | CN | =CHNMe₂ | | Me | |
| 1-838 | 3,3-dimethyl-oxetan-2-yl | F | CF₃ | =CHNMe₂ | | H | |
| 1-839 | 3,3-dimethyl-oxetan-2-yl | F | CF₃ | =CHNMe₂ | | Me | |
| 1-840 | 2,2-dimethyl-dioxolan-4-yl | H | Cl | H | H | H | |
| 1-841 | 2,2-dimethyl-dioxolan-4-yl | H | Cl | H | H | Me | |
| 1-842 | 2,2-dimethyl-dioxolan-4-yl | H | Cl | H | H | Et | |
| 1-843 | 2,2-dimethyl-dioxolan-4-yl | H | Br | H | H | H | |
| 1-844 | 2,2-dimethyl-dioxolan-4-yl | H | Br | H | H | Me | |
| 1-845 | 2,2-dimethyl-dioxolan-4-yl | H | Br | H | H | Et | |
| 1-846 | 2,2-dimethyl-dioxolan-4-yl | H | F | H | H | H | |
| 1-847 | 2,2-dimethyl-dioxolan-4-yl | H | F | H | H | Me | |
| 1-848 | 2,2-dimethyl-dioxolan-4-yl | H | I | H | H | H | |
| 1-849 | 2,2-dimethyl-dioxolan-4-yl | H | I | H | H | Me | |
| 1-850 | 2,2-dimethyl-dioxolan-4-yl | H | CN | H | H | H | |
| 1-851 | 2,2-dimethyl-dioxolan-4-yl | H | CN | H | H | Me | |
| 1-852 | 2,2-dimethyl-dioxolan-4-yl | H | CF₃ | H | H | H | |
| 1-853 | 2,2-dimethyl-dioxolan-4-yl | H | CF₃ | H | H | Me | |
| 1-854 | 2,2-dimethyl-dioxolan-4-yl | F | Cl | H | H | H | |
| 1-855 | 2,2-dimethyl-dioxolan-4-yl | F | Cl | H | H | Me | |
| 1-856 | 2,2-dimethyl-dioxolan-4-yl | F | Cl | H | H | Et | |
| 1-857 | 2,2-dimethyl-dioxolan-4-yl | F | Br | H | H | H | |
| 1-858 | 2,2-dimethyl-dioxolan-4-yl | F | Br | H | H | Me | |
| 1-859 | 2,2-dimethyl-dioxolan-4-yl | F | Br | H | H | Et | |
| 1-860 | 2,2-dimethyl-dioxolan-4-yl | F | F | H | H | H | |
| 1-861 | 2,2-dimethyl-dioxolan-4-yl | F | F | H | H | Me | |
| 1-862 | 2,2-dimethyl-dioxolan-4-yl | F | I | H | H | H | |
| 1-863 | 2,2-dimethyl-dioxolan-4-yl | F | I | H | H | Me | |
| 1-864 | 2,2-dimethyl-dioxolan-4-yl | F | CN | H | H | H | |
| 1-865 | 2,2-dimethyl-dioxolan-4-yl | F | CN | H | H | Me | |
| 1-866 | 2,2-dimethyl-dioxolan-4-yl | F | CF₃ | H | H | H | |
| 1-867 | 2,2-dimethyl-dioxolan-4-yl | F | CF₃ | H | H | Me | |
| 1-868 | 2,2-dimethyl-dioxolan-4-yl | H | Cl | H | Me | H | |

TABLE 1-continued

Hetarylpyridines:

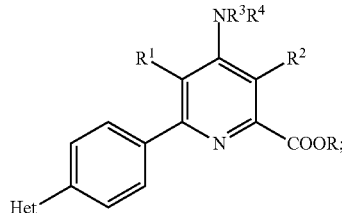

(I-vii)

| No. | Het | R¹ | R² | R³ | R⁴ | R | Physical data: $^1$H NMR: δ [CDCl$_3$] |
|---|---|---|---|---|---|---|---|
| 1-869 | 2,2-dimethyl-dioxolan-4-yl | H | Cl | H | Me | Me | |
| 1-870 | 2,2-dimethyl-dioxolan-4-yl | H | Cl | H | Me | Et | |
| 1-871 | 2,2-dimethyl-dioxolan-4-yl | H | Br | H | Me | H | |
| 1-872 | 2,2-dimethyl-dioxolan-4-yl | H | Br | H | Me | Me | |
| 1-873 | 2,2-dimethyl-dioxolan-4-yl | H | Br | H | Me | Et | |
| 1-874 | 2,2-dimethyl-dioxolan-4-yl | H | F | H | Me | H | |
| 1-875 | 2,2-dimethyl-dioxolan-4-yl | H | F | H | Me | Me | |
| 1-876 | 2,2-dimethyl-dioxolan-4-yl | H | I | H | Me | H | |
| 1-877 | 2,2-dimethyl-dioxolan-4-yl | H | I | H | Me | Me | |
| 1-878 | 2,2-dimethyl-dioxolan-4-yl | H | CN | H | Me | H | |
| 1-879 | 2,2-dimethyl-dioxolan-4-yl | H | CN | H | Me | Me | |
| 1-880 | 2,2-dimethyl-dioxolan-4-yl | H | CF$_3$ | H | Me | H | |
| 1-881 | 2,2-dimethyl-dioxolan-4-yl | H | CF$_3$ | H | Me | Me | |
| 1-882 | 2,2-dimethyl-dioxolan-4-yl | F | Cl | H | Me | H | |
| 1-883 | 2,2-dimethyl-dioxolan-4-yl | F | Cl | H | Me | Me | |
| 1-884 | 2,2-dimethyl-dioxolan-4-yl | F | Cl | H | Me | Et | |
| 1-885 | 2,2-dimethyl-dioxolan-4-yl | F | Br | H | Me | H | |
| 1-886 | 2,2-dimethyl-dioxolan-4-yl | F | Br | H | Me | Me | |
| 1-887 | 2,2-dimethyl-dioxolan-4-yl | F | Br | H | Me | Et | |
| 1-888 | 2,2-dimethyl-dioxolan-4-yl | F | F | H | Me | H | |
| 1-889 | 2,2-dimethyl-dioxolan-4-yl | F | F | H | Me | Me | |
| 1-890 | 2,2-dimethyl-dioxolan-4-yl | F | I | H | Me | H | |
| 1-891 | 2,2-dimethyl-dioxolan-4-yl | F | I | H | Me | Me | |
| 1-892 | 2,2-dimethyl-dioxolan-4-yl | F | CN | H | Me | H | |
| 1-893 | 2,2-dimethyl-dioxolan-4-yl | F | CN | H | Me | Me | |
| 1-894 | 2,2-dimethyl-dioxolan-4-yl | F | CF$_3$ | H | Me | H | |
| 1-895 | 2,2-dimethyl-dioxolan-4-yl | F | CF$_3$ | H | Me | Me | |
| 1-896 | 2,2-dimethyl-dioxolan-4-yl | H | Cl | Me | Me | H | |
| 1-897 | 2,2-dimethyl-dioxolan-4-yl | H | Cl | Me | Me | Me | |
| 1-898 | 2,2-dimethyl-dioxolan-4-yl | H | Cl | Me | Me | Et | |
| 1-899 | 2,2-dimethyl-dioxolan-4-yl | H | Br | Me | Me | H | |
| 1-900 | 2,2-dimethyl-dioxolan-4-yl | H | Br | Me | Me | Me | |
| 1-901 | 2,2-dimethyl-dioxolan-4-yl | H | Br | Me | Me | Et | |
| 1-902 | 2,2-dimethyl-dioxolan-4-yl | H | F | Me | Me | H | |
| 1-903 | 2,2-dimethyl-dioxolan-4-yl | H | F | Me | Me | Me | |
| 1-904 | 2,2-dimethyl-dioxolan-4-yl | H | I | Me | Me | H | |
| 1-905 | 2,2-dimethyl-dioxolan-4-yl | H | I | Me | Me | Me | |
| 1-906 | 2,2-dimethyl-dioxolan-4-yl | H | CN | Me | Me | H | |
| 1-907 | 2,2-dimethyl-dioxolan-4-yl | H | CN | Me | Me | Me | |
| 1-908 | 2,2-dimethyl-dioxolan-4-yl | H | CF$_3$ | Me | Me | H | |
| 1-909 | 2,2-dimethyl-dioxolan-4-yl | H | CF$_3$ | Me | Me | Me | |
| 1-910 | 2,2-dimethyl-dioxolan-4-yl | F | Cl | Me | Me | H | |
| 1-911 | 2,2-dimethyl-dioxolan-4-yl | F | Cl | Me | Me | Me | |
| 1-912 | 2,2-dimethyl-dioxolan-4-yl | F | Cl | Me | Me | Et | |
| 1-913 | 2,2-dimethyl-dioxolan-4-yl | F | Br | Me | Me | H | |
| 1-914 | 2,2-dimethyl-dioxolan-4-yl | F | Br | Me | Me | Me | |
| 1-915 | 2,2-dimethyl-dioxolan-4-yl | F | Br | Me | Me | Et | |
| 1-916 | 2,2-dimethyl-dioxolan-4-yl | F | F | Me | Me | H | |
| 1-917 | 2,2-dimethyl-dioxolan-4-yl | F | F | Me | Me | Me | |
| 1-918 | 2,2-dimethyl-dioxolan-4-yl | F | I | Me | Me | H | |
| 1-919 | 2,2-dimethyl-dioxolan-4-yl | F | I | Me | Me | Me | |
| 1-920 | 2,2-dimethyl-dioxolan-4-yl | F | CN | Me | Me | H | |
| 1-921 | 2,2-dimethyl-dioxolan-4-yl | F | CN | Me | Me | Me | |
| 1-922 | 2,2-dimethyl-dioxolan-4-yl | F | CF$_3$ | Me | Me | H | |
| 1-923 | 2,2-dimethyl-dioxolan-4-yl | F | CF$_3$ | Me | Me | Me | |
| 1-924 | 2,2-dimethyl-dioxolan-4-yl | H | Cl | =CHNMe$_2$ | | H | |
| 1-925 | 2,2-dimethyl-dioxolan-4-yl | H | Cl | =CHNMe$_2$ | | Me | |
| 1-926 | 2,2-dimethyl-dioxolan-4-yl | H | Cl | =CHNMe$_2$ | | Et | |
| 1-927 | 2,2-dimethyl-dioxolan-4-yl | H | Br | =CHNMe$_2$ | | H | |
| 1-928 | 2,2-dimethyl-dioxolan-4-yl | H | Br | =CHNMe$_2$ | | Me | |
| 1-929 | 2,2-dimethyl-dioxolan-4-yl | H | Br | =CHNMe$_2$ | | Et | |
| 1-930 | 2,2-dimethyl-dioxolan-4-yl | H | F | =CHNMe$_2$ | | H | |
| 1-931 | 2,2-dimethyl-dioxolan-4-yl | H | F | =CHNMe$_2$ | | Me | |

TABLE 1-continued

Hetarylpyridines:

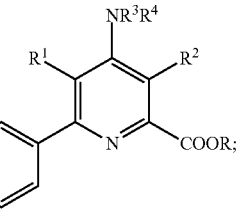

(I-vii)

| No. | Het | R$^1$ | R$^2$ | R$^3$ | R$^4$ | R | Physical data: $^1$H NMR: δ [CDCl$_3$] |
|---|---|---|---|---|---|---|---|
| 1-932 | 2,2-dimethyl-dioxolan-4-yl | H | I | =CHNMe$_2$ | H | | |
| 1-933 | 2,2-dimethyl-dioxolan-4-yl | H | I | =CHNMe$_2$ | Me | | |
| 1-934 | 2,2-dimethyl-dioxolan-4-yl | H | CN | =CHNMe$_2$ | H | | |
| 1-935 | 2,2-dimethyl-dioxolan-4-yl | H | CN | =CHNMe$_2$ | Me | | |
| 1-936 | 2,2-dimethyl-dioxolan-4-yl | H | CF$_3$ | =CHNMe$_2$ | H | | |
| 1-937 | 2,2-dimethyl-dioxolan-4-yl | H | CF$_3$ | =CHNMe$_2$ | Me | | |
| 1-938 | 2,2-dimethyl-dioxolan-4-yl | F | Cl | =CHNMe$_2$ | H | | |
| 1-939 | 2,2-dimethyl-dioxolan-4-yl | F | Cl | =CHNMe$_2$ | Me | | |
| 1-940 | 2,2-dimethyl-dioxolan-4-yl | F | Cl | =CHNMe$_2$ | Et | | |
| 1-941 | 2,2-dimethyl-dioxolan-4-yl | F | Br | =CHNMe$_2$ | H | | |
| 1-942 | 2,2-dimethyl-dioxolan-4-yl | F | Br | =CHNMe$_2$ | Me | | |
| 1-943 | 2,2-dimethyl-dioxolan-4-yl | F | Br | =CHNMe$_2$ | Et | | |
| 1-944 | 2,2-dimethyl-dioxolan-4-yl | F | F | =CHNMe$_2$ | H | | |
| 1-945 | 2,2-dimethyl-dioxolan-4-yl | F | F | =CHNMe$_2$ | Me | | |
| 1-946 | 2,2-dimethyl-dioxolan-4-yl | F | I | =CHNMe$_2$ | H | | |
| 1-947 | 2,2-dimethyl-dioxolan-4-yl | F | I | =CHNMe$_2$ | Me | | |
| 1-948 | 2,2-dimethyl-dioxolan-4-yl | F | CN | =CHNMe$_2$ | H | | |
| 1-949 | 2,2-dimethyl-dioxolan-4-yl | F | CN | =CHNMe$_2$ | Me | | |
| 1-950 | 2,2-dimethyl-dioxolan-4-yl | F | CF$_3$ | =CHNMe$_2$ | H | | |
| 1-951 | 2,2-dimethyl-dioxolan-4-yl | F | CF$_3$ | =CHNMe$_2$ | Me | | |

TABLE 2

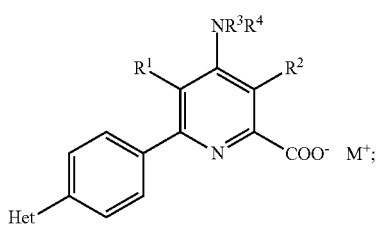

(I-viii)

| No. | Het | R$^1$ | R$^2$ | R$^3$ | R$^4$ | M$^+$ | Physical data: $^1$H NMR: δ [CDCl$_3$] |
|---|---|---|---|---|---|---|---|
| 2-1 | 3-tert-butyl-1,2,4-oxadiazol-5-yl | H | Cl | H | H | Na$^+$ | |
| 2-2 | 3-tert-butyl-1,2,4-oxadiazol-5-yl | H | Cl | H | H | K$^+$ | |
| 2-3 | 3-tert-butyl-1,2,4-oxadiazol-5-yl | H | Cl | H | H | NH$_4^+$ | |
| 2-4 | 3-tert-butyl-1,2,4-oxadiazol-5-yl | H | Br | H | H | Na$^+$ | |
| 2-5 | 3-tert-butyl-1,2,4-oxadiazol-5-yl | H | Br | H | H | K$^+$ | |
| 2-6 | 3-tert-butyl-1,2,4-oxadiazol-5-yl | H | Br | H | H | NH$_4^+$ | |
| 2-7 | 3-tert-butyl-1,2,4-oxadiazol-5-yl | H | F | H | H | Na$^+$ | |
| 2-8 | 3-tert-butyl-1,2,4-oxadiazol-5-yl | H | F | H | H | K$^+$ | |
| 2-9 | 3-tert-butyl-1,2,4-oxadiazol-5-yl | H | I | H | H | Na$^+$ | |
| 2-10 | 3-tert-butyl-1,2,4-oxadiazol-5-yl | H | I | H | H | K$^+$ | |
| 2-11 | 3-tert-butyl-1,2,4-oxadiazol-5-yl | H | CN | H | H | Na$^+$ | |
| 2-12 | 3-tert-butyl-1,2,4-oxadiazol-5-yl | H | CN | H | H | K$^+$ | |
| 2-13 | 3-tert-butyl-1,2,4-oxadiazol-5-yl | H | CF$_3$ | H | H | Na$^+$ | |
| 2-14 | 3-tert-butyl-1,2,4-oxadiazol-5-yl | H | CF$_3$ | H | H | K$^+$ | |
| 2-15 | 3-tert-butyl-1,2,4-oxadiazol-5-yl | F | Cl | H | H | Na$^+$ | |
| 2-16 | 3-tert-butyl-1,2,4-oxadiazol-5-yl | F | Cl | H | H | K$^+$ | |
| 2-17 | 3-tert-butyl-1,2,4-oxadiazol-5-yl | F | Cl | H | H | NH$_4^+$ | |
| 2-18 | 3-tert-butyl-1,2,4-oxadiazol-5-yl | F | Br | H | H | Na$^+$ | |
| 2-19 | 3-tert-butyl-1,2,4-oxadiazol-5-yl | F | Br | H | H | K$^+$ | |
| 2-20 | 3-tert-butyl-1,2,4-oxadiazol-5-yl | F | Br | H | H | NH$_4^+$ | |
| 2-21 | 3-tert-butyl-1,2,4-oxadiazol-5-yl | F | F | H | H | Na$^+$ | |
| 2-22 | 3-tert-butyl-1,2,4-oxadiazol-5-yl | F | F | H | H | K$^+$ | |

TABLE 2-continued

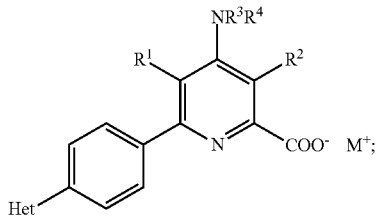

(I-viii)

| No. | Het | R¹ | R² | R³ | R⁴ | M⁺ | Physical data: ¹H NMR: δ [CDCl₃] |
|---|---|---|---|---|---|---|---|
| 2-23 | 3-tert-butyl-1,2,4-oxadiazol-5-yl | F | I | H | H | Na⁺ | |
| 2-24 | 3-tert-butyl-1,2,4-oxadiazol-5-yl | F | I | H | H | K⁺ | |
| 2-25 | 3-tert-butyl-1,2,4-oxadiazol-5-yl | F | CN | H | H | Na⁺ | |
| 2-26 | 3-tert-butyl-1,2,4-oxadiazol-5-yl | F | CN | H | H | K⁺ | |
| 2-27 | 3-tert-butyl-1,2,4-oxadiazol-5-yl | F | CF₃ | H | H | Na⁺ | |
| 2-28 | 3-tert-butyl-1,2,4-oxadiazol-5-yl | F | CF₃ | H | H | K⁺ | |
| 2-29 | 3-tert-butyl-1,2,4-oxadiazol-5-yl | Cl | Cl | H | H | Na⁺ | |
| 2-30 | 3-tert-butyl-1,2,4-oxadiazol-5-yl | Cl | Cl | H | H | K⁺ | |
| 2-31 | 3-tert-butyl-1,2,4-oxadiazol-5-yl | Cl | Cl | H | H | NH₄⁺ | |
| 2-32 | 3-tert-butyl-1,2,4-oxadiazol-5-yl | Cl | Br | H | H | Na⁺ | |
| 2-33 | 3-tert-butyl-1,2,4-oxadiazol-5-yl | Cl | Br | H | H | K⁺ | |
| 2-34 | 3-tert-butyl-1,2,4-oxadiazol-5-yl | Cl | Br | H | H | NH₄⁺ | |
| 2-35 | 3-tert-butyl-1,2,4-oxadiazol-5-yl | Cl | F | H | H | Na⁺ | |
| 2-36 | 3-tert-butyl-1,2,4-oxadiazol-5-yl | Cl | F | H | H | K⁺ | |
| 2-37 | 3-tert-butyl-1,2,4-oxadiazol-5-yl | Cl | I | H | H | Na⁺ | |
| 2-38 | 3-tert-butyl-1,2,4-oxadiazol-5-yl | Cl | I | H | H | K⁺ | |
| 2-39 | 3-tert-butyl-1,2,4-oxadiazol-5-yl | Cl | CN | H | H | Na⁺ | |
| 2-40 | 3-tert-butyl-1,2,4-oxadiazol-5-yl | Cl | CN | H | H | K⁺ | |
| 2-41 | 3-tert-butyl-1,2,4-oxadiazol-5-yl | Cl | CF₃ | H | H | Na⁺ | |
| 2-42 | 3-tert-butyl-1,2,4-oxadiazol-5-yl | Cl | CF₃ | H | H | K⁺ | |
| 2-43 | 3-tert-butyl-1,2,4-oxadiazol-5-yl | H | Cl | H | Me | Na⁺ | |
| 2-44 | 3-tert-butyl-1,2,4-oxadiazol-5-yl | H | Cl | H | Me | K⁺ | |
| 2-45 | 3-tert-butyl-1,2,4-oxadiazol-5-yl | H | Cl | H | Me | NH₄⁺ | |
| 2-46 | 3-tert-butyl-1,2,4-oxadiazol-5-yl | H | Br | H | Me | Na⁺ | |
| 2-47 | 3-tert-butyl-1,2,4-oxadiazol-5-yl | H | Br | H | Me | K⁺ | |
| 2-48 | 3-tert-butyl-1,2,4-oxadiazol-5-yl | H | Br | H | Me | NH₄⁺ | |
| 2-49 | 3-tert-butyl-1,2,4-oxadiazol-5-yl | H | F | H | Me | Na⁺ | |
| 2-50 | 3-tert-butyl-1,2,4-oxadiazol-5-yl | H | F | H | Me | K⁺ | |
| 2-51 | 3-tert-butyl-1,2,4-oxadiazol-5-yl | H | I | H | Me | Na⁺ | |
| 2-52 | 3-tert-butyl-1,2,4-oxadiazol-5-yl | H | I | H | Me | K⁺ | |
| 2-53 | 3-tert-butyl-1,2,4-oxadiazol-5-yl | H | CN | H | Me | Na⁺ | |
| 2-54 | 3-tert-butyl-1,2,4-oxadiazol-5-yl | H | CN | H | Me | K⁺ | |
| 2-55 | 3-tert-butyl-1,2,4-oxadiazol-5-yl | H | CF₃ | H | Me | Na⁺ | |
| 2-56 | 3-tert-butyl-1,2,4-oxadiazol-5-yl | H | CF₃ | H | Me | K⁺ | |
| 2-57 | 3-tert-butyl-1,2,4-oxadiazol-5-yl | F | Cl | H | Me | Na⁺ | |
| 2-58 | 3-tert-butyl-1,2,4-oxadiazol-5-yl | F | Cl | H | Me | K⁺ | |
| 2-59 | 3-tert-butyl-1,2,4-oxadiazol-5-yl | F | Cl | H | Me | NH₄⁺ | |
| 2-60 | 3-tert-butyl-1,2,4-oxadiazol-5-yl | F | Br | H | Me | Na⁺ | |
| 2-61 | 3-tert-butyl-1,2,4-oxadiazol-5-yl | F | Br | H | Me | K⁺ | |
| 2-62 | 3-tert-butyl-1,2,4-oxadiazol-5-yl | F | Br | H | Me | NH₄⁺ | |
| 2-63 | 3-tert-butyl-1,2,4-oxadiazol-5-yl | F | F | H | Me | Na⁺ | |
| 2-64 | 3-tert-butyl-1,2,4-oxadiazol-5-yl | F | F | H | Me | K⁺ | |
| 2-65 | 3-tert-butyl-1,2,4-oxadiazol-5-yl | F | I | H | Me | Na⁺ | |
| 2-66 | 3-tert-butyl-1,2,4-oxadiazol-5-yl | F | I | H | Me | K⁺ | |
| 2-67 | 3-tert-butyl-1,2,4-oxadiazol-5-yl | F | CN | H | Me | Na⁺ | |
| 2-68 | 3-tert-butyl-1,2,4-oxadiazol-5-yl | F | CN | H | Me | K⁺ | |
| 2-69 | 3-tert-butyl-1,2,4-oxadiazol-5-yl | F | CF₃ | H | Me | Na⁺ | |
| 2-70 | 3-tert-butyl-1,2,4-oxadiazol-5-yl | F | CF₃ | H | Me | K⁺ | |
| 2-71 | 3-tert-butyl-1,2,4-oxadiazol-5-yl | Cl | Cl | H | Me | Na⁺ | |
| 2-72 | 3-tert-butyl-1,2,4-oxadiazol-5-yl | Cl | Cl | H | Me | K⁺ | |
| 2-73 | 3-tert-butyl-1,2,4-oxadiazol-5-yl | Cl | Cl | H | Me | NH₄⁺ | |
| 2-74 | 3-tert-butyl-1,2,4-oxadiazol-5-yl | Cl | Br | H | Me | Na⁺ | |
| 2-75 | 3-tert-butyl-1,2,4-oxadiazol-5-yl | Cl | Br | H | Me | K⁺ | |
| 2-76 | 3-tert-butyl-1,2,4-oxadiazol-5-yl | Cl | Br | H | Me | NH₄⁺ | |
| 2-77 | 3-tert-butyl-1,2,4-oxadiazol-5-yl | Cl | F | H | Me | Na⁺ | |
| 2-78 | 3-tert-butyl-1,2,4-oxadiazol-5-yl | Cl | F | H | Me | K⁺ | |
| 2-79 | 3-tert-butyl-1,2,4-oxadiazol-5-yl | Cl | I | H | Me | Na⁺ | |
| 2-80 | 3-tert-butyl-1,2,4-oxadiazol-5-yl | Cl | I | H | Me | K⁺ | |
| 2-81 | 3-tert-butyl-1,2,4-oxadiazol-5-yl | Cl | CN | H | Me | Na⁺ | |
| 2-82 | 3-tert-butyl-1,2,4-oxadiazol-5-yl | Cl | CN | H | Me | K⁺ | |
| 2-83 | 3-tert-butyl-1,2,4-oxadiazol-5-yl | Cl | CF₃ | H | Me | Na⁺ | |
| 2-84 | 3-tert-butyl-1,2,4-oxadiazol-5-yl | Cl | CF₃ | H | Me | K⁺ | |
| 2-85 | 3-tert-butyl-1,2,4-oxadiazol-5-yl | H | Cl | Me | Me | Na⁺ | |
| 2-86 | 3-tert-butyl-1,2,4-oxadiazol-5-yl | H | Cl | Me | Me | K⁺ | |

TABLE 2-continued

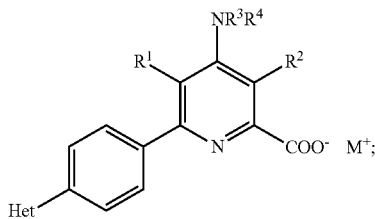

(I-viii)

| No. | Het | R¹ | R² | R³ | R⁴ | M⁺ | Physical data: $^1$H NMR: δ [CDCl$_3$] |
|---|---|---|---|---|---|---|---|
| 2-87 | 3-tert-butyl-1,2,4-oxadiazol-5-yl | H | Cl | Me | Me | NH$_4^+$ | |
| 2-88 | 3-tert-butyl-1,2,4-oxadiazol-5-yl | H | Br | Me | Me | Na$^+$ | |
| 2-89 | 3-tert-butyl-1,2,4-oxadiazol-5-yl | H | Br | Me | Me | K$^+$ | |
| 2-90 | 3-tert-butyl-1,2,4-oxadiazol-5-yl | H | Br | Me | Me | NH$_4^+$ | |
| 2-91 | 3-tert-butyl-1,2,4-oxadiazol-5-yl | H | F | Me | Me | Na$^+$ | |
| 2-92 | 3-tert-butyl-1,2,4-oxadiazol-5-yl | H | F | Me | Me | K$^+$ | |
| 2-93 | 3-tert-butyl-1,2,4-oxadiazol-5-yl | H | I | Me | Me | Na$^+$ | |
| 2-94 | 3-tert-butyl-1,2,4-oxadiazol-5-yl | H | I | Me | Me | K$^+$ | |
| 2-95 | 3-tert-butyl-1,2,4-oxadiazol-5-yl | H | CN | Me | Me | Na$^+$ | |
| 2-96 | 3-tert-butyl-1,2,4-oxadiazol-5-yl | H | CN | Me | Me | K$^+$ | |
| 2-97 | 3-tert-butyl-1,2,4-oxadiazol-5-yl | H | CF$_3$ | Me | Me | Na$^+$ | |
| 2-98 | 3-tert-butyl-1,2,4-oxadiazol-5-yl | H | CF$_3$ | Me | Me | K$^+$ | |
| 2-99 | 3-tert-butyl-1,2,4-oxadiazol-5-yl | F | Cl | Me | Me | Na$^+$ | |
| 2-100 | 3-tert-butyl-1,2,4-oxadiazol-5-yl | F | Cl | Me | Me | K$^+$ | |
| 2-101 | 3-tert-butyl-1,2,4-oxadiazol-5-yl | F | Cl | Me | Me | NH$_4^+$ | |
| 2-102 | 3-tert-butyl-1,2,4-oxadiazol-5-yl | F | Br | Me | Me | Na$^+$ | |
| 2-103 | 3-tert-butyl-1,2,4-oxadiazol-5-yl | F | Br | Me | Me | K$^+$ | |
| 2-104 | 3-tert-butyl-1,2,4-oxadiazol-5-yl | F | Br | Me | Me | NH$_4^+$ | |
| 2-105 | 3-tert-butyl-1,2,4-oxadiazol-5-yl | F | F | Me | Me | Na$^+$ | |
| 2-106 | 3-tert-butyl-1,2,4-oxadiazol-5-yl | F | F | Me | Me | K$^+$ | |
| 2-107 | 3-tert-butyl-1,2,4-oxadiazol-5-yl | F | I | Me | Me | Na$^+$ | |
| 2-108 | 3-tert-butyl-1,2,4-oxadiazol-5-yl | F | I | Me | Me | K$^+$ | |
| 2-109 | 3-tert-butyl-1,2,4-oxadiazol-5-yl | F | CN | Me | Me | Na$^+$ | |
| 2-110 | 3-tert-butyl-1,2,4-oxadiazol-5-yl | F | CN | Me | Me | K$^+$ | |
| 2-111 | 3-tert-butyl-1,2,4-oxadiazol-5-yl | F | CF$_3$ | Me | Me | Na$^+$ | |
| 2-112 | 3-tert-butyl-1,2,4-oxadiazol-5-yl | F | CF$_3$ | Me | Me | K$^+$ | |
| 2-113 | 3-tert-butyl-1,2,4-oxadiazol-5-yl | Cl | Cl | Me | Me | Na$^+$ | |
| 2-114 | 3-tert-butyl-1,2,4-oxadiazol-5-yl | Cl | Cl | Me | Me | K$^+$ | |
| 2-115 | 3-tert-butyl-1,2,4-oxadiazol-5-yl | Cl | Cl | Me | Me | NH$_4^+$ | |
| 2-116 | 3-tert-butyl-1,2,4-oxadiazol-5-yl | Cl | Br | Me | Me | Na$^+$ | |
| 2-117 | 3-tert-butyl-1,2,4-oxadiazol-5-yl | Cl | Br | Me | Me | K$^+$ | |
| 2-118 | 3-tert-butyl-1,2,4-oxadiazol-5-yl | Cl | Br | Me | Me | NH$_4^+$ | |
| 2-119 | 3-tert-butyl-1,2,4-oxadiazol-5-yl | Cl | F | Me | Me | Na$^+$ | |
| 2-120 | 3-tert-butyl-1,2,4-oxadiazol-5-yl | Cl | F | Me | Me | K$^+$ | |
| 2-121 | 3-tert-butyl-1,2,4-oxadiazol-5-yl | Cl | I | Me | Me | Na$^+$ | |
| 2-122 | 3-tert-butyl-1,2,4-oxadiazol-5-yl | Cl | I | Me | Me | K$^+$ | |
| 2-123 | 3-tert-butyl-1,2,4-oxadiazol-5-yl | Cl | CN | Me | Me | Na$^+$ | |
| 2-124 | 3-tert-butyl-1,2,4-oxadiazol-5-yl | Cl | CN | Me | Me | K$^+$ | |
| 2-125 | 3-tert-butyl-1,2,4-oxadiazol-5-yl | Cl | CF$_3$ | Me | Me | Na$^+$ | |
| 2-126 | 3-tert-butyl-1,2,4-oxadiazol-5-yl | Cl | CF$_3$ | Me | Me | K$^+$ | |
| 2-127 | 3-tert-butyl-1,2,4-oxadiazol-5-yl | H | Cl | =CHNMe$_2$ | | Na$^+$ | |
| 2-128 | 3-tert-butyl-1,2,4-oxadiazol-5-yl | H | Cl | =CHNMe$_2$ | | K$^+$ | |
| 2-129 | 3-tert-butyl-1,2,4-oxadiazol-5-yl | H | Cl | =CHNMe$_2$ | | NH$_4^+$ | |
| 2-130 | 3-tert-butyl-1,2,4-oxadiazol-5-yl | H | Br | =CHNMe$_2$ | | Na$^+$ | |
| 2-131 | 3-tert-butyl-1,2,4-oxadiazol-5-yl | H | Br | =CHNMe$_2$ | | K$^+$ | |
| 2-132 | 3-tert-butyl-1,2,4-oxadiazol-5-yl | H | Br | =CHNMe$_2$ | | NH$_4^+$ | |
| 2-133 | 3-tert-butyl-1,2,4-oxadiazol-5-yl | H | F | =CHNMe$_2$ | | Na$^+$ | |
| 2-134 | 3-tert-butyl-1,2,4-oxadiazol-5-yl | H | F | =CHNMe$_2$ | | K$^+$ | |
| 2-135 | 3-tert-butyl-1,2,4-oxadiazol-5-yl | H | I | =CHNMe$_2$ | | Na$^+$ | |
| 2-136 | 3-tert-butyl-1,2,4-oxadiazol-5-yl | H | I | =CHNMe$_2$ | | K$^+$ | |
| 2-137 | 3-tert-butyl-1,2,4-oxadiazol-5-yl | H | CN | =CHNMe$_2$ | | Na$^+$ | |
| 2-138 | 3-tert-butyl-1,2,4-oxadiazol-5-yl | H | CN | =CHNMe$_2$ | | K$^+$ | |
| 2-139 | 3-tert-butyl-1,2,4-oxadiazol-5-yl | H | CF$_3$ | =CHNMe$_2$ | | Na$^+$ | |
| 2-140 | 3-tert-butyl-1,2,4-oxadiazol-5-yl | H | CF$_3$ | =CHNMe$_2$ | | K$^+$ | |
| 2-141 | 3-tert-butyl-1,2,4-oxadiazol-5-yl | F | Cl | =CHNMe$_2$ | | Na$^+$ | |
| 2-142 | 3-tert-butyl-1,2,4-oxadiazol-5-yl | F | Cl | =CHNMe$_2$ | | K$^+$ | |
| 2-143 | 3-tert-butyl-1,2,4-oxadiazol-5-yl | F | Cl | =CHNMe$_2$ | | NH$_4^+$ | |
| 2-144 | 3-tert-butyl-1,2,4-oxadiazol-5-yl | F | Br | =CHNMe$_2$ | | Na$^+$ | |
| 2-145 | 3-tert-butyl-1,2,4-oxadiazol-5-yl | F | Br | =CHNMe$_2$ | | K$^+$ | |
| 2-146 | 3-tert-butyl-1,2,4-oxadiazol-5-yl | F | Br | =CHNMe$_2$ | | NH$_4^+$ | |
| 2-147 | 3-tert-butyl-1,2,4-oxadiazol-5-yl | F | F | =CHNMe$_2$ | | Na$^+$ | |
| 2-148 | 3-tert-butyl-1,2,4-oxadiazol-5-yl | F | F | =CHNMe$_2$ | | K$^+$ | |
| 2-149 | 3-tert-butyl-1,2,4-oxadiazol-5-yl | F | I | =CHNMe$_2$ | | Na$^+$ | |
| 2-150 | 3-tert-butyl-1,2,4-oxadiazol-5-yl | F | I | =CHNMe$_2$ | | K$^+$ | |

TABLE 2-continued

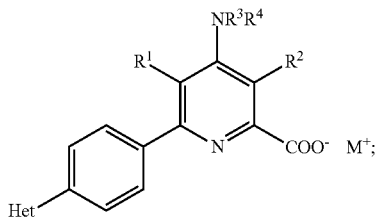

(I-viii)

| No. | Het | $R^1$ | $R^2$ | $R^3$ | $R^4$ | $M^+$ | Physical data: $^1$H NMR: δ [CDCl$_3$] |
|---|---|---|---|---|---|---|---|
| 2-151 | 3-tert-butyl-1,2,4-oxadiazol-5-yl | F | CN | =CHNMe$_2$ | | Na$^+$ | |
| 2-152 | 3-tert-butyl-1,2,4-oxadiazol-5-yl | F | CN | =CHNMe$_2$ | | K$^+$ | |
| 2-153 | 3-tert-butyl-1,2,4-oxadiazol-5-yl | F | CF$_3$ | =CHNMe$_2$ | | Na$^+$ | |
| 2-154 | 3-tert-butyl-1,2,4-oxadiazol-5-yl | F | CF$_3$ | =CHNMe$_2$ | | K$^+$ | |
| 2-155 | 3-tert-butyl-1,2,4-oxadiazol-5-yl | Cl | Cl | =CHNMe$_2$ | | Na$^+$ | |
| 2-156 | 3-tert-butyl-1,2,4-oxadiazol-5-yl | Cl | Cl | =CHNMe$_2$ | | K$^+$ | |
| 2-157 | 3-tert-butyl-1,2,4-oxadiazol-5-yl | Cl | Cl | =CHNMe$_2$ | | NH$_4^+$ | |
| 2-158 | 3-tert-butyl-1,2,4-oxadiazol-5-yl | Cl | Br | =CHNMe$_2$ | | Na$^+$ | |
| 2-159 | 3-tert-butyl-1,2,4-oxadiazol-5-yl | Cl | Br | =CHNMe$_2$ | | K$^+$ | |
| 2-160 | 3-tert-butyl-1,2,4-oxadiazol-5-yl | Cl | Br | =CHNMe$_2$ | | NH$_4^+$ | |
| 2-161 | 3-tert-butyl-1,2,4-oxadiazol-5-yl | Cl | F | =CHNMe$_2$ | | Na$^+$ | |
| 2-162 | 3-tert-butyl-1,2,4-oxadiazol-5-yl | Cl | F | =CHNMe$_2$ | | K$^+$ | |
| 2-163 | 3-tert-butyl-1,2,4-oxadiazol-5-yl | Cl | I | =CHNMe$_2$ | | Na$^+$ | |
| 2-164 | 3-tert-butyl-1,2,4-oxadiazol-5-yl | Cl | I | =CHNMe$_2$ | | K$^+$ | |
| 2-165 | 3-tert-butyl-1,2,4-oxadiazol-5-yl | Cl | CN | =CHNMe$_2$ | | Na$^+$ | |
| 2-166 | 3-tert-butyl-1,2,4-oxadiazol-5-yl | Cl | CN | =CHNMe$_2$ | | K$^+$ | |
| 2-167 | 3-tert-butyl-1,2,4-oxadiazol-5-yl | Cl | CF$_3$ | =CHNMe$_2$ | | Na$^+$ | |
| 2-168 | 3-tert-butyl-1,2,4-oxadiazol-5-yl | Cl | CF$_3$ | =CHNMe$_2$ | | K$^+$ | |
| 2-169 | thien-2-yl | H | Cl | H | H | Na$^+$ | |
| 2-170 | thien-2-yl | H | Cl | H | H | K$^+$ | |
| 2-171 | thien-2-yl | H | Cl | H | H | NH$_4^+$ | |
| 2-172 | thien-2-yl | H | Br | H | H | Na$^+$ | |
| 2-173 | thien-2-yl | H | Br | H | H | K$^+$ | |
| 2-174 | thien-2-yl | H | Br | H | H | NH$_4^+$ | |
| 2-175 | thien-2-yl | H | F | H | H | Na$^+$ | |
| 2-176 | thien-2-yl | H | F | H | H | K$^+$ | |
| 2-177 | thien-2-yl | H | I | H | H | Na$^+$ | |
| 2-178 | thien-2-yl | H | I | H | H | K$^+$ | |
| 2-179 | thien-2-yl | H | CN | H | H | Na$^+$ | |
| 2-180 | thien-2-yl | H | CN | H | H | K$^+$ | |
| 2-181 | thien-2-yl | H | CF$_3$ | H | H | Na$^+$ | |
| 2-182 | thien-2-yl | H | CF$_3$ | H | H | K$^+$ | |
| 2-183 | thien-2-yl | F | Cl | H | H | Na$^+$ | |
| 2-184 | thien-2-yl | F | Cl | H | H | K$^+$ | |
| 2-185 | thien-2-yl | F | Cl | H | H | NH$_4^+$ | |
| 2-186 | thien-2-yl | F | Br | H | H | Na$^+$ | |
| 2-187 | thien-2-yl | F | Br | H | H | K$^+$ | |
| 2-188 | thien-2-yl | F | Br | H | H | NH$_4^+$ | |
| 2-189 | thien-2-yl | F | F | H | H | Na$^+$ | |
| 2-190 | thien-2-yl | F | F | H | H | K$^+$ | |
| 2-191 | thien-2-yl | F | I | H | H | Na$^+$ | |
| 2-192 | thien-2-yl | F | I | H | H | K$^+$ | |
| 2-193 | thien-2-yl | F | CN | H | H | Na$^+$ | |
| 2-194 | thien-2-yl | F | CN | H | H | K$^+$ | |
| 2-195 | thien-2-yl | F | CF$_3$ | H | H | Na$^+$ | |
| 2-196 | thien-2-yl | F | CF$_3$ | H | H | K$^+$ | |
| 2-197 | thien-2-yl | H | Cl | H | Me | Na$^+$ | |
| 2-198 | thien-2-yl | H | Cl | H | Me | K$^+$ | |
| 2-199 | thien-2-yl | H | Cl | H | Me | NH$_4^+$ | |
| 2-200 | thien-2-yl | H | Br | H | Me | Na$^+$ | |
| 2-201 | thien-2-yl | H | Br | H | Me | K$^+$ | |
| 2-202 | thien-2-yl | H | Br | H | Me | NH$_4^+$ | |
| 2-203 | thien-2-yl | H | F | H | Me | Na$^+$ | |
| 2-204 | thien-2-yl | H | F | H | Me | K$^+$ | |
| 2-205 | thien-2-yl | H | I | H | Me | Na$^+$ | |
| 2-206 | thien-2-yl | H | I | H | Me | K$^+$ | |
| 2-207 | thien-2-yl | H | CN | H | Me | Na$^+$ | |
| 2-208 | thien-2-yl | H | CN | H | Me | K$^+$ | |
| 2-209 | thien-2-yl | H | CF$_3$ | H | Me | Na$^+$ | |
| 2-210 | thien-2-yl | H | CF$_3$ | H | Me | K$^+$ | |
| 2-211 | thien-2-yl | F | Cl | H | Me | Na$^+$ | |
| 2-212 | thien-2-yl | F | Cl | H | Me | K$^+$ | |
| 2-213 | thien-2-yl | F | Cl | H | Me | NH$_4^+$ | |
| 2-214 | thien-2-yl | F | Br | H | Me | Na$^+$ | |

TABLE 2-continued

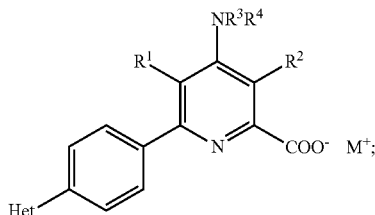

(I-viii)

| No. | Het | $R^1$ | $R^2$ | $R^3$ | $R^4$ | $M^+$ | Physical data: $^1H$ NMR: δ [CDCl$_3$] |
|---|---|---|---|---|---|---|---|
| 2-215 | thien-2-yl | F | Br | H | Me | K$^+$ | |
| 2-216 | thien-2-yl | F | Br | H | Me | NH$_4^+$ | |
| 2-217 | thien-2-yl | F | F | H | Me | Na$^+$ | |
| 2-218 | thien-2-yl | F | F | H | Me | K$^+$ | |
| 2-219 | thien-2-yl | F | I | H | Me | Na$^+$ | |
| 2-220 | thien-2-yl | F | I | H | Me | K$^+$ | |
| 2-221 | thien-2-yl | F | CN | H | Me | Na$^+$ | |
| 2-222 | thien-2-yl | F | CN | H | Me | K$^+$ | |
| 2-223 | thien-2-yl | F | CF$_3$ | H | Me | Na$^+$ | |
| 2-224 | thien-2-yl | F | CF$_3$ | H | Me | K$^+$ | |
| 2-225 | thien-2-yl | H | Cl | Me | Me | Na$^+$ | |
| 2-226 | thien-2-yl | H | Cl | Me | Me | K$^+$ | |
| 2-227 | thien-2-yl | H | Cl | Me | Me | NH$_4^+$ | |
| 2-228 | thien-2-yl | H | Br | Me | Me | Na$^+$ | |
| 2-229 | thien-2-yl | H | Br | Me | Me | K$^+$ | |
| 2-230 | thien-2-yl | H | Br | Me | Me | NH$_4^+$ | |
| 2-231 | thien-2-yl | H | F | Me | Me | Na$^+$ | |
| 2-232 | thien-2-yl | H | F | Me | Me | K$^+$ | |
| 2-233 | thien-2-yl | H | I | Me | Me | Na$^+$ | |
| 2-234 | thien-2-yl | H | I | Me | Me | K$^+$ | |
| 2-235 | thien-2-yl | H | CN | Me | Me | Na$^+$ | |
| 2-236 | thien-2-yl | H | CN | Me | Me | K$^+$ | |
| 2-237 | thien-2-yl | H | CF$_3$ | Me | Me | Na$^+$ | |
| 2-238 | thien-2-yl | H | CF$_3$ | Me | Me | K$^+$ | |
| 2-239 | thien-2-yl | F | Cl | Me | Me | Na$^+$ | |
| 2-240 | thien-2-yl | F | Cl | Me | Me | K$^+$ | |
| 2-241 | thien-2-yl | F | Cl | Me | Me | NH$_4^+$ | |
| 2-242 | thien-2-yl | F | Br | Me | Me | Na$^+$ | |
| 2-243 | thien-2-yl | F | Br | Me | Me | K$^+$ | |
| 2-244 | thien-2-yl | F | Br | Me | Me | NH$_4^+$ | |
| 2-245 | thien-2-yl | F | F | Me | Me | Na$^+$ | |
| 2-246 | thien-2-yl | F | F | Me | Me | K$^+$ | |
| 2-247 | thien-2-yl | F | I | Me | Me | Na$^+$ | |
| 2-248 | thien-2-yl | F | I | Me | Me | K$^+$ | |
| 2-249 | thien-2-yl | F | CN | Me | Me | Na$^+$ | |
| 2-250 | thien-2-yl | F | CN | Me | Me | K$^+$ | |
| 2-251 | thien-2-yl | F | CF$_3$ | Me | Me | Na$^+$ | |
| 2-252 | thien-2-yl | F | CF$_3$ | Me | Me | K$^+$ | |
| 2-253 | thien-2-yl | H | Cl | =CHNMe$_2$ | | Na$^+$ | |
| 2-254 | thien-2-yl | H | Cl | =CHNMe$_2$ | | K$^+$ | |
| 2-255 | thien-2-yl | H | Cl | =CHNMe$_2$ | | NH$_4^+$ | |
| 2-256 | thien-2-yl | H | Br | =CHNMe$_2$ | | Na$^+$ | |
| 2-257 | thien-2-yl | H | Br | =CHNMe$_2$ | | K$^+$ | |
| 2-258 | thien-2-yl | H | Br | =CHNMe$_2$ | | NH$_4^+$ | |
| 2-259 | thien-2-yl | H | F | =CHNMe$_2$ | | Na$^+$ | |
| 2-260 | thien-2-yl | H | F | =CHNMe$_2$ | | K$^+$ | |
| 2-261 | thien-2-yl | H | I | =CHNMe$_2$ | | Na$^+$ | |
| 2-262 | thien-2-yl | H | I | =CHNMe$_2$ | | K$^+$ | |
| 2-263 | thien-2-yl | H | CN | =CHNMe$_2$ | | Na$^+$ | |
| 2-264 | thien-2-yl | H | CN | =CHNMe$_2$ | | K$^+$ | |
| 2-265 | thien-2-yl | H | CF$_3$ | =CHNMe$_2$ | | Na$^+$ | |
| 2-266 | thien-2-yl | H | CF$_3$ | =CHNMe$_2$ | | K$^+$ | |
| 2-267 | thien-2-yl | F | Cl | =CHNMe$_2$ | | Na$^+$ | |
| 2-268 | thien-2-yl | F | Cl | =CHNMe$_2$ | | K$^+$ | |
| 2-269 | thien-2-yl | F | Cl | =CHNMe$_2$ | | NH$_4^+$ | |
| 2-270 | thien-2-yl | F | Br | =CHNMe$_2$ | | Na$^+$ | |
| 2-271 | thien-2-yl | F | Br | =CHNMe$_2$ | | K$^+$ | |
| 2-272 | thien-2-yl | F | Br | =CHNMe$_2$ | | NH$_4^+$ | |
| 2-273 | thien-2-yl | F | F | =CHNMe$_2$ | | Na$^+$ | |
| 2-274 | thien-2-yl | F | F | =CHNMe$_2$ | | K$^+$ | |
| 2-275 | thien-2-yl | F | I | =CHNMe$_2$ | | Na$^+$ | |
| 2-276 | thien-2-yl | F | I | =CHNMe$_2$ | | K$^+$ | |
| 2-277 | thien-2-yl | F | CN | =CHNMe$_2$ | | Na$^+$ | |
| 2-278 | thien-2-yl | F | CN | =CHNMe$_2$ | | K$^+$ | |

TABLE 2-continued

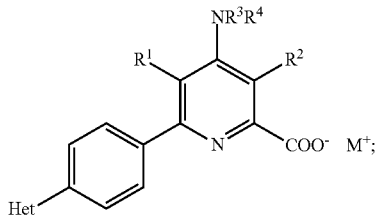

(I-viii)

| No. | Het | $R^1$ | $R^2$ | $R^3$ | $R^4$ | $M^+$ | Physical data: $^1$H NMR: δ [CDCl$_3$] |
|---|---|---|---|---|---|---|---|
| 2-279 | thien-2-yl | F | CF$_3$ | =CHNMe$_2$ | | Na$^+$ | |
| 2-280 | thien-2-yl | F | CF$_3$ | =CHNMe$_2$ | | K$^+$ | |
| 2-281 | pyrrol-1-yl | H | Cl | H | H | Na$^+$ | |
| 2-282 | pyrrol-1-yl | H | Cl | H | H | K$^+$ | |
| 2-283 | pyrrol-1-yl | H | Cl | H | H | NH$_4^+$ | |
| 2-284 | pyrrol-1-yl | H | Br | H | H | Na$^+$ | |
| 2-285 | pyrrol-1-yl | H | Br | H | H | K$^+$ | |
| 2-286 | pyrrol-1-yl | H | Br | H | H | NH$_4^+$ | |
| 2-287 | pyrrol-1-yl | H | F | H | H | Na$^+$ | |
| 2-288 | pyrrol-1-yl | H | F | H | H | K$^+$ | |
| 2-289 | pyrrol-1-yl | H | I | H | H | Na$^+$ | |
| 2-290 | pyrrol-1-yl | H | I | H | H | K$^+$ | |
| 2-291 | pyrrol-1-yl | H | CN | H | H | Na$^+$ | |
| 2-292 | pyrrol-1-yl | H | CN | H | H | K$^+$ | |
| 2-293 | pyrrol-1-yl | H | CF$_3$ | H | H | Na$^+$ | |
| 2-294 | pyrrol-1-yl | H | CF$_3$ | H | H | K$^+$ | |
| 2-295 | pyrrol-1-yl | F | Cl | H | H | Na$^+$ | |
| 2-296 | pyrrol-1-yl | F | Cl | H | H | K$^+$ | |
| 2-297 | pyrrol-1-yl | F | Cl | H | H | NH$_4^+$ | |
| 2-298 | pyrrol-1-yl | F | Br | H | H | Na$^+$ | |
| 2-299 | pyrrol-1-yl | F | Br | H | H | K$^+$ | |
| 2-300 | pyrrol-1-yl | F | Br | H | H | NH$_4^+$ | |
| 2-301 | pyrrol-1-yl | F | F | H | H | Na$^+$ | |
| 2-302 | pyrrol-1-yl | F | F | H | H | K$^+$ | |
| 2-303 | pyrrol-1-yl | F | I | H | H | Na$^+$ | |
| 2-304 | pyrrol-1-yl | F | I | H | H | K$^+$ | |
| 2-305 | pyrrol-1-yl | F | CN | H | H | Na$^+$ | |
| 2-306 | pyrrol-1-yl | F | CN | H | H | K$^+$ | |
| 2-307 | pyrrol-1-yl | F | CF$_3$ | H | H | Na$^+$ | |
| 2-308 | pyrrol-1-yl | F | CF$_3$ | H | H | K$^+$ | |
| 2-309 | pyrrol-1-yl | H | Cl | H | Me | Na$^+$ | |
| 2-310 | pyrrol-1-yl | H | Cl | H | Me | K$^+$ | |
| 2-311 | pyrrol-1-yl | H | Cl | H | Me | NH$_4^+$ | |
| 2-312 | pyrrol-1-yl | H | Br | H | Me | Na$^+$ | |
| 2-313 | pyrrol-1-yl | H | Br | H | Me | K$^+$ | |
| 2-314 | pyrrol-1-yl | H | Br | H | Me | NH$_4^+$ | |
| 2-315 | pyrrol-1-yl | H | F | H | Me | Na$^+$ | |
| 2-316 | pyrrol-1-yl | H | F | H | Me | K$^+$ | |
| 2-317 | pyrrol-1-yl | H | I | H | Me | Na$^+$ | |
| 2-318 | pyrrol-1-yl | H | I | H | Me | K$^+$ | |
| 2-319 | pyrrol-1-yl | H | CN | H | Me | Na$^+$ | |
| 2-320 | pyrrol-1-yl | H | CN | H | Me | K$^+$ | |
| 2-321 | pyrrol-1-yl | H | CF$_3$ | H | Me | Na$^+$ | |
| 2-322 | pyrrol-1-yl | H | CF$_3$ | H | Me | K$^+$ | |
| 2-323 | pyrrol-1-yl | F | Cl | H | Me | Na$^+$ | |
| 2-324 | pyrrol-1-yl | F | Cl | H | Me | K$^+$ | |
| 2-325 | pyrrol-1-yl | F | Cl | H | Me | NH$_4^+$ | |
| 2-326 | pyrrol-1-yl | F | Br | H | Me | Na$^+$ | |
| 2-327 | pyrrol-1-yl | F | Br | H | Me | K$^+$ | |
| 2-328 | pyrrol-1-yl | F | Br | H | Me | NH$_4^+$ | |
| 2-329 | pyrrol-1-yl | F | F | H | Me | Na$^+$ | |
| 2-330 | pyrrol-1-yl | F | F | H | Me | K$^+$ | |
| 2-331 | pyrrol-1-yl | F | I | H | Me | Na$^+$ | |
| 2-332 | pyrrol-1-yl | F | I | H | Me | K$^+$ | |
| 2-333 | pyrrol-1-yl | F | CN | H | Me | Na$^+$ | |
| 2-334 | pyrrol-1-yl | F | CN | H | Me | K$^+$ | |
| 2-335 | pyrrol-1-yl | F | CF$_3$ | H | Me | Na$^+$ | |
| 2-336 | pyrrol-1-yl | F | CF$_3$ | H | Me | K$^+$ | |
| 2-337 | pyrrol-1-yl | H | Cl | Me | Me | Na$^+$ | |
| 2-338 | pyrrol-1-yl | H | Cl | Me | Me | K$^+$ | |
| 2-339 | pyrrol-1-yl | H | Cl | Me | Me | NH$_4^+$ | |
| 2-340 | pyrrol-1-yl | H | Br | Me | Me | Na$^+$ | |
| 2-341 | pyrrol-1-yl | H | Br | Me | Me | K$^+$ | |
| 2-342 | pyrrol-1-yl | H | Br | Me | Me | NH$_4^+$ | |

TABLE 2-continued

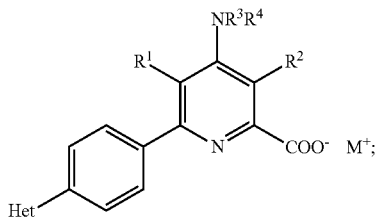

(I-viii)

| No. | Het | R¹ | R² | R³ | R⁴ | M⁺ | Physical data: $^1$H NMR: δ [CDCl$_3$] |
|---|---|---|---|---|---|---|---|
| 2-343 | pyrrol-1-yl | H | F | Me | Me | Na⁺ | |
| 2-344 | pyrrol-1-yl | H | F | Me | Me | K⁺ | |
| 2-345 | pyrrol-1-yl | H | I | Me | Me | Na⁺ | |
| 2-346 | pyrrol-1-yl | H | I | Me | Me | K⁺ | |
| 2-347 | pyrrol-1-yl | H | CN | Me | Me | Na⁺ | |
| 2-348 | pyrrol-1-yl | H | CN | Me | Me | K⁺ | |
| 2-349 | pyrrol-1-yl | H | CF$_3$ | Me | Me | Na⁺ | |
| 2-350 | pyrrol-1-yl | H | CF$_3$ | Me | Me | K⁺ | |
| 2-351 | pyrrol-1-yl | F | Cl | Me | Me | Na⁺ | |
| 2-352 | pyrrol-1-yl | F | Cl | Me | Me | K⁺ | |
| 2-353 | pyrrol-1-yl | F | Cl | Me | Me | NH$_4^+$ | |
| 2-354 | pyrrol-1-yl | F | Br | Me | Me | Na⁺ | |
| 2-355 | pyrrol-1-yl | F | Br | Me | Me | K⁺ | |
| 2-356 | pyrrol-1-yl | F | Br | Me | Me | NH$_4^+$ | |
| 2-357 | pyrrol-1-yl | F | F | Me | Me | Na⁺ | |
| 2-358 | pyrrol-1-yl | F | F | Me | Me | K⁺ | |
| 2-359 | pyrrol-1-yl | F | I | Me | Me | Na⁺ | |
| 2-360 | pyrrol-1-yl | F | I | Me | Me | K⁺ | |
| 2-361 | pyrrol-1-yl | F | CN | Me | Me | Na⁺ | |
| 2-362 | pyrrol-1-yl | F | CN | Me | Me | K⁺ | |
| 2-363 | pyrrol-1-yl | F | CF$_3$ | Me | Me | Na⁺ | |
| 2-364 | pyrrol-1-yl | F | CF$_3$ | Me | Me | K⁺ | |
| 2-365 | pyrrol-1-yl | H | Cl | =CHNMe$_2$ | | Na⁺ | |
| 2-366 | pyrrol-1-yl | H | Cl | =CHNMe$_2$ | | K⁺ | |
| 2-367 | pyrrol-1-yl | H | Cl | =CHNMe$_2$ | | NH$_4^+$ | |
| 2-368 | pyrrol-1-yl | H | Br | =CHNMe$_2$ | | Na⁺ | |
| 2-369 | pyrrol-1-yl | H | Br | =CHNMe$_2$ | | K⁺ | |
| 2-370 | pyrrol-1-yl | H | Br | =CHNMe$_2$ | | NH$_4^+$ | |
| 2-371 | pyrrol-1-yl | H | F | =CHNMe$_2$ | | Na⁺ | |
| 2-372 | pyrrol-1-yl | H | F | =CHNMe$_2$ | | K⁺ | |
| 2-373 | pyrrol-1-yl | H | I | =CHNMe$_2$ | | Na⁺ | |
| 2-374 | pyrrol-1-yl | H | I | =CHNMe$_2$ | | K⁺ | |
| 2-375 | pyrrol-1-yl | H | CN | =CHNMe$_2$ | | Na⁺ | |
| 2-376 | pyrrol-1-yl | H | CN | =CHNMe$_2$ | | K⁺ | |
| 2-377 | pyrrol-1-yl | H | CF$_3$ | =CHNMe$_2$ | | Na⁺ | |
| 2-378 | pyrrol-1-yl | H | CF$_3$ | =CHNMe$_2$ | | K⁺ | |
| 2-379 | pyrrol-1-yl | F | Cl | =CHNMe$_2$ | | Na⁺ | |
| 2-380 | pyrrol-1-yl | F | Cl | =CHNMe$_2$ | | K⁺ | |
| 2-381 | pyrrol-1-yl | F | Cl | =CHNMe$_2$ | | NH$_4^+$ | |
| 2-382 | pyrrol-1-yl | F | Br | =CHNMe$_2$ | | Na⁺ | |
| 2-383 | pyrrol-1-yl | F | Br | =CHNMe$_2$ | | K⁺ | |
| 2-384 | pyrrol-1-yl | F | Br | =CHNMe$_2$ | | NH$_4^+$ | |
| 2-385 | pyrrol-1-yl | F | F | =CHNMe$_2$ | | Na⁺ | |
| 2-386 | pyrrol-1-yl | F | F | =CHNMe$_2$ | | K⁺ | |
| 2-387 | pyrrol-1-yl | F | I | =CHNMe$_2$ | | Na⁺ | |
| 2-388 | pyrrol-1-yl | F | I | =CHNMe$_2$ | | K⁺ | |
| 2-389 | pyrrol-1-yl | F | CN | =CHNMe$_2$ | | Na⁺ | |
| 2-390 | pyrrol-1-yl | F | CN | =CHNMe$_2$ | | K⁺ | |
| 2-391 | pyrrol-1-yl | F | CF$_3$ | =CHNMe$_2$ | | Na⁺ | |
| 2-392 | pyrrol-1-yl | F | CF$_3$ | =CHNMe$_2$ | | K⁺ | |
| 2-393 | pyrazol-1-yl | H | Cl | H | H | Na⁺ | |
| 2-394 | pyrazol-1-yl | H | Cl | H | H | K⁺ | |
| 2-395 | pyrazol-1-yl | H | Cl | H | H | NH$_4^+$ | |
| 2-396 | pyrazol-1-yl | H | Br | H | H | Na⁺ | |
| 2-397 | pyrazol-1-yl | H | Br | H | H | K⁺ | |
| 2-398 | pyrazol-1-yl | H | Br | H | H | NH$_4^+$ | |
| 2-399 | pyrazol-1-yl | H | F | H | H | Na⁺ | |
| 2-400 | pyrazol-1-yl | H | F | H | H | K⁺ | |
| 2-401 | pyrazol-1-yl | H | I | H | H | Na⁺ | |
| 2-402 | pyrazol-1-yl | H | I | H | H | K⁺ | |
| 2-403 | pyrazol-1-yl | H | CN | H | H | Na⁺ | |
| 2-404 | pyrazol-1-yl | H | CN | H | H | K⁺ | |
| 2-405 | pyrazol-1-yl | H | CF$_3$ | H | H | Na⁺ | |
| 2-406 | pyrazol-1-yl | H | CF$_3$ | H | H | K⁺ | |

TABLE 2-continued

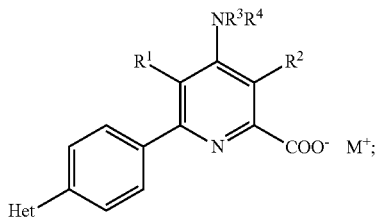

(I-viii)

| No. | Het | $R^1$ | $R^2$ | $R^3$ | $R^4$ | $M^+$ | Physical data: $^1$H NMR: δ [CDCl$_3$] |
|---|---|---|---|---|---|---|---|
| 2-407 | pyrazol-1-yl | F | Cl | H | H | Na$^+$ | |
| 2-408 | pyrazol-1-yl | F | Cl | H | H | K$^+$ | |
| 2-409 | pyrazol-1-yl | F | Cl | H | H | NH$_4^+$ | |
| 2-410 | pyrazol-1-yl | F | Br | H | H | Na$^+$ | |
| 2-411 | pyrazol-1-yl | F | Br | H | H | K$^+$ | |
| 2-412 | pyrazol-1-yl | F | Br | H | H | NH$_4^+$ | |
| 2-413 | pyrazol-1-yl | F | F | H | H | Na$^+$ | |
| 2-414 | pyrazol-1-yl | F | F | H | H | K$^+$ | |
| 2-415 | pyrazol-1-yl | F | I | H | H | Na$^+$ | |
| 2-416 | pyrazol-1-yl | F | I | H | H | K$^+$ | |
| 2-417 | pyrazol-1-yl | F | CN | H | H | Na$^+$ | |
| 2-418 | pyrazol-1-yl | F | CN | H | H | K$^+$ | |
| 2-419 | pyrazol-1-yl | F | CF$_3$ | H | H | Na$^+$ | |
| 2-420 | pyrazol-1-yl | F | CF$_3$ | H | H | K$^+$ | |
| 2-421 | pyrazol-1-yl | H | Cl | H | Me | Na$^+$ | |
| 2-422 | pyrazol-1-yl | H | Cl | H | Me | K$^+$ | |
| 2-423 | pyrazol-1-yl | H | Cl | H | Me | NH$_4^+$ | |
| 2-424 | pyrazol-1-yl | H | Br | H | Me | Na$^+$ | |
| 2-425 | pyrazol-1-yl | H | Br | H | Me | K$^+$ | |
| 2-426 | pyrazol-1-yl | H | Br | H | Me | NH$_4^+$ | |
| 2-427 | pyrazol-1-yl | H | F | H | Me | Na$^+$ | |
| 2-428 | pyrazol-1-yl | H | F | H | Me | K$^+$ | |
| 2-429 | pyrazol-1-yl | H | I | H | Me | Na$^+$ | |
| 2-430 | pyrazol-1-yl | H | I | H | Me | K$^+$ | |
| 2-431 | pyrazol-1-yl | H | CN | H | Me | Na$^+$ | |
| 2-432 | pyrazol-1-yl | H | CN | H | Me | K$^+$ | |
| 2-433 | pyrazol-1-yl | H | CF$_3$ | H | Me | Na$^+$ | |
| 2-434 | pyrazol-1-yl | H | CF$_3$ | H | Me | K$^+$ | |
| 2-435 | pyrazol-1-yl | F | Cl | H | Me | Na$^+$ | |
| 2-436 | pyrazol-1-yl | F | Cl | H | Me | K$^+$ | |
| 2-437 | pyrazol-1-yl | F | Cl | H | Me | NH$_4^+$ | |
| 2-438 | pyrazol-1-yl | F | Br | H | Me | Na$^+$ | |
| 2-439 | pyrazol-1-yl | F | Br | H | Me | K$^+$ | |
| 2-440 | pyrazol-1-yl | F | Br | H | Me | NH$_4^+$ | |
| 2-441 | pyrazol-1-yl | F | F | H | Me | Na$^+$ | |
| 2-442 | pyrazol-1-yl | F | F | H | Me | K$^+$ | |
| 2-443 | pyrazol-1-yl | F | I | H | Me | Na$^+$ | |
| 2-444 | pyrazol-1-yl | F | I | H | Me | K$^+$ | |
| 2-445 | pyrazol-1-yl | F | CN | H | Me | Na$^+$ | |
| 2-446 | pyrazol-1-yl | F | CN | H | Me | K$^+$ | |
| 2-447 | pyrazol-1-yl | F | CF$_3$ | H | Me | Na$^+$ | |
| 2-448 | pyrazol-1-yl | F | CF$_3$ | H | Me | K$^+$ | |
| 2-449 | pyrazol-1-yl | H | Cl | Me | Me | Na$^+$ | |
| 2-450 | pyrazol-1-yl | H | Cl | Me | Me | K$^+$ | |
| 2-451 | pyrazol-1-yl | H | Cl | Me | Me | NH$_4^+$ | |
| 2-452 | pyrazol-1-yl | H | Br | Me | Me | Na$^+$ | |
| 2-453 | pyrazol-1-yl | H | Br | Me | Me | K$^+$ | |
| 2-454 | pyrazol-1-yl | H | Br | Me | Me | NH$_4^+$ | |
| 2-455 | pyrazol-1-yl | H | F | Me | Me | Na$^+$ | |
| 2-456 | pyrazol-1-yl | H | F | Me | Me | K$^+$ | |
| 2-457 | pyrazol-1-yl | H | I | Me | Me | Na$^+$ | |
| 2-458 | pyrazol-1-yl | H | I | Me | Me | K$^+$ | |
| 2-459 | pyrazol-1-yl | H | CN | Me | Me | Na$^+$ | |
| 2-460 | pyrazol-1-yl | H | CN | Me | Me | K$^+$ | |
| 2-461 | pyrazol-1-yl | H | CF$_3$ | Me | Me | Na$^+$ | |
| 2-462 | pyrazol-1-yl | H | CF$_3$ | Me | Me | K$^+$ | |
| 2-463 | pyrazol-1-yl | F | Cl | Me | Me | Na$^+$ | |
| 2-464 | pyrazol-1-yl | F | Cl | Me | Me | K$^+$ | |
| 2-465 | pyrazol-1-yl | F | Cl | Me | Me | NH$_4^+$ | |
| 2-466 | pyrazol-1-yl | F | Br | Me | Me | Na$^+$ | |
| 2-467 | pyrazol-1-yl | F | Br | Me | Me | K$^+$ | |
| 2-468 | pyrazol-1-yl | F | Br | Me | Me | NH$_4^+$ | |
| 2-469 | pyrazol-1-yl | F | F | Me | Me | Na$^+$ | |
| 2-470 | pyrazol-1-yl | F | F | Me | Me | K$^+$ | |

TABLE 2-continued

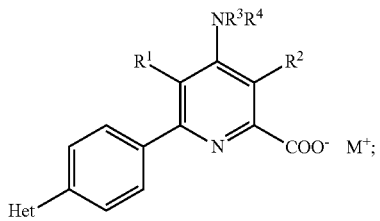

(I-viii)

| No. | Het | $R^1$ | $R^2$ | $R^3$ | $R^4$ | $M^+$ | Physical data: $^1$H NMR: δ [CDCl$_3$] |
|---|---|---|---|---|---|---|---|
| 2-471 | pyrazol-1-yl | F | I | Me | Me | Na$^+$ | |
| 2-472 | pyrazol-1-yl | F | I | Me | Me | K$^+$ | |
| 2-473 | pyrazol-1-yl | F | CN | Me | Me | Na$^+$ | |
| 2-474 | pyrazol-1-yl | F | CN | Me | Me | K$^+$ | |
| 2-475 | pyrazol-1-yl | F | CF$_3$ | Me | Me | Na$^+$ | |
| 2-476 | pyrazol-1-yl | F | CF$_3$ | Me | Me | K$^+$ | |
| 2-477 | pyrazol-1-yl | H | Cl | =CHNMe$_2$ | | Na$^+$ | |
| 2-478 | pyrazol-1-yl | H | Cl | =CHNMe$_2$ | | K$^+$ | |
| 2-479 | pyrazol-1-yl | H | Cl | =CHNMe$_2$ | | NH$_4^+$ | |
| 2-480 | pyrazol-1-yl | H | Br | =CHNMe$_2$ | | Na$^+$ | |
| 2-481 | pyrazol-1-yl | H | Br | =CHNMe$_2$ | | K$^+$ | |
| 2-482 | pyrazol-1-yl | H | Br | =CHNMe$_2$ | | NH$_4^+$ | |
| 2-483 | pyrazol-1-yl | H | F | =CHNMe$_2$ | | Na$^+$ | |
| 2-484 | pyrazol-1-yl | H | F | =CHNMe$_2$ | | K$^+$ | |
| 2-485 | pyrazol-1-yl | H | I | =CHNMe$_2$ | | Na$^+$ | |
| 2-486 | pyrazol-1-yl | H | I | =CHNMe$_2$ | | K$^+$ | |
| 2-487 | pyrazol-1-yl | H | CN | =CHNMe$_2$ | | Na$^+$ | |
| 2-488 | pyrazol-1-yl | H | CN | =CHNMe$_2$ | | K$^+$ | |
| 2-489 | pyrazol-1-yl | H | CF$_3$ | =CHNMe$_2$ | | Na$^+$ | |
| 2-490 | pyrazol-1-yl | H | CF$_3$ | =CHNMe$_2$ | | K$^+$ | |
| 2-491 | pyrazol-1-yl | F | Cl | =CHNMe$_2$ | | Na$^+$ | |
| 2-492 | pyrazol-1-yl | F | Cl | =CHNMe$_2$ | | K$^+$ | |
| 2-493 | pyrazol-1-yl | F | Cl | =CHNMe$_2$ | | NH$_4^+$ | |
| 2-494 | pyrazol-1-yl | F | Br | =CHNMe$_2$ | | Na$^+$ | |
| 2-495 | pyrazol-1-yl | F | Br | =CHNMe$_2$ | | K$^+$ | |
| 2-496 | pyrazol-1-yl | F | Br | =CHNMe$_2$ | | NH$_4^+$ | |
| 2-497 | pyrazol-1-yl | F | F | =CHNMe$_2$ | | Na$^+$ | |
| 2-498 | pyrazol-1-yl | F | F | =CHNMe$_2$ | | K$^+$ | |
| 2-499 | pyrazol-1-yl | F | I | =CHNMe$_2$ | | Na$^+$ | |
| 2-500 | pyrazol-1-yl | F | I | =CHNMe$_2$ | | K$^+$ | |
| 2-501 | pyrazol-1-yl | F | CN | =CHNMe$_2$ | | Na$^+$ | |
| 2-502 | pyrazol-1-yl | F | CN | =CHNMe$_2$ | | K$^+$ | |
| 2-503 | pyrazol-1-yl | F | CF$_3$ | =CHNMe$_2$ | | Na$^+$ | |
| 2-504 | pyrazol-1-yl | F | CF$_3$ | =CHNMe$_2$ | | K$^+$ | |
| 2-505 | pyridin-3-yl | H | Cl | H | H | Na$^+$ | |
| 2-506 | pyridin-3-yl | H | Cl | H | H | K$^+$ | |
| 2-507 | pyridin-3-yl | H | Cl | H | H | NH$_4^+$ | |
| 2-508 | pyridin-3-yl | H | Br | H | H | Na$^+$ | |
| 2-509 | pyridin-3-yl | H | Br | H | H | K$^+$ | |
| 2-510 | pyridin-3-yl | H | Br | H | H | NH$_4^+$ | |
| 2-511 | pyridin-3-yl | H | F | H | H | Na$^+$ | |
| 2-512 | pyridin-3-yl | H | F | H | H | K$^+$ | |
| 2-513 | pyridin-3-yl | H | I | H | H | Na$^+$ | |
| 2-514 | pyridin-3-yl | H | I | H | H | K$^+$ | |
| 2-515 | pyridin-3-yl | H | CN | H | H | Na$^+$ | |
| 2-516 | pyridin-3-yl | H | CN | H | H | K$^+$ | |
| 2-517 | pyridin-3-yl | H | CF$_3$ | H | H | Na$^+$ | |
| 2-518 | pyridin-3-yl | H | CF$_3$ | H | H | K$^+$ | |
| 2-519 | pyridin-3-yl | F | Cl | H | H | Na$^+$ | |
| 2-520 | pyridin-3-yl | F | Cl | H | H | K$^+$ | |
| 2-521 | pyridin-3-yl | F | Cl | H | H | NH$_4^+$ | |
| 2-522 | pyridin-3-yl | F | Br | H | H | Na$^+$ | |
| 2-523 | pyridin-3-yl | F | Br | H | H | K$^+$ | |
| 2-524 | pyridin-3-yl | F | Br | Me | H | NH$_4^+$ | |
| 2-525 | pyridin-3-yl | F | F | H | H | Na$^+$ | |
| 2-526 | pyridin-3-yl | F | F | H | H | K$^+$ | |
| 2-527 | pyridin-3-yl | F | I | H | H | Na$^+$ | |
| 2-528 | pyridin-3-yl | F | I | H | H | K$^+$ | |
| 2-529 | pyridin-3-yl | F | CN | H | H | Na$^+$ | |
| 2-530 | pyridin-3-yl | F | CN | H | H | K$^+$ | |
| 2-531 | pyridin-3-yl | F | CF$_3$ | H | H | Na$^+$ | |
| 2-532 | pyridin-3-yl | F | CF$_3$ | H | H | K$^+$ | |
| 2-533 | pyridin-3-yl | H | Cl | H | Me | Na$^+$ | |
| 2-534 | pyridin-3-yl | H | Cl | H | Me | K$^+$ | |

TABLE 2-continued

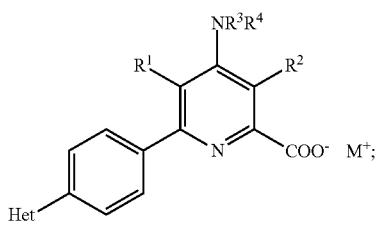

(I-viii)

| No. | Het | $R^1$ | $R^2$ | $R^3$ | $R^4$ | $M^+$ | Physical data: $^1$H NMR: δ [CDCl$_3$] |
|---|---|---|---|---|---|---|---|
| 2-535 | pyridin-3-yl | H | Cl | H | Me | $NH_4^+$ | |
| 2-536 | pyridin-3-yl | H | Br | H | Me | $Na^+$ | |
| 2-537 | pyridin-3-yl | H | Br | H | Me | $K^+$ | |
| 2-538 | pyridin-3-yl | H | Br | H | Me | $NH_4^+$ | |
| 2-539 | pyridin-3-yl | H | F | H | Me | $Na^+$ | |
| 2-540 | pyridin-3-yl | H | F | H | Me | $K^+$ | |
| 2-541 | pyridin-3-yl | H | I | H | Me | $Na^+$ | |
| 2-542 | pyridin-3-yl | H | I | H | Me | $K^+$ | |
| 2-543 | pyridin-3-yl | H | CN | H | Me | $Na^+$ | |
| 2-544 | pyridin-3-yl | H | CN | H | Me | $K^+$ | |
| 2-545 | pyridin-3-yl | H | $CF_3$ | H | Me | $Na^+$ | |
| 2-546 | pyridin-3-yl | H | $CF_3$ | H | Me | $K^+$ | |
| 2-547 | pyridin-3-yl | F | Cl | H | Me | $Na^+$ | |
| 2-548 | pyridin-3-yl | F | Cl | H | Me | $K^+$ | |
| 2-549 | pyridin-3-yl | F | Cl | H | Me | $NH_4^+$ | |
| 2-550 | pyridin-3-yl | F | Br | H | Me | $Na^+$ | |
| 2-551 | pyridin-3-yl | F | Br | H | Me | $K^+$ | |
| 2-552 | pyridin-3-yl | F | Br | H | Me | $NH_4^+$ | |
| 2-553 | pyridin-3-yl | F | F | H | Me | $Na^+$ | |
| 2-554 | pyridin-3-yl | F | F | H | Me | $K^+$ | |
| 2-555 | pyridin-3-yl | F | I | H | Me | $Na^+$ | |
| 2-556 | pyridin-3-yl | F | I | H | Me | $K^+$ | |
| 2-557 | pyridin-3-yl | F | CN | H | Me | $Na^+$ | |
| 2-558 | pyridin-3-yl | F | CN | H | Me | $K^+$ | |
| 2-559 | pyridin-3-yl | F | $CF_3$ | H | Me | $Na^+$ | |
| 2-560 | pyridin-3-yl | F | $CF_3$ | H | Me | $K^+$ | |
| 2-561 | pyridin-3-yl | H | Cl | Me | Me | $Na^+$ | |
| 2-562 | pyridin-3-yl | H | Cl | Me | Me | $K^+$ | |
| 2-563 | pyridin-3-yl | H | Cl | Me | Me | $NH_4^+$ | |
| 2-564 | pyridin-3-yl | H | Br | Me | Me | $Na^+$ | |
| 2-565 | pyridin-3-yl | H | Br | Me | Me | $K^+$ | |
| 2-566 | pyridin-3-yl | H | Br | Me | Me | $NH_4^+$ | |
| 2-567 | pyridin-3-yl | H | F | Me | Me | $Na^+$ | |
| 2-568 | pyridin-3-yl | H | F | Me | Me | $K^+$ | |
| 2-569 | pyridin-3-yl | H | I | Me | Me | $Na^+$ | |
| 2-570 | pyridin-3-yl | H | I | Me | Me | $K^+$ | |
| 2-571 | pyridin-3-yl | H | CN | Me | Me | $Na^+$ | |
| 2-572 | pyridin-3-yl | H | CN | Me | Me | $K^+$ | |
| 2-573 | pyridin-3-yl | H | $CF_3$ | Me | Me | $Na^+$ | |
| 2-574 | pyridin-3-yl | H | $CF_3$ | Me | Me | $K^+$ | |
| 2-575 | pyridin-3-yl | F | Cl | Me | Me | $Na^+$ | |
| 2-576 | pyridin-3-yl | F | Cl | Me | Me | $K^+$ | |
| 2-577 | pyridin-3-yl | F | Cl | Me | Me | $NH_4^+$ | |
| 2-578 | pyridin-3-yl | F | Br | Me | Me | $Na^+$ | |
| 2-579 | pyridin-3-yl | F | Br | Me | Me | $K^+$ | |
| 2-580 | pyridin-3-yl | F | Br | Me | Me | $NH_4^+$ | |
| 2-581 | pyridin-3-yl | F | F | Me | Me | $Na^+$ | |
| 2-582 | pyridin-3-yl | F | F | Me | Me | $K^+$ | |
| 2-583 | pyridin-3-yl | F | I | Me | Me | $Na^+$ | |
| 2-584 | pyridin-3-yl | F | I | Me | Me | $K^+$ | |
| 2-585 | pyridin-3-yl | F | CN | Me | Me | $Na^+$ | |
| 2-586 | pyridin-3-yl | F | CN | Me | Me | $K^+$ | |
| 2-587 | pyridin-3-yl | F | $CF_3$ | Me | Me | $Na^+$ | |
| 2-588 | pyridin-3-yl | F | $CF_3$ | Me | Me | $K^+$ | |
| 2-589 | pyridin-3-yl | H | Cl | =CHNMe$_2$ | | $Na^+$ | |
| 2-590 | pyridin-3-yl | H | Cl | =CHNMe$_2$ | | $K^+$ | |
| 2-591 | pyridin-3-yl | H | Cl | =CHNMe$_2$ | | $NH_4^+$ | |
| 2-592 | pyridin-3-yl | H | Br | =CHNMe$_2$ | | $Na^+$ | |
| 2-593 | pyridin-3-yl | H | Br | =CHNMe$_2$ | | $K^+$ | |
| 2-594 | pyridin-3-yl | H | Br | =CHNMe$_2$ | | $NH_4^+$ | |
| 2-595 | pyridin-3-yl | H | F | =CHNMe$_2$ | | $Na^+$ | |
| 2-596 | pyridin-3-yl | H | F | =CHNMe$_2$ | | $K^+$ | |
| 2-597 | pyridin-3-yl | H | I | =CHNMe$_2$ | | $Na^+$ | |
| 2-598 | pyridin-3-yl | H | I | =CHNMe$_2$ | | $K^+$ | |

TABLE 2-continued (I-viii)

| No. | Het | R¹ | R² | R³ | R⁴ | M⁺ | Physical data: ¹H NMR: δ [CDCl₃] |
|---|---|---|---|---|---|---|---|
| 2-599 | pyridin-3-yl | H | CN | =CHNMe₂ | | Na⁺ | |
| 2-600 | pyridin-3-yl | H | CN | =CHNMe₂ | | K⁺ | |
| 2-601 | pyridin-3-yl | H | CF₃ | =CHNMe₂ | | Na⁺ | |
| 2-602 | pyridin-3-yl | H | CF₃ | =CHNMe₂ | | K⁺ | |
| 2-603 | pyridin-3-yl | F | Cl | =CHNMe₂ | | Na⁺ | |
| 2-604 | pyridin-3-yl | F | Cl | =CHNMe₂ | | K⁺ | |
| 2-605 | pyridin-3-yl | F | Cl | =CHNMe₂ | | NH₄⁺ | |
| 2-606 | pyridin-3-yl | F | Br | =CHNMe₂ | | Na⁺ | |
| 2-607 | pyridin-3-yl | F | Br | =CHNMe₂ | | K⁺ | |
| 2-608 | pyridin-3-yl | F | Br | =CHNMe₂ | | NH₄⁺ | |
| 2-609 | pyridin-3-yl | F | F | =CHNMe₂ | | Na⁺ | |
| 2-610 | pyridin-3-yl | F | F | =CHNMe₂ | | K⁺ | |
| 2-611 | pyridin-3-yl | F | I | =CHNMe₂ | | Na⁺ | |
| 2-612 | pyridin-3-yl | F | I | =CHNMe₂ | | K⁺ | |
| 2-613 | pyridin-3-yl | F | CN | =CHNMe₂ | | Na⁺ | |
| 2-614 | pyridin-3-yl | F | CN | =CHNMe₂ | | K⁺ | |
| 2-615 | pyridin-3-yl | F | CF₃ | =CHNMe₂ | | Na⁺ | |
| 2-616 | pyridin-3-yl | F | CF₃ | =CHNMe₂ | | K⁺ | |
| 2-617 | oxiranyl | H | Cl | H | H | Na⁺ | |
| 2-618 | oxiranyl | H | Cl | H | H | K⁺ | |
| 2-619 | oxiranyl | H | Cl | H | H | NH₄⁺ | |
| 2-620 | oxiranyl | H | Br | H | H | Na⁺ | |
| 2-621 | oxiranyl | H | Br | H | H | K⁺ | |
| 2-622 | oxiranyl | H | Br | H | H | NH₄⁺ | |
| 2-623 | oxiranyl | H | F | H | H | Na⁺ | |
| 2-624 | oxiranyl | H | F | H | H | K⁺ | |
| 2-625 | oxiranyl | H | I | H | H | Na⁺ | |
| 2-626 | oxiranyl | H | I | H | H | K⁺ | |
| 2-627 | oxiranyl | H | CN | H | H | Na⁺ | |
| 2-628 | oxiranyl | H | CN | H | H | K⁺ | |
| 2-629 | oxiranyl | H | CF₃ | H | H | Na⁺ | |
| 2-630 | oxiranyl | H | CF₃ | H | H | K⁺ | |
| 2-631 | oxiranyl | F | Cl | H | H | Na⁺ | |
| 2-632 | oxiranyl | F | Cl | H | H | K⁺ | |
| 2-633 | oxiranyl | F | Cl | H | H | NH₄⁺ | |
| 2-634 | oxiranyl | F | Br | H | H | Na⁺ | |
| 2-635 | oxiranyl | F | Br | H | H | K⁺ | |
| 2-636 | oxiranyl | F | Br | H | H | NH₄⁺ | |
| 2-637 | oxiranyl | F | F | H | H | Na⁺ | |
| 2-638 | oxiranyl | F | F | H | H | K⁺ | |
| 2-639 | oxiranyl | F | I | H | H | Na⁺ | |
| 2-640 | oxiranyl | F | I | H | H | K⁺ | |
| 2-641 | oxiranyl | F | CN | H | H | Na⁺ | |
| 2-642 | oxiranyl | F | CN | H | H | K⁺ | |
| 2-643 | oxiranyl | F | CF₃ | H | H | Na⁺ | |
| 2-644 | oxiranyl | F | CF₃ | H | H | K⁺ | |
| 2-645 | oxiranyl | H | Cl | H | Me | Na⁺ | |
| 2-646 | oxiranyl | H | Cl | H | Me | K⁺ | |
| 2-647 | oxiranyl | H | Cl | H | Me | NH₄⁺ | |
| 2-648 | oxiranyl | H | Br | H | Me | Na⁺ | |
| 2-649 | oxiranyl | H | Br | H | Me | K⁺ | |
| 2-650 | oxiranyl | H | Br | H | Me | NH₄⁺ | |
| 2-651 | oxiranyl | H | F | H | Me | Na⁺ | |
| 2-652 | oxiranyl | H | F | H | Me | K⁺ | |
| 2-653 | oxiranyl | H | I | H | Me | Na⁺ | |
| 2-654 | oxiranyl | H | I | H | Me | K⁺ | |
| 2-655 | oxiranyl | H | CN | H | Me | Na⁺ | |
| 2-656 | oxiranyl | H | CN | H | Me | K⁺ | |
| 2-657 | oxiranyl | H | CF₃ | H | Me | Na⁺ | |
| 2-658 | oxiranyl | H | CF₃ | H | Me | K⁺ | |
| 2-659 | oxiranyl | F | Cl | H | Me | Na⁺ | |
| 2-660 | oxiranyl | F | Cl | H | Me | K⁺ | |
| 2-661 | oxiranyl | F | Cl | H | Me | NH₄⁺ | |
| 2-662 | oxiranyl | F | Br | H | Me | Na⁺ | |

TABLE 2-continued

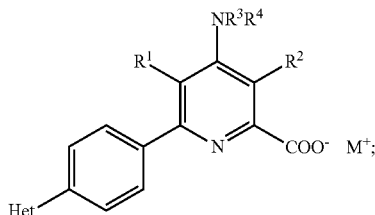

(I-viii)

| No. | Het | $R^1$ | $R^2$ | $R^3$ | $R^4$ | $M^+$ | Physical data: $^1$H NMR: δ [CDCl$_3$] |
|---|---|---|---|---|---|---|---|
| 2-663 | oxiranyl | F | Br | H | Me | K$^+$ | |
| 2-664 | oxiranyl | F | Br | H | Me | NH$_4^+$ | |
| 2-665 | oxiranyl | F | F | H | Me | Na$^+$ | |
| 2-666 | oxiranyl | F | F | H | Me | K$^+$ | |
| 2-667 | oxiranyl | F | I | H | Me | Na$^+$ | |
| 2-668 | oxiranyl | F | I | H | Me | K$^+$ | |
| 2-669 | oxiranyl | F | CN | H | Me | Na$^+$ | |
| 2-670 | oxiranyl | F | CN | H | Me | K$^+$ | |
| 2-671 | oxiranyl | F | CF$_3$ | H | Me | Na$^+$ | |
| 2-672 | oxiranyl | F | CF$_3$ | H | Me | K$^+$ | |
| 2-673 | oxiranyl | H | Cl | Me | Me | Na$^+$ | |
| 2-674 | oxiranyl | H | Cl | Me | Me | K$^+$ | |
| 2-675 | oxiranyl | H | Cl | Me | Me | NH$_4^+$ | |
| 2-676 | oxiranyl | H | Br | Me | Me | Na$^+$ | |
| 2-677 | oxiranyl | H | Br | Me | Me | K$^+$ | |
| 2-678 | oxiranyl | H | Br | Me | Me | NH$_4^+$ | |
| 2-679 | oxiranyl | H | F | Me | Me | Na$^+$ | |
| 2-680 | oxiranyl | H | F | Me | Me | K$^+$ | |
| 2-681 | oxiranyl | H | I | Me | Me | Na$^+$ | |
| 2-682 | oxiranyl | H | I | Me | Me | K$^+$ | |
| 2-683 | oxiranyl | H | CN | Me | Me | Na$^+$ | |
| 2-684 | oxiranyl | H | CN | Me | Me | K$^+$ | |
| 2-685 | oxiranyl | H | CF$_3$ | Me | Me | Na$^+$ | |
| 2-686 | oxiranyl | H | CF$_3$ | Me | Me | K$^+$ | |
| 2-687 | oxiranyl | F | Cl | Me | Me | Na$^+$ | |
| 2-688 | oxiranyl | F | Cl | Me | Me | K$^+$ | |
| 2-689 | oxiranyl | F | Cl | Me | Me | NH$_4^+$ | |
| 2-690 | oxiranyl | F | Br | Me | Me | Na$^+$ | |
| 2-691 | oxiranyl | F | Br | Me | Me | K$^+$ | |
| 2-692 | oxiranyl | F | Br | Me | Me | NH$_4^+$ | |
| 2-693 | oxiranyl | F | F | Me | Me | Na$^+$ | |
| 2-694 | oxiranyl | F | F | Me | Me | K$^+$ | |
| 2-695 | oxiranyl | F | I | Me | Me | Na$^+$ | |
| 2-696 | oxiranyl | F | I | Me | Me | K$^+$ | |
| 2-697 | oxiranyl | F | CN | Me | Me | Na$^+$ | |
| 2-698 | oxiranyl | F | CN | Me | Me | K$^+$ | |
| 2-699 | oxiranyl | F | CF$_3$ | Me | Me | Na$^+$ | |
| 2-700 | oxiranyl | F | CF$_3$ | Me | Me | K$^+$ | |
| 2-701 | oxiranyl | H | Cl | =CHNMe$_2$ | | Na$^+$ | |
| 2-702 | oxiranyl | H | Cl | =CHNMe$_2$ | | K$^+$ | |
| 2-703 | oxiranyl | H | Cl | =CHNMe$_2$ | | NH$_4^+$ | |
| 2-704 | oxiranyl | H | Br | =CHNMe$_2$ | | Na$^+$ | |
| 2-705 | oxiranyl | H | Br | =CHNMe$_2$ | | K$^+$ | |
| 2-706 | oxiranyl | H | Br | =CHNMe$_2$ | | NH$_4^+$ | |
| 2-707 | oxiranyl | H | F | =CHNMe$_2$ | | Na$^+$ | |
| 2-708 | oxiranyl | H | F | =CHNMe$_2$ | | K$^+$ | |
| 2-709 | oxiranyl | H | I | =CHNMe$_2$ | | Na$^+$ | |
| 2-710 | oxiranyl | H | I | =CHNMe$_2$ | | K$^+$ | |
| 2-711 | oxiranyl | H | CN | =CHNMe$_2$ | | Na$^+$ | |
| 2-712 | oxiranyl | H | CN | =CHNMe$_2$ | | K$^+$ | |
| 2-713 | oxiranyl | H | CF$_3$ | =CHNMe$_2$ | | Na$^+$ | |
| 2-714 | oxiranyl | H | CF$_3$ | =CHNMe$_2$ | | K$^+$ | |
| 2-715 | oxiranyl | F | Cl | =CHNMe$_2$ | | Na$^+$ | |
| 2-716 | oxiranyl | F | Cl | =CHNMe$_2$ | | K$^+$ | |
| 2-717 | oxiranyl | F | Cl | =CHNMe$_2$ | | NH$_4^+$ | |
| 2-718 | oxiranyl | F | Br | =CHNMe$_2$ | | Na$^+$ | |
| 2-719 | oxiranyl | F | Br | =CHNMe$_2$ | | K$^+$ | |
| 2-720 | oxiranyl | F | Br | =CHNMe$_2$ | | NH$_4^+$ | |
| 2-721 | oxiranyl | F | F | =CHNMe$_2$ | | Na$^+$ | |
| 2-722 | oxiranyl | F | F | =CHNMe$_2$ | | K$^+$ | |
| 2-723 | oxiranyl | F | I | =CHNMe$_2$ | | Na$^+$ | |
| 2-724 | oxiranyl | F | I | =CHNMe$_2$ | | K$^+$ | |
| 2-725 | oxiranyl | F | CN | =CHNMe$_2$ | | Na$^+$ | |
| 2-726 | oxiranyl | F | CN | =CHNMe$_2$ | | K$^+$ | |

TABLE 2-continued

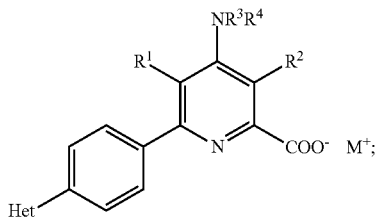

(I-viii)

| No. | Het | $R^1$ | $R^2$ | $R^3$ | $R^4$ | $M^+$ | Physical data: $^1H$ NMR: δ [$CDCl_3$] |
|---|---|---|---|---|---|---|---|
| 2-727 | oxiranyl | F | $CF_3$ | =$CHNMe_2$ | | $Na^+$ | |
| 2-728 | oxiranyl | F | $CF_3$ | =$CHNMe_2$ | | $K^+$ | |
| 2-729 | 3,3-dimethyl-oxetan-2-yl | H | Cl | H | H | $Na^+$ | |
| 2-730 | 3,3-dimethyl-oxetan-2-yl | H | Cl | H | H | $K^+$ | |
| 2-731 | 3,3-dimethyl-oxetan-2-yl | H | Cl | H | H | $NH_4^+$ | |
| 2-732 | 3,3-dimethyl-oxetan-2-yl | H | Br | H | H | $Na^+$ | |
| 2-733 | 3,3-dimethyl-oxetan-2-yl | H | Br | H | H | $K^+$ | |
| 2-734 | 3,3-dimethyl-oxetan-2-yl | H | Br | H | H | $NH_4^+$ | |
| 2-735 | 3,3-dimethyl-oxetan-2-yl | H | F | H | H | $Na^+$ | |
| 2-736 | 3,3-dimethyl-oxetan-2-yl | H | F | H | H | $K^+$ | |
| 2-737 | 3,3-dimethyl-oxetan-2-yl | H | I | H | H | $Na^+$ | |
| 2-738 | 3,3-dimethyl-oxetan-2-yl | H | I | H | H | $K^+$ | |
| 2-739 | 3,3-dimethyl-oxetan-2-yl | H | CN | H | H | $Na^+$ | |
| 2-740 | 3,3-dimethyl-oxetan-2-yl | H | CN | H | H | $K^+$ | |
| 2-741 | 3,3-dimethyl-oxetan-2-yl | H | $CF_3$ | H | H | $Na^+$ | |
| 2-742 | 3,3-dimethyl-oxetan-2-yl | H | $CF_3$ | H | H | $K^+$ | |
| 2-743 | 3,3-dimethyl-oxetan-2-yl | F | Cl | H | H | $Na^+$ | |
| 2-744 | 3,3-dimethyl-oxetan-2-yl | F | Cl | H | H | $K^+$ | |
| 2-745 | 3,3-dimethyl-oxetan-2-yl | F | Cl | H | H | $NH_4^+$ | |
| 2-746 | 3,3-dimethyl-oxetan-2-yl | F | Br | H | H | $Na^+$ | |
| 2-747 | 3,3-dimethyl-oxetan-2-yl | F | Br | H | H | $K^+$ | |
| 2-748 | 3,3-dimethyl-oxetan-2-yl | F | Br | H | H | $NH_4^+$ | |
| 2-749 | 3,3-dimethyl-oxetan-2-yl | F | F | H | H | $Na^+$ | |
| 2-750 | 3,3-dimethyl-oxetan-2-yl | F | F | H | H | $K^+$ | |
| 2-751 | 3,3-dimethyl-oxetan-2-yl | F | I | H | H | $Na^+$ | |
| 2-752 | 3,3-dimethyl-oxetan-2-yl | F | I | H | H | $K^+$ | |
| 2-753 | 3,3-dimethyl-oxetan-2-yl | F | CN | H | H | $Na^+$ | |
| 2-754 | 3,3-dimethyl-oxetan-2-yl | F | CN | H | H | $K^+$ | |
| 2-755 | 3,3-dimethyl-oxetan-2-yl | F | $CF_3$ | H | H | $Na^+$ | |
| 2-756 | 3,3-dimethyl-oxetan-2-yl | F | $CF_3$ | H | H | $K^+$ | |
| 2-757 | 3,3-dimethyl-oxetan-2-yl | H | Cl | H | Me | $Na^+$ | |
| 2-758 | 3,3-dimethyl-oxetan-2-yl | H | Cl | H | Me | $K^+$ | |
| 2-759 | 3,3-dimethyl-oxetan-2-yl | H | Cl | H | Me | $NH_4^+$ | |
| 2-760 | 3,3-dimethyl-oxetan-2-yl | H | Br | H | Me | $Na^+$ | |
| 2-761 | 3,3-dimethyl-oxetan-2-yl | H | Br | H | Me | $K^+$ | |
| 2-762 | 3,3-dimethyl-oxetan-2-yl | H | Br | H | Me | $NH_4^+$ | |
| 2-763 | 3,3-dimethyl-oxetan-2-yl | H | F | H | Me | $Na^+$ | |
| 2-764 | 3,3-dimethyl-oxetan-2-yl | H | F | H | Me | $K^+$ | |
| 2-765 | 3,3-dimethyl-oxetan-2-yl | H | I | H | Me | $Na^+$ | |
| 2-766 | 3,3-dimethyl-oxetan-2-yl | H | I | H | Me | $K^+$ | |
| 2-767 | 3,3-dimethyl-oxetan-2-yl | H | CN | H | Me | $Na^+$ | |
| 2-768 | 3,3-dimethyl-oxetan-2-yl | H | CN | H | Me | $K^+$ | |
| 2-769 | 3,3-dimethyl-oxetan-2-yl | H | $CF_3$ | H | Me | $Na^+$ | |
| 2-770 | 3,3-dimethyl-oxetan-2-yl | H | $CF_3$ | H | Me | $K^+$ | |
| 2-771 | 3,3-dimethyl-oxetan-2-yl | F | Cl | H | Me | $Na^+$ | |
| 2-772 | 3,3-dimethyl-oxetan-2-yl | F | Cl | H | Me | $K^+$ | |
| 2-773 | 3,3-dimethyl-oxetan-2-yl | F | Cl | H | Me | $NH_4^+$ | |
| 2-774 | 3,3-dimethyl-oxetan-2-yl | F | Br | H | Me | $Na^+$ | |
| 2-775 | 3,3-dimethyl-oxetan-2-yl | F | Br | H | Me | $K^+$ | |
| 2-776 | 3,3-dimethyl-oxetan-2-yl | F | Br | H | Me | $NH_4^+$ | |
| 2-777 | 3,3-dimethyl-oxetan-2-yl | F | F | H | Me | $Na^+$ | |
| 2-778 | 3,3-dimethyl-oxetan-2-yl | F | F | H | Me | $K^+$ | |
| 2-779 | 3,3-dimethyl-oxetan-2-yl | F | I | H | Me | $Na^+$ | |
| 2-780 | 3,3-dimethyl-oxetan-2-yl | F | I | H | Me | $K^+$ | |
| 2-781 | 3,3-dimethyl-oxetan-2-yl | F | CN | H | Me | $Na^+$ | |
| 2-782 | 3,3-dimethyl-oxetan-2-yl | F | CN | H | Me | $K^+$ | |
| 2-783 | 3,3-dimethyl-oxetan-2-yl | F | $CF_3$ | H | Me | $Na^+$ | |
| 2-784 | 3,3-dimethyl-oxetan-2-yl | F | $CF_3$ | H | Me | $K^+$ | |
| 2-785 | 3,3-dimethyl-oxetan-2-yl | H | Cl | Me | Me | $Na^+$ | |
| 2-786 | 3,3-dimethyl-oxetan-2-yl | H | Cl | Me | Me | $K^+$ | |
| 2-787 | 3,3-dimethyl-oxetan-2-yl | H | Cl | Me | Me | $NH_4^+$ | |
| 2-788 | 3,3-dimethyl-oxetan-2-yl | H | Br | Me | Me | $Na^+$ | |
| 2-789 | 3,3-dimethyl-oxetan-2-yl | H | Br | Me | Me | $K^+$ | |
| 2-790 | 3,3-dimethyl-oxetan-2-yl | H | Br | Me | Me | $NH_4^+$ | |

TABLE 2-continued

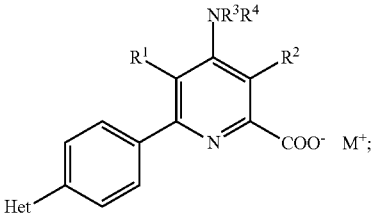

(I-viii)

| No. | Het | R¹ | R² | R³ | R⁴ | M⁺ | Physical data: ¹H NMR: δ [CDCl₃] |
|---|---|---|---|---|---|---|---|
| 2-791 | 3,3-dimethyl-oxetan-2-yl | H | F | Me | Me | Na⁺ | |
| 2-792 | 3,3-dimethyl-oxetan-2-yl | H | F | Me | Me | K⁺ | |
| 2-793 | 3,3-dimethyl-oxetan-2-yl | H | I | Me | Me | Na⁺ | |
| 2-794 | 3,3-dimethyl-oxetan-2-yl | H | I | Me | Me | K⁺ | |
| 2-795 | 3,3-dimethyl-oxetan-2-yl | H | CN | Me | Me | Na⁺ | |
| 2-796 | 3,3-dimethyl-oxetan-2-yl | H | CN | Me | Me | K⁺ | |
| 2-797 | 3,3-dimethyl-oxetan-2-yl | H | CF₃ | Me | Me | Na⁺ | |
| 2-798 | 3,3-dimethyl-oxetan-2-yl | H | CF₃ | Me | Me | K⁺ | |
| 2-799 | 3,3-dimethyl-oxetan-2-yl | F | Cl | Me | Me | Na⁺ | |
| 2-800 | 3,3-dimethyl-oxetan-2-yl | F | Cl | Me | Me | K⁺ | |
| 2-801 | 3,3-dimethyl-oxetan-2-yl | F | Cl | Me | Me | NH₄⁺ | |
| 2-802 | 3,3-dimethyl-oxetan-2-yl | F | Br | Me | Me | Na⁺ | |
| 2-803 | 3,3-dimethyl-oxetan-2-yl | F | Br | Me | Me | K⁺ | |
| 2-804 | 3,3-dimethyl-oxetan-2-yl | F | Br | Me | Me | NH₄⁺ | |
| 2-805 | 3,3-dimethyl-oxetan-2-yl | F | F | Me | Me | Na⁺ | |
| 2-806 | 3,3-dimethyl-oxetan-2-yl | F | F | Me | Me | K⁺ | |
| 2-807 | 3,3-dimethyl-oxetan-2-yl | F | I | Me | Me | Na⁺ | |
| 2-808 | 3,3-dimethyl-oxetan-2-yl | F | I | Me | Me | K⁺ | |
| 2-809 | 3,3-dimethyl-oxetan-2-yl | F | CN | Me | Me | Na⁺ | |
| 2-810 | 3,3-dimethyl-oxetan-2-yl | F | CN | Me | Me | K⁺ | |
| 2-811 | 3,3-dimethyl-oxetan-2-yl | F | CF₃ | Me | Me | Na⁺ | |
| 2-812 | 3,3-dimethyl-oxetan-2-yl | F | CF₃ | Me | Me | K⁺ | |
| 2-813 | 3,3-dimethyl-oxetan-2-yl | H | Cl | =CHNMe₂ | | Na⁺ | |
| 2-814 | 3,3-dimethyl-oxetan-2-yl | H | Cl | =CHNMe₂ | | K⁺ | |
| 2-815 | 3,3-dimethyl-oxetan-2-yl | H | Cl | =CHNMe₂ | | NH₄⁺ | |
| 2-816 | 3,3-dimethyl-oxetan-2-yl | H | Br | =CHNMe₂ | | Na⁺ | |
| 2-817 | 3,3-dimethyl-oxetan-2-yl | H | Br | =CHNMe₂ | | K⁺ | |
| 2-818 | 3,3-dimethyl-oxetan-2-yl | H | Br | =CHNMe₂ | | NH₄⁺ | |
| 2-819 | 3,3-dimethyl-oxetan-2-yl | H | F | =CHNMe₂ | | Na⁺ | |
| 2-820 | 3,3-dimethyl-oxetan-2-yl | H | F | =CHNMe₂ | | K⁺ | |
| 2-821 | 3,3-dimethyl-oxetan-2-yl | H | I | =CHNMe₂ | | Na⁺ | |
| 2-822 | 3,3-dimethyl-oxetan-2-yl | H | I | =CHNMe₂ | | K⁺ | |
| 2-823 | 3,3-dimethyl-oxetan-2-yl | H | CN | =CHNMe₂ | | Na⁺ | |
| 2-824 | 3,3-dimethyl-oxetan-2-yl | H | CN | =CHNMe₂ | | K⁺ | |
| 2-825 | 3,3-dimethyl-oxetan-2-yl | H | CF₃ | =CHNMe₂ | | Na⁺ | |
| 2-826 | 3,3-dimethyl-oxetan-2-yl | H | CF₃ | =CHNMe₂ | | K⁺ | |
| 2-827 | 3,3-dimethyl-oxetan-2-yl | F | Cl | =CHNMe₂ | | Na⁺ | |
| 2-828 | 3,3-dimethyl-oxetan-2-yl | F | Cl | =CHNMe₂ | | K⁺ | |
| 2-829 | 3,3-dimethyl-oxetan-2-yl | F | Cl | =CHNMe₂ | | NH₄⁺ | |
| 2-830 | 3,3-dimethyl-oxetan-2-yl | F | Br | =CHNMe₂ | | Na⁺ | |
| 2-831 | 3,3-dimethyl-oxetan-2-yl | F | Br | =CHNMe₂ | | K⁺ | |
| 2-832 | 3,3-dimethyl-oxetan-2-yl | F | Br | =CHNMe₂ | | NH₄⁺ | |
| 2-833 | 3,3-dimethyl-oxetan-2-yl | F | F | =CHNMe₂ | | Na⁺ | |
| 2-834 | 3,3-dimethyl-oxetan-2-yl | F | F | =CHNMe₂ | | K⁺ | |
| 2-835 | 3,3-dimethyl-oxetan-2-yl | F | I | =CHNMe₂ | | Na⁺ | |
| 2-836 | 3,3-dimethyl-oxetan-2-yl | F | I | =CHNMe₂ | | K⁺ | |
| 2-837 | 3,3-dimethyl-oxetan-2-yl | F | CN | =CHNMe₂ | | Na⁺ | |
| 2-838 | 3,3-dimethyl-oxetan-2-yl | F | CN | =CHNMe₂ | | K⁺ | |
| 2-839 | 3,3-dimethyl-oxetan-2-yl | F | CF₃ | =CHNMe₂ | | Na⁺ | |
| 2-840 | 3,3-dimethyl-oxetan-2-yl | F | CF₃ | =CHNMe₂ | | K⁺ | |
| 2-841 | 2,2-dimethyl-dioxolan-4-yl | H | Cl | H | H | Na⁺ | |
| 2-842 | 2,2-dimethyl-dioxolan-4-yl | H | Cl | H | H | K⁺ | |
| 2-843 | 2,2-dimethyl-dioxolan-4-yl | H | Cl | H | H | NH₄⁺ | |
| 2-844 | 2,2-dimethyl-dioxolan-4-yl | H | Br | H | H | Na⁺ | |
| 2-845 | 2,2-dimethyl-dioxolan-4-yl | H | Br | H | H | K⁺ | |
| 2-846 | 2,2-dimethyl-dioxolan-4-yl | H | Br | H | H | NH₄⁺ | |
| 2-847 | 2,2-dimethyl-dioxolan-4-yl | H | F | H | H | Na⁺ | |
| 2-848 | 2,2-dimethyl-dioxolan-4-yl | H | F | H | H | K⁺ | |
| 2-849 | 2,2-dimethyl-dioxolan-4-yl | H | I | H | H | Na⁺ | |
| 2-850 | 2,2-dimethyl-dioxolan-4-yl | H | I | H | H | K⁺ | |
| 2-851 | 2,2-dimethyl-dioxolan-4-yl | H | CN | H | H | Na⁺ | |
| 2-852 | 2,2-dimethyl-dioxolan-4-yl | H | CN | H | H | K⁺ | |
| 2-853 | 2,2-dimethyl-dioxolan-4-yl | H | CF₃ | H | H | Na⁺ | |
| 2-854 | 2,2-dimethyl-dioxolan-4-yl | H | CF₃ | H | H | K⁺ | |

TABLE 2-continued (I-viii)

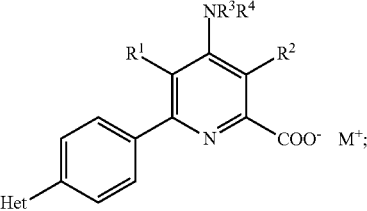

| No. | Het | R¹ | R² | R³ | R⁴ | M⁺ | Physical data: $^1$H NMR: δ [CDCl$_3$] |
|---|---|---|---|---|---|---|---|
| 2-855 | 2,2-dimethyl-dioxolan-4-yl | F | Cl | H | H | Na⁺ | |
| 2-856 | 2,2-dimethyl-dioxolan-4-yl | F | Cl | H | H | K⁺ | |
| 2-857 | 2,2-dimethyl-dioxolan-4-yl | F | Cl | H | H | NH₄⁺ | |
| 2-858 | 2,2-dimethyl-dioxolan-4-yl | F | Br | H | H | Na⁺ | |
| 2-859 | 2,2-dimethyl-dioxolan-4-yl | F | Br | H | H | K⁺ | |
| 2-860 | 2,2-dimethyl-dioxolan-4-yl | F | Br | H | H | NH₄⁺ | |
| 2-861 | 2,2-dimethyl-dioxolan-4-yl | F | F | H | H | Na⁺ | |
| 2-862 | 2,2-dimethyl-dioxolan-4-yl | F | F | H | H | K⁺ | |
| 2-863 | 2,2-dimethyl-dioxolan-4-yl | F | I | H | H | Na⁺ | |
| 2-864 | 2,2-dimethyl-dioxolan-4-yl | F | I | H | H | K⁺ | |
| 2-865 | 2,2-dimethyl-dioxolan-4-yl | F | CN | H | H | Na⁺ | |
| 2-866 | 2,2-dimethyl-dioxolan-4-yl | F | CN | H | H | K⁺ | |
| 2-867 | 2,2-dimethyl-dioxolan-4-yl | F | CF₃ | H | H | Na⁺ | |
| 2-868 | 2,2-dimethyl-dioxolan-4-yl | F | CF₃ | H | H | K⁺ | |
| 2-869 | 2,2-dimethyl-dioxolan-4-yl | H | Cl | H | Me | Na⁺ | |
| 2-870 | 2,2-dimethyl-dioxolan-4-yl | H | Cl | H | Me | K⁺ | |
| 2-871 | 2,2-dimethyl-dioxolan-4-yl | H | Cl | H | Me | NH₄⁺ | |
| 2-872 | 2,2-dimethyl-dioxolan-4-yl | H | Br | H | Me | Na⁺ | |
| 2-873 | 2,2-dimethyl-dioxolan-4-yl | H | Br | H | Me | K⁺ | |
| 2-874 | 2,2-dimethyl-dioxolan-4-yl | H | Br | H | Me | NH₄⁺ | |
| 2-875 | 2,2-dimethyl-dioxolan-4-yl | H | F | H | Me | Na⁺ | |
| 2-876 | 2,2-dimethyl-dioxolan-4-yl | H | F | H | Me | K⁺ | |
| 2-877 | 2,2-dimethyl-dioxolan-4-yl | H | I | H | Me | Na⁺ | |
| 2-878 | 2,2-dimethyl-dioxolan-4-yl | H | I | H | Me | K⁺ | |
| 2-879 | 2,2-dimethyl-dioxolan-4-yl | H | CN | H | Me | Na⁺ | |
| 2-880 | 2,2-dimethyl-dioxolan-4-yl | H | CN | H | Me | K⁺ | |
| 2-881 | 2,2-dimethyl-dioxolan-4-yl | H | CF₃ | H | Me | Na⁺ | |
| 2-882 | 2,2-dimethyl-dioxolan-4-yl | H | CF₃ | H | Me | K⁺ | |
| 2-883 | 2,2-dimethyl-dioxolan-4-yl | F | Cl | H | Me | Na⁺ | |
| 2-884 | 2,2-dimethyl-dioxolan-4-yl | F | Cl | H | Me | K⁺ | |
| 2-885 | 2,2-dimethyl-dioxolan-4-yl | F | Cl | H | Me | NH₄⁺ | |
| 2-886 | 2,2-dimethyl-dioxolan-4-yl | F | Br | H | Me | Na⁺ | |
| 2-887 | 2,2-dimethyl-dioxolan-4-yl | F | Br | H | Me | K⁺ | |
| 2-888 | 2,2-dimethyl-dioxolan-4-yl | F | Br | H | Me | NH₄⁺ | |
| 2-889 | 2,2-dimethyl-dioxolan-4-yl | F | F | H | Me | Na⁺ | |
| 2-890 | 2,2-dimethyl-dioxolan-4-yl | F | F | H | Me | K⁺ | |
| 2-891 | 2,2-dimethyl-dioxolan-4-yl | F | I | H | Me | Na⁺ | |
| 2-892 | 2,2-dimethyl-dioxolan-4-yl | F | I | H | Me | K⁺ | |
| 2-893 | 2,2-dimethyl-dioxolan-4-yl | F | CN | H | Me | Na⁺ | |
| 2-894 | 2,2-dimethyl-dioxolan-4-yl | F | CN | H | Me | K⁺ | |
| 2-895 | 2,2-dimethyl-dioxolan-4-yl | F | CF₃ | H | Me | Na⁺ | |
| 2-896 | 2,2-dimethyl-dioxolan-4-yl | F | CF₃ | H | Me | K⁺ | |
| 2-897 | 2,2-dimethyl-dioxolan-4-yl | H | Cl | Me | Me | Na⁺ | |
| 2-898 | 2,2-dimethyl-dioxolan-4-yl | H | Cl | Me | Me | K⁺ | |
| 2-899 | 2,2-dimethyl-dioxolan-4-yl | H | Cl | Me | Me | NH₄⁺ | |
| 2-900 | 2,2-dimethyl-dioxolan-4-yl | H | Br | Me | Me | Na⁺ | |
| 2-901 | 2,2-dimethyl-dioxolan-4-yl | H | Br | Me | Me | K⁺ | |
| 2-902 | 2,2-dimethyl-dioxolan-4-yl | H | Br | Me | Me | NH₄⁺ | |
| 2-903 | 2,2-dimethyl-dioxolan-4-yl | H | F | Me | Me | Na⁺ | |
| 2-904 | 2,2-dimethyl-dioxolan-4-yl | H | F | Me | Me | K⁺ | |
| 2-905 | 2,2-dimethyl-dioxolan-4-yl | H | I | Me | Me | Na⁺ | |
| 2-906 | 2,2-dimethyl-dioxolan-4-yl | H | I | Me | Me | K⁺ | |
| 2-907 | 2,2-dimethyl-dioxolan-4-yl | H | CN | Me | Me | Na⁺ | |
| 2-908 | 2,2-dimethyl-dioxolan-4-yl | H | CN | Me | Me | K⁺ | |
| 2-909 | 2,2-dimethyl-dioxolan-4-yl | H | CF₃ | Me | Me | Na⁺ | |
| 2-910 | 2,2-dimethyl-dioxolan-4-yl | H | CF₃ | Me | Me | K⁺ | |
| 2-911 | 2,2-dimethyl-dioxolan-4-yl | F | Cl | Me | Me | Na⁺ | |
| 2-912 | 2,2-dimethyl-dioxolan-4-yl | F | Cl | Me | Me | K⁺ | |
| 2-913 | 2,2-dimethyl-dioxolan-4-yl | F | Cl | Me | Me | NH₄⁺ | |
| 2-914 | 2,2-dimethyl-dioxolan-4-yl | F | Br | Me | Me | Na⁺ | |
| 2-915 | 2,2-dimethyl-dioxolan-4-yl | F | Br | Me | Me | K⁺ | |
| 2-916 | 2,2-dimethyl-dioxolan-4-yl | F | Br | Me | Me | NH₄⁺ | |
| 2-917 | 2,2-dimethyl-dioxolan-4-yl | F | F | Me | Me | Na⁺ | |
| 2-918 | 2,2-dimethyl-dioxolan-4-yl | F | F | Me | Me | K⁺ | |

TABLE 2-continued (I-viii)

| No. | Het | R¹ | R² | R³ | R⁴ | M⁺ | Physical data: ¹H NMR: δ [CDCl₃] |
|---|---|---|---|---|---|---|---|
| 2-919 | 2,2-dimethyl-dioxolan-4-yl | F | I | Me | Me | Na⁺ | |
| 2-920 | 2,2-dimethyl-dioxolan-4-yl | F | I | Me | Me | K⁺ | |
| 2-921 | 2,2-dimethyl-dioxolan-4-yl | F | CN | Me | Me | Na⁺ | |
| 2-922 | 2,2-dimethyl-dioxolan-4-yl | F | CN | Me | Me | K⁺ | |
| 2-923 | 2,2-dimethyl-dioxolan-4-yl | F | CF₃ | Me | Me | Na⁺ | |
| 2-924 | 2,2-dimethyl-dioxolan-4-yl | F | CF₃ | Me | Me | K⁺ | |
| 2-925 | 2,2-dimethyl-dioxolan-4-yl | H | Cl | =CHNMe₂ | | Na⁺ | |
| 2-926 | 2,2-dimethyl-dioxolan-4-yl | H | Cl | =CHNMe₂ | | K⁺ | |
| 2-927 | 2,2-dimethyl-dioxolan-4-yl | H | Cl | =CHNMe₂ | | NH₄⁺ | |
| 2-928 | 2,2-dimethyl-dioxolan-4-yl | H | Br | =CHNMe₂ | | Na⁺ | |
| 2-929 | 2,2-dimethyl-dioxolan-4-yl | H | Br | =CHNMe₂ | | K⁺ | |
| 2-930 | 2,2-dimethyl-dioxolan-4-yl | H | Br | =CHNMe₂ | | NH₄⁺ | |
| 2-931 | 2,2-dimethyl-dioxolan-4-yl | H | F | =CHNMe₂ | | Na⁺ | |
| 2-932 | 2,2-dimethyl-dioxolan-4-yl | H | F | =CHNMe₂ | | K⁺ | |
| 2-933 | 2,2-dimethyl-dioxolan-4-yl | H | I | =CHNMe₂ | | Na⁺ | |
| 2-934 | 2,2-dimethyl-dioxolan-4-yl | H | I | =CHNMe₂ | | K⁺ | |
| 2-935 | 2,2-dimethyl-dioxolan-4-yl | H | CN | =CHNMe₂ | | Na⁺ | |
| 2-936 | 2,2-dimethyl-dioxolan-4-yl | H | CN | =CHNMe₂ | | K⁺ | |
| 2-937 | 2,2-dimethyl-dioxolan-4-yl | H | CF₃ | =CHNMe₂ | | Na⁺ | |
| 2-938 | 2,2-dimethyl-dioxolan-4-yl | H | CF₃ | =CHNMe₂ | | K⁺ | |
| 2-939 | 2,2-dimethyl-dioxolan-4-yl | F | Cl | =CHNMe₂ | | Na⁺ | |
| 2-940 | 2,2-dimethyl-dioxolan-4-yl | F | Cl | =CHNMe₂ | | K⁺ | |
| 2-941 | 2,2-dimethyl-dioxolan-4-yl | F | Cl | =CHNMe₂ | | NH₄⁺ | |
| 2-942 | 2,2-dimethyl-dioxolan-4-yl | F | Br | =CHNMe₂ | | Na⁺ | |
| 2-943 | 2,2-dimethyl-dioxolan-4-yl | F | Br | =CHNMe₂ | | K⁺ | |
| 2-944 | 2,2-dimethyl-dioxolan-4-yl | F | Br | =CHNMe₂ | | NH₄⁺ | |
| 2-945 | 2,2-dimethyl-dioxolan-4-yl | F | F | =CHNMe₂ | | Na⁺ | |
| 2-946 | 2,2-dimethyl-dioxolan-4-yl | F | F | =CHNMe₂ | | K⁺ | |
| 2-947 | 2,2-dimethyl-dioxolan-4-yl | F | I | =CHNMe₂ | | Na⁺ | |
| 2-948 | 2,2-dimethyl-dioxolan-4-yl | F | I | =CHNMe₂ | | K⁺ | |
| 2-949 | 2,2-dimethyl-dioxolan-4-yl | F | CN | =CHNMe₂ | | Na⁺ | |
| 2-950 | 2,2-dimethyl-dioxolan-4-yl | F | CN | =CHNMe₂ | | K⁺ | |
| 2-951 | 2,2-dimethyl-dioxolan-4-yl | F | CF₃ | =CHNMe₂ | | Na⁺ | |
| 2-952 | 2,2-dimethyl-dioxolan-4-yl | F | CF₃ | =CHNMe₂ | | K⁺ | |

TABLE 3

(I-iii)

| No. | Het | R¹ | R² | R³ | R⁴ | R | Physical data: ¹H NMR: δ [CDCl₃] |
|---|---|---|---|---|---|---|---|
| 3-1 | 3-tert-butyl-1,2,4-oxadiazol-5-yl | H | Cl | H | H | H | |
| 3-2 | 3-tert-butyl-1,2,4-oxadiazol-5-yl | H | Cl | H | H | Me | |
| 3-3 | 3-tert-butyl-1,2,4-oxadiazol-5-yl | H | Cl | H | H | Et | |
| 3-4 | 3-tert-butyl-1,2,4-oxadiazol-5-yl | H | Br | H | H | H | |
| 3-5 | 3-tert-butyl-1,2,4-oxadiazol-5-yl | H | Br | H | H | Me | |
| 3-6 | 3-tert-butyl-1,2,4-oxadiazol-5-yl | H | Br | H | H | Et | |
| 3-7 | 3-tert-butyl-1,2,4-oxadiazol-5-yl | H | F | H | H | H | |
| 3-8 | 3-tert-butyl-1,2,4-oxadiazol-5-yl | H | F | H | H | Me | |

TABLE 3-continued

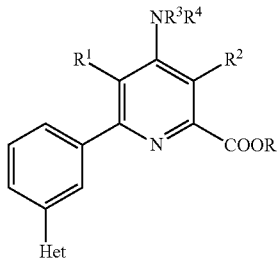

(I-iii)

| No. | Het | R¹ | R² | R³ | R⁴ | R | Physical data: ¹H NMR: δ [CDCl₃] |
|---|---|---|---|---|---|---|---|
| 3-9 | 3-tert-butyl-1,2,4-oxadiazol-5-yl | H | I | H | H | H | |
| 3-10 | 3-tert-butyl-1,2,4-oxadiazol-5-yl | H | I | H | H | Me | |
| 3-11 | 3-tert-butyl-1,2,4-oxadiazol-5-yl | H | CN | H | H | H | |
| 3-12 | 3-tert-butyl-1,2,4-oxadiazol-5-yl | H | CN | H | H | Me | |
| 3-13 | 3-tert-butyl-1,2,4-oxadiazol-5-yl | H | CF₃ | H | H | H | |
| 3-14 | 3-tert-butyl-1,2,4-oxadiazol-5-yl | H | CF₃ | H | H | Me | |
| 3-15 | 3-tert-butyl-1,2,4-oxadiazol-5-yl | F | Cl | H | H | H | |
| 3-16 | 3-tert-butyl-1,2,4-oxadiazol-5-yl | F | Cl | H | H | Me | |
| 3-17 | 3-tert-butyl-1,2,4-oxadiazol-5-yl | F | Cl | H | H | Et | |
| 3-18 | 3-tert-butyl-1,2,4-oxadiazol-5-yl | F | Br | H | H | H | |
| 3-19 | 3-tert-butyl-1,2,4-oxadiazol-5-yl | F | Br | H | H | Me | |
| 3-20 | 3-tert-butyl-1,2,4-oxadiazol-5-yl | F | Br | H | H | Et | |
| 3-21 | 3-tert-butyl-1,2,4-oxadiazol-5-yl | F | F | H | H | H | |
| 3-22 | 3-tert-butyl-1,2,4-oxadiazol-5-yl | F | F | H | H | Me | |
| 3-23 | 3-tert-butyl-1,2,4-oxadiazol-5-yl | F | I | H | H | H | |
| 3-24 | 3-tert-butyl-1,2,4-oxadiazol-5-yl | F | I | H | H | Me | |
| 3-25 | 3-tert-butyl-1,2,4-oxadiazol-5-yl | F | CN | H | H | H | |
| 3-26 | 3-tert-butyl-1,2,4-oxadiazol-5-yl | F | CN | H | H | Me | |
| 3-27 | 3-tert-butyl-1,2,4-oxadiazol-5-yl | F | CF₃ | H | H | H | |
| 3-28 | 3-tert-butyl-1,2,4-oxadiazol-5-yl | F | CF₃ | H | H | Me | |
| 3-29 | 3-tert-butyl-1,2,4-oxadiazol-5-yl | Cl | Cl | H | H | H | |
| 3-30 | 3-tert-butyl-1,2,4-oxadiazol-5-yl | Cl | Cl | H | H | Me | |
| 3-31 | 3-tert-butyl-1,2,4-oxadiazol-5-yl | Cl | Cl | H | H | Et | |
| 3-32 | 3-tert-butyl-1,2,4-oxadiazol-5-yl | Cl | Br | H | H | H | |
| 3-33 | 3-tert-butyl-1,2,4-oxadiazol-5-yl | Cl | Br | H | H | Me | |
| 3-34 | 3-tert-butyl-1,2,4-oxadiazol-5-yl | Cl | Br | H | H | Et | |
| 3-35 | 3-tert-butyl-1,2,4-oxadiazol-5-yl | Cl | F | H | H | H | |
| 3-36 | 3-tert-butyl-1,2,4-oxadiazol-5-yl | Cl | F | H | H | Me | |
| 3-37 | 3-tert-butyl-1,2,4-oxadiazol-5-yl | Cl | I | H | H | H | |
| 3-38 | 3-tert-butyl-1,2,4-oxadiazol-5-yl | Cl | I | H | H | Me | |
| 3-39 | 3-tert-butyl-1,2,4-oxadiazol-5-yl | Cl | CN | H | H | H | |
| 3-40 | 3-tert-butyl-1,2,4-oxadiazol-5-yl | Cl | CN | H | H | Me | |
| 3-41 | 3-tert-butyl-1,2,4-oxadiazol-5-yl | Cl | CF₃ | H | H | H | |
| 3-42 | 3-tert-butyl-1,2,4-oxadiazol-5-yl | Cl | CF₃ | H | H | Me | |
| 3-43 | 3-tert-butyl-1,2,4-oxadiazol-5-yl | H | Cl | H | Me | H | |
| 3-44 | 3-tert-butyl-1,2,4-oxadiazol-5-yl | H | Cl | H | Me | Me | |
| 3-45 | 3-tert-butyl-1,2,4-oxadiazol-5-yl | H | Cl | H | Me | Et | |
| 3-46 | 3-tert-butyl-1,2,4-oxadiazol-5-yl | H | Br | H | Me | H | |
| 3-47 | 3-tert-butyl-1,2,4-oxadiazol-5-yl | H | Br | H | Me | Me | |
| 3-48 | 3-tert-butyl-1,2,4-oxadiazol-5-yl | H | Br | H | Me | Et | |
| 3-49 | 3-tert-butyl-1,2,4-oxadiazol-5-yl | H | F | H | Me | H | |
| 3-50 | 3-tert-butyl-1,2,4-oxadiazol-5-yl | H | F | H | Me | Me | |
| 3-51 | 3-tert-butyl-1,2,4-oxadiazol-5-yl | H | I | H | Me | H | |
| 3-52 | 3-tert-butyl-1,2,4-oxadiazol-5-yl | H | I | H | Me | Me | |
| 3-53 | 3-tert-butyl-1,2,4-oxadiazol-5-yl | H | CN | H | Me | H | |
| 3-54 | 3-tert-butyl-1,2,4-oxadiazol-5-yl | H | CN | H | Me | Me | |
| 3-55 | 3-tert-butyl-1,2,4-oxadiazol-5-yl | H | CF₃ | H | Me | H | |
| 3-56 | 3-tert-butyl-1,2,4-oxadiazol-5-yl | H | CF₃ | H | Me | Me | |
| 3-57 | 3-tert-butyl-1,2,4-oxadiazol-5-yl | F | Cl | H | Me | H | |
| 3-58 | 3-tert-butyl-1,2,4-oxadiazol-5-yl | F | Cl | H | Me | Me | |
| 3-59 | 3-tert-butyl-1,2,4-oxadiazol-5-yl | F | Cl | H | Me | Et | |
| 3-60 | 3-tert-butyl-1,2,4-oxadiazol-5-yl | F | Br | H | Me | H | |
| 3-61 | 3-tert-butyl-1,2,4-oxadiazol-5-yl | F | Br | H | Me | Me | |
| 3-62 | 3-tert-butyl-1,2,4-oxadiazol-5-yl | F | Br | H | Me | Et | |
| 3-63 | 3-tert-butyl-1,2,4-oxadiazol-5-yl | F | F | H | Me | H | |
| 3-64 | 3-tert-butyl-1,2,4-oxadiazol-5-yl | F | F | H | Me | Me | |
| 3-65 | 3-tert-butyl-1,2,4-oxadiazol-5-yl | F | I | H | Me | H | |
| 3-66 | 3-tert-butyl-1,2,4-oxadiazol-5-yl | F | I | H | Me | Me | |
| 3-67 | 3-tert-butyl-1,2,4-oxadiazol-5-yl | F | CN | H | Me | H | |
| 3-68 | 3-tert-butyl-1,2,4-oxadiazol-5-yl | F | CN | H | Me | Me | |
| 3-69 | 3-tert-butyl-1,2,4-oxadiazol-5-yl | F | CF₃ | H | Me | H | |
| 3-70 | 3-tert-butyl-1,2,4-oxadiazol-5-yl | F | CF₃ | H | Me | Me | |
| 3-71 | 3-tert-butyl-1,2,4-oxadiazol-5-yl | Cl | Cl | H | Me | H | |

TABLE 3-continued

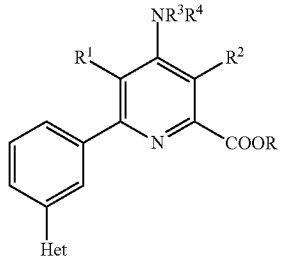

(I-iii)

| No. | Het | $R^1$ | $R^2$ | $R^3$ | $R^4$ | R | Physical data: $^1$H NMR: δ [CDCl$_3$] |
|---|---|---|---|---|---|---|---|
| 3-72 | 3-tert-butyl-1,2,4-oxadiazol-5-yl | Cl | Cl | H | Me | Me | |
| 3-73 | 3-tert-butyl-1,2,4-oxadiazol-5-yl | Cl | Cl | H | Me | Et | |
| 3-74 | 3-tert-butyl-1,2,4-oxadiazol-5-yl | Cl | Br | H | Me | H | |
| 3-75 | 3-tert-butyl-1,2,4-oxadiazol-5-yl | Cl | Br | H | Me | Me | |
| 3-76 | 3-tert-butyl-1,2,4-oxadiazol-5-yl | Cl | Br | H | Me | Et | |
| 3-77 | 3-tert-butyl-1,2,4-oxadiazol-5-yl | Cl | F | H | Me | H | |
| 3-78 | 3-tert-butyl-1,2,4-oxadiazol-5-yl | Cl | F | H | Me | Me | |
| 3-79 | 3-tert-butyl-1,2,4-oxadiazol-5-yl | Cl | I | H | Me | H | |
| 3-80 | 3-tert-butyl-1,2,4-oxadiazol-5-yl | Cl | I | H | Me | Me | |
| 3-81 | 3-tert-butyl-1,2,4-oxadiazol-5-yl | Cl | CN | H | Me | H | |
| 3-82 | 3-tert-butyl-1,2,4-oxadiazol-5-yl | Cl | CN | H | Me | Me | |
| 3-83 | 3-tert-butyl-1,2,4-oxadiazol-5-yl | Cl | CF$_3$ | H | Me | H | |
| 3-84 | 3-tert-butyl-1,2,4-oxadiazol-5-yl | Cl | CF$_3$ | H | Me | Me | |
| 3-85 | 3-tert-butyl-1,2,4-oxadiazol-5-yl | H | Cl | Me | Me | H | |
| 3-86 | 3-tert-butyl-1,2,4-oxadiazol-5-yl | H | Cl | Me | Me | Me | |
| 3-87 | 3-tert-butyl-1,2,4-oxadiazol-5-yl | H | Cl | Me | Me | Et | |
| 3-88 | 3-tert-butyl-1,2,4-oxadiazol-5-yl | H | Br | Me | Me | H | |
| 3-89 | 3-tert-butyl-1,2,4-oxadiazol-5-yl | H | Br | Me | Me | Me | |
| 3-90 | 3-tert-butyl-1,2,4-oxadiazol-5-yl | H | Br | Me | Me | Et | |
| 3-91 | 3-tert-butyl-1,2,4-oxadiazol-5-yl | H | F | Me | Me | H | |
| 3-92 | 3-tert-butyl-1,2,4-oxadiazol-5-yl | H | F | Me | Me | Me | |
| 3-93 | 3-tert-butyl-1,2,4-oxadiazol-5-yl | H | I | Me | Me | H | |
| 3-94 | 3-tert-butyl-1,2,4-oxadiazol-5-yl | H | I | Me | Me | Me | |
| 3-95 | 3-tert-butyl-1,2,4-oxadiazol-5-yl | H | CN | Me | Me | H | |
| 3-96 | 3-tert-butyl-1,2,4-oxadiazol-5-yl | H | CN | Me | Me | Me | |
| 3-97 | 3-tert-butyl-1,2,4-oxadiazol-5-yl | H | CF$_3$ | Me | Me | H | |
| 3-98 | 3-tert-butyl-1,2,4-oxadiazol-5-yl | H | CF$_3$ | Me | Me | Me | |
| 3-99 | 3-tert-butyl-1,2,4-oxadiazol-5-yl | F | Cl | Me | Me | H | |
| 3-100 | 3-tert-butyl-1,2,4-oxadiazol-5-yl | F | Cl | Me | Me | Me | |
| 3-101 | 3-tert-butyl-1,2,4-oxadiazol-5-yl | F | Cl | Me | Me | Et | |
| 3-102 | 3-tert-butyl-1,2,4-oxadiazol-5-yl | F | Br | Me | Me | H | |
| 3-103 | 3-tert-butyl-1,2,4-oxadiazol-5-yl | F | Br | Me | Me | Me | |
| 3-104 | 3-tert-butyl-1,2,4-oxadiazol-5-yl | F | Br | Me | Me | Et | |
| 3-105 | 3-tert-butyl-1,2,4-oxadiazol-5-yl | F | F | Me | Me | H | |
| 3-106 | 3-tert-butyl-1,2,4-oxadiazol-5-yl | F | F | Me | Me | Me | |
| 3-107 | 3-tert-butyl-1,2,4-oxadiazol-5-yl | F | I | Me | Me | H | |
| 3-108 | 3-tert-butyl-1,2,4-oxadiazol-5-yl | F | I | Me | Me | Me | |
| 3-109 | 3-tert-butyl-1,2,4-oxadiazol-5-yl | F | CN | Me | Me | H | |
| 3-110 | 3-tert-butyl-1,2,4-oxadiazol-5-yl | F | CN | Me | Me | Me | |
| 3-111 | 3-tert-butyl-1,2,4-oxadiazol-5-yl | F | CF$_3$ | Me | Me | H | |
| 3-112 | 3-tert-butyl-1,2,4-oxadiazol-5-yl | F | CF$_3$ | Me | Me | Me | |
| 3-113 | 3-tert-butyl-1,2,4-oxadiazol-5-yl | Cl | Cl | Me | Me | H | |
| 3-114 | 3-tert-butyl-1,2,4-oxadiazol-5-yl | Cl | Cl | Me | Me | Me | |
| 3-115 | 3-tert-butyl-1,2,4-oxadiazol-5-yl | Cl | Cl | Me | Me | Et | |
| 3-116 | 3-tert-butyl-1,2,4-oxadiazol-5-yl | Cl | Br | Me | Me | H | |
| 3-117 | 3-tert-butyl-1,2,4-oxadiazol-5-yl | Cl | Br | Me | Me | Me | |
| 3-118 | 3-tert-butyl-1,2,4-oxadiazol-5-yl | Cl | Br | Me | Me | Et | |
| 3-119 | 3-tert-butyl-1,2,4-oxadiazol-5-yl | Cl | F | Me | Me | H | |
| 3-120 | 3-tert-butyl-1,2,4-oxadiazol-5-yl | Cl | F | Me | Me | Me | |
| 3-121 | 3-tert-butyl-1,2,4-oxadiazol-5-yl | Cl | I | Me | Me | H | |
| 3-122 | 3-tert-butyl-1,2,4-oxadiazol-5-yl | Cl | I | Me | Me | Me | |
| 3-123 | 3-tert-butyl-1,2,4-oxadiazol-5-yl | Cl | CN | Me | Me | H | |
| 3-124 | 3-tert-butyl-1,2,4-oxadiazol-5-yl | Cl | CN | Me | Me | Me | |
| 3-125 | 3-tert-butyl-1,2,4-oxadiazol-5-yl | Cl | CF$_3$ | Me | Me | H | |
| 3-126 | 3-tert-butyl-1,2,4-oxadiazol-5-yl | Cl | CF$_3$ | Me | Me | Me | |
| 3-127 | 3-tert-butyl-1,2,4-oxadiazol-5-yl | H | Cl | =CHNMe$_2$ | | H | |
| 3-128 | 3-tert-butyl-1,2,4-oxadiazol-5-yl | H | Cl | =CHNMe$_2$ | | Me | |
| 3-129 | 3-tert-butyl-1,2,4-oxadiazol-5-yl | H | Cl | =CHNMe$_2$ | | Et | |
| 3-130 | 3-tert-butyl-1,2,4-oxadiazol-5-yl | H | Br | =CHNMe$_2$ | | H | |
| 3-131 | 3-tert-butyl-1,2,4-oxadiazol-5-yl | H | Br | =CHNMe$_2$ | | Me | |
| 3-132 | 3-tert-butyl-1,2,4-oxadiazol-5-yl | H | Br | =CHNMe$_2$ | | Et | |
| 3-133 | 3-tert-butyl-1,2,4-oxadiazol-5-yl | H | F | =CHNMe$_2$ | | H | |
| 3-134 | 3-tert-butyl-1,2,4-oxadiazol-5-yl | H | F | =CHNMe$_2$ | | Me | |

TABLE 3-continued

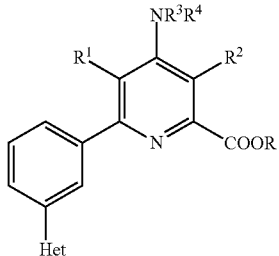
(I-iii)

| No. | Het | R$^1$ | R$^2$ | R$^3$ | R$^4$ | R | Physical data: $^1$H NMR: δ [CDCl$_3$] |
|---|---|---|---|---|---|---|---|
| 3-135 | 3-tert-butyl-1,2,4-oxadiazol-5-yl | H | I | =CHNMe$_2$ | | H | |
| 3-136 | 3-tert-butyl-1,2,4-oxadiazol-5-yl | H | I | =CHNMe$_2$ | | Me | |
| 3-137 | 3-tert-butyl-1,2,4-oxadiazol-5-yl | H | CN | =CHNMe$_2$ | | H | |
| 3-138 | 3-tert-butyl-1,2,4-oxadiazol-5-yl | H | CN | =CHNMe$_2$ | | Me | |
| 3-139 | 3-tert-butyl-1,2,4-oxadiazol-5-yl | H | CF$_3$ | =CHNMe$_2$ | | H | |
| 3-140 | 3-tert-butyl-1,2,4-oxadiazol-5-yl | H | CF$_3$ | =CHNMe$_2$ | | Me | |
| 3-141 | 3-tert-butyl-1,2,4-oxadiazol-5-yl | F | Cl | =CHNMe$_2$ | | H | |
| 3-142 | 3-tert-butyl-1,2,4-oxadiazol-5-yl | F | Cl | =CHNMe$_2$ | | Me | |
| 3-143 | 3-tert-butyl-1,2,4-oxadiazol-5-yl | F | Cl | =CHNMe$_2$ | | Et | |
| 3-144 | 3-tert-butyl-1,2,4-oxadiazol-5-yl | F | Br | =CHNMe$_2$ | | H | |
| 3-145 | 3-tert-butyl-1,2,4-oxadiazol-5-yl | F | Br | =CHNMe$_2$ | | Me | |
| 3-146 | 3-tert-butyl-1,2,4-oxadiazol-5-yl | F | Br | =CHNMe$_2$ | | Et | |
| 3-147 | 3-tert-butyl-1,2,4-oxadiazol-5-yl | F | F | =CHNMe$_2$ | | H | |
| 3-148 | 3-tert-butyl-1,2,4-oxadiazol-5-yl | F | F | =CHNMe$_2$ | | Me | |
| 3-149 | 3-tert-butyl-1,2,4-oxadiazol-5-yl | F | I | =CHNMe$_2$ | | H | |
| 3-150 | 3-tert-butyl-1,2,4-oxadiazol-5-yl | F | I | =CHNMe$_2$ | | Me | |
| 3-151 | 3-tert-butyl-1,2,4-oxadiazol-5-yl | F | CN | =CHNMe$_2$ | | H | |
| 3-152 | 3-tert-butyl-1,2,4-oxadiazol-5-yl | F | CN | =CHNMe$_2$ | | Me | |
| 3-153 | 3-tert-butyl-1,2,4-oxadiazol-5-yl | F | CF$_3$ | =CHNMe$_2$ | | H | |
| 3-154 | 3-tert-butyl-1,2,4-oxadiazol-5-yl | F | CF$_3$ | =CHNMe$_2$ | | Me | |
| 3-155 | 3-tert-butyl-1,2,4-oxadiazol-5-yl | Cl | Cl | =CHNMe$_2$ | | H | |
| 3-156 | 3-tert-butyl-1,2,4-oxadiazol-5-yl | Cl | Cl | =CHNMe$_2$ | | Me | |
| 3-157 | 3-tert-butyl-1,2,4-oxadiazol-5-yl | Cl | Cl | =CHNMe$_2$ | | Et | |
| 3-158 | 3-tert-butyl-1,2,4-oxadiazol-5-yl | Cl | Br | =CHNMe$_2$ | | H | |
| 3-159 | 3-tert-butyl-1,2,4-oxadiazol-5-yl | Cl | Br | =CHNMe$_2$ | | Me | |
| 3-160 | 3-tert-butyl-1,2,4-oxadiazol-5-yl | Cl | Br | =CHNMe$_2$ | | Et | |
| 3-161 | 3-tert-butyl-1,2,4-oxadiazol-5-yl | Cl | F | =CHNMe$_2$ | | H | |
| 3-162 | 3-tert-butyl-1,2,4-oxadiazol-5-yl | Cl | F | =CHNMe$_2$ | | Me | |
| 3-163 | 3-tert-butyl-1,2,4-oxadiazol-5-yl | Cl | I | =CHNMe$_2$ | | H | |
| 3-164 | 3-tert-butyl-1,2,4-oxadiazol-5-yl | Cl | I | =CHNMe$_2$ | | Me | |
| 3-165 | 3-tert-butyl-1,2,4-oxadiazol-5-yl | Cl | CN | =CHNMe$_2$ | | H | |
| 3-166 | 3-tert-butyl-1,2,4-oxadiazol-5-yl | Cl | CN | =CHNMe$_2$ | | Me | |
| 3-167 | 3-tert-butyl-1,2,4-oxadiazol-5-yl | Cl | CF$_3$ | =CHNMe$_2$ | | H | |
| 3-168 | 3-tert-butyl-1,2,4-oxadiazol-5-yl | Cl | CF$_3$ | =CHNMe$_2$ | | Me | |
| 3-169 | thien-2-yl | H | Cl | H | H | H | |
| 3-170 | thien-2-yl | H | Cl | H | H | Me | |
| 3-171 | thien-2-yl | H | Cl | H | H | Et | |
| 3-172 | thien-2-yl | H | Br | H | H | H | |
| 3-173 | thien-2-yl | H | Br | H | H | Me | |
| 3-174 | thien-2-yl | H | Br | H | H | Et | |
| 3-175 | thien-2-yl | H | F | H | H | H | |
| 3-176 | thien-2-yl | H | F | H | H | Me | |
| 3-177 | thien-2-yl | H | I | H | H | H | |
| 3-178 | thien-2-yl | H | I | H | H | Me | |
| 3-179 | thien-2-yl | H | CN | H | H | H | |
| 3-180 | thien-2-yl | H | CN | H | H | Me | |
| 3-181 | thien-2-yl | H | CF$_3$ | H | H | H | |
| 3-182 | thien-2-yl | H | CF$_3$ | H | H | Me | |
| 3-183 | thien-2-yl | F | Cl | H | H | H | |
| 3-184 | thien-2-yl | F | Cl | H | H | Me | |
| 3-185 | thien-2-yl | F | Cl | H | H | Et | |
| 3-186 | thien-2-yl | F | Br | H | H | H | |
| 3-187 | thien-2-yl | F | Br | H | H | Me | |
| 3-188 | thien-2-yl | F | Br | H | H | Et | |
| 3-189 | thien-2-yl | F | F | H | H | H | |
| 3-190 | thien-2-yl | F | F | H | H | Me | |
| 3-191 | thien-2-yl | F | I | H | H | H | |
| 3-192 | thien-2-yl | F | I | H | H | Me | |
| 3-193 | thien-2-yl | F | CN | H | H | H | |
| 3-194 | thien-2-yl | F | CN | H | H | Me | |
| 3-195 | thien-2-yl | F | CF$_3$ | H | H | H | |
| 3-196 | thien-2-yl | F | CF$_3$ | H | H | Me | |
| 3-197 | thien-2-yl | H | Cl | H | Me | H | |

TABLE 3-continued

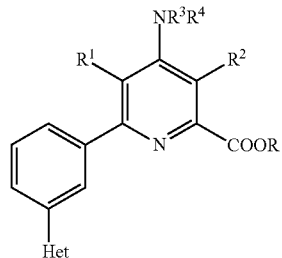

(I-iii)

| No. | Het | $R^1$ | $R^2$ | $R^3$ | $R^4$ | R | Physical data: $^1$H NMR: δ [CDCl$_3$] |
|---|---|---|---|---|---|---|---|
| 3-198 | thien-2-yl | H | Cl | H | Me | Me | |
| 3-199 | thien-2-yl | H | Cl | H | Me | Et | |
| 3-200 | thein-2-yl | H | Br | H | Me | H | |
| 3-201 | thien-2-yl | H | Br | H | Me | Me | |
| 3-202 | thien-2-yl | H | Br | H | Me | Et | |
| 3-203 | thien-2-yl | H | F | H | Me | H | |
| 3-204 | thien-2-yl | H | F | H | Me | Me | |
| 3-205 | thien-2-yl | H | I | H | Me | H | |
| 3-206 | thien-2-yl | H | I | H | Me | Me | |
| 3-207 | thien-2-yl | H | CN | H | Me | H | |
| 3-208 | thien-2-yl | H | CN | H | Me | Me | |
| 3-209 | thien-2-yl | H | CF$_3$ | H | Me | H | |
| 3-210 | thien-2-yl | H | CF$_3$ | H | Me | Me | |
| 3-211 | thien-2-yl | F | Cl | H | Me | H | |
| 3-212 | thien-2-yl | F | Cl | H | Me | Me | |
| 3-213 | thien-2-yl | F | Cl | H | Me | Et | |
| 3-214 | thien-2-yl | F | Br | H | Me | H | |
| 3-215 | thien-2-yl | F | Br | H | Me | Me | |
| 3-216 | thien-2-yl | F | Br | H | Me | Et | |
| 3-217 | thien-2-yl | F | F | H | Me | H | |
| 3-218 | thien-2-yl | F | F | H | Me | Me | |
| 3-219 | thien-2-yl | F | I | H | Me | H | |
| 3-220 | thien-2-yl | F | I | H | Me | Me | |
| 3-221 | thien-2-yl | F | CN | H | Me | H | |
| 3-222 | thien-2-yl | F | CN | H | Me | Me | |
| 3-223 | thien-2-yl | F | CF$_3$ | H | Me | H | |
| 3-224 | thien-2-yl | F | CF$_3$ | H | Me | Me | |
| 3-225 | thien-2-yl | H | Cl | Me | Me | H | |
| 3-226 | thien-2-yl | H | Cl | Me | Me | Me | |
| 3-227 | thien-2-yl | H | Cl | Me | Me | Et | |
| 3-228 | thien-2-yl | H | Br | Me | Me | H | |
| 3-229 | thien-2-yl | H | Br | Me | Me | Me | |
| 3-230 | thien-2-yl | H | Br | Me | Me | Et | |
| 3-231 | thien-2-yl | H | F | Me | Me | H | |
| 3-232 | thien-2-yl | H | F | Me | Me | Me | |
| 3-233 | thien-2-yl | H | I | Me | Me | H | |
| 3-234 | thien-2-yl | H | I | Me | Me | Me | |
| 3-235 | thien-2-yl | H | CN | Me | Me | H | |
| 3-236 | thien-2-yl | H | CN | Me | Me | Me | |
| 3-237 | thien-2-yl | H | CF$_3$ | Me | Me | H | |
| 3-238 | thien-2-yl | H | CF$_3$ | Me | Me | Me | |
| 3-239 | thien-2-yl | F | Cl | Me | Me | H | |
| 3-240 | thien-2-yl | F | Cl | Me | Me | Me | |
| 3-241 | thien-2-yl | F | Cl | Me | Me | Et | |
| 3-242 | thien-2-yl | F | Br | Me | Me | H | |
| 3-243 | thien-2-yl | F | Br | Me | Me | Me | |
| 3-244 | thien-2-yl | F | Br | Me | Me | Et | |
| 3-245 | thien-2-yl | F | F | Me | Me | H | |
| 3-246 | thien-2-yl | F | F | Me | Me | Me | |
| 3-247 | thien-2-yl | F | I | Me | Me | H | |
| 3-248 | thien-2-yl | F | I | Me | Me | Me | |
| 3-249 | thien-2-yl | F | CN | Me | Me | H | |
| 3-250 | thien-2-yl | F | CN | Me | Me | Me | |
| 3-251 | thien-2-yl | F | CF$_3$ | Me | Me | H | |
| 3-252 | thien-2-yl | F | CF$_3$ | Me | Me | Me | |
| 3-253 | thien-2-yl | H | Cl | =CHNMe$_2$ | | H | |
| 3-254 | thien-2-yl | H | Cl | =CHNMe$_2$ | | Me | |
| 3-255 | thien-2-yl | H | Cl | =CHNMe$_2$ | | Et | |
| 3-256 | thien-2-yl | H | Br | =CHNMe$_2$ | | H | |
| 3-257 | thien-2-yl | H | Br | =CHNMe$_2$ | | Me | |
| 3-258 | thien-2-yl | H | Br | =CHNMe$_2$ | | Et | |
| 3-259 | thien-2-yl | H | F | =CHNMe$_2$ | | H | |
| 3-260 | thien-2-yl | H | F | =CHNMe$_2$ | | Me | |

TABLE 3-continued (I-iii)

Structure: Pyridine with NR³R⁴ at position 4, R¹ at position 5, R² at position 3, COOR at position 2, and a phenyl group at position 6 bearing Het at the meta position.

| No. | Het | R¹ | R² | R³ | R⁴ | R | Physical data: ¹H NMR: δ [CDCl₃] |
|---|---|---|---|---|---|---|---|
| 3-261 | thien-2-yl | H | I | =CHNMe₂ | | H | |
| 3-262 | thien-2-yl | H | I | =CHNMe₂ | | Me | |
| 3-263 | thien-2-yl | H | CN | =CHNMe₂ | | H | |
| 3-264 | thien-2-yl | H | CN | =CHNMe₂ | | Me | |
| 3-265 | thien-2-yl | H | CF₃ | =CHNMe₂ | | H | |
| 3-266 | thien-2-yl | H | CF₃ | =CHNMe₂ | | Me | |
| 3-267 | thien-2-yl | F | Cl | =CHNMe₂ | | H | |
| 3-268 | thien-2-yl | F | Cl | =CHNMe₂ | | Me | |
| 3-269 | thien-2-yl | F | Cl | =CHNMe₂ | | Et | |
| 3-270 | thien-2-yl | F | Br | =CHNMe₂ | | H | |
| 3-271 | thien-2-yl | F | Br | =CHNMe₂ | | Me | |
| 3-272 | thien-2-yl | F | Br | =CHNMe₂ | | Et | |
| 3-273 | thien-2-yl | F | F | =CHNMe₂ | | H | |
| 3-274 | thien-2-yl | F | F | =CHNMe₂ | | Me | |
| 3-275 | thien-2-yl | F | I | =CHNMe₂ | | H | |
| 3-276 | thien-2-yl | F | I | =CHNMe₂ | | Me | |
| 3-277 | thien-2-yl | F | CN | =CHNMe₂ | | H | |
| 3-278 | thien-2-yl | F | CN | =CHNMe₂ | | Me | |
| 3-279 | thien-2-yl | F | CF₃ | =CHNMe₂ | | H | |
| 3-280 | thien-2-yl | F | CF₃ | =CHNMe₂ | | Me | |
| 3-281 | pyrrol-1-yl | H | Cl | H | H | H | |
| 3-282 | pyrrol-1-yl | H | Cl | H | H | Me | |
| 3-283 | pyrrol-1-yl | H | Cl | H | H | Et | |
| 3-284 | pyrrol-1-yl | H | Br | H | H | H | |
| 3-285 | pyrrol-1-yl | H | Br | H | H | Me | |
| 3-286 | pyrrol-1-yl | H | Br | H | H | Et | |
| 3-287 | pyrrol-1-yl | H | F | H | H | H | |
| 3-288 | pyrrol-1-yl | H | F | H | H | Me | |
| 3-289 | pyrrol-1-yl | H | I | H | H | H | |
| 3-290 | pyrrol-1-yl | H | I | H | H | Me | |
| 3-291 | pyrrol-1-yl | H | CN | H | H | H | |
| 3-292 | pyrrol-1-yl | H | CN | H | H | Me | |
| 3-293 | pyrrol-1-yl | H | CF₃ | H | H | H | |
| 3-294 | pyrrol-1-yl | H | CF₃ | H | H | Me | |
| 3-295 | pyrrol-1-yl | F | Cl | H | H | H | |
| 3-296 | pyrrol-1-yl | F | Cl | H | H | Me | |
| 3-297 | pyrrol-1-yl | F | Cl | H | H | Et | |
| 3-298 | pyrrol-1-yl | F | Br | H | H | H | |
| 3-299 | pyrrol-1-yl | F | Br | H | H | Me | |
| 3-300 | pyrrol-1-yl | F | Br | H | H | Et | |
| 3-301 | pyrrol-1-yl | F | F | H | H | H | |
| 3-302 | pyrrol-1-yl | F | F | H | H | Me | |
| 3-303 | pyrrol-1-yl | F | I | H | H | H | |
| 3-304 | pyrrol-1-yl | F | I | H | H | Me | |
| 3-305 | pyrrol-1-yl | F | CN | H | H | H | |
| 3-306 | pyrrol-1-yl | F | CN | H | H | Me | |
| 3-307 | pyrrol-1-yl | F | CF₃ | H | H | H | |
| 3-308 | pyrrol-1-yl | F | CF₃ | H | H | Me | |
| 3-309 | pyrrol-1-yl | H | Cl | H | Me | H | |
| 3-310 | pyrrol-1-yl | H | Cl | H | Me | Me | |
| 3-311 | pyrrol-1-yl | H | Cl | H | Me | Et | |
| 3-312 | pyrrol-1-yl | H | Br | H | Me | H | |
| 3-313 | pyrrol-1-yl | H | Br | H | Me | Me | |
| 3-314 | pyrrol-1-yl | H | Br | H | Me | Et | |
| 3-315 | pyrrol-1-yl | H | F | H | Me | H | |
| 3-316 | pyrrol-1-yl | H | F | H | Me | Me | |
| 3-317 | pyrrol-1-yl | H | I | H | Me | H | |
| 3-318 | pyrrol-1-yl | H | I | H | Me | Me | |
| 3-319 | pyrrol-1-yl | H | CN | H | Me | H | |
| 3-320 | pyrrol-1-yl | H | CN | H | Me | Me | |
| 3-321 | pyrrol-1-yl | H | CF₃ | H | Me | H | |
| 3-322 | pyrrol-1-yl | H | CF₃ | H | Me | Me | |
| 3-323 | pyrrol-1-yl | F | Cl | H | Me | H | |

TABLE 3-continued

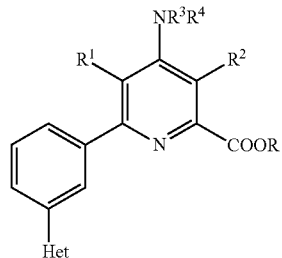

(I-iii)

| No. | Het | R$^1$ | R$^2$ | R$^3$ | R$^4$ | R | Physical data: $^1$H NMR: δ [CDCl$_3$] |
|---|---|---|---|---|---|---|---|
| 3-324 | pyrrol-1-yl | F | Cl | H | Me | Me | |
| 3-325 | pyrrol-1-yl | F | Cl | H | Me | Et | |
| 3-326 | pyrrol-1-yl | F | Br | H | Me | H | |
| 3-327 | pyrrol-1-yl | F | Br | H | Me | Me | |
| 3-328 | pyrrol-1-yl | F | Br | H | Me | Et | |
| 3-329 | pyrrol-1-yl | F | F | H | Me | H | |
| 3-330 | pyrrol-1-yl | F | F | H | Me | Me | |
| 3-331 | pyrrol-1-yl | F | I | H | Me | H | |
| 3-332 | pyrrol-1-yl | F | I | H | Me | Me | |
| 3-333 | pyrrol-1-yl | F | CN | H | Me | H | |
| 3-334 | pyrrol-1-yl | F | CN | H | Me | Me | |
| 3-335 | pyrrol-1-yl | F | CF$_3$ | H | Me | H | |
| 3-336 | pyrrol-1-yl | F | CF$_3$ | H | Me | Me | |
| 3-337 | pyrrol-1-yl | H | Cl | Me | Me | H | |
| 3-338 | pyrrol-1-yl | H | Cl | Me | Me | Me | |
| 3-339 | pyrrol-1-yl | H | Cl | Me | Me | Et | |
| 3-340 | pyrrol-1-yl | H | Br | Me | Me | H | |
| 3-341 | pyrrol-1-yl | H | Br | Me | Me | Me | |
| 3-342 | pyrrol-1-yl | H | Br | Me | Me | Et | |
| 3-343 | pyrrol-1-yl | H | F | Me | Me | H | |
| 3-344 | pyrrol-1-yl | H | F | Me | Me | Me | |
| 3-345 | pyrrol-1-yl | H | I | Me | Me | H | |
| 3-346 | pyrrol-1-yl | H | I | Me | Me | Me | |
| 3-347 | pyrrol-1-yl | H | CN | Me | Me | H | |
| 3-348 | pyrrol-1-yl | H | CN | Me | Me | Me | |
| 3-349 | pyrrol-1-yl | H | CF$_3$ | Me | Me | H | |
| 3-350 | pyrrol-1-yl | H | CF$_3$ | Me | Me | Me | |
| 3-351 | pyrrol-1-yl | F | Cl | Me | Me | H | |
| 3-352 | pyrrol-1-yl | F | Cl | Me | Me | Me | |
| 3-353 | pyrrol-1-yl | F | Cl | Me | Me | Et | |
| 3-354 | pyrrol-1-yl | F | Br | Me | Me | H | |
| 3-355 | pyrrol-1-yl | F | Br | Me | Me | Me | |
| 3-356 | pyrrol-1-yl | F | Br | Me | Me | Et | |
| 3-357 | pyrrol-1-yl | F | F | Me | Me | H | |
| 3-358 | pyrrol-1-yl | F | F | Me | Me | Me | |
| 3-359 | pyrrol-1-yl | F | I | Me | Me | H | |
| 3-360 | pyrrol-1-yl | F | I | Me | Me | Me | |
| 3-361 | pyrrol-1-yl | F | CN | Me | Me | H | |
| 3-362 | pyrrol-1-yl | F | CN | Me | Me | Me | |
| 3-363 | pyrrol-1-yl | F | CF$_3$ | Me | Me | H | |
| 3-364 | pyrrol-1-yl | F | CF$_3$ | Me | Me | Me | |
| 3-365 | pyrrol-1-yl | H | Cl | =CHNMe$_2$ | | H | |
| 3-366 | pyrrol-1-yl | H | Cl | =CHNMe$_2$ | | Me | |
| 3-367 | pyrrol-1-yl | H | Cl | =CHNMe$_2$ | | Et | |
| 3-368 | pyrrol-1-yl | H | Br | =CHNMe$_2$ | | H | |
| 3-369 | pyrrol-1-yl | H | Br | =CHNMe$_2$ | | Me | |
| 3-370 | pyrrol-1-yl | H | Br | =CHNMe$_2$ | | Et | |
| 3-371 | pyrrol-1-yl | H | F | =CHNMe$_2$ | | H | |
| 3-372 | pyrrol-1-yl | H | F | =CHNMe$_2$ | | Me | |
| 3-373 | pyrrol-1-yl | H | I | =CHNMe$_2$ | | H | |
| 3-374 | pyrrol-1-yl | H | I | =CHNMe$_2$ | | Me | |
| 3-375 | pyrrol-1-yl | H | CN | =CHNMe$_2$ | | H | |
| 3-376 | pyrrol-1-yl | H | CN | =CHNMe$_2$ | | Me | |
| 3-377 | pyrrol-1-yl | H | CF$_3$ | =CHNMe$_2$ | | H | |
| 3-378 | pyrrol-1-yl | H | CF$_3$ | =CHNMe$_2$ | | Me | |
| 3-379 | pyrrol-1-yl | F | Cl | =CHNMe$_2$ | | H | |
| 3-380 | pyrrol-1-yl | F | Cl | =CHNMe$_2$ | | Me | |
| 3-381 | pyrrol-1-yl | F | Cl | =CHNMe$_2$ | | Et | |
| 3-382 | pyrrol-1-yl | F | Br | =CHNMe$_2$ | | H | |
| 3-383 | pyrrol-1-yl | F | Br | =CHNMe$_2$ | | Me | |
| 3-384 | pyrrol-1-yl | F | Br | =CHNMe$_2$ | | Et | |
| 3-385 | pyrrol-1-yl | F | F | =CHNMe$_2$ | | H | |
| 3-386 | pyrrol-1-yl | F | F | =CHNMe$_2$ | | Me | |

TABLE 3-continued

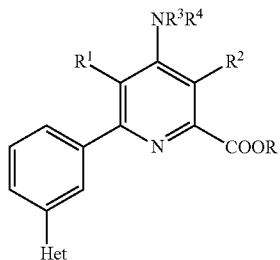

(I-iii)

| No. | Het | R¹ | R² | R³ | R⁴ | R | Physical data: $^1$H NMR: δ [CDCl$_3$] |
|---|---|---|---|---|---|---|---|
| 3-387 | pyrrol-1-yl | F | I | =CHNMe$_2$ | | H | |
| 3-388 | pyrrol-1-yl | F | I | =CHNMe$_2$ | | Me | |
| 3-389 | pyrrol-1-yl | F | CN | =CHNMe$_2$ | | H | |
| 3-390 | pyrrol-1-yl | F | CN | =CHNMe$_2$ | | Me | |
| 3-391 | pyrrol-1-yl | F | CF$_3$ | =CHNMe$_2$ | | H | |
| 3-392 | pyrrol-1-yl | F | CF$_3$ | =CHNMe$_2$ | | Me | |
| 3-393 | pyrazol-1-yl | H | Cl | H | H | H | |
| 3-394 | pyrazol-1-yl | H | Cl | H | H | Me | |
| 3-395 | pyrazol-1-yl | H | Cl | H | H | Et | |
| 3-396 | pyrazol-1-yl | H | Br | H | H | H | |
| 3-397 | pyrazol-1-yl | H | Br | H | H | Me | |
| 3-398 | pyrazol-1-yl | H | Br | H | H | Et | |
| 3-399 | pyrazol-1-yl | H | F | H | H | H | |
| 3-400 | pyrazol-1-yl | H | F | H | H | Me | |
| 3-401 | pyrazol-1-yl | H | I | H | H | H | |
| 3-402 | pyrazol-1-yl | H | I | H | H | Me | |
| 3-403 | pyrazol-1-yl | H | CN | H | H | H | |
| 3-404 | pyrazol-1-yl | H | CN | H | H | Me | |
| 3-405 | pyrazol-1-yl | H | CF$_3$ | H | H | H | |
| 3-406 | pyrazol-1-yl | H | CF$_3$ | H | H | Me | |
| 3-407 | pyrazol-1-yl | F | Cl | H | H | H | |
| 3-408 | pyrazol-1-yl | F | Cl | H | H | Me | |
| 3-409 | pyrazol-1-yl | F | Cl | H | H | Et | |
| 3-410 | pyrazol-1-yl | F | Br | H | H | H | |
| 3-411 | pyrazol-1-yl | F | Br | H | H | Me | |
| 3-412 | pyrazol-1-yl | F | Br | H | H | Et | |
| 3-413 | pyrazol-1-yl | F | F | H | H | H | |
| 3-414 | pyrazol-1-yl | F | F | H | H | Me | |
| 3-415 | pyrazol-1-yl | F | I | H | H | H | |
| 3-416 | pyrazol-1-yl | F | I | H | H | Me | |
| 3-417 | pyrazol-1-yl | F | CN | H | H | H | |
| 3-418 | pyrazol-1-yl | F | CN | H | H | Me | |
| 3-419 | pyrazol-1-yl | F | CF$_3$ | H | H | H | |
| 3-420 | pyrazol-1-yl | F | CF$_3$ | H | H | Me | |
| 3-421 | pyrazol-1-yl | H | Cl | H | Me | H | |
| 3-422 | pyrazol-1-yl | H | Cl | H | Me | Me | |
| 3-423 | pyrazol-1-yl | H | Cl | H | Me | Et | |
| 3-424 | pyrazol-1-yl | H | Br | H | Me | H | |
| 3-425 | pyrazol-1-yl | H | Br | H | Me | Me | |
| 3-426 | pyrazol-1-yl | H | Br | H | Me | Et | |
| 3-427 | pyrazol-1-yl | H | F | H | Me | H | |
| 3-428 | pyrazol-1-yl | H | F | H | Me | Me | |
| 3-429 | pyrazol-1-yl | H | I | H | Me | H | |
| 3-430 | pyrazol-1-yl | H | I | H | Me | Me | |
| 3-431 | pyrazol-1-yl | H | CN | H | Me | H | |
| 3-432 | pyrazol-1-yl | H | CN | H | Me | Me | |
| 3-433 | pyrazol-1-yl | H | CF$_3$ | H | Me | H | |
| 3-434 | pyrazol-1-yl | H | CF$_3$ | H | Me | Me | |
| 3-435 | pyrazol-1-yl | F | Cl | H | Me | H | |
| 3-436 | pyrazol-1-yl | F | Cl | H | Me | Me | |
| 3-437 | pyrazol-1-yl | F | Cl | H | Me | Et | |
| 3-438 | pyrazol-1-yl | F | Br | H | Me | H | |
| 3-439 | pyrazol-1-yl | F | Br | H | Me | Me | |
| 3-440 | pyrazol-1-yl | F | Br | H | Me | Et | |
| 3-441 | pyrazol-1-yl | F | F | H | Me | H | |
| 3-442 | pyrazol-1-yl | F | F | H | Me | Me | |
| 3-443 | pyrazol-1-yl | F | I | H | Me | H | |
| 3-444 | pyrazol-1-yl | F | I | H | Me | Me | |
| 3-445 | pyrazol-1-yl | F | CN | H | Me | H | |
| 3-446 | pyrazol-1-yl | F | CN | H | Me | Me | |
| 3-447 | pyrazol-1-yl | F | CF$_3$ | H | Me | H | |
| 3-448 | pyrazol-1-yl | F | CF$_3$ | H | Me | Me | |
| 3-449 | pyrazol-1-yl | H | Cl | Me | Me | H | |

TABLE 3-continued

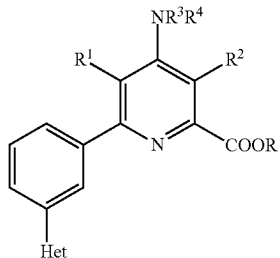

(I-iii)

| No. | Het | $R^1$ | $R^2$ | $R^3$ | $R^4$ | R | Physical data: $^1$H NMR: δ [CDCl$_3$] |
|---|---|---|---|---|---|---|---|
| 3-450 | pyrazol-1-yl | H | Cl | Me | Me | Me | |
| 3-451 | pyrazol-1-yl | H | Cl | Me | Me | Et | |
| 3-452 | pyrazol-1-yl | H | Br | Me | Me | H | |
| 3-453 | pyrazol-1-yl | H | Br | Me | Me | Me | |
| 3-454 | pyrazol-1-yl | H | Br | Me | Me | Et | |
| 3-455 | pyrazol-1-yl | H | F | Me | Me | H | |
| 3-456 | pyrazol-1-yl | H | F | Me | Me | Me | |
| 3-457 | pyrazol-1-yl | H | I | Me | Me | H | |
| 3-458 | pyrazol-1-yl | H | I | Me | Me | Me | |
| 3-459 | pyrazol-1-yl | H | CN | Me | Me | H | |
| 3-460 | pyrazol-1-yl | H | CN | Me | Me | Me | |
| 3-461 | pyrazol-1-yl | H | CF$_3$ | Me | Me | H | |
| 3-462 | pyrazol-1-yl | H | CF$_3$ | Me | Me | Me | |
| 3-463 | pyrazol-1-yl | F | Cl | Me | Me | H | |
| 3-464 | pyrazol-1-yl | F | Cl | Me | Me | Me | |
| 3-465 | pyrazol-1-yl | F | Cl | Me | Me | Et | |
| 3-466 | pyrazol-1-yl | F | Br | Me | Me | H | |
| 3-467 | pyrazol-1-yl | F | Br | Me | Me | Me | |
| 3-468 | pyrazol-1-yl | F | Br | Me | Me | Et | |
| 3-469 | pyrazol-1-yl | F | F | Me | Me | H | |
| 3-470 | pyrazol-1-yl | F | F | Me | Me | Me | |
| 3-471 | pyrazol-1-yl | F | I | Me | Me | H | |
| 3-472 | pyrazol-1-yl | F | I | Me | Me | Me | |
| 3-473 | pyrazol-1-yl | F | CN | Me | Me | H | |
| 3-474 | pyrazol-1-yl | F | CN | Me | Me | Me | |
| 3-475 | pyrazol-1-yl | F | CF$_3$ | Me | Me | H | |
| 3-476 | pyrazol-1-yl | F | CF$_3$ | Me | Me | Me | |
| 3-477 | pyrazol-1-yl | H | Cl | =CHNMe$_2$ | | H | |
| 3-478 | pyrazol-1-yl | H | Cl | =CHNMe$_2$ | | Me | |
| 3-479 | pyrazol-1-yl | H | Cl | =CHNMe$_2$ | | Et | |
| 3-480 | pyrazol-1-yl | H | Br | =CHNMe$_2$ | | H | |
| 3-481 | pyrazol-1-yl | H | Br | =CHNMe$_2$ | | Me | |
| 3-482 | pyrazol-1-yl | H | Br | =CHNMe$_2$ | | Et | |
| 3-483 | pyrazol-1-yl | H | F | =CHNMe$_2$ | | H | |
| 3-484 | pyrazol-1-yl | H | F | =CHNMe$_2$ | | Me | |
| 3-485 | pyrazol-1-yl | H | I | =CHNMe$_2$ | | H | |
| 3-486 | pyrazol-1-yl | H | I | =CHNMe$_2$ | | Me | |
| 3-487 | pyrazol-1-yl | H | CN | =CHNMe$_2$ | | H | |
| 3-488 | pyrazol-1-yl | H | CN | =CHNMe$_2$ | | Me | |
| 3-489 | pyrazol-1-yl | H | CF$_3$ | =CHNMe$_2$ | | H | |
| 3-490 | pyrazol-1-yl | H | CF$_3$ | =CHNMe$_2$ | | Me | |
| 3-491 | pyrazol-1-yl | F | Cl | =CHNMe$_2$ | | H | |
| 3-492 | pyrazol-1-yl | F | Cl | =CHNMe$_2$ | | Me | |
| 3-493 | pyrazol-1-yl | F | Cl | =CHNMe$_2$ | | Et | |
| 3-494 | pyrazol-1-yl | F | Br | =CHNMe$_2$ | | H | |
| 3-495 | pyrazol-1-yl | F | Br | =CHNMe$_2$ | | Me | |
| 3-496 | pyrazol-1-yl | F | Br | =CHNMe$_2$ | | Et | |
| 3-497 | pyrazol-1-yl | F | F | =CHNMe$_2$ | | H | |
| 3-498 | pyrazol-1-yl | F | F | =CHNMe$_2$ | | Me | |
| 3-499 | pyrazol-1-yl | F | I | =CHNMe$_2$ | | H | |
| 3-500 | pyrazol-1-yl | F | I | =CHNMe$_2$ | | Me | |
| 3-501 | pyrazol-1-yl | F | CN | =CHNMe$_2$ | | H | |
| 3-502 | pyrazol-1-yl | F | CN | =CHNMe$_2$ | | Me | |
| 3-503 | pyrazol-1-yl | F | CF$_3$ | =CHNMe$_2$ | | H | |
| 3-504 | pyrazol-1-yl | F | CF$_3$ | =CHNMe$_2$ | | Me | |
| 3-505 | pyridin-3-yl | H | Cl | H | H | H | |
| 3-506 | pyridin-3-yl | H | Cl | H | H | Me | |
| 3-507 | pyridin-3-yl | H | Cl | H | H | Et | |
| 3-508 | pyridin-3-yl | H | Br | H | H | H | |
| 3-509 | pyridin-3-yl | H | Br | H | H | Me | |
| 3-510 | pyridin-3-yl | H | Br | H | H | Et | |
| 3-511 | pyridin-3-yl | H | F | H | H | H | |
| 3-512 | pyridin-3-yl | H | F | H | H | Me | |

TABLE 3-continued

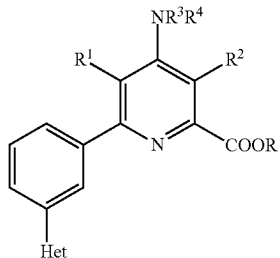
(I-iii)

| No. | Het | R¹ | R² | R³ | R⁴ | R | Physical data: $^1$H NMR: δ [CDCl$_3$] |
|---|---|---|---|---|---|---|---|
| 3-513 | pyridin-3-yl | H | I | H | H | H | |
| 3-514 | pyridin-3-yl | H | I | H | H | Me | |
| 3-515 | pyridin-3-yl | H | CN | H | H | H | |
| 3-516 | pyridin-3-yl | H | CN | H | H | Me | |
| 3-517 | pyridin-3-yl | H | CF$_3$ | H | H | H | |
| 3-518 | pyridin-3-yl | H | CF$_3$ | H | H | Me | |
| 3-519 | pyridin-3-yl | F | Cl | H | H | H | |
| 3-520 | pyridin-3-yl | F | Cl | H | H | Me | |
| 3-521 | pyridin-3-yl | F | Cl | H | H | Et | |
| 3-522 | pyridin-3-yl | F | Br | H | H | H | |
| 3-523 | pyridin-3-yl | F | Br | H | H | Me | |
| 3-524 | pyridin-3-yl | F | Br | H | H | Et | |
| 3-525 | pyridin-3-yl | F | F | H | H | H | |
| 3-526 | pyridin-3-yl | F | F | H | H | Me | |
| 3-527 | pyridin-3-yl | F | I | H | H | H | |
| 3-528 | pyridin-3-yl | F | I | H | H | Me | |
| 3-529 | pyridin-3-yl | F | CN | H | H | H | |
| 3-530 | pyridin-3-yl | F | CN | H | H | Me | |
| 3-531 | pyridin-3-yl | F | CF$_3$ | H | H | H | |
| 3-532 | pyridin-3-yl | F | CF$_3$ | H | H | Me | |
| 3-533 | pyridin-3-yl | H | Cl | H | Me | H | |
| 3-534 | pyridin-3-yl | H | Cl | H | Me | Me | |
| 3-535 | pyridin-3-yl | H | Cl | H | Me | Et | |
| 3-536 | pyridin-3-yl | H | Br | H | Me | H | |
| 3-537 | pyridin-3-yl | H | Br | H | Me | Me | |
| 3-538 | pyridin-3-yl | H | Br | H | Me | Et | |
| 3-539 | pyridin-3-yl | H | F | H | Me | H | |
| 3-540 | pyridin-3-yl | H | F | H | Me | Me | |
| 3-541 | pyridin-3-yl | H | I | H | Me | H | |
| 3-542 | pyridin-3-yl | H | I | H | Me | Me | |
| 3-543 | pyridin-3-yl | H | CN | H | Me | H | |
| 3-544 | pyridin-3-yl | H | CN | H | Me | Me | |
| 3-545 | pyridin-3-yl | H | CF$_3$ | H | Me | H | |
| 3-546 | pyridin-3-yl | H | CF$_3$ | H | Me | Me | |
| 3-547 | pyridin-3-yl | F | Cl | H | Me | H | |
| 3-548 | pyridin-3-yl | F | Cl | H | Me | Me | |
| 3-549 | pyridin-3-yl | F | Cl | H | Me | Et | |
| 3-550 | pyridin-3-yl | F | Br | H | Me | H | |
| 3-551 | pyridin-3-yl | F | Br | H | Me | Me | |
| 3-552 | pyridin-3-yl | F | Br | H | Me | Et | |
| 3-553 | pyridin-3-yl | F | F | H | Me | H | |
| 3-554 | pyridin-3-yl | F | F | H | Me | Me | |
| 3-555 | pyridin-3-yl | F | I | H | Me | H | |
| 3-556 | pyridin-3-yl | F | I | H | Me | Me | |
| 3-557 | pyridin-3-yl | F | CN | H | Me | H | |
| 3-558 | pyridin-3-yl | F | CN | H | Me | Me | |
| 3-559 | pyridin-3-yl | F | CF$_3$ | H | Me | H | |
| 3-560 | pyridin-3-yl | F | CF$_3$ | H | Me | Me | |
| 3-561 | pyridin-3-yl | H | Cl | Me | Me | H | |
| 3-562 | pyridin-3-yl | H | Cl | Me | Me | Me | |
| 3-563 | pyridin-3-yl | H | Cl | Me | Me | Et | |
| 3-564 | pyridin-3-yl | H | Br | Me | Me | H | |
| 3-565 | pyridin-3-yl | H | Br | Me | Me | Me | |
| 3-566 | pyridin-3-yl | H | Br | Me | Me | Et | |
| 3-567 | pyridin-3-yl | H | F | Me | Me | H | |
| 3-568 | pyridin-3-yl | H | F | Me | Me | Me | |
| 3-569 | pyridin-3-yl | H | I | Me | Me | H | |
| 3-570 | pyridin-3-yl | H | I | Me | Me | Me | |
| 3-571 | pyridin-3-yl | H | CN | Me | Me | H | |
| 3-572 | pyridin-3-yl | H | CN | Me | Me | Me | |
| 3-573 | pyridin-3-yl | H | CF$_3$ | Me | Me | H | |
| 3-574 | pyridin-3-yl | H | CF$_3$ | Me | Me | Me | |
| 3-575 | pyridin-3-yl | F | Cl | Me | Me | H | |

TABLE 3-continued

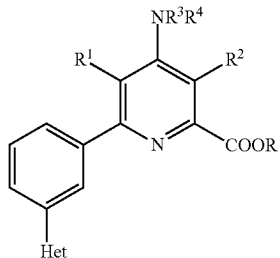

(I-iii)

| No. | Het | R¹ | R² | R³ | R⁴ | R | Physical data: $^1$H NMR: δ [CDCl$_3$] |
|---|---|---|---|---|---|---|---|
| 3-576 | pyridin-3-yl | F | Cl | Me | Me | Me | |
| 3-577 | pyridin-3-yl | F | Cl | Me | Me | Et | |
| 3-578 | pyridin-3-yl | F | Br | Me | Me | H | |
| 3-579 | pyridin-3-yl | F | Br | Me | Me | Me | |
| 3-580 | pyridin-3-yl | F | Br | Me | Me | Et | |
| 3-581 | pyridin-3-yl | F | F | Me | Me | H | |
| 3-582 | pyridin-3-yl | F | F | Me | Me | Me | |
| 3-583 | pyridin-3-yl | F | I | Me | Me | H | |
| 3-584 | pyridin-3-yl | F | I | Me | Me | Me | |
| 3-585 | pyridin-3-yl | F | CN | Me | Me | H | |
| 3-586 | pyridin-3-yl | F | CN | Me | Me | Me | |
| 3-587 | pyridin-3-yl | F | CF$_3$ | Me | Me | H | |
| 3-588 | pyridin-3-yl | F | CF$_3$ | Me | Me | Me | |
| 3-589 | pyridin-3-yl | H | Cl | =CHNMe$_2$ | | H | |
| 3-590 | pyridin-3-yl | H | Cl | =CHNMe$_2$ | | Me | |
| 3-591 | pyridin-3-yl | H | Cl | =CHNMe$_2$ | | Et | |
| 3-592 | pyridin-3-yl | H | Br | =CHNMe$_2$ | | H | |
| 3-593 | pyridin-3-yl | H | Br | =CHNMe$_2$ | | Me | |
| 3-594 | pyridin-3-yl | H | Br | =CHNMe$_2$ | | Et | |
| 3-595 | pyridin-3-yl | H | F | =CHNMe$_2$ | | H | |
| 3-596 | pyridin-3-yl | H | F | =CHNMe$_2$ | | Me | |
| 3-597 | pyridin-3-yl | H | I | =CHNMe$_2$ | | H | |
| 3-598 | pyridin-3-yl | H | I | =CHNMe$_2$ | | Me | |
| 3-599 | pyridin-3-yl | H | CN | =CHNMe$_2$ | | H | |
| 3-600 | pyridin-3-yl | H | CN | =CHNMe$_2$ | | Me | |
| 3-601 | pyridin-3-yl | H | CF$_3$ | =CHNMe$_2$ | | H | |
| 3-602 | pyridin-3-yl | H | CF$_3$ | =CHNMe$_2$ | | Me | |
| 3-603 | pyridin-3-yl | F | Cl | =CHNMe$_2$ | | H | |
| 3-604 | pyridin-3-yl | F | Cl | =CHNMe$_2$ | | Me | |
| 3-605 | pyridin-3-yl | F | Cl | =CHNMe$_2$ | | Et | |
| 3-606 | pyridin-3-yl | F | Br | =CHNMe$_2$ | | H | |
| 3-607 | pyridin-3-yl | F | Br | =CHNMe$_2$ | | Me | |
| 3-608 | pyridin-3-yl | F | Br | =CHNMe$_2$ | | Et | |
| 3-609 | pyridin-3-yl | F | F | =CHNMe$_2$ | | H | |
| 3-610 | pyridin-3-yl | F | F | =CHNMe$_2$ | | Me | |
| 3-611 | pyridin-3-yl | F | I | =CHNMe$_2$ | | H | |
| 3-612 | pyridin-3-yl | F | I | =CHNMe$_2$ | | Me | |
| 3-613 | pyridin-3-yl | F | CN | =CHNMe$_2$ | | H | |
| 3-614 | pyridin-3-yl | F | CN | =CHNMe$_2$ | | Me | |
| 3-615 | pyridin-3-yl | F | CF$_3$ | =CHNMe$_2$ | | H | |
| 3-616 | pyridin-3-yl | F | CF$_3$ | =CHNMe$_2$ | | Me | |
| 3-617 | oxiranyl | H | Cl | H | H | H | |
| 3-618 | oxiranyl | H | Cl | H | H | Me | |
| 3-619 | oxiranyl | H | Cl | H | H | Et | |
| 3-620 | oxiranyl | H | Br | H | H | H | |
| 3-621 | oxiranyl | H | Br | H | H | Me | |
| 3-622 | oxiranyl | H | Br | H | H | Et | |
| 3-623 | oxiranyl | H | F | H | H | H | |
| 3-624 | oxiranyl | H | F | H | H | Me | |
| 3-625 | oxiranyl | H | I | H | H | H | |
| 3-626 | oxiranyl | H | I | H | H | Me | |
| 3-627 | oxiranyl | H | CN | H | H | H | |
| 3-628 | oxiranyl | H | CN | H | H | Me | |
| 3-629 | oxiranyl | H | CF$_3$ | H | H | H | |
| 3-630 | oxiranyl | H | CF$_3$ | H | H | Me | |
| 3-631 | oxiranyl | F | Cl | H | H | H | |
| 3-632 | oxiranyl | F | Cl | H | H | Me | |
| 3-633 | oxiranyl | F | Cl | H | H | Et | |
| 3-634 | oxiranyl | F | Br | H | H | H | |
| 3-635 | oxiranyl | F | Br | H | H | Me | |
| 3-636 | oxiranyl | F | Br | H | H | Et | |
| 3-637 | oxiranyl | F | F | H | H | H | |
| 3-638 | oxiranyl | F | F | H | H | Me | |

TABLE 3-continued

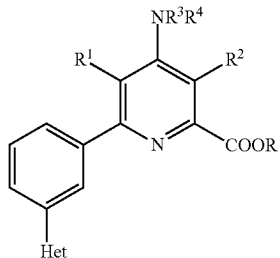

(I-iii)

| No. | Het | $R^1$ | $R^2$ | $R^3$ | $R^4$ | R | Physical data: $^1$H NMR: δ [CDCl$_3$] |
|---|---|---|---|---|---|---|---|
| 3-639 | oxiranyl | F | I | H | H | H | |
| 3-640 | oxiranyl | F | I | H | H | Me | |
| 3-641 | oxiranyl | F | CN | H | H | H | |
| 3-642 | oxiranyl | F | CN | H | H | Me | |
| 3-643 | oxiranyl | F | CF$_3$ | H | H | H | |
| 3-644 | oxiranyl | F | CF$_3$ | H | H | Me | |
| 3-645 | oxiranyl | H | Cl | H | Me | H | |
| 3-646 | oxiranyl | H | Cl | H | Me | Me | |
| 3-647 | oxiranyl | H | Cl | H | Me | Et | |
| 3-648 | oxiranyl | H | Br | H | Me | H | |
| 3-649 | oxiranyl | H | Br | H | Me | Me | |
| 3-650 | oxiranyl | H | Br | H | Me | Et | |
| 3-651 | oxiranyl | H | F | H | Me | H | |
| 3-652 | oxiranyl | H | F | H | Me | Me | |
| 3-653 | oxiranyl | H | I | H | Me | H | |
| 3-654 | oxiranyl | H | I | H | Me | Me | |
| 3-655 | oxiranyl | H | CN | H | Me | H | |
| 3-656 | oxiranyl | H | CN | H | Me | Me | |
| 3-657 | oxiranyl | H | CF$_3$ | H | Me | H | |
| 3-658 | oxiranyl | H | CF$_3$ | H | Me | Me | |
| 3-659 | oxiranyl | F | Cl | H | Me | H | |
| 3-660 | oxiranyl | F | Cl | H | Me | Me | |
| 3-661 | oxiranyl | F | Cl | H | Me | Et | |
| 3-662 | oxiranyl | F | Br | H | Me | H | |
| 3-663 | oxiranyl | F | Br | H | Me | Me | |
| 3-664 | oxiranyl | F | Br | H | Me | Et | |
| 3-665 | oxiranyl | F | F | H | Me | H | |
| 3-666 | oxiranyl | F | F | H | Me | Me | |
| 3-667 | oxiranyl | F | I | H | Me | H | |
| 3-668 | oxiranyl | F | I | H | Me | Me | |
| 3-669 | oxiranyl | F | CN | H | Me | H | |
| 3-670 | oxiranyl | F | CN | H | Me | Me | |
| 3-671 | oxiranyl | F | CF$_3$ | H | Me | H | |
| 3-672 | oxiranyl | F | CF$_3$ | H | Me | Me | |
| 3-673 | oxiranyl | H | Cl | Me | Me | H | |
| 3-674 | oxiranyl | H | Cl | Me | Me | Me | |
| 3-675 | oxiranyl | H | Cl | Me | Me | Et | |
| 3-676 | oxiranyl | H | Br | Me | Me | H | |
| 3-677 | oxiranyl | H | Br | Me | Me | Me | |
| 3-678 | oxiranyl | H | Br | Me | Me | Et | |
| 3-679 | oxiranyl | H | F | Me | Me | H | |
| 3-680 | oxiranyl | H | F | Me | Me | Me | |
| 3-681 | oxiranyl | H | I | Me | Me | H | |
| 3-682 | oxiranyl | H | I | Me | Me | Me | |
| 3-683 | oxiranyl | H | CN | Me | Me | H | |
| 3-684 | oxiranyl | H | CN | Me | Me | Me | |
| 3-685 | oxiranyl | H | CF$_3$ | Me | Me | H | |
| 3-686 | oxiranyl | H | CF$_3$ | Me | Me | Me | |
| 3-687 | oxiranyl | F | Cl | Me | Me | H | |
| 3-688 | oxiranyl | F | Cl | Me | Me | Me | |
| 3-689 | oxiranyl | F | Cl | Me | Me | Et | |
| 3-690 | oxiranyl | F | Br | Me | Me | H | |
| 3-691 | oxiranyl | F | Br | Me | Me | Me | |
| 3-692 | oxiranyl | F | Br | Me | Me | Et | |
| 3-693 | oxiranyl | F | F | Me | Me | H | |
| 3-694 | oxiranyl | F | F | Me | Me | Me | |
| 3-695 | oxiranyl | F | I | Me | Me | H | |
| 3-696 | oxiranyl | F | I | Me | Me | Me | |
| 3-697 | oxiranyl | F | CN | Me | Me | H | |
| 3-698 | oxiranyl | F | CN | Me | Me | Me | |
| 3-699 | oxiranyl | F | CF$_3$ | Me | Me | H | |
| 3-700 | oxiranyl | F | CF$_3$ | Me | Me | Me | |
| 3-701 | oxiranyl | H | Cl | =CHNMe$_2$ | | H | |

TABLE 3-continued

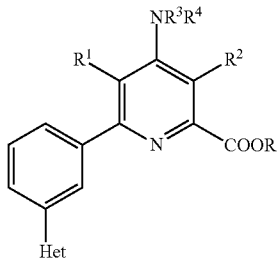

(I-iii)

| No. | Het | R¹ | R² | R³ | R⁴ | R | Physical data: $^1$H NMR: δ [CDCl$_3$] |
|---|---|---|---|---|---|---|---|
| 3-702 | oxiranyl | H | Cl | =CHNMe$_2$ | | Me | |
| 3-703 | oxiranyl | H | Cl | =CHNMe$_2$ | | Et | |
| 3-704 | oxiranyl | H | Br | =CHNMe$_2$ | | H | |
| 3-705 | oxiranyl | H | Br | =CHNMe$_2$ | | Me | |
| 3-706 | oxiranyl | H | Br | =CHNMe$_2$ | | Et | |
| 3-707 | oxiranyl | H | F | =CHNMe$_2$ | | H | |
| 3-708 | oxiranyl | H | F | =CHNMe$_2$ | | Me | |
| 3-709 | oxiranyl | H | I | =CHNMe$_2$ | | H | |
| 3-710 | oxiranyl | H | I | =CHNMe$_2$ | | Me | |
| 3-711 | oxiranyl | H | CN | =CHNMe$_2$ | | H | |
| 3-712 | oxiranyl | H | CN | =CHNMe$_2$ | | Me | |
| 3-713 | oxiranyl | H | CF$_3$ | =CHNMe$_2$ | | H | |
| 3-714 | oxiranyl | H | CF$_3$ | =CHNMe$_2$ | | Me | |
| 3-715 | oxiranyl | F | Cl | =CHNMe$_2$ | | H | |
| 3-716 | oxiranyl | F | Cl | =CHNMe$_2$ | | Me | |
| 3-717 | oxiranyl | F | Cl | =CHNMe$_2$ | | Et | |
| 3-718 | oxiranyl | F | Br | =CHNMe$_2$ | | H | |
| 3-719 | oxiranyl | F | Br | =CHNMe$_2$ | | Me | |
| 3-720 | oxiranyl | F | Br | =CHNMe$_2$ | | Et | |
| 3-721 | oxiranyl | F | F | =CHNMe$_2$ | | H | |
| 3-722 | oxiranyl | F | F | =CHNMe$_2$ | | Me | |
| 3-723 | oxiranyl | F | I | =CHNMe$_2$ | | H | |
| 3-724 | oxiranyl | F | I | =CHNMe$_2$ | | Me | |
| 3-725 | oxiranyl | F | CN | =CHNMe$_2$ | | H | |
| 3-726 | oxiranyl | F | CN | =CHNMe$_2$ | | Me | |
| 3-727 | oxiranyl | F | CF$_3$ | =CHNMe$_2$ | | H | |
| 3-728 | oxiranyl | F | CF$_3$ | =CHNMe$_2$ | | Me | |
| 3-729 | 3,3-dimethyl-oxetan-2-yl | H | Cl | H | H | H | |
| 3-730 | 3,3-dimethyl-oxetan-2-yl | H | Cl | H | H | Me | |
| 3-731 | 3,3-dimethyl-oxetan-2-yl | H | Cl | H | H | Et | |
| 3-732 | 3,3-dimethyl-oxetan-2-yl | H | Br | H | H | H | |
| 3-733 | 3,3-dimethyl-oxetan-2-yl | H | Br | H | H | Me | |
| 3-734 | 3,3-dimethyl-oxetan-2-yl | H | Br | H | H | Et | |
| 3-735 | 3,3-dimethyl-oxetan-2-yl | H | F | H | H | H | |
| 3-736 | 3,3-dimethyl-oxetan-2-yl | H | F | H | H | Me | |
| 3-737 | 3,3-dimethyl-oxetan-2-yl | H | I | H | H | H | |
| 3-738 | 3,3-dimethyl-oxetan-2-yl | H | I | H | H | Me | |
| 3-739 | 3,3-dimethyl-oxetan-2-yl | H | CN | H | H | H | |
| 3-740 | 3,3-dimethyl-oxetan-2-yl | H | CN | H | H | Me | |
| 3-741 | 3,3-dimethyl-oxetan-2-yl | H | CF$_3$ | H | H | H | |
| 3-742 | 3,3-dimethyl-oxetan-2-yl | H | CF$_3$ | H | H | Me | |
| 3-743 | 3,3-dimethyl-oxetan-2-yl | F | Cl | H | H | H | |
| 3-744 | 3,3-dimethyl-oxetan-2-yl | F | Cl | H | H | Me | |
| 3-745 | 3,3-dimethyl-oxetan-2-yl | F | Cl | H | H | Et | |
| 3-746 | 3,3-dimethyl-oxetan-2-yl | F | Br | H | H | H | |
| 3-747 | 3,3-dimethyl-oxetan-2-yl | F | Br | H | H | Me | |
| 3-748 | 3,3-dimethyl-oxetan-2-yl | F | Br | H | H | Et | |
| 3-749 | 3,3-dimethyl-oxetan-2-yl | F | F | H | H | H | |
| 3-750 | 3,3-dimethyl-oxetan-2-yl | F | F | H | H | Me | |
| 3-751 | 3,3-dimethyl-oxetan-2-yl | F | I | H | H | H | |
| 3-752 | 3,3-dimethyl-oxetan-2-yl | F | I | H | H | Me | |
| 3-753 | 3,3-dimethyl-oxetan-2-yl | F | CN | H | H | H | |
| 3-754 | 3,3-dimethyl-oxetan-2-yl | F | CN | H | H | Me | |
| 3-755 | 3,3-dimethyl-oxetan-2-yl | F | CF$_3$ | H | H | H | |
| 3-756 | 3,3-dimethyl-oxetan-2-yl | F | CF$_3$ | H | H | Me | |
| 3-757 | 3,3-dimethyl-oxetan-2-yl | H | Cl | H | Me | H | |
| 3-758 | 3,3-dimethyl-oxetan-2-yl | H | Cl | H | Me | Me | |
| 3-759 | 3,3-dimethyl-oxetan-2-yl | H | Cl | H | Me | Et | |
| 3-760 | 3,3-dimethyl-oxetan-2-yl | H | Br | H | Me | H | |
| 3-761 | 3,3-dimethyl-oxetan-2-yl | H | Br | H | Me | Me | |
| 3-762 | 3,3-dimethyl-oxetan-2-yl | H | Br | H | Me | Et | |
| 3-763 | 3,3-dimethyl-oxetan-2-yl | H | F | H | Me | H | |
| 3-764 | 3,3-dimethyl-oxetan-2-yl | H | F | H | Me | Me | |

TABLE 3-continued

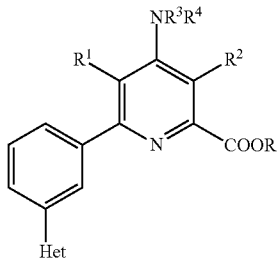

(I-iii)

| No. | Het | R¹ | R² | R³ | R⁴ | R | Physical data: $^1$H NMR: δ [CDCl$_3$] |
|---|---|---|---|---|---|---|---|
| 3-765 | 3,3-dimethyl-oxetan-2-yl | H | I | H | Me | H | |
| 3-766 | 3,3-dimethyl-oxetan-2-yl | H | I | H | Me | Me | |
| 3-767 | 3,3-dimethyl-oxetan-2-yl | H | CN | H | Me | H | |
| 3-768 | 3,3-dimethyl-oxetan-2-yl | H | CN | H | Me | Me | |
| 3-769 | 3,3-dimethyl-oxetan-2-yl | H | CF$_3$ | H | Me | H | |
| 3-770 | 3,3-dimethyl-oxetan-2-yl | H | CF$_3$ | H | Me | Me | |
| 3-771 | 3,3-dimethyl-oxetan-2-yl | F | Cl | H | Me | H | |
| 3-772 | 3,3-dimethyl-oxetan-2-yl | F | Cl | H | Me | Me | |
| 3-773 | 3,3-dimethyl-oxetan-2-yl | F | Cl | H | Me | Et | |
| 3-774 | 3,3-dimethyl-oxetan-2-yl | F | Br | H | Me | H | |
| 3-775 | 3,3-dimethyl-oxetan-2-yl | F | Br | H | Me | Me | |
| 3-776 | 3,3-dimethyl-oxetan-2-yl | F | Br | H | Me | Et | |
| 3-777 | 3,3-dimethyl-oxetan-2-yl | F | F | H | Me | H | |
| 3-778 | 3,3-dimethyl-oxetan-2-yl | F | F | H | Me | Me | |
| 3-779 | 3,3-dimethyl-oxetan-2-yl | F | I | H | Me | H | |
| 3-780 | 3,3-dimethyl-oxetan-2-yl | F | I | H | Me | Me | |
| 3-781 | 3,3-dimethyl-oxetan-2-yl | F | CN | H | Me | H | |
| 3-782 | 3,3-dimethyl-oxetan-2-yl | F | CN | H | Me | Me | |
| 3-783 | 3,3-dimethyl-oxetan-2-yl | F | CF$_3$ | H | Me | H | |
| 3-784 | 3,3-dimethyl-oxetan-2-yl | F | CF$_3$ | H | Me | Me | |
| 3-785 | 3,3-dimethyl-oxetan-2-yl | H | Cl | Me | Me | H | |
| 3-786 | 3,3-dimethyl-oxetan-2-yl | H | Cl | Me | Me | Me | |
| 3-787 | 3,3-dimethyl-oxetan-2-yl | H | Cl | Me | Me | Et | |
| 3-788 | 3,3-dimethyl-oxetan-2-yl | H | Br | Me | Me | H | |
| 3-789 | 3,3-dimethyl-oxetan-2-yl | H | Br | Me | Me | Me | |
| 3-790 | 3,3-dimethyl-oxetan-2-yl | H | Br | Me | Me | Et | |
| 3-791 | 3,3-dimethyl-oxetan-2-yl | H | F | Me | Me | H | |
| 3-792 | 3,3-dimethyl-oxetan-2-yl | H | F | Me | Me | Me | |
| 3-793 | 3,3-dimethyl-oxetan-2-yl | H | I | Me | Me | H | |
| 3-794 | 3,3-dimethyl-oxetan-2-yl | H | I | Me | Me | Me | |
| 3-795 | 3,3-dimethyl-oxetan-2-yl | H | CN | Me | Me | H | |
| 3-796 | 3,3-dimethyl-oxetan-2-yl | H | CN | Me | Me | Me | |
| 3-797 | 3,3-dimethyl-oxetan-2-yl | H | CF$_3$ | Me | Me | H | |
| 3-798 | 3,3-dimethyl-oxetan-2-yl | H | CF$_3$ | Me | Me | Me | |
| 3-799 | 3,3-dimethyl-oxetan-2-yl | F | Cl | Me | Me | H | |
| 3-800 | 3,3-dimethyl-oxetan-2-yl | F | Cl | Me | Me | Me | |
| 3-801 | 3,3-dimethyl-oxetan-2-yl | F | Cl | Me | Me | Et | |
| 3-802 | 3,3-dimethyl-oxetan-2-yl | F | Br | Me | Me | H | |
| 3-803 | 3,3-dimethyl-oxetan-2-yl | F | Br | Me | Me | Me | |
| 3-804 | 3,3-dimethyl-oxetan-2-yl | F | Br | Me | Me | Et | |
| 3-805 | 3,3-dimethyl-oxetan-2-yl | F | F | Me | Me | H | |
| 3-806 | 3,3-dimethyl-oxetan-2-yl | F | F | Me | Me | Me | |
| 3-807 | 3,3-dimethyl-oxetan-2-yl | F | I | Me | Me | H | |
| 3-808 | 3,3-dimethyl-oxetan-2-yl | F | I | Me | Me | Me | |
| 3-809 | 3,3-dimethyl-oxetan-2-yl | F | CN | Me | Me | H | |
| 3-810 | 3,3-dimethyl-oxetan-2-yl | F | CN | Me | Me | Me | |
| 3-811 | 3,3-dimethyl-oxetan-2-yl | F | CF$_3$ | Me | Me | H | |
| 3-812 | 3,3-dimethyl-oxetan-2-yl | F | CF$_3$ | Me | Me | Me | |
| 3-813 | 3,3-dimethyl-oxetan-2-yl | H | Cl | =CHNMe$_2$ | | H | |
| 3-814 | 3,3-dimethyl-oxetan-2-yl | H | Cl | =CHNMe$_2$ | | Me | |
| 3-815 | 3,3-dimethyl-oxetan-2-yl | H | Cl | =CHNMe$_2$ | | Et | |
| 3-816 | 3,3-dimethyl-oxetan-2-yl | H | Br | =CHNMe$_2$ | | H | |
| 3-817 | 3,3-dimethyl-oxetan-2-yl | H | Br | =CHNMe$_2$ | | Me | |
| 3-818 | 3,3-dimethyl-oxetan-2-yl | H | Br | =CHNMe$_2$ | | Et | |
| 3-819 | 3,3-dimethyl-oxetan-2-yl | H | F | =CHNMe$_2$ | | H | |
| 3-820 | 3,3-dimethyl-oxetan-2-yl | H | F | =CHNMe$_2$ | | Me | |
| 3-821 | 3,3-dimethyl-oxetan-2-yl | H | I | =CHNMe$_2$ | | H | |
| 3-822 | 3,3-dimethyl-oxetan-2-yl | H | I | =CHNMe$_2$ | | Me | |
| 3-823 | 3,3-dimethyl-oxetan-2-yl | H | CN | =CHNMe$_2$ | | H | |
| 3-824 | 3,3-dimethyl-oxetan-2-yl | H | CN | =CHNMe$_2$ | | Me | |
| 3-825 | 3,3-dimethyl-oxetan-2-yl | H | CF$_3$ | =CHNMe$_2$ | | H | |
| 3-826 | 3,3-dimethyl-oxetan-2-yl | H | CF$_3$ | =CHNMe$_2$ | | Me | |
| 3-827 | 3,3-dimethyl-oxetan-2-yl | F | Cl | =CHNMe$_2$ | | H | |

TABLE 3-continued

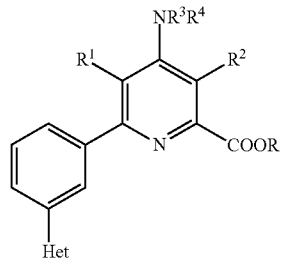

(I-iii)

| No. | Het | $R^1$ | $R^2$ | $R^3$ | $R^4$ | R | Physical data: $^1$H NMR: δ [CDCl$_3$] |
|---|---|---|---|---|---|---|---|
| 3-828 | 3,3-dimethyl-oxetan-2-yl | F | Cl | =CHNMe$_2$ | | Me | |
| 3-829 | 3,3-dimethyl-oxetan-2-yl | F | Cl | =CHNMe$_2$ | | Et | |
| 3-830 | 3,3-dimethyl-oxetan-2-yl | F | Br | =CHNMe$_2$ | | H | |
| 3-831 | 3,3-dimethyl-oxetan-2-yl | F | Br | =CHNMe$_2$ | | Me | |
| 3-832 | 3,3-dimethyl-oxetan-2-yl | F | Br | =CHNMe$_2$ | | Et | |
| 3-833 | 3,3-dimethyl-oxetan-2-yl | F | F | =CHNMe$_2$ | | H | |
| 3-834 | 3,3-dimethyl-oxetan-2-yl | F | F | =CHNMe$_2$ | | Me | |
| 3-835 | 3,3-dimethyl-oxetan-2-yl | F | I | =CHNMe$_2$ | | H | |
| 3-836 | 3,3-dimethyl-oxetan-2-yl | F | I | =CHNMe$_2$ | | Me | |
| 3-837 | 3,3-dimethyl-oxetan-2-yl | F | CN | =CHNMe$_2$ | | H | |
| 3-838 | 3,3-dimethyl-oxetan-2-yl | F | CN | =CHNMe$_2$ | | Me | |
| 3-839 | 3,3-dimethyl-oxetan-2-yl | F | CF$_3$ | =CHNMe$_2$ | | H | |
| 3-840 | 3,3-dimethyl-oxetan-2-yl | F | CF$_3$ | =CHNMe$_2$ | | Me | |
| 3-841 | 2,2-dimethyl-dioxolan-4-yl | H | Cl | H | H | H | |
| 3-842 | 2,2-dimethyl-dioxolan-4-yl | H | Cl | H | H | Me | |
| 3-843 | 2,2-dimethyl-dioxolan-4-yl | H | Cl | H | H | Et | |
| 3-844 | 2,2-dimethyl-dioxolan-4-yl | H | Br | H | H | H | |
| 3-845 | 2,2-dimethyl-dioxolan-4-yl | H | Br | H | H | Me | |
| 3-846 | 2,2-dimethyl-dioxolan-4-yl | H | Br | H | H | Et | |
| 3-847 | 2,2-dimethyl-dioxolan-4-yl | H | F | H | H | H | |
| 3-848 | 2,2-dimethyl-dioxolan-4-yl | H | F | H | H | Me | |
| 3-849 | 2,2-dimethyl-dioxolan-4-yl | H | I | H | H | H | |
| 3-850 | 2,2-dimethyl-dioxolan-4-yl | H | I | H | H | Me | |
| 3-851 | 2,2-dimethyl-dioxolan-4-yl | H | CN | H | H | H | |
| 3-852 | 2,2-dimethyl-dioxolan-4-yl | H | CN | H | H | Me | |
| 3-853 | 2,2-dimethyl-dioxolan-4-yl | H | CF$_3$ | H | H | H | |
| 3-854 | 2,2-dimethyl-dioxolan-4-yl | H | CF$_3$ | H | H | Me | |
| 3-855 | 2,2-dimethyl-dioxolan-4-yl | F | Cl | H | H | H | |
| 3-856 | 2,2-dimethyl-dioxolan-4-yl | F | Cl | H | H | Me | |
| 3-857 | 2,2-dimethyl-dioxolan-4-yl | F | Cl | H | H | Et | |
| 3-858 | 2,2-dimethyl-dioxolan-4-yl | F | Br | H | H | H | |
| 3-859 | 2,2-dimethyl-dioxolan-4-yl | F | Br | H | H | Me | |
| 3-860 | 2,2-dimethyl-dioxolan-4-yl | F | Br | H | H | Et | |
| 3-861 | 2,2-dimethyl-dioxolan-4-yl | F | F | H | H | H | |
| 3-862 | 2,2-dimethyl-dioxolan-4-yl | F | F | H | H | Me | |
| 3-863 | 2,2-dimethyl-dioxolan-4-yl | F | I | H | H | H | |
| 3-864 | 2,2-dimethyl-dioxolan-4-yl | F | I | H | H | Me | |
| 3-865 | 2,2-dimethyl-dioxolan-4-yl | F | CN | H | H | H | |
| 3-866 | 2,2-dimethyl-dioxolan-4-yl | F | CN | H | H | Me | |
| 3-867 | 2,2-dimethyl-dioxolan-4-yl | F | CF$_3$ | H | H | H | |
| 3-868 | 2,2-dimethyl-dioxolan-4-yl | F | CF$_3$ | H | H | Me | |
| 3-869 | 2,2-dimethyl-dioxolan-4-yl | H | Cl | H | Me | H | |
| 3-870 | 2,2-dimethyl-dioxolan-4-yl | H | Cl | H | Me | Me | |
| 3-871 | 2,2-dimethyl-dioxolan-4-yl | H | Cl | H | Me | Et | |
| 3-872 | 2,2-dimethyl-dioxolan-4-yl | H | Br | H | Me | H | |
| 3-873 | 2,2-dimethyl-dioxolan-4-yl | H | Br | H | Me | Me | |
| 3-874 | 2,2-dimethyl-dioxolan-4-yl | H | Br | H | Me | Et | |
| 3-875 | 2,2-dimethyl-dioxolan-4-yl | H | F | H | Me | H | |
| 3-876 | 2,2-dimethyl-dioxolan-4-yl | H | F | H | Me | Me | |
| 3-877 | 2,2-dimethyl-dioxolan-4-yl | H | I | H | Me | H | |
| 3-878 | 2,2-dimethyl-dioxolan-4-yl | H | I | H | Me | Me | |
| 3-879 | 2,2-dimethyl-dioxolan-4-yl | H | CN | H | Me | H | |
| 3-880 | 2,2-dimethyl-dioxolan-4-yl | H | CN | H | Me | Me | |
| 3-881 | 2,2-dimethyl-dioxolan-4-yl | H | CF$_3$ | H | Me | H | |
| 3-882 | 2,2-dimethyl-dioxolan-4-yl | H | CF$_3$ | H | Me | Me | |
| 3-883 | 2,2-dimethyl-dioxolan-4-yl | F | Cl | H | Me | H | |
| 3-884 | 2,2-dimethyl-dioxolan-4-yl | F | Cl | H | Me | Me | |
| 3-885 | 2,2-dimethyl-dioxolan-4-yl | F | Cl | H | Me | Et | |
| 3-886 | 2,2-dimethyl-dioxolan-4-yl | F | Br | H | Me | H | |
| 3-887 | 2,2-dimethyl-dioxolan-4-yl | F | Br | H | Me | Me | |
| 3-888 | 2,2-dimethyl-dioxolan-4-yl | F | Br | H | Me | Et | |
| 3-889 | 2,2-dimethyl-dioxolan-4-yl | F | F | H | Me | H | |
| 3-890 | 2,2-dimethyl-dioxolan-4-yl | F | F | H | Me | Me | |

TABLE 3-continued

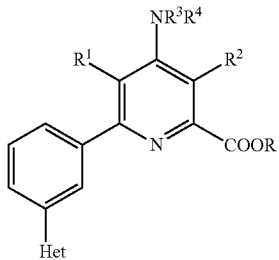

(I-iii)

| No. | Het | R¹ | R² | R³ | R⁴ | R | Physical data: $^1$H NMR: δ [CDCl$_3$] |
|---|---|---|---|---|---|---|---|
| 3-891 | 2,2-dimethyl-dioxolan-4-yl | F | I | H | Me | H | |
| 3-892 | 2,2-dimethyl-dioxolan-4-yl | F | I | H | Me | Me | |
| 3-893 | 2,2-dimethyl-dioxolan-4-yl | F | CN | H | Me | H | |
| 3-894 | 2,2-dimethyl-dioxolan-4-yl | F | CN | H | Me | Me | |
| 3-895 | 2,2-dimethyl-dioxolan-4-yl | F | CF$_3$ | H | Me | H | |
| 3-896 | 2,2-dimethyl-dioxolan-4-yl | F | CF$_3$ | H | Me | Me | |
| 3-897 | 2,2-dimethyl-dioxolan-4-yl | H | Cl | Me | Me | H | |
| 3-898 | 2,2-dimethyl-dioxolan-4-yl | H | Cl | Me | Me | Me | |
| 3-899 | 2,2-dimethyl-dioxolan-4-yl | H | Cl | Me | Me | Et | |
| 3-900 | 2,2-dimethyl-dioxolan-4-yl | H | Br | Me | Me | H | |
| 3-901 | 2,2-dimethyl-dioxolan-4-yl | H | Br | Me | Me | Me | |
| 3-902 | 2,2-dimethyl-dioxolan-4-yl | H | Br | Me | Me | Et | |
| 3-903 | 2,2-dimethyl-dioxolan-4-yl | H | F | Me | Me | H | |
| 3-904 | 2,2-dimethyl-dioxolan-4-yl | H | F | Me | Me | Me | |
| 3-905 | 2,2-dimethyl-dioxolan-4-yl | H | I | Me | Me | H | |
| 3-906 | 2,2-dimethyl-dioxolan-4-yl | H | I | Me | Me | Me | |
| 3-907 | 2,2-dimethyl-dioxolan-4-yl | H | CN | Me | Me | H | |
| 3-908 | 2,2-dimethyl-dioxolan-4-yl | H | CN | Me | Me | Me | |
| 3-909 | 2,2-dimethyl-dioxolan-4-yl | H | CF$_3$ | Me | Me | H | |
| 3-910 | 2,2-dimethyl-dioxolan-4-yl | H | CF$_3$ | Me | Me | Me | |
| 3-911 | 2,2-dimethyl-dioxolan-4-yl | F | Cl | Me | Me | H | |
| 3-912 | 2,2-dimethyl-dioxolan-4-yl | F | Cl | Me | Me | Me | |
| 3-913 | 2,2-dimethyl-dioxolan-4-yl | F | Cl | Me | Me | Et | |
| 3-914 | 2,2-dimethyl-dioxolan-4-yl | F | Br | Me | Me | H | |
| 3-915 | 2,2-dimethyl-dioxolan-4-yl | F | Br | Me | Me | Me | |
| 3-916 | 2,2-dimethyl-dioxolan-4-yl | F | Br | Me | Me | Et | |
| 3-917 | 2,2-dimethyl-dioxolan-4-yl | F | F | Me | Me | H | |
| 3-918 | 2,2-dimethyl-dioxolan-4-yl | F | F | Me | Me | Me | |
| 3-919 | 2,2-dimethyl-dioxolan-4-yl | F | I | Me | Me | H | |
| 3-920 | 2,2-dimethyl-dioxolan-4-yl | F | I | Me | Me | Me | |
| 3-921 | 2,2-dimethyl-dioxolan-4-yl | F | CN | Me | Me | H | |
| 3-922 | 2,2-dimethyl-dioxolan-4-yl | F | CN | Me | Me | Me | |
| 3-923 | 2,2-dimethyl-dioxolan-4-yl | F | CF$_3$ | Me | Me | H | |
| 3-924 | 2,2-dimethyl-dioxolan-4-yl | F | CF$_3$ | Me | Me | Me | |
| 3-925 | 2,2-dimethyl-dioxolan-4-yl | H | Cl | =CHNMe$_2$ | | H | |
| 3-926 | 2,2-dimethyl-dioxolan-4-yl | H | Cl | =CHNMe$_2$ | | Me | |
| 3-927 | 2,2-dimethyl-dioxolan-4-yl | H | Cl | =CHNMe$_2$ | | Et | |
| 3-928 | 2,2-dimethyl-dioxolan-4-yl | H | Br | =CHNMe$_2$ | | H | |
| 3-929 | 2,2-dimethyl-dioxolan-4-yl | H | Br | =CHNMe$_2$ | | Me | |
| 3-930 | 2,2-dimethyl-dioxolan-4-yl | H | Br | =CHNMe$_2$ | | Et | |
| 3-931 | 2,2-dimethyl-dioxolan-4-yl | H | F | =CHNMe$_2$ | | H | |
| 3-932 | 2,2-dimethyl-dioxolan-4-yl | H | F | =CHNMe$_2$ | | Me | |
| 3-933 | 2,2-dimethyl-dioxolan-4-yl | H | I | =CHNMe$_2$ | | H | |
| 3-934 | 2,2-dimethyl-dioxolan-4-yl | H | I | =CHNMe$_2$ | | Me | |
| 3-935 | 2,2-dimethyl-dioxolan-4-yl | H | CN | =CHNMe$_2$ | | H | |
| 3-936 | 2,2-dimethyl-dioxolan-4-yl | H | CN | =CHNMe$_2$ | | Me | |
| 3-937 | 2,2-dimethyl-dioxolan-4-yl | H | CF$_3$ | =CHNMe$_2$ | | H | |
| 3-938 | 2,2-dimethyl-dioxolan-4-yl | H | CF$_3$ | =CHNMe$_2$ | | Me | |
| 3-939 | 2,2-dimethyl-dioxolan-4-yl | F | Cl | =CHNMe$_2$ | | H | |
| 3-940 | 2,2-dimethyl-dioxolan-4-yl | F | Cl | =CHNMe$_2$ | | Me | |
| 3-941 | 2,2-dimethyl-dioxolan-4-yl | F | Cl | =CHNMe$_2$ | | Et | |
| 3-942 | 2,2-dimethyl-dioxolan-4-yl | F | Br | =CHNMe$_2$ | | H | |
| 3-943 | 2,2-dimethyl-dioxolan-4-yl | F | Br | =CHNMe$_2$ | | Me | |
| 3-944 | 2,2-dimethyl-dioxolan-4-yl | F | Br | =CHNMe$_2$ | | Et | |
| 3-945 | 2,2-dimethyl-dioxolan-4-yl | F | F | =CHNMe$_2$ | | H | |
| 3-946 | 2,2-dimethyl-dioxolan-4-yl | F | F | =CHNMe$_2$ | | Me | |
| 3-947 | 2,2-dimethyl-dioxolan-4-yl | F | I | =CHNMe$_2$ | | H | |
| 3-948 | 2,2-dimethyl-dioxolan-4-yl | F | I | =CHNMe$_2$ | | Me | |
| 3-949 | 2,2-dimethyl-dioxolan-4-yl | F | CN | =CHNMe$_2$ | | H | |
| 3-950 | 2,2-dimethyl-dioxolan-4-yl | F | CN | =CHNMe$_2$ | | Me | |
| 3-951 | 2,2-dimethyl-dioxolan-4-yl | F | CF$_3$ | =CHNMe$_2$ | | H | |
| 3-952 | 2,2-dimethyl-dioxolan-4-yl | F | CF$_3$ | =CHNMe$_2$ | | Me | |

TABLE 4

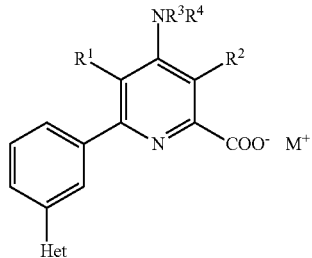

(I-iv)

| No. | Het | R¹ | R² | R³ | R⁴ | M⁺ | Physical data: $^1$H NMR: δ [CDCl$_3$] |
|---|---|---|---|---|---|---|---|
| 4-1 | 3-tert-butyl-1,2,4-oxadiazol-5-yl | H | Cl | H | H | Na⁺ | |
| 4-2 | 3-tert-butyl-1,2,4-oxadiazol-5-yl | H | Cl | H | H | K⁺ | |
| 4-3 | 3-tert-butyl-1,2,4-oxadiazol-5-yl | H | Cl | H | H | NH₄⁺ | |
| 4-4 | 3-tert-butyl-1,2,4-oxadiazol-5-yl | H | Br | H | H | Na⁺ | |
| 4-5 | 3-tert-butyl-1,2,4-oxadiazol-5-yl | H | Br | H | H | K⁺ | |
| 4-6 | 3-tert-butyl-1,2,4-oxadiazol-5-yl | H | Br | H | H | NH₄⁺ | |
| 4-7 | 3-tert-butyl-1,2,4-oxadiazol-5-yl | H | F | H | H | Na⁺ | |
| 4-8 | 3-tert-butyl-1,2,4-oxadiazol-5-yl | H | F | H | H | K⁺ | |
| 4-9 | 3-tert-butyl-1,2,4-oxadiazol-5-yl | H | I | H | H | Na⁺ | |
| 4-10 | 3-tert-butyl-1,2,4-oxadiazol-5-yl | H | I | H | H | K⁺ | |
| 4-11 | 3-tert-butyl-1,2,4-oxadiazol-5-yl | H | CN | H | H | Na⁺ | |
| 4-12 | 3-tert-butyl-1,2,4-oxadiazol-5-yl | H | CN | H | H | K⁺ | |
| 4-13 | 3-tert-butyl-1,2,4-oxadiazol-5-yl | H | CF₃ | H | H | Na⁺ | |
| 4-14 | 3-tert-butyl-1,2,4-oxadiazol-5-yl | H | CF₃ | H | H | K⁺ | |
| 4-15 | 3-tert-butyl-1,2,4-oxadiazol-5-yl | F | Cl | H | H | Na⁺ | |
| 4-16 | 3-tert-butyl-1,2,4-oxadiazol-5-yl | F | Cl | H | H | K⁺ | |
| 4-17 | 3-tert-butyl-1,2,4-oxadiazol-5-yl | F | Cl | H | H | NH₄⁺ | |
| 4-18 | 3-tert-butyl-1,2,4-oxadiazol-5-yl | F | Br | H | H | Na⁺ | |
| 4-19 | 3-tert-butyl-1,2,4-oxadiazol-5-yl | F | Br | H | H | K⁺ | |
| 4-20 | 3-tert-butyl-1,2,4-oxadiazol-5-yl | F | Br | H | H | NH₄⁺ | |
| 4-21 | 3-tert-butyl-1,2,4-oxadiazol-5-yl | F | F | H | H | Na⁺ | |
| 4-22 | 3-tert-butyl-1,2,4-oxadiazol-5-yl | F | F | H | H | K⁺ | |
| 4-23 | 3-tert-butyl-1,2,4-oxadiazol-5-yl | F | I | H | H | Na⁺ | |
| 4-24 | 3-tert-butyl-1,2,4-oxadiazol-5-yl | F | I | H | H | K⁺ | |
| 4-25 | 3-tert-butyl-1,2,4-oxadiazol-5-yl | F | CN | H | H | Na⁺ | |
| 4-26 | 3-tert-butyl-1,2,4-oxadiazol-5-yl | F | CN | H | H | K⁺ | |
| 4-27 | 3-tert-butyl-1,2,4-oxadiazol-5-yl | F | CF₃ | H | H | Na⁺ | |
| 4-28 | 3-tert-butyl-1,2,4-oxadiazol-5-yl | F | CF₃ | H | H | K⁺ | |
| 4-29 | 3-tert-butyl-1,2,4-oxadiazol-5-yl | Cl | Cl | H | H | Na⁺ | |
| 4-30 | 3-tert-butyl-1,2,4-oxadiazol-5-yl | Cl | Cl | H | H | K⁺ | |
| 4-31 | 3-tert-butyl-1,2,4-oxadiazol-5-yl | Cl | Cl | H | H | NH₄⁺ | |
| 4-32 | 3-tert-butyl-1,2,4-oxadiazol-5-yl | Cl | Br | H | H | Na⁺ | |
| 4-33 | 3-tert-butyl-1,2,4-oxadiazol-5-yl | Cl | Br | H | H | K⁺ | |
| 4-34 | 3-tert-butyl-1,2,4-oxadiazol-5-yl | Cl | Br | H | H | NH₄⁺ | |
| 4-35 | 3-tert-butyl-1,2,4-oxadiazol-5-yl | Cl | F | H | H | Na⁺ | |
| 4-36 | 3-tert-butyl-1,2,4-oxadiazol-5-yl | Cl | F | H | H | K⁺ | |
| 4-37 | 3-tert-butyl-1,2,4-oxadiazol-5-yl | Cl | I | H | H | Na⁺ | |
| 4-38 | 3-tert-butyl-1,2,4-oxadiazol-5-yl | Cl | I | H | H | K⁺ | |
| 4-39 | 3-tert-butyl-1,2,4-oxadiazol-5-yl | Cl | CN | H | H | Na⁺ | |
| 4-40 | 3-tert-butyl-1,2,4-oxadiazol-5-yl | Cl | CN | H | H | K⁺ | |
| 4-41 | 3-tert-butyl-1,2,4-oxadiazol-5-yl | Cl | CF₃ | H | H | Na⁺ | |
| 4-42 | 3-tert-butyl-1,2,4-oxadiazol-5-yl | Cl | CF₃ | H | H | K⁺ | |
| 4-43 | 3-tert-butyl-1,2,4-oxadiazol-5-yl | H | Cl | H | Me | Na⁺ | |
| 4-44 | 3-tert-butyl-1,2,4-oxadiazol-5-yl | H | Cl | H | Me | K⁺ | |
| 4-45 | 3-tert-butyl-1,2,4-oxadiazol-5-yl | H | Cl | H | Me | NH₄⁺ | |
| 4-46 | 3-tert-butyl-1,2,4-oxadiazol-5-yl | H | Br | H | Me | Na⁺ | |
| 4-47 | 3-tert-butyl-1,2,4-oxadiazol-5-yl | H | Br | H | Me | K⁺ | |
| 4-48 | 3-tert-butyl-1,2,4-oxadiazol-5-yl | H | Br | H | Me | NH₄⁺ | |
| 4-49 | 3-tert-butyl-1,2,4-oxadiazol-5-yl | H | F | H | Me | Na⁺ | |
| 4-50 | 3-tert-butyl-1,2,4-oxadiazol-5-yl | H | F | H | Me | K⁺ | |
| 4-51 | 3-tert-butyl-1,2,4-oxadiazol-5-yl | H | I | H | Me | Na⁺ | |
| 4-52 | 3-tert-butyl-1,2,4-oxadiazol-5-yl | H | I | H | Me | K⁺ | |
| 4-53 | 3-tert-butyl-1,2,4-oxadiazol-5-yl | H | CN | H | Me | Na⁺ | |
| 4-54 | 3-tert-butyl-1,2,4-oxadiazol-5-yl | H | CN | H | Me | K⁺ | |
| 4-55 | 3-tert-butyl-1,2,4-oxadiazol-5-yl | H | CF₃ | H | Me | Na⁺ | |
| 4-56 | 3-tert-butyl-1,2,4-oxadiazol-5-yl | H | CF₃ | H | Me | K⁺ | |
| 4-57 | 3-tert-butyl-1,2,4-oxadiazol-5-yl | F | Cl | H | Me | Na⁺ | |
| 4-58 | 3-tert-butyl-1,2,4-oxadiazol-5-yl | F | Cl | H | Me | K⁺ | |
| 4-59 | 3-tert-butyl-1,2,4-oxadiazol-5-yl | F | Cl | H | Me | NH₄⁺ | |
| 4-60 | 3-tert-butyl-1,2,4-oxadiazol-5-yl | F | Br | H | Me | Na⁺ | |
| 4-61 | 3-tert-butyl-1,2,4-oxadiazol-5-yl | F | Br | H | Me | K⁺ | |
| 4-62 | 3-tert-butyl-1,2,4-oxadiazol-5-yl | F | Br | H | Me | NH₄⁺ | |
| 4-63 | 3-tert-butyl-1,2,4-oxadiazol-5-yl | F | F | H | Me | Na⁺ | |

TABLE 4-continued

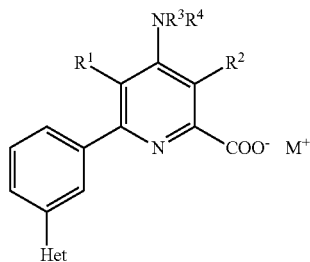

(I-iv)

| No. | Het | R¹ | R² | R³ | R⁴ | M⁺ | Physical data: $^1$H NMR: δ [CDCl$_3$] |
|---|---|---|---|---|---|---|---|
| 4-64 | 3-tert-butyl-1,2,4-oxadiazol-5-yl | F | F | H | Me | K⁺ | |
| 4-65 | 3-tert-butyl-1,2,4-oxadiazol-5-yl | F | I | H | Me | Na⁺ | |
| 4-66 | 3-tert-butyl-1,2,4-oxadiazol-5-yl | F | I | H | Me | K⁺ | |
| 4-67 | 3-tert-butyl-1,2,4-oxadiazol-5-yl | F | CN | H | Me | Na⁺ | |
| 4-68 | 3-tert-butyl-1,2,4-oxadiazol-5-yl | F | CN | H | Me | K⁺ | |
| 4-69 | 3-tert-butyl-1,2,4-oxadiazol-5-yl | F | CF₃ | H | Me | Na⁺ | |
| 4-70 | 3-tert-butyl-1,2,4-oxadiazol-5-yl | F | CF₃ | H | Me | K⁺ | |
| 4-71 | 3-tert-butyl-1,2,4-oxadiazol-5-yl | Cl | Cl | H | Me | Na⁺ | |
| 4-72 | 3-tert-butyl-1,2,4-oxadiazol-5-yl | Cl | Cl | H | Me | K⁺ | |
| 4-73 | 3-tert-butyl-1,2,4-oxadiazol-5-yl | Cl | Cl | H | Me | NH₄⁺ | |
| 4-74 | 3-tert-butyl-1,2,4-oxadiazol-5-yl | Cl | Br | H | Me | Na⁺ | |
| 4-75 | 3-tert-butyl-1,2,4-oxadiazol-5-yl | Cl | Br | H | Me | K⁺ | |
| 4-76 | 3-tert-butyl-1,2,4-oxadiazol-5-yl | Cl | Br | H | Me | NH₄⁺ | |
| 4-77 | 3-tert-butyl-1,2,4-oxadiazol-5-yl | Cl | F | H | Me | Na⁺ | |
| 4-78 | 3-tert-butyl-1,2,4-oxadiazol-5-yl | Cl | F | H | Me | K⁺ | |
| 4-79 | 3-tert-butyl-1,2,4-oxadiazol-5-yl | Cl | I | H | Me | Na⁺ | |
| 4-80 | 3-tert-butyl-1,2,4-oxadiazol-5-yl | Cl | I | H | Me | K⁺ | |
| 4-81 | 3-tert-butyl-1,2,4-oxadiazol-5-yl | Cl | CN | H | Me | Na⁺ | |
| 4-82 | 3-tert-butyl-1,2,4-oxadiazol-5-yl | Cl | CN | H | Me | K⁺ | |
| 4-83 | 3-tert-butyl-1,2,4-oxadiazol-5-yl | Cl | CF₃ | H | Me | Na⁺ | |
| 4-84 | 3-tert-butyl-1,2,4-oxadiazol-5-yl | Cl | CF₃ | H | Me | K⁺ | |
| 4-85 | 3-tert-butyl-1,2,4-oxadiazol-5-yl | H | Cl | Me | Me | Na⁺ | |
| 4-86 | 3-tert-butyl-1,2,4-oxadiazol-5-yl | H | Cl | Me | Me | K⁺ | |
| 4-87 | 3-tert-butyl-1,2,4-oxadiazol-5-yl | H | Cl | Me | Me | NH₄⁺ | |
| 4-88 | 3-tert-butyl-1,2,4-oxadiazol-5-yl | H | Br | Me | Me | Na⁺ | |
| 4-89 | 3-tert-butyl-1,2,4-oxadiazol-5-yl | H | Br | Me | Me | K⁺ | |
| 4-90 | 3-tert-butyl-1,2,4-oxadiazol-5-yl | H | Br | Me | Me | NH₄⁺ | |
| 4-91 | 3-tert-butyl-1,2,4-oxadiazol-5-yl | H | F | Me | Me | Na⁺ | |
| 4-92 | 3-tert-butyl-1,2,4-oxadiazol-5-yl | H | F | Me | Me | K⁺ | |
| 4-93 | 3-tert-butyl-1,2,4-oxadiazol-5-yl | H | I | Me | Me | Na⁺ | |
| 4-94 | 3-tert-butyl-1,2,4-oxadiazol-5-yl | H | I | Me | Me | K⁺ | |
| 4-95 | 3-tert-butyl-1,2,4-oxadiazol-5-yl | H | CN | Me | Me | Na⁺ | |
| 4-96 | 3-tert-butyl-1,2,4-oxadiazol-5-yl | H | CN | Me | Me | K⁺ | |
| 4-97 | 3-tert-butyl-1,2,4-oxadiazol-5-yl | H | CF₃ | Me | Me | Na⁺ | |
| 4-98 | 3-tert-butyl-1,2,4-oxadiazol-5-yl | H | CF₃ | Me | Me | K⁺ | |
| 4-99 | 3-tert-butyl-1,2,4-oxadiazol-5-yl | F | Cl | Me | Me | Na⁺ | |
| 4-100 | 3-tert-butyl-1,2,4-oxadiazol-5-yl | F | Cl | Me | Me | K⁺ | |
| 4-101 | 3-tert-butyl-1,2,4-oxadiazol-5-yl | F | Cl | Me | Me | NH₄⁺ | |
| 4-102 | 3-tert-butyl-1,2,4-oxadiazol-5-yl | F | Br | Me | Me | Na⁺ | |
| 4-103 | 3-tert-butyl-1,2,4-oxadiazol-5-yl | F | Br | Me | Me | K⁺ | |
| 4-104 | 3-tert-butyl-1,2,4-oxadiazol-5-yl | F | Br | Me | Me | NH₄⁺ | |
| 4-105 | 3-tert-butyl-1,2,4-oxadiazol-5-yl | F | F | Me | Me | Na⁺ | |
| 4-106 | 3-tert-butyl-1,2,4-oxadiazol-5-yl | F | F | Me | Me | K⁺ | |
| 4-107 | 3-tert-butyl-1,2,4-oxadiazol-5-yl | F | I | Me | Me | Na⁺ | |
| 4-108 | 3-tert-butyl-1,2,4-oxadiazol-5-yl | F | I | Me | Me | K⁺ | |
| 4-109 | 3-tert-butyl-1,2,4-oxadiazol-5-yl | F | CN | Me | Me | Na⁺ | |
| 4-110 | 3-tert-butyl-1,2,4-oxadiazol-5-yl | F | CN | Me | Me | K⁺ | |
| 4-111 | 3-tert-butyl-1,2,4-oxadiazol-5-yl | F | CF₃ | Me | Me | Na⁺ | |
| 4-112 | 3-tert-butyl-1,2,4-oxadiazol-5-yl | F | CF₃ | Me | Me | K⁺ | |
| 4-113 | 3-tert-butyl-1,2,4-oxadiazol-5-yl | Cl | Cl | Me | Me | Na⁺ | |
| 4-114 | 3-tert-butyl-1,2,4-oxadiazol-5-yl | Cl | Cl | Me | Me | K⁺ | |
| 4-115 | 3-tert-butyl-1,2,4-oxadiazol-5-yl | Cl | Cl | Me | Me | NH₄⁺ | |
| 4-116 | 3-tert-butyl-1,2,4-oxadiazol-5-yl | Cl | Br | Me | Me | Na⁺ | |
| 4-117 | 3-tert-butyl-1,2,4-oxadiazol-5-yl | Cl | Br | Me | Me | K⁺ | |
| 4-118 | 3-tert-butyl-1,2,4-oxadiazol-5-yl | Cl | Br | Me | Me | NH₄⁺ | |
| 4-119 | 3-tert-butyl-1,2,4-oxadiazol-5-yl | Cl | F | Me | Me | Na⁺ | |
| 4-120 | 3-tert-butyl-1,2,4-oxadiazol-5-yl | Cl | F | Me | Me | K⁺ | |
| 4-121 | 3-tert-butyl-1,2,4-oxadiazol-5-yl | Cl | I | Me | Me | Na⁺ | |
| 4-122 | 3-tert-butyl-1,2,4-oxadiazol-5-yl | Cl | I | Me | Me | K⁺ | |
| 4-123 | 3-tert-butyl-1,2,4-oxadiazol-5-yl | Cl | CN | Me | Me | Na⁺ | |
| 4-124 | 3-tert-butyl-1,2,4-oxadiazol-5-yl | Cl | CN | Me | Me | K⁺ | |
| 4-125 | 3-tert-butyl-1,2,4-oxadiazol-5-yl | Cl | CF₃ | Me | Me | Na⁺ | |
| 4-126 | 3-tert-butyl-1,2,4-oxadiazol-5-yl | Cl | CF₃ | Me | Me | K⁺ | |

TABLE 4-continued

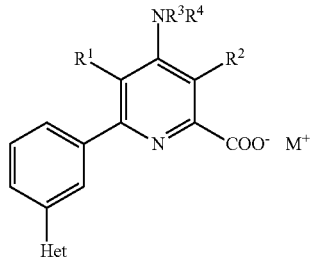

(I-iv)

| No. | Het | R$^1$ | R$^2$ | R$^3$ | R$^4$ | M$^+$ | Physical data: $^1$H NMR: δ [CDCl$_3$] |
|---|---|---|---|---|---|---|---|
| 4-127 | 3-tert-butyl-1,2,4-oxadiazol-5-yl | H | Cl | =CHNMe$_2$ | | Na$^+$ | |
| 4-128 | 3-tert-butyl-1,2,4-oxadiazol-5-yl | H | Cl | =CHNMe$_2$ | | K$^+$ | |
| 4-129 | 3-tert-butyl-1,2,4-oxadiazol-5-yl | H | Cl | =CHNMe$_2$ | | NH$_4^+$ | |
| 4-130 | 3-tert-butyl-1,2,4-oxadiazol-5-yl | H | Br | =CHNMe$_2$ | | Na$^+$ | |
| 4-131 | 3-tert-butyl-1,2,4-oxadiazol-5-yl | H | Br | =CHNMe$_2$ | | K$^+$ | |
| 4-132 | 3-tert-butyl-1,2,4-oxadiazol-5-yl | H | Br | =CHNMe$_2$ | | NH$_4^+$ | |
| 4-133 | 3-tert-butyl-1,2,4-oxadiazol-5-yl | H | F | =CHNMe$_2$ | | Na$^+$ | |
| 4-134 | 3-tert-butyl-1,2,4-oxadiazol-5-yl | H | F | =CHNMe$_2$ | | K$^+$ | |
| 4-135 | 3-tert-butyl-1,2,4-oxadiazol-5-yl | H | I | =CHNMe$_2$ | | Na$^+$ | |
| 4-136 | 3-tert-butyl-1,2,4-oxadiazol-5-yl | H | I | =CHNMe$_2$ | | K$^+$ | |
| 4-137 | 3-tert-butyl-1,2,4-oxadiazol-5-yl | H | CN | =CHNMe$_2$ | | Na$^+$ | |
| 4-138 | 3-tert-butyl-1,2,4-oxadiazol-5-yl | H | CN | =CHNMe$_2$ | | K$^+$ | |
| 4-139 | 3-tert-butyl-1,2,4-oxadiazol-5-yl | H | CF$_3$ | =CHNMe$_2$ | | Na$^+$ | |
| 4-140 | 3-tert-butyl-1,2,4-oxadiazol-5-yl | H | CF$_3$ | =CHNMe$_2$ | | K$^+$ | |
| 4-141 | 3-tert-butyl-1,2,4-oxadiazol-5-yl | F | Cl | =CHNMe$_2$ | | Na$^+$ | |
| 4-142 | 3-tert-butyl-1,2,4-oxadiazol-5-yl | F | Cl | =CHNMe$_2$ | | K$^+$ | |
| 4-143 | 3-tert-butyl-1,2,4-oxadiazol-5-yl | F | Cl | =CHNMe$_2$ | | NH$_4^+$ | |
| 4-144 | 3-tert-butyl-1,2,4-oxadiazol-5-yl | F | Br | =CHNMe$_2$ | | Na$^+$ | |
| 4-145 | 3-tert-butyl-1,2,4-oxadiazol-5-yl | F | Br | =CHNMe$_2$ | | K$^+$ | |
| 4-146 | 3-tert-butyl-1,2,4-oxadiazol-5-yl | F | Br | =CHNMe$_2$ | | NH$_4^+$ | |
| 4-147 | 3-tert-butyl-1,2,4-oxadiazol-5-yl | F | F | =CHNMe$_2$ | | Na$^+$ | |
| 4-148 | 3-tert-butyl-1,2,4-oxadiazol-5-yl | F | F | =CHNMe$_2$ | | K$^+$ | |
| 4-149 | 3-tert-butyl-1,2,4-oxadiazol-5-yl | F | I | =CHNMe$_2$ | | Na$^+$ | |
| 4-150 | 3-tert-butyl-1,2,4-oxadiazol-5-yl | F | I | =CHNMe$_2$ | | K$^+$ | |
| 4-151 | 3-tert-butyl-1,2,4-oxadiazol-5-yl | F | CN | =CHNMe$_2$ | | Na$^+$ | |
| 4-152 | 3-tert-butyl-1,2,4-oxadiazol-5-yl | F | CN | =CHNMe$_2$ | | K$^+$ | |
| 4-153 | 3-tert-butyl-1,2,4-oxadiazol-5-yl | F | CF$_3$ | =CHNMe$_2$ | | Na$^+$ | |
| 4-154 | 3-tert-butyl-1,2,4-oxadiazol-5-yl | F | CF$_3$ | =CHNMe$_2$ | | K$^+$ | |
| 4-155 | 3-tert-butyl-1,2,4-oxadiazol-5-yl | Cl | Cl | =CHNMe$_2$ | | Na$^+$ | |
| 4-156 | 3-tert-butyl-1,2,4-oxadiazol-5-yl | Cl | Cl | =CHNMe$_2$ | | K$^+$ | |
| 4-157 | 3-tert-butyl-1,2,4-oxadiazol-5-yl | Cl | Cl | =CHNMe$_2$ | | NH$_4^+$ | |
| 4-158 | 3-tert-butyl-1,2,4-oxadiazol-5-yl | Cl | Br | =CHNMe$_2$ | | Na$^+$ | |
| 4-159 | 3-tert-butyl-1,2,4-oxadiazol-5-yl | Cl | Br | =CHNMe$_2$ | | K$^+$ | |
| 4-160 | 3-tert-butyl-1,2,4-oxadiazol-5-yl | Cl | Br | =CHNMe$_2$ | | NH$_4^+$ | |
| 4-161 | 3-tert-butyl-1,2,4-oxadiazol-5-yl | Cl | F | =CHNMe$_2$ | | Na$^+$ | |
| 4-162 | 3-tert-butyl-1,2,4-oxadiazol-5-yl | Cl | F | =CHNMe$_2$ | | K$^+$ | |
| 4-163 | 3-tert-butyl-1,2,4-oxadiazol-5-yl | Cl | I | =CHNMe$_2$ | | Na$^+$ | |
| 4-164 | 3-tert-butyl-1,2,4-oxadiazol-5-yl | Cl | I | =CHNMe$_2$ | | K$^+$ | |
| 4-165 | 3-tert-butyl-1,2,4-oxadiazol-5-yl | Cl | CN | =CHNMe$_2$ | | Na$^+$ | |
| 4-166 | 3-tert-butyl-1,2,4-oxadiazol-5-yl | Cl | CN | =CHNMe$_2$ | | K$^+$ | |
| 4-167 | 3-tert-butyl-1,2,4-oxadiazol-5-yl | Cl | CF$_3$ | =CHNMe$_2$ | | Na$^+$ | |
| 4-168 | 3-tert-butyl-1,2,4-oxadiazol-5-yl | Cl | CF$_3$ | =CHNMe$_2$ | | K$^+$ | |
| 4-169 | thien-2-yl | H | Cl | H | H | Na$^+$ | |
| 4-170 | thien-2-yl | H | Cl | H | H | K$^+$ | |
| 4-171 | thien-2-yl | H | Cl | H | H | NH$_4^+$ | |
| 4-172 | thien-2-yl | H | Br | H | H | Na$^+$ | |
| 4-173 | thien-2-yl | H | Br | H | H | K$^+$ | |
| 4-174 | thien-2-yl | H | Br | H | H | NH$_4^+$ | |
| 4-175 | thien-2-yl | H | F | H | H | Na$^+$ | |
| 4-176 | thien-2-yl | H | F | H | H | K$^+$ | |
| 4-177 | thien-2-yl | H | I | H | H | Na$^+$ | |
| 4-178 | thien-2-yl | H | I | H | H | K$^+$ | |
| 4-179 | thien-2-yl | H | CN | H | H | Na$^+$ | |
| 4-180 | thien-2-yl | H | CN | H | H | K$^+$ | |
| 4-181 | thien-2-yl | H | CF$_3$ | H | H | Na$^+$ | |
| 4-182 | thien-2-yl | H | CF$_3$ | H | H | K$^+$ | |
| 4-183 | thien-2-yl | F | Cl | H | H | Na$^+$ | |
| 4-184 | thien-2-yl | F | Cl | H | H | K$^+$ | |
| 4-185 | thien-2-yl | F | Cl | H | H | NH$_4^+$ | |
| 4-186 | thien-2-yl | F | Br | H | H | Na$^+$ | |
| 4-187 | thien-2-yl | F | Br | H | H | K$^+$ | |
| 4-188 | thien-2-yl | F | Br | H | H | NH$_4^+$ | |
| 4-189 | thien-2-yl | F | F | H | H | Na$^+$ | |

TABLE 4-continued

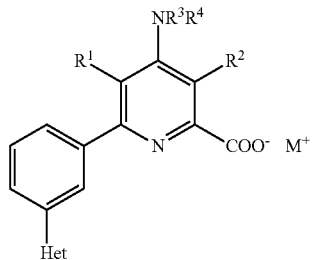

(I-iv)

| No. | Het | R¹ | R² | R³ | R⁴ | M⁺ | Physical data: ¹H NMR: δ [CDCl₃] |
|---|---|---|---|---|---|---|---|
| 4-190 | thien-2-yl | F | F | H | H | K⁺ | |
| 4-191 | thien-2-yl | F | I | H | H | Na⁺ | |
| 4-192 | thien-2-yl | F | I | H | H | K⁺ | |
| 4-193 | thien-2-yl | F | CN | H | H | Na⁺ | |
| 4-194 | thien-2-yl | F | CN | H | H | K⁺ | |
| 4-195 | thien-2-yl | F | CF₃ | H | H | Na⁺ | |
| 4-196 | thien-2-yl | F | CF₃ | H | H | K⁺ | |
| 4-197 | thien-2-yl | H | Cl | H | Me | Na⁺ | |
| 4-198 | thien-2-yl | H | Cl | H | Me | K⁺ | |
| 4-199 | thien-2-yl | H | Cl | H | Me | NH₄⁺ | |
| 4-200 | thien-2-yl | H | Br | H | Me | Na⁺ | |
| 4-201 | thien-2-yl | H | Br | H | Me | K⁺ | |
| 4-202 | thien-2-yl | H | Br | H | Me | NH₄⁺ | |
| 4-203 | thien-2-yl | H | F | H | Me | Na⁺ | |
| 4-204 | thien-2-yl | H | F | H | Me | K⁺ | |
| 4-205 | thien-2-yl | H | I | H | Me | Na⁺ | |
| 4-206 | thien-2-yl | H | I | H | Me | K⁺ | |
| 4-207 | thien-2-yl | H | CN | H | Me | Na⁺ | |
| 4-208 | thien-2-yl | H | CN | H | Me | K⁺ | |
| 4-209 | thien-2-yl | H | CF₃ | H | Me | Na⁺ | |
| 4-210 | thien-2-yl | H | CF₃ | H | Me | K⁺ | |
| 4-211 | thien-2-yl | F | Cl | H | Me | Na⁺ | |
| 4-212 | thien-2-yl | F | Cl | H | Me | K⁺ | |
| 4-213 | thien-2-yl | F | Cl | H | Me | NH₄⁺ | |
| 4-214 | thien-2-yl | F | Br | H | Me | Na⁺ | |
| 4-215 | thien-2-yl | F | Br | H | Me | K⁺ | |
| 4-216 | thien-2-yl | F | Br | H | Me | NH₄⁺ | |
| 4-217 | thien-2-yl | F | F | H | Me | Na⁺ | |
| 4-218 | thien-2-yl | F | F | H | Me | K⁺ | |
| 4-219 | thien-2-yl | F | I | H | Me | Na⁺ | |
| 4-220 | thien-2-yl | F | I | H | Me | K⁺ | |
| 4-221 | thien-2-yl | F | CN | H | Me | Na⁺ | |
| 4-222 | thien-2-yl | F | CN | H | Me | K⁺ | |
| 4-223 | thien-2-yl | F | CF₃ | H | Me | Na⁺ | |
| 4-224 | thien-2-yl | F | CF₃ | H | Me | K⁺ | |
| 4-225 | thien-2-yl | H | Cl | Me | Me | Na⁺ | |
| 4-226 | thien-2-yl | H | Cl | Me | Me | K⁺ | |
| 4-227 | thien-2-yl | H | Cl | Me | Me | NH₄⁺ | |
| 4-228 | thien-2-yl | H | Br | Me | Me | Na⁺ | |
| 4-229 | thien-2-yl | H | Br | Me | Me | K⁺ | |
| 4-230 | thien-2-yl | H | Br | Me | Me | NH₄⁺ | |
| 4-231 | thien-2-yl | H | F | Me | Me | Na⁺ | |
| 4-232 | thien-2-yl | H | F | Me | Me | K⁺ | |
| 4-233 | thien-2-yl | H | I | Me | Me | Na⁺ | |
| 4-234 | thien-2-yl | H | I | Me | Me | K⁺ | |
| 4-235 | thien-2-yl | H | CN | Me | Me | Na⁺ | |
| 4-236 | thien-2-yl | H | CN | Me | Me | K⁺ | |
| 4-237 | thien-2-yl | H | CF₃ | Me | Me | Na⁺ | |
| 4-238 | thien-2-yl | H | CF₃ | Me | Me | K⁺ | |
| 4-239 | thien-2-yl | F | Cl | Me | Me | Na⁺ | |
| 4-240 | thien-2-yl | F | Cl | Me | Me | K⁺ | |
| 4-241 | thien-2-yl | F | Cl | Me | Me | NH₄⁺ | |
| 4-242 | thien-2-yl | F | Br | Me | Me | Na⁺ | |
| 4-243 | thien-2-yl | F | Br | Me | Me | K⁺ | |
| 4-244 | thien-2-yl | F | Br | Me | Me | NH₄⁺ | |
| 4-245 | thien-2-yl | F | F | Me | Me | Na⁺ | |
| 4-246 | thien-2-yl | F | F | Me | Me | K⁺ | |
| 4-247 | thien-2-yl | F | I | Me | Me | Na⁺ | |
| 4-248 | thien-2-yl | F | I | Me | Me | K⁺ | |
| 4-249 | thien-2-yl | F | CN | Me | Me | Na⁺ | |
| 4-250 | thien-2-yl | F | CN | Me | Me | K⁺ | |
| 4-251 | thien-2-yl | F | CF₃ | Me | Me | Na⁺ | |
| 4-252 | thien-2-yl | F | CF₃ | Me | Me | K⁺ | |

TABLE 4-continued

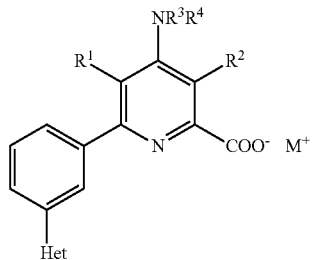

(I-iv)

| No. | Het | R¹ | R² | R³ | R⁴ | M⁺ | Physical data: $^1$H NMR: δ [CDCl$_3$] |
|---|---|---|---|---|---|---|---|
| 4-253 | thien-2-yl | H | Cl | =CHNMe$_2$ | | Na⁺ | |
| 4-254 | thien-2-yl | H | Cl | =CHNMe$_2$ | | K⁺ | |
| 4-255 | thien-2-yl | H | Cl | =CHNMe$_2$ | | NH$_4^+$ | |
| 4-256 | thien-2-yl | H | Br | =CHNMe$_2$ | | Na⁺ | |
| 4-257 | thien-2-yl | H | Br | =CHNMe$_2$ | | K⁺ | |
| 4-258 | thien-2-yl | H | Br | =CHNMe$_2$ | | NH$_4^+$ | |
| 4-259 | thien-2-yl | H | F | =CHNMe$_2$ | | Na⁺ | |
| 4-260 | thien-2-yl | H | F | =CHNMe$_2$ | | K⁺ | |
| 4-261 | thien-2-yl | H | I | =CHNMe$_2$ | | Na⁺ | |
| 4-262 | thien-2-yl | H | I | =CHNMe$_2$ | | K⁺ | |
| 4-263 | thien-2-yl | H | CN | =CHNMe$_2$ | | Na⁺ | |
| 4-264 | thien-2-yl | H | CN | =CHNMe$_2$ | | K⁺ | |
| 4-265 | thien-2-yl | H | CF$_3$ | =CHNMe$_2$ | | Na⁺ | |
| 4-266 | thien-2-yl | H | CF$_3$ | =CHNMe$_2$ | | K⁺ | |
| 4-267 | thien-2-yl | F | Cl | =CHNMe$_2$ | | Na⁺ | |
| 4-268 | thien-2-yl | F | Cl | =CHNMe$_2$ | | K⁺ | |
| 4-269 | thien-2-yl | F | Cl | =CHNMe$_2$ | | NH$_4^+$ | |
| 4-270 | thien-2-yl | F | Br | =CHNMe$_2$ | | Na⁺ | |
| 4-271 | thien-2-yl | F | Br | =CHNMe$_2$ | | K⁺ | |
| 4-272 | thien-2-yl | F | Br | =CHNMe$_2$ | | NH$_4^+$ | |
| 4-273 | thien-2-yl | F | F | =CHNMe$_2$ | | Na⁺ | |
| 4-274 | thien-2-yl | F | F | =CHNMe$_2$ | | K⁺ | |
| 4-275 | thien-2-yl | F | I | =CHNMe$_2$ | | Na⁺ | |
| 4-276 | thien-2-yl | F | I | =CHNMe$_2$ | | K⁺ | |
| 4-277 | thien-2-yl | F | CN | =CHNMe$_2$ | | Na⁺ | |
| 4-278 | thien-2-yl | F | CN | =CHNMe$_2$ | | K⁺ | |
| 4-279 | thien-2-yl | F | CF$_3$ | =CHNMe$_2$ | | Na⁺ | |
| 4-280 | thien-2-yl | F | CF$_3$ | =CHNMe$_2$ | | K⁺ | |
| 4-281 | pyrrol-1-yl | H | Cl | H | H | Na⁺ | |
| 4-282 | pyrrol-1-yl | H | Cl | H | H | K⁺ | |
| 4-283 | pyrrol-1-yl | H | Cl | H | H | NH$_4^+$ | |
| 4-284 | pyrrol-1-yl | H | Br | H | H | Na⁺ | |
| 4-285 | pyrrol-1-yl | H | Br | H | H | K⁺ | |
| 4-286 | pyrrol-1-yl | H | Br | H | H | NH$_4^+$ | |
| 4-287 | pyrrol-1-yl | H | F | H | H | Na⁺ | |
| 4-288 | pyrrol-1-yl | H | F | H | H | K⁺ | |
| 4-289 | pyrrol-1-yl | H | I | H | H | Na⁺ | |
| 4-290 | pyrrol-1-yl | H | I | H | H | K⁺ | |
| 4-291 | pyrrol-1-yl | H | CN | H | H | Na⁺ | |
| 4-292 | pyrrol-1-yl | H | CN | H | H | K⁺ | |
| 4-293 | pyrrol-1-yl | H | CF$_3$ | H | H | Na⁺ | |
| 4-294 | pyrrol-1-yl | H | CF$_3$ | H | H | K⁺ | |
| 4-295 | pyrrol-1-yl | F | Cl | H | H | Na⁺ | |
| 4-296 | pyrrol-1-yl | F | Cl | H | H | K⁺ | |
| 4-297 | pyrrol-1-yl | F | Cl | H | H | NH$_4^+$ | |
| 4-298 | pyrrol-1-yl | F | Br | H | H | Na⁺ | |
| 4-299 | pyrrol-1-yl | F | Br | H | H | K⁺ | |
| 4-300 | pyrrol-1-yl | F | Br | H | H | NH$_4^+$ | |
| 4-301 | pyrrol-1-yl | F | F | H | H | Na⁺ | |
| 4-302 | pyrrol-1-yl | F | F | H | H | K⁺ | |
| 4-303 | pyrrol-1-yl | F | I | H | H | Na⁺ | |
| 4-304 | pyrrol-1-yl | F | I | H | H | K⁺ | |
| 4-305 | pyrrol-1-yl | F | CN | H | H | Na⁺ | |
| 4-306 | pyrrol-1-yl | F | CN | H | H | K⁺ | |
| 4-307 | pyrrol-1-yl | F | CF$_3$ | H | H | Na⁺ | |
| 4-308 | pyrrol-1-yl | F | CF$_3$ | H | H | K⁺ | |
| 4-309 | pyrrol-1-yl | H | Cl | H | Me | Na⁺ | |
| 4-310 | pyrrol-1-yl | H | Cl | H | Me | K⁺ | |
| 4-311 | pyrrol-1-yl | H | Cl | H | Me | NH$_4^+$ | |
| 4-312 | pyrrol-1-yl | H | Br | H | Me | Na⁺ | |
| 4-313 | pyrrol-1-yl | H | Br | H | Me | K⁺ | |
| 4-314 | pyrrol-1-yl | H | Br | H | Me | NH$_4^+$ | |
| 4-315 | pyrrol-1-yl | H | F | H | Me | Na⁺ | |

TABLE 4-continued

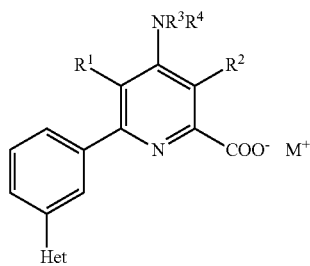

(I-iv)

| No. | Het | $R^1$ | $R^2$ | $R^3$ | $R^4$ | $M^+$ | Physical data: $^1$H NMR: δ [CDCl$_3$] |
|---|---|---|---|---|---|---|---|
| 4-316 | pyrrol-1-yl | H | F | H | Me | K$^+$ | |
| 4-317 | pyrrol-1-yl | H | I | H | Me | Na$^+$ | |
| 4-318 | pyrrol-1-yl | H | I | H | Me | K$^+$ | |
| 4-319 | pyrrol-1-yl | H | CN | H | Me | Na$^+$ | |
| 4-320 | pyrrol-1-yl | H | CN | H | Me | K$^+$ | |
| 4-321 | pyrrol-1-yl | H | CF$_3$ | H | Me | Na$^+$ | |
| 4-322 | pyrrol-1-yl | H | CF$_3$ | H | Me | K$^+$ | |
| 4-323 | pyrrol-1-yl | F | Cl | H | Me | Na$^+$ | |
| 4-324 | pyrrol-1-yl | F | Cl | H | Me | K$^+$ | |
| 4-325 | pyrrol-1-yl | F | Cl | H | Me | NH$_4^+$ | |
| 4-326 | pyrrol-1-yl | F | Br | H | Me | Na$^+$ | |
| 4-327 | pyrrol-1-yl | F | Br | H | Me | K$^+$ | |
| 4-328 | pyrrol-1-yl | F | Br | H | Me | NH$_4^+$ | |
| 4-329 | pyrrol-1-yl | F | F | H | Me | Na$^+$ | |
| 4-330 | pyrrol-1-yl | F | F | H | Me | K$^+$ | |
| 4-331 | pyrrol-1-yl | F | I | H | Me | Na$^+$ | |
| 4-332 | pyrrol-1-yl | F | I | H | Me | K$^+$ | |
| 4-333 | pyrrol-1-yl | F | CN | H | Me | Na$^+$ | |
| 4-334 | pyrrol-1-yl | F | CN | H | Me | K$^+$ | |
| 4-335 | pyrrol-1-yl | F | CF$_3$ | H | Me | Na$^+$ | |
| 4-336 | pyrrol-1-yl | F | CF$_3$ | H | Me | K$^+$ | |
| 4-337 | pyrrol-1-yl | H | Cl | Me | Me | Na$^+$ | |
| 4-338 | pyrrol-1-yl | H | Cl | Me | Me | K$^+$ | |
| 4-339 | pyrrol-1-yl | H | Cl | Me | Me | NH$_4^+$ | |
| 4-340 | pyrrol-1-yl | H | Br | Me | Me | Na$^+$ | |
| 4-341 | pyrrol-1-yl | H | Br | Me | Me | K$^+$ | |
| 4-342 | pyrrol-1-yl | H | Br | Me | Me | NH$_4^+$ | |
| 4-343 | pyrrol-1-yl | H | F | Me | Me | Na$^+$ | |
| 4-344 | pyrrol-1-yl | H | F | Me | Me | K$^+$ | |
| 4-345 | pyrrol-1-yl | H | I | Me | Me | Na$^+$ | |
| 4-346 | pyrrol-1-yl | H | I | Me | Me | K$^+$ | |
| 4-347 | pyrrol-1-yl | H | CN | Me | Me | Na$^+$ | |
| 4-348 | pyrrol-1-yl | H | CN | Me | Me | K$^+$ | |
| 4-349 | pyrrol-1-yl | H | CF$_3$ | Me | Me | Na$^+$ | |
| 4-350 | pyrrol-1-yl | H | CF$_3$ | Me | Me | K$^+$ | |
| 4-351 | pyrrol-1-yl | F | Cl | Me | Me | Na$^+$ | |
| 4-352 | pyrrol-1-yl | F | Cl | Me | Me | K$^+$ | |
| 4-353 | pyrrol-1-yl | F | Cl | Me | Me | NH$_4^+$ | |
| 4-354 | pyrrol-1-yl | F | Br | Me | Me | Na$^+$ | |
| 4-355 | pyrrol-1-yl | F | Br | Me | Me | K$^+$ | |
| 4-356 | pyrrol-1-yl | F | Br | Me | Me | NH$_4^+$ | |
| 4-357 | pyrrol-1-yl | F | F | Me | Me | Na$^+$ | |
| 4-358 | pyrrol-1-yl | F | F | Me | Me | K$^+$ | |
| 4-359 | pyrrol-1-yl | F | I | Me | Me | Na$^+$ | |
| 4-360 | pyrrol-1-yl | F | I | Me | Me | K$^+$ | |
| 4-361 | pyrrol-1-yl | F | CN | Me | Me | Na$^+$ | |
| 4-362 | pyrrol-1-yl | F | CN | Me | Me | K$^+$ | |
| 4-363 | pyrrol-1-yl | F | CF$_3$ | Me | Me | Na$^+$ | |
| 4-364 | pyrrol-1-yl | F | CF$_3$ | Me | Me | K$^+$ | |
| 4-365 | pyrrol-1-yl | H | Cl | =CHNMe$_2$ | | Na$^+$ | |
| 4-366 | pyrrol-1-yl | H | Cl | =CHNMe$_2$ | | K$^+$ | |
| 4-367 | pyrrol-1-yl | H | Cl | =CHNMe$_2$ | | NH$_4^+$ | |
| 4-368 | pyrrol-1-yl | H | Br | =CHNMe$_2$ | | Na$^+$ | |
| 4-369 | pyrrol-1-yl | H | Br | =CHNMe$_2$ | | K$^+$ | |
| 4-370 | pyrrol-1-yl | H | Br | =CHNMe$_2$ | | NH$_4^+$ | |
| 4-371 | pyrrol-1-yl | H | F | =CHNMe$_2$ | | Na$^+$ | |
| 4-372 | pyrrol-1-yl | H | F | =CHNMe$_2$ | | K$^+$ | |
| 4-373 | pyrrol-1-yl | H | I | =CHNMe$_2$ | | Na$^+$ | |
| 4-374 | pyrrol-1-yl | H | I | =CHNMe$_2$ | | K$^+$ | |
| 4-375 | pyrrol-1-yl | H | CN | =CHNMe$_2$ | | Na$^+$ | |
| 4-376 | pyrrol-1-yl | H | CN | =CHNMe$_2$ | | K$^+$ | |
| 4-377 | pyrrol-1-yl | H | CF$_3$ | =CHNMe$_2$ | | Na$^+$ | |
| 4-378 | pyrrol-1-yl | H | CF$_3$ | =CHNMe$_2$ | | K$^+$ | |

TABLE 4-continued

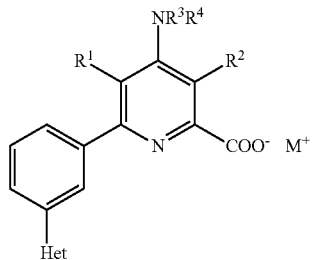

(I-iv)

| No. | Het | R¹ | R² | R³ | R⁴ | M⁺ | Physical data: $^1$H NMR: δ [CDCl$_3$] |
|---|---|---|---|---|---|---|---|
| 4-379 | pyrrol-1-yl | F | Cl | =CHNMe$_2$ | | Na⁺ | |
| 4-380 | pyrrol-1-yl | F | Cl | =CHNMe$_2$ | | K⁺ | |
| 4-381 | pyrrol-1-yl | F | Cl | =CHNMe$_2$ | | NH$_4$⁺ | |
| 4-382 | pyrrol-1-yl | F | Br | =CHNMe$_2$ | | Na⁺ | |
| 4-383 | pyrrol-1-yl | F | Br | =CHNMe$_2$ | | K⁺ | |
| 4-384 | pyrrol-1-yl | F | Br | =CHNMe$_2$ | | NH$_4$⁺ | |
| 4-385 | pyrrol-1-yl | F | F | =CHNMe$_2$ | | Na⁺ | |
| 4-386 | pyrrol-1-yl | F | F | =CHNMe$_2$ | | K⁺ | |
| 4-387 | pyrrol-1-yl | F | I | =CHNMe$_2$ | | Na⁺ | |
| 4-388 | pyrrol-1-yl | F | I | =CHNMe$_2$ | | K⁺ | |
| 4-389 | pyrrol-1-yl | F | CN | =CHNMe$_2$ | | Na⁺ | |
| 4-390 | pyrrol-1-yl | F | CN | =CHNMe$_2$ | | K⁺ | |
| 4-391 | pyrrol-1-yl | F | CF$_3$ | =CHNMe$_2$ | | Na⁺ | |
| 4-392 | pyrrol-1-yl | F | CF$_3$ | =CHNMe$_2$ | | K⁺ | |
| 4-393 | pyrazol-1-yl | H | Cl | H | H | Na⁺ | |
| 4-394 | pyrazol-1-yl | H | Cl | H | H | K⁺ | |
| 4-395 | pyrazol-1-yl | H | Cl | H | H | NH$_4$⁺ | |
| 4-396 | pyrazol-1-yl | H | Br | H | H | Na⁺ | |
| 4-397 | pyrazol-1-yl | H | Br | H | H | K⁺ | |
| 4-398 | pyrazol-1-yl | H | Br | H | H | NH$_4$⁺ | |
| 4-399 | pyrazol-1-yl | H | F | H | H | Na⁺ | |
| 4-400 | pyrazol-1-yl | H | F | H | H | K⁺ | |
| 4-401 | pyrazol-1-yl | H | I | H | H | Na⁺ | |
| 4-402 | pyrazol-1-yl | H | I | H | H | K⁺ | |
| 4-403 | pyrazol-1-yl | H | CN | H | H | Na⁺ | |
| 4-404 | pyrazol-1-yl | H | CN | H | H | K⁺ | |
| 4-405 | pyrazol-1-yl | H | CF$_3$ | H | H | Na⁺ | |
| 4-406 | pyrazol-1-yl | H | CF$_3$ | H | H | K⁺ | |
| 4-407 | pyrazol-1-yl | F | Cl | H | H | Na⁺ | |
| 4-408 | pyrazol-1-yl | F | Cl | H | H | K⁺ | |
| 4-409 | pyrazol-1-yl | F | Cl | H | H | NH$_4$⁺ | |
| 4-410 | pyrazol-1-yl | F | Br | H | H | Na⁺ | |
| 4-411 | pyrazol-1-yl | F | Br | H | H | K⁺ | |
| 4-412 | pyrazol-1-yl | F | Br | H | H | NH$_4$⁺ | |
| 4-413 | pyrazol-1-yl | F | F | H | H | Na⁺ | |
| 4-414 | pyrazol-1-yl | F | F | H | H | K⁺ | |
| 4-415 | pyrazol-1-yl | F | I | H | H | Na⁺ | |
| 4-416 | pyrazol-1-yl | F | I | H | H | K⁺ | |
| 4-417 | pyrazol-1-yl | F | CN | H | H | Na⁺ | |
| 4-418 | pyrazol-1-yl | F | CN | H | H | K⁺ | |
| 4-419 | pyrazol-1-yl | F | CF$_3$ | H | H | Na⁺ | |
| 4-420 | pyrazol-1-yl | F | CF$_3$ | H | H | K⁺ | |
| 4-421 | pyrazol-1-yl | H | Cl | H | Me | Na⁺ | |
| 4-422 | pyrazol-1-yl | H | Cl | H | Me | K⁺ | |
| 4-423 | pyrazol-1-yl | H | Cl | H | Me | NH$_4$⁺ | |
| 4-424 | pyrazol-1-yl | H | Br | H | Me | Na⁺ | |
| 4-425 | pyrazol-1-yl | H | Br | H | Me | K⁺ | |
| 4-426 | pyrazol-1-yl | H | Br | H | Me | NH$_4$⁺ | |
| 4-427 | pyrazol-1-yl | H | F | H | Me | Na⁺ | |
| 4-428 | pyrazol-1-yl | H | F | H | Me | K⁺ | |
| 4-429 | pyrazol-1-yl | H | I | H | Me | Na⁺ | |
| 4-430 | pyrazol-1-yl | H | I | H | Me | K⁺ | |
| 4-431 | pyrazol-1-yl | H | CN | H | Me | Na⁺ | |
| 4-432 | pyrazol-1-yl | H | CN | H | Me | K⁺ | |
| 4-433 | pyrazol-1-yl | H | CF$_3$ | H | Me | Na⁺ | |
| 4-434 | pyrazol-1-yl | H | CF$_3$ | H | Me | K⁺ | |
| 4-435 | pyrazol-1-yl | F | Cl | H | Me | Na⁺ | |
| 4-436 | pyrazol-1-yl | F | Cl | H | Me | K⁺ | |
| 4-437 | pyrazol-1-yl | F | Cl | H | Me | NH$_4$⁺ | |
| 4-438 | pyrazol-1-yl | F | Br | H | Me | Na⁺ | |
| 4-439 | pyrazol-1-yl | F | Br | H | Me | K⁺ | |
| 4-440 | pyrazol-1-yl | F | Br | H | Me | NH$_4$⁺ | |
| 4-441 | pyrazol-1-yl | F | F | H | Me | Na⁺ | |

TABLE 4-continued

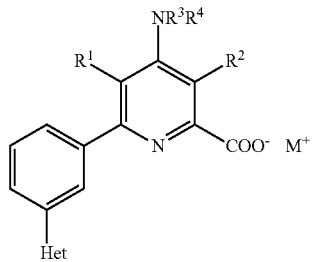

(I-iv)

| No. | Het | $R^1$ | $R^2$ | $R^3$ | $R^4$ | $M^+$ | Physical data: $^1$H NMR: δ [CDCl$_3$] |
|---|---|---|---|---|---|---|---|
| 4-442 | pyrazol-1-yl | F | F | H | Me | K$^+$ | |
| 4-443 | pyrazol-1-yl | F | I | H | Me | Na$^+$ | |
| 4-444 | pyrazol-1-yl | F | I | H | Me | K$^+$ | |
| 4-445 | pyrazol-1-yl | F | CN | H | Me | Na$^+$ | |
| 4-446 | pyrazol-1-yl | F | CN | H | Me | K$^+$ | |
| 4-447 | pyrazol-1-yl | F | CF$_3$ | H | Me | Na$^+$ | |
| 4-448 | pyrazol-1-yl | F | CF$_3$ | H | Me | K$^+$ | |
| 4-449 | pyrazol-1-yl | H | Cl | Me | Me | Na$^+$ | |
| 4-450 | pyrazol-1-yl | H | Cl | Me | Me | K$^+$ | |
| 4-451 | pyrazol-1-yl | H | Cl | Me | Me | NH$_4^+$ | |
| 4-452 | pyrazol-1-yl | H | Br | Me | Me | Na$^+$ | |
| 4-453 | pyrazol-1-yl | H | Br | Me | Me | K$^+$ | |
| 4-454 | pyrazol-1-yl | H | Br | Me | Me | NH$_4^+$ | |
| 4-455 | pyrazol-1-yl | H | F | Me | Me | Na$^+$ | |
| 4-456 | pyrazol-1-yl | H | F | Me | Me | K$^+$ | |
| 4-457 | pyrazol-1-yl | H | I | Me | Me | Na$^+$ | |
| 4-458 | pyrazol-1-yl | H | I | Me | Me | K$^+$ | |
| 4-459 | pyrazol-1-yl | H | CN | Me | Me | Na$^+$ | |
| 4-460 | pyrazol-1-yl | H | CN | Me | Me | K$^+$ | |
| 4-461 | pyrazol-1-yl | H | CF$_3$ | Me | Me | Na$^+$ | |
| 4-462 | pyrazol-1-yl | H | CF$_3$ | Me | Me | K$^+$ | |
| 4-463 | pyrazol-1-yl | F | Cl | Me | Me | Na$^+$ | |
| 4-464 | pyrazol-1-yl | F | Cl | Me | Me | K$^+$ | |
| 4-465 | pyrazol-1-yl | F | Cl | Me | Me | NH$_4^+$ | |
| 4-466 | pyrazol-1-yl | F | Br | Me | Me | Na$^+$ | |
| 4-467 | pyrazol-1-yl | F | Br | Me | Me | K$^+$ | |
| 4-468 | pyrazol-1-yl | F | Br | Me | Me | NH$_4^+$ | |
| 4-469 | pyrazol-1-yl | F | F | Me | Me | Na$^+$ | |
| 4-470 | pyrazol-1-yl | F | F | Me | Me | K$^+$ | |
| 4-471 | pyrazol-1-yl | F | I | Me | Me | Na$^+$ | |
| 4-472 | pyrazol-1-yl | F | I | Me | Me | K$^+$ | |
| 4-473 | pyrazol-1-yl | F | CN | Me | Me | Na$^+$ | |
| 4-474 | pyrazol-1-yl | F | CN | Me | Me | K$^+$ | |
| 4-475 | pyrazol-1-yl | F | CF$_3$ | Me | Me | Na$^+$ | |
| 4-476 | pyrazol-1-yl | F | CF$_3$ | Me | Me | K$^+$ | |
| 4-477 | pyrazol-1-yl | H | Cl | =CHNMe$_2$ | | Na$^+$ | |
| 4-478 | pyrazol-1-yl | H | Cl | =CHNMe$_2$ | | K$^+$ | |
| 4-479 | pyrazol-1-yl | H | Cl | =CHNMe$_2$ | | NH$_4^+$ | |
| 4-480 | pyrazol-1-yl | H | Br | =CHNMe$_2$ | | Na$^+$ | |
| 4-481 | pyrazol-1-yl | H | Br | =CHNMe$_2$ | | K$^+$ | |
| 4-482 | pyrazol-1-yl | H | Br | =CHNMe$_2$ | | NH$_4^+$ | |
| 4-483 | pyrazol-1-yl | H | F | =CHNMe$_2$ | | Na$^+$ | |
| 4-484 | pyrazol-1-yl | H | F | =CHNMe$_2$ | | K$^+$ | |
| 4-485 | pyrazol-1-yl | H | I | =CHNMe$_2$ | | Na$^+$ | |
| 4-486 | pyrazol-1-yl | H | I | =CHNMe$_2$ | | K$^+$ | |
| 4-487 | pyrazol-1-yl | H | CN | =CHNMe$_2$ | | Na$^+$ | |
| 4-488 | pyrazol-1-yl | H | CN | =CHNMe$_2$ | | K$^+$ | |
| 4-489 | pyrazol-1-yl | H | CF$_3$ | =CHNMe$_2$ | | Na$^+$ | |
| 4-490 | pyrazol-1-yl | H | CF$_3$ | =CHNMe$_2$ | | K$^+$ | |
| 4-491 | pyrazol-1-yl | F | Cl | =CHNMe$_2$ | | Na$^+$ | |
| 4-492 | pyrazol-1-yl | F | Cl | =CHNMe$_2$ | | K$^+$ | |
| 4-493 | pyrazol-1-yl | F | Cl | =CHNMe$_2$ | | NH$_4^+$ | |
| 4-494 | pyrazol-1-yl | F | Br | =CHNMe$_2$ | | Na$^+$ | |
| 4-495 | pyrazol-1-yl | F | Br | =CHNMe$_2$ | | K$^+$ | |
| 4-496 | pyrazol-1-yl | F | Br | =CHNMe$_2$ | | NH$_4^+$ | |
| 4-497 | pyrazol-1-yl | F | F | =CHNMe$_2$ | | Na$^+$ | |
| 4-498 | pyrazol-1-yl | F | F | =CHNMe$_2$ | | K$^+$ | |
| 4-499 | pyrazol-1-yl | F | I | =CHNMe$_2$ | | Na$^+$ | |
| 4-500 | pyrazol-1-yl | F | I | =CHNMe$_2$ | | K$^+$ | |
| 4-501 | pyrazol-1-yl | F | CN | =CHNMe$_2$ | | Na$^+$ | |
| 4-502 | pyrazol-1-yl | F | CN | =CHNMe$_2$ | | K$^+$ | |
| 4-503 | pyrazol-1-yl | F | CF$_3$ | =CHNMe$_2$ | | Na$^+$ | |
| 4-504 | pyrazol-1-yl | F | CF$_3$ | =CHNMe$_2$ | | K$^+$ | |

TABLE 4-continued

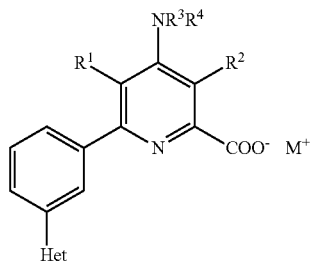

(I-iv)

| No. | Het | R¹ | R² | R³ | R⁴ | M⁺ | Physical data: $^1$H NMR: δ [CDCl$_3$] |
|---|---|---|---|---|---|---|---|
| 4-505 | pyridin-3-yl | H | Cl | H | H | Na⁺ | |
| 4-506 | pyridin-3-yl | H | Cl | H | H | K⁺ | |
| 4-507 | pyridin-3-yl | H | Cl | H | H | NH$_4$⁺ | |
| 4-508 | pyridin-3-yl | H | Br | H | H | Na⁺ | |
| 4-509 | pyridin-3-yl | H | Br | H | H | K⁺ | |
| 4-510 | pyridin-3-yl | H | Br | H | H | NH$_4$⁺ | |
| 4-511 | pyridin-3-yl | H | F | H | H | Na⁺ | |
| 4-512 | pyridin-3-yl | H | F | H | H | K⁺ | |
| 4-513 | pyridin-3-yl | H | I | H | H | Na⁺ | |
| 4-514 | pyridin-3-yl | H | I | H | H | K⁺ | |
| 4-515 | pyridin-3-yl | H | CN | H | H | Na⁺ | |
| 4-516 | pyridin-3-yl | H | CN | H | H | K⁺ | |
| 4-517 | pyridin-3-yl | H | CF$_3$ | H | H | Na⁺ | |
| 4-518 | pyridin-3-yl | H | CF$_3$ | H | H | K⁺ | |
| 4-519 | pyridin-3-yl | F | Cl | H | H | Na⁺ | |
| 4-520 | pyridin-3-yl | F | Cl | H | H | K⁺ | |
| 4-521 | pyridin-3-yl | F | Cl | H | H | NH$_4$⁺ | |
| 4-522 | pyridin-3-yl | F | Br | H | H | Na⁺ | |
| 4-523 | pyridin-3-yl | F | Br | H | H | K⁺ | |
| 4-524 | pyridin-3-yl | F | Br | H | H | NH$_4$⁺ | |
| 4-525 | pyridin-3-yl | F | F | H | H | Na⁺ | |
| 4-526 | pyridin-3-yl | F | F | H | H | K⁺ | |
| 4-527 | pyridin-3-yl | F | I | H | H | Na⁺ | |
| 4-528 | pyridin-3-yl | F | I | H | H | K⁺ | |
| 4-529 | pyridin-3-yl | F | CN | H | H | Na⁺ | |
| 4-530 | pyridin-3-yl | F | CN | H | H | K⁺ | |
| 4-531 | pyridin-3-yl | F | CF$_3$ | H | H | Na⁺ | |
| 4-532 | pyridin-3-yl | F | CF$_3$ | H | H | K⁺ | |
| 4-533 | pyridin-3-yl | H | Cl | H | Me | Na⁺ | |
| 4-534 | pyridin-3-yl | H | Cl | H | Me | K⁺ | |
| 4-535 | pyridin-3-yl | H | Cl | H | Me | NH$_4$⁺ | |
| 4-536 | pyridin-3-yl | H | Br | H | Me | Na⁺ | |
| 4-537 | pyridin-3-yl | H | Br | H | Me | K⁺ | |
| 4-538 | pyridin-3-yl | H | Br | H | Me | NH$_4$⁺ | |
| 4-539 | pyridin-3-yl | H | F | H | Me | Na⁺ | |
| 4-540 | pyridin-3-yl | H | F | H | Me | K⁺ | |
| 4-541 | pyridin-3-yl | H | I | H | Me | Na⁺ | |
| 4-542 | pyridin-3-yl | H | I | H | Me | K⁺ | |
| 4-543 | pyridin-3-yl | H | CN | H | Me | Na⁺ | |
| 4-544 | pyridin-3-yl | H | CN | H | Me | K⁺ | |
| 4-545 | pyridin-3-yl | H | CF$_3$ | H | Me | Na⁺ | |
| 4-546 | pyridin-3-yl | H | CF$_3$ | H | Me | K⁺ | |
| 4-547 | pyridin-3-yl | F | Cl | H | Me | Na⁺ | |
| 4-548 | pyridin-3-yl | F | Cl | H | Me | K⁺ | |
| 4-549 | pyridin-3-yl | F | Cl | H | Me | NH$_4$⁺ | |
| 4-550 | pyridin-3-yl | F | Br | H | Me | Na⁺ | |
| 4-551 | pyridin-3-yl | F | Br | H | Me | K⁺ | |
| 4-552 | pyridin-3-yl | F | Br | H | Me | NH$_4$⁺ | |
| 4-553 | pyridin-3-yl | F | F | H | Me | Na⁺ | |
| 4-554 | pyridin-3-yl | F | F | H | Me | K⁺ | |
| 4-555 | pyridin-3-yl | F | I | H | Me | Na⁺ | |
| 4-556 | pyridin-3-yl | F | I | H | Me | K⁺ | |
| 4-557 | pyridin-3-yl | F | CN | H | Me | Na⁺ | |
| 4-558 | pyridin-3-yl | F | CN | H | Me | K⁺ | |
| 4-559 | pyridin-3-yl | F | CF$_3$ | H | Me | Na⁺ | |
| 4-560 | pyridin-3-yl | F | CF$_3$ | H | Me | K⁺ | |
| 4-561 | pyridin-3-yl | H | Cl | Me | Me | Na⁺ | |
| 4-562 | pyridin-3-yl | H | Cl | Me | Me | K⁺ | |
| 4-563 | pyridin-3-yl | H | Cl | Me | Me | NH$_4$⁺ | |
| 4-564 | pyridin-3-yl | H | Br | Me | Me | Na⁺ | |
| 4-565 | pyridin-3-yl | H | Br | Me | Me | K⁺ | |
| 4-566 | pyridin-3-yl | H | Br | Me | Me | NH$_4$⁺ | |
| 4-567 | pyridin-3-yl | H | F | Me | Me | Na⁺ | |

TABLE 4-continued

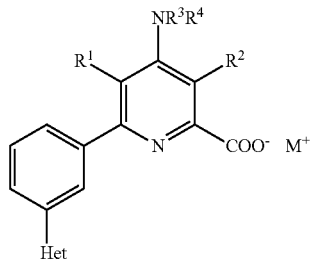

(I-iv)

| No. | Het | R¹ | R² | R³ | R⁴ | M⁺ | Physical data: $^1$H NMR: δ [CDCl$_3$] |
|---|---|---|---|---|---|---|---|
| 4-568 | pyridin-3-yl | H | F | Me | Me | K⁺ | |
| 4-569 | pyridin-3-yl | H | I | Me | Me | Na⁺ | |
| 4-570 | pyridin-3-yl | H | I | Me | Me | K⁺ | |
| 4-571 | pyridin-3-yl | H | CN | Me | Me | Na⁺ | |
| 4-572 | pyridin-3-yl | H | CN | Me | Me | K⁺ | |
| 4-573 | pyridin-3-yl | H | CF₃ | Me | Me | Na⁺ | |
| 4-574 | pyridin-3-yl | H | CF₃ | Me | Me | K⁺ | |
| 4-575 | pyridin-3-yl | F | Cl | Me | Me | Na⁺ | |
| 4-576 | pyridin-3-yl | F | Cl | Me | Me | K⁺ | |
| 4-577 | pyridin-3-yl | F | Cl | Me | Me | NH₄⁺ | |
| 4-578 | pyridin-3-yl | F | Br | Me | Me | Na⁺ | |
| 4-579 | pyridin-3-yl | F | Br | Me | Me | K⁺ | |
| 4-580 | pyridin-3-yl | F | Br | Me | Me | NH₄⁺ | |
| 4-581 | pyridin-3-yl | F | F | Me | Me | Na⁺ | |
| 4-582 | pyridin-3-yl | F | F | Me | Me | K⁺ | |
| 4-583 | pyridin-3-yl | F | I | Me | Me | Na⁺ | |
| 4-584 | pyridin-3-yl | F | I | Me | Me | K⁺ | |
| 4-585 | pyridin-3-yl | F | CN | Me | Me | Na⁺ | |
| 4-586 | pyridin-3-yl | F | CN | Me | Me | K⁺ | |
| 4-587 | pyridin-3-yl | F | CF₃ | Me | Me | Na⁺ | |
| 4-588 | pyridin-3-yl | F | CF₃ | Me | Me | K⁺ | |
| 4-589 | pyridin-3-yl | H | Cl | =CHNMe₂ | | Na⁺ | |
| 4-590 | pyridin-3-yl | H | Cl | =CHNMe₂ | | K⁺ | |
| 4-591 | pyridin-3-yl | H | Cl | =CHNMe₂ | | NH₄⁺ | |
| 4-592 | pyridin-3-yl | H | Br | =CHNMe₂ | | Na⁺ | |
| 4-593 | pyridin-3-yl | H | Br | =CHNMe₂ | | K⁺ | |
| 4-594 | pyridin-3-yl | H | Br | =CHNMe₂ | | NH₄⁺ | |
| 4-595 | pyridin-3-yl | H | F | =CHNMe₂ | | Na⁺ | |
| 4-596 | pyridin-3-yl | H | F | =CHNMe₂ | | K⁺ | |
| 4-597 | pyridin-3-yl | H | I | =CHNMe₂ | | Na⁺ | |
| 4-598 | pyridin-3-yl | H | I | =CHNMe₂ | | K⁺ | |
| 4-599 | pyridin-3-yl | H | CN | =CHNMe₂ | | Na⁺ | |
| 4-600 | pyridin-3-yl | H | CN | =CHNMe₂ | | K⁺ | |
| 4-601 | pyridin-3-yl | H | CF₃ | =CHNMe₂ | | Na⁺ | |
| 4-602 | pyridin-3-yl | H | CF₃ | =CHNMe₂ | | K⁺ | |
| 4-603 | pyridin-3-yl | F | Cl | =CHNMe₂ | | Na⁺ | |
| 4-604 | pyridin-3-yl | F | Cl | =CHNMe₂ | | K⁺ | |
| 4-605 | pyridin-3-yl | F | Cl | =CHNMe₂ | | NH₄⁺ | |
| 4-606 | pyridin-3-yl | F | Br | =CHNMe₂ | | Na⁺ | |
| 4-607 | pyridin-3-yl | F | Br | =CHNMe₂ | | K⁺ | |
| 4-608 | pyridin-3-yl | F | Br | =CHNMe₂ | | NH₄⁺ | |
| 4-609 | pyridin-3-yl | F | F | =CHNMe₂ | | Na⁺ | |
| 4-610 | pyridin-3-yl | F | F | =CHNMe₂ | | K⁺ | |
| 4-611 | pyridin-3-yl | F | I | =CHNMe₂ | | Na⁺ | |
| 4-612 | pyridin-3-yl | F | I | =CHNMe₂ | | K⁺ | |
| 4-613 | pyridin-3-yl | F | CN | =CHNMe₂ | | Na⁺ | |
| 4-614 | pyridin-3-yl | F | CN | =CHNMe₂ | | K⁺ | |
| 4-615 | pyridin-3-yl | F | CF₃ | =CHNMe₂ | | Na⁺ | |
| 4-616 | pyridin-3-yl | F | CF₃ | =CHNMe₂ | | K⁺ | |
| 4-617 | oxiranyl | H | Cl | H | H | Na⁺ | |
| 4-618 | oxiranyl | H | Cl | H | H | K⁺ | |
| 4-619 | oxiranyl | H | Cl | H | H | NH₄⁺ | |
| 4-620 | oxiranyl | H | Br | H | H | Na⁺ | |
| 4-621 | oxiranyl | H | Br | H | H | K⁺ | |
| 4-622 | oxiranyl | H | Br | H | H | NH₄⁺ | |
| 4-623 | oxiranyl | H | F | H | H | Na⁺ | |
| 4-624 | oxiranyl | H | F | H | H | K⁺ | |
| 4-625 | oxiranyl | H | I | H | H | Na⁺ | |
| 4-626 | oxiranyl | H | I | H | H | K⁺ | |
| 4-627 | oxiranyl | H | CN | H | H | Na⁺ | |
| 4-628 | oxiranyl | H | CN | H | H | K⁺ | |
| 4-629 | oxiranyl | H | CF₃ | H | H | Na⁺ | |
| 4-630 | oxiranyl | H | CF₃ | H | H | K⁺ | |

TABLE 4-continued (I-iv)

| No. | Het | R¹ | R² | R³ | R⁴ | M⁺ | Physical data: $^1$H NMR: δ [CDCl$_3$] |
|---|---|---|---|---|---|---|---|
| 4-631 | oxiranyl | F | Cl | H | H | Na⁺ | |
| 4-632 | oxiranyl | F | Cl | H | H | K⁺ | |
| 4-633 | oxiranyl | F | Cl | H | H | NH$_4$⁺ | |
| 4-634 | oxiranyl | F | Br | H | H | Na⁺ | |
| 4-635 | oxiranyl | F | Br | H | H | K⁺ | |
| 4-636 | oxiranyl | F | Br | H | H | NH$_4$⁺ | |
| 4-637 | oxiranyl | F | F | H | H | Na⁺ | |
| 4-638 | oxiranyl | F | F | H | H | K⁺ | |
| 4-639 | oxiranyl | F | I | H | H | Na⁺ | |
| 4-640 | oxiranyl | F | I | H | H | K⁺ | |
| 4-641 | oxiranyl | F | CN | H | H | Na⁺ | |
| 4-642 | oxiranyl | F | CN | H | H | K⁺ | |
| 4-643 | oxiranyl | F | CF$_3$ | H | H | Na⁺ | |
| 4-644 | oxiranyl | F | CF$_3$ | H | H | K⁺ | |
| 4-645 | oxiranyl | H | Cl | H | Me | Na⁺ | |
| 4-646 | oxiranyl | H | Cl | H | Me | K⁺ | |
| 4-647 | oxiranyl | H | Cl | H | Me | NH$_4$⁺ | |
| 4-648 | oxiranyl | H | Br | H | Me | Na⁺ | |
| 4-649 | oxiranyl | H | Br | H | Me | K⁺ | |
| 4-650 | oxiranyl | H | Br | H | Me | NH$_4$⁺ | |
| 4-651 | oxiranyl | H | F | H | Me | Na⁺ | |
| 4-652 | oxiranyl | H | F | H | Me | K⁺ | |
| 4-653 | oxiranyl | H | I | H | Me | Na⁺ | |
| 4-654 | oxiranyl | H | I | H | Me | K⁺ | |
| 4-655 | oxiranyl | H | CN | H | Me | Na⁺ | |
| 4-656 | oxiranyl | H | CN | H | Me | K⁺ | |
| 4-657 | oxiranyl | H | CF$_3$ | H | Me | Na⁺ | |
| 4-658 | oxiranyl | H | CF$_3$ | H | Me | K⁺ | |
| 4-659 | oxiranyl | F | Cl | H | Me | Na⁺ | |
| 4-660 | oxiranyl | F | Cl | H | Me | K⁺ | |
| 4-661 | oxiranyl | F | Cl | H | Me | NH$_4$⁺ | |
| 4-662 | oxiranyl | F | Br | H | Me | Na⁺ | |
| 4-663 | oxiranyl | F | Br | H | Me | K⁺ | |
| 4-664 | oxiranyl | F | Br | H | Me | NH$_4$⁺ | |
| 4-665 | oxiranyl | F | F | H | Me | Na⁺ | |
| 4-666 | oxiranyl | F | F | H | Me | K⁺ | |
| 4-667 | oxiranyl | F | I | H | Me | Na⁺ | |
| 4-668 | oxiranyl | F | I | H | Me | K⁺ | |
| 4-669 | oxiranyl | F | CN | H | Me | Na⁺ | |
| 4-670 | oxiranyl | F | CN | H | Me | K⁺ | |
| 4-671 | oxiranyl | F | CF$_3$ | H | Me | Na⁺ | |
| 4-672 | oxiranyl | F | CF$_3$ | H | Me | K⁺ | |
| 4-673 | oxiranyl | H | Cl | Me | Me | Na⁺ | |
| 4-674 | oxiranyl | H | Cl | Me | Me | K⁺ | |
| 4-675 | oxiranyl | H | Cl | Me | Me | NH$_4$⁺ | |
| 4-676 | oxiranyl | H | Br | Me | Me | Na⁺ | |
| 4-677 | oxiranyl | H | Br | Me | Me | K⁺ | |
| 4-678 | oxiranyl | H | Br | Me | Me | NH$_4$⁺ | |
| 4-679 | oxiranyl | H | F | Me | Me | Na⁺ | |
| 4-680 | oxiranyl | H | F | Me | Me | K⁺ | |
| 4-681 | oxiranyl | H | I | Me | Me | Na⁺ | |
| 4-682 | oxiranyl | H | I | Me | Me | K⁺ | |
| 4-683 | oxiranyl | H | CN | Me | Me | Na⁺ | |
| 4-684 | oxiranyl | H | CN | Me | Me | K⁺ | |
| 4-685 | oxiranyl | H | CF$_3$ | Me | Me | Na⁺ | |
| 4-686 | oxiranyl | H | CF$_3$ | Me | Me | K⁺ | |
| 4-687 | oxiranyl | F | Cl | Me | Me | Na⁺ | |
| 4-688 | oxiranyl | F | Cl | Me | Me | K⁺ | |
| 4-689 | oxiranyl | F | Cl | Me | Me | NH$_4$⁺ | |
| 4-690 | oxiranyl | F | Br | Me | Me | Na⁺ | |
| 4-691 | oxiranyl | F | Br | Me | Me | K⁺ | |
| 4-692 | oxiranyl | F | Br | Me | Me | NH$_4$⁺ | |
| 4-693 | oxiranyl | F | F | Me | Me | Na⁺ | |

TABLE 4-continued

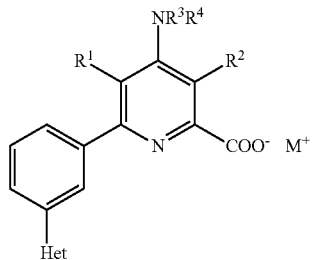

(I-iv)

| No. | Het | $R^1$ | $R^2$ | $R^3$ | $R^4$ | $M^+$ | Physical data: $^1$H NMR: δ [CDCl$_3$] |
|---|---|---|---|---|---|---|---|
| 4-694 | oxiranyl | F | F | Me | Me | K$^+$ | |
| 4-695 | oxiranyl | F | I | Me | Me | Na$^+$ | |
| 4-696 | oxiranyl | F | I | Me | Me | K$^+$ | |
| 4-697 | oxiranyl | F | CN | Me | Me | Na$^+$ | |
| 4-698 | oxiranyl | F | CN | Me | Me | K$^+$ | |
| 4-699 | oxiranyl | F | CF$_3$ | Me | Me | Na$^+$ | |
| 4-700 | oxiranyl | F | CF$_3$ | Me | Me | K$^+$ | |
| 4-701 | oxiranyl | H | Cl | =CHNMe$_2$ | | Na$^+$ | |
| 4-702 | oxiranyl | H | Cl | =CHNMe$_2$ | | K$^+$ | |
| 4-703 | oxiranyl | H | Cl | =CHNMe$_2$ | | NH$_4^+$ | |
| 4-704 | oxiranyl | H | Br | =CHNMe$_2$ | | Na$^+$ | |
| 4-705 | oxiranyl | H | Br | =CHNMe$_2$ | | K$^+$ | |
| 4-706 | oxiranyl | H | Br | =CHNMe$_2$ | | NH$_4^+$ | |
| 4-707 | oxiranyl | H | F | =CHNMe$_2$ | | Na$^+$ | |
| 4-708 | oxiranyl | H | F | =CHNMe$_2$ | | K$^+$ | |
| 4-709 | oxiranyl | H | I | =CHNMe$_2$ | | Na$^+$ | |
| 4-710 | oxiranyl | H | I | =CHNMe$_2$ | | K$^+$ | |
| 4-711 | oxiranyl | H | CN | =CHNMe$_2$ | | Na$^+$ | |
| 4-712 | oxiranyl | H | CN | =CHNMe$_2$ | | K$^+$ | |
| 4-713 | oxiranyl | H | CF$_3$ | =CHNMe$_2$ | | Na$^+$ | |
| 4-714 | oxiranyl | H | CF$_3$ | =CHNMe$_2$ | | K$^+$ | |
| 4-715 | oxiranyl | F | Cl | =CHNMe$_2$ | | Na$^+$ | |
| 4-716 | oxiranyl | F | Cl | =CHNMe$_2$ | | K$^+$ | |
| 4-717 | oxiranyl | F | Cl | =CHNMe$_2$ | | NH$_4^+$ | |
| 4-718 | oxiranyl | F | Br | =CHNMe$_2$ | | Na$^+$ | |
| 4-719 | oxiranyl | F | Br | =CHNMe$_2$ | | K$^+$ | |
| 4-720 | oxiranyl | F | Br | =CHNMe$_2$ | | NH$_4^+$ | |
| 4-721 | oxiranyl | F | F | =CHNMe$_2$ | | Na$^+$ | |
| 4-722 | oxiranyl | F | F | =CHNMe$_2$ | | K$^+$ | |
| 4-723 | oxiranyl | F | I | =CHNMe$_2$ | | Na$^+$ | |
| 4-724 | oxiranyl | F | I | =CHNMe$_2$ | | K$^+$ | |
| 4-725 | oxiranyl | F | CN | =CHNMe$_2$ | | Na$^+$ | |
| 4-726 | oxiranyl | F | CN | =CHNMe$_2$ | | K$^+$ | |
| 4-727 | oxiranyl | F | CF$_3$ | =CHNMe$_2$ | | Na$^+$ | |
| 4-728 | oxiranyl | F | CF$_3$ | =CHNMe$_2$ | | K$^+$ | |
| 4-729 | 3,3-dimethyl-oxetan-2-yl | H | Cl | H | H | Na$^+$ | |
| 4-730 | 3,3-dimethyl-oxetan-2-yl | H | Cl | H | H | K$^+$ | |
| 4-731 | 3,3-dimethyl-oxetan-2-yl | H | Cl | H | H | NH$_4^+$ | |
| 4-732 | 3,3-dimethyl-oxetan-2-yl | H | Br | H | H | Na$^+$ | |
| 4-733 | 3,3-dimethyl-oxetan-2-yl | H | Br | H | H | K$^+$ | |
| 4-734 | 3,3-dimethyl-oxetan-2-yl | H | Br | H | H | NH$_4^+$ | |
| 4-735 | 3,3-dimethyl-oxetan-2-yl | H | F | H | H | Na$^+$ | |
| 4-736 | 3,3-dimethyl-oxetan-2-yl | H | F | H | H | K$^+$ | |
| 4-737 | 3,3-dimethyl-oxetan-2-yl | H | I | H | H | Na$^+$ | |
| 4-738 | 3,3-dimethyl-oxetan-2-yl | H | I | H | H | K$^+$ | |
| 4-739 | 3,3-dimethyl-oxetan-2-yl | H | CN | H | H | Na$^+$ | |
| 4-740 | 3,3-dimethyl-oxetan-2-yl | H | CN | H | H | K$^+$ | |
| 4-741 | 3,3-dimethyl-oxetan-2-yl | H | CF$_3$ | H | H | Na$^+$ | |
| 4-742 | 3,3-dimethyl-oxetan-2-yl | H | CF$_3$ | H | H | K$^+$ | |
| 4-743 | 3,3-dimethyl-oxetan-2-yl | F | Cl | H | H | Na$^+$ | |
| 4-744 | 3,3-dimethyl-oxetan-2-yl | F | Cl | H | H | K$^+$ | |
| 4-745 | 3,3-dimethyl-oxetan-2-yl | F | Cl | H | H | NH$_4^+$ | |
| 4-746 | 3,3-dimethyl-oxetan-2-yl | F | Br | H | H | Na$^+$ | |
| 4-747 | 3,3-dimethyl-oxetan-2-yl | F | Br | H | H | K$^+$ | |
| 4-748 | 3,3-dimethyl-oxetan-2-yl | F | Br | H | H | NH$_4^+$ | |
| 4-749 | 3,3-dimethyl-oxetan-2-yl | F | F | H | H | Na$^+$ | |
| 4-750 | 3,3-dimethyl-oxetan-2-yl | F | F | H | H | K$^+$ | |
| 4-751 | 3,3-dimethyl-oxetan-2-yl | F | I | H | H | Na$^+$ | |
| 4-752 | 3,3-dimethyl-oxetan-2-yl | F | I | H | H | K$^+$ | |
| 4-753 | 3,3-dimethyl-oxetan-2-yl | F | CN | H | H | Na$^+$ | |
| 4-754 | 3,3-dimethyl-oxetan-2-yl | F | CN | H | H | K$^+$ | |
| 4-755 | 3,3-dimethyl-oxetan-2-yl | F | CF$_3$ | H | H | Na$^+$ | |
| 4-756 | 3,3-dimethyl-oxetan-2-yl | F | CF$_3$ | H | H | K$^+$ | |

TABLE 4-continued

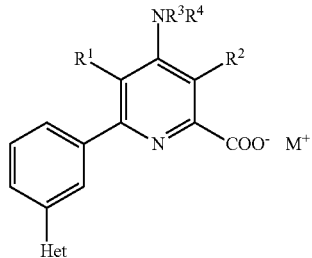

(I-iv)

| No. | Het | R¹ | R² | R³ | R⁴ | M⁺ | Physical data: $^1$H NMR: δ [CDCl$_3$] |
|---|---|---|---|---|---|---|---|
| 4-757 | 3,3-dimethyl-oxetan-2-yl | H | Cl | H | Me | Na⁺ | |
| 4-758 | 3,3-dimethyl-oxetan-2-yl | H | Cl | H | Me | K⁺ | |
| 4-759 | 3,3-dimethyl-oxetan-2-yl | H | Cl | H | Me | NH₄⁺ | |
| 4-760 | 3,3-dimethyl-oxetan-2-yl | H | Br | H | Me | Na⁺ | |
| 4-761 | 3,3-dimethyl-oxetan-2-yl | H | Br | H | Me | K⁺ | |
| 4-762 | 3,3-dimethyl-oxetan-2-yl | H | Br | H | Me | NH₄⁺ | |
| 4-763 | 3,3-dimethyl-oxetan-2-yl | H | F | H | Me | Na⁺ | |
| 4-764 | 3,3-dimethyl-oxetan-2-yl | H | F | H | Me | K⁺ | |
| 4-765 | 3,3-dimethyl-oxetan-2-yl | H | I | H | Me | Na⁺ | |
| 4-766 | 3,3-dimethyl-oxetan-2-yl | H | I | H | Me | K⁺ | |
| 4-767 | 3,3-dimethyl-oxetan-2-yl | H | CN | H | Me | Na⁺ | |
| 4-768 | 3,3-dimethyl-oxetan-2-yl | H | CN | H | Me | K⁺ | |
| 4-769 | 3,3-dimethyl-oxetan-2-yl | H | CF₃ | H | Me | Na⁺ | |
| 4-770 | 3,3-dimethyl-oxetan-2-yl | H | CF₃ | H | Me | K⁺ | |
| 4-771 | 3,3-dimethyl-oxetan-2-yl | F | Cl | H | Me | Na⁺ | |
| 4-772 | 3,3-dimethyl-oxetan-2-yl | F | Cl | H | Me | K⁺ | |
| 4-773 | 3,3-dimethyl-oxetan-2-yl | F | Cl | H | Me | NH₄⁺ | |
| 4-774 | 3,3-dimethyl-oxetan-2-yl | F | Br | H | Me | Na⁺ | |
| 4-775 | 3,3-dimethyl-oxetan-2-yl | F | Br | H | Me | K⁺ | |
| 4-776 | 3,3-dimethyl-oxetan-2-yl | F | Br | H | Me | NH₄⁺ | |
| 4-777 | 3,3-dimethyl-oxetan-2-yl | F | F | H | Me | Na⁺ | |
| 4-778 | 3,3-dimethyl-oxetan-2-yl | F | F | H | Me | K⁺ | |
| 4-779 | 3,3-dimethyl-oxetan-2-yl | F | I | H | Me | Na⁺ | |
| 4-780 | 3,3-dimethyl-oxetan-2-yl | F | I | H | Me | K⁺ | |
| 4-781 | 3,3-dimethyl-oxetan-2-yl | F | CN | H | Me | Na⁺ | |
| 4-782 | 3,3-dimethyl-oxetan-2-yl | F | CN | H | Me | K⁺ | |
| 4-783 | 3,3-dimethyl-oxetan-2-yl | F | CF₃ | H | Me | Na⁺ | |
| 4-784 | 3,3-dimethyl-oxetan-2-yl | F | CF₃ | H | Me | K⁺ | |
| 4-785 | 3,3-dimethyl-oxetan-2-yl | H | Cl | Me | Me | Na⁺ | |
| 4-786 | 3,3-dimethyl-oxetan-2-yl | H | Cl | Me | Me | K⁺ | |
| 4-787 | 3,3-dimethyl-oxetan-2-yl | H | Cl | Me | Me | NH₄⁺ | |
| 4-788 | 3,3-dimethyl-oxetan-2-yl | H | Br | Me | Me | Na⁺ | |
| 4-789 | 3,3-dimethyl-oxetan-2-yl | H | Br | Me | Me | K⁺ | |
| 4-790 | 3,3-dimethyl-oxetan-2-yl | H | Br | Me | Me | NH₄⁺ | |
| 4-791 | 3,3-dimethyl-oxetan-2-yl | H | F | Me | Me | Na⁺ | |
| 4-792 | 3,3-dimethyl-oxetan-2-yl | H | F | Me | Me | K⁺ | |
| 4-793 | 3,3-dimethyl-oxetan-2-yl | H | I | Me | Me | Na⁺ | |
| 4-794 | 3,3-dimethyl-oxetan-2-yl | H | I | Me | Me | K⁺ | |
| 4-795 | 3,3-dimethyl-oxetan-2-yl | H | CN | Me | Me | Na⁺ | |
| 4-796 | 3,3-dimethyl-oxetan-2-yl | H | CN | Me | Me | K⁺ | |
| 4-797 | 3,3-dimethyl-oxetan-2-yl | H | CF₃ | Me | Me | Na⁺ | |
| 4-798 | 3,3-dimethyl-oxetan-2-yl | H | CF₃ | Me | Me | K⁺ | |
| 4-799 | 3,3-dimethyl-oxetan-2-yl | F | Cl | Me | Me | Na⁺ | |
| 4-800 | 3,3-dimethyl-oxetan-2-yl | F | Cl | Me | Me | K⁺ | |
| 4-801 | 3,3-dimethyl-oxetan-2-yl | F | Cl | Me | Me | NH₄⁺ | |
| 4-802 | 3,3-dimethyl-oxetan-2-yl | F | Br | Me | Me | Na⁺ | |
| 4-803 | 3,3-dimethyl-oxetan-2-yl | F | Br | Me | Me | K⁺ | |
| 4-804 | 3,3-dimethyl-oxetan-2-yl | F | Br | Me | Me | NH₄⁺ | |
| 4-805 | 3,3-dimethyl-oxetan-2-yl | F | F | Me | Me | Na⁺ | |
| 4-806 | 3,3-dimethyl-oxetan-2-yl | F | F | Me | Me | K⁺ | |
| 4-807 | 3,3-dimethyl-oxetan-2-yl | F | I | Me | Me | Na⁺ | |
| 4-808 | 3,3-dimethyl-oxetan-2-yl | F | I | Me | Me | K⁺ | |
| 4-809 | 3,3-dimethyl-oxetan-2-yl | F | CN | Me | Me | Na⁺ | |
| 4-810 | 3,3-dimethyl-oxetan-2-yl | F | CN | Me | Me | K⁺ | |
| 4-811 | 3,3-dimethyl-oxetan-2-yl | F | CF₃ | Me | Me | Na⁺ | |
| 4-812 | 3,3-dimethyl-oxetan-2-yl | F | CF₃ | Me | Me | K⁺ | |
| 4-813 | 3,3-dimethyl-oxetan-2-yl | H | Cl | =CHNMe₂ | | Na⁺ | |
| 4-814 | 3,3-dimethyl-oxetan-2-yl | H | Cl | =CHNMe₂ | | K⁺ | |
| 4-815 | 3,3-dimethyl-oxetan-2-yl | H | Cl | =CHNMe₂ | | NH₄⁺ | |
| 4-816 | 3,3-dimethyl-oxetan-2-yl | H | Br | =CHNMe₂ | | Na⁺ | |
| 4-817 | 3,3-dimethyl-oxetan-2-yl | H | Br | =CHNMe₂ | | K⁺ | |
| 4-818 | 3,3-dimethyl-oxetan-2-yl | H | Br | =CHNMe₂ | | NH₄⁺ | |
| 4-819 | 3,3-dimethyl-oxetan-2-yl | H | F | =CHNMe₂ | | Na⁺ | |

TABLE 4-continued

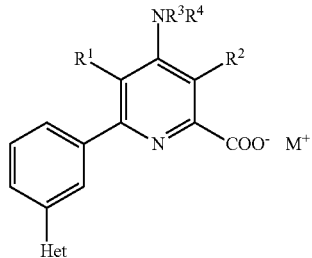

(I-iv)

| No. | Het | R¹ | R² | R³ | R⁴ | M⁺ | Physical data: $^1$H NMR: δ [CDCl$_3$] |
|---|---|---|---|---|---|---|---|
| 4-820 | 3,3-dimethyl-oxetan-2-yl | H | F | =CHNMe$_2$ | | K⁺ | |
| 4-821 | 3,3-dimethyl-oxetan-2-yl | H | I | =CHNMe$_2$ | | Na⁺ | |
| 4-822 | 3,3-dimethyl-oxetan-2-yl | H | I | =CHNMe$_2$ | | K⁺ | |
| 4-823 | 3,3-dimethyl-oxetan-2-yl | H | CN | =CHNMe$_2$ | | Na⁺ | |
| 4-824 | 3,3-dimethyl-oxetan-2-yl | H | CN | =CHNMe$_2$ | | K⁺ | |
| 4-825 | 3,3-dimethyl-oxetan-2-yl | H | CF$_3$ | =CHNMe$_2$ | | Na⁺ | |
| 4-826 | 3,3-dimethyl-oxetan-2-yl | H | CF$_3$ | =CHNMe$_2$ | | K⁺ | |
| 4-827 | 3,3-dimethyl-oxetan-2-yl | F | Cl | =CHNMe$_2$ | | Na⁺ | |
| 4-828 | 3,3-dimethyl-oxetan-2-yl | F | Cl | =CHNMe$_2$ | | K⁺ | |
| 4-829 | 3,3-dimethyl-oxetan-2-yl | F | Cl | =CHNMe$_2$ | | NH$_4^+$ | |
| 4-830 | 3,3-dimethyl-oxetan-2-yl | F | Br | =CHNMe$_2$ | | Na⁺ | |
| 4-831 | 3,3-dimethyl-oxetan-2-yl | F | Br | =CHNMe$_2$ | | K⁺ | |
| 4-832 | 3,3-dimethyl-oxetan-2-yl | F | Br | =CHNMe$_2$ | | NH$_4^+$ | |
| 4-833 | 3,3-dimethyl-oxetan-2-yl | F | F | =CHNMe$_2$ | | Na⁺ | |
| 4-834 | 3,3-dimethyl-oxetan-2-yl | F | F | =CHNMe$_2$ | | K⁺ | |
| 4-835 | 3,3-dimethyl-oxetan-2-yl | F | I | =CHNMe$_2$ | | Na⁺ | |
| 4-836 | 3,3-dimethyl-oxetan-2-yl | F | I | =CHNMe$_2$ | | K⁺ | |
| 4-837 | 3,3-dimethyl-oxetan-2-yl | F | CN | =CHNMe$_2$ | | Na⁺ | |
| 4-838 | 3,3-dimethyl-oxetan-2-yl | F | CN | =CHNMe$_2$ | | K⁺ | |
| 4-839 | 3,3-dimethyl-oxetan-2-yl | F | CF$_3$ | =CHNMe$_2$ | | Na⁺ | |
| 4-840 | 3,3-dimethyl-oxetan-2-yl | F | CF$_3$ | =CHNMe$_2$ | | K⁺ | |
| 4-841 | 2,2-dimethyl-dioxolan-4-yl | H | Cl | H | H | Na⁺ | |
| 4-842 | 2,2-dimethyl-dioxolan-4-yl | H | Cl | H | H | K⁺ | |
| 4-843 | 2,2-dimethyl-dioxolan-4-yl | H | Cl | H | H | NH$_4^+$ | |
| 4-844 | 2,2-dimethyl-dioxolan-4-yl | H | Br | H | H | Na⁺ | |
| 4-845 | 2,2-dimethyl-dioxolan-4-yl | H | Br | H | H | K⁺ | |
| 4-846 | 2,2-dimethyl-dioxolan-4-yl | H | Br | H | H | NH$_4^+$ | |
| 4-847 | 2,2-dimethyl-dioxolan-4-yl | H | F | H | H | Na⁺ | |
| 4-848 | 2,2-dimethyl-dioxolan-4-yl | H | F | H | H | K⁺ | |
| 4-849 | 2,2-dimethyl-dioxolan-4-yl | H | I | H | H | Na⁺ | |
| 4-850 | 2,2-dimethyl-dioxolan-4-yl | H | I | H | H | K⁺ | |
| 4-851 | 2,2-dimethyl-dioxolan-4-yl | H | CN | H | H | Na⁺ | |
| 4-852 | 2,2-dimethyl-dioxolan-4-yl | H | CN | H | H | K⁺ | |
| 4-853 | 2,2-dimethyl-dioxolan-4-yl | H | CF$_3$ | H | H | Na⁺ | |
| 4-854 | 2,2-dimethyl-dioxolan-4-yl | H | CF$_3$ | H | H | K⁺ | |
| 4-855 | 2,2-dimethyl-dioxolan-4-yl | F | Cl | H | H | Na⁺ | |
| 4-856 | 2,2-dimethyl-dioxolan-4-yl | F | Cl | H | H | K⁺ | |
| 4-857 | 2,2-dimethyl-dioxolan-4-yl | F | Cl | H | H | NH$_4^+$ | |
| 4-858 | 2,2-dimethyl-dioxolan-4-yl | F | Br | H | H | Na⁺ | |
| 4-859 | 2,2-dimethyl-dioxolan-4-yl | F | Br | H | H | K⁺ | |
| 4-860 | 2,2-dimethyl-dioxolan-4-yl | F | Br | H | H | NH$_4^+$ | |
| 4-861 | 2,2-dimethyl-dioxolan-4-yl | F | F | H | H | Na⁺ | |
| 4-862 | 2,2-dimethyl-dioxolan-4-yl | F | F | H | H | K⁺ | |
| 4-863 | 2,2-dimethyl-dioxolan-4-yl | F | I | H | H | Na⁺ | |
| 4-864 | 2,2-dimethyl-dioxolan-4-yl | F | I | H | H | K⁺ | |
| 4-865 | 2,2-dimethyl-dioxolan-4-yl | F | CN | H | H | Na⁺ | |
| 4-866 | 2,2-dimethyl-dioxolan-4-yl | F | CN | H | H | K⁺ | |
| 4-867 | 2,2-dimethyl-dioxolan-4-yl | F | CF$_3$ | H | H | Na⁺ | |
| 4-868 | 2,2-dimethyl-dioxolan-4-yl | F | CF$_3$ | H | H | K⁺ | |
| 4-869 | 2,2-dimethyl-dioxolan-4-yl | H | Cl | H | Me | Na⁺ | |
| 4-870 | 2,2-dimethyl-dioxolan-4-yl | H | Cl | H | Me | K⁺ | |
| 4-871 | 2,2-dimethyl-dioxolan-4-yl | H | Cl | H | Me | NH$_4^+$ | |
| 4-872 | 2,2-dimethyl-dioxolan-4-yl | H | Br | H | Me | Na⁺ | |
| 4-873 | 2,2-dimethyl-dioxolan-4-yl | H | Br | H | Me | K⁺ | |
| 4-874 | 2,2-dimethyl-dioxolan-4-yl | H | Br | H | Me | NH$_4^+$ | |
| 4-875 | 2,2-dimethyl-dioxolan-4-yl | H | F | H | Me | Na⁺ | |
| 4-876 | 2,2-dimethyl-dioxolan-4-yl | H | F | H | Me | K⁺ | |
| 4-877 | 2,2-dimethyl-dioxolan-4-yl | H | I | H | Me | Na⁺ | |
| 4-878 | 2,2-dimethyl-dioxolan-4-yl | H | I | H | Me | K⁺ | |
| 4-879 | 2,2-dimethyl-dioxolan-4-yl | H | CN | H | Me | Na⁺ | |
| 4-880 | 2,2-dimethyl-dioxolan-4-yl | H | CN | H | Me | K⁺ | |
| 4-881 | 2,2-dimethyl-dioxolan-4-yl | H | CF$_3$ | H | Me | Na⁺ | |
| 4-882 | 2,2-dimethyl-dioxolan-4-yl | H | CF$_3$ | H | Me | K⁺ | |

TABLE 4-continued

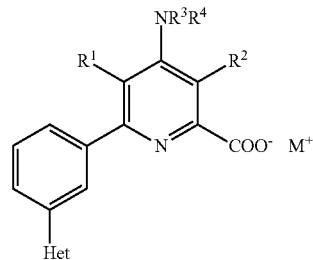

(I-iv)

| No. | Het | $R^1$ | $R^2$ | $R^3$ | $R^4$ | $M^+$ | Physical data: $^1$H NMR: δ [CDCl$_3$] |
|---|---|---|---|---|---|---|---|
| 4-883 | 2,2-dimethyl-dioxolan-4-yl | F | Cl | H | Me | Na$^+$ | |
| 4-884 | 2,2-dimethyl-dioxolan-4-yl | F | Cl | H | Me | K$^+$ | |
| 4-885 | 2,2-dimethyl-dioxolan-4-yl | F | Cl | H | Me | NH$_4^+$ | |
| 4-886 | 2,2-dimethyl-dioxolan-4-yl | F | Br | H | Me | Na$^+$ | |
| 4-887 | 2,2-dimethyl-dioxolan-4-yl | F | Br | H | Me | K$^+$ | |
| 4-888 | 2,2-dimethyl-dioxolan-4-yl | F | Br | H | Me | NH$_4^+$ | |
| 4-889 | 2,2-dimethyl-dioxolan-4-yl | F | F | H | Me | Na$^+$ | |
| 4-890 | 2,2-dimethyl-dioxolan-4-yl | F | F | H | Me | K$^+$ | |
| 4-891 | 2,2-dimethyl-dioxolan-4-yl | F | I | H | Me | Na$^+$ | |
| 4-892 | 2,2-dimethyl-dioxolan-4-yl | F | I | H | Me | K$^+$ | |
| 4-893 | 2,2-dimethyl-dioxolan-4-yl | F | CN | H | Me | Na$^+$ | |
| 4-894 | 2,2-dimethyl-dioxolan-4-yl | F | CN | H | Me | K$^+$ | |
| 4-895 | 2,2-dimethyl-dioxolan-4-yl | F | CF$_3$ | H | Me | Na$^+$ | |
| 4-896 | 2,2-dimethyl-dioxolan-4-yl | F | CF$_3$ | H | Me | K$^+$ | |
| 4-897 | 2,2-dimethyl-dioxolan-4-yl | H | Cl | Me | Me | Na$^+$ | |
| 4-898 | 2,2-dimethyl-dioxolan-4-yl | H | Cl | Me | Me | K$^+$ | |
| 4-899 | 2,2-dimethyl-dioxolan-4-yl | H | Cl | Me | Me | NH$_4^+$ | |
| 4-900 | 2,2-dimethyl-dioxolan-4-yl | H | Br | Me | Me | Na$^+$ | |
| 4-901 | 2,2-dimethyl-dioxolan-4-yl | H | Br | Me | Me | K$^+$ | |
| 4-902 | 2,2-dimethyl-dioxolan-4-yl | H | Br | Me | Me | NH$_4^+$ | |
| 4-903 | 2,2-dimethyl-dioxolan-4-yl | H | F | Me | Me | Na$^+$ | |
| 4-904 | 2,2-dimethyl-dioxolan-4-yl | H | F | Me | Me | K$^+$ | |
| 4-905 | 2,2-dimethyl-dioxolan-4-yl | H | I | Me | Me | Na$^+$ | |
| 4-906 | 2,2-dimethyl-dioxolan-4-yl | H | I | Me | Me | K$^+$ | |
| 4-907 | 2,2-dimethyl-dioxolan-4-yl | H | CN | Me | Me | Na$^+$ | |
| 4-908 | 2,2-dimethyl-dioxolan-4-yl | H | CN | Me | Me | K$^+$ | |
| 4-909 | 2,2-dimethyl-dioxolan-4-yl | H | CF$_3$ | Me | Me | Na$^+$ | |
| 4-910 | 2,2-dimethyl-dioxolan-4-yl | H | CF$_3$ | Me | Me | K$^+$ | |
| 4-911 | 2,2-dimethyl-dioxolan-4-yl | F | Cl | Me | Me | Na$^+$ | |
| 4-912 | 2,2-dimethyl-dioxolan-4-yl | F | Cl | Me | Me | K$^+$ | |
| 4-913 | 2,2-dimethyl-dioxolan-4-yl | F | Cl | Me | Me | NH$_4^+$ | |
| 4-914 | 2,2-dimethyl-dioxolan-4-yl | F | Br | Me | Me | Na$^+$ | |
| 4-915 | 2,2-dimethyl-dioxolan-4-yl | F | Br | Me | Me | K$^+$ | |
| 4-916 | 2,2-dimethyl-dioxolan-4-yl | F | Br | Me | Me | NH$_4^+$ | |
| 4-917 | 2,2-dimethyl-dioxolan-4-yl | F | F | Me | Me | Na$^+$ | |
| 4-918 | 2,2-dimethyl-dioxolan-4-yl | F | F | Me | Me | K$^+$ | |
| 4-919 | 2,2-dimethyl-dioxolan-4-yl | F | I | Me | Me | Na$^+$ | |
| 4-920 | 2,2-dimethyl-dioxolan-4-yl | F | I | Me | Me | K$^+$ | |
| 4-921 | 2,2-dimethyl-dioxolan-4-yl | F | CN | Me | Me | Na$^+$ | |
| 4-922 | 2,2-dimethyl-dioxolan-4-yl | F | CN | Me | Me | K$^+$ | |
| 4-923 | 2,2-dimethyl-dioxolan-4-yl | F | CF$_3$ | Me | Me | Na$^+$ | |
| 4-924 | 2,2-dimethyl-dioxolan-4-yl | F | CF$_3$ | Me | Me | K$^+$ | |
| 4-925 | 2,2-dimethyl-dioxolan-4-yl | H | Cl | =CHNMe$_2$ | | Na$^+$ | |
| 4-926 | 2,2-dimethyl-dioxolan-4-yl | H | Cl | =CHNMe$_2$ | | K$^+$ | |
| 4-927 | 2,2-dimethyl-dioxolan-4-yl | H | Cl | =CHNMe$_2$ | | NH$_4^+$ | |
| 4-928 | 2,2-dimethyl-dioxolan-4-yl | H | Br | =CHNMe$_2$ | | Na$^+$ | |
| 4-929 | 2,2-dimethyl-dioxolan-4-yl | H | Br | =CHNMe$_2$ | | K$^+$ | |
| 4-930 | 2,2-dimethyl-dioxolan-4-yl | H | Br | =CHNMe$_2$ | | NH$_4^+$ | |
| 4-931 | 2,2-dimethyl-dioxolan-4-yl | H | F | =CHNMe$_2$ | | Na$^+$ | |
| 4-932 | 2,2-dimethyl-dioxolan-4-yl | H | F | =CHNMe$_2$ | | K$^+$ | |
| 4-933 | 2,2-dimethyl-dioxolan-4-yl | H | I | =CHNMe$_2$ | | Na$^+$ | |
| 4-934 | 2,2-dimethyl-dioxolan-4-yl | H | I | =CHNMe$_2$ | | K$^+$ | |
| 4-935 | 2,2-dimethyl-dioxolan-4-yl | H | CN | =CHNMe$_2$ | | Na$^+$ | |
| 4-936 | 2,2-dimethyl-dioxolan-4-yl | H | CN | =CHNMe$_2$ | | K$^+$ | |
| 4-937 | 2,2-dimethyl-dioxolan-4-yl | H | CF$_3$ | =CHNMe$_2$ | | Na$^+$ | |
| 4-938 | 2,2-dimethyl-dioxolan-4-yl | H | CF$_3$ | =CHNMe$_2$ | | K$^+$ | |
| 4-939 | 2,2-dimethyl-dioxolan-4-yl | F | Cl | =CHNMe$_2$ | | Na$^+$ | |
| 4-940 | 2,2-dimethyl-dioxolan-4-yl | F | Cl | =CHNMe$_2$ | | K$^+$ | |
| 4-941 | 2,2-dimethyl-dioxolan-4-yl | F | Cl | =CHNMe$_2$ | | NH$_4^+$ | |
| 4-942 | 2,2-dimethyl-dioxolan-4-yl | F | Br | =CHNMe$_2$ | | Na$^+$ | |
| 4-943 | 2,2-dimethyl-dioxolan-4-yl | F | Br | =CHNMe$_2$ | | K$^+$ | |
| 4-944 | 2,2-dimethyl-dioxolan-4-yl | F | Br | =CHNMe$_2$ | | NH$_4^+$ | |
| 4-945 | 2,2-dimethyl-dioxolan-4-yl | F | F | =CHNMe$_2$ | | Na$^+$ | |

TABLE 4-continued

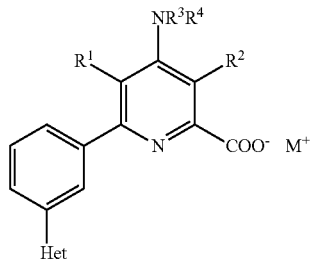

(I-iv)

| No. | Het | R¹ | R² | R³ | R⁴ | M⁺ | Physical data: ¹H NMR: δ [CDCl₃] |
|---|---|---|---|---|---|---|---|
| 4-946 | 2,2-dimethyl-dioxolan-4-yl | F | F | =CHNMe₂ | | K⁺ | |
| 4-947 | 2,2-dimethyl-dioxolan-4-yl | F | I | =CHNMe₂ | | Na⁺ | |
| 4-948 | 2,2-dimethyl-dioxolan-4-yl | F | I | =CHNMe₂ | | K⁺ | |
| 4-949 | 2,2-dimethyl-dioxolan-4-yl | F | CN | =CHNMe₂ | | Na⁺ | |
| 4-950 | 2,2-dimethyl-dioxolan-4-yl | F | CN | =CHNMe₂ | | K⁺ | |
| 4-951 | 2,2-dimethyl-dioxolan-4-yl | F | CF₃ | =CHNMe₂ | | Na⁺ | |
| 4-952 | 2,2-dimethyl-dioxolan-4-yl | F | CF₃ | =CHNMe₂ | | K⁺ | |

TABLE 5

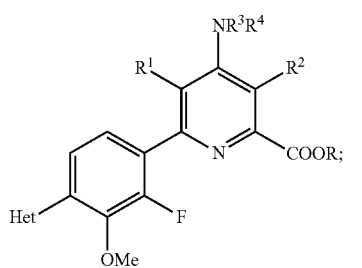

(I-v)

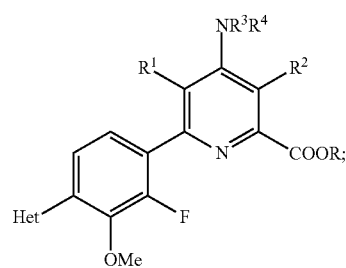

(I-v)

| No. | Het | R¹ | R² | R³ | R⁴ | R | Physical data: ¹H NMR: δ [CDCl₃] |
|---|---|---|---|---|---|---|---|
| 5-1 | 3-tert-butyl-1,2,4-oxadiazol-5-yl | H | Cl | H | H | H | |
| 5-2 | 3-tert-butyl-1,2,4-oxadiazol-5-yl | H | Cl | H | H | Me | |
| 5-3 | 3-tert-butyl-1,2,4-oxadiazol-5-yl | H | Cl | H | H | Et | |
| 5-4 | 3-tert-butyl-1,2,4-oxadiazol-5-yl | H | Br | H | H | H | |
| 5-5 | 3-tert-butyl-1,2,4-oxadiazol-5-yl | H | Br | H | H | Me | |
| 5-6 | 3-tert-butyl-1,2,4-oxadiazol-5-yl | H | Br | H | H | Et | |
| 5-7 | 3-tert-butyl-1,2,4-oxadiazol-5-yl | H | F | H | H | H | |
| 5-8 | 3-tert-butyl-1,2,4-oxadiazol-5-yl | H | F | H | H | Me | |
| 5-9 | 3-tert-butyl-1,2,4-oxadiazol-5-yl | H | I | H | H | H | |
| 5-10 | 3-tert-butyl-1,2,4-oxadiazol-5-yl | H | I | H | H | Me | |
| 5-11 | 3-tert-butyl-1,2,4-oxadiazol-5-yl | H | CN | H | H | H | |
| 5-12 | 3-tert-butyl-1,2,4-oxadiazol-5-yl | H | CN | H | H | Me | |
| 5-13 | 3-tert-butyl-1,2,4-oxadiazol-5-yl | H | CF₃ | H | H | H | |
| 5-14 | 3-tert-butyl-1,2,4-oxadiazol-5-yl | H | CF₃ | H | H | Me | |
| 5-15 | 3-tert-butyl-1,2,4-oxadiazol-5-yl | F | Cl | H | H | H | |
| 5-16 | 3-tert-butyl-1,2,4-oxadiazol-5-yl | F | Cl | H | H | Me | |
| 5-17 | 3-tert-butyl-1,2,4-oxadiazol-5-yl | F | Cl | H | H | Et | |
| 5-18 | 3-tert-butyl-1,2,4-oxadiazol-5-yl | F | Br | H | H | H | |
| 5-19 | 3-tert-butyl-1,2,4-oxadiazol-5-yl | F | Br | H | H | Me | |
| 5-20 | 3-tert-butyl-1,2,4-oxadiazol-5-yl | F | Br | H | H | Et | |
| 5-21 | 3-tert-butyl-1,2,4-oxadiazol-5-yl | F | F | H | H | H | |
| 5-22 | 3-tert-butyl-1,2,4-oxadiazol-5-yl | F | F | H | H | Me | |
| 5-23 | 3-tert-butyl-1,2,4-oxadiazol-5-yl | F | I | H | H | H | |
| 5-24 | 3-tert-butyl-1,2,4-oxadiazol-5-yl | F | I | H | H | Me | |
| 5-25 | 3-tert-butyl-1,2,4-oxadiazol-5-yl | F | CN | H | H | H | |
| 5-26 | 3-tert-butyl-1,2,4-oxadiazol-5-yl | F | CN | H | H | Me | |
| 5-27 | 3-tert-butyl-1,2,4-oxadiazol-5-yl | F | CF₃ | H | H | H | |
| 5-28 | 3-tert-butyl-1,2,4-oxadiazol-5-yl | F | CF₃ | H | H | Me | |
| 5-29 | 3-tert-butyl-1,2,4-oxadiazol-5-yl | Cl | Cl | H | H | H | |
| 5-30 | 3-tert-butyl-1,2,4-oxadiazol-5-yl | Cl | Cl | H | H | Me | |

TABLE 5-continued

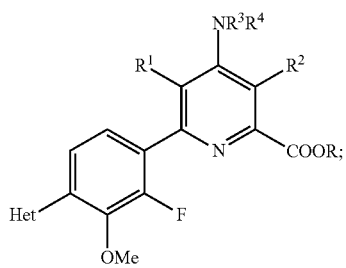

(I-v)

| No. | Het | $R^1$ | $R^2$ | $R^3$ | $R^4$ | R | Physical data: $^1$H NMR: δ [CDCl$_3$] |
|---|---|---|---|---|---|---|---|
| 5-31 | 3-tert-butyl-1,2,4-oxadiazol-5-yl | Cl | Cl | H | H | Et | |
| 5-32 | 3-tert-butyl-1,2,4-oxadiazol-5-yl | Cl | Br | H | H | H | |
| 5-33 | 3-tert-butyl-1,2,4-oxadiazol-5-yl | Cl | Br | H | H | Me | |
| 5-34 | 3-tert-butyl-1,2,4-oxadiazol-5-yl | Cl | Br | H | H | Et | |
| 5-35 | 3-tert-butyl-1,2,4-oxadiazol-5-yl | Cl | F | H | H | H | |
| 5-36 | 3-tert-butyl-1,2,4-oxadiazol-5-yl | Cl | F | H | H | Me | |
| 5-37 | 3-tert-butyl-1,2,4-oxadiazol-5-yl | Cl | I | H | H | H | |
| 5-38 | 3-tert-butyl-1,2,4-oxadiazol-5-yl | Cl | I | H | H | Me | |
| 5-39 | 3-tert-butyl-1,2,4-oxadiazol-5-yl | Cl | CN | H | H | H | |
| 5-40 | 3-tert-butyl-1,2,4-oxadiazol-5-yl | Cl | CN | H | H | Me | |
| 5-41 | 3-tert-butyl-1,2,4-oxadiazol-5-yl | Cl | CF$_3$ | H | H | H | |
| 5-42 | 3-tert-butyl-1,2,4-oxadiazol-5-yl | Cl | CF$_3$ | H | H | Me | |
| 5-43 | 3-tert-butyl-1,2,4-oxadiazol-5-yl | H | Cl | H | Me | H | |
| 5-44 | 3-tert-butyl-1,2,4-oxadiazol-5-yl | H | Cl | H | Me | Me | |
| 5-45 | 3-tert-butyl-1,2,4-oxadiazol-5-yl | H | Cl | H | Me | Et | |
| 5-46 | 3-tert-butyl-1,2,4-oxadiazol-5-yl | H | Br | H | Me | H | |
| 5-47 | 3-tert-butyl-1,2,4-oxadiazol-5-yl | H | Br | H | Me | Me | |
| 5-48 | 3-tert-butyl-1,2,4-oxadiazol-5-yl | H | Br | H | Me | Et | |
| 5-49 | 3-tert-butyl-1,2,4-oxadiazol-5-yl | H | F | H | Me | H | |
| 5-50 | 3-tert-butyl-1,2,4-oxadiazol-5-yl | H | F | H | Me | Me | |
| 5-51 | 3-tert-butyl-1,2,4-oxadiazol-5-yl | H | I | H | Me | H | |
| 5-52 | 3-tert-butyl-1,2,4-oxadiazol-5-yl | H | I | H | Me | Me | |
| 5-53 | 3-tert-butyl-1,2,4-oxadiazol-5-yl | H | CN | H | Me | H | |
| 5-54 | 3-tert-butyl-1,2,4-oxadiazol-5-yl | H | CN | H | Me | Me | |
| 5-55 | 3-tert-butyl-1,2,4-oxadiazol-5-yl | H | CF$_3$ | H | Me | H | |
| 5-56 | 3-tert-butyl-1,2,4-oxadiazol-5-yl | H | CF$_3$ | H | Me | Me | |
| 5-57 | 3-tert-butyl-1,2,4-oxadiazol-5-yl | F | Cl | H | Me | H | |
| 5-58 | 3-tert-butyl-1,2,4-oxadiazol-5-yl | F | Cl | H | Me | Me | |
| 5-59 | 3-tert-butyl-1,2,4-oxadiazol-5-yl | F | Cl | H | Me | Et | |
| 5-60 | 3-tert-butyl-1,2,4-oxadiazol-5-yl | F | Br | H | Me | H | |
| 5-61 | 3-tert-butyl-1,2,4-oxadiazol-5-yl | F | Br | H | Me | Me | |
| 5-62 | 3-tert-butyl-1,2,4-oxadiazol-5-yl | F | Br | H | Me | Et | |
| 5-63 | 3-tert-butyl-1,2,4-oxadiazol-5-yl | F | F | H | Me | H | |
| 5-64 | 3-tert-butyl-1,2,4-oxadiazol-5-yl | F | F | H | Me | Me | |
| 5-65 | 3-tert-butyl-1,2,4-oxadiazol-5-yl | F | I | H | Me | H | |
| 5-66 | 3-tert-butyl-1,2,4-oxadiazol-5-yl | F | I | H | Me | Me | |
| 5-67 | 3-tert-butyl-1,2,4-oxadiazol-5-yl | F | CN | H | Me | H | |
| 5-68 | 3-tert-butyl-1,2,4-oxadiazol-5-yl | F | CN | H | Me | Me | |
| 5-69 | 3-tert-butyl-1,2,4-oxadiazol-5-yl | F | CF$_3$ | H | Me | H | |
| 5-70 | 3-tert-butyl-1,2,4-oxadiazol-5-yl | F | CF$_3$ | H | Me | Me | |
| 5-71 | 3-tert-butyl-1,2,4-oxadiazol-5-yl | Cl | Cl | H | Me | H | |
| 5-72 | 3-tert-butyl-1,2,4-oxadiazol-5-yl | Cl | Cl | H | Me | Me | |
| 5-73 | 3-tert-butyl-1,2,4-oxadiazol-5-yl | Cl | Cl | H | Me | Et | |
| 5-74 | 3-tert-butyl-1,2,4-oxadiazol-5-yl | Cl | Br | H | Me | H | |
| 5-75 | 3-tert-butyl-1,2,4-oxadiazol-5-yl | Cl | Br | H | Me | Me | |
| 5-76 | 3-tert-butyl-1,2,4-oxadiazol-5-yl | Cl | Br | H | Me | Et | |
| 5-77 | 3-tert-butyl-1,2,4-oxadiazol-5-yl | Cl | F | H | Me | H | |
| 5-78 | 3-tert-butyl-1,2,4-oxadiazol-5-yl | Cl | F | H | Me | Me | |
| 5-79 | 3-tert-butyl-1,2,4-oxadiazol-5-yl | Cl | I | H | Me | H | |
| 5-80 | 3-tert-butyl-1,2,4-oxadiazol-5-yl | Cl | I | H | Me | Me | |
| 5-81 | 3-tert-butyl-1,2,4-oxadiazol-5-yl | Cl | CN | H | Me | H | |
| 5-82 | 3-tert-butyl-1,2,4-oxadiazol-5-yl | Cl | CN | H | Me | Me | |
| 5-83 | 3-tert-butyl-1,2,4-oxadiazol-5-yl | Cl | CF$_3$ | H | Me | H | |
| 5-84 | 3-tert-butyl-1,2,4-oxadiazol-5-yl | Cl | CF$_3$ | H | Me | Me | |
| 5-85 | 3-tert-butyl-1,2,4-oxadiazol-5-yl | H | Cl | Me | Me | H | |
| 5-86 | 3-tert-butyl-1,2,4-oxadiazol-5-yl | H | Cl | Me | Me | Me | |
| 5-87 | 3-tert-butyl-1,2,4-oxadiazol-5-yl | H | Cl | Me | Me | Et | |
| 5-88 | 3-tert-butyl-1,2,4-oxadiazol-5-yl | H | Br | Me | Me | H | |
| 5-89 | 3-tert-butyl-1,2,4-oxadiazol-5-yl | H | Br | Me | Me | Me | |
| 5-90 | 3-tert-butyl-1,2,4-oxadiazol-5-yl | H | Br | Me | Me | Et | |

TABLE 5-continued

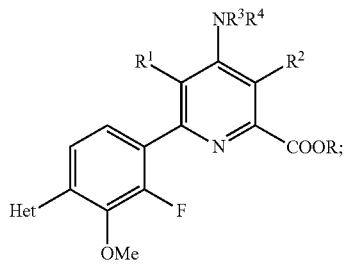

(I-v)

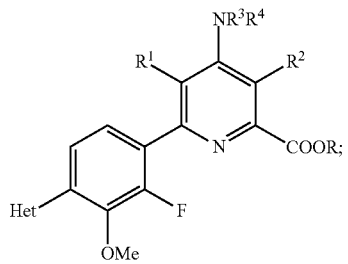

(I-v)

| No. | Het | R¹ | R² | R³ | R⁴ | R | Physical data: ¹H NMR: δ [CDCl₃] |
|---|---|---|---|---|---|---|---|
| 5-91 | 3-tert-butyl-1,2,4-oxadiazol-5-yl | H | F | Me | Me | H | |
| 5-92 | 3-tert-butyl-1,2,4-oxadiazol-5-yl | H | F | Me | Me | Me | |
| 5-93 | 3-tert-butyl-1,2,4-oxadiazol-5-yl | H | I | Me | Me | H | |
| 5-94 | 3-tert-butyl-1,2,4-oxadiazol-5-yl | H | I | Me | Me | Me | |
| 5-95 | 3-tert-butyl-1,2,4-oxadiazol-5-yl | H | CN | Me | Me | H | |
| 5-96 | 3-tert-butyl-1,2,4-oxadiazol-5-yl | H | CN | Me | Me | Me | |
| 5-97 | 3-tert-butyl-1,2,4-oxadiazol-5-yl | H | CF₃ | Me | Me | H | |
| 5-98 | 3-tert-butyl-1,2,4-oxadiazol-5-yl | H | CF₃ | Me | Me | Me | |
| 5-99 | 3-tert-butyl-1,2,4-oxadiazol-5-yl | F | Cl | Me | Me | H | |
| 5-100 | 3-tert-butyl-1,2,4-oxadiazol-5-yl | F | Cl | Me | Me | Me | |
| 5-101 | 3-tert-butyl-1,2,4-oxadiazol-5-yl | F | Cl | Me | Me | Et | |
| 5-102 | 3-tert-butyl-1,2,4-oxadiazol-5-yl | F | Br | Me | Me | H | |
| 5-103 | 3-tert-butyl-1,2,4-oxadiazol-5-yl | F | Br | Me | Me | Me | |
| 5-104 | 3-tert-butyl-1,2,4-oxadiazol-5-yl | F | Br | Me | Me | Et | |
| 5-105 | 3-tert-butyl-1,2,4-oxadiazol-5-yl | F | F | Me | Me | H | |
| 5-106 | 3-tert-butyl-1,2,4-oxadiazol-5-yl | F | F | Me | Me | Me | |
| 5-107 | 3-tert-butyl-1,2,4-oxadiazol-5-yl | F | I | Me | Me | H | |
| 5-108 | 3-tert-butyl-1,2,4-oxadiazol-5-yl | F | I | Me | Me | Me | |
| 5-109 | 3-tert-butyl-1,2,4-oxadiazol-5-yl | F | CN | Me | Me | H | |
| 5-110 | 3-tert-butyl-1,2,4-oxadiazol-5-yl | F | CN | Me | Me | Me | |
| 5-111 | 3-tert-butyl-1,2,4-oxadiazol-5-yl | F | CF₃ | Me | Me | H | |
| 5-112 | 3-tert-butyl-1,2,4-oxadiazol-5-yl | F | CF₃ | Me | Me | Me | |
| 5-113 | 3-tert-butyl-1,2,4-oxadiazol-5-yl | Cl | Cl | Me | Me | H | |
| 5-114 | 3-tert-butyl-1,2,4-oxadiazol-5-yl | Cl | Cl | Me | Me | Me | |
| 5-115 | 3-tert-butyl-1,2,4-oxadiazol-5-yl | Cl | Cl | Me | Me | Et | |
| 5-116 | 3-tert-butyl-1,2,4-oxadiazol-5-yl | Cl | Br | Me | Me | H | |
| 5-117 | 3-tert-butyl-1,2,4-oxadiazol-5-yl | Cl | Br | Me | Me | Me | |
| 5-118 | 3-tert-butyl-1,2,4-oxadiazol-5-yl | Cl | Br | Me | Me | Et | |
| 5-119 | 3-tert-butyl-1,2,4-oxadiazol-5-yl | Cl | F | Me | Me | H | |
| 5-120 | 3-tert-butyl-1,2,4-oxadiazol-5-yl | Cl | F | Me | Me | Me | |
| 5-121 | 3-tert-butyl-1,2,4-oxadiazol-5-yl | Cl | I | Me | Me | H | |
| 5-122 | 3-tert-butyl-1,2,4-oxadiazol-5-yl | Cl | I | Me | Me | Me | |
| 5-123 | 3-tert-butyl-1,2,4-oxadiazol-5-yl | Cl | CN | Me | Me | H | |
| 5-124 | 3-tert-butyl-1,2,4-oxadiazol-5-yl | Cl | CN | Me | Me | Me | |
| 5-125 | 3-tert-butyl-1,2,4-oxadiazol-5-yl | Cl | CF₃ | Me | Me | H | |
| 5-126 | 3-tert-butyl-1,2,4-oxadiazol-5-yl | Cl | CF₃ | Me | Me | Me | |
| 5-127 | 3-tert-butyl-1,2,4-oxadiazol-5-yl | H | Cl | =CHNMe₂ | | H | |
| 5-128 | 3-tert-butyl-1,2,4-oxadiazol-5-yl | H | Cl | =CHNMe₂ | | Me | |
| 5-129 | 3-tert-butyl-1,2,4-oxadiazol-5-yl | H | Cl | =CHNMe₂ | | Et | |
| 5-130 | 3-tert-butyl-1,2,4-oxadiazol-5-yl | H | Br | =CHNMe₂ | | H | |
| 5-131 | 3-tert-butyl-1,2,4-oxadiazol-5-yl | H | Br | =CHNMe₂ | | Me | |
| 5-132 | 3-tert-butyl-1,2,4-oxadiazol-5-yl | H | Br | =CHNMe₂ | | Et | |
| 5-133 | 3-tert-butyl-1,2,4-oxadiazol-5-yl | H | F | =CHNMe₂ | | H | |
| 5-134 | 3-tert-butyl-1,2,4-oxadiazol-5-yl | H | F | =CHNMe₂ | | Me | |
| 5-135 | 3-tert-butyl-1,2,4-oxadiazol-5-yl | H | I | =CHNMe₂ | | H | |
| 5-136 | 3-tert-butyl-1,2,4-oxadiazol-5-yl | H | I | =CHNMe₂ | | Me | |
| 5-137 | 3-tert-butyl-1,2,4-oxadiazol-5-yl | H | CN | =CHNMe₂ | | H | |
| 5-138 | 3-tert-butyl-1,2,4-oxadiazol-5-yl | H | CN | =CHNMe₂ | | Me | |
| 5-139 | 3-tert-butyl-1,2,4-oxadiazol-5-yl | H | CF₃ | =CHNMe₂ | | H | |
| 5-140 | 3-tert-butyl-1,2,4-oxadiazol-5-yl | H | CF₃ | =CHNMe₂ | | Me | |
| 5-141 | 3-tert-butyl-1,2,4-oxadiazol-5-yl | F | Cl | =CHNMe₂ | | H | |
| 5-142 | 3-tert-butyl-1,2,4-oxadiazol-5-yl | F | Cl | =CHNMe₂ | | Me | |
| 5-143 | 3-tert-butyl-1,2,4-oxadiazol-5-yl | F | Cl | =CHNMe₂ | | Et | |
| 5-144 | 3-tert-butyl-1,2,4-oxadiazol-5-yl | F | Br | =CHNMe₂ | | H | |
| 5-145 | 3-tert-butyl-1,2,4-oxadiazol-5-yl | F | Br | =CHNMe₂ | | Me | |
| 5-146 | 3-tert-butyl-1,2,4-oxadiazol-5-yl | F | Br | =CHNMe₂ | | Et | |
| 5-147 | 3-tert-butyl-1,2,4-oxadiazol-5-yl | F | F | =CHNMe₂ | | H | |
| 5-148 | 3-tert-butyl-1,2,4-oxadiazol-5-yl | F | F | =CHNMe₂ | | Me | |
| 5-149 | 3-tert-butyl-1,2,4-oxadiazol-5-yl | F | I | =CHNMe₂ | | H | |
| 5-150 | 3-tert-butyl-1,2,4-oxadiazol-5-yl | F | I | =CHNMe₂ | | Me | |

TABLE 5-continued

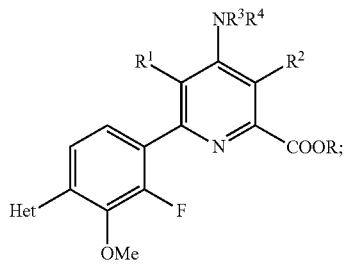

(I-v)

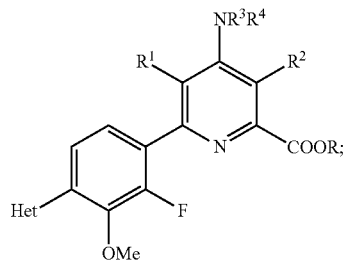

(I-v)

| No. | Het | R¹ | R² | R³ | R⁴ | R | Physical data: ¹H NMR: δ [CDCl₃] |
|---|---|---|---|---|---|---|---|
| 5-151 | 3-tert-butyl-1,2,4-oxadiazol-5-yl | F | CN | =CHNMe₂ | | H | |
| 5-152 | 3-tert-butyl-1,2,4-oxadiazol-5-yl | F | CN | =CHNMe₂ | | Me | |
| 5-153 | 3-tert-butyl-1,2,4-oxadiazol-5-yl | F | CF₃ | =CHNMe₂ | | H | |
| 5-154 | 3-tert-butyl-1,2,4-oxadiazol-5-yl | F | CF₃ | =CHNMe₂ | | Me | |
| 5-155 | 3-tert-butyl-1,2,4-oxadiazol-5-yl | Cl | Cl | =CHNMe₂ | | H | |
| 5-156 | 3-tert-butyl-1,2,4-oxadiazol-5-yl | Cl | Cl | =CHNMe₂ | | Me | |
| 5-157 | 3-tert-butyl-1,2,4-oxadiazol-5-yl | Cl | Cl | =CHNMe₂ | | Et | |
| 5-158 | 3-tert-butyl-1,2,4-oxadiazol-5-yl | Cl | Br | =CHNMe₂ | | H | |
| 5-159 | 3-tert-butyl-1,2,4-oxadiazol-5-yl | Cl | Br | =CHNMe₂ | | Me | |
| 5-160 | 3-tert-butyl-1,2,4-oxadiazol-5-yl | Cl | Br | =CHNMe₂ | | Et | |
| 5-161 | 3-tert-butyl-1,2,4-oxadiazol-5-yl | Cl | F | =CHNMe₂ | | H | |
| 5-162 | 3-tert-butyl-1,2,4-oxadiazol-5-yl | Cl | F | =CHNMe₂ | | Me | |
| 5-163 | 3-tert-butyl-1,2,4-oxadiazol-5-yl | Cl | I | =CHNMe₂ | | H | |
| 5-164 | 3-tert-butyl-1,2,4-oxadiazol-5-yl | Cl | I | =CHNMe₂ | | Me | |
| 5-165 | 3-tert-butyl-1,2,4-oxadiazol-5-yl | Cl | CN | =CHNMe₂ | | H | |
| 5-166 | 3-tert-butyl-1,2,4-oxadiazol-5-yl | Cl | CN | =CHNMe₂ | | Me | |
| 5-167 | 3-tert-butyl-1,2,4-oxadiazol-5-yl | Cl | CF₃ | =CHNMe₂ | | H | |
| 5-168 | 3-tert-butyl-1,2,4-oxadiazol-5-yl | Cl | CF₃ | =CHNMe₂ | | Me | |
| 5-169 | thien-2-yl | H | Cl | H | H | H | |
| 5-170 | thien-2-yl | H | Cl | H | H | Me | |
| 5-171 | thien-2-yl | H | Cl | H | H | Et | |
| 5-172 | thien-2-yl | H | Br | H | H | H | |
| 5-173 | thien-2-yl | H | Br | H | H | Me | |
| 5-174 | thien-2-yl | H | Br | H | H | Et | |
| 5-175 | thien-2-yl | H | F | H | H | H | |
| 5-176 | thien-2-yl | H | F | H | H | Me | |
| 5-177 | thien-2-yl | H | I | H | H | H | |
| 5-178 | thien-2-yl | H | I | H | H | Me | |
| 5-179 | thien-2-yl | H | CN | H | H | H | |
| 5-180 | thien-2-yl | H | CN | H | H | Me | |
| 5-181 | thien-2-yl | H | CF₃ | H | H | H | |
| 5-182 | thien-2-yl | H | CF₃ | H | H | Me | |
| 5-183 | thien-2-yl | F | Cl | H | H | H | |
| 5-184 | thien-2-yl | F | Cl | H | H | Me | |
| 5-185 | thien-2-yl | F | Cl | H | H | Et | |
| 5-186 | thien-2-yl | F | Br | H | H | H | |
| 5-187 | thien-2-yl | F | Br | H | H | Me | |
| 5-188 | thien-2-yl | F | Br | H | H | Et | |
| 5-189 | thien-2-yl | F | F | H | H | H | |
| 5-190 | thien-2-yl | F | F | H | H | Me | |
| 5-191 | thien-2-yl | F | I | H | H | H | |
| 5-192 | thien-2-yl | F | I | H | H | Me | |
| 5-193 | thien-2-yl | F | CN | H | H | H | |
| 5-194 | thien-2-yl | F | CN | H | H | Me | |
| 5-195 | thien-2-yl | F | CF₃ | H | H | H | |
| 5-196 | thien-2-yl | F | CF₃ | H | H | Me | |
| 5-197 | thien-2-yl | H | Cl | H | Me | H | |
| 5-198 | thien-2-yl | H | Cl | H | Me | Me | |
| 5-199 | thien-2-yl | H | Cl | H | Me | Et | |
| 5-200 | thien-2-y! | H | Br | H | Me | H | |
| 5-201 | thien-2-yl | H | Br | H | Me | Me | |
| 5-202 | thien-2-yl | H | Br | H | Me | Et | |
| 5-203 | thien-2-yl | H | F | H | Me | H | |
| 5-204 | thien-2-yl | H | F | H | Me | Me | |
| 5-205 | thien-2-yl | H | I | H | Me | H | |
| 5-206 | thien-2-yl | H | I | H | Me | Me | |
| 5-207 | thien-2-yl | H | CN | H | Me | H | |
| 5-208 | thien-2-yl | H | CN | H | Me | Me | |
| 5-209 | thien-2-yl | H | CF₃ | H | Me | H | |
| 5-210 | thien-2-yl | H | CF₃ | H | Me | Me | |
| 5-211 | thien-2-yl | F | Cl | H | Me | H | |
| 5-212 | thien-2-yl | F | Cl | H | Me | Me | |
| 5-213 | thien-2-yl | F | Cl | H | Me | Et | |
| 5-214 | thien-2-yl | F | Br | H | Me | H | |
| 5-215 | thien-2-yl | F | Br | H | Me | Me | |
| 5-216 | thien-2-yl | F | Br | H | Me | Et | |
| 5-217 | thien-2-yl | F | F | H | Me | H | |
| 5-218 | thien-2-yl | F | F | H | Me | Me | |
| 5-219 | thien-2-yl | F | I | H | Me | H | |
| 5-220 | thien-2-yl | F | I | H | Me | Me | |
| 5-221 | thien-2-yl | F | CN | H | Me | H | |
| 5-222 | thien-2-yl | F | CN | H | Me | Me | |
| 5-223 | thien-2-yl | F | CF₃ | H | Me | H | |
| 5-224 | thien-2-yl | F | CF₃ | H | Me | Me | |
| 5-225 | thien-2-yl | H | Cl | Me | Me | H | |
| 5-226 | thien-2-yl | H | Cl | Me | Me | Me | |
| 5-227 | thien-2-yl | H | Cl | Me | Me | Et | |
| 5-228 | thien-2-yl | H | Br | Me | Me | H | |
| 5-229 | thien-2-yl | H | Br | Me | Me | Me | |
| 5-230 | thien-2-yl | H | Br | Me | Me | Et | |
| 5-231 | thien-2-yl | H | F | Me | Me | H | |
| 5-232 | thien-2-yl | H | F | Me | Me | Me | |
| 5-233 | thien-2-yl | H | I | Me | Me | H | |
| 5-234 | thien-2-yl | H | I | Me | Me | Me | |
| 5-235 | thien-2-yl | H | CN | Me | Me | H | |
| 5-236 | thien-2-yl | H | CN | Me | Me | Me | |
| 5-237 | thien-2-yl | H | CF₃ | Me | Me | H | |
| 5-238 | thien-2-yl | H | CF₃ | Me | Me | Me | |
| 5-239 | thien-2-yl | F | Cl | Me | Me | H | |
| 5-240 | thien-2-yl | F | Cl | Me | Me | Me | |
| 5-241 | thien-2-yl | F | Cl | Me | Me | Et | |
| 5-242 | thien-2-yl | F | Br | Me | Me | H | |
| 5-243 | thien-2-yl | F | Br | Me | Me | Me | |
| 5-244 | thien-2-yl | F | Br | Me | Me | Et | |
| 5-245 | thien-2-yl | F | F | Me | Me | H | |
| 5-246 | thien-2-yl | F | F | Me | Me | Me | |
| 5-247 | thien-2-yl | F | I | Me | Me | H | |
| 5-248 | thien-2-yl | F | I | Me | Me | Me | |
| 5-249 | thien-2-yl | F | CN | Me | Me | H | |
| 5-250 | thien-2-yl | F | CN | Me | Me | Me | |
| 5-251 | thien-2-yl | F | CF₃ | Me | Me | H | |
| 5-252 | thien-2-yl | F | CF₃ | Me | Me | Me | |

TABLE 5-continued

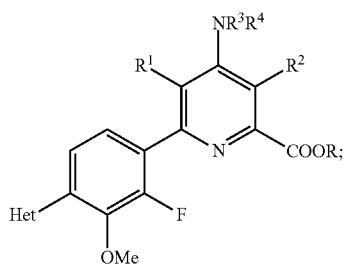

(I-v)

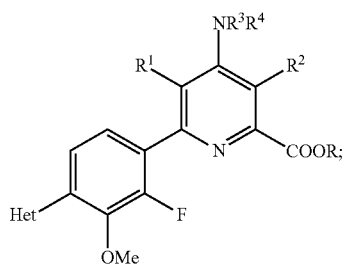

(I-v)

| No. | Het | R¹ | R² | R³ | R⁴ | R | Physical data: ¹H NMR: δ [CDCl₃] |
|---|---|---|---|---|---|---|---|
| 5-253 | thien-2-yl | H | Cl | =CHNMe₂ | | H | |
| 5-254 | thien-2-yl | H | Cl | =CHNMe₂ | | Me | |
| 5-255 | thien-2-yl | H | Cl | =CHNMe₂ | | Et | |
| 5-256 | thien-2-yl | H | Br | =CHNMe₂ | | H | |
| 5-257 | thien-2-yl | H | Br | =CHNMe₂ | | Me | |
| 5-258 | thien-2-yl | H | Br | =CHNMe₂ | | Et | |
| 5-259 | thien-2-yl | H | F | =CHNMe₂ | | H | |
| 5-260 | thien-2-yl | H | F | =CHNMe₂ | | Me | |
| 5-261 | thien-2-yl | H | I | =CHNMe₂ | | H | |
| 5-262 | thien-2-yl | H | I | =CHNMe₂ | | Me | |
| 5-263 | thien-2-yl | H | CN | =CHNMe₂ | | H | |
| 5-264 | thien-2-yl | H | CN | =CHNMe₂ | | Me | |
| 5-265 | thien-2-yl | H | CF₃ | =CHNMe₂ | | H | |
| 5-266 | thien-2-yl | H | CF₃ | =CHNMe₂ | | Me | |
| 5-267 | thien-2-yl | F | Cl | =CHNMe₂ | | H | |
| 5-268 | thien-2-yl | F | Cl | =CHNMe₂ | | Me | |
| 5-269 | thien-2-yl | F | Cl | =CHNMe₂ | | Et | |
| 5-270 | thien-2-yl | F | Br | =CHNMe₂ | | H | |
| 5-271 | thien-2-yl | F | Br | =CHNMe₂ | | Me | |
| 5-272 | thien-2-yl | F | Br | =CHNMe₂ | | Et | |
| 5-273 | thien-2-yl | F | F | =CHNMe₂ | | H | |
| 5-274 | thien-2-yl | F | F | =CHNMe₂ | | Me | |
| 5-275 | thien-2-yl | F | I | =CHNMe₂ | | H | |
| 5-276 | thien-2-yl | F | I | =CHNMe₂ | | Me | |
| 5-277 | thien-2-yl | F | CN | =CHNMe₂ | | H | |
| 5-278 | thien-2-yl | F | CN | =CHNMe₂ | | Me | |
| 5-279 | thien-2-yl | F | CF₃ | =CHNMe₂ | | H | |
| 5-280 | thien-2-yl | F | CF₃ | =CHNMe₂ | | Me | |
| 5-281 | pyrrol-1-yl | H | Cl | H | H | H | |
| 5-282 | pyrrol-1-yl | H | Cl | H | H | Me | |
| 5-283 | pyrrol-1-yl | H | Cl | H | H | Et | |
| 5-284 | pyrrol-1-yl | H | Br | H | H | H | |
| 5-285 | pyrrol-1-yl | H | Br | H | H | Me | |
| 5-286 | pyrrol-1-yl | H | Br | H | H | Et | |
| 5-287 | pyrrol-1-yl | H | F | H | H | H | |
| 5-288 | pyrrol-1-yl | H | F | H | H | Me | |
| 5-289 | pyrrol-1-yl | H | I | H | H | H | |
| 5-290 | pyrrol-1-yl | H | I | H | H | Me | |
| 5-291 | pyrrol-1-yl | H | CN | H | H | H | |
| 5-292 | pyrrol-1-yl | H | CN | H | H | Me | |
| 5-293 | pyrrol-1-yl | H | CF₃ | H | H | H | |
| 5-294 | pyrrol-1-yl | H | CF₃ | H | H | Me | |
| 5-295 | pyrrol-1-yl | F | Cl | H | H | H | |
| 5-296 | pyrrol-1-yl | F | Cl | H | H | Me | |
| 5-297 | pyrrol-1-yl | F | Cl | H | H | Et | |
| 5-298 | pyrrol-1-yl | F | Br | H | H | H | |
| 5-299 | pyrrol-1-yl | F | Br | H | H | Me | |
| 5-300 | pyrrol-1-yl | F | Br | H | H | Et | |
| 5-301 | pyrrol-1-yl | F | F | H | H | H | |
| 5-302 | pyrrol-1-yl | F | F | H | H | Me | |
| 5-303 | pyrrol-1-yl | F | I | H | H | H | |
| 5-304 | pyrrol-1-yl | F | I | H | H | Me | |
| 5-305 | pyrrol-1-yl | F | CN | H | H | H | |
| 5-306 | pyrrol-1-yl | F | CN | H | H | Me | |
| 5-307 | pyrrol-1-yl | F | CF₃ | H | H | H | |
| 5-308 | pyrrol-1-yl | F | CF₃ | H | H | Me | |
| 5-309 | pyrrol-1-yl | H | Cl | H | Me | H | |
| 5-310 | pyrrol-1-yl | H | Cl | H | Me | Me | |
| 5-311 | pyrrol-1-yl | H | Cl | H | Me | Et | |
| 5-312 | pyrrol-1-yl | H | Br | H | Me | H | |
| 5-313 | pyrrol-1-yl | H | Br | H | Me | Me | |
| 5-314 | pyrrol-1-yl | H | Br | H | Me | Et | |
| 5-315 | pyrrol-1-yl | H | F | H | Me | H | |
| 5-316 | pyrrol-1-yl | H | F | H | Me | Me | |
| 5-317 | pyrrol-1-yl | H | I | H | Me | H | |
| 5-318 | pyrrol-1-yl | H | I | H | Me | Me | |
| 5-319 | pyrrol-1-yl | H | CN | H | Me | H | |
| 5-320 | pyrrol-1-yl | H | CN | H | Me | Me | |
| 5-321 | pyrrol-1-yl | H | CF₃ | H | Me | H | |
| 5-322 | pyrrol-1-yl | H | CF₃ | H | Me | Me | |
| 5-323 | pyrrol-1-yl | F | Cl | H | Me | H | |
| 5-324 | pyrrol-1-yl | F | Cl | H | Me | Me | |
| 5-325 | pyrrol-1-yl | F | Cl | H | Me | Et | |
| 5-326 | pyrrol-1-yl | F | Br | H | Me | H | |
| 5-327 | pyrrol-1-yl | F | Br | H | Me | Me | |
| 5-328 | pyrrol-1-yl | F | Br | H | Me | Et | |
| 5-329 | pyrrol-1-yl | F | F | H | Me | H | |
| 5-330 | pyrrol-1-yl | F | F | H | Me | Me | |
| 5-331 | pyrrol-1-yl | F | I | H | Me | H | |
| 5-332 | pyrrol-1-yl | F | I | H | Me | Me | |
| 5-333 | pyrrol-1-yl | F | CN | H | Me | H | |
| 5-334 | pyrrol-1-yl | F | CN | H | Me | Me | |
| 5-335 | pyrrol-1-yl | F | CF₃ | H | Me | H | |
| 5-336 | pyrrol-1-yl | F | CF₃ | H | Me | Me | |
| 5-337 | pyrrol-1-yl | H | Cl | Me | Me | H | |
| 5-338 | pyrrol-1-yl | H | Cl | Me | Me | Me | |
| 5-339 | pyrrol-1-yl | H | Cl | Me | Me | Et | |
| 5-340 | pyrrol-1-yl | H | Br | Me | Me | H | |
| 5-341 | pyrrol-1-yl | H | Br | Me | Me | Me | |
| 5-342 | pyrrol-1-yl | H | Br | Me | Me | Et | |
| 5-343 | pyrrol-1-yl | H | F | Me | Me | H | |
| 5-344 | pyrrol-1-yl | H | F | Me | Me | Me | |
| 5-345 | pyrrol-1-yl | H | I | Me | Me | H | |
| 5-346 | pyrrol-1-yl | H | I | Me | Me | Me | |
| 5-347 | pyrrol-1-yl | H | CN | Me | Me | H | |
| 5-348 | pyrrol-1-yl | H | CN | Me | Me | Me | |
| 5-349 | pyrrol-1-yl | H | CF₃ | Me | Me | H | |
| 5-350 | pyrrol-1-yl | H | CF₃ | Me | Me | Me | |
| 5-351 | pyrrol-1-yl | F | Cl | Me | Me | H | |
| 5-352 | pyrrol-1-yl | F | Cl | Me | Me | Me | |
| 5-353 | pyrrol-1-yl | F | Cl | Me | Me | Et | |
| 5-354 | pyrrol-1-yl | F | Br | Me | Me | H | |
| 5-355 | pyrrol-1-yl | F | Br | Me | Me | Me | |
| 5-356 | pyrrol-1-yl | F | Br | Me | Me | Et | |
| 5-357 | pyrrol-1-yl | F | F | Me | Me | H | |
| 5-358 | pyrrol-1-yl | F | F | Me | Me | Me | |
| 5-359 | pyrrol-1-yl | F | I | Me | Me | H | |
| 5-360 | pyrrol-1-yl | F | I | Me | Me | Me | |
| 5-361 | pyrrol-1-yl | F | CN | Me | Me | H | |
| 5-362 | pyrrol-1-yl | F | CN | Me | Me | Me | |
| 5-363 | pyrrol-1-yl | F | CF₃ | Me | Me | H | |
| 5-364 | pyrrol-1-yl | F | CF₃ | Me | Me | Me | |
| 5-365 | pyrrol-1-yl | H | Cl | =CHNMe₂ | | H | |
| 5-366 | pyrrol-1-yl | H | Cl | =CHNMe₂ | | Me | |
| 5-367 | pyrrol-1-yl | H | Cl | =CHNMe₂ | | Et | |
| 5-368 | pyrrol-1-yl | H | Br | =CHNMe₂ | | H | |
| 5-369 | pyrrol-1-yl | H | Br | =CHNMe₂ | | Me | |
| 5-370 | pyrrol-1-yl | H | Br | =CHNMe₂ | | Et | |
| 5-371 | pyrrol-1-yl | H | F | =CHNMe₂ | | H | |
| 5-372 | pyrrol-1-yl | H | F | =CHNMe₂ | | Me | |

TABLE 5-continued

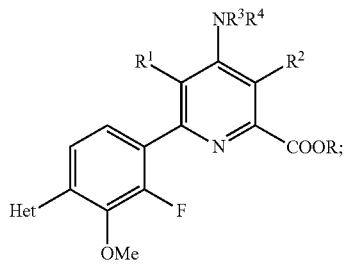

(I-v)

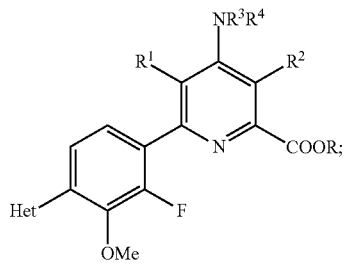

(I-v)

| No. | Het | R¹ | R² | R³ | R⁴ | R | Physical data: $^1$H NMR: δ [CDCl$_3$] | No. | Het | R¹ | R² | R³ | R⁴ | R | Physical data: $^1$H NMR: δ [CDCl$_3$] |
|---|---|---|---|---|---|---|---|---|---|---|---|---|---|---|---|
| 5-373 | pyrrol-1-yl | H | I | =CHNMe$_2$ | | H | | 5-433 | pyrazol-1-yl | H | CF$_3$ | H | Me | H | |
| 5-374 | pyrrol-1-yl | H | I | =CHNMe$_2$ | | Me | | 5-434 | pyrazol-1-yl | H | CF$_3$ | H | Me | Me | |
| 5-375 | pyrrol-1-yl | H | CN | =CHNMe$_2$ | | H | | 5-435 | pyrazol-1-yl | F | Cl | H | Me | H | |
| 5-376 | pyrrol-1-yl | H | CN | =CHNMe$_2$ | | Me | | 5-436 | pyrazol-1-yl | F | Cl | H | Me | Me | |
| 5-377 | pyrrol-1-yl | H | CF$_3$ | =CHNMe$_2$ | | H | | 5-437 | pyrazol-1-yl | F | Cl | H | Me | Et | |
| 5-378 | pyrrol-1-yl | H | CF$_3$ | =CHNMe$_2$ | | Me | | 5-438 | pyrazol-1-yl | F | Br | H | Me | H | |
| 5-379 | pyrrol-1-yl | F | Cl | =CHNMe$_2$ | | H | | 5-439 | pyrazol-1-yl | F | Br | H | Me | Me | |
| 5-380 | pyrrol-1-yl | F | Cl | =CHNMe$_2$ | | Me | | 5-440 | pyrazol-1-yl | F | Br | H | Me | Et | |
| 5-381 | pyrrol-1-yl | F | Cl | =CHNMe$_2$ | | Et | | 5-441 | pyrazol-1-yl | F | F | H | Me | H | |
| 5-382 | pyrrol-1-yl | F | Br | =CHNMe$_2$ | | H | | 5-442 | pyrazol-1-yl | F | F | H | Me | Me | |
| 5-383 | pyrrol-1-yl | F | Br | =CHNMe$_2$ | | Me | | 5-443 | pyrazol-1-yl | F | I | H | Me | H | |
| 5-384 | pyrrol-1-yl | F | Br | =CHNMe$_2$ | | Et | | 5-444 | pyrazol-1-yl | F | I | H | Me | Me | |
| 5-385 | pyrrol-1-yl | F | F | =CHNMe$_2$ | | H | | 5-445 | pyrazol-1-yl | F | CN | H | Me | H | |
| 5-386 | pyrrol-1-yl | F | F | =CHNMe$_2$ | | Me | | 5-446 | pyrazol-1-yl | F | CN | H | Me | Me | |
| 5-387 | pyrrol-1-yl | F | I | =CHNMe$_2$ | | H | | 5-447 | pyrazol-1-yl | F | CF$_3$ | H | Me | H | |
| 5-388 | pyrrol-1-yl | F | I | =CHNMe$_2$ | | Me | | 5-448 | pyrazol-1-yl | F | CF$_3$ | H | Me | Me | |
| 5-389 | pyrrol-1-yl | F | CN | =CHNMe$_2$ | | H | | 5-449 | pyrazol-1-yl | H | Cl | Me | Me | H | |
| 5-390 | pyrrol-1-yl | F | CN | =CHNMe$_2$ | | Me | | 5-450 | pyrazol-1-yl | H | Cl | Me | Me | Me | |
| 5-391 | pyrrol-1-yl | F | CF$_3$ | =CHNMe$_2$ | | H | | 5-451 | pyrazol-1-yl | H | Cl | Me | Me | Et | |
| 5-392 | pyrrol-1-yl | F | CF$_3$ | =CHNMe$_2$ | | Me | | 5-452 | pyrazol-1-yl | H | Br | Me | Me | H | |
| 5-393 | pyrazol-1-yl | H | Cl | H | H | H | | 5-453 | pyrazol-1-yl | H | Br | Me | Me | Me | |
| 5-394 | pyrazol-1-yl | H | Cl | H | H | Me | | 5-454 | pyrazol-1-yl | H | Br | Me | Me | Et | |
| 5-395 | pyrazol-1-yl | H | Cl | H | H | Et | | 5-455 | pyrazol-1-yl | H | F | Me | Me | H | |
| 5-396 | pyrazol-1-yl | H | Br | H | H | H | | 5-456 | pyrazol-1-yl | H | F | Me | Me | Me | |
| 5-397 | pyrazol-1-yl | H | Br | H | H | Me | | 5-457 | pyrazol-1-yl | H | I | Me | Me | H | |
| 5-398 | pyrazol-1-yl | H | Br | H | H | Et | | 5-458 | pyrazol-1-yl | H | I | Me | Me | Me | |
| 5-399 | pyrazol-1-yl | H | F | H | H | H | | 5-459 | pyrazol-1-yl | H | CN | Me | Me | H | |
| 5-400 | pyrazol-1-yl | H | F | H | H | Me | | 5-460 | pyrazol-1-yl | H | CN | Me | Me | Me | |
| 5-401 | pyrazol-1-yl | H | I | H | H | H | | 5-461 | pyrazol-1-yl | H | CF$_3$ | Me | Me | H | |
| 5-402 | pyrazol-1-yl | H | I | H | H | Me | | 5-462 | pyrazol-1-yl | H | CF$_3$ | Me | Me | Me | |
| 5-403 | pyrazol-1-yl | H | CN | H | H | H | | 5-463 | pyrazol-1-yl | F | Cl | Me | Me | H | |
| 5-404 | pyrazol-1-yl | H | CN | H | H | Me | | 5-464 | pyrazol-1-yl | F | Cl | Me | Me | Me | |
| 5-405 | pyrazol-1-yl | H | CF$_3$ | H | H | H | | 5-465 | pyrazol-1-yl | F | Cl | Me | Me | Et | |
| 5-406 | pyrazol-1-yl | H | CF$_3$ | H | H | Me | | 5-466 | pyrazol-1-yl | F | Br | Me | Me | H | |
| 5-407 | pyrazol-1-yl | F | Cl | H | H | H | | 5-467 | pyrazol-1-yl | F | Br | Me | Me | Me | |
| 5-408 | pyrazol-1-yl | F | Cl | H | H | Me | | 5-468 | pyrazol-1-yl | F | Br | Me | Me | Et | |
| 5-409 | pyrazol-1-yl | F | Cl | H | H | Et | | 5-469 | pyrazol-1-yl | F | F | Me | Me | H | |
| 5-410 | pyrazol-1-yl | F | Br | H | H | H | | 5-470 | pyrazol-1-yl | F | F | Me | Me | Me | |
| 5-411 | pyrazol-1-yl | F | Br | H | H | Me | | 5-471 | pyrazol-1-yl | F | I | Me | Me | H | |
| 5-412 | pyrazol-1-yl | F | Br | H | H | Et | | 5-472 | pyrazol-1-yl | F | I | Me | Me | Me | |
| 5-413 | pyrazol-1-yl | F | F | H | H | H | | 5-473 | pyrazol-1-yl | F | CN | Me | Me | H | |
| 5-414 | pyrazol-1-yl | F | F | H | H | Me | | 5-474 | pyrazol-1-yl | F | CN | Me | Me | Me | |
| 5-415 | pyrazol-1-yl | F | I | H | H | H | | 5-475 | pyrazol-1-yl | F | CF$_3$ | Me | Me | H | |
| 5-416 | pyrazol-1-yl | F | I | H | H | Me | | 5-476 | pyrazol-1-yl | F | CF$_3$ | Me | Me | Me | |
| 5-417 | pyrazol-1-yl | F | CN | H | H | H | | 5-477 | pyrazol-1-yl | H | Cl | =CHNMe$_2$ | | H | |
| 5-418 | pyrazol-1-yl | F | CN | H | H | Me | | 5-478 | pyrazol-1-yl | H | Cl | =CHNMe$_2$ | | Me | |
| 5-419 | pyrazol-1-yl | F | CF$_3$ | H | H | H | | 5-479 | pyrazol-1-yl | H | Cl | =CHNMe$_2$ | | Et | |
| 5-420 | pyrazol-1-yl | F | CF$_3$ | H | H | Me | | 5-480 | pyrazol-1-yl | H | Br | =CHNMe$_2$ | | H | |
| 5-421 | pyrazol-1-yl | H | Cl | H | Me | H | | 5-481 | pyrazol-1-yl | H | Br | =CHNMe$_2$ | | Me | |
| 5-422 | pyrazol-1-yl | H | Cl | H | Me | Me | | 5-482 | pyrazol-1-yl | H | Br | =CHNMe$_2$ | | Et | |
| 5-423 | pyrazol-1-yl | H | Cl | H | Me | Et | | 5-483 | pyrazol-1-yl | H | F | =CHNMe$_2$ | | H | |
| 5-424 | pyrazol-1-yl | H | Br | H | Me | H | | 5-484 | pyrazol-1-yl | H | F | =CHNMe$_2$ | | Me | |
| 5-425 | pyrazol-1-yl | H | Br | H | Me | Me | | 5-485 | pyrazol-1-yl | H | I | =CHNMe$_2$ | | H | |
| 5-426 | pyrazol-1-yl | H | Br | H | Me | Et | | 5-486 | pyrazol-1-yl | H | I | =CHNMe$_2$ | | Me | |
| 5-427 | pyrazol-1-yl | H | F | H | Me | H | | 5-487 | pyrazol-1-yl | H | CN | =CHNMe$_2$ | | H | |
| 5-428 | pyrazol-1-yl | H | F | H | Me | Me | | 5-488 | pyrazol-1-yl | H | CN | =CHNMe$_2$ | | Me | |
| 5-429 | pyrazol-1-yl | H | I | H | Me | H | | 5-489 | pyrazol-1-yl | H | CF$_3$ | =CHNMe$_2$ | | H | |
| 5-430 | pyrazol-1-yl | H | I | H | Me | Me | | 5-490 | pyrazol-1-yl | H | CF$_3$ | =CHNMe$_2$ | | Me | |
| 5-431 | pyrazol-1-yl | H | CN | H | Me | H | | 5-491 | pyrazol-1-yl | F | Cl | =CHNMe$_2$ | | H | |
| 5-432 | pyrazol-1-yl | H | CN | H | Me | Me | | 5-492 | pyrazol-1-yl | F | Cl | =CHNMe$_2$ | | Me | |

TABLE 5-continued

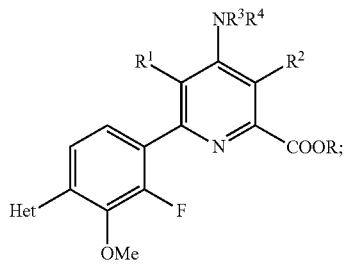

(I-v)

| No. | Het | R¹ | R² | R³ | R⁴ | R | Physical data: ¹H NMR: δ [CDCl₃] |
|---|---|---|---|---|---|---|---|
| 5-493 | pyrazol-1-yl | F | Cl | =CHNMe₂ | | Et | |
| 5-494 | pyrazol-1-yl | F | Br | =CHNMe₂ | | H | |
| 5-495 | pyrazol-1-yl | F | Br | =CHNMe₂ | | Me | |
| 5-496 | pyrazol-1-yl | F | Br | =CHNMe₂ | | Et | |
| 5-497 | pyrazol-1-yl | F | F | =CHNMe₂ | | H | |
| 5-498 | pyrazol-1-yl | F | F | =CHNMe₂ | | Me | |
| 5-499 | pyrazol-1-yl | F | I | =CHNMe₂ | | H | |
| 5-500 | pyrazol-1-yl | F | I | =CHNMe₂ | | Me | |
| 5-501 | pyrazol-1-yl | F | CN | =CHNMe₂ | | H | |
| 5-502 | pyrazol-1-yl | F | CN | =CHNMe₂ | | Me | |
| 5-503 | pyrazol-1-yl | F | CF₃ | =CHNMe₂ | | H | |
| 5-504 | pyrazol-1-yl | F | CF₃ | =CHNMe₂ | | Me | |
| 5-505 | pyridin-3-yl | H | Cl | H | H | H | |
| 5-506 | pyridin-3-yl | H | Cl | H | H | Me | |
| 5-507 | pyridin-3-yl | H | Cl | H | H | Et | |
| 5-508 | pyridin-3-yl | H | Br | H | H | H | |
| 5-509 | pyridin-3-yl | H | Br | H | H | Me | |
| 5-510 | pyridin-3-yl | H | Br | H | H | Et | |
| 5-511 | pyridin-3-yl | H | F | H | H | H | |
| 5-512 | pyridin-3-yl | H | F | H | H | Me | |
| 5-513 | pyridin-3-yl | H | I | H | H | H | |
| 5-514 | pyridin-3-yl | H | I | H | H | Me | |
| 5-515 | pyridin-3-yl | H | CN | H | H | H | |
| 5-516 | pyridin-3-yl | H | CN | H | H | Me | |
| 5-517 | pyridin-3-yl | H | CF₃ | H | H | H | |
| 5-518 | pyridin-3-yl | H | CF₃ | H | H | Me | |
| 5-519 | pyridin-3-yl | F | Cl | H | H | H | |
| 5-520 | pyridin-3-yl | F | Cl | H | H | Me | |
| 5-521 | pyridin-3-yl | F | Cl | H | H | Et | |
| 5-522 | pyridin-3-yl | F | Br | H | H | H | |
| 5-523 | pyridin-3-yl | F | Br | H | H | Me | |
| 5-524 | pyridin-3-yl | F | Br | H | H | Et | |
| 5-525 | pyridin-3-yl | F | F | H | H | H | |
| 5-526 | pyridin-3-yl | F | F | H | H | Me | |
| 5-527 | pyridin-3-yl | F | I | H | H | H | |
| 5-528 | pyridin-3-yl | F | I | H | H | Me | |
| 5-529 | pyridin-3-yl | F | CN | H | H | H | |
| 5-530 | pyridin-3-yl | F | CN | H | H | Me | |
| 5-531 | pyridin-3-yl | F | CF₃ | H | H | H | |
| 5-532 | pyridin-3-yl | F | CF₃ | H | H | Me | |
| 5-533 | pyridin-3-yl | H | Cl | H | Me | H | |
| 5-534 | pyridin-3-yl | H | Cl | H | Me | Me | |
| 5-535 | pyridin-3-yl | H | Cl | H | Me | Et | |
| 5-536 | pyridin-3-yl | H | Br | H | Me | H | |
| 5-537 | pyridin-3-yl | H | Br | H | Me | Me | |
| 5-538 | pyridin-3-yl | H | Br | H | Me | Et | |
| 5-539 | pyridin-3-yl | H | F | H | Me | H | |
| 5-540 | pyridin-3-yl | H | F | H | Me | Me | |
| 5-541 | pyridin-3-yl | H | I | H | Me | H | |
| 5-542 | pyridin-3-yl | H | I | H | Me | Me | |
| 5-543 | pyridin-3-yl | H | CN | H | Me | H | |
| 5-544 | pyridin-3-yl | H | CN | H | Me | Me | |
| 5-545 | pyridin-3-yl | H | CF₃ | H | Me | H | |
| 5-546 | pyridin-3-yl | H | CF₃ | H | Me | Me | |
| 5-547 | pyridin-3-yl | F | Cl | H | Me | H | |
| 5-548 | pyridin-3-yl | F | Cl | H | Me | Me | |
| 5-549 | pyridin-3-yl | F | Cl | H | Me | Et | |
| 5-550 | pyridin-3-yl | F | Br | H | Me | H | |
| 5-551 | pyridin-3-yl | F | Br | H | Me | Me | |
| 5-552 | pyridin-3-yl | F | Br | H | Me | Et | |

TABLE 5-continued

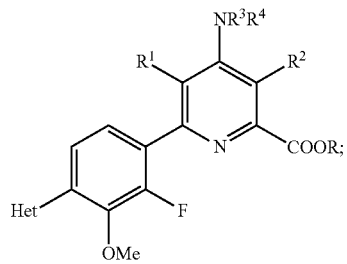

(I-v)

| No. | Het | R¹ | R² | R³ | R⁴ | R | Physical data: ¹H NMR: δ [CDCl₃] |
|---|---|---|---|---|---|---|---|
| 5-553 | pyridin-3-yl | F | F | H | Me | H | |
| 5-554 | pyridin-3-yl | F | F | H | Me | Me | |
| 5-555 | pyridin-3-yl | F | I | H | Me | H | |
| 5-556 | pyridin-3-yl | F | I | H | Me | Me | |
| 5-557 | pyridin-3-yl | F | CN | H | Me | H | |
| 5-558 | pyridin-3-yl | F | CN | H | Me | Me | |
| 5-559 | pyridin-3-yl | F | CF₃ | H | Me | H | |
| 5-560 | pyridin-3-yl | F | CF₃ | H | Me | Me | |
| 5-561 | pyridin-3-yl | H | Cl | Me | Me | H | |
| 5-562 | pyridin-3-yl | H | Cl | Me | Me | Me | |
| 5-563 | pyridin-3-yl | H | Cl | Me | Me | Et | |
| 5-564 | pyridin-3-yl | H | Br | Me | Me | H | |
| 5-565 | pyridin-3-yl | H | Br | Me | Me | Me | |
| 5-566 | pyridin-3-yl | H | Br | Me | Me | Et | |
| 5-567 | pyridin-3-yl | H | F | Me | Me | H | |
| 5-568 | pyridin-3-yl | H | F | Me | Me | Me | |
| 5-569 | pyridin-3-yl | H | I | Me | Me | H | |
| 5-570 | pyridin-3-yl | H | I | Me | Me | Me | |
| 5-571 | pyridin-3-yl | H | CN | Me | Me | H | |
| 5-572 | pyridin-3-yl | H | CN | Me | Me | Me | |
| 5-573 | pyridin-3-yl | H | CF₃ | Me | Me | H | |
| 5-574 | pyridin-3-yl | H | CF₃ | Me | Me | Me | |
| 5-575 | pyridin-3-yl | F | Cl | Me | Me | H | |
| 5-576 | pyridin-3-yl | F | Cl | Me | Me | Me | |
| 5-577 | pyridin-3-yl | F | Cl | Me | Me | Et | |
| 5-578 | pyridin-3-yl | F | Br | Me | Me | H | |
| 5-579 | pyridin-3-yl | F | Br | Me | Me | Me | |
| 5-580 | pyridin-3-yl | F | Br | Me | Me | Et | |
| 5-581 | pyridin-3-yl | F | F | Me | Me | H | |
| 5-582 | pyridin-3-yl | F | F | Me | Me | Me | |
| 5-583 | pyridin-3-yl | F | I | Me | Me | H | |
| 5-584 | pyridin-3-yl | F | I | Me | Me | Me | |
| 5-585 | pyridin-3-yl | F | CN | Me | Me | H | |
| 5-586 | pyridin-3-yl | F | CN | Me | Me | Me | |
| 5-587 | pyridin-3-yl | F | CF₃ | Me | Me | H | |
| 5-588 | pyridin-3-yl | F | CF₃ | Me | Me | Me | |
| 5-589 | pyridin-3-yl | H | Cl | =CHNMe₂ | | H | |
| 5-590 | pyridin-3-yl | H | Cl | =CHNMe₂ | | Me | |
| 5-591 | pyridin-3-yl | H | Cl | =CHNMe₂ | | Et | |
| 5-592 | pyridin-3-yl | H | Br | =CHNMe₂ | | H | |
| 5-593 | pyridin-3-yl | H | Br | =CHNMe₂ | | Me | |
| 5-594 | pyridin-3-yl | H | Br | =CHNMe₂ | | Et | |
| 5-595 | pyridin-3-yl | H | F | =CHNMe₂ | | H | |
| 5-596 | pyridin-3-yl | H | F | =CHNMe₂ | | Me | |
| 5-597 | pyridin-3-yl | H | I | =CHNMe₂ | | H | |
| 5-598 | pyridin-3-yl | H | I | =CHNMe₂ | | Me | |
| 5-599 | pyridin-3-yl | H | CN | =CHNMe₂ | | H | |
| 5-600 | pyridin-3-yl | H | CN | =CHNMe₂ | | Me | |
| 5-601 | pyridin-3-yl | H | CF₃ | =CHNMe₂ | | H | |
| 5-602 | pyridin-3-yl | H | CF₃ | =CHNMe₂ | | Me | |
| 5-603 | pyridin-3-yl | F | Cl | =CHNMe₂ | | H | |
| 5-604 | pyridin-3-yl | F | Cl | =CHNMe₂ | | Me | |
| 5-605 | pyridin-3-yl | F | Cl | =CHNMe₂ | | Et | |
| 5-606 | pyridin-3-yl | F | Br | =CHNMe₂ | | H | |
| 5-607 | pyridin-3-yl | F | Br | =CHNMe₂ | | Me | |
| 5-608 | pyridin-3-yl | F | Br | =CHNMe₂ | | Et | |
| 5-609 | pyridin-3-yl | F | F | =CHNMe₂ | | H | |
| 5-610 | pyridin-3-yl | F | F | =CHNMe₂ | | Me | |
| 5-611 | pyridin-3-yl | F | I | =CHNMe₂ | | H | |
| 5-612 | pyridin-3-yl | F | I | =CHNMe₂ | | Me | |

TABLE 5-continued

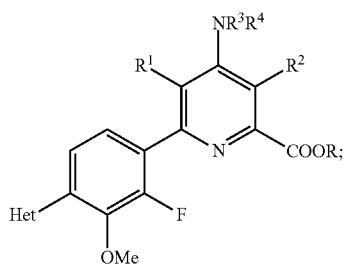

(I-v)

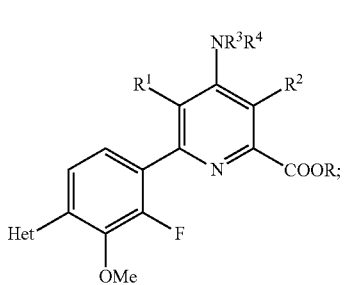

(I-v)

| No. | Het | R¹ | R² | R³ | R⁴ | R | Physical data: ¹H NMR: δ [CDCl₃] |
|---|---|---|---|---|---|---|---|
| 5-613 | pyridin-3-yl | F | CN | =CHNMe₂ | | H | |
| 5-614 | pyridin-3-yl | F | CN | =CHNMe₂ | | Me | |
| 5-615 | pyridin-3-yl | F | CF₃ | =CHNMe₂ | | H | |
| 5-616 | pyridin-3-yl | F | CF₃ | =CHNMe₂ | | Me | |
| 5-617 | oxiranyl | H | Cl | H | H | H | |
| 5-618 | oxiranyl | H | Cl | H | H | Me | |
| 5-619 | oxiranyl | H | Cl | H | H | Et | |
| 5-620 | oxiranyl | H | Br | H | H | H | |
| 5-621 | oxiranyl | H | Br | H | H | Me | |
| 5-622 | oxiranyl | H | Br | H | H | Et | |
| 5-623 | oxiranyl | H | F | H | H | H | |
| 5-624 | oxiranyl | H | F | H | H | Me | |
| 5-625 | oxiranyl | H | I | H | H | H | |
| 5-626 | oxiranyl | H | I | H | H | Me | |
| 5-627 | oxiranyl | H | CN | H | H | H | |
| 5-628 | oxiranyl | H | CN | H | H | Me | |
| 5-629 | oxiranyl | H | CF₃ | H | H | H | |
| 5-630 | oxiranyl | H | CF₃ | H | H | Me | |
| 5-631 | oxiranyl | F | Cl | H | H | H | |
| 5-632 | oxiranyl | F | Cl | H | H | Me | |
| 5-633 | oxiranyl | F | Cl | H | H | Et | |
| 5-634 | oxiranyl | F | Br | H | H | H | |
| 5-635 | oxiranyl | F | Br | H | H | Me | |
| 5-636 | oxiranyl | F | Br | H | H | Et | |
| 5-637 | oxiranyl | F | F | H | H | H | |
| 5-638 | oxiranyl | F | F | H | H | Me | |
| 5-639 | oxiranyl | F | I | H | H | H | |
| 5-640 | oxiranyl | F | I | H | H | Me | |
| 5-641 | oxiranyl | F | CN | H | H | H | |
| 5-642 | oxiranyl | F | CN | H | H | Me | |
| 5-643 | oxiranyl | F | CF₃ | H | H | H | |
| 5-644 | oxiranyl | F | CF₃ | H | H | Me | |
| 5-645 | oxiranyl | H | Cl | H | Me | H | |
| 5-646 | oxiranyl | H | Cl | H | Me | Me | |
| 5-647 | oxiranyl | H | Cl | H | Me | Et | |
| 5-648 | oxiranyl | H | Br | H | Me | H | |
| 5-649 | oxiranyl | H | Br | H | Me | Me | |
| 5-650 | oxiranyl | H | Br | H | Me | Et | |
| 5-651 | oxiranyl | H | F | H | Me | H | |
| 5-652 | oxiranyl | H | F | H | Me | Me | |
| 5-653 | oxiranyl | H | I | H | Me | H | |
| 5-654 | oxiranyl | H | I | H | Me | Me | |
| 5-655 | oxiranyl | H | CN | H | Me | H | |
| 5-656 | oxiranyl | H | CN | H | Me | Me | |
| 5-657 | oxiranyl | H | CF₃ | H | Me | H | |
| 5-658 | oxiranyl | H | CF₃ | H | Me | Me | |
| 5-659 | oxiranyl | F | Cl | H | Me | H | |
| 5-660 | oxiranyl | F | Cl | H | Me | Me | |
| 5-661 | oxiranyl | F | Cl | H | Me | Et | |
| 5-662 | oxiranyl | F | Br | H | Me | H | |
| 5-663 | oxiranyl | F | Br | H | Me | Me | |
| 5-664 | oxiranyl | F | Br | H | Me | Et | |
| 5-665 | oxiranyl | F | F | H | Me | H | |
| 5-666 | oxiranyl | F | F | H | Me | Me | |
| 5-667 | oxiranyl | F | I | H | Me | H | |
| 5-668 | oxiranyl | F | I | H | Me | Me | |
| 5-669 | oxiranyl | F | CN | H | Me | H | |
| 5-670 | oxiranyl | F | CN | H | Me | Me | |
| 5-671 | oxiranyl | F | CF₃ | H | Me | H | |
| 5-672 | oxiranyl | F | CF₃ | H | Me | Me | |
| 5-673 | oxiranyl | H | Cl | Me | Me | H | |
| 5-674 | oxiranyl | H | Cl | Me | Me | Me | |
| 5-675 | oxiranyl | H | Cl | Me | Me | Et | |
| 5-676 | oxiranyl | H | Br | Me | Me | H | |
| 5-677 | oxiranyl | H | Br | Me | Me | Me | |
| 5-678 | oxiranyl | H | Br | Me | Me | Et | |
| 5-679 | oxiranyl | H | F | Me | Me | H | |
| 5-680 | oxiranyl | H | F | Me | Me | Me | |
| 5-681 | oxiranyl | H | I | Me | Me | H | |
| 5-682 | oxiranyl | H | I | Me | Me | Me | |
| 5-683 | oxiranyl | H | CN | Me | Me | H | |
| 5-684 | oxiranyl | H | CN | Me | Me | Me | |
| 5-685 | oxiranyl | H | CF₃ | Me | Me | H | |
| 5-686 | oxiranyl | H | CF₃ | Me | Me | Me | |
| 5-687 | oxiranyl | F | Cl | Me | Me | H | |
| 5-688 | oxiranyl | F | Cl | Me | Me | Me | |
| 5-689 | oxiranyl | F | Cl | Me | Me | Et | |
| 5-690 | oxiranyl | F | Br | Me | Me | H | |
| 5-691 | oxiranyl | F | Br | Me | Me | Me | |
| 5-692 | oxiranyl | F | Br | Me | Me | Et | |
| 5-693 | oxiranyl | F | F | Me | Me | H | |
| 5-694 | oxiranyl | F | F | Me | Me | Me | |
| 5-695 | oxiranyl | F | I | Me | Me | H | |
| 5-696 | oxiranyl | F | I | Me | Me | Me | |
| 5-697 | oxiranyl | F | CN | Me | Me | H | |
| 5-698 | oxiranyl | F | CN | Me | Me | Me | |
| 5-699 | oxiranyl | F | CF₃ | Me | Me | H | |
| 5-700 | oxiranyl | F | CF₃ | Me | Me | Me | |
| 5-701 | oxiranyl | H | Cl | =CHNMe₂ | | H | |
| 5-702 | oxiranyl | H | Cl | =CHNMe₂ | | Me | |
| 5-703 | oxiranyl | H | Cl | =CHNMe₂ | | Et | |
| 5-704 | oxiranyl | H | Br | =CHNMe₂ | | H | |
| 5-705 | oxiranyl | H | Br | =CHNMe₂ | | Me | |
| 5-706 | oxiranyl | H | Br | =CHNMe₂ | | Et | |
| 5-707 | oxiranyl | H | F | =CHNMe₂ | | H | |
| 5-708 | oxiranyl | H | F | =CHNMe₂ | | Me | |
| 5-709 | oxiranyl | H | I | =CHNMe₂ | | H | |
| 5-710 | oxiranyl | H | I | =CHNMe₂ | | Me | |
| 5-711 | oxiranyl | H | CN | =CHNMe₂ | | H | |
| 5-712 | oxiranyl | H | CN | =CHNMe₂ | | Me | |
| 5-713 | oxiranyl | H | CF₃ | =CHNMe₂ | | H | |
| 5-714 | oxiranyl | H | CF₃ | =CHNMe₂ | | Me | |
| 5-715 | oxiranyl | F | Cl | =CHNMe₂ | | H | |
| 5-716 | oxiranyl | F | Cl | =CHNMe₂ | | Me | |
| 5-717 | oxiranyl | F | Cl | =CHNMe₂ | | Et | |
| 5-718 | oxiranyl | F | Br | =CHNMe₂ | | H | |
| 5-719 | oxiranyl | F | Br | =CHNMe₂ | | Me | |
| 5-720 | oxiranyl | F | Br | =CHNMe₂ | | Et | |
| 5-721 | oxiranyl | F | F | =CHNMe₂ | | H | |
| 5-722 | oxiranyl | F | F | =CHNMe₂ | | Me | |
| 5-723 | oxiranyl | F | I | =CHNMe₂ | | H | |
| 5-724 | oxiranyl | F | I | =CHNMe₂ | | Me | |
| 5-725 | oxiranyl | F | CN | =CHNMe₂ | | H | |
| 5-726 | oxiranyl | F | CN | =CHNMe₂ | | Me | |
| 5-727 | oxiranyl | F | CF₃ | =CHNMe₂ | | H | |
| 5-728 | oxiranyl | F | CF₃ | =CHNMe₂ | | Me | |
| 5-729 | 3,3-dimethyl-oxetan-2-yl | H | Cl | H | H | H | |
| 5-730 | 3,3-dimethyl-oxetan-2-yl | H | Cl | H | H | Me | |

TABLE 5-continued

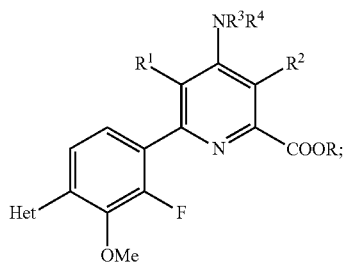

(I-v)

| No. | Het | R¹ | R² | R³ | R⁴ | R | Physical data: ¹H NMR: δ [CDCl₃] |
|---|---|---|---|---|---|---|---|
| 5-731 | 3,3-dimethyl-oxetan-2-yl | H | Cl | H | H | Et | |
| 5-732 | 3,3-dimethyl-oxetan-2-yl | H | Br | H | H | H | |
| 5-733 | 3,3-dimethyl-oxetan-2-yl | H | Br | H | H | Me | |
| 5-734 | 3,3-dimethyl-oxetan-2-yl | H | Br | H | H | Et | |
| 5-735 | 3,3-dimethyl-oxetan-2-yl | H | F | H | H | H | |
| 5-736 | 3,3-dimethyl-oxetan-2-yl | H | F | H | H | Me | |
| 5-737 | 3,3-dimethyl-oxetan-2-yl | H | I | H | H | H | |
| 5-738 | 3,3-dimethyl-oxetan-2-yl | H | I | H | H | Me | |
| 5-739 | 3,3-dimethyl-oxetan-2-yl | H | CN | H | H | H | |
| 5-740 | 3,3-dimethyl-oxetan-2-yl | H | CN | H | H | Me | |
| 5-741 | 3,3-dimethyl-oxetan-2-yl | H | CF₃ | H | H | H | |
| 5-742 | 3,3-dimethyl-oxetan-2-yl | H | CF₃ | H | H | Me | |
| 5-743 | 3,3-dimethyl-oxetan-2-yl | F | Cl | H | H | H | |
| 5-744 | 3,3-dimethyl-oxetan-2-yl | F | Cl | H | H | Me | |
| 5-745 | 3,3-dimethyl-oxetan-2-yl | F | Cl | H | H | Et | |
| 5-746 | 3,3-dimethyl-oxetan-2-yl | F | Br | H | H | H | |
| 5-747 | 3,3-dimethyl-oxetan-2-yl | F | Br | H | H | Me | |
| 5-748 | 3,3-dimethyl-oxetan-2-yl | F | Br | H | H | Et | |
| 5-749 | 3,3-dimethyl-oxetan-2-yl | F | F | H | H | H | |
| 5-750 | 3,3-dimethyl-oxetan-2-yl | F | F | H | H | Me | |
| 5-751 | 3,3-dimethyl-oxetan-2-yl | F | I | H | H | H | |
| 5-752 | 3,3-dimethyl-oxetan-2-yl | F | I | H | H | Me | |
| 5-753 | 3,3-dimethyl-oxetan-2-yl | F | CN | H | H | H | |
| 5-754 | 3,3-dimethyl-oxetan-2-yl | F | CN | H | H | Me | |
| 5-755 | 3,3-dimethyl-oxetan-2-yl | F | CF₃ | H | H | H | |
| 5-756 | 3,3-dimethyl-oxetan-2-yl | F | CF₃ | H | H | Me | |
| 5-757 | 3,3-dimethyl-oxetan-2-yl | H | Cl | H | Me | H | |
| 5-758 | 3,3-dimethyl-oxetan-2-yl | H | Cl | H | Me | Me | |
| 5-759 | 3,3-dimethyl-oxetan-2-yl | H | Cl | H | Me | Et | |
| 5-760 | 3,3-dimethyl-oxetan-2-yl | H | Br | H | Me | H | |

TABLE 5-continued

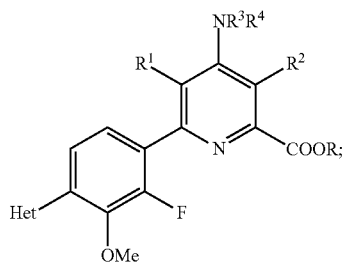

(I-v)

| No. | Het | R¹ | R² | R³ | R⁴ | R | Physical data: ¹H NMR: δ [CDCl₃] |
|---|---|---|---|---|---|---|---|
| 5-761 | 3,3-dimethyl-oxetan-2-yl | H | Br | H | Me | Me | |
| 5-762 | 3,3-dimethyl-oxetan-2-yl | H | Br | H | Me | Et | |
| 5-763 | 3,3-dimethyl-oxetan-2-yl | H | F | H | Me | H | |
| 5-764 | 3,3-dimethyl-oxetan-2-yl | H | F | H | Me | Me | |
| 5-765 | 3,3-dimethyl-oxetan-2-yl | H | I | H | Me | H | |
| 5-766 | 3,3-dimethyl-oxetan-2-yl | H | I | H | Me | Me | |
| 5-767 | 3,3-dimethyl-oxetan-2-yl | H | CN | H | Me | H | |
| 5-768 | 3,3-dimethyl-oxetan-2-yl | H | CN | H | Me | Me | |
| 5-769 | 3,3-dimethyl-oxetan-2-yl | H | CF₃ | H | Me | H | |
| 5-770 | 3,3-dimethyl-oxetan-2-yl | H | CF₃ | H | Me | Me | |
| 5-771 | 3,3-dimethyl-oxetan-2-yl | F | Cl | H | Me | H | |
| 5-772 | 3,3-dimethyl-oxetan-2-yl | F | Cl | H | Me | Me | |
| 5-773 | 3,3-dimethyl-oxetan-2-yl | F | Cl | H | Me | Et | |
| 5-774 | 3,3-dimethyl-oxetan-2-yl | F | Br | H | Me | H | |
| 5-775 | 3,3-dimethyl-oxetan-2-yl | F | Br | H | Me | Me | |
| 5-776 | 3,3-dimethyl-oxetan-2-yl | F | Br | H | Me | Et | |
| 5-777 | 3,3-dimethyl-oxetan-2-yl | F | F | H | Me | H | |
| 5-778 | 3,3-dimethyl-oxetan-2-yl | F | F | H | Me | Me | |
| 5-779 | 3,3-dimethyl-oxetan-2-yl | F | I | H | Me | H | |
| 5-780 | 3,3-dimethyl-oxetan-2-yl | F | I | H | Me | Me | |
| 5-781 | 3,3-dimethyl-oxetan-2-yl | F | CN | H | Me | H | |
| 5-782 | 3,3-dimethyl-oxetan-2-yl | F | CN | H | Me | Me | |
| 5-783 | 3,3-dimethyl-oxetan-2-yl | F | CF₃ | H | Me | H | |
| 5-784 | 3,3-dimethyl-oxetan-2-yl | F | CF₃ | H | Me | Me | |
| 5-785 | 3,3-dimethyl-oxetan-2-yl | H | Cl | Me | Me | H | |
| 5-786 | 3,3-dimethyl-oxetan-2-yl | H | Cl | Me | Me | Me | |
| 5-787 | 3,3-dimethyl-oxetan-2-yl | H | Cl | Me | Me | Et | |
| 5-788 | 3,3-dimethyl-oxetan-2-yl | H | Br | Me | Me | H | |
| 5-789 | 3,3-dimethyl-oxetan-2-yl | H | Br | Me | Me | Me | |
| 5-790 | 3,3-dimethyl-oxetan-2-yl | H | Br | Me | Me | Et | |

TABLE 5-continued

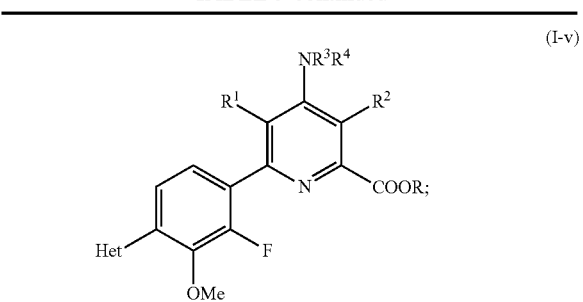

(I-v)

| No. | Het | R¹ | R² | R³ | R⁴ | R | Physical data: ¹H NMR: δ [CDCl₃] |
|---|---|---|---|---|---|---|---|
| 5-791 | 3,3-dimethyl-oxetan-2-yl | H | F | Me | Me | H | |
| 5-792 | 3,3-dimethyl-oxetan-2-yl | H | F | Me | Me | Me | |
| 5-793 | 3,3-dimethyl-oxetan-2-yl | H | I | Me | Me | H | |
| 5-794 | 3,3-dimethyl-oxetan-2-yl | H | I | Me | Me | Me | |
| 5-795 | 3,3-dimethyl-oxetan-2-yl | H | CN | Me | Me | H | |
| 5-796 | 3,3-dimethyl-oxetan-2-yl | H | CN | Me | Me | Me | |
| 5-797 | 3,3-dimethyl-oxetan-2-yl | H | CF₃ | Me | Me | H | |
| 5-798 | 3,3-dimethyl-oxetan-2-yl | H | CF₃ | Me | Me | Me | |
| 5-799 | 3,3-dimethyl-oxetan-2-yl | F | Cl | Me | Me | H | |
| 5-800 | 3,3-dimethyl-oxetan-2-yl | F | Cl | Me | Me | Me | |
| 5-801 | 3,3-dimethyl-oxetan-2-yl | F | Cl | Me | Me | Et | |
| 5-802 | 3,3-dimethyl-oxetan-2-yl | F | Br | Me | Me | H | |
| 5-803 | 3,3-dimethyl-oxetan-2-yl | F | Br | Me | Me | Me | |
| 5-804 | 3,3-dimethyl-oxetan-2-yl | F | Br | Me | Me | Et | |
| 5-805 | 3,3-dimethyl-oxetan-2-yl | F | F | Me | Me | H | |
| 5-806 | 3,3-dimethyl-oxetan-2-yl | F | F | Me | Me | Me | |
| 5-807 | 3,3-dimethyl-oxetan-2-yl | F | I | Me | Me | H | |
| 5-808 | 3,3-dimethyl-oxetan-2-yl | F | I | Me | Me | Me | |
| 5-809 | 3,3-dimethyl-oxetan-2-yl | F | CN | Me | Me | H | |
| 5-810 | 3,3-dimethyl-oxetan-2-yl | F | CN | Me | Me | Me | |
| 5-811 | 3,3-dimethyl-oxetan-2-yl | F | CF₃ | Me | Me | H | |
| 5-812 | 3,3-dimethyl-oxetan-2-yl | F | CF₃ | Me | Me | Me | |
| 5-813 | 3,3-dimethyl-oxetan-2-yl | H | Cl | =CHNMe₂ | | H | |
| 5-814 | 3,3-dimethyl-oxetan-2-yl | H | Cl | =CHNMe₂ | | Me | |
| 5-815 | 3,3-dimethyl-oxetan-2-yl | H | Cl | =CHNMe₂ | | Et | |
| 5-816 | 3,3-dimethyl-oxetan-2-yl | H | Br | =CHNMe₂ | | H | |
| 5-817 | 3,3-dimethyl-oxetan-2-yl | H | Br | =CHNMe₂ | | Me | |
| 5-818 | 3,3-dimethyl-oxetan-2-yl | H | Br | =CHNMe₂ | | Et | |
| 5-819 | 3,3-dimethyl-oxetan-2-yl | H | F | =CHNMe₂ | | H | |
| 5-820 | 3,3-dimethyl-oxetan-2-yl | H | F | =CHNMe₂ | | Me | |
| 5-821 | 3,3-dimethyl-oxetan-2-yl | H | I | =CHNMe₂ | | H | |
| 5-822 | 3,3-dimethyl-oxetan-2-yl | H | I | =CHNMe₂ | | Me | |
| 5-823 | 3,3-dimethyl-oxetan-2-yl | H | CN | =CHNMe₂ | | H | |
| 5-824 | 3,3-dimethyl-oxetan-2-yl | H | CN | =CHNMe₂ | | Me | |
| 5-825 | 3,3-dimethyl-oxetan-2-yl | H | CF₃ | =CHNMe₂ | | H | |
| 5-826 | 3,3-dimethyl-oxetan-2-yl | H | CF₃ | =CHNMe₂ | | Me | |
| 5-827 | 3,3-dimethyl-oxetan-2-yl | F | Cl | =CHNMe₂ | | H | |
| 5-828 | 3,3-dimethyl-oxetan-2-yl | F | Cl | =CHNMe₂ | | Me | |
| 5-829 | 3,3-dimethyl-oxetan-2-yl | F | Cl | =CHNMe₂ | | Et | |
| 5-830 | 3,3-dimethyl-oxetan-2-yl | F | Br | =CHNMe₂ | | H | |
| 5-831 | 3,3-dimethyl-oxetan-2-yl | F | Br | =CHNMe₂ | | Me | |
| 5-832 | 3,3-dimethyl-oxetan-2-yl | F | Br | =CHNMe₂ | | Et | |
| 5-833 | 3,3-dimethyl-oxetan-2-yl | F | F | =CHNMe₂ | | H | |
| 5-834 | 3,3-dimethyl-oxetan-2-yl | F | F | =CHNMe₂ | | Me | |
| 5-835 | 3,3-dimethyl-oxetan-2-yl | F | I | =CHNMe₂ | | H | |
| 5-836 | 3,3-dimethyl-oxetan-2-yl | F | I | =CHNMe₂ | | Me | |
| 5-837 | 3,3-dimethyl-oxetan-2-yl | F | CN | =CHNMe₂ | | H | |
| 5-838 | 3,3-dimethyl-oxetan-2-yl | F | CN | =CHNMe₂ | | Me | |
| 5-839 | 3,3-dimethyl-oxetan-2-yl | F | CF₃ | =CHNMe₂ | | H | |
| 5-840 | 3,3-dimethyl-oxetan-2-yl | F | CF₃ | =CHNMe₂ | | Me | |
| 5-841 | 2,2-dimethyl-dioxolan-4-yl | H | Cl | H | H | H | |
| 5-842 | 2,2-dimethyl-dioxolan-4-yl | H | Cl | H | H | Me | |
| 5-843 | 2,2-dimethyl-dioxolan-4-yl | H | Cl | H | H | Et | |
| 5-844 | 2,2-dimethyl-dioxolan-4-yl | H | Br | H | H | H | |
| 5-845 | 2,2-dimethyl-dioxolan-4-yl | H | Br | H | H | Me | |
| 5-846 | 2,2-dimethyl-dioxolan-4-yl | H | Br | H | H | Et | |
| 5-847 | 2,2-dimethyl-dioxolan-4-yl | H | F | H | H | H | |
| 5-848 | 2,2-dimethyl-dioxolan-4-yl | H | F | H | H | Me | |
| 5-849 | 2,2-dimethyl-dioxolan-4-yl | H | I | H | H | H | |
| 5-850 | 2,2-dimethyl-dioxolan-4-yl | H | I | H | H | Me | |

TABLE 5-continued

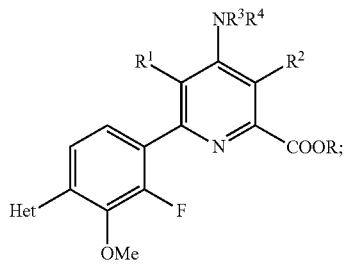

(I-v)

| No. | Het | R¹ | R² | R³ | R⁴ | R | Physical data: ¹H NMR: δ [CDCl₃] |
|---|---|---|---|---|---|---|---|
| 5-851 | 2,2-dimethyl-dioxolan-4-yl | H | CN | H | H | H | |
| 5-852 | 2,2-dimethyl-dioxolan-4-yl | H | CN | H | H | Me | |
| 5-853 | 2,2-dimethyl-dioxolan-4-yl | H | CF₃ | H | H | H | |
| 5-854 | 2,2-dimethyl-dioxolan-4-yl | H | CF₃ | H | H | Me | |
| 5-855 | 2,2-dimethyl-dioxolan-4-yl | F | Cl | H | H | H | |
| 5-856 | 2,2-dimethyl-dioxolan-4-yl | F | Cl | H | H | Me | |
| 5-857 | 2,2-dimethyl-dioxolan-4-yl | F | Cl | H | H | Et | |
| 5-858 | 2,2-dimethyl-dioxolan-4-yl | F | Br | H | H | H | |
| 5-859 | 2,2-dimethyl-dioxolan-4-yl | F | Br | H | H | Me | |
| 5-860 | 2,2-dimethyl-dioxolan-4-yl | F | Br | H | H | Et | |
| 5-861 | 2,2-dimethyl-dioxolan-4-yl | F | F | H | H | H | |
| 5-862 | 2,2-dimethyl-dioxolan-4-yl | F | F | H | H | Me | |
| 5-863 | 2,2-dimethyl-dioxolan-4-yl | F | I | H | H | H | |
| 5-864 | 2,2-dimethyl-dioxolan-4-yl | F | I | H | H | Me | |
| 5-865 | 2,2-dimethyl-dioxolan-4-yl | F | CN | H | H | H | |
| 5-866 | 2,2-dimethyl-dioxolan-4-yl | F | CN | H | H | Me | |
| 5-867 | 2,2-dimethyl-dioxolan-4-yl | F | CF₃ | H | H | H | |
| 5-868 | 2,2-dimethyl-dioxolan-4-yl | F | CF₃ | H | H | Me | |
| 5-869 | 2,2-dimethyl-dioxolan-4-yl | H | Cl | H | Me | H | |
| 5-870 | 2,2-dimethyl-dioxolan-4-yl | H | Cl | H | Me | Me | |
| 5-871 | 2,2-dimethyl-dioxolan-4-yl | H | Cl | H | Me | Et | |
| 5-872 | 2,2-dimethyl-dioxolan-4-yl | H | Br | H | Me | H | |
| 5-873 | 2,2-dimethyl-dioxolan-4-yl | H | Br | H | Me | Me | |
| 5-874 | 2,2-dimethyl-dioxolan-4-yl | H | Br | H | Me | Et | |
| 5-875 | 2,2-dimethyl-dioxolan-4-yl | H | F | H | Me | H | |
| 5-876 | 2,2-dimethyl-dioxolan-4-yl | H | F | H | Me | Me | |
| 5-877 | 2,2-dimethyl-dioxolan-4-yl | H | I | H | Me | H | |
| 5-878 | 2,2-dimethyl-dioxolan-4-yl | H | I | H | Me | Me | |
| 5-879 | 2,2-dimethyl-dioxolan-4-yl | H | CN | H | Me | H | |
| 5-880 | 2,2-dimethyl-dioxolan-4-yl | H | CN | H | Me | Me | |

TABLE 5-continued

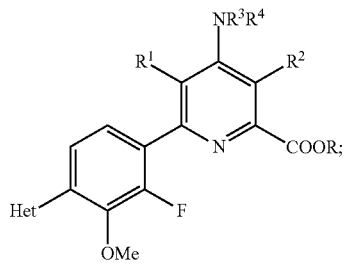

(I-v)

| No. | Het | R¹ | R² | R³ | R⁴ | R | Physical data: ¹H NMR: δ [CDCl₃] |
|---|---|---|---|---|---|---|---|
| 5-881 | 2,2-dimethyl-dioxolan-4-yl | H | CF₃ | H | Me | H | |
| 5-882 | 2,2-dimethyl-dioxolan-4-yl | H | CF₃ | H | Me | Me | |
| 5-883 | 2,2-dimethyl-dioxolan-4-yl | F | Cl | H | Me | H | |
| 5-884 | 2,2-dimethyl-dioxolan-4-yl | F | Cl | H | Me | Me | |
| 5-885 | 2,2-dimethyl-dioxolan-4-yl | F | Cl | H | Me | Et | |
| 5-886 | 2,2-dimethyl-dioxolan-4-yl | F | Br | H | Me | H | |
| 5-887 | 2,2-dimethyl-dioxolan-4-yl | F | Br | H | Me | Me | |
| 5-888 | 2,2-dimethyl-dioxolan-4-yl | F | Br | H | Me | Et | |
| 5-889 | 2,2-dimethyl-dioxolan-4-yl | F | F | H | Me | H | |
| 5-890 | 2,2-dimethyl-dioxolan-4-yl | F | F | H | Me | Me | |
| 5-891 | 2,2-dimethyl-dioxolan-4-yl | F | I | H | Me | H | |
| 5-892 | 2,2-dimethyl-dioxolan-4-yl | F | I | H | Me | Me | |
| 5-893 | 2,2-dimethyl-dioxolan-4-yl | F | CN | H | Me | H | |
| 5-894 | 2,2-dimethyl-dioxolan-4-yl | F | CN | H | Me | Me | |
| 5-895 | 2,2-dimethyl-dioxolan-4-yl | F | CF₃ | H | Me | H | |
| 5-896 | 2,2-dimethyl-dioxolan-4-yl | F | CF₃ | H | Me | Me | |
| 5-897 | 2,2-dimethyl-dioxolan-4-yl | H | Cl | Me | Me | H | |
| 5-898 | 2,2-dimethyl-dioxolan-4-yl | H | Cl | Me | Me | Me | |
| 5-899 | 2,2-dimethyl-dioxolan-4-yl | H | Cl | Me | Me | Et | |
| 5-900 | 2,2-dimethyl-dioxolan-4-yl | H | Br | Me | Me | H | |
| 5-901 | 2,2-dimethyl-dioxolan-4-yl | H | Br | Me | Me | Me | |
| 5-902 | 2,2-dimethyl-dioxolan-4-yl | H | Br | Me | Me | Et | |
| 5-903 | 2,2-dimethyl-dioxolan-4-yl | H | F | Me | Me | H | |
| 5-904 | 2,2-dimethyl-dioxolan-4-yl | H | F | Me | Me | Me | |
| 5-905 | 2,2-dimethyl-dioxolan-4-yl | H | I | Me | Me | H | |
| 5-906 | 2,2-dimethyl-dioxolan-4-yl | H | I | Me | Me | Me | |
| 5-907 | 2,2-dimethyl-dioxolan-4-yl | H | CN | Me | Me | H | |
| 5-908 | 2,2-dimethyl-dioxolan-4-yl | H | CN | Me | Me | Me | |
| 5-909 | 2,2-dimethyl-dioxolan-4-yl | H | CF₃ | Me | Me | H | |
| 5-910 | 2,2-dimethyl-dioxolan-4-yl | H | CF₃ | Me | Me | Me | |

TABLE 5-continued

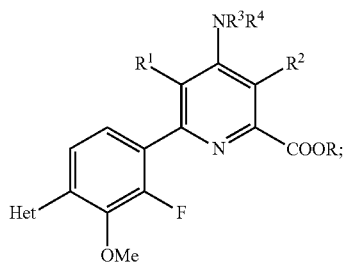

(I-v)

| No. | Het | R¹ | R² | R³ | R⁴ | R | Physical data: ¹H NMR: δ [CDCl₃] |
|---|---|---|---|---|---|---|---|
| 5-911 | 2,2-dimethyl-dioxolan-4-yl | F | Cl | Me | Me | H | |
| 5-912 | 2,2-dimethyl-dioxolan-4-yl | F | Cl | Me | Me | Me | |
| 5-913 | 2,2-dimethyl-dioxolan-4-yl | F | Cl | Me | Me | Et | |
| 5-914 | 2,2-dimethyl-dioxolan-4-yl | F | Br | Me | Me | H | |
| 5-915 | 2,2-dimethyl-dioxolan-4-yl | F | Br | Me | Me | Me | |
| 5-916 | 2,2-dimethyl-dioxolan-4-yl | F | Br | Me | Me | Et | |
| 5-917 | 2,2-dimethyl-dioxolan-4-yl | F | F | Me | Me | H | |
| 5-918 | 2,2-dimethyl-dioxolan-4-yl | F | F | Me | Me | Me | |
| 5-919 | 2,2-dimethyl-dioxolan-4-yl | F | I | Me | Me | H | |
| 5-920 | 2,2-dimethyl-dioxolan-4-yl | F | I | Me | Me | Me | |
| 5-921 | 2,2-dimethyl-dioxolan-4-yl | F | CN | Me | Me | H | |
| 5-922 | 2,2-dimethyl-dioxolan-4-yl | F | CN | Me | Me | Me | |
| 5-923 | 2,2-dimethyl-dioxolan-4-yl | F | CF₃ | Me | Me | H | |
| 5-924 | 2,2-dimethyl-dioxolan-4-yl | F | CF₃ | Me | Me | Me | |
| 5-925 | 2,2-dimethyl-dioxolan-4-yl | H | Cl | =CHNMe₂ | | H | |
| 5-926 | 2,2-dimethyl-dioxolan-4-yl | H | Cl | =CHNMe₂ | | Me | |
| 5-927 | 2,2-dimethyl-dioxolan-4-yl | H | Cl | =CHNMe₂ | | Et | |
| 5-928 | 2,2-dimethyl-dioxolan-4-yl | H | Br | =CHNMe₂ | | H | |
| 5-929 | 2,2-dimethyl-dioxolan-4-yl | H | Br | =CHNMe₂ | | Me | |
| 5-930 | 2,2-dimethyl-dioxolan-4-yl | H | Br | =CHNMe₂ | | Et | |
| 5-931 | 2,2-dimethyl-dioxolan-4-yl | H | F | =CHNMe₂ | | H | |
| 5-932 | 2,2-dimethyl-dioxolan-4-yl | H | F | =CHNMe₂ | | Me | |
| 5-933 | 2,2-dimethyl-dioxolan-4-yl | H | I | =CHNMe₂ | | H | |
| 5-934 | 2,2-dimethyl-dioxolan-4-yl | H | I | =CHNMe₂ | | Me | |
| 5-935 | 2,2-dimethyl-dioxolan-4-yl | H | CN | =CHNMe₂ | | H | |
| 5-936 | 2,2-dimethyl-dioxolan-4-yl | H | CN | =CHNMe₂ | | Me | |
| 5-937 | 2,2-dimethyl-dioxolan-4-yl | H | CF₃ | =CHNMe₂ | | H | |
| 5-938 | 2,2-dimethyl-dioxolan-4-yl | H | CF₃ | =CHNMe₂ | | Me | |
| 5-939 | 2,2-dimethyl-dioxolan-4-yl | F | Cl | =CHNMe₂ | | H | |
| 5-940 | 2,2-dimethyl-dioxolan-4-yl | F | Cl | =CHNMe₂ | | Me | |
| 5-941 | 2,2-dimethyl-dioxolan-4-yl | F | Cl | =CHNMe₂ | | Et | |
| 5-942 | 2,2-dimethyl-dioxolan-4-yl | F | Br | =CHNMe₂ | | H | |
| 5-943 | 2,2-dimethyl-dioxolan-4-yl | F | Br | =CHNMe₂ | | Me | |
| 5-944 | 2,2-dimethyl-dioxolan-4-yl | F | Br | =CHNMe₂ | | Et | |
| 5-945 | 2,2-dimethyl-dioxolan-4-yl | F | F | =CHNMe₂ | | H | |
| 5-946 | 2,2-dimethyl-dioxolan-4-yl | F | F | =CHNMe₂ | | Me | |
| 5-947 | 2,2-dimethyl-dioxolan-4-yl | F | I | =CHNMe₂ | | H | |
| 5-948 | 2,2-dimethyl-dioxolan-4-yl | F | I | =CHNMe₂ | | Me | |
| 5-949 | 2,2-dimethyl-dioxolan-4-yl | F | CN | =CHNMe₂ | | H | |
| 5-950 | 2,2-dimethyl-dioxolan-4-yl | F | CN | =CHNMe₂ | | Me | |
| 5-951 | 2,2-dimethyl-dioxolan-4-yl | F | CF₃ | =CHNMe₂ | | H | |
| 5-952 | 2,2-dimethyl-dioxolan-4-yl | F | CF₃ | =CHNMe₂ | | Me | |

TABLE 6

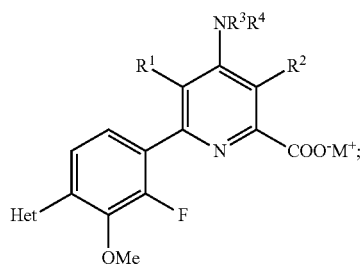

(I-vi)

| No. | Het | R¹ | R² | R³ | R⁴ | M⁺ | Physical data: ¹H NMR: δ [CDCl₃] |
|---|---|---|---|---|---|---|---|
| 6-1 | 3-tert-butyl-1,2,4-oxadiazol-5-yl | H | Cl | H | H | Na⁺ | |
| 6-2 | 3-tert-butyl-1,2,4-oxadiazol-5-yl | H | Cl | H | H | K⁺ | |
| 6-3 | 3-tert-butyl-1,2,4-oxadiazol-5-yl | H | Cl | H | H | NH₄⁺ | |
| 6-4 | 3-tert-butyl-1,2,4-oxadiazol-5-yl | H | Br | H | H | Na⁺ | |
| 6-5 | 3-tert-butyl-1,2,4-oxadiazol-5-yl | H | Br | H | H | K⁺ | |
| 6-6 | 3-tert-butyl-1,2,4-oxadiazol-5-yl | H | Br | H | H | NH₄⁺ | |

TABLE 6-continued

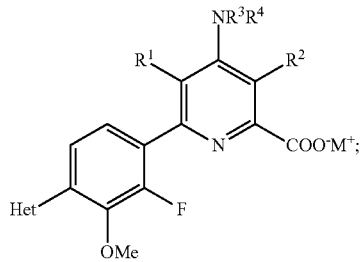

(I-vi)

| No. | Het | $R^1$ | $R^2$ | $R^3$ | $R^4$ | $M^+$ | Physical data: $^1$H NMR: δ [CDCl$_3$] |
|---|---|---|---|---|---|---|---|
| 6-7 | 3-tert-butyl-1,2,4-oxadiazol-5-yl | H | F | H | H | Na$^+$ | |
| 6-8 | 3-tert-butyl-1,2,4-oxadiazol-5-yl | H | F | H | H | K$^+$ | |
| 6-9 | 3-tert-butyl-1,2,4-oxadiazol-5-yl | H | I | H | H | Na$^+$ | |
| 6-10 | 3-tert-butyl-1,2,4-oxadiazol-5-yl | H | I | H | H | K$^+$ | |
| 6-11 | 3-tert-butyl-1,2,4-oxadiazol-5-yl | H | CN | H | H | Na$^+$ | |
| 6-12 | 3-tert-butyl-1,2,4-oxadiazol-5-yl | H | CN | H | H | K$^+$ | |
| 6-13 | 3-tert-butyl-1,2,4-oxadiazol-5-yl | H | CF$_3$ | H | H | Na$^+$ | |
| 6-14 | 3-tert-butyl-1,2,4-oxadiazol-5-yl | H | CF$_3$ | H | H | K$^+$ | |
| 6-15 | 3-tert-butyl-1,2,4-oxadiazol-5-yl | F | Cl | H | H | Na$^+$ | |
| 6-16 | 3-tert-butyl-1,2,4-oxadiazol-5-yl | F | Cl | H | H | K$^+$ | |
| 6-17 | 3-tert-butyl-1,2,4-oxadiazol-5-yl | F | Cl | H | H | NH$_4^+$ | |
| 6-18 | 3-tert-butyl-1,2,4-oxadiazol-5-yl | F | Br | H | H | Na$^+$ | |
| 6-19 | 3-tert-butyl-1,2,4-oxadiazol-5-yl | F | Br | H | H | K$^+$ | |
| 6-20 | 3-tert-butyl-1,2,4-oxadiazol-5-yl | F | Br | H | H | NH$_4^+$ | |
| 6-21 | 3-tert-butyl-1,2,4-oxadiazol-5-yl | F | F | H | H | Na$^+$ | |
| 6-22 | 3-tert-butyl-1,2,4-oxadiazol-5-yl | F | F | H | H | K$^+$ | |
| 6-23 | 3-tert-butyl-1,2,4-oxadiazol-5-yl | F | I | H | H | Na$^+$ | |
| 6-24 | 3-tert-butyl-1,2,4-oxadiazol-5-yl | F | I | H | H | K$^+$ | |
| 6-25 | 3-tert-butyl-1,2,4-oxadiazol-5-yl | F | CN | H | H | Na$^+$ | |
| 6-26 | 3-tert-butyl-1,2,4-oxadiazol-5-yl | F | CN | H | H | K$^+$ | |
| 6-27 | 3-tert-butyl-1,2,4-oxadiazol-5-yl | F | CF$_3$ | H | H | Na$^+$ | |
| 6-28 | 3-tert-butyl-1,2,4-oxadiazol-5-yl | F | CF$_3$ | H | H | K$^+$ | |
| 6-29 | 3-tert-butyl-1,2,4-oxadiazol-5-yl | Cl | Cl | H | H | Na$^+$ | |
| 6-30 | 3-tert-butyl-1,2,4-oxadiazol-5-yl | Cl | Cl | H | H | K$^+$ | |
| 6-31 | 3-tert-butyl-1,2,4-oxadiazol-5-yl | Cl | Cl | H | H | NH$_4^+$ | |
| 6-32 | 3-tert-butyl-1,2,4-oxadiazol-5-yl | Cl | Br | H | H | Na$^+$ | |
| 6-33 | 3-tert-butyl-1,2,4-oxadiazol-5-yl | Cl | Br | H | H | K$^+$ | |
| 6-34 | 3-tert-butyl-1,2,4-oxadiazol-5-yl | Cl | Br | H | H | NH$_4^+$ | |
| 6-35 | 3-tert-butyl-1,2,4-oxadiazol-5-yl | Cl | F | H | H | Na$^+$ | |
| 6-36 | 3-tert-butyl-1,2,4-oxadiazol-5-yl | Cl | F | H | H | K$^+$ | |
| 6-37 | 3-tert-butyl-1,2,4-oxadiazol-5-yl | Cl | I | H | H | Na$^+$ | |
| 6-38 | 3-tert-butyl-1,2,4-oxadiazol-5-yl | Cl | I | H | H | K$^+$ | |
| 6-39 | 3-tert-butyl-1,2,4-oxadiazol-5-yl | Cl | CN | H | H | Na$^+$ | |
| 6-40 | 3-tert-butyl-1,2,4-oxadiazol-5-yl | Cl | CN | H | H | K$^+$ | |
| 6-41 | 3-tert-butyl-1,2,4-oxadiazol-5-yl | Cl | CF$_3$ | H | H | Na$^+$ | |
| 6-42 | 3-tert-butyl-1,2,4-oxadiazol-5-yl | Cl | CF$_3$ | H | H | K$^+$ | |
| 6-43 | 3-tert-butyl-1,2,4-oxadiazol-5-yl | H | Cl | H | Me | Na$^+$ | |
| 6-44 | 3-tert-butyl-1,2,4-oxadiazol-5-yl | H | Cl | H | Me | K$^+$ | |
| 6-45 | 3-tert-butyl-1,2,4-oxadiazol-5-yl | H | Cl | H | Me | NH$_4^+$ | |
| 6-46 | 3-tert-butyl-1,2,4-oxadiazol-5-yl | H | Br | H | Me | Na$^+$ | |
| 6-47 | 3-tert-butyl-1,2,4-oxadiazol-5-yl | H | Br | H | Me | K$^+$ | |
| 6-48 | 3-tert-butyl-1,2,4-oxadiazol-5-yl | H | Br | H | Me | NH$_4^+$ | |
| 6-49 | 3-tert-butyl-1,2,4-oxadiazol-5-yl | H | F | H | Me | Na$^+$ | |
| 6-50 | 3-tert-butyl-1,2,4-oxadiazol-5-yl | H | F | H | Me | K$^+$ | |
| 6-51 | 3-tert-butyl-1,2,4-oxadiazol-5-yl | H | I | H | Me | Na$^+$ | |
| 6-52 | 3-tert-butyl-1,2,4-oxadiazol-5-yl | H | I | H | Me | K$^+$ | |
| 6-53 | 3-tert-butyl-1,2,4-oxadiazol-5-yl | H | CN | H | Me | Na$^+$ | |
| 6-54 | 3-tert-butyl-1,2,4-oxadiazol-5-yl | H | CN | H | Me | K$^+$ | |
| 6-55 | 3-tert-butyl-1,2,4-oxadiazol-5-yl | H | CF$_3$ | H | Me | Na$^+$ | |
| 6-56 | 3-tert-butyl-1,2,4-oxadiazol-5-yl | H | CF$_3$ | H | Me | K$^+$ | |
| 6-57 | 3-tert-butyl-1,2,4-oxadiazol-5-yl | F | Cl | H | Me | Na$^+$ | |
| 6-58 | 3-tert-butyl-1,2,4-oxadiazol-5-yl | F | Cl | H | Me | K$^+$ | |
| 6-59 | 3-tert-butyl-1,2,4-oxadiazol-5-yl | F | Cl | H | Me | NH$_4^+$ | |
| 6-60 | 3-tert-butyl-1,2,4-oxadiazol-5-yl | F | Br | H | Me | Na$^+$ | |
| 6-61 | 3-tert-butyl-1,2,4-oxadiazol-5-yl | F | Br | H | Me | K$^+$ | |
| 6-62 | 3-tert-butyl-1,2,4-oxadiazol-5-yl | F | Br | H | Me | NH$_4^+$ | |
| 6-63 | 3-tert-butyl-1,2,4-oxadiazol-5-yl | F | F | H | Me | Na$^+$ | |
| 6-64 | 3-tert-butyl-1,2,4-oxadiazol-5-yl | F | F | H | Me | K$^+$ | |
| 6-65 | 3-tert-butyl-1,2,4-oxadiazol-5-yl | F | I | H | Me | Na$^+$ | |
| 6-66 | 3-tert-butyl-1,2,4-oxadiazol-5-yl | F | I | H | Me | K$^+$ | |
| 6-67 | 3-tert-butyl-1,2,4-oxadiazol-5-yl | F | CN | H | Me | Na$^+$ | |

TABLE 6-continued

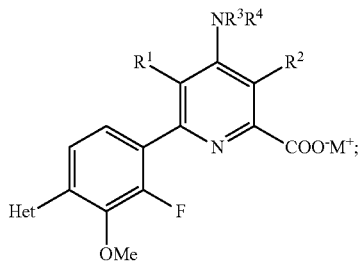

(I-vi)

| No. | Het | R¹ | R² | R³ | R⁴ | M⁺ | Physical data: ¹H NMR: δ [CDCl₃] |
|---|---|---|---|---|---|---|---|
| 6-68 | 3-tert-butyl-1,2,4-oxadiazol-5-yl | F | CN | H | Me | K⁺ | |
| 6-69 | 3-tert-butyl-1,2,4-oxadiazol-5-yl | F | CF₃ | H | Me | Na⁺ | |
| 6-70 | 3-tert-butyl-1,2,4-oxadiazol-5-yl | F | CF₃ | H | Me | K⁺ | |
| 6-71 | 3-tert-butyl-1,2,4-oxadiazol-5-yl | Cl | Cl | H | Me | Na⁺ | |
| 6-72 | 3-tert-butyl-1,2,4-oxadiazol-5-yl | Cl | Cl | H | Me | K⁺ | |
| 6-73 | 3-tert-butyl-1,2,4-oxadiazol-5-yl | Cl | Cl | H | Me | NH₄⁺ | |
| 6-74 | 3-tert-butyl-1,2,4-oxadiazol-5-yl | Cl | Br | H | Me | Na⁺ | |
| 6-75 | 3-tert-butyl-1,2,4-oxadiazol-5-yl | Cl | Br | H | Me | K⁺ | |
| 6-76 | 3-tert-butyl-1,2,4-oxadiazol-5-yl | Cl | Br | H | Me | NH₄⁺ | |
| 6-77 | 3-tert-butyl-1,2,4-oxadiazol-5-yl | Cl | F | H | Me | Na⁺ | |
| 6-78 | 3-tert-butyl-1,2,4-oxadiazol-5-yl | Cl | F | H | Me | K⁺ | |
| 6-79 | 3-tert-butyl-1,2,4-oxadiazol-5-yl | Cl | I | H | Me | Na⁺ | |
| 6-80 | 3-tert-butyl-1,2,4-oxadiazol-5-yl | Cl | I | H | Me | K⁺ | |
| 6-81 | 3-tert-butyl-1,2,4-oxadiazol-5-yl | Cl | CN | H | Me | Na⁺ | |
| 6-82 | 3-tert-butyl-1,2,4-oxadiazol-5-yl | Cl | CN | H | Me | K⁺ | |
| 6-83 | 3-tert-butyl-1,2,4-oxadiazol-5-yl | Cl | CF₃ | H | Me | Na⁺ | |
| 6-84 | 3-tert-butyl-1,2,4-oxadiazol-5-yl | Cl | CF₃ | H | Me | K⁺ | |
| 6-85 | 3-tert-butyl-1,2,4-oxadiazol-5-yl | H | Cl | Me | Me | Na⁺ | |
| 6-86 | 3-tert-butyl-1,2,4-oxadiazol-5-yl | H | Cl | Me | Me | K⁺ | |
| 6-87 | 3-tert-butyl-1,2,4-oxadiazol-5-yl | H | Cl | Me | Me | NH₄⁺ | |
| 6-88 | 3-tert-butyl-1,2,4-oxadiazol-5-yl | H | Br | Me | Me | Na⁺ | |
| 6-89 | 3-tert-butyl-1,2,4-oxadiazol-5-yl | H | Br | Me | Me | K⁺ | |
| 6-90 | 3-tert-butyl-1,2,4-oxadiazol-5-yl | H | Br | Me | Me | NH₄⁺ | |
| 6-91 | 3-tert-butyl-1,2,4-oxadiazol-5-yl | H | F | Me | Me | Na⁺ | |
| 6-92 | 3-tert-butyl-1,2,4-oxadiazol-5-yl | H | F | Me | Me | K⁺ | |
| 6-93 | 3-tert-butyl-1,2,4-oxadiazol-5-yl | H | I | Me | Me | Na⁺ | |
| 6-94 | 3-tert-butyl-1,2,4-oxadiazol-5-yl | H | I | Me | Me | K⁺ | |
| 6-95 | 3-tert-butyl-1,2,4-oxadiazol-5-yl | H | CN | Me | Me | Na⁺ | |
| 6-96 | 3-tert-butyl-1,2,4-oxadiazol-5-yl | H | CN | Me | Me | K⁺ | |
| 6-97 | 3-tert-butyl-1,2,4-oxadiazol-5-yl | H | CF₃ | Me | Me | Na⁺ | |
| 6-98 | 3-tert-butyl-1,2,4-oxadiazol-5-yl | H | CF₃ | Me | Me | K⁺ | |
| 6-99 | 3-tert-butyl-1,2,4-oxadiazol-5-yl | F | Cl | Me | Me | Na⁺ | |
| 6-100 | 3-tert-butyl-1,2,4-oxadiazol-5-yl | F | Cl | Me | Me | K⁺ | |
| 6-101 | 3-tert-butyl-1,2,4-oxadiazol-5-yl | F | Cl | Me | Me | NH₄⁺ | |
| 6-102 | 3-tert-butyl-1,2,4-oxadiazol-5-yl | F | Br | Me | Me | Na⁺ | |
| 6-103 | 3-tert-butyl-1,2,4-oxadiazol-5-yl | F | Br | Me | Me | K⁺ | |
| 6-104 | 3-tert-butyl-1,2,4-oxadiazol-5-yl | F | Br | Me | Me | NH₄⁺ | |
| 6-105 | 3-tert-butyl-1,2,4-oxadiazol-5-yl | F | F | Me | Me | Na⁺ | |
| 6-106 | 3-tert-butyl-1,2,4-oxadiazol-5-yl | F | F | Me | Me | K⁺ | |
| 6-107 | 3-tert-butyl-1,2,4-oxadiazol-5-yl | F | I | Me | Me | Na⁺ | |
| 6-108 | 3-tert-butyl-1,2,4-oxadiazol-5-yl | F | I | Me | Me | K⁺ | |
| 6-109 | 3-tert-butyl-1,2,4-oxadiazol-5-yl | F | CN | Me | Me | Na⁺ | |
| 6-110 | 3-tert-butyl-1,2,4-oxadiazol-5-yl | F | CN | Me | Me | K⁺ | |
| 6-111 | 3-tert-butyl-1,2,4-oxadiazol-5-yl | F | CF₃ | Me | Me | Na⁺ | |
| 6-112 | 3-tert-butyl-1,2,4-oxadiazol-5-yl | F | CF₃ | Me | Me | K⁺ | |
| 6-113 | 3-tert-butyl-1,2,4-oxadiazol-5-yl | Cl | Cl | Me | Me | Na⁺ | |
| 6-114 | 3-tert-butyl-1,2,4-oxadiazol-5-yl | Cl | Cl | Me | Me | K⁺ | |
| 6-115 | 3-tert-butyl-1,2,4-oxadiazol-5-yl | Cl | Cl | Me | Me | NH₄⁺ | |
| 6-116 | 3-tert-butyl-1,2,4-oxadiazol-5-yl | Cl | Br | Me | Me | Na⁺ | |
| 6-117 | 3-tert-butyl-1,2,4-oxadiazol-5-yl | Cl | Br | Me | Me | K⁺ | |
| 6-118 | 3-tert-butyl-1,2,4-oxadiazol-5-yl | Cl | Br | Me | Me | NH₄⁺ | |
| 6-119 | 3-tert-butyl-1,2,4-oxadiazol-5-yl | Cl | F | Me | Me | Na⁺ | |
| 6-120 | 3-tert-butyl-1,2,4-oxadiazol-5-yl | Cl | F | Me | Me | K⁺ | |
| 6-121 | 3-tert-butyl-1,2,4-oxadiazol-5-yl | Cl | I | Me | Me | Na⁺ | |
| 6-122 | 3-tert-butyl-1,2,4-oxadiazol-5-yl | Cl | I | Me | Me | K⁺ | |
| 6-123 | 3-tert-butyl-1,2,4-oxadiazol-5-yl | Cl | CN | Me | Me | Na⁺ | |
| 6-124 | 3-tert-butyl-1,2,4-oxadiazol-5-yl | Cl | CN | Me | Me | K⁺ | |
| 6-125 | 3-tert-butyl-1,2,4-oxadiazol-5-yl | Cl | CF₃ | Me | Me | Na⁺ | |
| 6-126 | 3-tert-butyl-1,2,4-oxadiazol-5-yl | Cl | CF₃ | Me | Me | K⁺ | |
| 6-127 | 3-tert-butyl-1,2,4-oxadiazol-5-yl | H | Cl | =CHNMe₂ | | Na⁺ | |
| 6-128 | 3-tert-butyl-1,2,4-oxadiazol-5-yl | H | Cl | =CHNMe₂ | | K⁺ | |

TABLE 6-continued

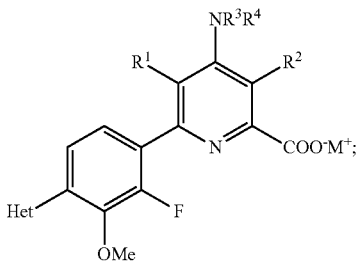

(I-vi)

| No. | Het | R¹ | R² | R³ | R⁴ | M⁺ | Physical data: ¹H NMR: δ [CDCl₃] |
|---|---|---|---|---|---|---|---|
| 6-129 | 3-tert-butyl-1,2,4-oxadiazol-5-yl | H | Cl | =CHNMe₂ | | NH₄⁺ | |
| 6-130 | 3-tert-butyl-1,2,4-oxadiazol-5-yl | H | Br | =CHNMe₂ | | Na⁺ | |
| 6-131 | 3-tert-butyl-1,2,4-oxadiazol-5-yl | H | Br | =CHNMe₂ | | K⁺ | |
| 6-132 | 3-tert-butyl-1,2,4-oxadiazol-5-yl | H | Br | =CHNMe₂ | | NH₄⁺ | |
| 6-133 | 3-tert-butyl-1,2,4-oxadiazol-5-yl | H | F | =CHNMe₂ | | Na⁺ | |
| 6-134 | 3-tert-butyl-1,2,4-oxadiazol-5-yl | H | F | =CHNMe₂ | | K⁺ | |
| 6-135 | 3-tert-butyl-1,2,4-oxadiazol-5-yl | H | I | =CHNMe₂ | | Na⁺ | |
| 6-136 | 3-tert-butyl-1,2,4-oxadiazol-5-yl | H | I | =CHNMe₂ | | K⁺ | |
| 6-137 | 3-tert-butyl-1,2,4-oxadiazol-5-yl | H | CN | =CHNMe₂ | | Na⁺ | |
| 6-138 | 3-tert-butyl-1,2,4-oxadiazol-5-yl | H | CN | =CHNMe₂ | | K⁺ | |
| 6-139 | 3-tert-butyl-1,2,4-oxadiazol-5-yl | H | CF₃ | =CHNMe₂ | | Na⁺ | |
| 6-140 | 3-tert-butyl-1,2,4-oxadiazol-5-yl | H | CF₃ | =CHNMe₂ | | K⁺ | |
| 6-141 | 3-tert-butyl-1,2,4-oxadiazol-5-yl | F | Cl | =CHNMe₂ | | Na⁺ | |
| 6-142 | 3-tert-butyl-1,2,4-oxadiazol-5-yl | F | Cl | =CHNMe₂ | | K⁺ | |
| 6-143 | 3-tert-butyl-1,2,4-oxadiazol-5-yl | F | Cl | =CHNMe₂ | | NH₄⁺ | |
| 6-144 | 3-tert-butyl-1,2,4-oxadiazol-5-yl | F | Br | =CHNMe₂ | | Na⁺ | |
| 6-145 | 3-tert-butyl-1,2,4-oxadiazol-5-yl | F | Br | =CHNMe₂ | | K⁺ | |
| 6-146 | 3-tert-butyl-1,2,4-oxadiazol-5-yl | F | Br | =CHNMe₂ | | NH₄⁺ | |
| 6-147 | 3-tert-butyl-1,2,4-oxadiazol-5-yl | F | F | =CHNMe₂ | | Na⁺ | |
| 6-148 | 3-tert-butyl-1,2,4-oxadiazol-5-yl | F | F | =CHNMe₂ | | K⁺ | |
| 6-149 | 3-tert-butyl-1,2,4-oxadiazol-5-yl | F | I | =CHNMe₂ | | Na⁺ | |
| 6-150 | 3-tert-butyl-1,2,4-oxadiazol-5-yl | F | I | =CHNMe₂ | | K⁺ | |
| 6-151 | 3-tert-butyl-1,2,4-oxadiazol-5-yl | F | CN | =CHNMe₂ | | Na⁺ | |
| 6-152 | 3-tert-butyl-1,2,4-oxadiazol-5-yl | F | CN | =CHNMe₂ | | K⁺ | |
| 6-153 | 3-tert-butyl-1,2,4-oxadiazol-5-yl | F | CF₃ | =CHNMe₂ | | Na⁺ | |
| 6-154 | 3-tert-butyl-1,2,4-oxadiazol-5-yl | F | CF₃ | =CHNMe₂ | | K⁺ | |
| 6-155 | 3-tert-butyl-1,2,4-oxadiazol-5-yl | Cl | Cl | =CHNMe₂ | | Na⁺ | |
| 6-156 | 3-tert-butyl-1,2,4-oxadiazol-5-yl | Cl | Cl | =CHNMe₂ | | K⁺ | |
| 6-157 | 3-tert-butyl-1,2,4-oxadiazol-5-yl | Cl | Cl | =CHNMe₂ | | NH₄⁺ | |
| 6-158 | 3-tert-butyl-1,2,4-oxadiazol-5-yl | Cl | Br | =CHNMe₂ | | Na⁺ | |
| 6-159 | 3-tert-butyl-1,2,4-oxadiazol-5-yl | Cl | Br | =CHNMe₂ | | K⁺ | |
| 6-160 | 3-tert-butyl-1,2,4-oxadiazol-5-yl | Cl | Br | =CHNMe₂ | | NH₄⁺ | |
| 6-161 | 3-tert-butyl-1,2,4-oxadiazol-5-yl | Cl | F | =CHNMe₂ | | Na⁺ | |
| 6-162 | 3-tert-butyl-1,2,4-oxadiazol-5-yl | Cl | F | =CHNMe₂ | | K⁺ | |
| 6-163 | 3-tert-butyl-1,2,4-oxadiazol-5-yl | Cl | I | =CHNMe₂ | | Na⁺ | |
| 6-164 | 3-tert-butyl-1,2,4-oxadiazol-5-yl | Cl | I | =CHNMe₂ | | K⁺ | |
| 6-165 | 3-tert-butyl-1,2,4-oxadiazol-5-yl | Cl | CN | =CHNMe₂ | | Na⁺ | |
| 6-166 | 3-tert-butyl-1,2,4-oxadiazol-5-yl | Cl | CN | =CHNMe₂ | | K⁺ | |
| 6-167 | 3-tert-butyl-1,2,4-oxadiazol-5-yl | Cl | CF₃ | =CHNMe₂ | | Na⁺ | |
| 6-168 | 3-tert-butyl-1,2,4-oxadiazol-5-yl | Cl | CF₃ | =CHNMe₂ | | K⁺ | |
| 6-169 | thien-2-yl | H | Cl | H | H | Na⁺ | |
| 6-170 | thien-2-yl | H | Cl | H | H | K⁺ | |
| 6-171 | thien-2-yl | H | Cl | H | H | NH₄⁺ | |
| 6-172 | thien-2-yl | H | Br | H | H | Na⁺ | |
| 6-173 | thien-2-yl | H | Br | H | H | K⁺ | |
| 6-174 | thien-2-yl | H | Br | H | H | NH₄⁺ | |
| 6-175 | thien-2-yl | H | F | H | H | Na⁺ | |
| 6-176 | thien-2-yl | H | F | H | H | K⁺ | |
| 6-177 | thien-2-yl | H | I | H | H | Na⁺ | |
| 6-178 | thien-2-yl | H | I | H | H | K⁺ | |
| 6-179 | thien-2-yl | H | CN | H | H | Na⁺ | |
| 6-180 | thien-2-yl | H | CN | H | H | K⁺ | |
| 6-181 | thien-2-yl | H | CF₃ | H | H | Na⁺ | |
| 6-182 | thien-2-yl | H | CF₃ | H | H | K⁺ | |
| 6-183 | thien-2-yl | F | Cl | H | H | Na⁺ | |
| 6-184 | thien-2-yl | F | Cl | H | H | K⁺ | |
| 6-185 | thien-2-yl | F | Cl | H | H | NH₄⁺ | |
| 6-186 | thien-2-yl | F | Br | H | H | Na⁺ | |
| 6-187 | thien-2-yl | F | Br | H | H | K⁺ | |
| 6-188 | thien-2-yl | F | Br | H | H | NH₄⁺ | |
| 6-189 | thien-2-yl | F | F | H | H | Na⁺ | |
| 6-190 | thien-2-yl | F | F | H | H | K⁺ | |
| 6-191 | thien-2-yl | F | I | H | H | Na⁺ | |
| 6-192 | thien-2-yl | F | I | H | H | K⁺ | |
| 6-193 | thien-2-yl | F | CN | H | H | Na⁺ | |
| 6-194 | thien-2-yl | F | CN | H | H | K⁺ | |
| 6-195 | thien-2-yl | F | CF₃ | H | H | Na⁺ | |
| 6-196 | thien-2-yl | F | CF₃ | H | H | K⁺ | |
| 6-197 | thien-2-yl | H | Cl | H | Me | Na⁺ | |
| 6-198 | thien-2-yl | H | Cl | H | Me | K⁺ | |
| 6-199 | thien-2-yl | H | Cl | H | Me | NH₄⁺ | |
| 6-200 | thien-2-yl | H | Br | H | Me | Na⁺ | |
| 6-201 | thien-2-yl | H | Br | H | Me | K⁺ | |
| 6-202 | thien-2-yl | H | Br | H | Me | NH₄⁺ | |
| 6-203 | thien-2-yl | H | F | H | Me | Na⁺ | |
| 6-204 | thien-2-yl | H | F | H | Me | K⁺ | |
| 6-205 | thien-2-yl | H | I | H | Me | Na⁺ | |
| 6-206 | thien-2-yl | H | I | H | Me | K⁺ | |
| 6-207 | thien-2-yl | H | CN | H | Me | Na⁺ | |
| 6-208 | thien-2-yl | H | CN | H | Me | K⁺ | |
| 6-209 | thien-2-yl | H | CF₃ | H | Me | Na⁺ | |

TABLE 6-continued

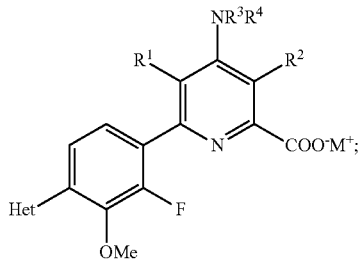

(I-vi)

| No. | Het | R¹ | R² | R³ | R⁴ | M⁺ | Physical data: ¹H NMR: δ [CDCl₃] |
|---|---|---|---|---|---|---|---|
| 6-210 | thien-2-yl | H | CF₃ | H | Me | K⁺ | |
| 6-211 | thien-2-yl | F | Cl | H | Me | Na⁺ | |
| 6-212 | thien-2-yl | F | Cl | H | Me | K⁺ | |
| 6-213 | thien-2-yl | F | Cl | H | Me | NH₄⁺ | |
| 6-214 | thien-2-yl | F | Br | H | Me | Na⁺ | |
| 6-215 | thien-2-yl | F | Br | H | Me | K⁺ | |
| 6-216 | thien-2-yl | F | Br | H | Me | NH₄⁺ | |
| 6-217 | thien-2-yl | F | F | H | Me | Na⁺ | |
| 6-218 | thien-2-yl | F | F | H | Me | K⁺ | |
| 6-219 | thien-2-yl | F | I | H | Me | Na⁺ | |
| 6-220 | thien-2-yl | F | I | H | Me | K⁺ | |
| 6-221 | thien-2-yl | F | CN | H | Me | Na⁺ | |
| 6-222 | thien-2-yl | F | CN | H | Me | K⁺ | |
| 6-223 | thien-2-yl | F | CF₃ | H | Me | Na⁺ | |
| 6-224 | thien-2-yl | F | CF₃ | H | Me | K⁺ | |
| 6-225 | thien-2-yl | H | Cl | Me | Me | Na⁺ | |
| 6-226 | thien-2-yl | H | Cl | Me | Me | K⁺ | |
| 6-227 | thien-2-yl | H | Cl | Me | Me | NH₄⁺ | |
| 6-228 | thien-2-yl | H | Br | Me | Me | Na⁺ | |
| 6-229 | thien-2-yl | H | Br | Me | Me | K⁺ | |
| 6-230 | thien-2-yl | H | Br | Me | Me | NH₄⁺ | |
| 6-231 | thien-2-yl | H | F | Me | Me | Na⁺ | |
| 6-232 | thien-2-yl | H | F | Me | Me | K⁺ | |
| 6-233 | thien-2-yl | H | I | Me | Me | Na⁺ | |
| 6-234 | thien-2-yl | H | I | Me | Me | K⁺ | |
| 6-235 | thien-2-yl | H | CN | Me | Me | Na⁺ | |
| 6-236 | thien-2-yl | H | CN | Me | Me | K⁺ | |
| 6-237 | thien-2-yl | H | CF₃ | Me | Me | Na⁺ | |
| 6-238 | thien-2-yl | H | CF₃ | Me | Me | K⁺ | |
| 6-239 | thien-2-yl | F | Cl | Me | Me | Na⁺ | |
| 6-240 | thien-2-yl | F | Cl | Me | Me | K⁺ | |
| 6-241 | thien-2-yl | F | Cl | Me | Me | NH₄⁺ | |
| 6-242 | thien-2-yl | F | Br | Me | Me | Na⁺ | |
| 6-243 | thien-2-yl | F | Br | Me | Me | K⁺ | |
| 6-244 | thien-2-yl | F | Br | Me | Me | NH₄⁺ | |
| 6-245 | thien-2-yl | F | F | Me | Me | Na⁺ | |
| 6-246 | thien-2-yl | F | F | Me | Me | K⁺ | |
| 6-247 | thien-2-yl | F | I | Me | Me | Na⁺ | |
| 6-248 | thien-2-yl | F | I | Me | Me | K⁺ | |
| 6-249 | thien-2-yl | F | CN | Me | Me | Na⁺ | |
| 6-250 | thien-2-yl | F | CN | Me | Me | K⁺ | |
| 6-251 | thien-2-yl | F | CF₃ | Me | Me | Na⁺ | |
| 6-252 | thien-2-yl | F | CF₃ | Me | Me | K⁺ | |
| 6-253 | thien-2-yl | H | Cl | =CHNMe₂ | | Na⁺ | |
| 6-254 | thien-2-yl | H | Cl | =CHNMe₂ | | K⁺ | |
| 6-255 | thien-2-yl | H | Cl | =CHNMe₂ | | NH₄⁺ | |
| 6-256 | thien-2-yl | H | Br | =CHNMe₂ | | Na⁺ | |
| 6-257 | thien-2-yl | H | Br | =CHNMe₂ | | K⁺ | |
| 6-258 | thien-2-yl | H | Br | =CHNMe₂ | | NH₄⁺ | |
| 6-259 | thien-2-yl | H | F | =CHNMe₂ | | Na⁺ | |
| 6-260 | thien-2-yl | H | F | =CHNMe₂ | | K⁺ | |
| 6-261 | thien-2-yl | H | I | =CHNMe₂ | | Na⁺ | |
| 6-262 | thien-2-yl | H | I | =CHNMe₂ | | K⁺ | |
| 6-263 | thien-2-yl | H | CN | =CHNMe₂ | | Na⁺ | |
| 6-264 | thien-2-yl | H | CN | =CHNMe₂ | | K⁺ | |
| 6-265 | thien-2-yl | H | CF₃ | =CHNMe₂ | | Na⁺ | |
| 6-266 | thien-2-yl | H | CF₃ | =CHNMe₂ | | K⁺ | |
| 6-267 | thien-2-yl | F | Cl | =CHNMe₂ | | Na⁺ | |
| 6-268 | thien-2-yl | F | Cl | =CHNMe₂ | | K⁺ | |
| 6-269 | thien-2-yl | F | Cl | =CHNMe₂ | | NH₄⁺ | |
| 6-270 | thien-2-yl | F | Br | =CHNMe₂ | | Na⁺ | |

TABLE 6-continued

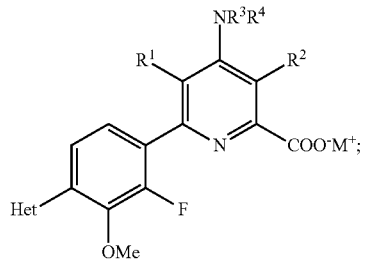

(I-vi)

| No. | Het | R¹ | R² | R³ | R⁴ | M⁺ | Physical data: ¹H NMR: δ [CDCl₃] |
|---|---|---|---|---|---|---|---|
| 6-271 | thien-2-yl | F | Br | =CHNMe₂ | | K⁺ | |
| 6-272 | thien-2-yl | F | Br | =CHNMe₂ | | NH₄⁺ | |
| 6-273 | thien-2-yl | F | F | =CHNMe₂ | | Na⁺ | |
| 6-274 | thien-2-yl | F | F | =CHNMe₂ | | K⁺ | |
| 6-275 | thien-2-yl | F | I | =CHNMe₂ | | Na⁺ | |
| 6-276 | thien-2-yl | F | I | =CHNMe₂ | | K⁺ | |
| 6-277 | thien-2-yl | F | CN | =CHNMe₂ | | Na⁺ | |
| 6-278 | thien-2-yl | F | CN | =CHNMe₂ | | K⁺ | |
| 6-279 | thien-2-yl | F | CF₃ | =CHNMe₂ | | Na⁺ | |
| 6-280 | thien-2-yl | F | CF₃ | =CHNMe₂ | | K⁺ | |
| 6-281 | pyrrol-1-yl | H | Cl | H | H | Na⁺ | |
| 6-282 | pyrrol-1-yl | H | Cl | H | H | K⁺ | |
| 6-283 | pyrrol-1-yl | H | Cl | H | H | NH₄⁺ | |
| 6-284 | pyrrol-1-yl | H | Br | H | H | Na⁺ | |
| 6-285 | pyrrol-1-yl | H | Br | H | H | K⁺ | |
| 6-286 | pyrrol-1-yl | H | Br | H | H | NH₄⁺ | |
| 6-287 | pyrrol-1-yl | H | F | H | H | Na⁺ | |
| 6-288 | pyrrol-1-yl | H | F | H | H | K⁺ | |
| 6-289 | pyrrol-1-yl | H | I | H | H | Na⁺ | |
| 6-290 | pyrrol-1-yl | H | I | H | H | K⁺ | |
| 6-291 | pyrrol-1-yl | H | CN | H | H | Na⁺ | |
| 6-292 | pyrrol-1-yl | H | CN | H | H | K⁺ | |
| 6-293 | pyrrol-1-yl | H | CF₃ | H | H | Na⁺ | |
| 6-294 | pyrrol-1-yl | H | CF₃ | H | H | K⁺ | |
| 6-295 | pyrrol-1-yl | F | Cl | H | H | Na⁺ | |
| 6-296 | pyrrol-1-yl | F | Cl | H | H | K⁺ | |
| 6-297 | pyrrol-1-yl | F | Cl | H | H | NH₄⁺ | |
| 6-298 | pyrrol-1-yl | F | Br | H | H | Na⁺ | |
| 6-299 | pyrrol-1-yl | F | Br | H | H | K⁺ | |
| 6-300 | pyrrol-1-yl | F | Br | H | H | NH₄⁺ | |
| 6-301 | pyrrol-1-yl | F | F | H | H | Na⁺ | |
| 6-302 | pyrrol-1-yl | F | F | H | H | K⁺ | |
| 6-303 | pyrrol-1-yl | F | I | H | H | Na⁺ | |
| 6-304 | pyrrol-1-yl | F | I | H | H | K⁺ | |
| 6-305 | pyrrol-1-yl | F | CN | H | H | Na⁺ | |
| 6-306 | pyrrol-1-yl | F | CN | H | H | K⁺ | |
| 6-307 | pyrrol-1-yl | F | CF₃ | H | H | Na⁺ | |
| 6-308 | pyrrol-1-yl | F | CF₃ | H | H | K⁺ | |
| 6-309 | pyrrol-1-yl | H | Cl | H | Me | Na⁺ | |
| 6-310 | pyrrol-1-yl | H | Cl | H | Me | K⁺ | |
| 6-311 | pyrrol-1-yl | H | Cl | H | Me | NH₄⁺ | |
| 6-312 | pyrrol-1-yl | H | Br | H | Me | Na⁺ | |
| 6-313 | pyrrol-1-yl | H | Br | H | Me | K⁺ | |
| 6-314 | pyrrol-1-yl | H | Br | H | Me | NH₄⁺ | |
| 6-315 | pyrrol-1-yl | H | F | H | Me | Na⁺ | |
| 6-316 | pyrrol-1-yl | H | F | H | Me | K⁺ | |
| 6-317 | pyrrol-1-yl | H | I | H | Me | Na⁺ | |
| 6-318 | pyrrol-1-yl | H | I | H | Me | K⁺ | |
| 6-319 | pyrrol-1-yl | H | CN | H | Me | Na⁺ | |
| 6-320 | pyrrol-1-yl | H | CN | H | Me | K⁺ | |
| 6-321 | pyrrol-1-yl | H | CF³ | H | Me | Na⁺ | |
| 6-322 | pyrrol-1-yl | H | CF₃ | H | Me | K⁺ | |
| 6-323 | pyrrol-1-yl | F | Cl | H | Me | Na⁺ | |
| 6-324 | pyrrol-1-yl | F | Cl | H | Me | K⁺ | |
| 6-325 | pyrrol-1-yl | F | Cl | H | Me | NH₄⁺ | |
| 6-326 | pyrrol-1-yl | F | Br | H | Me | Na⁺ | |
| 6-327 | pyrrol-1-yl | F | Br | H | Me | K⁺ | |
| 6-328 | pyrrol-1-yl | F | Br | H | Me | NH₄⁺ | |
| 6-329 | pyrrol-1-yl | F | F | H | Me | Na⁺ | |
| 6-330 | pyrrol-1-yl | F | F | H | Me | K⁺ | |
| 6-331 | pyrrol-1-yl | F | I | H | Me | Na⁺ | |

TABLE 6-continued

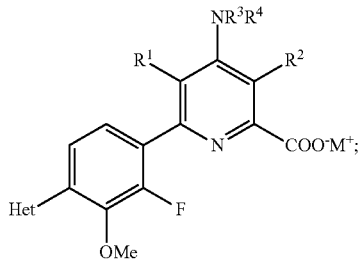

(I-vi)

| No. | Het | R¹ | R² | R³ | R⁴ | M⁺ | Physical data: ¹H NMR: δ [CDCl₃] |
|---|---|---|---|---|---|---|---|
| 6-332 | pyrrol-1-yl | F | I | H | Me | K⁺ | |
| 6-333 | pyrrol-1-yl | F | CN | H | Me | Na⁺ | |
| 6-334 | pyrrol-1-yl | F | CN | H | Me | K⁺ | |
| 6-335 | pyrrol-1-yl | F | CF₃ | H | Me | Na⁺ | |
| 6-336 | pyrrol-1-yl | F | CF₃ | H | Me | K⁺ | |
| 6-337 | pyrrol-1-yl | H | Cl | Me | Me | Na | |
| 6-338 | pyrrol-1-yl | H | Cl | Me | Me | K⁺ | |
| 6-339 | pyrrol-1-yl | H | Cl | Me | Me | NH₄⁺ | |
| 6-340 | pyrrol-1-yl | H | Br | Me | Me | Na⁺ | |
| 6-341 | pyrrol-1-yl | H | Br | Me | Me | K⁺ | |
| 6-342 | pyrrol-1-yl | H | Br | Me | Me | NH₄⁺ | |
| 6-343 | pyrrol-1-yl | H | F | Me | Me | Na⁺ | |
| 6-344 | pyrrol-1-yl | H | F | Me | Me | K⁺ | |
| 6-345 | pyrrol-1-yl | H | I | Me | Me | Na⁺ | |
| 6-346 | pyrrol-1-yl | H | I | Me | Me | K⁺ | |
| 6-347 | pyrrol-1-yl | H | CN | Me | Me | Na⁺ | |
| 6-348 | pyrrol-1-yl | H | CN | Me | Me | K⁺ | |
| 6-349 | pyrrol-1-yl | H | CF₃ | Me | Me | Na⁺ | |
| 6-350 | pyrrol-1-yl | H | CF₃ | Me | Me | K⁺ | |
| 6-351 | pyrrol-1-yl | F | Cl | Me | Me | Na⁺ | |
| 6-352 | pyrrol-1-yl | F | Cl | Me | Me | K⁺ | |
| 6-353 | pyrrol-1-yl | F | Cl | Me | Me | NH₄⁺ | |
| 6-354 | pyrrol-1-yl | F | Br | Me | Me | Na⁺ | |
| 6-355 | pyrrol-1-yl | F | Br | Me | Me | K⁺ | |
| 6-356 | pyrrol-1-yl | F | Br | Me | Me | NH₄⁺ | |
| 6-357 | pyrrol-1-yl | F | F | Me | Me | Na⁺ | |
| 6-358 | pyrrol-1-yl | F | F | Me | Me | K⁺ | |
| 6-359 | pyrrol-1-yl | F | I | Me | Me | Na⁺ | |
| 6-360 | pyrrol-1-yl | F | I | Me | Me | K⁺ | |
| 6-361 | pyrrol-1-yl | F | CN | Me | Me | Na⁺ | |
| 6-362 | pyrrol-1-yl | F | CN | Me | Me | K⁺ | |
| 6-363 | pyrrol-1-yl | F | CF₃ | Me | Me | Na⁺ | |
| 6-364 | pyrrol-1-yl | F | CF₃ | Me | Me | K⁺ | |
| 6-365 | pyrrol-1-yl | H | Cl | =CHNMe₂ | | Na⁺ | |
| 6-366 | pyrrol-1-yl | H | Cl | =CHNMe₂ | | K⁺ | |
| 6-367 | pyrrol-1-yl | H | Cl | =CHNMe₂ | | NH₄⁺ | |
| 6-368 | pyrrol-1-yl | H | Br | =CHNMe₂ | | Na⁺ | |
| 6-369 | pyrrol-1-yl | H | Br | =CHNMe₂ | | K⁺ | |
| 6-370 | pyrrol-1-yl | H | Br | =CHNMe₂ | | NH₄⁺ | |
| 6-371 | pyrrol-1-yl | H | F | =CHNMe₂ | | Na⁺ | |
| 6-372 | pyrrol-1-yl | H | F | =CHNMe₂ | | K⁺ | |
| 6-373 | pyrrol-1-yl | H | I | =CHNMe₂ | | Na⁺ | |
| 6-374 | pyrrol-1-yl | H | I | =CHNMe₂ | | K⁺ | |
| 6-375 | pyrrol-1-yl | H | CN | =CHNMe₂ | | Na⁺ | |
| 6-376 | pyrrol-1-yl | H | CN | =CHNMe₂ | | K⁺ | |
| 6-377 | pyrrol-1-yl | H | CF₃ | =CHNMe₂ | | Na⁺ | |
| 6-378 | pyrrol-1-yl | H | CF₃ | =CHNMe₂ | | K⁺ | |
| 6-379 | pyrrol-1-yl | F | Cl | =CHNMe₂ | | Na⁺ | |
| 6-380 | pyrrol-1-yl | F | Cl | =CHNMe₂ | | K⁺ | |
| 6-381 | pyrrol-1-yl | F | Cl | =CHNMe₂ | | NH₄⁺ | |
| 6-382 | pyrrol-1-yl | F | Br | =CHNMe₂ | | Na⁺ | |
| 6-383 | pyrrol-1-yl | F | Br | =CHNMe₂ | | K⁺ | |
| 6-384 | pyrrol-1-yl | F | Br | =CHNMe₂ | | NH₄⁺ | |
| 6-385 | pyrrol-1-yl | F | F | =CHNMe₂ | | Na⁺ | |
| 6-386 | pyrrol-1-yl | F | F | =CHNMe₂ | | K⁺ | |
| 6-387 | pyrrol-1-yl | F | I | =CHNMe₂ | | Na⁺ | |
| 6-388 | pyrrol-1-yl | F | I | =CHNMe₂ | | K⁺ | |
| 6-389 | pyrrol-1-yl | F | CN | =CHNMe₂ | | Na⁺ | |
| 6-390 | pyrrol-1-yl | F | CN | =CHNMe₂ | | K⁺ | |
| 6-391 | pyrrol-1-yl | F | CF₃ | =CHNMe₂ | | Na⁺ | |
| 6-392 | pyrrol-1-yl | F | CF₃ | =CHNMe₂ | | K⁺ | |

TABLE 6-continued

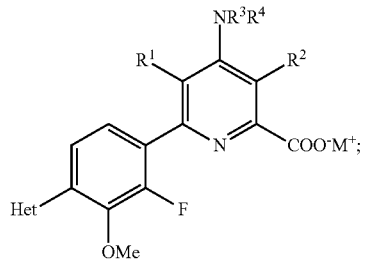

(I-vi)

| No. | Het | R¹ | R² | R³ | R⁴ | M⁺ | Physical data: ¹H NMR: δ [CDCl₃] |
|---|---|---|---|---|---|---|---|
| 6-393 | pyrazol-1-yl | H | Cl | H | H | Na⁺ | |
| 6-394 | pyrazol-1-yl | H | Cl | H | H | K⁺ | |
| 6-395 | pyrazol-1-yl | H | Cl | H | H | NH₄⁺ | |
| 6-396 | pyrazol-1-yl | H | Br | H | H | Na⁺ | |
| 6-397 | pyrazol-1-yl | H | Br | H | H | K⁺ | |
| 6-398 | pyrazol-1-yl | H | Br | H | H | NH₄⁺ | |
| 6-399 | pyrazol-1-yl | H | F | H | H | Na⁺ | |
| 6-400 | pyrazol-1-yl | H | F | H | H | K⁺ | |
| 6-401 | pyrazol-1-yl | H | I | H | H | Na⁺ | |
| 6-402 | pyrazol-1-yl | H | I | H | H | K⁺ | |
| 6-403 | pyrazol-1-yl | H | CN | H | H | Na⁺ | |
| 6-404 | pyrazol-1-yl | H | CN | H | H | K⁺ | |
| 6-405 | pyrazol-1-yl | H | CF₃ | H | H | Na⁺ | |
| 6-406 | pyrazol-1-yl | H | CF₃ | H | H | K⁺ | |
| 6-407 | pyrazol-1-yl | F | Cl | H | H | Na⁺ | |
| 6-408 | pyrazol-1-yl | F | Cl | H | H | K⁺ | |
| 6-409 | pyrazol-1-yl | F | Cl | H | H | NH₄⁺ | |
| 6-410 | pyrazol-1-yl | F | Br | H | H | Na⁺ | |
| 6-411 | pyrazol-1-yl | F | Br | H | H | K⁺ | |
| 6-412 | pyrazol-1-yl | F | Br | H | H | NH₄⁺ | |
| 6-413 | pyrazol-1-yl | F | F | H | H | Na⁺ | |
| 6-414 | pyrazol-1-yl | F | F | H | H | K⁺ | |
| 6-415 | pyrazol-1-yl | F | I | H | H | Na⁺ | |
| 6-416 | pyrazol-1-yl | F | I | H | H | K⁺ | |
| 6-417 | pyrazol-1-yl | F | CN | H | H | Na⁺ | |
| 6-418 | pyrazol-1-yl | F | CN | H | H | K⁺ | |
| 6-419 | pyrazol-1-yl | F | CF₃ | H | H | Na⁺ | |
| 6-420 | pyrazol-1-yl | F | CF₃ | H | H | K⁺ | |
| 6-421 | pyrazol-1-yl | H | Cl | H | Me | Na⁺ | |
| 6-422 | pyrazol-1-yl | H | Cl | H | Me | K⁺ | |
| 6-423 | pyrazol-1-yl | H | Cl | H | Me | NH₄⁺ | |
| 6-424 | pyrazol-1-yl | H | Br | H | Me | Na⁺ | |
| 6-425 | pyrazol-1-yl | H | Br | H | Me | K⁺ | |
| 6-426 | pyrazol-1-yl | H | Br | H | Me | NH₄⁺ | |
| 6-427 | pyrazol-1-yl | H | F | H | Me | Na⁺ | |
| 6-428 | pyrazol-1-yl | H | F | H | Me | K⁺ | |
| 6-429 | pyrazol-1-yl | H | I | H | Me | Na⁺ | |
| 6-430 | pyrazol-1-yl | H | I | H | Me | K⁺ | |
| 6-431 | pyrazol-1-yl | H | CN | H | Me | Na⁺ | |
| 6-432 | pyrazol-1-yl | H | CN | H | Me | K⁺ | |
| 6-433 | pyrazol-1-yl | H | CF₃ | H | Me | Na⁺ | |
| 6-434 | pyrazol-1-yl | H | CF₃ | H | Me | K⁺ | |
| 6-435 | pyrazol-1-yl | F | Cl | H | Me | Na⁺ | |
| 6-436 | pyrazol-1-yl | F | Cl | H | Me | K⁺ | |
| 6-437 | pyrazol-1-yl | F | Cl | H | Me | NH₄⁺ | |
| 6-438 | pyrazol-1-yl | F | Br | H | Me | Na⁺ | |
| 6-439 | pyrazol-1-yl | F | Br | H | Me | K⁺ | |
| 6-440 | pyrazol-1-yl | F | Br | H | Me | NH₄⁺ | |
| 6-441 | pyrazol-1-yl | F | F | H | Me | Na⁺ | |
| 6-442 | pyrazol-1-yl | F | F | H | Me | K⁺ | |
| 6-443 | pyrazol-1-yl | F | I | H | Me | Na⁺ | |
| 6-444 | pyrazol-1-yl | F | I | H | Me | K⁺ | |
| 6-445 | pyrazol-1-yl | F | CN | H | Me | Na⁺ | |
| 6-446 | pyrazol-1-yl | F | CN | H | Me | K⁺ | |
| 6-447 | pyrazol-1-yl | F | CF₃ | H | Me | Na⁺ | |
| 6-448 | pyrazol-1-yl | F | CF₃ | H | Me | K⁺ | |
| 6-449 | pyrazol-1-yl | H | Cl | Me | Me | Na⁺ | |
| 6-450 | pyrazol-1-yl | H | Cl | Me | Me | K⁺ | |
| 6-451 | pyrazol-1-yl | H | Cl | Me | Me | NH₄⁺ | |
| 6-452 | pyrazol-1-yl | H | Br | Me | Me | Na⁺ | |
| 6-453 | pyrazol-1-yl | H | Br | Me | Me | K⁺ | |

TABLE 6-continued

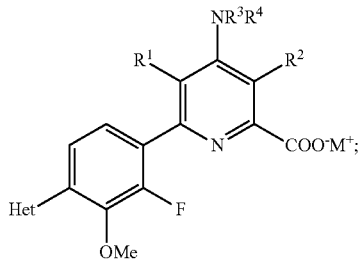

(I-vi)

| No. | Het | R¹ | R² | R³ | R⁴ | M⁺ | Physical data: ¹H NMR: δ [CDCl₃] |
|---|---|---|---|---|---|---|---|
| 6-454 | pyrazol-1-yl | H | Br | Me | Me | NH₄⁺ | |
| 6-455 | pyrazol-1-yl | H | F | Me | Me | Na⁺ | |
| 6-456 | pyrazol-1-yl | H | F | Me | Me | K⁺ | |
| 6-457 | pyrazol-1-yl | H | I | Me | Me | Na⁺ | |
| 6-458 | pyrazol-1-yl | H | I | Me | Me | K⁺ | |
| 6-459 | pyrazol-1-yl | H | CN | Me | Me | Na⁺ | |
| 6-460 | pyrazol-1-yl | H | CN | Me | Me | K⁺ | |
| 6-461 | pyrazol-1-yl | H | CF₃ | Me | Me | Na⁺ | |
| 6-462 | pyrazol-1-yl | H | CF₃ | Me | Me | K⁺ | |
| 6-463 | pyrazol-1-yl | F | Cl | Me | Me | Na⁺ | |
| 6-464 | pyrazol-1-yl | F | Cl | Me | Me | K⁺ | |
| 6-465 | pyrazol-1-yl | F | Cl | Me | Me | NH₄⁺ | |
| 6-466 | pyrazol-1-yl | F | Br | Me | Me | Na⁺ | |
| 6-467 | pyrazol-1-yl | F | Br | Me | Me | K⁺ | |
| 6-468 | pyrazol-1-yl | F | Br | Me | Me | NH₄⁺ | |
| 6-469 | pyrazol-1-yl | F | F | Me | Me | Na⁺ | |
| 6-470 | pyrazol-1-yl | F | F | Me | Me | K⁺ | |
| 6-471 | pyrazol-1-yl | F | I | Me | Me | Na⁺ | |
| 6-472 | pyrazol-1-yl | F | I | Me | Me | K⁺ | |
| 6-473 | pyrazol-1-yl | F | CN | Me | Me | Na⁺ | |
| 6-474 | pyrazol-1-yl | F | CN | Me | Me | K⁺ | |
| 6-475 | pyrazol-1-yl | F | CF₃ | Me | Me | Na⁺ | |
| 6-476 | pyrazol-1-yl | F | CF₃ | Me | Me | K⁺ | |
| 6-477 | pyrazol-1-yl | H | Cl | =CHNMe₂ | | Na⁺ | |
| 6-478 | pyrazol-1-yl | H | Cl | =CHNMe₂ | | K⁺ | |
| 6-479 | pyrazol-1-yl | H | Cl | =CHNMe₂ | | NH₄⁺ | |
| 6-480 | pyrazol-1-yl | H | Br | =CHNMe₂ | | Na⁺ | |
| 6-481 | pyrazol-1-yl | H | Br | =CHNMe₂ | | K⁺ | |
| 6-482 | pyrazol-1-yl | H | Br | =CHNMe₂ | | NH₄⁺ | |
| 6-483 | pyrazol-1-yl | H | F | =CHNMe₂ | | Na⁺ | |
| 6-484 | pyrazol-1-yl | H | F | =CHNMe₂ | | K⁺ | |
| 6-485 | pyrazol-1-yl | H | I | =CHNMe₂ | | Na⁺ | |
| 6-486 | pyrazol-1-yl | H | I | =CHNMe₂ | | K⁺ | |
| 6-487 | pyrazol-1-yl | H | CN | =CHNMe₂ | | Na⁺ | |
| 6-488 | pyrazol-1-yl | H | CN | =CHNMe₂ | | K⁺ | |
| 6-489 | pyrazol-1-yl | H | CF₃ | =CHNMe₂ | | Na⁺ | |
| 6-490 | pyrazol-1-yl | H | CF₃ | =CHNMe₂ | | K⁺ | |
| 6-491 | pyrazol-1-yl | F | Cl | =CHNMe₂ | | Na⁺ | |
| 6-492 | pyrazol-1-yl | F | Cl | =CHNMe₂ | | K⁺ | |
| 6-493 | pyrazol-1-yl | F | Cl | =CHNMe₂ | | NH₄⁺ | |
| 6-494 | pyrazol-1-yl | F | Br | =CHNMe₂ | | Na⁺ | |
| 6-495 | pyrazol-1-yl | F | Br | =CHNMe₂ | | K⁺ | |
| 6-496 | pyrazol-1-yl | F | Br | =CHNMe₂ | | NH₄⁺ | |
| 6-497 | pyrazol-1-yl | F | F | =CHNMe₂ | | Na⁺ | |
| 6-498 | pyrazol-1-yl | F | F | =CHNMe₂ | | K⁺ | |
| 6-499 | pyrazol-1-yl | F | I | =CHNMe₂ | | Na⁺ | |
| 6-500 | pyrazol-1-yl | F | I | =CHNMe₂ | | K⁺ | |
| 6-501 | pyrazol-1-yl | F | CN | =CHNMe₂ | | Na⁺ | |
| 6-502 | pyrazol-1-yl | F | CN | =CHNMe₂ | | K⁺ | |
| 6-503 | pyrazol-1-yl | F | CF₃ | =CHNMe₂ | | Na⁺ | |
| 6-504 | pyrazol-1-yl | F | CF₃ | =CHNMe₂ | | K⁺ | |
| 6-505 | pyridin-3-yl | H | Cl | H | H | Na⁺ | |
| 6-506 | pyridin-3-yl | H | Cl | H | H | K⁺ | |
| 6-507 | pyridin-3-yl | H | Cl | H | H | NH₄⁺ | |
| 6-508 | pyridin-3-yl | H | Br | H | H | Na⁺ | |
| 6-509 | pyridin-3-yl | H | Br | H | H | K⁺ | |
| 6-510 | pyridin-3-yl | H | Br | H | H | NH₄⁺ | |
| 6-511 | pyridin-3-yl | H | F | H | H | Na⁺ | |
| 6-512 | pyridin-3-yl | H | F | H | H | K⁺ | |
| 6-513 | pyridin-3-yl | H | I | H | H | Na⁺ | |
| 6-514 | pyridin-3-yl | H | I | H | H | K⁺ | |
| 6-515 | pyridin-3-yl | H | CN | H | H | Na⁺ | |
| 6-516 | pyridin-3-yl | H | CN | H | H | K⁺ | |
| 6-517 | pyridin-3-yl | H | CF₃ | H | H | Na⁺ | |
| 6-518 | pyridin-3-yl | H | CF₃ | H | H | K⁺ | |
| 6-519 | pyridin-3-yl | F | Cl | H | H | Na⁺ | |
| 6-520 | pyridin-3-yl | F | Cl | H | H | K⁺ | |
| 6-521 | pyridin-3-yl | F | Cl | H | H | NH₄⁺ | |
| 6-522 | pyridin-3-yl | F | Br | H | H | Na⁺ | |
| 6-523 | pyridin-3-yl | F | Br | H | H | K⁺ | |
| 6-524 | pyridin-3-yl | F | Br | H | H | NH₄⁺ | |
| 6-525 | pyridin-3-yl | F | F | H | H | Na⁺ | |
| 6-526 | pyridin-3-yl | F | F | H | H | K⁺ | |
| 6-527 | pyridin-3-yl | F | I | H | H | Na⁺ | |
| 6-528 | pyridin-3-yl | F | I | H | H | K⁺ | |
| 6-529 | pyridin-3-yl | F | CN | H | H | Na⁺ | |
| 6-530 | pyridin-3-yl | F | CN | H | H | K⁺ | |
| 6-531 | pyridin-3-yl | F | CF₃ | H | H | Na⁺ | |
| 6-532 | pyridin-3-yl | F | CF₃ | H | H | K⁺ | |
| 6-533 | pyridin-3-yl | H | Cl | H | Me | Na⁺ | |
| 6-534 | pyridin-3-yl | H | Cl | H | Me | K⁺ | |
| 6-535 | pyridin-3-yl | H | Cl | H | Me | NH₄⁺ | |
| 6-536 | pyridin-3-yl | H | Br | H | Me | Na⁺ | |
| 6-537 | pyridin-3-yl | H | Br | H | Me | K⁺ | |
| 6-538 | pyridin-3-yl | H | Br | H | Me | NH₄⁺ | |
| 6-539 | pyridin-3-yl | H | F | H | Me | Na⁺ | |
| 6-540 | pyridin-3-yl | H | F | H | Me | K⁺ | |
| 6-541 | pyridin-3-yl | H | I | H | Me | Na⁺ | |
| 6-542 | pyridin-3-yl | H | I | H | Me | K⁺ | |
| 6-543 | pyridin-3-yl | H | CN | H | Me | Na⁺ | |
| 6-544 | pyridin-3-yl | H | CN | H | Me | K⁺ | |
| 6-545 | pyridin-3-yl | H | CF₃ | H | Me | Na⁺ | |
| 6-546 | pyridin-3-yl | H | CF₃ | H | Me | K⁺ | |
| 6-547 | pyridin-3-yl | F | Cl | H | Me | Na⁺ | |
| 6-548 | pyridin-3-yl | F | Cl | H | Me | K⁺ | |
| 6-549 | pyridin-3-yl | F | Cl | H | Me | NH₄⁺ | |
| 6-550 | pyridin-3-yl | F | Br | H | Me | Na⁺ | |
| 6-551 | pyridin-3-yl | F | Br | H | Me | K⁺ | |
| 6-552 | pyridin-3-yl | F | Br | H | Me | NH₄⁺ | |
| 6-553 | pyridin-3-yl | F | F | H | Me | Na⁺ | |
| 6-554 | pyridin-3-yl | F | F | H | Me | K⁺ | |
| 6-555 | pyridin-3-yl | F | I | H | Me | Na⁺ | |
| 6-556 | pyridin-3-yl | F | I | H | Me | K⁺ | |
| 6-557 | pyridin-3-yl | F | CN | H | Me | Na⁺ | |
| 6-558 | pyridin-3-yl | F | CN | H | Me | K⁺ | |
| 6-559 | pyridin-3-yl | F | CF₃ | H | Me | Na⁺ | |
| 6-560 | pyridin-3-yl | F | CF₃ | H | Me | K⁺ | |
| 6-561 | pyridin-3-yl | H | Cl | Me | Me | Na⁺ | |
| 6-562 | pyridin-3-yl | H | Cl | Me | Me | K⁺ | |
| 6-563 | pyridin-3-yl | H | Cl | Me | Me | NH₄⁺ | |
| 6-564 | pyridin-3-yl | H | Br | Me | Me | Na⁺ | |
| 6-565 | pyridin-3-yl | H | Br | Me | Me | K⁺ | |
| 6-566 | pyridin-3-yl | H | Br | Me | Me | NH₄⁺ | |
| 6-567 | pyridin-3-yl | H | F | Me | Me | Na⁺ | |
| 6-568 | pyridin-3-yl | H | F | Me | Me | K⁺ | |
| 6-569 | pyridin-3-yl | H | I | Me | Me | Na⁺ | |
| 6-570 | pyridin-3-yl | H | I | Me | Me | K⁺ | |
| 6-571 | pyridin-3-yl | H | CN | Me | Me | Na⁺ | |
| 6-572 | pyridin-3-yl | H | CN | Me | Me | K⁺ | |
| 6-573 | pyridin-3-yl | H | CF₃ | Me | Me | Na⁺ | |
| 6-574 | pyridin-3-yl | H | CF₃ | Me | Me | K⁺ | |
| 6-575 | pyridin-3-yl | F | Cl | Me | Me | Na⁺ | |

TABLE 6-continued

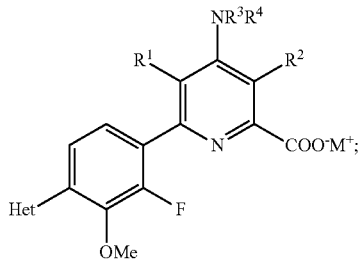

(I-vi)

| No. | Het | R¹ | R² | R³ | R⁴ | M⁺ | Physical data: ¹H NMR: δ [CDCl₃] |
|---|---|---|---|---|---|---|---|
| 6-576 | pyridin-3-yl | F | Cl | Me | Me | K⁺ | |
| 6-577 | pyridin-3-yl | F | Cl | Me | Me | NH₄⁺ | |
| 6-578 | pyridin-3-yl | F | Br | Me | Me | Na⁺ | |
| 6-579 | pyridin-3-yl | F | Br | Me | Me | K⁺ | |
| 6-580 | pyridin-3-yl | F | Br | Me | Me | NH₄⁺ | |
| 6-581 | pyridin-3-yl | F | F | Me | Me | Na⁺ | |
| 6-582 | pyridin-3-yl | F | F | Me | Me | K⁺ | |
| 6-583 | pyridin-3-yl | F | I | Me | Me | Na⁺ | |
| 6-584 | pyridin-3-yl | F | I | Me | Me | K⁺ | |
| 6-585 | pyridin-3-yl | F | CN | Me | Me | Na⁺ | |
| 6-586 | pyridin-3-yl | F | CN | Me | Me | K⁺ | |
| 6-587 | pyridin-3-yl | F | CF₃ | Me | Me | Na⁺ | |
| 6-588 | pyridin-3-yl | F | CF₃ | Me | Me | K⁺ | |
| 6-589 | pyridin-3-yl | H | Cl | =CHNMe₂ | | Na⁺ | |
| 6-590 | pyridin-3-yl | H | Cl | =CHNMe₂ | | K⁺ | |
| 6-591 | pyridin-3-yl | H | Cl | =CHNMe₂ | | NH₄⁺ | |
| 6-592 | pyridin-3-yl | H | Br | =CHNMe₂ | | Na⁺ | |
| 6-593 | pyridin-3-yl | H | Br | =CHNMe₂ | | K⁺ | |
| 6-594 | pyridin-3-yl | H | Br | =CHNMe₂ | | NH₄⁺ | |
| 6-595 | pyridin-3-yl | H | F | =CHNMe₂ | | Na⁺ | |
| 6-596 | pyridin-3-yl | H | F | =CHNMe₂ | | K⁺ | |
| 6-597 | pyridin-3-yl | H | I | =CHNMe₂ | | Na⁺ | |
| 6-598 | pyridin-3-yl | H | I | =CHNMe₂ | | K⁺ | |
| 6-599 | pyridin-3-yl | H | CN | =CHNMe₂ | | Na⁺ | |
| 6-600 | pyridin-3-yl | H | CN | =CHNMe₂ | | K⁺ | |
| 6-601 | pyridin-3-yl | H | CF₃ | =CHNMe₂ | | Na⁺ | |
| 6-602 | pyridin-3-yl | H | CF₃ | =CHNMe₂ | | K⁺ | |
| 6-603 | pyridin-3-yl | F | Cl | =CHNMe₂ | | Na⁺ | |
| 6-604 | pyridin-3-yl | F | Cl | =CHNMe₂ | | K⁺ | |
| 6-605 | pyridin-3-yl | F | Cl | =CHNMe₂ | | NH₄⁺ | |
| 6-606 | pyridin-3-yl | F | Br | =CHNMe₂ | | Na⁺ | |
| 6-607 | pyridin-3-yl | F | Br | =CHNMe₂ | | K⁺ | |
| 6-608 | pyridin-3-yl | F | Br | =CHNMe₂ | | NH₄⁺ | |
| 6-609 | pyridin-3-yl | F | F | =CHNMe₂ | | Na⁺ | |
| 6-610 | pyridin-3-yl | F | F | =CHNMe₂ | | K⁺ | |
| 6-611 | pyridin-3-yl | F | I | =CHNMe₂ | | Na⁺ | |
| 6-612 | pyridin-3-yl | F | I | =CHNMe₂ | | K⁺ | |
| 6-613 | pyridin-3-yl | F | CN | =CHNMe₂ | | Na⁺ | |
| 6-614 | pyridin-3-yl | F | CN | =CHNMe₂ | | K⁺ | |
| 6-615 | pyridin-3-yl | F | CF₃ | =CHNMe₂ | | Na⁺ | |
| 6-616 | pyridin-3-yl | F | CF₃ | =CHNMe₂ | | K⁺ | |
| 6-617 | oxiranyl | H | Cl | H | H | Na⁺ | |
| 6-618 | oxiranyl | H | Cl | H | H | K⁺ | |
| 6-619 | oxiranyl | H | Cl | H | H | NH₄⁺ | |
| 6-620 | oxiranyl | H | Br | H | H | Na⁺ | |
| 6-621 | oxiranyl | H | Br | H | H | K⁺ | |
| 6-622 | oxiranyl | H | Br | H | H | NH₄⁺ | |
| 6-623 | oxiranyl | H | F | H | H | Na⁺ | |
| 6-624 | oxiranyl | H | F | H | H | K⁺ | |
| 6-625 | oxiranyl | H | I | H | H | Na⁺ | |
| 6-626 | oxiranyl | H | I | H | H | K⁺ | |
| 6-627 | oxiranyl | H | CN | H | H | Na⁺ | |
| 6-628 | oxiranyl | H | CN | H | H | K⁺ | |
| 6-629 | oxiranyl | H | CF₃ | H | H | Na⁺ | |
| 6-630 | oxiranyl | H | CF₃ | H | H | K⁺ | |
| 6-631 | oxiranyl | F | Cl | H | H | Na⁺ | |
| 6-632 | oxiranyl | F | Cl | H | H | K⁺ | |
| 6-633 | oxiranyl | F | Cl | H | H | NH₄⁺ | |
| 6-634 | oxiranyl | F | Br | H | H | Na⁺ | |
| 6-635 | oxiranyl | F | Br | H | H | K⁺ | |
| 6-636 | oxiranyl | F | Br | H | H | NH₄⁺ | |

TABLE 6-continued

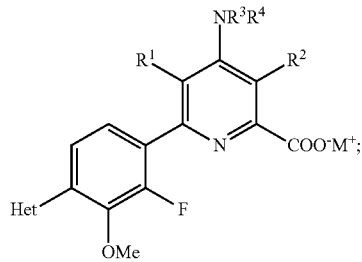

(I-vi)

| No. | Het | R¹ | R² | R³ | R⁴ | M⁺ | Physical data: ¹H NMR: δ [CDCl₃] |
|---|---|---|---|---|---|---|---|
| 6-637 | oxiranyl | F | F | H | H | Na⁺ | |
| 6-638 | oxiranyl | F | F | H | H | K⁺ | |
| 6-639 | oxiranyl | F | I | H | H | Na⁺ | |
| 6-640 | oxiranyl | F | I | H | H | K⁺ | |
| 6-641 | oxiranyl | F | CN | H | H | Na⁺ | |
| 6-642 | oxiranyl | F | CN | H | H | K⁺ | |
| 6-643 | oxiranyl | F | CF₃ | H | H | Na⁺ | |
| 6-644 | oxiranyl | F | CF₃ | H | H | K⁺ | |
| 6-645 | oxiranyl | H | Cl | H | Me | Na⁺ | |
| 6-646 | oxiranyl | H | Cl | H | Me | K⁺ | |
| 6-647 | oxiranyl | H | Cl | H | Me | NH₄⁺ | |
| 6-648 | oxiranyl | H | Br | H | Me | Na⁺ | |
| 6-649 | oxiranyl | H | Br | H | Me | K⁺ | |
| 6-650 | oxiranyl | H | Br | H | Me | NH₄⁺ | |
| 6-651 | oxiranyl | H | F | H | Me | Na⁺ | |
| 6-652 | oxiranyl | H | F | H | Me | K⁺ | |
| 6-653 | oxiranyl | H | I | H | Me | Na⁺ | |
| 6-654 | oxiranyl | H | I | H | Me | K⁺ | |
| 6-655 | oxiranyl | H | CN | H | Me | Na⁺ | |
| 6-656 | oxiranyl | H | CN | H | Me | K⁺ | |
| 6-657 | oxiranyl | H | CF₃ | H | Me | Na⁺ | |
| 6-658 | oxiranyl | H | CF₃ | H | Me | K⁺ | |
| 6-659 | oxiranyl | F | Cl | H | Me | Na⁺ | |
| 6-660 | oxiranyl | F | Cl | H | Me | K⁺ | |
| 6-661 | oxiranyl | F | Cl | H | Me | NH₄⁺ | |
| 6-662 | oxiranyl | F | Br | H | Me | Na⁺ | |
| 6-663 | oxiranyl | F | Br | H | Me | K⁺ | |
| 6-664 | oxiranyl | F | Br | H | Me | NH₄⁺ | |
| 6-665 | oxiranyl | F | F | H | Me | Na⁺ | |
| 6-666 | oxiranyl | F | F | H | Me | K⁺ | |
| 6-667 | oxiranyl | F | I | H | Me | Na⁺ | |
| 6-668 | oxiranyl | F | I | H | Me | K⁺ | |
| 6-669 | oxiranyl | F | CN | H | Me | Na⁺ | |
| 6-670 | oxiranyl | F | CN | H | Me | K⁺ | |
| 6-671 | oxiranyl | F | CF₃ | H | Me | Na⁺ | |
| 6-672 | oxiranyl | F | CF₃ | H | Me | K⁺ | |
| 6-673 | oxiranyl | H | Cl | Me | Me | Na⁺ | |
| 6-674 | oxiranyl | H | Cl | Me | Me | K⁺ | |
| 6-675 | oxiranyl | H | Cl | Me | Me | NH₄⁺ | |
| 6-676 | oxiranyl | H | Br | Me | Me | Na⁺ | |
| 6-677 | oxiranyl | H | Br | Me | Me | K⁺ | |
| 6-678 | oxiranyl | H | Br | Me | Me | NH₄⁺ | |
| 6-679 | oxiranyl | H | F | Me | Me | Na⁺ | |
| 6-680 | oxiranyl | H | F | Me | Me | K⁺ | |
| 6-681 | oxiranyl | H | I | Me | Me | Na⁺ | |
| 6-682 | oxiranyl | H | I | Me | Me | K⁺ | |
| 6-683 | oxiranyl | H | CN | Me | Me | Na⁺ | |
| 6-684 | oxiranyl | H | CN | Me | Me | K⁺ | |
| 6-685 | oxiranyl | H | CF₃ | Me | Me | Na⁺ | |
| 6-686 | oxiranyl | H | CF₃ | Me | Me | K⁺ | |
| 6-687 | oxiranyl | F | Cl | Me | Me | Na⁺ | |
| 6-688 | oxiranyl | F | Cl | Me | Me | K⁺ | |
| 6-689 | oxiranyl | F | Cl | Me | Me | NH₄⁺ | |
| 6-690 | oxiranyl | F | Br | Me | Me | Na⁺ | |
| 6-691 | oxiranyl | F | Br | Me | Me | K⁺ | |
| 6-692 | oxiranyl | F | Br | Me | Me | NH₄⁺ | |
| 6-693 | oxiranyl | F | F | Me | Me | Na⁺ | |
| 6-694 | oxiranyl | F | F | Me | Me | K⁺ | |
| 6-695 | oxiranyl | F | I | Me | Me | Na⁺ | |
| 6-696 | oxiranyl | F | I | Me | Me | K⁺ | |
| 6-697 | oxiranyl | F | CN | Me | Me | Na⁺ | |

TABLE 6-continued

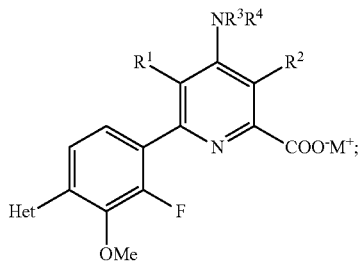

(I-vi)

| No. | Het | R¹ | R² | R³ | R⁴ | M⁺ | Physical data: ¹H NMR: δ [CDCl₃] |
|---|---|---|---|---|---|---|---|
| 6-698 | oxiranyl | F | CN | Me | Me | K⁺ | |
| 6-699 | oxiranyl | F | CF₃ | Me | Me | Na⁺ | |
| 6-700 | oxiranyl | F | CF₃ | Me | Me | K⁺ | |
| 6-701 | oxiranyl | H | Cl | =CHNMe₂ | | Na⁺ | |
| 6-702 | oxiranyl | H | Cl | =CHNMe₂ | | K⁺ | |
| 6-703 | oxiranyl | H | Cl | =CHNMe₂ | | NH₄⁺ | |
| 6-704 | oxiranyl | H | Br | =CHNMe₂ | | Na⁺ | |
| 6-705 | oxiranyl | H | Br | =CHNMe₂ | | K⁺ | |
| 6-706 | oxiranyl | H | Br | =CHNMe₂ | | NH₄⁺ | |
| 6-707 | oxiranyl | H | F | =CHNMe₂ | | Na⁺ | |
| 6-708 | oxiranyl | H | F | =CHNMe₂ | | K⁺ | |
| 6-709 | oxiranyl | H | I | =CHNMe₂ | | Na⁺ | |
| 6-710 | oxiranyl | H | I | =CHNMe₂ | | K⁺ | |
| 6-711 | oxiranyl | H | CN | =CHNMe₂ | | Na⁺ | |
| 6-712 | oxiranyl | H | CN | =CHNMe₂ | | K⁺ | |
| 6-713 | oxiranyl | H | CF₃ | =CHNMe₂ | | Na⁺ | |
| 6-714 | oxiranyl | H | CF₃ | =CHNMe₂ | | K⁺ | |
| 6-715 | oxiranyl | F | Cl | =CHNMe₂ | | Na⁺ | |
| 6-716 | oxiranyl | F | Cl | =CHNMe₂ | | K⁺ | |
| 6-717 | oxiranyl | F | Cl | =CHNMe₂ | | NH₄⁺ | |
| 6-718 | oxiranyl | F | Br | =CHNMe₂ | | Na⁺ | |
| 6-719 | oxiranyl | F | Br | =CHNMe₂ | | K⁺ | |
| 6-720 | oxiranyl | F | Br | =CHNMe₂ | | NH₄⁺ | |
| 6-721 | oxiranyl | F | F | =CHNMe₂ | | Na⁺ | |
| 6-722 | oxiranyl | F | F | =CHNMe₂ | | K⁺ | |
| 6-723 | oxiranyl | F | I | =CHNMe₂ | | Na⁺ | |
| 6-724 | oxiranyl | F | I | =CHNMe₂ | | K⁺ | |
| 6-725 | oxiranyl | F | CN | =CHNMe₂ | | Na⁺ | |
| 6-726 | oxiranyl | F | CN | =CHNMe₂ | | K⁺ | |
| 6-727 | oxiranyl | F | CF₃ | =CHNMe₂ | | Na⁺ | |
| 6-728 | oxiranyl | F | CF₃ | =CHNMe₂ | | K⁺ | |
| 6-729 | 3,3-dimethyl-oxetan-2-yl | H | Cl | H | H | Na⁺ | |
| 6-730 | 3,3-dimethyl-oxetan-2-yl | H | Cl | H | H | K⁺ | |
| 6-731 | 3,3-dimethyl-oxetan-2-yl | H | Cl | H | H | NH₄⁺ | |
| 6-732 | 3,3-dimethyl-oxetan-2-yl | H | Br | H | H | Na⁺ | |
| 6-733 | 3,3-dimethyl-oxetan-2-yl | H | Br | H | H | K⁺ | |
| 6-734 | 3,3-dimethyl-oxetan-2-yl | H | Br | H | H | NH₄⁺ | |
| 6-735 | 3,3-dimethyl-oxetan-2-yl | H | F | H | H | Na⁺ | |
| 6-736 | 3,3-dimethyl-oxetan-2-yl | H | F | H | H | K⁺ | |
| 6-737 | 3,3-dimethyl-oxetan-2-yl | H | I | H | H | Na⁺ | |
| 6-738 | 3,3-dimethyl-oxetan-2-yl | H | I | H | H | K⁺ | |
| 6-739 | 3,3-dimethyl-oxetan-2-yl | H | CN | H | H | Na⁺ | |
| 6-740 | 3,3-dimethyl-oxetan-2-yl | H | CN | H | H | K⁺ | |
| 6-741 | 3,3-dimethyl-oxetan-2-yl | H | CF₃ | H | H | Na⁺ | |
| 6-742 | 3,3-dimethyl-oxetan-2-yl | H | CF₃ | H | H | K⁺ | |
| 6-743 | 3,3-dimethyl-oxetan-2-yl | F | Cl | H | H | Na⁺ | |
| 6-744 | 3,3-dimethyl-oxetan-2-yl | F | Cl | H | H | K⁺ | |
| 6-745 | 3,3-dimethyl-oxetan-2-yl | F | Cl | H | H | NH₄⁺ | |
| 6-746 | 3,3-dimethyl-oxetan-2-yl | F | Br | H | H | Na⁺ | |
| 6-747 | 3,3-dimethyl-oxetan-2-yl | F | Br | H | H | K⁺ | |
| 6-748 | 3,3-dimethyl-oxetan-2-yl | F | Br | H | H | NH₄⁺ | |
| 6-749 | 3,3-dimethyl-oxetan-2-yl | F | F | H | H | Na⁺ | |
| 6-750 | 3,3-dimethyl-oxetan-2-yl | F | F | H | H | K⁺ | |
| 6-751 | 3,3-dimethyl-oxetan-2-yl | F | I | H | H | Na⁺ | |
| 6-752 | 3,3-dimethyl-oxetan-2-yl | F | I | H | H | K⁺ | |
| 6-753 | 3,3-dimethyl-oxetan-2-yl | F | CN | H | H | Na⁺ | |
| 6-754 | 3,3-dimethyl-oxetan-2-yl | F | CN | H | H | K⁺ | |
| 6-755 | 3,3-dimethyl-oxetan-2-yl | F | CF₃ | H | H | Na⁺ | |
| 6-756 | 3,3-dimethyl-oxetan-2-yl | F | CF₃ | H | H | K⁺ | |
| 6-757 | 3,3-dimethyl-oxetan-2-yl | H | Cl | H | Me | Na⁺ | |
| 6-758 | 3,3-dimethyl-oxetan-2-yl | H | Cl | H | Me | K⁺ | |
| 6-759 | 3,3-dimethyl-oxetan-2-yl | H | Cl | H | Me | NH₄⁺ | |
| 6-760 | 3,3-dimethyl-oxetan-2-yl | H | Br | H | Me | Na⁺ | |
| 6-761 | 3,3-dimethyl-oxetan-2-yl | H | Br | H | Me | K⁺ | |
| 6-762 | 3,3-dimethyl-oxetan-2-yl | H | Br | H | Me | NH₄⁺ | |
| 6-763 | 3,3-dimethyl-oxetan-2-yl | H | F | H | Me | Na⁺ | |
| 6-764 | 3,3-dimethyl-oxetan-2-yl | H | F | H | Me | K⁺ | |
| 6-765 | 3,3-dimethyl-oxetan-2-yl | H | I | H | Me | Na⁺ | |
| 6-766 | 3,3-dimethyl-oxetan-2-yl | H | I | H | Me | K⁺ | |
| 6-767 | 3,3-dimethyl-oxetan-2-yl | H | CN | H | Me | Na⁺ | |
| 6-768 | 3,3-dimethyl-oxetan-2-yl | H | CN | H | Me | K⁺ | |
| 6-769 | 3,3-dimethyl-oxetan-2-yl | H | CF₃ | H | Me | Na⁺ | |
| 6-770 | 3,3-dimethyl-oxetan-2-yl | H | CF₃ | H | Me | K⁺ | |
| 6-771 | 3,3-dimethyl-oxetan-2-yl | F | Cl | H | Me | Na⁺ | |
| 6-772 | 3,3-dimethyl-oxetan-2-yl | F | Cl | H | Me | K⁺ | |
| 6-773 | 3,3-dimethyl-oxetan-2-yl | F | Cl | H | Me | NH₄⁺ | |

TABLE 6-continued

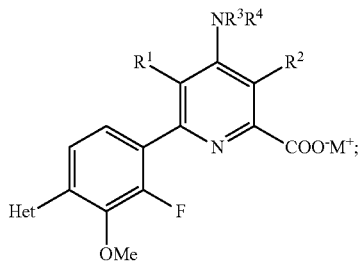

(I-vi)

| No. | Het | $R^1$ | $R^2$ | $R^3$ | $R^4$ | $M^+$ | Physical data: $^1$H NMR: δ [CDCl$_3$] |
|---|---|---|---|---|---|---|---|
| 6-774 | 3,3-dimethyl-oxetan-2-yl | F | Br | H | Me | Na$^+$ | |
| 6-775 | 3,3-dimethyl-oxetan-2-yl | F | Br | H | Me | K$^+$ | |
| 6-776 | 3,3-dimethyl-oxetan-2-yl | F | Br | H | Me | NH$_4^+$ | |
| 6-777 | 3,3-dimethyl-oxetan-2-yl | F | F | H | Me | Na$^+$ | |
| 6-778 | 3,3-dimethyl-oxetan-2-yl | F | F | H | Me | K$^+$ | |
| 6-779 | 3,3-dimethyl-oxetan-2-yl | F | I | H | Me | Na$^+$ | |
| 6-780 | 3,3-dimethyl-oxetan-2-yl | F | I | H | Me | K$^+$ | |
| 6-781 | 3,3-dimethyl-oxetan-2-yl | F | CN | H | Me | Na$^+$ | |
| 6-782 | 3,3-dimethyl-oxetan-2-yl | F | CN | H | Me | K$^+$ | |
| 6-783 | 3,3-dimethyl-oxetan-2-yl | F | CF$_3$ | H | Me | Na$^+$ | |
| 6-784 | 3,3-dimethyl-oxetan-2-yl | F | CF$_3$ | H | Me | K$^+$ | |
| 6-785 | 3,3-dimethyl-oxetan-2-yl | H | Cl | Me | Me | Na$^+$ | |
| 6-786 | 3,3-dimethyl-oxetan-2-yl | H | Cl | Me | Me | K$^+$ | |
| 6-787 | 3,3-dimethyl-oxetan-2-yl | H | Cl | Me | Me | NH$_4^+$ | |
| 6-788 | 3,3-dimethyl-oxetan-2-yl | H | Br | Me | Me | Na$^+$ | |
| 6-789 | 3,3-dimethyl-oxetan-2-yl | H | Br | Me | Me | K$^+$ | |
| 6-790 | 3,3-dimethyl-oxetan-2-yl | H | Br | Me | Me | NH$_4^+$ | |
| 6-791 | 3,3-dimethyl-oxetan-2-yl | H | F | Me | Me | Na$^+$ | |
| 6-792 | 3,3-dimethyl-oxetan-2-yl | H | F | Me | Me | K$^+$ | |
| 6-793 | 3,3-dimethyl-oxetan-2-yl | H | I | Me | Me | Na$^+$ | |
| 6-794 | 3,3-dimethyl-oxetan-2-yl | H | I | Me | Me | K$^+$ | |
| 6-795 | 3,3-dimethyl-oxetan-2-yl | H | CN | Me | Me | Na$^+$ | |
| 6-796 | 3,3-dimethyl-oxetan-2-yl | H | CN | Me | Me | K$^+$ | |
| 6-797 | 3,3-dimethyl-oxetan-2-yl | H | CF$_3$ | Me | Me | Na$^+$ | |
| 6-798 | 3,3-dimethyl-oxetan-2-yl | H | CF$_3$ | Me | Me | K$^+$ | |
| 6-799 | 3,3-dimethyl-oxetan-2-yl | F | Cl | Me | Me | Na$^+$ | |
| 6-800 | 3,3-dimethyl-oxetan-2-yl | F | Cl | Me | Me | K$^+$ | |
| 6-801 | 3,3-dimethyl-oxetan-2-yl | F | Cl | Me | Me | NH$_4^+$ | |
| 6-802 | 3,3-dimethyl-oxetan-2-yl | F | Br | Me | Me | Na$^+$ | |
| 6-803 | 3,3-dimethyl-oxetan-2-yl | F | Br | Me | Me | K$^+$ | |
| 6-804 | 3,3-dimethyl-oxetan-2-yl | F | Br | Me | Me | NH$_4^+$ | |
| 6-805 | 3,3-dimethyl-oxetan-2-yl | F | F | Me | Me | Na$^+$ | |
| 6-806 | 3,3-dimethyl-oxetan-2-yl | F | F | Me | Me | K$^+$ | |
| 6-807 | 3,3-dimethyl-oxetan-2-yl | F | I | Me | Me | Na$^+$ | |
| 6-808 | 3,3-dimethyl-oxetan-2-yl | F | I | Me | Me | K$^+$ | |
| 6-809 | 3,3-dimethyl-oxetan-2-yl | F | CN | Me | Me | Na$^+$ | |
| 6-810 | 3,3-dimethyl-oxetan-2-yl | F | CN | Me | Me | K$^+$ | |
| 6-811 | 3,3-dimethyl-oxetan-2-yl | F | CF$_3$ | Me | Me | Na$^+$ | |
| 6-812 | 3,3-dimethyl-oxetan-2-yl | F | CF$_3$ | Me | Me | K$^+$ | |
| 6-813 | 3,3-dimethyl-oxetan-2-yl | H | Cl | =CHNMe$_2$ | | Na$^+$ | |
| 6-814 | 3,3-dimethyl-oxetan-2-yl | H | Cl | =CHNMe$_2$ | | K$^+$ | |
| 6-815 | 3,3-dimethyl-oxetan-2-yl | H | Cl | =CHNMe$_2$ | | NH$_4^+$ | |
| 6-816 | 3,3-dimethyl-oxetan-2-yl | H | Br | =CHNMe$_2$ | | Na$^+$ | |
| 6-817 | 3,3-dimethyl-oxetan-2-yl | H | Br | =CHNMe$_2$ | | K$^+$ | |
| 6-818 | 3,3-dimethyl-oxetan-2-yl | H | Br | =CHNMe$_2$ | | NH$_4^+$ | |
| 6-819 | 3,3-dimethyl-oxetan-2-yl | H | F | =CHNMe$_2$ | | Na$^+$ | |
| 6-820 | 3,3-dimethyl-oxetan-2-yl | H | F | =CHNMe$_2$ | | K$^+$ | |
| 6-821 | 3,3-dimethyl-oxetan-2-yl | H | I | =CHNMe$_2$ | | Na$^+$ | |
| 6-822 | 3,3-dimethyl-oxetan-2-yl | H | I | =CHNMe$_2$ | | K$^+$ | |
| 6-823 | 3,3-dimethyl-oxetan-2-yl | H | CN | =CHNMe$_2$ | | Na$^+$ | |
| 6-824 | 3,3-dimethyl-oxetan-2-yl | H | CN | =CHNMe$_2$ | | K$^+$ | |
| 6-825 | 3,3-dimethyl-oxetan-2-yl | H | CF$_3$ | =CHNMe$_2$ | | Na$^+$ | |
| 6-826 | 3,3-dimethyl-oxetan-2-yl | H | CF$_3$ | =CHNMe$_2$ | | K$^+$ | |
| 6-827 | 3,3-dimethyl-oxetan-2-yl | F | Cl | =CHNMe$_2$ | | Na$^+$ | |
| 6-828 | 3,3-dimethyl-oxetan-2-yl | F | Cl | =CHNMe$_2$ | | K$^+$ | |
| 6-829 | 3,3-dimethyl-oxetan-2-yl | F | Cl | =CHNMe$_2$ | | NH$_4^+$ | |
| 6-830 | 3,3-dimethyl-oxetan-2-yl | F | Br | =CHNMe$_2$ | | Na$^+$ | |
| 6-831 | 3,3-dimethyl-oxetan-2-yl | F | Br | =CHNMe$_2$ | | K$^+$ | |
| 6-832 | 3,3-dimethyl-oxetan-2-yl | F | Br | =CHNMe$_2$ | | NH$_4^+$ | |
| 6-833 | 3,3-dimethyl-oxetan-2-yl | F | F | =CHNMe$_2$ | | Na$^+$ | |
| 6-834 | 3,3-dimethyl-oxetan-2-yl | F | F | =CHNMe$_2$ | | K$^+$ | |

TABLE 6-continued

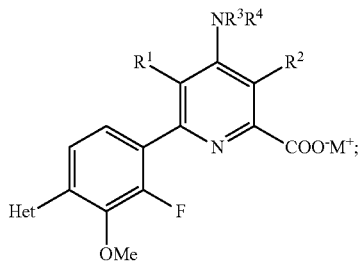

(I-vi)

| No. | Het | $R^1$ | $R^2$ | $R^3$ | $R^4$ | $M^+$ | Physical data: $^1$H NMR: δ [CDCl$_3$] |
|---|---|---|---|---|---|---|---|
| 6-835 | 3,3-dimethyl-oxetan-2-yl | F | I | =CHNMe$_2$ | | Na$^+$ | |
| 6-836 | 3,3-dimethyl-oxetan-2-yl | F | I | =CHNMe$_2$ | | K$^+$ | |
| 6-837 | 3,3-dimethyl-oxetan-2-yl | F | CN | =CHNMe$_2$ | | Na$^+$ | |
| 6-838 | 3,3-dimethyl-oxetan-2-yl | F | CN | =CHNMe$_2$ | | K$^+$ | |
| 6-839 | 3,3-dimethyl-oxetan-2-yl | F | CF$_3$ | =CHNMe$_2$ | | Na$^+$ | |
| 6-840 | 3,3-dimethyl-oxetan-2-yl | F | CF$_3$ | =CHNMe$_2$ | | K$^+$ | |
| 6-841 | 2,2-dimethyl-dioxolan-4-yl | H | Cl | H | H | Na$^+$ | |
| 6-842 | 2,2-dimethyl-dioxolan-4-yl | H | Cl | H | H | K$^+$ | |
| 6-843 | 2,2-dimethyl-dioxolan-4-yl | H | Cl | H | H | NH$_4^+$ | |
| 6-844 | 2,2-dimethyl-dioxolan-4-yl | H | Br | H | H | Na$^+$ | |
| 6-845 | 2,2-dimethyl-dioxolan-4-yl | H | Br | H | H | K$^+$ | |
| 6-846 | 2,2-dimethyl-dioxolan-4-yl | H | Br | H | H | NH$_4^+$ | |
| 6-847 | 2,2-dimethyl-dioxolan-4-yl | H | F | H | H | Na$^+$ | |
| 6-848 | 2,2-dimethyl-dioxolan-4-yl | H | F | H | H | K$^+$ | |
| 6-849 | 2,2-dimethyl-dioxolan-4-yl | H | I | H | H | Na$^+$ | |
| 6-850 | 2,2-dimethyl-dioxolan-4-yl | H | I | H | H | K$^+$ | |
| 6-851 | 2,2-dimethyl-dioxolan-4-yl | H | CN | H | H | Na$^+$ | |
| 6-852 | 2,2-dimethyl-dioxolan-4-yl | H | CN | H | H | K$^+$ | |
| 6-853 | 2,2-dimethyl-dioxolan-4-yl | H | CF$_3$ | H | H | Na$^+$ | |
| 6-854 | 2,2-dimethyl-dioxolan-4-yl | H | CF$_3$ | H | H | K$^+$ | |
| 6-855 | 2,2-dimethyl-dioxolan-4-yl | F | Cl | H | H | Na$^+$ | |
| 6-856 | 2,2-dimethyl-dioxolan-4-yl | F | Cl | H | H | K$^+$ | |
| 6-857 | 2,2-dimethyl-dioxolan-4-yl | F | Cl | H | H | NH$_4^+$ | |
| 6-858 | 2,2-dimethyl-dioxolan-4-yl | F | Br | H | H | Na$^+$ | |
| 6-859 | 2,2-dimethyl-dioxolan-4-yl | F | Br | H | H | K$^+$ | |
| 6-860 | 2,2-dimethyl-dioxolan-4-yl | F | Br | H | H | NH$_4^+$ | |
| 6-861 | 2,2-dimethyl-dioxolan-4-yl | F | F | H | H | Na$^+$ | |
| 6-862 | 2,2-dimethyl-dioxolan-4-yl | F | F | H | H | K$^+$ | |
| 6-863 | 2,2-dimethyl-dioxolan-4-yl | F | I | H | H | Na$^+$ | |
| 6-864 | 2,2-dimethyl-dioxolan-4-yl | F | I | H | H | K$^+$ | |

TABLE 6-continued

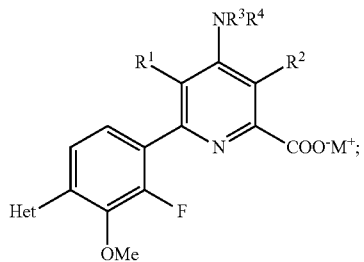

(I-vi)

| No. | Het | $R^1$ | $R^2$ | $R^3$ | $R^4$ | $M^+$ | Physical data: $^1$H NMR: δ [CDCl$_3$] |
|---|---|---|---|---|---|---|---|
| 6-865 | 2,2-dimethyl-dioxolan-4-yl | F | CN | H | H | Na$^+$ | |
| 6-866 | 2,2-dimethyl-dioxolan-4-yl | F | CN | H | H | K$^+$ | |
| 6-867 | 2,2-dimethyl-dioxolan-4-yl | F | CF$_3$ | H | H | Na$^+$ | |
| 6-868 | 2,2-dimethyl-dioxolan-4-yl | F | CF$_3$ | H | H | K$^+$ | |
| 6-869 | 2,2-dimethyl-dioxolan-4-yl | H | Cl | H | Me | Na$^+$ | |
| 6-870 | 2,2-dimethyl-dioxolan-4-yl | H | Cl | H | Me | K$^+$ | |
| 6-871 | 2,2-dimethyl-dioxolan-4-yl | H | Cl | H | Me | NH$_4^+$ | |
| 6-872 | 2,2-dimethyl-dioxolan-4-yl | H | Br | H | Me | Na$^+$ | |
| 6-873 | 2,2-dimethyl-dioxolan-4-yl | H | Br | H | Me | K$^+$ | |
| 6-874 | 2,2-dimethyl-dioxolan-4-yl | H | Br | H | Me | NH$_4^+$ | |
| 6-875 | 2,2-dimethyl-dioxolan-4-yl | H | F | H | Me | Na$^+$ | |
| 6-876 | 2,2-dimethyl-dioxolan-4-yl | H | F | H | Me | K$^+$ | |
| 6-877 | 2,2-dimethyl-dioxolan-4-yl | H | I | H | Me | Na$^+$ | |
| 6-878 | 2,2-dimethyl-dioxolan-4-yl | H | I | H | Me | K$^+$ | |
| 6-879 | 2,2-dimethyl-dioxolan-4-yl | H | CN | H | Me | Na$^+$ | |
| 6-880 | 2,2-dimethyl-dioxolan-4-yl | H | CN | H | Me | K$^+$ | |
| 6-881 | 2,2-dimethyl-dioxolan-4-yl | H | CF$_3$ | H | Me | Na$^+$ | |
| 6-882 | 2,2-dimethyl-dioxolan-4-yl | H | CF$_3$ | H | Me | K$^+$ | |
| 6-883 | 2,2-dimethyl-dioxolan-4-yl | F | Cl | H | Me | Na$^+$ | |
| 6-884 | 2,2-dimethyl-dioxolan-4-yl | F | Cl | H | Me | K$^+$ | |
| 6-885 | 2,2-dimethyl-dioxolan-4-yl | F | Cl | H | Me | NH$_4^+$ | |
| 6-886 | 2,2-dimethyl-dioxolan-4-yl | F | Br | H | Me | Na$^+$ | |
| 6-887 | 2,2-dimethyl-dioxolan-4-yl | F | Br | H | Me | K$^+$ | |
| 6-888 | 2,2-dimethyl-dioxolan-4-yl | F | Br | H | Me | NH$_4^+$ | |
| 6-889 | 2,2-dimethyl-dioxolan-4-yl | F | F | H | Me | Na$^+$ | |
| 6-890 | 2,2-dimethyl-dioxolan-4-yl | F | F | H | Me | K$^+$ | |
| 6-891 | 2,2-dimethyl-dioxolan-4-yl | F | I | H | Me | Na$^+$ | |
| 6-892 | 2,2-dimethyl-dioxolan-4-yl | F | I | H | Me | K$^+$ | |
| 6-893 | 2,2-dimethyl-dioxolan-4-yl | F | CN | H | Me | Na$^+$ | |
| 6-894 | 2,2-dimethyl-dioxolan-4-yl | F | CN | H | Me | K$^+$ | |
| 6-895 | 2,2-dimethyl-dioxolan-4-yl | F | CF$_3$ | H | Me | Na$^+$ | |

TABLE 6-continued (I-vi)

Structure: pyridine with NR³R⁴ at 4-position, R¹ at 5, R² at 3, COO⁻M⁺ at 2; 6-position attached to phenyl ring with F (ortho), OMe (meta), Het (para).

| No. | Het | R¹ | R² | R³ | R⁴ | M⁺ | Physical data: ¹H NMR: δ [CDCl₃] |
|---|---|---|---|---|---|---|---|
| 6-896 | 2,2-dimethyl-dioxolan-4-yl | F | CF₃ | H | Me | K⁺ | |
| 6-897 | 2,2-dimethyl-dioxolan-4-yl | H | Cl | Me | Me | Na⁺ | |
| 6-898 | 2,2-dimethyl-dioxolan-4-yl | H | Cl | Me | Me | K⁺ | |
| 6-899 | 2,2-dimethyl-dioxolan-4-yl | H | Cl | Me | Me | NH₄⁺ | |
| 6-900 | 2,2-dimethyl-dioxolan-4-yl | H | Br | Me | Me | Na⁺ | |
| 6-901 | 2,2-dimethyl-dioxolan-4-yl | H | Br | Me | Me | K⁺ | |
| 6-902 | 2,2-dimethyl-dioxolan-4-yl | H | Br | Me | Me | NH₄⁺ | |
| 6-903 | 2,2-dimethyl-dioxolan-4-yl | H | F | Me | Me | Na⁺ | |
| 6-904 | 2,2-dimethyl-dioxolan-4-yl | H | F | Me | Me | K⁺ | |
| 6-905 | 2,2-dimethyl-dioxolan-4-yl | H | I | Me | Me | Na⁺ | |
| 6-906 | 2,2-dimethyl-dioxolan-4-yl | H | I | Me | Me | K⁺ | |
| 6-907 | 2,2-dimethyl-dioxolan-4-yl | H | CN | Me | Me | Na⁺ | |
| 6-908 | 2,2-dimethyl-dioxolan-4-yl | H | CN | Me | Me | K⁺ | |
| 6-909 | 2,2-dimethyl-dioxolan-4-yl | H | CF₃ | Me | Me | Na⁺ | |
| 6-910 | 2,2-dimethyl-dioxolan-4-yl | H | CF₃ | Me | Me | K⁺ | |
| 6-911 | 2,2-dimethyl-dioxolan-4-yl | F | Cl | Me | Me | Na⁺ | |
| 6-912 | 2,2-dimethyl-dioxolan-4-yl | F | Cl | Me | Me | K⁺ | |
| 6-913 | 2,2-dimethyl-dioxolan-4-yl | F | Cl | Me | Me | NH₄⁺ | |
| 6-914 | 2,2-dimethyl-dioxolan-4-yl | F | Br | Me | Me | Na⁺ | |
| 6-915 | 2,2-dimethyl-dioxolan-4-yl | F | Br | Me | Me | K⁺ | |
| 6-916 | 2,2-dimethyl-dioxolan-4-yl | F | Br | Me | Me | NH₄⁺ | |
| 6-917 | 2,2-dimethyl-dioxolan-4-yl | F | F | Me | Me | Na⁺ | |
| 6-918 | 2,2-dimethyl-dioxolan-4-yl | F | F | Me | Me | K⁺ | |
| 6-919 | 2,2-dimethyl-dioxolan-4-yl | F | I | Me | Me | Na⁺ | |
| 6-920 | 2,2-dimethyl-dioxolan-4-yl | F | I | Me | Me | K⁺ | |
| 6-921 | 2,2-dimethyl-dioxolan-4-yl | F | CN | Me | Me | Na⁺ | |
| 6-922 | 2,2-dimethyl-dioxolan-4-yl | F | CN | Me | Me | K⁺ | |
| 6-923 | 2,2-dimethyl-dioxolan-4-yl | F | CF₃ | Me | Me | Na⁺ | |
| 6-924 | 2,2-dimethyl-dioxolan-4-yl | F | CF₃ | Me | Me | K⁺ | |
| 6-925 | 2,2-dimethyl-dioxolan-4-yl | H | Cl | =CHNMe₂ | | Na⁺ | |
| 6-926 | 2,2-dimethyl-dioxolan-4-yl | H | Cl | =CHNMe₂ | | K⁺ | |
| 6-927 | 2,2-dimethyl-dioxolan-4-yl | H | Cl | =CHNMe₂ | | NH₄⁺ | |
| 6-928 | 2,2-dimethyl-dioxolan-4-yl | H | Br | =CHNMe₂ | | Na⁺ | |
| 6-929 | 2,2-dimethyl-dioxolan-4-yl | H | Br | =CHNMe₂ | | K⁺ | |
| 6-930 | 2,2-dimethyl-dioxolan-4-yl | H | Br | =CHNMe₂ | | NH₄⁺ | |
| 6-931 | 2,2-dimethyl-dioxolan-4-yl | H | F | =CHNMe₂ | | Na⁺ | |
| 6-932 | 2,2-dimethyl-dioxolan-4-yl | H | F | =CHNMe₂ | | K⁺ | |
| 6-933 | 2,2-dimethyl-dioxolan-4-yl | H | I | =CHNMe₂ | | Na⁺ | |
| 6-934 | 2,2-dimethyl-dioxolan-4-yl | H | I | =CHNMe₂ | | K⁺ | |
| 6-935 | 2,2-dimethyl-dioxolan-4-yl | H | CN | =CHNMe₂ | | Na⁺ | |
| 6-936 | 2,2-dimethyl-dioxolan-4-yl | H | CN | =CHNMe₂ | | K⁺ | |
| 6-937 | 2,2-dimethyl-dioxolan-4-yl | H | CF₃ | =CHNMe₂ | | Na⁺ | |
| 6-938 | 2,2-dimethyl-dioxolan-4-yl | H | CF₃ | =CHNMe₂ | | K⁺ | |
| 6-939 | 2,2-dimethyl-dioxolan-4-yl | F | Cl | =CHNMe₂ | | Na⁺ | |
| 6-940 | 2,2-dimethyl-dioxolan-4-yl | F | Cl | =CHNMe₂ | | K⁺ | |
| 6-941 | 2,2-dimethyl-dioxolan-4-yl | F | Cl | =CHNMe₂ | | NH₄⁺ | |
| 6-942 | 2,2-dimethyl-dioxolan-4-yl | F | Br | =CHNMe₂ | | Na⁺ | |
| 6-943 | 2,2-dimethyl-dioxolan-4-yl | F | Br | =CHNMe₂ | | K⁺ | |
| 6-944 | 2,2-dimethyl-dioxolan-4-yl | F | Br | =CHNMe₂ | | NH₄⁺ | |
| 6-945 | 2,2-dimethyl-dioxolan-4-yl | F | F | =CHNMe₂ | | Na⁺ | |
| 6-946 | 2,2-dimethyl-dioxolan-4-yl | F | F | =CHNMe₂ | | K⁺ | |
| 6-947 | 2,2-dimethyl-dioxolan-4-yl | F | I | =CHNMe₂ | | Na⁺ | |
| 6-948 | 2,2-dimethyl-dioxolan-4-yl | F | I | =CHNMe₂ | | K⁺ | |
| 6-949 | 2,2-dimethyl-dioxolan-4-yl | F | CN | =CHNMe₂ | | Na⁺ | |
| 6-950 | 2,2-dimethyl-dioxolan-4-yl | F | CN | =CHNMe₂ | | K⁺ | |
| 6-951 | 2,2-dimethyl-dioxolan-4-yl | F | CF₃ | =CHNMe₂ | | Na⁺ | |
| 6-952 | 2,2-dimethyl-dioxolan-4-yl | F | CF₃ | =CHNMe₂ | | K⁺ | |

TABLE 7

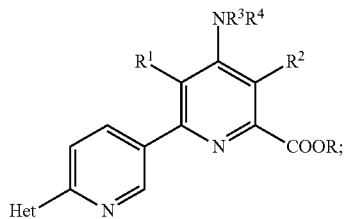

(i-vii)

| No. | Het | R¹ | R² | R³ | R⁴ | R | Physical data: $^1$H NMR: δ [CDCl$_3$] |
|---|---|---|---|---|---|---|---|
| 7-1 | 3-tert-butyl-1,2,4-oxadiazol-5-yl | H | Cl | H | H | H | |
| 7-2 | 3-tert-butyl-1,2,4-oxadiazol-5-yl | H | Cl | H | H | Me | |
| 7-3 | 3-tert-butyl-1,2,4-oxadiazol-5-yl | H | Cl | H | H | Et | |
| 7-4 | 3-tert-butyl-1,2,4-oxadiazol-5-yl | H | Br | H | H | H | |
| 7-5 | 3-tert-butyl-1,2,4-oxadiazol-5-yl | H | Br | H | H | Me | |
| 7-6 | 3-tert-butyl-1,2,4-oxadiazol-5-yl | H | Br | H | H | Et | |
| 7-7 | 3-tert-butyl-1,2,4-oxadiazol-5-yl | H | F | H | H | H | |
| 7-8 | 3-tert-butyl-1,2,4-oxadiazol-5-yl | H | F | H | H | Me | |
| 7-9 | 3-tert-butyl-1,2,4-oxadiazol-5-yl | H | I | H | H | H | |
| 7-10 | 3-tert-butyl-1,2,4-oxadiazol-5-yl | H | I | H | H | Me | |
| 7-11 | 3-tert-butyl-1,2,4-oxadiazol-5-yl | H | CN | H | H | H | |
| 7-12 | 3-tert-butyl-1,2,4-oxadiazol-5-yl | H | CN | H | H | Me | |
| 7-13 | 3-tert-butyl-1,2,4-oxadiazol-5-yl | H | CF$_3$ | H | H | H | |
| 7-14 | 3-tert-butyl-1,2,4-oxadiazol-5-yl | H | CF$_3$ | H | H | Me | |
| 7-15 | 3-tert-butyl-1,2,4-oxadiazol-5-yl | F | Cl | H | H | H | |
| 7-16 | 3-tert-butyl-1,2,4-oxadiazol-5-yl | F | Cl | H | H | Me | |
| 7-17 | 3-tert-butyl-1,2,4-oxadiazol-5-yl | F | Cl | H | H | Et | |
| 7-18 | 3-tert-butyl-1,2,4-oxadiazol-5-yl | F | Br | H | H | H | |
| 7-19 | 3-tert-butyl-1,2,4-oxadiazol-5-yl | F | Br | H | H | Me | |
| 7-20 | 3-tert-butyl-1,2,4-oxadiazol-5-yl | F | Br | H | H | Et | |
| 7-21 | 3-tert-butyl-1,2,4-oxadiazol-5-yl | F | F | H | H | H | |
| 7-22 | 3-tert-butyl-1,2,4-oxadiazol-5-yl | F | F | H | H | Me | |
| 7-23 | 3-tert-butyl-1,2,4-oxadiazol-5-yl | F | I | H | H | H | |
| 7-24 | 3-tert-butyl-1,2,4-oxadiazol-5-yl | F | I | H | H | Me | |
| 7-25 | 3-tert-butyl-1,2,4-oxadiazol-5-yl | F | CN | H | H | H | |
| 7-26 | 3-tert-butyl-1,2,4-oxadiazol-5-yl | F | CN | H | H | Me | |
| 7-27 | 3-tert-butyl-1,2,4-oxadiazol-5-yl | F | CF$_3$ | H | H | H | |
| 7-28 | 3-tert-butyl-1,2,4-oxadiazol-5-yl | F | CF$_3$ | H | H | Me | |
| 7-29 | 3-tert-butyl-1,2,4-oxadiazol-5-yl | Cl | Cl | H | H | H | |
| 7-30 | 3-tert-butyl-1,2,4-oxadiazol-5-yl | Cl | Cl | H | H | Me | |
| 7-31 | 3-tert-butyl-1,2,4-oxadiazol-5-yl | Cl | Cl | H | H | Et | |
| 7-32 | 3-tert-butyl-1,2,4-oxadiazol-5-yl | Cl | Br | H | H | H | |
| 7-33 | 3-tert-butyl-1,2,4-oxadiazol-5-yl | Cl | Br | H | H | Me | |
| 7-34 | 3-tert-butyl-1,2,4-oxadiazol-5-yl | Cl | Br | H | H | Et | |
| 7-35 | 3-tert-butyl-1,2,4-oxadiazol-5-yl | Cl | F | H | H | H | |
| 7-36 | 3-tert-butyl-1,2,4-oxadiazol-5-yl | Cl | F | H | H | Me | |
| 7-37 | 3-tert-butyl-1,2,4-oxadiazol-5-yl | Cl | I | H | H | H | |
| 7-38 | 3-tert-butyl-1,2,4-oxadiazol-5-yl | Cl | I | H | H | Me | |
| 7-39 | 3-tert-butyl-1,2,4-oxadiazol-5-yl | Cl | CN | H | H | H | |
| 7-40 | 3-tert-butyl-1,2,4-oxadiazol-5-yl | Cl | CN | H | H | Me | |
| 7-41 | 3-tert-butyl-1,2,4-oxadiazol-5-yl | Cl | CF$_3$ | H | H | H | |
| 7-42 | 3-tert-butyl-1,2,4-oxadiazol-5-yl | Cl | CF$_3$ | H | H | Me | |
| 7-43 | 3-tert-butyl-1,2,4-oxadiazol-5-yl | H | Cl | H | Me | H | |
| 7-44 | 3-tert-butyl-1,2,4-oxadiazol-5-yl | H | Cl | H | Me | Me | |
| 7-45 | 3-tert-butyl-1,2,4-oxadiazol-5-yl | H | Cl | H | Me | Et | |
| 7-46 | 3-tert-butyl-1,2,4-oxadiazol-5-yl | H | Br | H | Me | H | |
| 7-47 | 3-tert-butyl-1,2,4-oxadiazol-5-yl | H | Br | H | Me | Me | |
| 7-48 | 3-tert-butyl-1,2,4-oxadiazol-5-yl | H | Br | H | Me | Et | |
| 7-49 | 3-tert-butyl-1,2,4-oxadiazol-5-yl | H | F | H | Me | H | |
| 7-50 | 3-tert-butyl-1,2,4-oxadiazol-5-yl | H | F | H | Me | Me | |
| 7-51 | 3-tert-butyl-1,2,4-oxadiazol-5-yl | H | I | H | Me | H | |
| 7-52 | 3-tert-butyl-1,2,4-oxadiazol-5-yl | H | I | H | Me | Me | |
| 7-53 | 3-tert-butyl-1,2,4-oxadiazol-5-yl | H | CN | H | Me | H | |
| 7-54 | 3-tert-butyl-1,2,4-oxadiazol-5-yl | H | CN | H | Me | Me | |
| 7-55 | 3-tert-butyl-1,2,4-oxadiazol-5-yl | H | CF$_3$ | H | Me | H | |
| 7-56 | 3-tert-butyl-1,2,4-oxadiazol-5-yl | H | CF$_3$ | H | Me | Me | |
| 7-57 | 3-tert-butyl-1,2,4-oxadiazol-5-yl | F | Cl | H | Me | H | |
| 7-58 | 3-tert-butyl-1,2,4-oxadiazol-5-yl | F | Cl | H | Me | Me | |
| 7-59 | 3-tert-butyl-1,2,4-oxadiazol-5-yl | F | Cl | H | Me | Et | |
| 7-60 | 3-tert-butyl-1,2,4-oxadiazol-5-yl | F | Br | H | Me | H | |

TABLE 7-continued

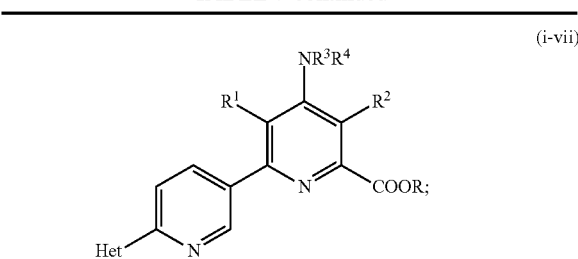

(i-vii)

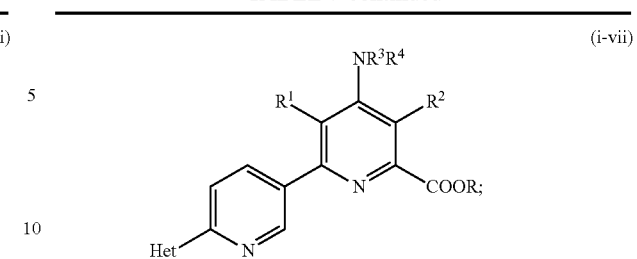

(i-vii)

| No. | Het | $R^1$ | $R^2$ | $R^3$ | $R^4$ | R | Physical data: $^1$H NMR: δ [CDCl$_3$] | No. | Het | $R^1$ | $R^2$ | $R^3$ | $R^4$ | R | Physical data: $^1$H NMR: δ [CDCl$_3$] |
|---|---|---|---|---|---|---|---|---|---|---|---|---|---|---|---|
| 7-61 | 3-tert-butyl-1,2,4-oxadiazol-5-yl | F | Br | H | Me | Me | | 7-91 | 3-tert-butyl-1,2,4-oxadiazol-5-yl | H | F | Me | Me | H | |
| 7-62 | 3-tert-butyl-1,2,4-oxadiazol-5-yl | F | Br | H | Me | Et | | 7-92 | 3-tert-butyl-1,2,4-oxadiazol-5-yl | H | F | Me | Me | Me | |
| 7-63 | 3-tert-butyl-1,2,4-oxadiazol-5-yl | F | F | H | Me | H | | 7-93 | 3-tert-butyl-1,2,4-oxadiazol-5-yl | H | I | Me | Me | H | |
| 7-64 | 3-tert-butyl-1,2,4-oxadiazol-5-yl | F | F | H | Me | Me | | 7-94 | 3-tert-butyl-1,2,4-oxadiazol-5-yl | H | I | Me | Me | Me | |
| 7-65 | 3-tert-butyl-1,2,4-oxadiazol-5-yl | F | I | H | Me | H | | 7-95 | 3-tert-butyl-1,2,4-oxadiazol-5-yl | H | CN | Me | Me | H | |
| 7-66 | 3-tert-butyl-1,2,4-oxadiazol-5-yl | F | I | H | Me | Me | | 7-96 | 3-tert-butyl-1,2,4-oxadiazol-5-yl | H | CN | Me | Me | Me | |
| 7-67 | 3-tert-butyl-1,2,4-oxadiazol-5-yl | F | CN | H | Me | H | | 7-97 | 3-tert-butyl-1,2,4-oxadiazol-5-yl | H | CF$_3$ | Me | Me | H | |
| 7-68 | 3-tert-butyl-1,2,4-oxadiazol-5-yl | F | CN | H | Me | Me | | 7-98 | 3-tert-butyl-1,2,4-oxadiazol-5-yl | H | CF$_3$ | Me | Me | Me | |
| 7-69 | 3-tert-butyl-1,2,4-oxadiazol-5-yl | F | CF$_3$ | H | Me | H | | 7-99 | 3-tert-butyl-1,2,4-oxadiazol-5-yl | F | Cl | Me | Me | H | |
| 7-70 | 3-tert-butyl-1,2,4-oxadiazol-5-yl | F | CF$_3$ | H | Me | Me | | 7-100 | 3-tert-butyl-1,2,4-oxadiazol-5-yl | F | Cl | Me | Me | Me | |
| 7-71 | 3-tert-butyl-1,2,4-oxadiazol-5-yl | Cl | Cl | H | Me | H | | 7-101 | 3-tert-butyl-1,2,4-oxadiazol-5-yl | F | Cl | Me | Me | Et | |
| 7-72 | 3-tert-butyl-1,2,4-oxadiazol-5-yl | Cl | Cl | H | Me | Me | | 7-102 | 3-tert-butyl-1,2,4-oxadiazol-5-yl | F | Br | Me | Me | H | |
| 7-73 | 3-tert-butyl-1,2,4-oxadiazol-5-yl | Cl | Cl | H | Me | Et | | 7-103 | 3-tert-butyl-1,2,4-oxadiazol-5-yl | F | Br | Me | Me | Me | |
| 7-74 | 3-tert-butyl-1,2,4-oxadiazol-5-yl | Cl | Br | H | Me | H | | 7-104 | 3-tert-butyl-1,2,4-oxadiazol-5-yl | F | Br | Me | Me | Et | |
| 7-75 | 3-tert-butyl-1,2,4-oxadiazol-5-yl | Cl | Br | H | Me | Me | | 7-105 | 3-tert-butyl-1,2,4-oxadiazol-5-yl | F | F | Me | Me | H | |
| 7-76 | 3-tert-butyl-1,2,4-oxadiazol-5-yl | Cl | Br | H | Me | Et | | 7-106 | 3-tert-butyl-1,2,4-oxadiazol-5-yl | F | F | Me | Me | Me | |
| 7-77 | 3-tert-butyl-1,2,4-oxadiazol-5-yl | Cl | F | H | Me | H | | 7-107 | 3-tert-butyl-1,2,4-oxadiazol-5-yl | F | I | Me | Me | H | |
| 7-78 | 3-tert-butyl-1,2,4-oxadiazol-5-yl | Cl | F | H | Me | Me | | 7-108 | 3-tert-butyl-1,2,4-oxadiazol-5-yl | F | I | Me | Me | Me | |
| 7-79 | 3-tert-butyl-1,2,4-oxadiazol-5-yl | Cl | I | H | Me | H | | 7-109 | 3-tert-butyl-1,2,4-oxadiazol-5-yl | F | CN | Me | Me | H | |
| 7-80 | 3-tert-butyl-1,2,4-oxadiazol-5-yl | Cl | I | H | Me | Me | | 7-110 | 3-tert-butyl-1,2,4-oxadiazol-5-yl | F | CN | Me | Me | Me | |
| 7-81 | 3-tert-butyl-1,2,4-oxadiazol-5-yl | Cl | CN | H | Me | H | | 7-111 | 3-tert-butyl-1,2,4-oxadiazol-5-yl | F | CF$_3$ | Me | Me | H | |
| 7-82 | 3-tert-butyl-1,2,4-oxadiazol-5-yl | Cl | CN | H | Me | Me | | 7-112 | 3-tert-butyl-1,2,4-oxadiazol-5-yl | F | CF$_3$ | Me | Me | Me | |
| 7-83 | 3-tert-butyl-1,2,4-oxadiazol-5-yl | Cl | CF$_3$ | H | Me | H | | 7-113 | 3-tert-butyl-1,2,4-oxadiazol-5-yl | Cl | Cl | Me | Me | H | |
| 7-84 | 3-tert-butyl-1,2,4-oxadiazol-5-yl | Cl | CF$_3$ | H | Me | Me | | 7-114 | 3-tert-butyl-1,2,4-oxadiazol-5-yl | Cl | Cl | Me | Me | Me | |
| 7-85 | 3-tert-butyl-1,2,4-oxadiazol-5-yl | H | Cl | Me | Me | H | | 7-115 | 3-tert-butyl-1,2,4-oxadiazol-5-yl | Cl | Cl | Me | Me | Et | |
| 7-86 | 3-tert-butyl-1,2,4-oxadiazol-5-yl | H | Cl | Me | Me | Me | | 7-116 | 3-tert-butyl-1,2,4-oxadiazol-5-yl | Cl | Br | Me | Me | H | |
| 7-87 | 3-tert-butyl-1,2,4-oxadiazol-5-yl | H | Cl | Me | Me | Et | | 7-117 | 3-tert-butyl-1,2,4-oxadiazol-5-yl | Cl | Br | Me | Me | Me | |
| 7-88 | 3-tert-butyl-1,2,4-oxadiazol-5-yl | H | Br | Me | Me | H | | 7-118 | 3-tert-butyl-1,2,4-oxadiazol-5-yl | Cl | Br | Me | Me | Et | |
| 7-89 | 3-tert-butyl-1,2,4-oxadiazol-5-yl | H | Br | Me | Me | Me | | 7-119 | 3-tert-butyl-1,2,4-oxadiazol-5-yl | Cl | F | Me | Me | H | |
| 7-90 | 3-tert-butyl-1,2,4-oxadiazol-5-yl | H | Br | Me | Me | Et | | 7-120 | 3-tert-butyl-1,2,4-oxadiazol-5-yl | Cl | F | Me | Me | Me | |

TABLE 7-continued

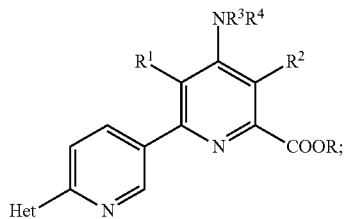

(i-vii)

| No. | Het | R¹ | R² | R³ | R⁴ | R |
|---|---|---|---|---|---|---|
| 7-121 | 3-tert-butyl-1,2,4-oxadiazol-5-yl | Cl | I | Me | Me | H |
| 7-122 | 3-tert-butyl-1,2,4-oxadiazol-5-yl | Cl | I | Me | Me | Me |
| 7-123 | 3-tert-butyl-1,2,4-oxadiazol-5-yl | Cl | CN | Me | Me | H |
| 7-124 | 3-tert-butyl-1,2,4-oxadiazol-5-yl | Cl | CN | Me | Me | Me |
| 7-125 | 3-tert-butyl-1,2,4-oxadiazol-5-yl | Cl | CF₃ | Me | Me | H |
| 7-126 | 3-tert-butyl-1,2,4-oxadiazol-5-yl | Cl | CF₃ | Me | Me | Me |
| 7-127 | 3-tert-butyl-1,2,4-oxadiazol-5-yl | H | Cl | =CHNMe₂ | H | |
| 7-128 | 3-tert-butyl-1,2,4-oxadiazol-5-yl | H | Cl | =CHNMe₂ | Me | |
| 7-129 | 3-tert-butyl-1,2,4-oxadiazol-5-yl | H | Cl | =CHNMe₂ | Et | |
| 7-130 | 3-tert-butyl-1,2,4-oxadiazol-5-yl | H | Br | =CHNMe₂ | H | |
| 7-131 | 3-tert-butyl-1,2,4-oxadiazol-5-yl | H | Br | =CHNMe₂ | Me | |
| 7-132 | 3-tert-butyl-1,2,4-oxadiazol-5-yl | H | Br | =CHNMe₂ | Et | |
| 7-133 | 3-tert-butyl-1,2,4-oxadiazol-5-yl | H | F | =CHNMe₂ | H | |
| 7-134 | 3-tert-butyl-1,2,4-oxadiazol-5-yl | H | F | =CHNMe₂ | Me | |
| 7-135 | 3-tert-butyl-1,2,4-oxadiazol-5-yl | H | I | =CHNMe₂ | H | |
| 7-136 | 3-tert-butyl-1,2,4-oxadiazol-5-yl | H | I | =CHNMe₂ | Me | |
| 7-137 | 3-tert-butyl-1,2,4-oxadiazol-5-yl | H | CN | =CHNMe₂ | H | |
| 7-138 | 3-tert-butyl-1,2,4-oxadiazol-5-yl | H | CN | =CHNMe₂ | Me | |
| 7-139 | 3-tert-butyl-1,2,4-oxadiazol-5-yl | H | CF₃ | =CHNMe₂ | H | |
| 7-140 | 3-tert-butyl-1,2,4-oxadiazol-5-yl | H | CF₃ | =CHNMe₂ | Me | |
| 7-141 | 3-tert-butyl-1,2,4-oxadiazol-5-yl | F | Cl | =CHNMe₂ | H | |
| 7-142 | 3-tert-butyl-1,2,4-oxadiazol-5-yl | F | Cl | =CHNMe₂ | Me | |
| 7-143 | 3-tert-butyl-1,2,4-oxadiazol-5-yl | F | Cl | =CHNMe₂ | Et | |
| 7-144 | 3-tert-butyl-1,2,4-oxadiazol-5-yl | F | Br | =CHNMe₂ | H | |
| 7-145 | 3-tert-butyl-1,2,4-oxadiazol-5-yl | F | Br | =CHNMe₂ | Me | |
| 7-146 | 3-tert-butyl-1,2,4-oxadiazol-5-yl | F | Br | =CHNMe₂ | Et | |
| 7-147 | 3-tert-butyl-1,2,4-oxadiazol-5-yl | F | F | =CHNMe₂ | H | |
| 7-148 | 3-tert-butyl-1,2,4-oxadiazol-5-yl | F | F | =CHNMe₂ | Me | |
| 7-149 | 3-tert-butyl-1,2,4-oxadiazol-5-yl | F | I | =CHNMe₂ | H | |
| 7-150 | 3-tert-butyl-1,2,4-oxadiazol-5-yl | F | I | =CHNMe₂ | Me | |
| 7-151 | 3-tert-butyl-1,2,4-oxadiazol-5-yl | F | CN | =CHNMe₂ | H | |
| 7-152 | 3-tert-butyl-1,2,4-oxadiazol-5-yl | F | CN | =CHNMe₂ | Me | |
| 7-153 | 3-tert-butyl-1,2,4-oxadiazol-5-yl | F | CF₃ | =CHNMe₂ | H | |
| 7-154 | 3-tert-butyl-1,2,4-oxadiazol-5-yl | F | CF₃ | =CHNMe₂ | Me | |
| 7-155 | 3-tert-butyl-1,2,4-oxadiazol-5-yl | Cl | Cl | =CHNMe₂ | H | |
| 7-156 | 3-tert-butyl-1,2,4-oxadiazol-5-yl | Cl | Cl | =CHNMe₂ | Me | |
| 7-157 | 3-tert-butyl-1,2,4-oxadiazol-5-yl | Cl | Cl | =CHNMe₂ | Et | |
| 7-158 | 3-tert-butyl-1,2,4-oxadiazol-5-yl | Cl | Br | =CHNMe₂ | H | |
| 7-159 | 3-tert-butyl-1,2,4-oxadiazol-5-yl | Cl | Br | =CHNMe₂ | Me | |
| 7-160 | 3-tert-butyl-1,2,4-oxadiazol-5-yl | Cl | Br | =CHNMe₂ | Et | |
| 7-161 | 3-tert-butyl-1,2,4-oxadiazol-5-yl | Cl | F | =CHNMe₂ | H | |
| 7-162 | 3-tert-butyl-1,2,4-oxadiazol-5-yl | Cl | F | =CHNMe₂ | Me | |
| 7-163 | 3-tert-butyl-1,2,4-oxadiazol-5-yl | Cl | I | =CHNMe₂ | H | |
| 7-164 | 3-tert-butyl-1,2,4-oxadiazol-5-yl | Cl | I | =CHNMe₂ | Me | |
| 7-165 | 3-tert-butyl-1,2,4-oxadiazol-5-yl | Cl | CN | =CHNMe₂ | H | |
| 7-166 | 3-tert-butyl-1,2,4-oxadiazol-5-yl | Cl | CN | =CHNMe₂ | Me | |
| 7-167 | 3-tert-butyl-1,2,4-oxadiazol-5-yl | Cl | CF₃ | =CHNMe₂ | H | |
| 7-168 | 3-tert-butyl-1,2,4-oxadiazol-5-yl | Cl | CF₃ | =CHNMe₂ | Me | |
| 7-169 | thien-2-yl | H | Cl | H | H | H |
| 7-170 | thien-2-yl | H | Cl | H | H | Me |
| 7-171 | thien-2-yl | H | Cl | H | H | Et |
| 7-172 | thien-2-yl | H | Br | H | H | H |
| 7-173 | thien-2-yl | H | Br | H | H | Me |
| 7-174 | thien-2-yl | H | Br | H | H | Et |
| 7-175 | thien-2-yl | H | F | H | H | H |
| 7-176 | thien-2-yl | H | F | H | H | Me |
| 7-177 | thien-2-yl | H | I | H | H | H |
| 7-178 | thien-2-yl | H | I | H | H | Me |
| 7-179 | thien-2-yl | H | CN | H | H | H |
| 7-180 | thien-2-yl | H | CN | H | H | Me |
| 7-181 | thien-2-yl | H | CF₃ | H | H | H |
| 7-182 | thien-2-yl | H | CF₃ | H | H | Me |
| 7-183 | thien-2-yl | F | Cl | H | H | H |
| 7-184 | thien-2-yl | F | Cl | H | H | Me |
| 7-185 | thien-2-yl | F | Cl | H | H | Et |
| 7-186 | thien-2-yl | F | Br | H | H | H |
| 7-187 | thien-2-yl | F | Br | H | H | Me |
| 7-188 | thien-2-yl | F | Br | H | H | Et |
| 7-189 | thien-2-yl | F | F | H | H | H |
| 7-190 | thien-2-yl | F | F | H | H | Me |
| 7-191 | thien-2-yl | F | I | H | H | H |
| 7-192 | thien-2-yl | F | I | H | H | Me |
| 7-193 | thien-2-yl | F | CN | H | H | H |
| 7-194 | thien-2-yl | F | CN | H | H | Me |
| 7-195 | thien-2-yl | F | CF₃ | H | H | H |
| 7-196 | thien-2-yl | F | CF₃ | H | H | Me |
| 7-197 | thien-2-yl | H | Cl | H | Me | H |

TABLE 7-continued

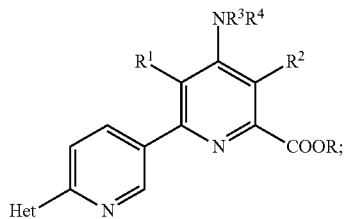

(i-vii)

| No. | Het | $R^1$ | $R^2$ | $R^3$ | $R^4$ | R | Physical data: $^1$H NMR: δ [CDCl$_3$] |
|---|---|---|---|---|---|---|---|
| 7-198 | thien-2-yl | H | Cl | H | Me | Me | |
| 7-199 | thien-2-yl | H | Cl | H | Me | Et | |
| 7-200 | thien-2-yl | H | Br | H | Me | H | |
| 7-201 | thien-2-yl | H | Br | H | Me | Me | |
| 7-202 | thien-2-yl | H | Br | H | Me | Et | |
| 7-203 | thien-2-yl | H | F | H | Me | H | |
| 7-204 | thien-2-yl | H | F | H | Me | Me | |
| 7-205 | thien-2-yl | H | I | H | Me | H | |
| 7-206 | thien-2-yl | H | I | H | Me | Me | |
| 7-207 | thien-2-yl | H | CN | H | Me | H | |
| 7-208 | thien-2-yl | H | CN | H | Me | Me | |
| 7-209 | thien-2-yl | H | CF$_3$ | H | Me | H | |
| 7-210 | thien-2-yl | H | CF$_3$ | H | Me | Me | |
| 7-211 | thien-2-yl | F | Cl | H | Me | H | |
| 7-212 | thien-2-yl | F | Cl | H | Me | Me | |
| 7-213 | thien-2-yl | F | Cl | H | Me | Et | |
| 7-214 | thien-2-yl | F | Br | H | Me | H | |
| 7-215 | thien-2-yl | F | Br | H | Me | Me | |
| 7-216 | thien-2-yl | F | Br | H | Me | Et | |
| 7-217 | thien-2-yl | F | F | H | Me | H | |
| 7-218 | thien-2-yl | F | F | H | Me | Me | |
| 7-219 | thien-2-yl | F | I | H | Me | H | |
| 7-220 | thien-2-yl | F | I | H | Me | Me | |
| 7-221 | thien-2-yl | F | CN | H | Me | H | |
| 7-222 | thien-2-yl | F | CN | H | Me | Me | |
| 7-223 | thien-2-yl | F | CF$_3$ | H | Me | H | |
| 7-224 | thien-2-yl | F | CF$_3$ | H | Me | Me | |
| 7-225 | thien-2-yl | H | Cl | Me | Me | H | |
| 7-226 | thien-2-yl | H | Cl | Me | Me | Me | |
| 7-227 | thien-2-yl | H | Cl | Me | Me | Et | |
| 7-228 | thien-2-yl | H | Br | Me | Me | H | |
| 7-229 | thien-2-yl | H | Br | Me | Me | Me | |
| 7-230 | thien-2-yl | H | Br | Me | Me | Et | |
| 7-231 | thien-2-yl | H | F | Me | Me | H | |
| 7-232 | thien-2-yl | H | F | Me | Me | Me | |
| 7-233 | thien-2-yl | H | I | Me | Me | H | |
| 7-234 | thien-2-yl | H | I | Me | Me | Me | |
| 7-235 | thien-2-yl | H | CN | Me | Me | H | |
| 7-236 | thien-2-yl | H | CN | Me | Me | Me | |
| 7-237 | thien-2-yl | H | CF$_3$ | Me | Me | H | |
| 7-238 | thien-2-yl | H | CF$_3$ | Me | Me | Me | |
| 7-239 | thien-2-yl | F | Cl | Me | Me | H | |
| 7-240 | thien-2-yl | F | Cl | Me | Me | Me | |
| 7-241 | thien-2-yl | F | Cl | Me | Me | Et | |
| 7-242 | thien-2-yl | F | Br | Me | Me | H | |
| 7-243 | thien-2-yl | F | Br | Me | Me | Me | |
| 7-244 | thien-2-yl | F | Br | Me | Me | Et | |
| 7-245 | thien-2-yl | F | F | Me | Me | H | |
| 7-246 | thien-2-yl | F | F | Me | Me | Me | |
| 7-247 | thien-2-yl | F | I | Me | Me | H | |
| 7-248 | thien-2-yl | F | I | Me | Me | Me | |
| 7-249 | thien-2-yl | F | CN | Me | Me | H | |
| 7-250 | thien-2-yl | F | CN | Me | Me | Me | |
| 7-251 | thien-2-yl | F | CF$_3$ | Me | Me | H | |
| 7-252 | thien-2-yl | F | CF$_3$ | Me | Me | Me | |
| 7-253 | thien-2-yl | H | Cl | =CHNMe$_2$ | H | | |
| 7-254 | thien-2-yl | H | Cl | =CHNMe$_2$ | Me | | |
| 7-255 | thien-2-yl | H | Cl | =CHNMe$_2$ | Et | | |
| 7-256 | thien-2-yl | H | Br | =CHNMe$_2$ | H | | |
| 7-257 | thien-2-yl | H | Br | =CHNMe$_2$ | Me | | |
| 7-258 | thien-2-yl | H | Br | =CHNMe$_2$ | Et | | |
| 7-259 | thien-2-yl | H | F | =CHNMe$_2$ | H | | |
| 7-260 | thien-2-yl | H | F | =CHNMe$_2$ | Me | | |
| 7-261 | thien-2-yl | H | I | =CHNMe$_2$ | H | | |
| 7-262 | thien-2-yl | H | I | =CHNMe$_2$ | Me | | |
| 7-263 | thien-2-yl | H | CN | =CHNMe$_2$ | H | | |
| 7-264 | thien-2-yl | H | CN | =CHNMe$_2$ | Me | | |
| 7-265 | thien-2-yl | H | CF$_3$ | =CHNMe$_2$ | H | | |
| 7-266 | thien-2-yl | H | CF$_3$ | =CHNMe$_2$ | Me | | |
| 7-267 | thien-2-yl | F | Cl | =CHNMe$_2$ | H | | |
| 7-268 | thien-2-yl | F | Cl | =CHNMe$_2$ | Me | | |
| 7-269 | thien-2-yl | F | Cl | =CHNMe$_2$ | Et | | |
| 7-270 | thien-2-yl | F | Br | =CHNMe$_2$ | H | | |
| 7-271 | thien-2-yl | F | Br | =CHNMe$_2$ | Me | | |
| 7-272 | thien-2-yl | F | Br | =CHNMe$_2$ | Et | | |
| 7-273 | thien-2-yl | F | F | =CHNMe$_2$ | H | | |
| 7-274 | thien-2-yl | F | F | =CHNMe$_2$ | Me | | |
| 7-275 | thien-2-yl | F | I | =CHNMe$_2$ | H | | |
| 7-276 | thien-2-yl | F | I | =CHNMe$_2$ | Me | | |
| 7-277 | thien-2-yl | F | CN | =CHNMe$_2$ | H | | |
| 7-278 | thien-2-yl | F | CN | =CHNMe$_2$ | Me | | |
| 7-279 | thien-2-yl | F | CF$_3$ | =CHNMe$_2$ | H | | |
| 7-280 | thien-2-yl | F | CF$_3$ | =CHNMe$_2$ | Me | | |
| 7-281 | pyrrol-1-yl | H | Cl | H | H | H | |
| 7-282 | pyrrol-1-yl | H | Cl | H | H | Me | |
| 7-283 | pyrrol-1-yl | H | Cl | H | H | Et | |
| 7-284 | pyrrol-1-yl | H | Br | H | H | H | |
| 7-285 | pyrrol-1-yl | H | Br | H | H | Me | |
| 7-286 | pyrrol-1-yl | H | Br | H | H | Et | |
| 7-287 | pyrrol-1-yl | H | F | H | H | H | |
| 7-288 | pyrrol-1-yl | H | F | H | H | Me | |
| 7-289 | pyrrol-1-yl | H | I | H | H | H | |
| 7-290 | pyrrol-1-yl | H | I | H | H | Me | |
| 7-291 | pyrrol-1-yl | H | CN | H | H | H | |
| 7-292 | pyrrol-1-yl | H | CN | H | H | Me | |
| 7-293 | pyrrol-1-yl | H | CF$_3$ | H | H | H | |
| 7-294 | pyrrol-1-yl | H | CF$_3$ | H | H | Me | |
| 7-295 | pyrrol-1-yl | F | Cl | H | H | H | |
| 7-296 | pyrrol-1-yl | F | Cl | H | H | Me | |
| 7-297 | pyrrol-1-yl | F | Cl | H | H | Et | |
| 7-298 | pyrrol-1-yl | F | Br | H | H | H | |
| 7-299 | pyrrol-1-yl | F | Br | H | H | Me | |
| 7-300 | pyrrol-1-yl | F | Br | H | H | Et | |
| 7-301 | pyrrol-1-yl | F | F | H | H | H | |
| 7-302 | pyrrol-1-yl | F | F | H | H | Me | |
| 7-303 | pyrrol-1-yl | F | I | H | H | H | |
| 7-304 | pyrrol-1-yl | F | I | H | H | Me | |
| 7-305 | pyrrol-1-yl | F | CN | H | H | H | |
| 7-306 | pyrrol-1-yl | F | CN | H | H | Me | |
| 7-307 | pyrrol-1-yl | F | CF$_3$ | H | H | H | |
| 7-308 | pyrrol-1-yl | F | CF$_3$ | H | H | Me | |
| 7-309 | pyrrol-1-yl | H | Cl | H | Me | H | |
| 7-310 | pyrrol-1-yl | H | Cl | H | Me | Me | |
| 7-311 | pyrrol-1-yl | H | Cl | H | Me | Et | |
| 7-312 | pyrrol-1-yl | H | Br | H | Me | H | |
| 7-313 | pyrrol-1-yl | H | Br | H | Me | Me | |
| 7-314 | pyrrol-1-yl | H | Br | H | Me | Et | |
| 7-315 | pyrrol-1-yl | H | F | H | Me | H | |
| 7-316 | pyrrol-1-yl | H | F | H | Me | Me | |
| 7-317 | pyrrol-1-yl | H | I | H | Me | H | |
| 7-318 | pyrrol-1-yl | H | I | H | Me | Me | |
| 7-319 | pyrrol-1-yl | H | CN | H | Me | H | |
| 7-320 | pyrrol-1-yl | H | CN | H | Me | Me | |
| 7-321 | pyrrol-1-yl | H | CF$_3$ | H | Me | H | |
| 7-322 | pyrrol-1-yl | H | CF$_3$ | H | Me | Me | |
| 7-323 | pyrrol-1-yl | F | Cl | H | Me | H | |

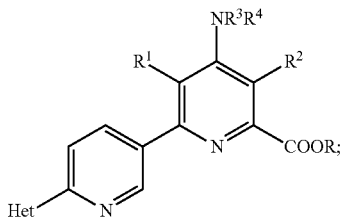

TABLE 7-continued

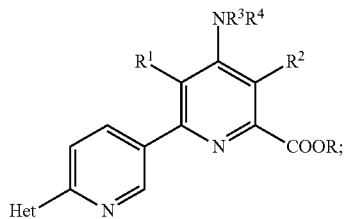

(i-vii)

| No. | Het | R¹ | R² | R³ | R⁴ | R | Physical data: ¹H NMR: δ [CDCl₃] |
|---|---|---|---|---|---|---|---|
| 7-324 | pyrrol-1-yl | F | Cl | H | Me | Me | |
| 7-325 | pyrrol-1-yl | F | Cl | H | Me | Et | |
| 7-326 | pyrrol-1-yl | F | Br | H | Me | H | |
| 7-327 | pyrrol-1-yl | F | Br | H | Me | Me | |
| 7-328 | pyrrol-1-yl | F | Br | H | Me | Et | |
| 7-329 | pyrrol-1-yl | F | F | H | Me | H | |
| 7-330 | pyrrol-1-yl | F | F | H | Me | Me | |
| 7-331 | pyrrol-1-yl | F | I | H | Me | H | |
| 7-332 | pyrrol-1-yl | F | I | H | Me | Me | |
| 7-333 | pyrrol-1-yl | F | CN | H | Me | H | |
| 7-334 | pyrrol-1-yl | F | CN | H | Me | Me | |
| 7-335 | pyrrol-1-yl | F | CF₃ | H | Me | H | |
| 7-336 | pyrrol-1-yl | F | CF₃ | H | Me | Me | |
| 7-337 | pyrrol-1-yl | H | Cl | Me | Me | H | |
| 7-338 | pyrrol-1-yl | H | Cl | Me | Me | Me | |
| 7-339 | pyrrol-1-yl | H | Cl | Me | Me | Et | |
| 7-340 | pyrrol-1-yl | H | Br | Me | Me | H | |
| 7-341 | pyrrol-1-yl | H | Br | Me | Me | Me | |
| 7-342 | pyrrol-1-yl | H | Br | Me | Me | Et | |
| 7-343 | pyrrol-1-yl | H | F | Me | Me | H | |
| 7-344 | pyrrol-1-yl | H | F | Me | Me | Me | |
| 7-345 | pyrrol-1-yl | H | I | Me | Me | H | |
| 7-346 | pyrrol-1-yl | H | I | Me | Me | Me | |
| 7-347 | pyrrol-1-yl | H | CN | Me | Me | H | |
| 7-348 | pyrrol-1-yl | H | CN | Me | Me | Me | |
| 7-349 | pyrrol-1-yl | H | CF₃ | Me | Me | H | |
| 7-350 | pyrrol-1-yl | H | CF₃ | Me | Me | Me | |
| 7-351 | pyrrol-1-yl | F | Cl | Me | Me | H | |
| 7-352 | pyrrol-1-yl | F | Cl | Me | Me | Me | |
| 7-353 | pyrrol-1-yl | F | Cl | Me | Me | Et | |
| 7-354 | pyrrol-1-yl | F | Br | Me | Me | H | |
| 7-355 | pyrrol-1-yl | F | Br | Me | Me | Me | |
| 7-356 | pyrrol-1-yl | F | Br | Me | Me | Et | |
| 7-357 | pyrrol-1-yl | F | F | Me | Me | H | |
| 7-358 | pyrrol-1-yl | F | F | Me | Me | Me | |
| 7-359 | pyrrol-1-yl | F | I | Me | Me | H | |
| 7-360 | pyrrol-1-yl | F | I | Me | Me | Me | |
| 7-361 | pyrrol-1-yl | F | CN | Me | Me | H | |
| 7-362 | pyrrol-1-yl | F | CN | Me | Me | Me | |
| 7-363 | pyrrol-1-yl | F | CF₃ | Me | Me | H | |
| 7-364 | pyrrol-1-yl | F | CF₃ | Me | Me | Me | |
| 7-365 | pyrrol-1-yl | H | Cl | =CHNMe₂ | | H | |
| 7-366 | pyrrol-1-yl | H | Cl | =CHNMe₂ | | Me | |
| 7-367 | pyrrol-1-yl | H | Cl | =CHNMe₂ | | Et | |
| 7-368 | pyrrol-1-yl | H | Br | =CHNMe₂ | | H | |
| 7-369 | pyrrol-1-yl | H | Br | =CHNMe₂ | | Me | |
| 7-370 | pyrrol-1-yl | H | Br | =CHNMe₂ | | Et | |
| 7-371 | pyrrol-1-yl | H | F | =CHNMe₂ | | H | |
| 7-372 | pyrrol-1-yl | H | F | =CHNMe₂ | | Me | |
| 7-373 | pyrrol-1-yl | H | I | =CHNMe₂ | | H | |
| 7-374 | pyrrol-1-yl | H | I | =CHNMe₂ | | Me | |
| 7-375 | pyrrol-1-yl | H | CN | =CHNMe₂ | | H | |
| 7-376 | pyrrol-1-yl | H | CN | =CHNMe₂ | | Me | |
| 7-377 | pyrrol-1-yl | H | CF₃ | =CHNMe₂ | | H | |
| 7-378 | pyrrol-1-yl | H | CF₃ | =CHNMe₂ | | Me | |
| 7-379 | pyrrol-1-yl | F | Cl | =CHNMe₂ | | H | |
| 7-380 | pyrrol-1-yl | F | Cl | =CHNMe₂ | | Me | |
| 7-381 | pyrrol-1-yl | F | Cl | =CHNMe₂ | | Et | |
| 7-382 | pyrrol-1-yl | F | Br | =CHNMe₂ | | H | |
| 7-383 | pyrrol-1-yl | F | Br | =CHNMe₂ | | Me | |
| 7-384 | pyrrol-1-yl | F | Br | =CHNMe₂ | | Et | |
| 7-385 | pyrrol-1-yl | F | F | =CHNMe₂ | | H | |
| 7-386 | pyrrol-1-yl | F | F | =CHNMe₂ | | Me | |
| 7-387 | pyrrol-1-yl | F | I | =CHNMe₂ | | H | |
| 7-388 | pyrrol-1-yl | F | I | =CHNMe₂ | | Me | |
| 7-389 | pyrrol-1-yl | F | CN | =CHNMe₂ | | H | |
| 7-390 | pyrrol-1-yl | F | CN | =CHNMe₂ | | Me | |
| 7-391 | pyrrol-1-yl | F | CF₃ | =CHNMe₂ | | H | |
| 7-392 | pyrrol-1-yl | F | CF₃ | =CHNMe₂ | | Me | |
| 7-393 | pyrazol-1-yl | H | Cl | H | H | H | |
| 7-394 | pyrazol-1-yl | H | Cl | H | H | Me | |
| 7-395 | pyrazol-1-yl | H | Cl | H | H | Et | |
| 7-396 | pyrazol-1-yl | H | Br | H | H | H | |
| 7-397 | pyrazol-1-yl | H | Br | H | H | Me | |
| 7-398 | pyrazol-1-yl | H | Br | H | H | Et | |
| 7-399 | pyrazol-1-yl | H | F | H | H | H | |
| 7-400 | pyrazol-1-yl | H | F | H | H | Me | |
| 7-401 | pyrazol-1-yl | H | I | H | H | H | |
| 7-402 | pyrazol-1-yl | H | I | H | H | Me | |
| 7-403 | pyrazol-1-yl | H | CN | H | H | H | |
| 7-404 | pyrazol-1-yl | H | CN | H | H | Me | |
| 7-405 | pyrazol-1-yl | H | CF₃ | H | H | H | |
| 7-406 | pyrazol-1-yl | H | CF₃ | H | H | Me | |
| 7-407 | pyrazol-1-yl | F | Cl | H | H | H | |
| 7-408 | pyrazol-1-yl | F | Cl | H | H | Me | |
| 7-409 | pyrazol-1-yl | F | Cl | H | H | Et | |
| 7-410 | pyrazol-1-yl | F | Br | H | H | H | |
| 7-411 | pyrazol-1-yl | F | Br | H | H | Me | |
| 7-412 | pyrazol-1-yl | F | Br | H | H | Et | |
| 7-413 | pyrazol-1-yl | F | F | H | H | H | |
| 7-414 | pyrazol-1-yl | F | F | H | H | Me | |
| 7-415 | pyrazol-1-yl | F | I | H | H | H | |
| 7-416 | pyrazol-1-yl | F | I | H | H | Me | |
| 7-417 | pyrazol-1-yl | F | CN | H | H | H | |
| 7-418 | pyrazol-1-yl | F | CN | H | H | Me | |
| 7-419 | pyrazol-1-yl | F | CF₃ | H | H | H | |
| 7-420 | pyrazol-1-yl | F | CF₃ | H | H | Me | |
| 7-421 | pyrazol-1-yl | H | Cl | H | Me | H | |
| 7-422 | pyrazol-1-yl | H | Cl | H | Me | Me | |
| 7-423 | pyrazol-1-yl | H | Cl | H | Me | Et | |
| 7-424 | pyrazol-1-yl | H | Br | H | Me | H | |
| 7-425 | pyrazol-1-yl | H | Br | H | Me | Me | |
| 7-426 | pyrazol-1-yl | H | Br | H | Me | Et | |
| 7-427 | pyrazol-1-yl | H | F | H | Me | H | |
| 7-428 | pyrazol-1-yl | H | F | H | Me | Me | |
| 7-429 | pyrazol-1-yl | H | I | H | Me | H | |
| 7-430 | pyrazol-1-yl | H | I | H | Me | Me | |
| 7-431 | pyrazol-1-yl | H | CN | H | Me | H | |
| 7-432 | pyrazol-1-yl | H | CN | H | Me | Me | |
| 7-433 | pyrazol-1-yl | H | CF₃ | H | Me | H | |
| 7-434 | pyrazol-1-yl | H | CF₃ | H | Me | Me | |
| 7-435 | pyrazol-1-yl | F | Cl | H | Me | H | |
| 7-436 | pyrazol-1-yl | F | Cl | H | Me | Me | |
| 7-437 | pyrazol-1-yl | F | Cl | H | Me | Et | |
| 7-438 | pyrazol-1-yl | F | Br | H | Me | H | |
| 7-439 | pyrazol-1-yl | F | Br | H | Me | Me | |
| 7-440 | pyrazol-1-yl | F | Br | H | Me | Et | |
| 7-441 | pyrazol-1-yl | F | F | H | Me | H | |
| 7-442 | pyrazol-1-yl | F | F | H | Me | Me | |
| 7-443 | pyrazol-1-yl | F | I | H | Me | H | |
| 7-444 | pyrazol-1-yl | F | I | H | Me | Me | |
| 7-445 | pyrazol-1-yl | F | CN | H | Me | H | |
| 7-446 | pyrazol-1-yl | F | CN | H | Me | Me | |
| 7-447 | pyrazol-1-yl | F | CF₃ | H | Me | H | |
| 7-448 | pyrazol-1-yl | F | CF₃ | H | Me | Me | |
| 7-449 | pyrazol-1-yl | H | Cl | Me | Me | H | |

TABLE 7-continued

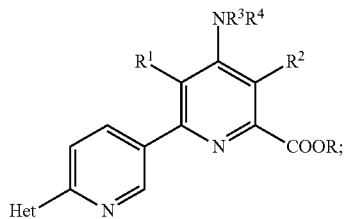

(i-vii)

| No. | Het | R¹ | R² | R³ | R⁴ | R | Physical data: ¹H NMR: δ [CDCl₃] |
|---|---|---|---|---|---|---|---|
| 7-450 | pyrazol-1-yl | H | Cl | Me | Me | Me | |
| 7-451 | pyrazol-1-yl | H | Cl | Me | Me | Et | |
| 7-452 | pyrazol-1-yl | H | Br | Me | Me | H | |
| 7-453 | pyrazol-1-yl | H | Br | Me | Me | Me | |
| 7-454 | pyrazol-1-yl | H | Br | Me | Me | Et | |
| 7-455 | pyrazol-1-yl | H | F | Me | Me | H | |
| 7-456 | pyrazol-1-yl | H | F | Me | Me | Me | |
| 7-457 | pyrazol-1-yl | H | I | Me | Me | H | |
| 7-458 | pyrazol-1-yl | H | I | Me | Me | Me | |
| 7-459 | pyrazol-1-yl | H | CN | Me | Me | H | |
| 7-460 | pyrazol-1-yl | H | CN | Me | Me | Me | |
| 7-461 | pyrazol-1-yl | H | CF₃ | Me | Me | H | |
| 7-462 | pyrazol-1-yl | H | CF₃ | Me | Me | Me | |
| 7-463 | pyrazol-1-yl | F | Cl | Me | Me | H | |
| 7-464 | pyrazol-1-yl | F | Cl | Me | Me | Me | |
| 7-465 | pyrazol-1-yl | F | Cl | Me | Me | Et | |
| 7-466 | pyrazol-1-yl | F | Br | Me | Me | H | |
| 7-467 | pyrazol-1-yl | F | Br | Me | Me | Me | |
| 7-468 | pyrazol-1-yl | F | Br | Me | Me | Et | |
| 7-469 | pyrazol-1-yl | F | F | Me | Me | H | |
| 7-470 | pyrazol-1-yl | F | F | Me | Me | Me | |
| 7-471 | pyrazol-1-yl | F | I | Me | Me | H | |
| 7-472 | pyrazol-1-yl | F | I | Me | Me | Me | |
| 7-473 | pyrazol-1-yl | F | CN | Me | Me | H | |
| 7-474 | pyrazol-1-yl | F | CN | Me | Me | Me | |
| 7-475 | pyrazol-1-yl | F | CF₃ | Me | Me | H | |
| 7-476 | pyrazol-1-yl | F | CF₃ | Me | Me | Me | |
| 7-477 | pyrazol-1-yl | H | Cl | =CHNMe₂ | | H | |
| 7-478 | pyrazol-1-yl | H | Cl | =CHNMe₂ | | Me | |
| 7-479 | pyrazol-1-yl | H | Cl | =CHNMe₂ | | Et | |
| 7-480 | pyrazol-1-yl | H | Br | =CHNMe₂ | | H | |
| 7-481 | pyrazol-1-yl | H | Br | =CHNMe₂ | | Me | |
| 7-482 | pyrazol-1-yl | H | Br | =CHNMe₂ | | Et | |
| 7-483 | pyrazol-1-yl | H | F | =CHNMe₂ | | H | |
| 7-484 | pyrazol-1-yl | H | F | =CHNMe₂ | | Me | |
| 7-485 | pyrazol-1-yl | H | I | =CHNMe₂ | | H | |
| 7-486 | pyrazol-1-yl | H | I | =CHNMe₂ | | Me | |
| 7-487 | pyrazol-1-yl | H | CN | =CHNMe₂ | | H | |
| 7-488 | pyrazol-1-yl | H | CN | =CHNMe₂ | | Me | |
| 7-489 | pyrazol-1-yl | H | CF₃ | =CHNMe₂ | | H | |
| 7-490 | pyrazol-1-yl | H | CF₃ | =CHNMe₂ | | Me | |
| 7-491 | pyrazol-1-yl | F | Cl | =CHNMe₂ | | H | |
| 7-492 | pyrazol-1-yl | F | Cl | =CHNMe₂ | | Me | |
| 7-493 | pyrazol-1-yl | F | Cl | =CHNMe₂ | | Et | |
| 7-494 | pyrazol-1-yl | F | Br | =CHNMe₂ | | H | |
| 7-495 | pyrazol-1-yl | F | Br | =CHNMe₂ | | Me | |
| 7-496 | pyrazol-1-yl | F | Br | =CHNMe₂ | | Et | |
| 7-497 | pyrazol-1-yl | F | F | =CHNMe₂ | | H | |
| 7-498 | pyrazol-1-yl | F | F | =CHNMe₂ | | Me | |
| 7-499 | pyrazol-1-yl | F | I | =CHNMe₂ | | H | |
| 7-500 | pyrazol-1-yl | F | I | =CHNMe₂ | | Me | |
| 7-501 | pyrazol-1-yl | F | CN | =CHNMe₂ | | H | |
| 7-502 | pyrazol-1-yl | F | CN | =CHNMe₂ | | Me | |
| 7-503 | pyrazol-1-yl | F | CF₃ | =CHNMe₂ | | H | |
| 7-504 | pyrazol-1-yl | F | CF₃ | =CHNMe₂ | | Me | |
| 7-505 | pyridin-3-yl | H | Cl | H | H | H | |
| 7-506 | pyridin-3-yl | H | Cl | H | H | Me | |
| 7-507 | pyridin-3-yl | H | Cl | H | H | Et | |
| 7-508 | pyridin-3-yl | H | Br | H | H | H | |
| 7-509 | pyridin-3-yl | H | Br | H | H | Me | |
| 7-510 | pyridin-3-yl | H | Br | H | H | Et | |
| 7-511 | pyridin-3-yl | H | F | H | H | H | |
| 7-512 | pyridin-3-yl | H | F | H | H | Me | |
| 7-513 | pyridin-3-yl | H | I | H | H | H | |
| 7-514 | pyridin-3-yl | H | I | H | H | Me | |
| 7-515 | pyridin-3-yl | H | CN | H | H | H | |
| 7-516 | pyridin-3-yl | H | CN | H | H | Me | |
| 7-517 | pyridin-3-yl | H | CF₃ | H | H | H | |
| 7-518 | pyridin-3-yl | H | CF₃ | H | H | Me | |
| 7-519 | pyridin-3-yl | F | Cl | H | H | H | |
| 7-520 | pyridin-3-yl | F | Cl | H | H | Me | |
| 7-521 | pyridin-3-yl | F | Cl | H | H | Et | |
| 7-522 | pyridin-3-yl | F | Br | H | H | H | |
| 7-523 | pyridin-3-yl | F | Br | H | H | Me | |
| 7-524 | pyridin-3-yl | F | Br | H | H | Et | |
| 7-525 | pyridin-3-yl | F | F | H | H | H | |
| 7-526 | pyridin-3-yl | F | F | H | H | Me | |
| 7-527 | pyridin-3-yl | F | I | H | H | H | |
| 7-528 | pyridin-3-yl | F | I | H | H | Me | |
| 7-529 | pyridin-3-yl | F | CN | H | H | H | |
| 7-530 | pyridin-3-yl | F | CN | H | H | Me | |
| 7-531 | pyridin-3-yl | F | CF₃ | H | H | H | |
| 7-532 | pyridin-3-yl | F | CF₃ | H | H | Me | |
| 7-533 | pyridin-3-yl | H | Cl | H | Me | H | |
| 7-534 | pyridin-3-yl | H | Cl | H | Me | Me | |
| 7-535 | pyridin-3-yl | H | Cl | H | Me | Et | |
| 7-536 | pyridin-3-yl | H | Br | H | Me | H | |
| 7-537 | pyridin-3-yl | H | Br | H | Me | Me | |
| 7-538 | pyridin-3-yl | H | Br | H | Me | Et | |
| 7-539 | pyridin-3-yl | H | F | H | Me | H | |
| 7-540 | pyridin-3-yl | H | F | H | Me | Me | |
| 7-541 | pyridin-3-yl | H | I | H | Me | H | |
| 7-542 | pyridin-3-yl | H | I | H | Me | Me | |
| 7-543 | pyridin-3-yl | H | CN | H | Me | H | |
| 7-544 | pyridin-3-yl | H | CN | H | Me | Me | |
| 7-545 | pyridin-3-yl | H | CF₃ | H | Me | H | |
| 7-546 | pyridin-3-yl | H | CF₃ | H | Me | Me | |
| 7-547 | pyridin-3-yl | F | Cl | H | Me | H | |
| 7-548 | pyridin-3-yl | F | Cl | H | Me | Me | |
| 7-549 | pyridin-3-yl | F | Cl | H | Me | Et | |
| 7-550 | pyridin-3-yl | F | Br | H | Me | H | |
| 7-551 | pyridin-3-yl | F | Br | H | Me | Me | |
| 7-552 | pyridin-3-yl | F | Br | H | Me | Et | |
| 7-553 | pyridin-3-yl | F | F | H | Me | H | |
| 7-554 | pyridin-3-yl | F | F | H | Me | Me | |
| 7-555 | pyridin-3-yl | F | I | H | Me | H | |
| 7-556 | pyridin-3-yl | F | I | H | Me | Me | |
| 7-557 | pyridin-3-yl | F | CN | H | Me | H | |
| 7-558 | pyridin-3-yl | F | CN | H | Me | Me | |
| 7-559 | pyridin-3-yl | F | CF₃ | H | Me | H | |
| 7-560 | pyridin-3-yl | F | CF₃ | H | Me | Me | |
| 7-561 | pyridin-3-yl | H | Cl | Me | Me | H | |
| 7-562 | pyridin-3-yl | H | Cl | Me | Me | Me | |
| 7-563 | pyridin-3-yl | H | Cl | Me | Me | Et | |
| 7-564 | pyridin-3-yl | H | Br | Me | Me | H | |
| 7-565 | pyridin-3-yl | H | Br | Me | Me | Me | |
| 7-566 | pyridin-3-yl | H | Br | Me | Me | Et | |
| 7-567 | pyridin-3-yl | H | F | Me | Me | H | |
| 7-568 | pyridin-3-yl | H | F | Me | Me | Me | |
| 7-569 | pyridin-3-yl | H | I | Me | Me | H | |
| 7-570 | pyridin-3-yl | H | I | Me | Me | Me | |
| 7-571 | pyridin-3-yl | H | CN | Me | Me | H | |
| 7-572 | pyridin-3-yl | H | CN | Me | Me | Me | |
| 7-573 | pyridin-3-yl | H | CF₃ | Me | Me | H | |
| 7-574 | pyridin-3-yl | H | CF₃ | Me | Me | Me | |
| 7-575 | pyridin-3-yl | F | Cl | Me | Me | H | |

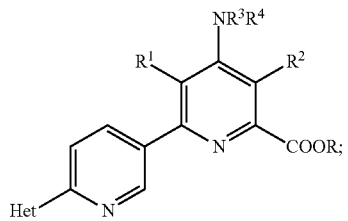

TABLE 7-continued

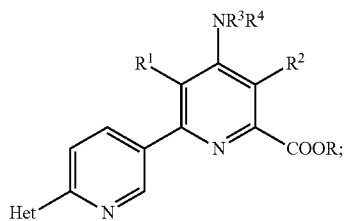

(i-vii)

| No. | Het | $R^1$ | $R^2$ | $R^3$ | $R^4$ | R | Physical data: $^1$H NMR: δ [CDCl$_3$] |
|---|---|---|---|---|---|---|---|
| 7-576 | pyridin-3-yl | F | Cl | Me | Me | Me | |
| 7-577 | pyridin-3-yl | F | Cl | Me | Me | Et | |
| 7-578 | pyridin-3-yl | F | Br | Me | Me | H | |
| 7-579 | pyridin-3-yl | F | Br | Me | Me | Me | |
| 7-580 | pyridin-3-yl | F | Br | Me | Me | Et | |
| 7-581 | pyridin-3-yl | F | F | Me | Me | H | |
| 7-582 | pyridin-3-yl | F | F | Me | Me | Me | |
| 7-583 | pyridin-3-yl | F | I | Me | Me | H | |
| 7-584 | pyridin-3-yl | F | I | Me | Me | Me | |
| 7-585 | pyridin-3-yl | F | CN | Me | Me | H | |
| 7-586 | pyridin-3-yl | F | CN | Me | Me | Me | |
| 7-587 | pyridin-3-yl | F | CF$_3$ | Me | Me | H | |
| 7-588 | pyridin-3-yl | F | CF$_3$ | Me | Me | Me | |
| 7-589 | pyridin-3-yl | H | Cl | =CHNMe$_2$ | | H | |
| 7-590 | pyridin-3-yl | H | Cl | =CHNMe$_2$ | | Me | |
| 7-591 | pyridin-3-yl | H | Cl | =CHNMe$_2$ | | Et | |
| 7-592 | pyridin-3-yl | H | Br | =CHNMe$_2$ | | H | |
| 7-593 | pyridin-3-yl | H | Br | =CHNMe$_2$ | | Me | |
| 7-594 | pyridin-3-yl | H | Br | =CHNMe$_2$ | | Et | |
| 7-595 | pyridin-3-yl | H | F | =CHNMe$_2$ | | H | |
| 7-596 | pyridin-3-yl | H | F | =CHNMe$_2$ | | Me | |
| 7-597 | pyridin-3-yl | H | I | =CHNMe$_2$ | | H | |
| 7-598 | pyridin-3-yl | H | I | =CHNMe$_2$ | | Me | |
| 7-599 | pyridin-3-yl | H | CN | =CHNMe$_2$ | | H | |
| 7-600 | pyridin-3-yl | H | CN | =CHNMe$_2$ | | Me | |
| 7-601 | pyridin-3-yl | H | CF$_3$ | =CHNMe$_2$ | | H | |
| 7-602 | pyridin-3-yl | H | CF$_3$ | =CHNMe$_2$ | | Me | |
| 7-603 | pyridin-3-yl | F | Cl | =CHNMe$_2$ | | H | |
| 7-604 | pyridin-3-yl | F | Cl | =CHNMe$_2$ | | Me | |
| 7-605 | pyridin-3-yl | F | Cl | =CHNMe$_2$ | | Et | |
| 7-606 | pyridin-3-yl | F | Br | =CHNMe$_2$ | | H | |
| 7-607 | pyridin-3-yl | F | Br | =CHNMe$_2$ | | Me | |
| 7-608 | pyridin-3-yl | F | Br | =CHNMe$_2$ | | Et | |
| 7-609 | pyridin-3-yl | F | F | =CHNMe$_2$ | | H | |
| 7-610 | pyridin-3-yl | F | F | =CHNMe$_2$ | | Me | |
| 7-611 | pyridin-3-yl | F | I | =CHNMe$_2$ | | H | |
| 7-612 | pyridin-3-yl | F | I | =CHNMe$_2$ | | Me | |
| 7-613 | pyridin-3-yl | F | CN | =CHNMe$_2$ | | H | |
| 7-614 | pyridin-3-yl | F | CN | =CHNMe$_2$ | | Me | |
| 7-615 | pyridin-3-yl | F | CF$_3$ | =CHNMe$_2$ | | H | |
| 7-616 | pyridin-3-yl | F | CF$_3$ | =CHNMe$_2$ | | Me | |
| 7-617 | oxiranyl | H | Cl | H | H | H | |
| 7-618 | oxiranyl | H | Cl | H | H | Me | |
| 7-619 | oxiranyl | H | Cl | H | H | Et | |
| 7-620 | oxiranyl | H | Br | H | H | H | |
| 7-621 | oxiranyl | H | Br | H | H | Me | |
| 7-622 | oxiranyl | H | Br | H | H | Et | |
| 7-623 | oxiranyl | H | F | H | H | H | |
| 7-624 | oxiranyl | H | F | H | H | Me | |
| 7-625 | oxiranyl | H | I | H | H | H | |
| 7-626 | oxiranyl | H | I | H | H | Me | |
| 7-627 | oxiranyl | H | CN | H | H | H | |
| 7-628 | oxiranyl | H | CN | H | H | Me | |
| 7-629 | oxiranyl | H | CF$_3$ | H | H | H | |
| 7-630 | oxiranyl | H | CF$_3$ | H | H | Me | |
| 7-631 | oxiranyl | F | Cl | H | H | H | |
| 7-632 | oxiranyl | F | Cl | H | H | Me | |
| 7-633 | oxiranyl | F | Cl | H | H | Et | |
| 7-634 | oxiranyl | F | Br | H | H | H | |
| 7-635 | oxiranyl | F | Br | H | H | Me | |
| 7-636 | oxiranyl | F | Br | H | H | Et | |
| 7-637 | oxiranyl | F | F | H | H | H | |
| 7-638 | oxiranyl | F | F | H | H | Me | |
| 7-639 | oxiranyl | F | I | H | H | H | |
| 7-640 | oxiranyl | F | I | H | H | Me | |
| 7-641 | oxiranyl | F | CN | H | H | H | |
| 7-642 | oxiranyl | F | CN | H | H | Me | |
| 7-643 | oxiranyl | F | CF$_3$ | H | H | H | |
| 7-644 | oxiranyl | F | CF$_3$ | H | H | Me | |
| 7-645 | oxiranyl | H | Cl | H | Me | H | |
| 7-646 | oxiranyl | H | Cl | H | Me | Me | |
| 7-647 | oxiranyl | H | Cl | H | Me | Et | |
| 7-648 | oxiranyl | H | Br | H | Me | H | |
| 7-649 | oxiranyl | H | Br | H | Me | Me | |
| 7-650 | oxiranyl | H | Br | H | Me | Et | |
| 7-651 | oxiranyl | H | F | H | Me | H | |
| 7-652 | oxiranyl | H | F | H | Me | Me | |
| 7-653 | oxiranyl | H | I | H | Me | H | |
| 7-654 | oxiranyl | H | I | H | Me | Me | |
| 7-655 | oxiranyl | H | CN | H | Me | H | |
| 7-656 | oxiranyl | H | CN | H | Me | Me | |
| 7-657 | oxiranyl | H | CF$_3$ | H | Me | H | |
| 7-658 | oxiranyl | H | CF$_3$ | H | Me | Me | |
| 7-659 | oxiranyl | F | Cl | H | Me | H | |
| 7-660 | oxiranyl | F | Cl | H | Me | Me | |
| 7-661 | oxiranyl | F | Cl | H | Me | Et | |
| 7-662 | oxiranyl | F | Br | H | Me | H | |
| 7-663 | oxiranyl | F | Br | H | Me | Me | |
| 7-664 | oxiranyl | F | Br | H | Me | Et | |
| 7-665 | oxiranyl | F | F | H | Me | H | |
| 7-666 | oxiranyl | F | F | H | Me | Me | |
| 7-667 | oxiranyl | F | I | H | Me | H | |
| 7-668 | oxiranyl | F | I | H | Me | Me | |
| 7-669 | oxiranyl | F | CN | H | Me | H | |
| 7-670 | oxiranyl | F | CN | H | Me | Me | |
| 7-671 | oxiranyl | F | CF$_3$ | H | Me | H | |
| 7-672 | oxiranyl | F | CF$_3$ | H | Me | Me | |
| 7-673 | oxiranyl | H | Cl | Me | Me | H | |
| 7-674 | oxiranyl | H | Cl | Me | Me | Me | |
| 7-675 | oxiranyl | H | Cl | Me | Me | Et | |
| 7-676 | oxiranyl | H | Br | Me | Me | H | |
| 7-677 | oxiranyl | H | Br | Me | Me | Me | |
| 7-678 | oxiranyl | H | Br | Me | Me | Et | |
| 7-679 | oxiranyl | H | F | Me | Me | H | |
| 7-680 | oxiranyl | H | F | Me | Me | Me | |
| 7-681 | oxiranyl | H | I | Me | Me | H | |
| 7-682 | oxiranyl | H | I | Me | Me | Me | |
| 7-683 | oxiranyl | H | CN | Me | Me | H | |
| 7-684 | oxiranyl | H | CN | Me | Me | Me | |
| 7-685 | oxiranyl | H | CF$_3$ | Me | Me | H | |
| 7-686 | oxiranyl | H | CF$_3$ | Me | Me | Me | |
| 7-687 | oxiranyl | F | Cl | Me | Me | H | |
| 7-688 | oxiranyl | F | Cl | Me | Me | Me | |
| 7-689 | oxiranyl | F | Cl | Me | Me | Et | |
| 7-690 | oxiranyl | F | Br | Me | Me | H | |
| 7-691 | oxiranyl | F | Br | Me | Me | Me | |
| 7-692 | oxiranyl | F | Br | Me | Me | Et | |
| 7-693 | oxiranyl | F | F | Me | Me | H | |
| 7-694 | oxiranyl | F | F | Me | Me | Me | |
| 7-695 | oxiranyl | F | I | Me | Me | H | |
| 7-696 | oxiranyl | F | I | Me | Me | Me | |
| 7-697 | oxiranyl | F | CN | Me | Me | H | |
| 7-698 | oxiranyl | F | CN | Me | Me | Me | |
| 7-699 | oxiranyl | F | CF$_3$ | Me | Me | H | |
| 7-700 | oxiranyl | F | CF$_3$ | Me | Me | Me | |
| 7-701 | oxiranyl | H | Cl | =CHNMe$_2$ | | H | |

TABLE 7-continued

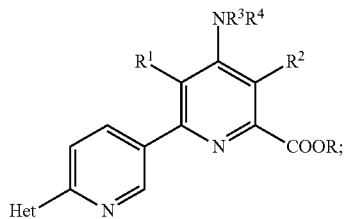

| No. | Het | R¹ | R² | R³ | R⁴ | R | Physical data: ¹H NMR: δ [CDCl₃] |
|---|---|---|---|---|---|---|---|
| 7-702 | oxiranyl | H | Cl | =CHNMe₂ | | Me | |
| 7-703 | oxiranyl | H | Cl | =CHNMe₂ | | Et | |
| 7-704 | oxiranyl | H | Br | =CHNMe₂ | | H | |
| 7-705 | oxiranyl | H | Br | =CHNMe₂ | | Me | |
| 7-706 | oxiranyl | H | Br | =CHNMe₂ | | Et | |
| 7-707 | oxiranyl | H | F | =CHNMe₂ | | H | |
| 7-708 | oxiranyl | H | F | =CHNMe₂ | | Me | |
| 7-709 | oxiranyl | H | I | =CHNMe₂ | | H | |
| 7-710 | oxiranyl | H | I | =CHNMe₂ | | Me | |
| 7-711 | oxiranyl | H | CN | =CHNMe₂ | | H | |
| 7-712 | oxiranyl | H | CN | =CHNMe₂ | | Me | |
| 7-713 | oxiranyl | H | CF₃ | =CHNMe₂ | | H | |
| 7-714 | oxiranyl | H | CF₃ | =CHNMe₂ | | Me | |
| 7-715 | oxiranyl | F | Cl | =CHNMe₂ | | H | |
| 7-716 | oxiranyl | F | Cl | =CHNMe₂ | | Me | |
| 7-717 | oxiranyl | F | Cl | =CHNMe₂ | | Et | |
| 7-718 | oxiranyl | F | Br | =CHNMe₂ | | H | |
| 7-719 | oxiranyl | F | Br | =CHNMe₂ | | Me | |
| 7-720 | oxiranyl | F | Br | =CHNMe₂ | | Et | |
| 7-721 | oxiranyl | F | F | =CHNMe₂ | | H | |
| 7-722 | oxiranyl | F | F | =CHNMe₂ | | Me | |
| 7-723 | oxiranyl | F | I | =CHNMe₂ | | H | |
| 7-724 | oxiranyl | F | I | =CHNMe₂ | | Me | |
| 7-725 | oxiranyl | F | CN | =CHNMe₂ | | H | |
| 7-726 | oxiranyl | F | CN | =CHNMe₂ | | Me | |
| 7-727 | oxiranyl | F | CF₃ | =CHNMe₂ | | H | |
| 7-728 | oxiranyl | F | CF₃ | =CHNMe₂ | | Me | |
| 7-729 | 3,3-dimethyl-oxetan-2-yl | H | Cl | H | H | H | |
| 7-730 | 3,3-dimethyl-oxetan-2-yl | H | Cl | H | H | Me | |
| 7-731 | 3,3-dimethyl-oxetan-2-yl | H | Cl | H | H | Et | |
| 7-732 | 3,3-dimethyl-oxetan-2-yl | H | Br | H | H | H | |
| 7-733 | 3,3-dimethyl-oxetan-2-yl | H | Br | H | H | Me | |
| 7-734 | 3,3-dimethyl-oxetan-2-yl | H | Br | H | H | Et | |
| 7-735 | 3,3-dimethyl-oxetan-2-yl | H | F | H | H | H | |
| 7-736 | 3,3-dimethyl-oxetan-2-yl | H | F | H | H | Me | |
| 7-737 | 3,3-dimethyl-oxetan-2-yl | H | I | H | H | H | |
| 7-738 | 3,3-dimethyl-oxetan-2-yl | H | I | H | H | Me | |
| 7-739 | 3,3-dimethyl-oxetan-2-yl | H | CN | H | H | H | |
| 7-740 | 3,3-dimethyl-oxetan-2-yl | H | CN | H | H | Me | |
| 7-741 | 3,3-dimethyl-oxetan-2-yl | H | CF₃ | H | H | H | |
| 7-742 | 3,3-dimethyl-oxetan-2-yl | H | CF₃ | H | H | Me | |
| 7-743 | 3,3-dimethyl-oxetan-2-yl | F | Cl | H | H | H | |
| 7-744 | 3,3-dimethyl-oxetan-2-yl | F | Cl | H | H | Me | |
| 7-745 | 3,3-dimethyl-oxetan-2-yl | F | Cl | H | H | Et | |
| 7-746 | 3,3-dimethyl-oxetan-2-yl | F | Br | H | H | H | |
| 7-747 | 3,3-dimethyl-oxetan-2-yl | F | Br | H | H | Me | |
| 7-748 | 3,3-dimethyl-oxetan-2-yl | F | Br | H | H | Et | |
| 7-749 | 3,3-dimethyl-oxetan-2-yl | F | F | H | H | H | |
| 7-750 | 3,3-dimethyl-oxetan-2-yl | F | F | H | H | Me | |
| 7-751 | 3,3-dimethyl-oxetan-2-yl | F | I | H | H | H | |
| 7-752 | 3,3-dimethyl-oxetan-2-yl | F | I | H | H | Me | |
| 7-753 | 3,3-dimethyl-oxetan-2-yl | F | CN | H | H | H | |
| 7-754 | 3,3-dimethyl-oxetan-2-yl | F | CN | H | H | Me | |
| 7-755 | 3,3-dimethyl-oxetan-2-yl | F | CF₃ | H | H | H | |
| 7-756 | 3,3-dimethyl-oxetan-2-yl | F | CF₃ | H | H | Me | |
| 7-757 | 3,3-dimethyl-oxetan-2-yl | H | Cl | H | Me | H | |
| 7-758 | 3,3-dimethyl-oxetan-2-yl | H | Cl | H | Me | Me | |
| 7-759 | 3,3-dimethyl-oxetan-2-yl | H | Cl | H | Me | Et | |
| 7-760 | 3,3-dimethyl-oxetan-2-yl | H | Br | H | Me | H | |
| 7-761 | 3,3-dimethyl-oxetan-2-yl | H | Br | H | Me | Me | |
| 7-762 | 3,3-dimethyl-oxetan-2-yl | H | Br | H | Me | Et | |
| 7-763 | 3,3-dimethyl-oxetan-2-yl | H | F | H | Me | H | |
| 7-764 | 3,3-dimethyl-oxetan-2-yl | H | F | H | Me | Me | |
| 7-765 | 3,3-dimethyl-oxetan-2-yl | H | I | H | Me | H | |
| 7-766 | 3,3-dimethyl-oxetan-2-yl | H | I | H | Me | Me | |
| 7-767 | 3,3-dimethyl-oxetan-2-yl | H | CN | H | Me | H | |
| 7-768 | 3,3-dimethyl-oxetan-2-yl | H | CN | H | Me | Me | |
| 7-769 | 3,3-dimethyl-oxetan-2-yl | H | CF₃ | H | Me | H | |
| 7-770 | 3,3-dimethyl-oxetan-2-yl | H | CF₃ | H | Me | Me | |
| 7-771 | 3,3-dimethyl-oxetan-2-yl | F | Cl | H | Me | H | |
| 7-772 | 3,3-dimethyl-oxetan-2-yl | F | Cl | H | Me | Me | |
| 7-773 | 3,3-dimethyl-oxetan-2-yl | F | Cl | H | Me | Et | |
| 7-774 | 3,3-dimethyl-oxetan-2-yl | F | Br | H | Me | H | |

TABLE 7-continued

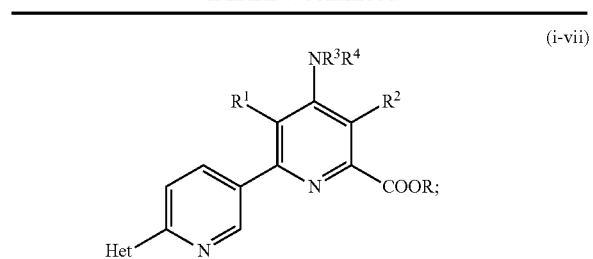

(i-vii)

| No. | Het | $R^1$ | $R^2$ | $R^3$ | $R^4$ | R | Physical data: $^1$H NMR: δ [CDCl$_3$] |
|---|---|---|---|---|---|---|---|
| 7-775 | 3,3-dimethyl-oxetan-2-yl | F | Br | H | Me | Me | |
| 7-776 | 3,3-dimethyl-oxetan-2-yl | F | Br | H | Me | Et | |
| 7-777 | 3,3-dimethyl-oxetan-2-yl | F | F | H | Me | H | |
| 7-778 | 3,3-dimethyl-oxetan-2-yl | F | F | H | Me | Me | |
| 7-779 | 3,3-dimethyl-oxetan-2-yl | F | I | H | Me | H | |
| 7-780 | 3,3-dimethyl-oxetan-2-yl | F | I | H | Me | Me | |
| 7-781 | 3,3-dimethyl-oxetan-2-yl | F | CN | H | Me | H | |
| 7-782 | 3,3-dimethyl-oxetan-2-yl | F | CN | H | Me | Me | |
| 7-783 | 3,3-dimethyl-oxetan-2-yl | F | CF$_3$ | H | Me | H | |
| 7-784 | 3,3-dimethyl-oxetan-2-yl | F | CF$_3$ | H | Me | Me | |
| 7-785 | 3,3-dimethyl-oxetan-2-yl | H | Cl | Me | Me | H | |
| 7-786 | 3,3-dimethyl-oxetan-2-yl | H | Cl | Me | Me | Me | |
| 7-787 | 3,3-dimethyl-oxetan-2-yl | H | Cl | Me | Me | Et | |
| 7-788 | 3,3-dimethyl-oxetan-2-yl | H | Br | Me | Me | H | |
| 7-789 | 3,3-dimethyl-oxetan-2-yl | H | Br | Me | Me | Me | |
| 7-790 | 3,3-dimethyl-oxetan-2-yl | H | Br | Me | Me | Et | |
| 7-791 | 3,3-dimethyl-oxetan-2-yl | H | F | Me | Me | H | |
| 7-792 | 3,3-dimethyl-oxetan-2-yl | H | F | Me | Me | Me | |
| 7-793 | 3,3-dimethyl-oxetan-2-yl | H | I | Me | Me | H | |
| 7-794 | 3,3-dimethyl-oxetan-2-yl | H | I | Me | Me | Me | |
| 7-795 | 3,3-dimethyl-oxetan-2-yl | H | CN | Me | Me | H | |
| 7-796 | 3,3-dimethyl-oxetan-2-yl | H | CN | Me | Me | Me | |
| 7-797 | 3,3-dimethyl-oxetan-2-yl | H | CF$_3$ | Me | Me | H | |
| 7-798 | 3,3-dimethyl-oxetan-2-yl | H | CF$_3$ | Me | Me | Me | |
| 7-799 | 3,3-dimethyl-oxetan-2-yl | F | Cl | Me | Me | H | |
| 7-800 | 3,3-dimethyl-oxetan-2-yl | F | Cl | Me | Me | Me | |
| 7-801 | 3,3-dimethyl-oxetan-2-yl | F | Cl | Me | Me | Et | |
| 7-802 | 3,3-dimethyl-oxetan-2-yl | F | Br | Me | Me | H | |
| 7-803 | 3,3-dimethyl-oxetan-2-yl | F | Br | Me | Me | Me | |
| 7-804 | 3,3-dimethyl-oxetan-2-yl | F | Br | Me | Me | Et | |
| 7-805 | 3,3-dimethyl-oxetan-2-yl | F | F | Me | Me | H | |
| 7-806 | 3,3-dimethyl-oxetan-2-yl | F | F | Me | Me | Me | |
| 7-807 | 3,3-dimethyl-oxetan-2-yl | F | I | Me | Me | H | |
| 7-808 | 3,3-dimethyl-oxetan-2-yl | F | I | Me | Me | Me | |
| 7-809 | 3,3-dimethyl-oxetan-2-yl | F | CN | Me | Me | H | |
| 7-810 | 3,3-dimethyl-oxetan-2-yl | F | CN | Me | Me | Me | |
| 7-811 | 3,3-dimethyl-oxetan-2-yl | F | CF$_3$ | Me | Me | H | |
| 7-812 | 3,3-dimethyl-oxetan-2-yl | F | CF$_3$ | Me | Me | Me | |
| 7-813 | 3,3-dimethyl-oxetan-2-yl | H | Cl | =CHNMe$_2$ | | H | |
| 7-814 | 3,3-dimethyl-oxetan-2-yl | H | Cl | =CHNMe$_2$ | | Me | |
| 7-815 | 3,3-dimethyl-oxetan-2-yl | H | Cl | =CHNMe$_2$ | | Et | |
| 7-816 | 3,3-dimethyl-oxetan-2-yl | H | Br | =CHNMe$_2$ | | H | |
| 7-817 | 3,3-dimethyl-oxetan-2-yl | H | Br | =CHNMe$_2$ | | Me | |
| 7-818 | 3,3-dimethyl-oxetan-2-yl | H | Br | =CHNMe$_2$ | | Et | |
| 7-819 | 3,3-dimethyl-oxetan-2-yl | H | F | =CHNMe$_2$ | | H | |
| 7-820 | 3,3-dimethyl-oxetan-2-yl | H | F | =CHNMe$_2$ | | Me | |
| 7-821 | 3,3-dimethyl-oxetan-2-yl | H | I | =CHNMe$_2$ | | H | |
| 7-822 | 3,3-dimethyl-oxetan-2-yl | H | I | =CHNMe$_2$ | | Me | |
| 7-823 | 3,3-dimethyl-oxetan-2-yl | H | CN | =CHNMe$_2$ | | H | |
| 7-824 | 3,3-dimethyl-oxetan-2-yl | H | CN | =CHNMe$_2$ | | Me | |
| 7-825 | 3,3-dimethyl-oxetan-2-yl | H | CF$_3$ | =CHNMe$_2$ | | H | |
| 7-826 | 3,3-dimethyl-oxetan-2-yl | H | CF$_3$ | =CHNMe$_2$ | | Me | |
| 7-827 | 3,3-dimethyl-oxetan-2-yl | F | Cl | =CHNMe$_2$ | | H | |
| 7-828 | 3,3-dimethyl-oxetan-2-yl | F | Cl | =CHNMe$_2$ | | Me | |
| 7-829 | 3,3-dimethyl-oxetan-2-yl | F | Cl | =CHNMe$_2$ | | Et | |
| 7-830 | 3,3-dimethyl-oxetan-2-yl | F | Br | =CHNMe$_2$ | | H | |
| 7-831 | 3,3-dimethyl-oxetan-2-yl | F | Br | =CHNMe$_2$ | | Me | |
| 7-832 | 3,3-dimethyl-oxetan-2-yl | F | Br | =CHNMe$_2$ | | Et | |
| 7-833 | 3,3-dimethyl-oxetan-2-yl | F | F | =CHNMe$_2$ | | H | |

TABLE 7-continued

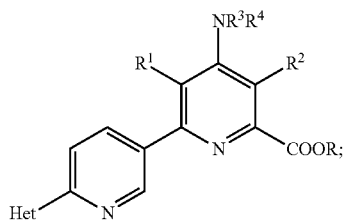

(i-vii)

| No. | Het | R¹ | R² | R³ | R⁴ | R | Physical data: ¹H NMR: δ [CDCl₃] |
|---|---|---|---|---|---|---|---|
| 7-834 | 3,3-dimethyl-oxetan-2-yl | F | F | =CHNMe₂ | | Me | |
| 7-835 | 3,3-dimethyl-oxetan-2-yl | F | I | =CHNMe₂ | | H | |
| 7-836 | 3,3-dimethyl-oxetan-2-yl | F | I | =CHNMe₂ | | Me | |
| 7-837 | 3,3-dimethyl-oxetan-2-yl | F | CN | =CHNMe₂ | | H | |
| 7-838 | 3,3-dimethyl-oxetan-2-yl | F | CN | =CHNMe₂ | | Me | |
| 7-839 | 3,3-dimethyl-oxetan-2-yl | F | CF₃ | =CHNMe₂ | | H | |
| 7-840 | 3,3-dimethyl-oxetan-2-yl | F | CF₃ | =CHNMe₂ | | Me | |
| 7-841 | 2,2-dimethyl-dioxolan-4-yl | H | Cl | H | H | H | |
| 7-842 | 2,2-dimethyl-dioxolan-4-yl | H | Cl | H | H | Me | |
| 7-843 | 2,2-dimethyl-dioxolan-4-yl | H | Cl | H | H | Et | |
| 7-844 | 2,2-dimethyl-dioxolan-4-yl | H | Br | H | H | H | |
| 7-845 | 2,2-dimethyl-dioxolan-4-yl | H | Br | H | H | Me | |
| 7-846 | 2,2-dimethyl-dioxolan-4-yl | H | Br | H | H | Et | |
| 7-847 | 2,2-dimethyl-dioxolan-4-yl | H | F | H | H | H | |
| 7-848 | 2,2-dimethyl-dioxolan-4-yl | H | F | H | H | Me | |
| 7-849 | 2,2-dimethyl-dioxolan-4-yl | H | I | H | H | H | |
| 7-850 | 2,2-dimethyl-dioxolan-4-yl | H | I | H | H | Me | |
| 7-851 | 2,2-dimethyl-dioxolan-4-yl | H | CN | H | H | H | |
| 7-852 | 2,2-dimethyl-dioxolan-4-yl | H | CN | H | H | Me | |
| 7-853 | 2,2-dimethyl-dioxolan-4-yl | H | CF₃ | H | H | H | |
| 7-854 | 2,2-dimethyl-dioxolan-4-yl | H | CF₃ | H | H | Me | |
| 7-855 | 2,2-dimethyl-dioxolan-4-yl | F | Cl | H | H | H | |
| 7-856 | 2,2-dimethyl-dioxolan-4-yl | F | Cl | H | H | Me | |
| 7-857 | 2,2-dimethyl-dioxolan-4-yl | F | Cl | H | H | Et | |
| 7-858 | 2,2-dimethyl-dioxolan-4-yl | F | Br | H | H | H | |
| 7-859 | 2,2-dimethyl-dioxolan-4-yl | F | Br | H | H | Me | |
| 7-860 | 2,2-dimethyl-dioxolan-4-yl | F | Br | H | H | Et | |
| 7-861 | 2,2-dimethyl-dioxolan-4-yl | F | F | H | H | H | |
| 7-862 | 2,2-dimethyl-dioxolan-4-yl | F | F | H | H | Me | |

TABLE 7-continued

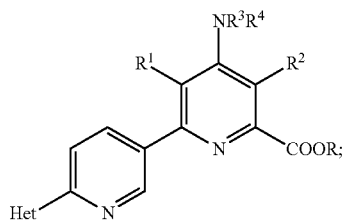

(i-vii)

| No. | Het | R¹ | R² | R³ | R⁴ | R | Physical data: ¹H NMR: δ [CDCl₃] |
|---|---|---|---|---|---|---|---|
| 7-863 | 2,2-dimethyl-dioxolan-4-yl | F | I | H | H | H | |
| 7-864 | 2,2-dimethyl-dioxolan-4-yl | F | I | H | H | Me | |
| 7-865 | 2,2-dimethyl-dioxolan-4-yl | F | CN | H | H | H | |
| 7-866 | 2,2-dimethyl-dioxolan-4-yl | F | CN | H | H | Me | |
| 7-867 | 2,2-dimethyl-dioxolan-4-yl | F | CF₃ | H | H | H | |
| 7-868 | 2,2-dimethyl-dioxolan-4-yl | F | CF₃ | H | H | Me | |
| 7-869 | 2,2-dimethyl-dioxolan-4-yl | H | Cl | H | Me | H | |
| 7-870 | 2,2-dimethyl-dioxolan-4-yl | H | Cl | H | Me | Me | |
| 7-871 | 2,2-dimethyl-dioxolan-4-yl | H | Cl | H | Me | Et | |
| 7-872 | 2,2-dimethyl-dioxolan-4-yl | H | Br | H | Me | H | |
| 7-873 | 2,2-dimethyl-dioxolan-4-yl | H | Br | H | Me | Me | |
| 7-874 | 2,2-dimethyl-dioxolan-4-yl | H | Br | H | Me | Et | |
| 7-875 | 2,2-dimethyl-dioxolan-4-yl | H | F | H | Me | H | |
| 7-876 | 2,2-dimethyl-dioxolan-4-yl | H | F | H | Me | Me | |
| 7-877 | 2,2-dimethyl-dioxolan-4-yl | H | I | H | Me | H | |
| 7-878 | 2,2-dimethyl-dioxolan-4-yl | H | I | H | Me | Me | |
| 7-879 | 2,2-dimethyl-dioxolan-4-yl | H | CN | H | Me | H | |
| 7-880 | 2,2-dimethyl-dioxolan-4-yl | H | CN | H | Me | Me | |
| 7-881 | 2,2-dimethyl-dioxolan-4-yl | H | CF₃ | H | Me | H | |
| 7-882 | 2,2-dimethyl-dioxolan-4-yl | H | CF₃ | H | Me | Me | |
| 7-883 | 2,2-dimethyl-dioxolan-4-yl | F | Cl | H | Me | H | |
| 7-884 | 2,2-dimethyl-dioxolan-4-yl | F | Cl | H | Me | Me | |
| 7-885 | 2,2-dimethyl-dioxolan-4-yl | F | Cl | H | Me | Et | |
| 7-886 | 2,2-dimethyl-dioxolan-4-yl | F | Br | H | Me | H | |
| 7-887 | 2,2-dimethyl-dioxolan-4-yl | F | Br | H | Me | Me | |
| 7-888 | 2,2-dimethyl-dioxolan-4-yl | F | Br | H | Me | Et | |
| 7-889 | 2,2-dimethyl-dioxolan-4-yl | F | F | H | Me | H | |
| 7-890 | 2,2-dimethyl-dioxolan-4-yl | F | F | H | Me | Me | |

TABLE 7-continued (i-vii)

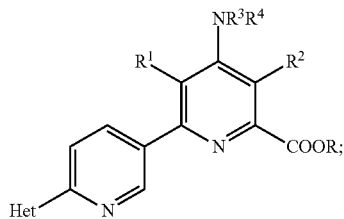
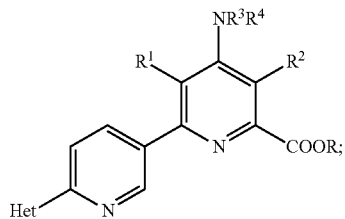

| No. | Het | R¹ | R² | R³ | R⁴ | R | Physical data: ¹H NMR: δ [CDCl₃] |
|---|---|---|---|---|---|---|---|
| 7-891 | 2,2-dimethyl-dioxolan-4-yl | F | I | H | Me | H | |
| 7-892 | 2,2-dimethyl-dioxolan-4-yl | F | I | H | Me | Me | |
| 7-893 | 2,2-dimethyl-dioxolan-4-yl | F | CN | H | Me | H | |
| 7-894 | 2,2-dimethyl-dioxolan-4-yl | F | CN | H | Me | Me | |
| 7-895 | 2,2-dimethyl-dioxolan-4-yl | F | CF₃ | H | Me | H | |
| 7-896 | 2,2-dimethyl-dioxolan-4-yl | F | CF₃ | H | Me | Me | |
| 7-897 | 2,2-dimethyl-dioxolan-4-yl | H | Cl | Me | Me | H | |
| 7-898 | 2,2-dimethyl-dioxolan-4-yl | H | Cl | Me | Me | Me | |
| 7-899 | 2,2-dimethyl-dioxolan-4-yl | H | Cl | Me | Me | Et | |
| 7-900 | 2,2-dimethyl-dioxolan-4-yl | H | Br | Me | Me | H | |
| 7-901 | 2,2-dimethyl-dioxolan-4-yl | H | Br | Me | Me | Me | |
| 7-902 | 2,2-dimethyl-dioxolan-4-yl | H | Br | Me | Me | Et | |
| 7-903 | 2,2-dimethyl-dioxolan-4-yl | H | F | Me | Me | H | |
| 7-904 | 2,2-dimethyl-dioxolan-4-yl | H | F | Me | Me | Me | |
| 7-905 | 2,2-dimethyl-dioxolan-4-yl | H | I | Me | Me | H | |
| 7-906 | 2,2-dimethyl-dioxolan-4-yl | H | I | Me | Me | Me | |
| 7-907 | 2,2-dimethyl-dioxolan-4-yl | H | CN | Me | Me | H | |
| 7-908 | 2,2-dimethyl-dioxolan-4-yl | H | CN | Me | Me | Me | |
| 7-909 | 2,2-dimethyl-dioxolan-4-yl | H | CF₃ | Me | Me | H | |
| 7-910 | 2,2-dimethyl-dioxolan-4-yl | H | CF₃ | Me | Me | Me | |
| 7-911 | 2,2-dimethyl-dioxolan-4-yl | F | Cl | Me | Me | H | |
| 7-912 | 2,2-dimethyl-dioxolan-4-yl | F | Cl | Me | Me | Me | |
| 7-913 | 2,2-dimethyl-dioxolan-4-yl | F | Cl | Me | Me | Et | |
| 7-914 | 2,2-dimethyl-dioxolan-4-yl | F | Br | Me | Me | H | |
| 7-915 | 2,2-dimethyl-dioxolan-4-yl | F | Br | Me | Me | Me | |
| 7-916 | 2,2-dimethyl-dioxolan-4-yl | F | Br | Me | Me | Et | |
| 7-917 | 2,2-dimethyl-dioxolan-4-yl | F | F | Me | Me | H | |
| 7-918 | 2,2-dimethyl-dioxolan-4-yl | F | F | Me | Me | Me | |
| 7-919 | 2,2-dimethyl-dioxolan-4-yl | F | I | Me | Me | H | |
| 7-920 | 2,2-dimethyl-dioxolan-4-yl | F | I | Me | Me | Me | |
| 7-921 | 2,2-dimethyl-dioxolan-4-yl | F | CN | Me | Me | H | |
| 7-922 | 2,2-dimethyl-dioxolan-4-yl | F | CN | Me | Me | Me | |
| 7-923 | 2,2-dimethyl-dioxolan-4-yl | F | CF₃ | Me | Me | H | |
| 7-924 | 2,2-dimethyl-dioxolan-4-yl | F | CF₃ | Me | Me | Me | |
| 7-925 | 2,2-dimethyl-dioxolan-4-yl | H | Cl | =CHNMe₂ | | H | |
| 7-926 | 2,2-dimethyl-dioxolan-4-yl | H | Cl | =CHNMe₂ | | Me | |
| 7-927 | 2,2-dimethyl-dioxolan-4-yl | H | Cl | =CHNMe₂ | | Et | |
| 7-928 | 2,2-dimethyl-dioxolan-4-yl | H | Br | =CHNMe₂ | | H | |
| 7-929 | 2,2-dimethyl-dioxolan-4-yl | H | Br | =CHNMe₂ | | Me | |
| 7-930 | 2,2-dimethyl-dioxolan-4-yl | H | Br | =CHNMe₂ | | Et | |
| 7-931 | 2,2-dimethyl-dioxolan-4-yl | H | F | =CHNMe₂ | | H | |
| 7-932 | 2,2-dimethyl-dioxolan-4-yl | H | F | =CHNMe₂ | | Me | |
| 7-933 | 2,2-dimethyl-dioxolan-4-yl | H | I | =CHNMe₂ | | H | |
| 7-934 | 2,2-dimethyl-dioxolan-4-yl | H | I | =CHNMe₂ | | Me | |
| 7-935 | 2,2-dimethyl-dioxolan-4-yl | H | CN | =CHNMe₂ | | H | |
| 7-936 | 2,2-dimethyl-dioxolan-4-yl | H | CN | =CHNMe₂ | | Me | |
| 7-937 | 2,2-dimethyl-dioxolan-4-yl | H | CF₃ | =CHNMe₂ | | H | |
| 7-938 | 2,2-dimethyl-dioxolan-4-yl | H | CF₃ | =CHNMe₂ | | Me | |
| 7-939 | 2,2-dimethyl-dioxolan-4-yl | F | Cl | =CHNMe₂ | | H | |
| 7-940 | 2,2-dimethyl-dioxolan-4-yl | F | Cl | =CHNMe₂ | | Me | |
| 7-941 | 2,2-dimethyl-dioxolan-4-yl | F | Cl | =CHNMe₂ | | Et | |
| 7-942 | 2,2-dimethyl-dioxolan-4-yl | F | Br | =CHNMe₂ | | H | |
| 7-943 | 2,2-dimethyl-dioxolan-4-yl | F | Br | =CHNMe₂ | | Me | |
| 7-944 | 2,2-dimethyl-dioxolan-4-yl | F | Br | =CHNMe₂ | | Et | |
| 7-945 | 2,2-dimethyl-dioxolan-4-yl | F | F | =CHNMe₂ | | H | |
| 7-946 | 2,2-dimethyl-dioxolan-4-yl | F | F | =CHNMe₂ | | Me | |
| 7-947 | 2,2-dimethyl-dioxolan-4-yl | F | I | =CHNMe₂ | | H | |
| 7-948 | 2,2-dimethyl-dioxolan-4-yl | F | I | =CHNMe₂ | | Me | |
| 7-949 | 2,2-dimethyl-dioxolan-4-yl | F | CN | =CHNMe₂ | | H | |
| 7-950 | 2,2-dimethyl-dioxolan-4-yl | F | CN | =CHNMe₂ | | Me | |
| 7-951 | 2,2-dimethyl-dioxolan-4-yl | F | CF₃ | =CHNMe₂ | | H | |
| 7-952 | 2,2-dimethyl-dioxolan-4-yl | F | CF₃ | =CHNMe₂ | | Me | |

TABLE 8

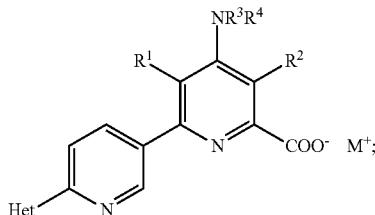

(I-iia)

| No. | Het | R¹ | R² | R³ | R⁴ | M⁺ | Physical data: $^1$H-NMR: δ [CDCl$_3$] |
|---|---|---|---|---|---|---|---|
| 8-1 | 3-tert-butyl-1,2,4-oxadiazol-5-yl | H | Cl | H | H | Na⁺ | |
| 8-2 | 3-tert-butyl-1,2,4-oxadiazol-5-yl | H | Cl | H | H | K⁺ | |
| 8-3 | 3-tert-butyl-1,2,4-oxadiazol-5-yl | H | Cl | H | H | NH$_4^+$ | |
| 8-4 | 3-tert-butyl-1,2,4-oxadiazol-5-yl | H | Br | H | H | Na⁺ | |
| 8-5 | 3-tert-butyl-1,2,4-oxadiazol-5-yl | H | Br | H | H | K⁺ | |
| 8-6 | 3-tert-butyl-1,2,4-oxadiazol-5-yl | H | Br | H | H | NH$_4^+$ | |
| 8-7 | 3-tert-butyl-1,2,4-oxadiazol-5-yl | H | F | H | H | Na⁺ | |
| 8-8 | 3-tert-butyl-1,2,4-oxadiazol-5-yl | H | F | H | H | K⁺ | |
| 8-9 | 3-tert-butyl-1,2,4-oxadiazol-5-yl | H | I | H | H | Na⁺ | |
| 8-10 | 3-tert-butyl-1,2,4-oxadiazol-5-yl | H | I | H | H | K⁺ | |
| 8-11 | 3-tert-butyl-1,2,4-oxadiazol-5-yl | H | CN | H | H | Na⁺ | |
| 8-12 | 3-tert-butyl-1,2,4-oxadiazol-5-yl | H | CN | H | H | K⁺ | |
| 8-13 | 3-tert-butyl-1,2,4-oxadiazol-5-yl | H | CF$_3$ | H | H | Na⁺ | |
| 8-14 | 3-tert-butyl-1,2,4-oxadiazol-5-yl | H | CF$_3$ | H | H | K⁺ | |
| 8-15 | 3-tert-butyl-1,2,4-oxadiazol-5-yl | F | Cl | H | H | Na⁺ | |
| 8-16 | 3-tert-butyl-1,2,4-oxadiazol-5-yl | F | Cl | H | H | K⁺ | |
| 8-17 | 3-tert-butyl-1,2,4-oxadiazol-5-yl | F | Cl | H | H | NH$_4^+$ | |
| 8-18 | 3-tert-butyl-1,2,4-oxadiazol-5-yl | F | Br | H | H | Na⁺ | |
| 8-19 | 3-tert-butyl-1,2,4-oxadiazol-5-yl | F | Br | H | H | K⁺ | |
| 8-20 | 3-tert-butyl-1,2,4-oxadiazol-5-yl | F | Br | H | H | NH$_4^+$ | |
| 8-21 | 3-tert-butyl-1,2,4-oxadiazol-5-yl | F | F | H | H | Na⁺ | |
| 8-22 | 3-tert-butyl-1,2,4-oxadiazol-5-yl | F | F | H | H | K⁺ | |
| 8-23 | 3-tert-butyl-1,2,4-oxadiazol-5-yl | F | I | H | H | Na⁺ | |
| 8-24 | 3-tert-butyl-1,2,4-oxadiazol-5-yl | F | I | H | H | K⁺ | |
| 8-25 | 3-tert-butyl-1,2,4-oxadiazol-5-yl | F | CN | H | H | Na⁺ | |
| 8-26 | 3-tert-butyl-1,2,4-oxadiazol-5-yl | F | CN | H | H | K⁺ | |
| 8-27 | 3-tert-butyl-1,2,4-oxadiazol-5-yl | F | CF$_3$ | H | H | Na⁺ | |
| 8-28 | 3-tert-butyl-1,2,4-oxadiazol-5-yl | F | CF$_3$ | H | H | K⁺ | |
| 8-29 | 3-tert-butyl-1,2,4-oxadiazol-5-yl | Cl | Cl | H | H | Na⁺ | |
| 8-30 | 3-tert-butyl-1,2,4-oxadiazol-5-yl | Cl | Cl | H | H | K⁺ | |
| 8-31 | 3-tert-butyl-1,2,4-oxadiazol-5-yl | Cl | Cl | H | H | NH$_4^+$ | |
| 8-32 | 3-tert-butyl-1,2,4-oxadiazol-5-yl | Cl | Br | H | H | Na⁺ | |
| 8-33 | 3-tert-butyl-1,2,4-oxadiazol-5-yl | Cl | Br | H | H | K⁺ | |
| 8-34 | 3-tert-butyl-1,2,4-oxadiazol-5-yl | Cl | Br | H | H | NH$_4^+$ | |
| 8-35 | 3-tert-butyl-1,2,4-oxadiazol-5-yl | Cl | F | H | H | Na⁺ | |
| 8-36 | 3-tert-butyl-1,2,4-oxadiazol-5-yl | Cl | F | H | H | K⁺ | |
| 8-37 | 3-tert-butyl-1,2,4-oxadiazol-5-yl | Cl | I | H | H | Na⁺ | |
| 8-38 | 3-tert-butyl-1,2,4-oxadiazol-5-yl | Cl | I | H | H | K⁺ | |
| 8-39 | 3-tert-butyl-1,2,4-oxadiazol-5-yl | Cl | CN | H | H | Na⁺ | |
| 8-40 | 3-tert-butyl-1,2,4-oxadiazol-5-yl | Cl | CN | H | H | K⁺ | |
| 8-41 | 3-tert-butyl-1,2,4-oxadiazol-5-yl | Cl | CF$_3$ | H | H | Na⁺ | |
| 8-42 | 3-tert-butyl-1,2,4-oxadiazol-5-yl | Cl | CF$_3$ | H | H | K⁺ | |
| 8-43 | 3-tert-butyl-1,2,4-oxadiazol-5-yl | H | Cl | H | Me | Na⁺ | |
| 8-44 | 3-tert-butyl-1,2,4-oxadiazol-5-yl | H | Cl | H | Me | K⁺ | |
| 8-45 | 3-tert-butyl-1,2,4-oxadiazol-5-yl | H | Cl | H | Me | NH$_4^+$ | |
| 8-46 | 3-tert-butyl-1,2,4-oxadiazol-5-yl | H | Br | H | Me | Na⁺ | |
| 8-47 | 3-tert-butyl-1,2,4-oxadiazol-5-yl | H | Br | H | Me | K⁺ | |
| 8-48 | 3-tert-butyl-1,2,4-oxadiazol-5-yl | H | Br | H | Me | NH$_4^+$ | |
| 8-49 | 3-tert-butyl-1,2,4-oxadiazol-5-yl | H | F | H | Me | Na⁺ | |
| 8-50 | 3-tert-butyl-1,2,4-oxadiazol-5-yl | H | F | H | Me | K⁺ | |
| 8-51 | 3-tert-butyl-1,2,4-oxadiazol-5-yl | H | I | H | Me | Na⁺ | |
| 8-52 | 3-tert-butyl-1,2,4-oxadiazol-5-yl | H | I | H | Me | K⁺ | |
| 8-53 | 3-tert-butyl-1,2,4-oxadiazol-5-yl | H | CN | H | Me | Na⁺ | |
| 8-54 | 3-tert-butyl-1,2,4-oxadiazol-5-yl | H | CN | H | Me | K⁺ | |
| 8-55 | 3-tert-butyl-1,2,4-oxadiazol-5-yl | H | CF$_3$ | H | Me | Na⁺ | |
| 8-56 | 3-tert-butyl-1,2,4-oxadiazol-5-yl | H | CF$_3$ | H | Me | K⁺ | |
| 8-57 | 3-tert-butyl-1,2,4-oxadiazol-5-yl | F | Cl | H | Me | Na⁺ | |
| 8-58 | 3-tert-butyl-1,2,4-oxadiazol-5-yl | F | Cl | H | Me | K⁺ | |
| 8-59 | 3-tert-butyl-1,2,4-oxadiazol-5-yl | F | Cl | H | Me | NH$_4^+$ | |
| 8-60 | 3-tert-butyl-1,2,4-oxadiazol-5-yl | F | Br | H | Me | Na⁺ | |
| 8-61 | 3-tert-butyl-1,2,4-oxadiazol-5-yl | F | Br | H | Me | K⁺ | |
| 8-62 | 3-tert-butyl-1,2,4-oxadiazol-5-yl | F | Br | H | Me | NH$_4^+$ | |
| 8-63 | 3-tert-butyl-1,2,4-oxadiazol-5-yl | F | F | H | Me | Na⁺ | |
| 8-64 | 3-tert-butyl-1,2,4-oxadiazol-5-yl | F | F | H | Me | K⁺ | |

TABLE 8-continued (I-iia)

| No. | Het | R¹ | R² | R³ | R⁴ | M⁺ | Physical data: ¹H-NMR: δ [CDCl₃] |
|---|---|---|---|---|---|---|---|
| 8-65 | 3-tert-butyl-1,2,4-oxadiazol-5-yl | F | I | H | Me | Na⁺ | |
| 8-66 | 3-tert-butyl-1,2,4-oxadiazol-5-yl | F | I | H | Me | K⁺ | |
| 8-67 | 3-tert-butyl-1,2,4-oxadiazol-5-yl | F | CN | H | Me | Na⁺ | |
| 8-68 | 3-tert-butyl-1,2,4-oxadiazol-5-yl | F | CN | H | Me | K⁺ | |
| 8-69 | 3-tert-butyl-1,2,4-oxadiazol-5-yl | F | CF₃ | H | Me | Na⁺ | |
| 8-70 | 3-tert-butyl-1,2,4-oxadiazol-5-yl | F | CF₃ | H | Me | K⁺ | |
| 8-71 | 3-tert-butyl-1,2,4-oxadiazol-5-yl | Cl | Cl | H | Me | Na⁺ | |
| 8-72 | 3-tert-butyl-1,2,4-oxadiazol-5-yl | Cl | Cl | H | Me | K⁺ | |
| 8-73 | 3-tert-butyl-1,2,4-oxadiazol-5-yl | Cl | Cl | H | Me | NH₄⁺ | |
| 8-74 | 3-tert-butyl-1,2,4-oxadiazol-5-yl | Cl | Br | H | Me | Na⁺ | |
| 8-75 | 3-tert-butyl-1,2,4-oxadiazol-5-yl | Cl | Br | H | Me | K⁺ | |
| 8-76 | 3-tert-butyl-1,2,4-oxadiazol-5-yl | Cl | Br | H | Me | NH₄⁺ | |
| 8-77 | 3-tert-butyl-1,2,4-oxadiazol-5-yl | Cl | F | H | Me | Na⁺ | |
| 8-78 | 3-tert-butyl-1,2,4-oxadiazol-5-yl | Cl | F | H | Me | K⁺ | |
| 8-79 | 3-tert-butyl-1,2,4-oxadiazol-5-yl | Cl | I | H | Me | Na⁺ | |
| 8-80 | 3-tert-butyl-1,2,4-oxadiazol-5-yl | Cl | I | H | Me | K⁺ | |
| 8-81 | 3-tert-butyl-1,2,4-oxadiazol-5-yl | Cl | CN | H | Me | Na⁺ | |
| 8-82 | 3-tert-butyl-1,2,4-oxadiazol-5-yl | Cl | CN | H | Me | K⁺ | |
| 8-83 | 3-tert-butyl-1,2,4-oxadiazol-5-yl | Cl | CF₃ | H | Me | Na⁺ | |
| 8-84 | 3-tert-butyl-1,2,4-oxadiazol-5-yl | Cl | CF₃ | H | Me | K⁺ | |
| 8-85 | 3-tert-butyl-1,2,4-oxadiazol-5-yl | H | Cl | Me | Me | Na⁺ | |
| 8-86 | 3-tert-butyl-1,2,4-oxadiazol-5-yl | H | Cl | Me | Me | K⁺ | |
| 8-87 | 3-tert-butyl-1,2,4-oxadiazol-5-yl | H | Cl | Me | Me | NH₄⁺ | |
| 8-88 | 3-tert-butyl-1,2,4-oxadiazol-5-yl | H | Br | Me | Me | Na⁺ | |
| 8-89 | 3-tert-butyl-1,2,4-oxadiazol-5-yl | H | Br | Me | Me | K⁺ | |
| 8-90 | 3-tert-butyl-1,2,4-oxadiazol-5-yl | H | Br | Me | Me | NH₄⁺ | |
| 8-91 | 3-tert-butyl-1,2,4-oxadiazol-5-yl | H | F | Me | Me | Na⁺ | |
| 8-92 | 3-tert-butyl-1,2,4-oxadiazol-5-yl | H | F | Me | Me | K⁺ | |
| 8-93 | 3-tert-butyl-1,2,4-oxadiazol-5-yl | H | I | Me | Me | Na⁺ | |
| 8-94 | 3-tert-butyl-1,2,4-oxadiazol-5-yl | H | I | Me | Me | K⁺ | |
| 8-95 | 3-tert-butyl-1,2,4-oxadiazol-5-yl | H | CN | Me | Me | Na⁺ | |
| 8-96 | 3-tert-butyl-1,2,4-oxadiazol-5-yl | H | CN | Me | Me | K⁺ | |
| 8-97 | 3-tert-butyl-1,2,4-oxadiazol-5-yl | H | CF₃ | Me | Me | Na⁺ | |
| 8-98 | 3-tert-butyl-1,2,4-oxadiazol-5-yl | H | CF₃ | Me | Me | K⁺ | |
| 8-99 | 3-tert-butyl-1,2,4-oxadiazol-5-yl | F | Cl | Me | Me | Na⁺ | |
| 8-100 | 3-tert-butyl-1,2,4-oxadiazol-5-yl | F | Cl | Me | Me | K⁺ | |
| 8-101 | 3-tert-butyl-1,2,4-oxadiazol-5-yl | F | Cl | Me | Me | NH₄⁺ | |
| 8-102 | 3-tert-butyl-1,2,4-oxadiazol-5-yl | F | Br | Me | Me | Na⁺ | |
| 8-103 | 3-tert-butyl-1,2,4-oxadiazol-5-yl | F | Br | Me | Me | K⁺ | |
| 8-104 | 3-tert-butyl-1,2,4-oxadiazol-5-yl | F | Br | Me | Me | NH₄⁺ | |
| 8-105 | 3-tert-butyl-1,2,4-oxadiazol-5-yl | F | F | Me | Me | Na⁺ | |
| 8-106 | 3-tert-butyl-1,2,4-oxadiazol-5-yl | F | F | Me | Me | K⁺ | |
| 8-107 | 3-tert-butyl-1,2,4-oxadiazol-5-yl | F | I | Me | Me | Na⁺ | |
| 8-108 | 3-tert-butyl-1,2,4-oxadiazol-5-yl | F | I | Me | Me | K⁺ | |
| 8-109 | 3-tert-butyl-1,2,4-oxadiazol-5-yl | F | CN | Me | Me | Na⁺ | |
| 8-110 | 3-tert-butyl-1,2,4-oxadiazol-5-yl | F | CN | Me | Me | K⁺ | |
| 8-111 | 3-tert-butyl-1,2,4-oxadiazol-5-yl | F | CF₃ | Me | Me | Na⁺ | |
| 8-112 | 3-tert-butyl-1,2,4-oxadiazol-5-yl | F | CF₃ | Me | Me | K⁺ | |
| 8-113 | 3-tert-butyl-1,2,4-oxadiazol-5-yl | Cl | Cl | Me | Me | Na⁺ | |
| 8-114 | 3-tert-butyl-1,2,4-oxadiazol-5-yl | Cl | Cl | Me | Me | K⁺ | |
| 8-115 | 3-tert-butyl-1,2,4-oxadiazol-5-yl | Cl | Cl | Me | Me | NH₄⁺ | |
| 8-116 | 3-tert-butyl-1,2,4-oxadiazol-5-yl | Cl | Br | Me | Me | Na⁺ | |
| 8-117 | 3-tert-butyl-1,2,4-oxadiazol-5-yl | Cl | Br | Me | Me | K⁺ | |
| 8-118 | 3-tert-butyl-1,2,4-oxadiazol-5-yl | Cl | Br | Me | Me | NH₄⁺ | |
| 8-119 | 3-tert-butyl-1,2,4-oxadiazol-5-yl | Cl | F | Me | Me | Na⁺ | |
| 8-120 | 3-tert-butyl-1,2,4-oxadiazol-5-yl | Cl | F | Me | Me | K⁺ | |
| 8-121 | 3-tert-butyl-1,2,4-oxadiazol-5-yl | Cl | I | Me | Me | Na⁺ | |
| 8-122 | 3-tert-butyl-1,2,4-oxadiazol-5-yl | Cl | I | Me | Me | K⁺ | |
| 8-123 | 3-tert-butyl-1,2,4-oxadiazol-5-yl | Cl | CN | Me | Me | Na⁺ | |
| 8-124 | 3-tert-butyl-1,2,4-oxadiazol-5-yl | Cl | CN | Me | Me | K⁺ | |
| 8-125 | 3-tert-butyl-1,2,4-oxadiazol-5-yl | Cl | CF₃ | Me | Me | Na⁺ | |
| 8-126 | 3-tert-butyl-1,2,4-oxadiazol-5-yl | Cl | CF₃ | Me | Me | K⁺ | |
| 8-127 | 3-tert-butyl-1,2,4-oxadiazol-5-yl | H | Cl | =CHNMe₂ | | Na⁺ | |
| 8-128 | 3-tert-butyl-1,2,4-oxadiazol-5-yl | H | Cl | =CHNMe₂ | | K⁺ | |

TABLE 8-continued

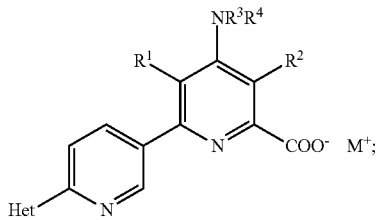

(I-iia)

| No. | Het | R¹ | R² | R³ | R⁴ | M⁺ | Physical data: $^1$H-NMR: δ [CDCl$_3$] |
|---|---|---|---|---|---|---|---|
| 8-129 | 3-tert-butyl-1,2,4-oxadiazol-5-yl | H | Cl | =CHNMe$_2$ | | NH$_4^+$ | |
| 8-130 | 3-tert-butyl-1,2,4-oxadiazol-5-yl | H | Br | =CHNMe$_2$ | | Na$^+$ | |
| 8-131 | 3-tert-butyl-1,2,4-oxadiazol-5-yl | H | Br | =CHNMe$_2$ | | K$^+$ | |
| 8-132 | 3-tert-butyl-1,2,4-oxadiazol-5-yl | H | Br | =CHNMe$_2$ | | NH$_4^+$ | |
| 8-133 | 3-tert-butyl-1,2,4-oxadiazol-5-yl | H | F | =CHNMe$_2$ | | Na$^+$ | |
| 8-134 | 3-tert-butyl-1,2,4-oxadiazol-5-yl | H | F | =CHNMe$_2$ | | K$^+$ | |
| 8-135 | 3-tert-butyl-1,2,4-oxadiazol-5-yl | H | I | =CHNMe$_2$ | | Na$^+$ | |
| 8-136 | 3-tert-butyl-1,2,4-oxadiazol-5-yl | H | I | =CHNMe$_2$ | | K$^+$ | |
| 8-137 | 3-tert-butyl-1,2,4-oxadiazol-5-yl | H | CN | =CHNMe$_2$ | | Na$^+$ | |
| 8-138 | 3-tert-butyl-1,2,4-oxadiazol-5-yl | H | CN | =CHNMe$_2$ | | K$^+$ | |
| 8-139 | 3-tert-butyl-1,2,4-oxadiazol-5-yl | H | CF$_3$ | =CHNMe$_2$ | | Na$^+$ | |
| 8-140 | 3-tert-butyl-1,2,4-oxadiazol-5-yl | H | CF$_3$ | =CHNMe$_2$ | | K$^+$ | |
| 8-141 | 3-tert-butyl-1,2,4-oxadiazol-5-yl | F | Cl | =CHNMe$_2$ | | Na$^+$ | |
| 8-142 | 3-tert-butyl-1,2,4-oxadiazol-5-yl | F | Cl | =CHNMe$_2$ | | K$^+$ | |
| 8-143 | 3-tert-butyl-1,2,4-oxadiazol-5-yl | F | Cl | =CHNMe$_2$ | | NH$_4^+$ | |
| 8-144 | 3-tert-butyl-1,2,4-oxadiazol-5-yl | F | Br | =CHNMe$_2$ | | Na$^+$ | |
| 8-145 | 3-tert-butyl-1,2,4-oxadiazol-5-yl | F | Br | =CHNMe$_2$ | | K$^+$ | |
| 8-146 | 3-tert-butyl-1,2,4-oxadiazol-5-yl | F | Br | =CHNMe$_2$ | | NH$_4^+$ | |
| 8-147 | 3-tert-butyl-1,2,4-oxadiazol-5-yl | F | F | =CHNMe$_2$ | | Na$^+$ | |
| 8-148 | 3-tert-butyl-1,2,4-oxadiazol-5-yl | F | F | =CHNMe$_2$ | | K$^+$ | |
| 8-149 | 3-tert-butyl-1,2,4-oxadiazol-5-yl | F | I | =CHNMe$_2$ | | Na$^+$ | |
| 8-150 | 3-tert-butyl-1,2,4-oxadiazol-5-yl | F | I | =CHNMe$_2$ | | K$^+$ | |
| 8-151 | 3-tert-butyl-1,2,4-oxadiazol-5-yl | F | CN | =CHNMe$_2$ | | Na$^+$ | |
| 8-152 | 3-tert-butyl-1,2,4-oxadiazol-5-yl | F | CN | =CHNMe$_2$ | | K$^+$ | |
| 8-153 | 3-tert-butyl-1,2,4-oxadiazol-5-yl | F | CF$_3$ | =CHNMe$_2$ | | Na$^+$ | |
| 8-154 | 3-tert-butyl-1,2,4-oxadiazol-5-yl | F | CF$_3$ | =CHNMe$_2$ | | K$^+$ | |
| 8-155 | 3-tert-butyl-1,2,4-oxadiazol-5-yl | Cl | Cl | =CHNMe$_2$ | | Na$^+$ | |
| 8-156 | 3-tert-butyl-1,2,4-oxadiazol-5-yl | Cl | Cl | =CHNMe$_2$ | | K$^+$ | |
| 8-157 | 3-tert-butyl-1,2,4-oxadiazol-5-yl | Cl | Cl | =CHNMe$_2$ | | NH$_4^+$ | |
| 8-158 | 3-tert-butyl-1,2,4-oxadiazol-5-yl | Cl | Br | =CHNMe$_2$ | | Na$^+$ | |
| 8-159 | 3-tert-butyl-1,2,4-oxadiazol-5-yl | Cl | Br | =CHNMe$_2$ | | K$^+$ | |
| 8-160 | 3-tert-butyl-1,2,4-oxadiazol-5-yl | Cl | Br | =CHNMe$_2$ | | NH$_4^+$ | |
| 8-161 | 3-tert-butyl-1,2,4-oxadiazol-5-yl | Cl | F | =CHNMe$_2$ | | Na$^+$ | |
| 8-162 | 3-tert-butyl-1,2,4-oxadiazol-5-yl | Cl | F | =CHNMe$_2$ | | K$^+$ | |
| 8-163 | 3-tert-butyl-1,2,4-oxadiazol-5-yl | Cl | I | =CHNMe$_2$ | | Na$^+$ | |
| 8-164 | 3-tert-butyl-1,2,4-oxadiazol-5-yl | Cl | I | =CHNMe$_2$ | | K$^+$ | |
| 8-165 | 3-tert-butyl-1,2,4-oxadiazol-5-yl | Cl | CN | =CHNMe$_2$ | | Na$^+$ | |
| 8-166 | 3-tert-butyl-1,2,4-oxadiazol-5-yl | Cl | CN | =CHNMe$_2$ | | K$^+$ | |
| 8-167 | 3-tert-butyl-1,2,4-oxadiazol-5-yl | Cl | CF$_3$ | =CHNMe$_2$ | | Na$^+$ | |
| 8-168 | 3-tert-butyl-1,2,4-oxadiazol-5-yl | Cl | CF$_3$ | =CHNMe$_2$ | | K$^+$ | |
| 8-169 | thien-2-yl | H | Cl | H | H | Na$^+$ | |
| 8-170 | thien-2-yl | H | Cl | H | H | K$^+$ | |
| 8-171 | thien-2-yl | H | Cl | H | H | NH$_4^+$ | |
| 8-172 | thien-2-yl | H | Br | H | H | Na$^+$ | |
| 8-173 | thien-2-yl | H | Br | H | H | K$^+$ | |
| 8-174 | thien-2-yl | H | Br | H | H | NH$_4^+$ | |
| 8-175 | thien-2-yl | H | F | H | H | Na$^+$ | |
| 8-176 | thien-2-yl | H | F | H | H | K$^+$ | |
| 8-177 | thien-2-yl | H | I | H | H | Na$^+$ | |
| 8-178 | thien-2-yl | H | I | H | H | K$^+$ | |
| 8-179 | thien-2-yl | H | CN | H | H | Na$^+$ | |
| 8-180 | thien-2-yl | H | CN | H | H | K$^+$ | |
| 8-181 | thien-2-yl | H | CF$_3$ | H | H | Na$^+$ | |
| 8-182 | thien-2-yl | H | CF$_3$ | H | H | K$^+$ | |
| 8-183 | thien-2-yl | F | Cl | H | H | Na$^+$ | |
| 8-184 | thien-2-yl | F | Cl | H | H | K$^+$ | |
| 8-185 | thien-2-yl | F | Cl | H | H | NH$_4^+$ | |
| 8-186 | thien-2-yl | F | Br | H | H | Na$^+$ | |
| 8-187 | thien-2-yl | F | Br | H | H | K$^+$ | |
| 8-188 | thien-2-yl | F | Br | H | H | NH$_4^+$ | |
| 8-189 | thien-2-yl | F | F | H | H | Na$^+$ | |
| 8-190 | thien-2-yl | F | F | H | H | K$^+$ | |
| 8-191 | thien-2-yl | F | I | H | H | Na$^+$ | |
| 8-192 | thien-2-yl | F | I | H | H | K$^+$ | |

TABLE 8-continued

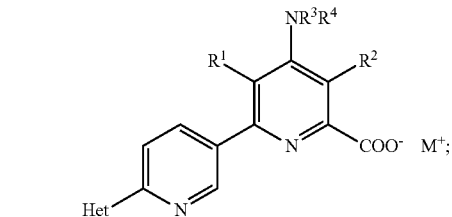

(I-iia)

| No. | Het | $R^1$ | $R^2$ | $R^3$ | $R^4$ | $M^+$ | Physical data: $^1$H-NMR: δ [CDCl$_3$] |
|---|---|---|---|---|---|---|---|
| 8-193 | thien-2-yl | F | CN | H | H | Na$^+$ | |
| 8-194 | thien-2-yl | F | CN | H | H | K$^+$ | |
| 8-195 | thien-2-yl | F | CF$_3$ | H | H | Na$^+$ | |
| 8-196 | thien-2-yl | F | CF$_3$ | H | H | K$^+$ | |
| 8-197 | thien-2-yl | H | Cl | H | Me | Na$^+$ | |
| 8-198 | thien-2-yl | H | Cl | H | Me | K$^+$ | |
| 8-199 | thien-2-yl | H | Cl | H | Me | NH$_4^+$ | |
| 8-200 | thien-2-y! | H | Br | H | Me | Na$^+$ | |
| 8-201 | thien-2-yl | H | Br | H | Me | K$^+$ | |
| 8-202 | thien-2-yl | H | Br | H | Me | NH$_4^+$ | |
| 8-203 | thien-2-yl | H | F | H | Me | Na$^+$ | |
| 8-204 | thien-2-yl | H | F | H | Me | K$^+$ | |
| 8-205 | thien-2-yl | H | I | H | Me | Na$^+$ | |
| 8-206 | thien-2-yl | H | I | H | Me | K$^+$ | |
| 8-207 | thien-2-yl | H | CN | H | Me | Na$^+$ | |
| 8-208 | thien-2-yl | H | CN | H | Me | K$^+$ | |
| 8-209 | thien-2-yl | H | CF$_3$ | H | Me | Na$^+$ | |
| 8-210 | thien-2-yl | H | CF$_3$ | H | Me | K$^+$ | |
| 8-211 | thien-2-yl | F | Cl | H | Me | Na$^+$ | |
| 8-212 | thien-2-yl | F | Cl | H | Me | K$^+$ | |
| 8-213 | thien-2-yl | F | Cl | H | Me | NH$_4^+$ | |
| 8-214 | thien-2-yl | F | Br | H | Me | Na$^+$ | |
| 8-215 | thien-2-yl | F | Br | H | Me | K$^+$ | |
| 8-216 | thien-2-yl | F | Br | H | Me | NH$_4^+$ | |
| 8-217 | thien-2-yl | F | F | H | Me | Na$^+$ | |
| 8-218 | thien-2-yl | F | F | H | Me | K$^+$ | |
| 8-219 | thien-2-yl | F | I | H | Me | Na$^+$ | |
| 8-220 | thien-2-yl | F | I | H | Me | K$^+$ | |
| 8-221 | thien-2-yl | F | CN | H | Me | Na$^+$ | |
| 8-222 | thien-2-yl | F | CN | H | Me | K$^+$ | |
| 8-223 | thien-2-yl | F | CF$_3$ | H | Me | Na$^+$ | |
| 8-224 | thien-2-yl | F | CF$_3$ | H | Me | K$^+$ | |
| 8-225 | thien-2-yl | H | Cl | Me | Me | Na$^+$ | |
| 8-226 | thien-2-yl | H | Cl | Me | Me | K$^+$ | |
| 8-227 | thien-2-yl | H | Cl | Me | Me | NH$_4^+$ | |
| 8-228 | thien-2-yl | H | Br | Me | Me | Na$^+$ | |
| 8-229 | thien-2-yl | H | Br | Me | Me | K$^+$ | |
| 8-230 | thien-2-yl | H | Br | Me | Me | NH$_4^+$ | |
| 8-231 | thien-2-yl | H | F | Me | Me | Na$^+$ | |
| 8-232 | thien-2-yl | H | F | Me | Me | K$^+$ | |
| 8-233 | thien-2-yl | H | I | Me | Me | Na$^+$ | |
| 8-234 | thien-2-yl | H | I | Me | Me | K$^+$ | |
| 8-235 | thien-2-yl | H | CN | Me | Me | Na$^+$ | |
| 8-236 | thien-2-yl | H | CN | Me | Me | K$^+$ | |
| 8-237 | thien-2-yl | H | CF$_3$ | Me | Me | Na$^+$ | |
| 8-238 | thien-2-yl | H | CF$_3$ | Me | Me | K$^+$ | |
| 8-239 | thien-2-yl | F | Cl | Me | Me | Na$^+$ | |
| 8-240 | thien-2-yl | F | Cl | Me | Me | K$^+$ | |
| 8-241 | thien-2-yl | F | Cl | Me | Me | NH$_4^+$ | |
| 8-242 | thien-2-yl | F | Br | Me | Me | Na$^+$ | |
| 8-243 | thien-2-yl | F | Br | Me | Me | K$^+$ | |
| 8-244 | thien-2-yl | F | Br | Me | Me | NH$_4^+$ | |
| 8-245 | thien-2-yl | F | F | Me | Me | Na$^+$ | |
| 8-246 | thien-2-yl | F | F | Me | Me | K$^+$ | |
| 8-247 | thien-2-yl | F | I | Me | Me | Na$^+$ | |
| 8-248 | thien-2-yl | F | I | Me | Me | K$^+$ | |
| 8-249 | thien-2-yl | F | CN | Me | Me | Na$^+$ | |
| 8-250 | thien-2-yl | F | CN | Me | Me | K$^+$ | |
| 8-251 | thien-2-yl | F | CF$_3$ | Me | Me | Na$^+$ | |
| 8-252 | thien-2-yl | F | CF$_3$ | Me | Me | K$^+$ | |
| 8-253 | thien-2-yl | H | Cl | =CHNMe$_2$ | | Na$^+$ | |
| 8-254 | thien-2-yl | H | Cl | =CHNMe$_2$ | | K$^+$ | |
| 8-255 | thien-2-yl | H | Cl | =CHNMe$_2$ | | NH$_4^+$ | |
| 8-256 | thien-2-yl | H | Br | =CHNMe$_2$ | | Na$^+$ | |

TABLE 8-continued

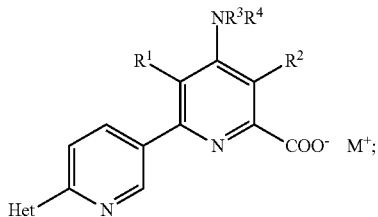

(I-iia)

| No. | Het | R¹ | R² | R³ | R⁴ | M⁺ | Physical data: $^1$H-NMR: δ [CDCl₃] |
|---|---|---|---|---|---|---|---|
| 8-257 | thien-2-yl | H | Br | =CHNMe₂ | | K⁺ | |
| 8-258 | thien-2-yl | H | Br | =CHNMe₂ | | NH₄⁺ | |
| 8-259 | thien-2-yl | H | F | =CHNMe₂ | | Na⁺ | |
| 8-260 | thien-2-yl | H | F | =CHNMe₂ | | K⁺ | |
| 8-261 | thien-2-yl | H | I | =CHNMe₂ | | Na⁺ | |
| 8-262 | thien-2-yl | H | I | =CHNMe₂ | | K⁺ | |
| 8-263 | thien-2-yl | H | CN | =CHNMe₂ | | Na⁺ | |
| 8-264 | thien-2-yl | H | CN | =CHNMe₂ | | K⁺ | |
| 8-265 | thien-2-yl | H | CF₃ | =CHNMe₂ | | Na⁺ | |
| 8-266 | thien-2-yl | H | CF₃ | =CHNMe₂ | | K⁺ | |
| 8-267 | thien-2-yl | F | Cl | =CHNMe₂ | | Na⁺ | |
| 8-268 | thien-2-yl | F | Cl | =CHNMe₂ | | K⁺ | |
| 8-269 | thien-2-yl | F | Cl | =CHNMe₂ | | NH₄⁺ | |
| 8-270 | thien-2-yl | F | Br | =CHNMe₂ | | Na⁺ | |
| 8-271 | thien-2-yl | F | Br | =CHNMe₂ | | K⁺ | |
| 8-272 | thien-2-yl | F | Br | =CHNMe₂ | | NH₄⁺ | |
| 8-273 | thien-2-yl | F | F | =CHNMe₂ | | Na⁺ | |
| 8-274 | thien-2-yl | F | F | =CHNMe₂ | | K⁺ | |
| 8-275 | thien-2-yl | F | I | =CHNMe₂ | | Na⁺ | |
| 8-276 | thien-2-yl | F | I | =CHNMe₂ | | K⁺ | |
| 8-277 | thien-2-yl | F | CN | =CHNMe₂ | | Na⁺ | |
| 8-278 | thien-2-yl | F | CN | =CHNMe₂ | | K⁺ | |
| 8-279 | thien-2-yl | F | CF₃ | =CHNMe₂ | | Na⁺ | |
| 8-280 | thien-2-yl | F | CF₃ | =CHNMe₂ | | K⁺ | |
| 8-281 | pyrrol-1-yl | H | Cl | H | H | Na⁺ | |
| 8-282 | pyrrol-1-yl | H | Cl | H | H | K⁺ | |
| 8-283 | pyrrol-1-yl | H | Cl | H | H | NH₄⁺ | |
| 8-284 | pyrrol-1-yl | H | Br | H | H | Na⁺ | |
| 8-285 | pyrrol-1-yl | H | Br | H | H | K⁺ | |
| 8-286 | pyrrol-1-yl | H | Br | H | H | NH₄⁺ | |
| 8-287 | pyrrol-1-yl | H | F | H | H | Na⁺ | |
| 8-288 | pyrrol-1-yl | H | F | H | H | K⁺ | |
| 8-289 | pyrrol-1-yl | H | I | H | H | Na⁺ | |
| 8-290 | pyrrol-1-yl | H | I | H | H | K⁺ | |
| 8-291 | pyrrol-1-yl | H | CN | H | H | Na⁺ | |
| 8-292 | pyrrol-1-yl | H | CN | H | H | K⁺ | |
| 8-293 | pyrrol-1-yl | H | CF₃ | H | H | Na⁺ | |
| 8-294 | pyrrol-1-yl | H | CF₃ | H | H | K⁺ | |
| 8-295 | pyrrol-1-yl | F | Cl | H | H | Na⁺ | |
| 8-296 | pyrrol-1-yl | F | Cl | H | H | K⁺ | |
| 8-297 | pyrrol-1-yl | F | Cl | H | H | NH₄⁺ | |
| 8-298 | pyrrol-1-yl | F | Br | H | H | Na⁺ | |
| 8-299 | pyrrol-1-yl | F | Br | H | H | K⁺ | |
| 8-300 | pyrrol-1-yl | F | Br | H | H | NH₄⁺ | |
| 8-301 | pyrrol-1-yl | F | F | H | H | Na⁺ | |
| 8-302 | pyrrol-1-yl | F | F | H | H | K⁺ | |
| 8-303 | pyrrol-1-yl | F | I | H | H | Na⁺ | |
| 8-304 | pyrrol-1-yl | F | I | H | H | K⁺ | |
| 8-305 | pyrrol-1-yl | F | CN | H | H | Na⁺ | |
| 8-306 | pyrrol-1-yl | F | CN | H | H | K⁺ | |
| 8-307 | pyrrol-1-yl | F | CF₃ | H | H | Na⁺ | |
| 8-308 | pyrrol-1-yl | F | CF₃ | H | H | K⁺ | |
| 8-309 | pyrrol-1-yl | H | Cl | H | Me | Na⁺ | |
| 8-310 | pyrrol-1-yl | H | Cl | H | Me | K⁺ | |
| 8-311 | pyrrol-1-yl | H | Cl | H | Me | NH₄⁺ | |
| 8-312 | pyrrol-1-yl | H | Br | H | Me | Na⁺ | |
| 8-313 | pyrrol-1-yl | H | Br | H | Me | K⁺ | |
| 8-314 | pyrrol-1-yl | H | Br | H | Me | NH₄⁺ | |
| 8-315 | pyrrol-1-yl | H | F | H | Me | Na⁺ | |
| 8-316 | pyrrol-1-yl | H | F | H | Me | K⁺ | |
| 8-317 | pyrrol-1-yl | H | I | H | Me | Na⁺ | |
| 8-318 | pyrrol-1-yl | H | I | H | Me | K⁺ | |
| 8-319 | pyrrol-1-yl | H | CN | H | Me | Na⁺ | |
| 8-320 | pyrrol-1-yl | H | CN | H | Me | K⁺ | |

TABLE 8-continued

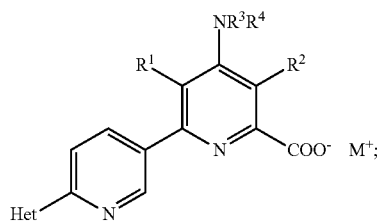

(I-iia)

| No. | Het | R$^1$ | R$^2$ | R$^3$ | R$^4$ | M$^+$ | Physical data: $^1$H-NMR: δ [CDCl$_3$] |
|---|---|---|---|---|---|---|---|
| 8-321 | pyrrol-1-yl | H | CF$_3$ | H | Me | Na$^+$ | |
| 8-322 | pyrrol-1-yl | H | CF$_3$ | H | Me | K$^+$ | |
| 8-323 | pyrrol-1-yl | F | Cl | H | Me | Na$^+$ | |
| 8-324 | pyrrol-1-yl | F | Cl | H | Me | K$^+$ | |
| 8-325 | pyrrol-1-yl | F | Cl | H | Me | NH$_4^+$ | |
| 8-326 | pyrrol-1-yl | F | Br | H | Me | Na$^+$ | |
| 8-327 | pyrrol-1-yl | F | Br | H | Me | K$^+$ | |
| 8-328 | pyrrol-1-yl | F | Br | H | Me | NH$_4^+$ | |
| 8-329 | pyrrol-1-yl | F | F | H | Me | Na$^+$ | |
| 8-330 | pyrrol-1-yl | F | F | H | Me | K$^+$ | |
| 8-331 | pyrrol-1-yl | F | I | H | Me | Na$^+$ | |
| 8-332 | pyrrol-1-yl | F | I | H | Me | K$^+$ | |
| 8-333 | pyrrol-1-yl | F | CN | H | Me | Na$^+$ | |
| 8-334 | pyrrol-1-yl | F | CN | H | Me | K$^+$ | |
| 8-335 | pyrrol-1-yl | F | CF$_3$ | H | Me | Na$^+$ | |
| 8-336 | pyrrol-1-yl | F | CF$_3$ | H | Me | K$^+$ | |
| 8-337 | pyrrol-1-yl | H | Cl | Me | Me | Na$^+$ | |
| 8-338 | pyrrol-1-yl | H | Cl | Me | Me | K$^+$ | |
| 8-339 | pyrrol-1-yl | H | Cl | Me | Me | NH$_4^+$ | |
| 8-340 | pyrrol-1-yl | H | Br | Me | Me | Na$^+$ | |
| 8-341 | pyrrol-1-yl | H | Br | Me | Me | K$^+$ | |
| 8-342 | pyrrol-1-yl | H | Br | Me | Me | NH$_4^+$ | |
| 8-343 | pyrrol-1-yl | H | F | Me | Me | Na$^+$ | |
| 8-344 | pyrrol-1-yl | H | F | Me | Me | K$^+$ | |
| 8-345 | pyrrol-1-yl | H | I | Me | Me | Na$^+$ | |
| 8-346 | pyrrol-1-yl | H | I | Me | Me | K$^+$ | |
| 8-347 | pyrrol-1-yl | H | CN | Me | Me | Na$^+$ | |
| 8-348 | pyrrol-1-yl | H | CN | Me | Me | K$^+$ | |
| 8-349 | pyrrol-1-yl | H | CF$_3$ | Me | Me | Na$^+$ | |
| 8-350 | pyrrol-1-yl | H | CF$_3$ | Me | Me | K$^+$ | |
| 8-351 | pyrrol-1-yl | F | Cl | Me | Me | Na$^+$ | |
| 8-352 | pyrrol-1-yl | F | Cl | Me | Me | K$^+$ | |
| 8-353 | pyrrol-1-yl | F | Cl | Me | Me | NH$_4^+$ | |
| 8-354 | pyrrol-1-yl | F | Br | Me | Me | Na$^+$ | |
| 8-355 | pyrrol-1-yl | F | Br | Me | Me | K$^+$ | |
| 8-356 | pyrrol-1-yl | F | Br | Me | Me | NH$_4^+$ | |
| 8-357 | pyrrol-1-yl | F | F | Me | Me | Na$^+$ | |
| 8-358 | pyrrol-1-yl | F | F | Me | Me | K$^+$ | |
| 8-359 | pyrrol-1-yl | F | I | Me | Me | Na$^+$ | |
| 8-360 | pyrrol-1-yl | F | I | Me | Me | K$^+$ | |
| 8-361 | pyrrol-1-yl | F | CN | Me | Me | Na$^+$ | |
| 8-362 | pyrrol-1-yl | F | CN | Me | Me | K$^+$ | |
| 8-363 | pyrrol-1-yl | F | CF$_3$ | Me | Me | Na$^+$ | |
| 8-364 | pyrrol-1-yl | F | CF$_3$ | Me | Me | K$^+$ | |
| 8-365 | pyrrol-1-yl | H | Cl | =CHNMe$_2$ | | Na$^+$ | |
| 8-366 | pyrrol-1-yl | H | Cl | =CHNMe$_2$ | | K$^+$ | |
| 8-367 | pyrrol-1-yl | H | Cl | =CHNMe$_2$ | | NH$_4^+$ | |
| 8-368 | pyrrol-1-yl | H | Br | =CHNMe$_2$ | | Na$^+$ | |
| 8-369 | pyrrol-1-yl | H | Br | =CHNMe$_2$ | | K$^+$ | |
| 8-370 | pyrrol-1-yl | H | Br | =CHNMe$_2$ | | NH$_4^+$ | |
| 8-371 | pyrrol-1-yl | H | F | =CHNMe$_2$ | | Na$^+$ | |
| 8-372 | pyrrol-1-yl | H | F | =CHNMe$_2$ | | K$^+$ | |
| 8-373 | pyrrol-1-yl | H | I | =CHNMe$_2$ | | Na$^+$ | |
| 8-374 | pyrrol-1-yl | H | I | =CHNMe$_2$ | | K$^+$ | |
| 8-375 | pyrrol-1-yl | H | CN | =CHNMe$_2$ | | Na$^+$ | |
| 8-376 | pyrrol-1-yl | H | CN | =CHNMe$_2$ | | K$^+$ | |
| 8-377 | pyrrol-1-yl | H | CF$_3$ | =CHNMe$_2$ | | Na$^+$ | |
| 8-378 | pyrrol-1-yl | H | CF$_3$ | =CHNMe$_2$ | | K$^+$ | |
| 8-379 | pyrrol-1-yl | F | Cl | =CHNMe$_2$ | | Na$^+$ | |
| 8-380 | pyrrol-1-yl | F | Cl | =CHNMe$_2$ | | K$^+$ | |
| 8-381 | pyrrol-1-yl | F | Cl | =CHNMe$_2$ | | NH$_4^+$ | |
| 8-382 | pyrrol-1-yl | F | Br | =CHNMe$_2$ | | Na$^+$ | |
| 8-383 | pyrrol-1-yl | F | Br | =CHNMe$_2$ | | K$^+$ | |
| 8-384 | pyrrol-1-yl | F | Br | =CHNMe$_2$ | | NH$_4^+$ | |

TABLE 8-continued

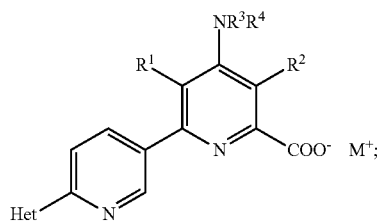

(I-iia)

| No. | Het | $R^1$ | $R^2$ | $R^3$ | $R^4$ | $M^+$ | Physical data: $^1$H-NMR: δ [CDCl$_3$] |
|---|---|---|---|---|---|---|---|
| 8-385 | pyrrol-1-yl | F | F | =CHNMe$_2$ | | Na$^+$ | |
| 8-386 | pyrrol-1-yl | F | F | =CHNMe$_2$ | | K$^+$ | |
| 8-387 | pyrrol-1-yl | F | I | =CHNMe$_2$ | | Na$^+$ | |
| 8-388 | pyrrol-1-yl | F | I | =CHNMe$_2$ | | K$^+$ | |
| 8-389 | pyrrol-1-yl | F | CN | =CHNMe$_2$ | | Na$^+$ | |
| 8-390 | pyrrol-1-yl | F | CN | =CHNMe$_2$ | | K$^+$ | |
| 8-391 | pyrrol-1-yl | F | CF$_3$ | =CHNMe$_2$ | | Na$^+$ | |
| 8-392 | pyrrol-1-yl | F | CF$_3$ | =CHNMe$_2$ | | K$^+$ | |
| 8-393 | pyrazol-1-yl | H | Cl | H | H | Na$^+$ | |
| 8-394 | pyrazol-1-yl | H | Cl | H | H | | |
| 8-395 | pyrazol-1-yl | H | Cl | H | H | NH$_4^+$ | |
| 8-396 | pyrazol-1-yl | H | Br | H | H | Na$^+$ | |
| 8-397 | pyrazol-1-yl | H | Br | H | H | K$^+$ | |
| 8-398 | pyrazol-1-yl | H | Br | H | H | NH$_4^+$ | |
| 8-399 | pyrazol-1-yl | H | F | H | H | Na$^+$ | |
| 8-400 | pyrazol-1-yl | H | F | H | H | K$^+$ | |
| 8-401 | pyrazol-1-yl | H | I | H | H | Na$^+$ | |
| 8-402 | pyrazol-1-yl | H | I | H | H | K$^+$ | |
| 8-403 | pyrazol-1-yl | H | CN | H | H | Na$^+$ | |
| 8-404 | pyrazol-1-yl | H | CN | H | H | K$^+$ | |
| 8-405 | pyrazol-1-yl | H | CF$_3$ | H | H | Na$^+$ | |
| 8-406 | pyrazol-1-yl | H | CF$_3$ | H | H | K$^+$ | |
| 8-407 | pyrazol-1-yl | F | Cl | H | H | Na$^+$ | |
| 8-408 | pyrazol-1-yl | F | Cl | H | H | K$^+$ | |
| 8-409 | pyrazol-1-yl | F | Cl | H | H | NH$_4^+$ | |
| 8-410 | pyrazol-1-yl | F | Br | H | H | Na$^+$ | |
| 8-411 | pyrazol-1-yl | F | Br | H | H | K$^+$ | |
| 8-412 | pyrazol-1-yl | F | Br | H | H | NH$_4^+$ | |
| 8-413 | pyrazol-1-yl | F | F | H | H | Na$^+$ | |
| 8-414 | pyrazol-1-yl | F | F | H | H | K$^+$ | |
| 8-415 | pyrazol-1-yl | F | I | H | H | Na$^+$ | |
| 8-416 | pyrazol-1-yl | F | I | H | H | K$^+$ | |
| 8-417 | pyrazol-1-yl | F | CN | H | H | Na$^+$ | |
| 8-418 | pyrazol-1-yl | F | CN | H | H | K$^+$ | |
| 8-419 | pyrazol-1-yl | F | CF$_3$ | H | H | Na$^+$ | |
| 8-420 | pyrazol-1-yl | F | CF$_3$ | H | H | K$^+$ | |
| 8-421 | pyrazol-1-yl | H | Cl | H | Me | Na$^+$ | |
| 8-422 | pyrazol-1-yl | H | Cl | H | Me | K$^+$ | |
| 8-423 | pyrazol-1-yl | H | Cl | H | Me | NH$_4^+$ | |
| 8-424 | pyrazol-1-yl | H | Br | H | Me | Na$^+$ | |
| 8-425 | pyrazol-1-yl | H | Br | H | Me | K$^+$ | |
| 8-426 | pyrazol-1-yl | H | Br | H | Me | NH$_4^+$ | |
| 8-427 | pyrazol-1-yl | H | F | H | Me | Na$^+$ | |
| 8-428 | pyrazol-1-yl | H | F | H | Me | K$^+$ | |
| 8-429 | pyrazol-1-yl | H | I | H | Me | Na$^+$ | |
| 8-430 | pyrazol-1-yl | H | I | H | Me | K$^+$ | |
| 8-431 | pyrazol-1-yl | H | CN | H | Me | Na$^+$ | |
| 8-432 | pyrazol-1-yl | H | CN | H | Me | K$^+$ | |
| 8-433 | pyrazol-1-yl | H | CF$_3$ | H | Me | Na$^+$ | |
| 8-434 | pyrazol-1-yl | H | CF$_3$ | H | Me | K$^+$ | |
| 8-435 | pyrazol-1-yl | F | Cl | H | Me | Na$^+$ | |
| 8-436 | pyrazol-1-yl | F | Cl | H | Me | K$^+$ | |
| 8-437 | pyrazol-1-yl | F | Cl | H | Me | NH$_4^+$ | |
| 8-438 | pyrazol-1-yl | F | Br | H | Me | Na$^+$ | |
| 8-439 | pyrazol-1-yl | F | Br | H | Me | K$^+$ | |
| 8-440 | pyrazol-1-yl | F | Br | H | Me | NH$_4^+$ | |
| 8-441 | pyrazol-1-yl | F | F | H | Me | Na$^+$ | |
| 8-442 | pyrazol-1-yl | F | F | H | Me | K$^+$ | |
| 8-443 | pyrazol-1-yl | F | I | H | Me | Na$^+$ | |
| 8-444 | pyrazol-1-yl | F | I | H | Me | K$^+$ | |
| 8-445 | pyrazol-1-yl | F | CN | H | Me | Na$^+$ | |
| 8-446 | pyrazol-1-yl | F | CN | H | Me | K$^+$ | |
| 8-447 | pyrazol-1-yl | F | CF$_3$ | H | Me | Na$^+$ | |
| 8-448 | pyrazol-1-yl | F | CF$_3$ | H | Me | K$^+$ | |

TABLE 8-continued

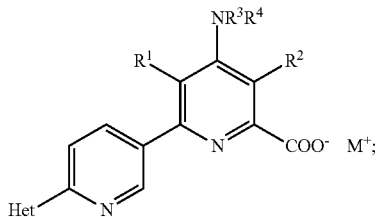

(I-iia)

| No. | Het | $R^1$ | $R^2$ | $R^3$ | $R^4$ | $M^+$ | Physical data: $^1$H-NMR: δ [CDCl$_3$] |
|---|---|---|---|---|---|---|---|
| 8-449 | pyrazol-1-yl | H | Cl | Me | Me | Na$^+$ | |
| 8-450 | pyrazol-1-yl | H | Cl | Me | Me | K$^+$ | |
| 8-451 | pyrazol-1-yl | H | Cl | Me | Me | NH$_4^+$ | |
| 8-452 | pyrazol-1-yl | H | Br | Me | Me | Na$^+$ | |
| 8-453 | pyrazol-1-yl | H | Br | Me | Me | K$^+$ | |
| 8-454 | pyrazol-1-yl | H | Br | Me | Me | NH$_4^+$ | |
| 8-455 | pyrazol-1-yl | H | F | Me | Me | Na$^+$ | |
| 8-456 | pyrazol-1-yl | H | F | Me | Me | K$^+$ | |
| 8-457 | pyrazol-1-yl | H | I | Me | Me | Na$^+$ | |
| 8-458 | pyrazol-1-yl | H | I | Me | Me | K$^+$ | |
| 8-459 | pyrazol-1-yl | H | CN | Me | Me | Na$^+$ | |
| 8-460 | pyrazol-1-yl | H | CN | Me | Me | K$^+$ | |
| 8-461 | pyrazol-1-yl | H | CF$_3$ | Me | Me | Na$^+$ | |
| 8-462 | pyrazol-1-yl | H | CF$_3$ | Me | Me | K$^+$ | |
| 8-463 | pyrazol-1-yl | F | Cl | Me | Me | Na$^+$ | |
| 8-464 | pyrazol-1-yl | F | Cl | Me | Me | K$^+$ | |
| 8-465 | pyrazol-1-yl | F | Cl | Me | Me | NH$_4^+$ | |
| 8-466 | pyrazol-1-yl | F | Br | Me | Me | Na$^+$ | |
| 8-467 | pyrazol-1-yl | F | Br | Me | Me | K$^+$ | |
| 8-468 | pyrazol-1-yl | F | Br | Me | Me | NH$_4^+$ | |
| 8-469 | pyrazol-1-yl | F | F | Me | Me | Na$^+$ | |
| 8-470 | pyrazol-1-yl | F | F | Me | Me | K$^+$ | |
| 8-471 | pyrazol-1-yl | F | I | Me | Me | Na$^+$ | |
| 8-472 | pyrazol-1-yl | F | I | Me | Me | K$^+$ | |
| 8-473 | pyrazol-1-yl | F | CN | Me | Me | Na$^+$ | |
| 8-474 | pyrazol-1-yl | F | CN | Me | Me | K$^+$ | |
| 8-475 | pyrazol-1-yl | F | CF$_3$ | Me | Me | Na$^+$ | |
| 8-476 | pyrazol-1-yl | F | CF$_3$ | Me | Me | K$^+$ | |
| 8-477 | pyrazol-1-yl | H | Cl | =CHNMe$_2$ | | Na$^+$ | |
| 8-478 | pyrazol-1-yl | H | Cl | =CHNMe$_2$ | | K$^+$ | |
| 8-479 | pyrazol-1-yl | H | Cl | =CHNMe$_2$ | | NH$_4^+$ | |
| 8-480 | pyrazol-1-yl | H | Br | =CHNMe$_2$ | | Na$^+$ | |
| 8-481 | pyrazol-1-yl | H | Br | =CHNMe$_2$ | | K$^+$ | |
| 8-482 | pyrazol-1-yl | H | Br | =CHNMe$_2$ | | NH$_4^+$ | |
| 8-483 | pyrazol-1-yl | H | F | =CHNMe$_2$ | | Na$^+$ | |
| 8-484 | pyrazol-1-yl | H | F | =CHNMe$_2$ | | K$^+$ | |
| 8-485 | pyrazol-1-yl | H | I | =CHNMe$_2$ | | Na$^+$ | |
| 8-486 | pyrazol-1-yl | H | I | =CHNMe$_2$ | | K$^+$ | |
| 8-487 | pyrazol-1-yl | H | CN | =CHNMe$_2$ | | Na$^+$ | |
| 8-488 | pyrazol-1-yl | H | CN | =CHNMe$_2$ | | K$^+$ | |
| 8-489 | pyrazol-1-yl | H | CF$_3$ | =CHNMe$_2$ | | Na$^+$ | |
| 8-490 | pyrazol-1-yl | H | CF$_3$ | =CHNMe$_2$ | | K$^+$ | |
| 8-491 | pyrazol-1-yl | F | Cl | =CHNMe$_2$ | | Na$^+$ | |
| 8-492 | pyrazol-1-yl | F | Cl | =CHNMe$_2$ | | K$^+$ | |
| 8-493 | pyrazol-1-yl | F | Cl | =CHNMe$_2$ | | NH$_4^+$ | |
| 8-494 | pyrazol-1-yl | F | Br | =CHNMe$_2$ | | Na$^+$ | |
| 8-495 | pyrazol-1-yl | F | Br | =CHNMe$_2$ | | K$^+$ | |
| 8-496 | pyrazol-1-yl | F | Br | =CHNMe$_2$ | | NH$_4^+$ | |
| 8-497 | pyrazol-1-yl | F | F | =CHNMe$_2$ | | Na$^+$ | |
| 8-498 | pyrazol-1-yl | F | F | =CHNMe$_2$ | | K$^+$ | |
| 8-499 | pyrazol-1-yl | F | I | =CHNMe$_2$ | | Na$^+$ | |
| 8-500 | pyrazol-1-yl | F | I | =CHNMe$_2$ | | K$^+$ | |
| 8-501 | pyrazol-1-yl | F | CN | =CHNMe$_2$ | | Na$^+$ | |
| 8-502 | pyrazol-1-yl | F | CN | =CHNMe$_2$ | | K$^+$ | |
| 8-503 | pyrazol-1-yl | F | CF$_3$ | =CHNMe$_2$ | | Na$^+$ | |
| 8-504 | pyrazol-1-yl | F | CF$_3$ | =CHNMe$_2$ | | K$^+$ | |
| 8-505 | pyridin-3-yl | H | Cl | H | H | Na$^+$ | |
| 8-506 | pyridin-3-yl | H | Cl | H | H | K$^+$ | |
| 8-507 | pyridin-3-yl | H | Cl | H | H | NH$_4^+$ | |
| 8-508 | pyridin-3-yl | H | Br | H | H | Na$^+$ | |
| 8-509 | pyridin-3-yl | H | Br | H | H | K$^+$ | |
| 8-510 | pyridin-3-yl | H | Br | H | H | NH$_4^+$ | |
| 8-511 | pyridin-3-yl | H | F | H | H | Na$^+$ | |
| 8-512 | pyridin-3-yl | H | F | H | H | K$^+$ | |

TABLE 8-continued

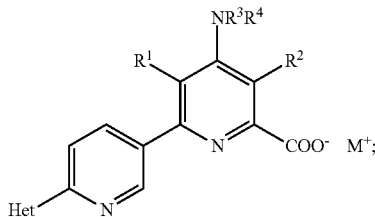

(I-iia)

| No. | Het | R¹ | R² | R³ | R⁴ | M⁺ | Physical data: ¹H-NMR: δ [CDCl₃] |
|---|---|---|---|---|---|---|---|
| 8-513 | pyridin-3-yl | H | I | H | H | Na⁺ | |
| 8-514 | pyridin-3-yl | H | I | H | H | K⁺ | |
| 8-515 | pyridin-3-yl | H | CN | H | H | Na⁺ | |
| 8-516 | pyridin-3-yl | H | CN | H | H | K⁺ | |
| 8-517 | pyridin-3-yl | H | CF₃ | H | H | Na⁺ | |
| 8-518 | pyridin-3-yl | H | CF₃ | H | H | K⁺ | |
| 8-519 | pyridin-3-yl | F | Cl | H | H | Na⁺ | |
| 8-520 | pyridin-3-yl | F | Cl | H | H | K⁺ | |
| 8-521 | pyridin-3-yl | F | Cl | H | H | NH₄⁺ | |
| 8-522 | pyridin-3-yl | F | Br | H | H | Na⁺ | |
| 8-523 | pyridin-3-yl | F | Br | H | H | K⁺ | |
| 8-524 | pyridin-3-yl | F | Br | H | H | NH₄⁺ | |
| 8-525 | pyridin-3-yl | F | F | H | H | Na⁺ | |
| 8-526 | pyridin-3-yl | F | F | H | H | K⁺ | |
| 8-527 | pyridin-3-yl | F | I | H | H | Na⁺ | |
| 8-528 | pyridin-3-yl | F | I | H | H | K⁺ | |
| 8-529 | pyridin-3-yl | F | CN | H | H | Na⁺ | |
| 8-530 | pyridin-3-yl | F | CN | H | H | K⁺ | |
| 8-531 | pyridin-3-yl | F | CF₃ | H | H | Na⁺ | |
| 8-532 | pyridin-3-yl | F | CF₃ | H | H | K⁺ | |
| 8-533 | pyridin-3-yl | H | Cl | H | Me | Na⁺ | |
| 8-534 | pyridin-3-yl | H | Cl | H | Me | K⁺ | |
| 8-535 | pyridin-3-yl | H | Cl | H | Me | NH₄⁺ | |
| 8-536 | pyridin-3-yl | H | Br | H | Me | Na⁺ | |
| 8-537 | pyridin-3-yl | H | Br | H | Me | K⁺ | |
| 8-538 | pyridin-3-yl | H | Br | H | Me | NH₄⁺ | |
| 8-539 | pyridin-3-yl | H | F | H | Me | Na⁺ | |
| 8-540 | pyridin-3-yl | H | F | H | Me | K⁺ | |
| 8-541 | pyridin-3-yl | H | I | H | Me | Na⁺ | |
| 8-542 | pyridin-3-yl | H | I | H | Me | K⁺ | |
| 8-543 | pyridin-3-yl | H | CN | H | Me | Na⁺ | |
| 8-544 | pyridin-3-yl | H | CN | H | Me | K⁺ | |
| 8-545 | pyridin-3-yl | H | CF₃ | H | Me | Na⁺ | |
| 8-546 | pyridin-3-yl | H | CF₃ | H | Me | K⁺ | |
| 8-547 | pyridin-3-yl | F | Cl | H | Me | Na⁺ | |
| 8-548 | pyridin-3-yl | F | Cl | H | Me | K⁺ | |
| 8-549 | pyridin-3-yl | F | Cl | H | Me | NH₄⁺ | |
| 8-550 | pyridin-3-yl | F | Br | H | Me | Na⁺ | |
| 8-551 | pyridin-3-yl | F | Br | H | Me | K⁺ | |
| 8-552 | pyridin-3-yl | F | Br | H | Me | NH₄⁺ | |
| 8-553 | pyridin-3-yl | F | F | H | Me | Na⁺ | |
| 8-554 | pyridin-3-yl | F | F | H | Me | K⁺ | |
| 8-555 | pyridin-3-yl | F | I | H | Me | Na⁺ | |
| 8-556 | pyridin-3-yl | F | I | H | Me | K⁺ | |
| 8-557 | pyridin-3-yl | F | CN | H | Me | Na⁺ | |
| 8-558 | pyridin-3-yl | F | CN | H | Me | K⁺ | |
| 8-559 | pyridin-3-yl | F | CF₃ | H | Me | Na⁺ | |
| 8-560 | pyridin-3-yl | F | CF₃ | H | Me | K⁺ | |
| 8-561 | pyridin-3-yl | H | Cl | Me | Me | Na⁺ | |
| 8-562 | pyridin-3-yl | H | Cl | Me | Me | K⁺ | |
| 8-563 | pyridin-3-yl | H | Cl | Me | Me | NH₄⁺ | |
| 8-564 | pyridin-3-yl | H | Br | Me | Me | Na⁺ | |
| 8-565 | pyridin-3-yl | H | Br | Me | Me | K⁺ | |
| 8-566 | pyridin-3-yl | H | Br | Me | Me | NH₄⁺ | |
| 8-567 | pyridin-3-yl | H | F | Me | Me | Na⁺ | |
| 8-568 | pyridin-3-yl | H | F | Me | Me | K⁺ | |
| 8-569 | pyridin-3-yl | H | I | Me | Me | Na⁺ | |
| 8-570 | pyridin-3-yl | H | I | Me | Me | K⁺ | |
| 8-571 | pyridin-3-yl | H | CN | Me | Me | Na⁺ | |
| 8-572 | pyridin-3-yl | H | CN | Me | Me | K⁺ | |
| 8-573 | pyridin-3-yl | H | CF₃ | Me | Me | Na⁺ | |
| 8-574 | pyridin-3-yl | H | CF₃ | Me | Me | K⁺ | |
| 8-575 | pyridin-3-yl | F | Cl | Me | Me | Na⁺ | |
| 8-576 | pyridin-3-yl | F | Cl | Me | Me | K⁺ | |

TABLE 8-continued

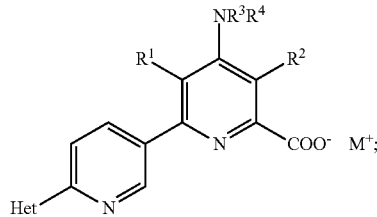

(I-iia)

| No. | Het | $R^1$ | $R^2$ | $R^3$ | $R^4$ | $M^+$ | Physical data: $^1$H-NMR: δ [CDCl$_3$] |
|---|---|---|---|---|---|---|---|
| 8-577 | pyridin-3-yl | F | Cl | Me | Me | NH$_4^+$ | |
| 8-578 | pyridin-3-yl | F | Br | Me | Me | Na$^+$ | |
| 8-579 | pyridin-3-yl | F | Br | Me | Me | K$^+$ | |
| 8-580 | pyridin-3-yl | F | Br | Me | Me | NH$_4^+$ | |
| 8-581 | pyridin-3-yl | F | F | Me | Me | Na$^+$ | |
| 8-582 | pyridin-3-yl | F | F | Me | Me | K$^+$ | |
| 8-583 | pyridin-3-yl | F | I | Me | Me | Na$^+$ | |
| 8-584 | pyridin-3-yl | F | I | Me | Me | K$^+$ | |
| 8-585 | pyridin-3-yl | F | CN | Me | Me | Na$^+$ | |
| 8-586 | pyridin-3-yl | F | CN | Me | Me | K$^+$ | |
| 8-587 | pyridin-3-yl | F | CF$_3$ | Me | Me | Na$^+$ | |
| 8-588 | pyridin-3-yl | F | CF$_3$ | Me | Me | K$^+$ | |
| 8-589 | pyridin-3-yl | H | Cl | =CHNMe$_2$ | | Na$^+$ | |
| 8-590 | pyridin-3-yl | H | Cl | =CHNMe$_2$ | | K$^+$ | |
| 8-591 | pyridin-3-yl | H | Cl | =CHNMe$_2$ | | NH$_4^+$ | |
| 8-592 | pyridin-3-yl | H | Br | =CHNMe$_2$ | | Na$^+$ | |
| 8-593 | pyridin-3-yl | H | Br | =CHNMe$_2$ | | K$^+$ | |
| 8-594 | pyridin-3-yl | H | Br | =CHNMe$_2$ | | NH$_4^+$ | |
| 8-595 | pyridin-3-yl | H | F | =CHNMe$_2$ | | Na$^+$ | |
| 8-596 | pyridin-3-yl | H | F | =CHNMe$_2$ | | K$^+$ | |
| 8-597 | pyridin-3-yl | H | I | =CHNMe$_2$ | | Na$^+$ | |
| 8-598 | pyridin-3-yl | H | I | =CHNMe$_2$ | | K$^+$ | |
| 8-599 | pyridin-3-yl | H | CN | =CHNMe$_2$ | | Na$^+$ | |
| 8-600 | pyridin-3-yl | H | CN | =CHNMe$_2$ | | K$^+$ | |
| 8-601 | pyridin-3-yl | H | CF$_3$ | =CHNMe$_2$ | | Na$^+$ | |
| 8-602 | pyridin-3-yl | H | CF$_3$ | =CHNMe$_2$ | | K$^+$ | |
| 8-603 | pyridin-3-yl | F | Cl | =CHNMe$_2$ | | Na$^+$ | |
| 8-604 | pyridin-3-yl | F | Cl | =CHNMe$_2$ | | K$^+$ | |
| 8-605 | pyridin-3-yl | F | Cl | =CHNMe$_2$ | | NH$_4^+$ | |
| 8-606 | pyridin-3-yl | F | Br | =CHNMe$_2$ | | Na$^+$ | |
| 8-607 | pyridin-3-yl | F | Br | =CHNMe$_2$ | | K$^+$ | |
| 8-608 | pyridin-3-yl | F | Br | =CHNMe$_2$ | | NH$_4^+$ | |
| 8-609 | pyridin-3-yl | F | F | =CHNMe$_2$ | | Na$^+$ | |
| 8-610 | pyridin-3-yl | F | F | =CHNMe$_2$ | | K$^+$ | |
| 8-611 | pyridin-3-yl | F | I | =CHNMe$_2$ | | Na$^+$ | |
| 8-612 | pyridin-3-yl | F | I | =CHNMe$_2$ | | K$^+$ | |
| 8-613 | pyridin-3-yl | F | CN | =CHNMe$_2$ | | Na$^+$ | |
| 8-614 | pyridin-3-yl | F | CN | =CHNMe$_2$ | | K$^+$ | |
| 8-615 | pyridin-3-yl | F | CF$_3$ | =CHNMe$_2$ | | Na$^+$ | |
| 8-616 | pyridin-3-yl | F | CF$_3$ | =CHNMe$_2$ | | K$^+$ | |
| 8-617 | oxiranyl | H | Cl | H | H | Na$^+$ | |
| 8-618 | oxiranyl | H | Cl | H | H | K$^+$ | |
| 8-619 | oxiranyl | H | Cl | H | H | NH$_4^+$ | |
| 8-620 | oxiranyl | H | Br | H | H | Na$^+$ | |
| 8-621 | oxiranyl | H | Br | H | H | K$^+$ | |
| 8-622 | oxiranyl | H | Br | H | H | NH$_4^+$ | |
| 8-623 | oxiranyl | H | F | H | H | Na$^+$ | |
| 8-624 | oxiranyl | H | F | H | H | K$^+$ | |
| 8-625 | oxiranyl | H | I | H | H | Na$^+$ | |
| 8-626 | oxiranyl | H | I | H | H | K$^+$ | |
| 8-627 | oxiranyl | H | CN | H | H | Na$^+$ | |
| 8-628 | oxiranyl | H | CN | H | H | K$^+$ | |
| 8-629 | oxiranyl | H | CF$_3$ | H | H | Na$^+$ | |
| 8-630 | oxiranyl | H | CF$_3$ | H | H | K$^+$ | |
| 8-631 | oxiranyl | F | Cl | H | H | Na$^+$ | |
| 8-632 | oxiranyl | F | Cl | H | H | K$^+$ | |
| 8-633 | oxiranyl | F | Cl | H | H | NH$_4^+$ | |
| 8-634 | oxiranyl | F | Br | H | H | Na$^+$ | |
| 8-635 | oxiranyl | F | Br | H | H | K$^+$ | |
| 8-636 | oxiranyl | F | Br | H | H | NH$_4^+$ | |
| 8-637 | oxiranyl | F | F | H | H | Na$^+$ | |
| 8-638 | oxiranyl | F | F | H | H | K$^+$ | |
| 8-639 | oxiranyl | F | I | H | H | Na$^+$ | |
| 8-640 | oxiranyl | F | I | H | H | K$^+$ | |

TABLE 8-continued

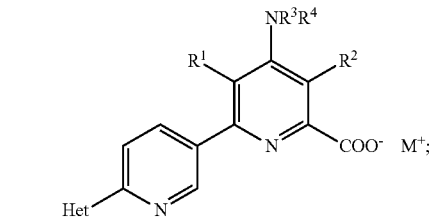

(I-iia)

| No. | Het | R¹ | R² | R³ | R⁴ | M⁺ | Physical data: ¹H-NMR: δ [CDCl₃] |
|---|---|---|---|---|---|---|---|
| 8-641 | oxiranyl | F | CN | H | H | Na⁺ | |
| 8-642 | oxiranyl | F | CN | H | H | K⁺ | |
| 8-643 | oxiranyl | F | CF₃ | H | H | Na⁺ | |
| 8-644 | oxiranyl | F | CF₃ | H | H | K⁺ | |
| 8-645 | oxiranyl | H | Cl | H | Me | Na⁺ | |
| 8-646 | oxiranyl | H | Cl | H | Me | K⁺ | |
| 8-647 | oxiranyl | H | Cl | H | Me | NH₄⁺ | |
| 8-648 | oxiranyl | H | Br | H | Me | Na⁺ | |
| 8-649 | oxiranyl | H | Br | H | Me | K⁺ | |
| 8-650 | oxiranyl | H | Br | H | Me | NH₄⁺ | |
| 8-651 | oxiranyl | H | F | H | Me | Na⁺ | |
| 8-652 | oxiranyl | H | F | H | Me | K⁺ | |
| 8-653 | oxiranyl | H | I | H | Me | Na⁺ | |
| 8-654 | oxiranyl | H | I | H | Me | K⁺ | |
| 8-655 | oxiranyl | H | CN | H | Me | Na⁺ | |
| 8-656 | oxiranyl | H | CN | H | Me | K⁺ | |
| 8-657 | oxiranyl | H | CF₃ | H | Me | Na⁺ | |
| 8-658 | oxiranyl | H | CF₃ | H | Me | K⁺ | |
| 8-659 | oxiranyl | F | Cl | H | Me | Na⁺ | |
| 8-660 | oxiranyl | F | Cl | H | Me | K⁺ | |
| 8-661 | oxiranyl | F | Cl | H | Me | NH₄⁺ | |
| 8-662 | oxiranyl | F | Br | H | Me | Na⁺ | |
| 8-663 | oxiranyl | F | Br | H | Me | K⁺ | |
| 8-664 | oxiranyl | F | Br | H | Me | NH₄⁺ | |
| 8-665 | oxiranyl | F | F | H | Me | Na⁺ | |
| 8-666 | oxiranyl | F | F | H | Me | K⁺ | |
| 8-667 | oxiranyl | F | I | H | Me | Na⁺ | |
| 8-668 | oxiranyl | F | I | H | Me | K⁺ | |
| 8-669 | oxiranyl | F | CN | H | Me | Na⁺ | |
| 8-670 | oxiranyl | F | CN | H | Me | K⁺ | |
| 8-671 | oxiranyl | F | CF₃ | H | Me | Na⁺ | |
| 8-672 | oxiranyl | F | CF₃ | H | Me | K⁺ | |
| 8-673 | oxiranyl | H | Cl | Me | Me | Na⁺ | |
| 8-674 | oxiranyl | H | Cl | Me | Me | K⁺ | |
| 8-675 | oxiranyl | H | Cl | Me | Me | NH₄⁺ | |
| 8-676 | oxiranyl | H | Br | Me | Me | Na⁺ | |
| 8-677 | oxiranyl | H | Br | Me | Me | K⁺ | |
| 8-678 | oxiranyl | H | Br | Me | Me | NH₄⁺ | |
| 8-679 | oxiranyl | H | F | Me | Me | Na⁺ | |
| 8-680 | oxiranyl | H | F | Me | Me | K⁺ | |
| 8-681 | oxiranyl | H | I | Me | Me | Na⁺ | |
| 8-682 | oxiranyl | H | I | Me | Me | K⁺ | |
| 8-683 | oxiranyl | H | CN | Me | Me | Na⁺ | |
| 8-684 | oxiranyl | H | CN | Me | Me | K⁺ | |
| 8-685 | oxiranyl | H | CF₃ | Me | Me | Na⁺ | |
| 8-686 | oxiranyl | H | CF₃ | Me | Me | K⁺ | |
| 8-687 | oxiranyl | F | Cl | Me | Me | Na⁺ | |
| 8-688 | oxiranyl | F | Cl | Me | Me | K⁺ | |
| 8-689 | oxiranyl | F | Cl | Me | Me | NH₄⁺ | |
| 8-690 | oxiranyl | F | Br | Me | Me | Na⁺ | |
| 8-691 | oxiranyl | F | Br | Me | Me | K⁺ | |
| 8-692 | oxiranyl | F | Br | Me | Me | NH₄⁺ | |
| 8-693 | oxiranyl | F | F | Me | Me | Na⁺ | |
| 8-694 | oxiranyl | F | F | Me | Me | K⁺ | |
| 8-695 | oxiranyl | F | I | Me | Me | Na⁺ | |
| 8-696 | oxiranyl | F | I | Me | Me | K⁺ | |
| 8-697 | oxiranyl | F | CN | Me | Me | Na⁺ | |
| 8-698 | oxiranyl | F | CN | Me | Me | K⁺ | |
| 8-699 | oxiranyl | F | CF₃ | Me | Me | Na⁺ | |
| 8-700 | oxiranyl | F | CF₃ | Me | Me | K⁺ | |
| 8-701 | oxiranyl | H | Cl | =CHNMe₂ | | Na⁺ | |
| 8-702 | oxiranyl | H | Cl | =CHNMe₂ | | K⁺ | |
| 8-703 | oxiranyl | H | Cl | =CHNMe₂ | | NH₄⁺ | |
| 8-704 | oxiranyl | H | Br | =CHNMe₂ | | Na⁺ | |

TABLE 8-continued

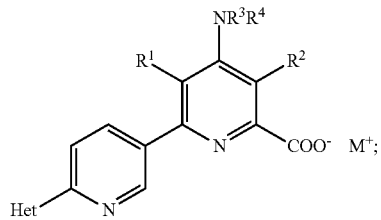

(I-iia)

| No. | Het | R¹ | R² | R³ | R⁴ | M⁺ | Physical data: $^1$H-NMR: δ [CDCl$_3$] |
|---|---|---|---|---|---|---|---|
| 8-705 | oxiranyl | H | Br | =CHNMe$_2$ | | K⁺ | |
| 8-706 | oxiranyl | H | Br | =CHNMe$_2$ | | NH$_4^+$ | |
| 8-707 | oxiranyl | H | F | =CHNMe$_2$ | | Na⁺ | |
| 8-708 | oxiranyl | H | F | =CHNMe$_2$ | | K⁺ | |
| 8-709 | oxiranyl | H | I | =CHNMe$_2$ | | Na⁺ | |
| 8-710 | oxiranyl | H | I | =CHNMe$_2$ | | K⁺ | |
| 8-711 | oxiranyl | H | CN | =CHNMe$_2$ | | Na⁺ | |
| 8-712 | oxiranyl | H | CN | =CHNMe$_2$ | | K⁺ | |
| 8-713 | oxiranyl | H | CF$_3$ | =CHNMe$_2$ | | Na⁺ | |
| 8-714 | oxiranyl | H | CF$_3$ | =CHNMe$_2$ | | K⁺ | |
| 8-715 | oxiranyl | F | Cl | =CHNMe$_2$ | | Na⁺ | |
| 8-716 | oxiranyl | F | Cl | =CHNMe$_2$ | | K⁺ | |
| 8-717 | oxiranyl | F | Cl | =CHNMe$_2$ | | NH$_4^+$ | |
| 8-718 | oxiranyl | F | Br | =CHNMe$_2$ | | Na⁺ | |
| 8-719 | oxiranyl | F | Br | =CHNMe$_2$ | | K⁺ | |
| 8-720 | oxiranyl | F | Br | =CHNMe$_2$ | | NH$_4^+$ | |
| 8-721 | oxiranyl | F | F | =CHNMe$_2$ | | Na⁺ | |
| 8-722 | oxiranyl | F | F | =CHNMe$_2$ | | K⁺ | |
| 8-723 | oxiranyl | F | I | =CHNMe$_2$ | | Na⁺ | |
| 8-724 | oxiranyl | F | I | =CHNMe$_2$ | | K⁺ | |
| 8-725 | oxiranyl | F | CN | =CHNMe$_2$ | | Na⁺ | |
| 8-726 | oxiranyl | F | CN | =CHNMe$_2$ | | K⁺ | |
| 8-727 | oxiranyl | F | CF$_3$ | =CHNMe$_2$ | | Na⁺ | |
| 8-728 | oxiranyl | F | CF$_3$ | =CHNMe$_2$ | | K⁺ | |
| 8-729 | 3,3-dimethyl-oxetan-2-yl | H | Cl | H | H | Na⁺ | |
| 8-730 | 3,3-dimethyl-oxetan-2-yl | H | Cl | H | H | K⁺ | |
| 8-731 | 3,3-dimethyl-oxetan-2-yl | H | Cl | H | H | NH$_4^+$ | |
| 8-732 | 3,3-dimethyl-oxetan-2-yl | H | Br | H | H | Na⁺ | |
| 8-733 | 3,3-dimethyl-oxetan-2-yl | H | Br | H | H | K⁺ | |
| 8-734 | 3,3-dimethyl-oxetan-2-yl | H | Br | H | H | NH$_4^+$ | |
| 8-735 | 3,3-dimethyl-oxetan-2-yl | H | F | H | H | Na⁺ | |
| 8-736 | 3,3-dimethyl-oxetan-2-yl | H | F | H | H | K⁺ | |
| 8-737 | 3,3-dimethyl-oxetan-2-yl | H | I | H | H | Na⁺ | |
| 8-738 | 3,3-dimethyl-oxetan-2-yl | H | I | H | H | K⁺ | |
| 8-739 | 3,3-dimethyl-oxetan-2-yl | H | CN | H | H | Na⁺ | |
| 8-740 | 3,3-dimethyl-oxetan-2-yl | H | CN | H | H | K⁺ | |
| 8-741 | 3,3-dimethyl-oxetan-2-yl | H | CF$_3$ | H | H | Na⁺ | |
| 8-742 | 3,3-dimethyl-oxetan-2-yl | H | CF$_3$ | H | H | K⁺ | |
| 8-743 | 3,3-dimethyl-oxetan-2-yl | F | Cl | H | H | Na⁺ | |
| 8-744 | 3,3-dimethyl-oxetan-2-yl | F | Cl | H | H | K⁺ | |
| 8-745 | 3,3-dimethyl-oxetan-2-yl | F | Cl | H | H | NH$_4^+$ | |
| 8-746 | 3,3-dimethyl-oxetan-2-yl | F | Br | H | H | Na⁺ | |
| 8-747 | 3,3-dimethyl-oxetan-2-yl | F | Br | H | H | K⁺ | |
| 8-748 | 3,3-dimethyl-oxetan-2-yl | F | Br | H | H | NH$_4^+$ | |
| 8-749 | 3,3-dimethyl-oxetan-2-yl | F | F | H | H | Na⁺ | |
| 8-750 | 3,3-dimethyl-oxetan-2-yl | F | F | H | H | K⁺ | |
| 8-751 | 3,3-dimethyl-oxetan-2-yl | F | I | H | H | Na⁺ | |
| 8-752 | 3,3-dimethyl-oxetan-2-yl | F | I | H | H | K⁺ | |
| 8-753 | 3,3-dimethyl-oxetan-2-yl | F | CN | H | H | Na⁺ | |
| 8-754 | 3,3-dimethyl-oxetan-2-yl | F | CN | H | H | K⁺ | |
| 8-755 | 3,3-dimethyl-oxetan-2-yl | F | CF$_3$ | H | H | Na⁺ | |
| 8-756 | 3,3-dimethyl-oxetan-2-yl | F | CF$_3$ | H | H | K⁺ | |
| 8-757 | 3,3-dimethyl-oxetan-2-yl | H | Cl | H | Me | Na⁺ | |
| 8-758 | 3,3-dimethyl-oxetan-2-yl | H | Cl | H | Me | K⁺ | |
| 8-759 | 3,3-dimethyl-oxetan-2-yl | H | Cl | H | Me | NH$_4^+$ | |
| 8-760 | 3,3-dimethyl-oxetan-2-yl | H | Br | H | Me | Na⁺ | |
| 8-761 | 3,3-dimethyl-oxetan-2-yl | H | Br | H | Me | K⁺ | |
| 8-762 | 3,3-dimethyl-oxetan-2-yl | H | Br | H | Me | NH$_4^+$ | |
| 8-763 | 3,3-dimethyl-oxetan-2-yl | H | F | H | Me | Na⁺ | |
| 8-764 | 3,3-dimethyl-oxetan-2-yl | H | F | H | Me | K⁺ | |
| 8-765 | 3,3-dimethyl-oxetan-2-yl | H | I | H | Me | Na⁺ | |
| 8-766 | 3,3-dimethyl-oxetan-2-yl | H | I | H | Me | K⁺ | |
| 8-767 | 3,3-dimethyl-oxetan-2-yl | H | CN | H | Me | Na⁺ | |
| 8-768 | 3,3-dimethyl-oxetan-2-yl | H | CN | H | Me | K⁺ | |

TABLE 8-continued

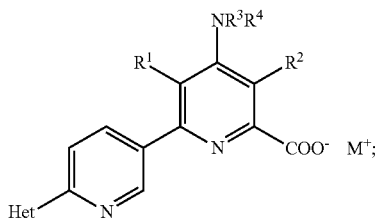

(I-iia)

| No. | Het | $R^1$ | $R^2$ | $R^3$ | $R^4$ | $M^+$ | Physical data: $^1$H-NMR: δ [CDCl$_3$] |
|---|---|---|---|---|---|---|---|
| 8-769 | 3,3-dimethyl-oxetan-2-yl | H | CF$_3$ | H | Me | Na$^+$ | |
| 8-770 | 3,3-dimethyl-oxetan-2-yl | H | CF$_3$ | H | Me | K$^+$ | |
| 8-771 | 3,3-dimethyl-oxetan-2-yl | F | Cl | H | Me | Na$^+$ | |
| 8-772 | 3,3-dimethyl-oxetan-2-yl | F | Cl | H | Me | K$^+$ | |
| 8-773 | 3,3-dimethyl-oxetan-2-yl | F | Cl | H | Me | NH$_4^+$ | |
| 8-774 | 3,3-dimethyl-oxetan-2-yl | F | Br | H | Me | Na$^+$ | |
| 8-775 | 3,3-dimethyl-oxetan-2-yl | F | Br | H | Me | K$^+$ | |
| 8-776 | 3,3-dimethyl-oxetan-2-yl | F | Br | H | Me | NH$_4^+$ | |
| 8-777 | 3,3-dimethyl-oxetan-2-yl | F | F | H | Me | Na$^+$ | |
| 8-778 | 3,3-dimethyl-oxetan-2-yl | F | F | H | Me | K$^+$ | |
| 8-779 | 3,3-dimethyl-oxetan-2-yl | F | I | H | Me | Na$^+$ | |
| 8-780 | 3,3-dimethyl-oxetan-2-yl | F | I | H | Me | K$^+$ | |
| 8-781 | 3,3-dimethyl-oxetan-2-yl | F | CN | H | Me | Na$^+$ | |
| 8-782 | 3,3-dimethyl-oxetan-2-yl | F | CN | H | Me | K$^+$ | |
| 8-783 | 3,3-dimethyl-oxetan-2-yl | F | CF$_3$ | H | Me | Na$^+$ | |
| 8-784 | 3,3-dimethyl-oxetan-2-yl | F | CF$_3$ | H | Me | K$^+$ | |
| 8-785 | 3,3-dimethyl-oxetan-2-yl | H | Cl | Me | Me | Na$^+$ | |
| 8-786 | 3,3-dimethyl-oxetan-2-yl | H | Cl | Me | Me | K$^+$ | |
| 8-787 | 3,3-dimethyl-oxetan-2-yl | H | Cl | Me | Me | NH$_4^+$ | |
| 8-788 | 3,3-dimethyl-oxetan-2-yl | H | Br | Me | Me | Na$^+$ | |
| 8-789 | 3,3-dimethyl-oxetan-2-yl | H | Br | Me | Me | K$^+$ | |
| 8-790 | 3,3-dimethyl-oxetan-2-yl | H | Br | Me | Me | NH$_4^+$ | |
| 8-791 | 3,3-dimethyl-oxetan-2-yl | H | F | Me | Me | Na$^+$ | |
| 8-792 | 3,3-dimethyl-oxetan-2-yl | H | F | Me | Me | K$^+$ | |
| 8-793 | 3,3-dimethyl-oxetan-2-yl | H | I | Me | Me | Na$^+$ | |
| 8-794 | 3,3-dimethyl-oxetan-2-yl | H | I | Me | Me | K$^+$ | |
| 8-795 | 3,3-dimethyl-oxetan-2-yl | H | CN | Me | Me | Na$^+$ | |
| 8-796 | 3,3-dimethyl-oxetan-2-yl | H | CN | Me | Me | K$^+$ | |
| 8-797 | 3,3-dimethyl-oxetan-2-yl | H | CF$_3$ | Me | Me | Na$^+$ | |
| 8-798 | 3,3-dimethyl-oxetan-2-yl | H | CF$_3$ | Me | Me | K$^+$ | |
| 8-799 | 3,3-dimethyl-oxetan-2-yl | F | Cl | Me | Me | Na$^+$ | |
| 8-800 | 3,3-dimethyl-oxetan-2-yl | F | Cl | Me | Me | K$^+$ | |
| 8-801 | 3,3-dimethyl-oxetan-2-yl | F | Cl | Me | Me | NH$_4^+$ | |
| 8-802 | 3,3-dimethyl-oxetan-2-yl | F | Br | Me | Me | Na$^+$ | |
| 8-803 | 3,3-dimethyl-oxetan-2-yl | F | Br | Me | Me | K$^+$ | |
| 8-804 | 3,3-dimethyl-oxetan-2-yl | F | Br | Me | Me | NH$_4^+$ | |
| 8-805 | 3,3-dimethyl-oxetan-2-yl | F | F | Me | Me | Na$^+$ | |
| 8-806 | 3,3-dimethyl-oxetan-2-yl | F | F | Me | Me | K$^+$ | |
| 8-807 | 3,3-dimethyl-oxetan-2-yl | F | I | Me | Me | Na$^+$ | |
| 8-808 | 3,3-dimethyl-oxetan-2-yl | F | I | Me | Me | K$^+$ | |
| 8-809 | 3,3-dimethyl-oxetan-2-yl | F | CN | Me | Me | Na$^+$ | |
| 8-810 | 3,3-dimethyl-oxetan-2-yl | F | CN | Me | Me | K$^+$ | |
| 8-811 | 3,3-dimethyl-oxetan-2-yl | F | CF$_3$ | Me | Me | Na$^+$ | |
| 8-812 | 3,3-dimethyl-oxetan-2-yl | F | CF$_3$ | Me | Me | K$^+$ | |
| 8-813 | 3,3-dimethyl-oxetan-2-yl | H | Cl | =CHNMe$_2$ | | Na$^+$ | |
| 8-814 | 3,3-dimethyl-oxetan-2-yl | H | Cl | =CHNMe$_2$ | | K$^+$ | |
| 8-815 | 3,3-dimethyl-oxetan-2-yl | H | Cl | =CHNMe$_2$ | | NH$_4^+$ | |
| 8-816 | 3,3-dimethyl-oxetan-2-yl | H | Br | =CHNMe$_2$ | | Na$^+$ | |
| 8-817 | 3,3-dimethyl-oxetan-2-yl | H | Br | =CHNMe$_2$ | | K$^+$ | |
| 8-818 | 3,3-dimethyl-oxetan-2-yl | H | Br | =CHNMe$_2$ | | NH$_4^+$ | |
| 8-819 | 3,3-dimethyl-oxetan-2-yl | H | F | =CHNMe$_2$ | | Na$^+$ | |
| 8-820 | 3,3-dimethyl-oxetan-2-yl | H | F | =CHNMe$_2$ | | K$^+$ | |
| 8-821 | 3,3-dimethyl-oxetan-2-yl | H | I | =CHNMe$_2$ | | Na$^+$ | |
| 8-822 | 3,3-dimethyl-oxetan-2-yl | H | I | =CHNMe$_2$ | | K$^+$ | |
| 8-823 | 3,3-dimethyl-oxetan-2-yl | H | CN | =CHNMe$_2$ | | Na$^+$ | |
| 8-824 | 3,3-dimethyl-oxetan-2-yl | H | CN | =CHNMe$_2$ | | K$^+$ | |
| 8-825 | 3,3-dimethyl-oxetan-2-yl | H | CF$_3$ | =CHNMe$_2$ | | Na$^+$ | |

TABLE 8-continued

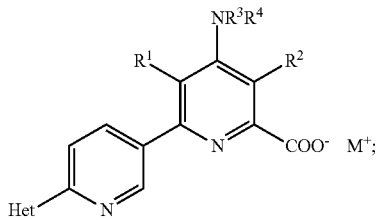

(I-iia)

| No. | Het | $R^1$ | $R^2$ | $R^3$ | $R^4$ | $M^+$ | Physical data: $^1$H-NMR: δ [CDCl$_3$] |
|---|---|---|---|---|---|---|---|
| 8-826 | 3,3-dimethyl-oxetan-2-yl | H | CF$_3$ | =CHNMe$_2$ | | K$^+$ | |
| 8-827 | 3,3-dimethyl-oxetan-2-yl | F | Cl | =CHNMe$_2$ | | Na$^+$ | |
| 8-828 | 3,3-dimethyl-oxetan-2-yl | F | Cl | =CHNMe$_2$ | | K$^+$ | |
| 8-829 | 3,3-dimethyl-oxetan-2-yl | F | Cl | =CHNMe$_2$ | | NH$_4^+$ | |
| 8-830 | 3,3-dimethyl-oxetan-2-yl | F | Br | =CHNMe$_2$ | | Na$^+$ | |
| 8-831 | 3,3-dimethyl-oxetan-2-yl | F | Br | =CHNMe$_2$ | | K$^+$ | |
| 8-832 | 3,3-dimethyl-oxetan-2-yl | F | Br | =CHNMe$_2$ | | NH$_4^+$ | |
| 8-833 | 3,3-dimethyl-oxetan-2-yl | F | F | =CHNMe$_2$ | | Na$^+$ | |
| 8-834 | 3,3-dimethyl-oxetan-2-yl | F | F | =CHNMe$_2$ | | K$^+$ | |
| 8-835 | 3,3-dimethyl-oxetan-2-yl | F | I | =CHNMe$_2$ | | Na$^+$ | |
| 8-836 | 3,3-dimethyl-oxetan-2-yl | F | I | =CHNMe$_2$ | | K$^+$ | |
| 8-837 | 3,3-dimethyl-oxetan-2-yl | F | CN | =CHNMe$_2$ | | Na$^+$ | |
| 8-838 | 3,3-dimethyl-oxetan-2-yl | F | CN | =CHNMe$_2$ | | K$^+$ | |
| 8-839 | 3,3-dimethyl-oxetan-2-yl | F | CF$_3$ | =CHNMe$_2$ | | Na$^+$ | |
| 8-840 | 3,3-dimethyl-oxetan-2-yl | F | CF$_3$ | =CHNMe$_2$ | | K$^+$ | |
| 8-841 | 2,2-dimethyl-dioxolan-4-yl | H | Cl | H | H | Na$^+$ | |
| 8-842 | 2,2-dimethyl-dioxolan-4-yl | H | Cl | H | H | K$^+$ | |
| 8-843 | 2,2-dimethyl-dioxolan-4-yl | H | Cl | H | H | NH$_4^+$ | |
| 8-844 | 2,2-dimethyl-dioxolan-4-yl | H | Br | H | H | Na$^+$ | |
| 8-845 | 2,2-dimethyl-dioxolan-4-yl | H | Br | H | H | K$^+$ | |
| 8-846 | 2,2-dimethyl-dioxolan-4-yl | H | Br | H | H | NH$_4^+$ | |
| 8-847 | 2,2-dimethyl-dioxolan-4-yl | H | F | H | H | Na$^+$ | |
| 8-848 | 2,2-dimethyl-dioxolan-4-yl | H | F | H | H | K$^+$ | |
| 8-849 | 2,2-dimethyl-dioxolan-4-yl | H | I | H | H | Na$^+$ | |
| 8-850 | 2,2-dimethyl-dioxolan-4-yl | H | I | H | H | K$^+$ | |
| 8-851 | 2,2-dimethyl-dioxolan-4-yl | H | CN | H | H | Na$^+$ | |
| 8-852 | 2,2-dimethyl-dioxolan-4-yl | H | CN | H | H | K$^+$ | |
| 8-853 | 2,2-dimethyl-dioxolan-4-yl | H | CF$_3$ | H | H | Na$^+$ | |
| 8-854 | 2,2-dimethyl-dioxolan-4-yl | H | CF$_3$ | H | H | K$^+$ | |
| 8-855 | 2,2-dimethyl-dioxolan-4-yl | F | Cl | H | H | Na$^+$ | |
| 8-856 | 2,2-dimethyl-dioxolan-4-yl | F | Cl | H | H | K$^+$ | |
| 8-857 | 2,2-dimethyl-dioxolan-4-yl | F | Cl | H | H | NH$_4^+$ | |
| 8-858 | 2,2-dimethyl-dioxolan-4-yl | F | Br | H | H | Na$^+$ | |
| 8-859 | 2,2-dimethyl-dioxolan-4-yl | F | Br | H | H | K$^+$ | |
| 8-860 | 2,2-dimethyl-dioxolan-4-yl | F | Br | H | H | NH$_4^+$ | |
| 8-861 | 2,2-dimethyl-dioxolan-4-yl | F | F | H | H | Na$^+$ | |
| 8-862 | 2,2-dimethyl-dioxolan-4-yl | F | F | H | H | K$^+$ | |
| 8-863 | 2,2-dimethyl-dioxolan-4-yl | F | I | H | H | Na$^+$ | |
| 8-864 | 2,2-dimethyl-dioxolan-4-yl | F | I | H | H | K$^+$ | |
| 8-865 | 2,2-dimethyl-dioxolan-4-yl | F | CN | H | H | Na$^+$ | |
| 8-866 | 2,2-dimethyl-dioxolan-4-yl | F | CN | H | H | K$^+$ | |
| 8-867 | 2,2-dimethyl-dioxolan-4-yl | F | CF$_3$ | H | H | Na$^+$ | |
| 8-868 | 2,2-dimethyl-dioxolan-4-yl | F | CF$_3$ | H | H | K$^+$ | |
| 8-869 | 2,2-dimethyl-dioxolan-4-yl | H | Cl | H | Me | Na$^+$ | |
| 8-870 | 2,2-dimethyl-dioxolan-4-yl | H | Cl | H | Me | K$^+$ | |
| 8-871 | 2,2-dimethyl-dioxolan-4-yl | H | Cl | H | Me | NH$_4^+$ | |
| 8-872 | 2,2-dimethyl-dioxolan-4-yl | H | Br | H | Me | Na$^+$ | |
| 8-873 | 2,2-dimethyl-dioxolan-4-yl | H | Br | H | Me | K$^+$ | |
| 8-874 | 2,2-dimethyl-dioxolan-4-yl | H | Br | H | Me | NH$_4^+$ | |
| 8-875 | 2,2-dimethyl-dioxolan-4-yl | H | F | H | Me | Na$^+$ | |
| 8-876 | 2,2-dimethyl-dioxolan-4-yl | H | F | H | Me | K$^+$ | |
| 8-877 | 2,2-dimethyl-dioxolan-4-yl | H | I | H | Me | Na$^+$ | |
| 8-878 | 2,2-dimethyl-dioxolan-4-yl | H | I | H | Me | K$^+$ | |
| 8-879 | 2,2-dimethyl-dioxolan-4-yl | H | CN | H | Me | Na$^+$ | |
| 8-880 | 2,2-dimethyl-dioxolan-4-yl | H | CN | H | Me | K$^+$ | |
| 8-881 | 2,2-dimethyl-dioxolan-4-yl | H | CF$_3$ | H | Me | Na$^+$ | |
| 8-882 | 2,2-dimethyl-dioxolan-4-yl | H | CF$_3$ | H | Me | K$^+$ | |
| 8-883 | 2,2-dimethyl-dioxolan-4-yl | F | Cl | H | Me | Na$^+$ | |
| 8-884 | 2,2-dimethyl-dioxolan-4-yl | F | Cl | H | Me | K$^+$ | |
| 8-885 | 2,2-dimethyl-dioxolan-4-yl | F | Cl | H | Me | NH$_4^+$ | |
| 8-886 | 2,2-dimethyl-dioxolan-4-yl | F | Br | H | Me | Na$^+$ | |
| 8-887 | 2,2-dimethyl-dioxolan-4-yl | F | Br | H | Me | K$^+$ | |
| 8-888 | 2,2-dimethyl-dioxolan-4-yl | F | Br | H | Me | NH$_4^+$ | |
| 8-889 | 2,2-dimethyl-dioxolan-4-yl | F | F | H | Me | Na$^+$ | |

TABLE 8-continued

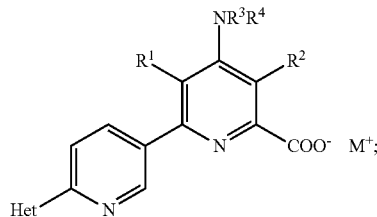

(I-iia)

| No. | Het | $R^1$ | $R^2$ | $R^3$ | $R^4$ | $M^+$ | Physical data: $^1$H-NMR: δ [CDCl$_3$] |
|---|---|---|---|---|---|---|---|
| 8-890 | 2,2-dimethyl-dioxolan-4-yl | F | F | H | Me | K$^+$ | |
| 8-891 | 2,2-dimethyl-dioxolan-4-yl | F | I | H | Me | Na$^+$ | |
| 8-892 | 2,2-dimethyl-dioxolan-4-yl | F | I | H | Me | K$^+$ | |
| 8-893 | 2,2-dimethyl-dioxolan-4-yl | F | CN | H | Me | Na$^+$ | |
| 8-894 | 2,2-dimethyl-dioxolan-4-yl | F | CN | H | Me | K$^+$ | |
| 8-895 | 2,2-dimethyl-dioxolan-4-yl | F | CF$_3$ | H | Me | Na$^+$ | |
| 8-896 | 2,2-dimethyl-dioxolan-4-yl | F | CF$_3$ | H | Me | K$^+$ | |
| 8-897 | 2,2-dimethyl-dioxolan-4-yl | H | Cl | Me | Me | Na$^+$ | |
| 8-898 | 2,2-dimethyl-dioxolan-4-yl | H | Cl | Me | Me | K$^+$ | |
| 8-899 | 2,2-dimethyl-dioxolan-4-yl | H | Cl | Me | Me | NH$_4^+$ | |
| 8-900 | 2,2-dimethyl-dioxolan-4-yl | H | Br | Me | Me | Na$^+$ | |
| 8-901 | 2,2-dimethyl-dioxolan-4-yl | H | Br | Me | Me | K$^+$ | |
| 8-902 | 2,2-dimethyl-dioxolan-4-yl | H | Br | Me | Me | NH$_4^+$ | |
| 8-903 | 2,2-dimethyl-dioxolan-4-yl | H | F | Me | Me | Na$^+$ | |
| 8-904 | 2,2-dimethyl-dioxolan-4-yl | H | F | Me | Me | K$^+$ | |
| 8-905 | 2,2-dimethyl-dioxolan-4-yl | H | I | Me | Me | Na$^+$ | |
| 8-906 | 2,2-dimethyl-dioxolan-4-yl | H | I | Me | Me | K$^+$ | |
| 8-907 | 2,2-dimethyl-dioxolan-4-yl | H | CN | Me | Me | Na$^+$ | |
| 8-908 | 2,2-dimethyl-dioxolan-4-yl | H | CN | Me | Me | K$^+$ | |
| 8-909 | 2,2-dimethyl-dioxolan-4-yl | H | CF$_3$ | Me | Me | Na$^+$ | |
| 8-910 | 2,2-dimethyl-dioxolan-4-yl | H | CF$_3$ | Me | Me | K$^+$ | |
| 8-911 | 2,2-dimethyl-dioxolan-4-yl | F | Cl | Me | Me | Na$^+$ | |
| 8-912 | 2,2-dimethyl-dioxolan-4-yl | F | Cl | Me | Me | K$^+$ | |
| 8-913 | 2,2-dimethyl-dioxolan-4-yl | F | Cl | Me | Me | NH$_4^+$ | |
| 8-914 | 2,2-dimethyl-dioxolan-4-yl | F | Br | Me | Me | Na$^+$ | |
| 8-915 | 2,2-dimethyl-dioxolan-4-yl | F | Br | Me | Me | K$^+$ | |
| 8-916 | 2,2-dimethyl-dioxolan-4-yl | F | Br | Me | Me | NH$_4^+$ | |
| 8-917 | 2,2-dimethyl-dioxolan-4-yl | F | F | Me | Me | Na$^+$ | |
| 8-918 | 2,2-dimethyl-dioxolan-4-yl | F | F | Me | Me | K$^+$ | |
| 8-919 | 2,2-dimethyl-dioxolan-4-yl | F | I | Me | Me | Na$^+$ | |
| 8-920 | 2,2-dimethyl-dioxolan-4-yl | F | I | Me | Me | K$^+$ | |
| 8-921 | 2,2-dimethyl-dioxolan-4-yl | F | CN | Me | Me | Na$^+$ | |
| 8-922 | 2,2-dimethyl-dioxolan-4-yl | F | CN | Me | Me | K$^+$ | |
| 8-923 | 2,2-dimethyl-dioxolan-4-yl | F | CF$_3$ | Me | Me | Na$^+$ | |
| 8-924 | 2,2-dimethyl-dioxolan-4-yl | F | CF$_3$ | Me | Me | K$^+$ | |
| 8-925 | 2,2-dimethyl-dioxolan-4-yl | H | Cl | =CHNMe$_2$ | | Na$^+$ | |
| 8-926 | 2,2-dimethyl-dioxolan-4-yl | H | Cl | =CHNMe$_2$ | | K$^+$ | |
| 8-927 | 2,2-dimethyl-dioxolan-4-yl | H | Cl | =CHNMe$_2$ | | NH$_4^+$ | |
| 8-928 | 2,2-dimethyl-dioxolan-4-yl | H | Br | =CHNMe$_2$ | | Na$^+$ | |
| 8-929 | 2,2-dimethyl-dioxolan-4-yl | H | Br | =CHNMe$_2$ | | K$^+$ | |
| 8-930 | 2,2-dimethyl-dioxolan-4-yl | H | Br | =CHNMe$_2$ | | NH$_4^+$ | |
| 8-931 | 2,2-dimethyl-dioxolan-4-yl | H | F | =CHNMe$_2$ | | Na$^+$ | |
| 8-932 | 2,2-dimethyl-dioxolan-4-yl | H | F | =CHNMe$_2$ | | K$^+$ | |
| 8-933 | 2,2-dimethyl-dioxolan-4-yl | H | I | =CHNMe$_2$ | | Na$^+$ | |
| 8-934 | 2,2-dimethyl-dioxolan-4-yl | H | I | =CHNMe$_2$ | | K$^+$ | |
| 8-935 | 2,2-dimethyl-dioxolan-4-yl | H | CN | =CHNMe$_2$ | | Na$^+$ | |
| 8-936 | 2,2-dimethyl-dioxolan-4-yl | H | CN | =CHNMe$_2$ | | K$^+$ | |
| 8-937 | 2,2-dimethyl-dioxolan-4-yl | H | CF$_3$ | =CHNMe$_2$ | | Na$^+$ | |
| 8-938 | 2,2-dimethyl-dioxolan-4-yl | H | CF$_3$ | =CHNMe$_2$ | | K$^+$ | |
| 8-939 | 2,2-dimethyl-dioxolan-4-yl | F | Cl | =CHNMe$_2$ | | Na$^+$ | |
| 8-940 | 2,2-dimethyl-dioxolan-4-yl | F | Cl | =CHNMe$_2$ | | K$^+$ | |
| 8-941 | 2,2-dimethyl-dioxolan-4-yl | F | Cl | =CHNMe$_2$ | | NH$_4^+$ | |
| 8-942 | 2,2-dimethyl-dioxolan-4-yl | F | Br | =CHNMe$_2$ | | Na$^+$ | |
| 8-943 | 2,2-dimethyl-dioxolan-4-yl | F | Br | =CHNMe$_2$ | | K$^+$ | |
| 8-944 | 2,2-dimethyl-dioxolan-4-yl | F | Br | =CHNMe$_2$ | | NH$_4^+$ | |
| 8-945 | 2,2-dimethyl-dioxolan-4-yl | F | F | =CHNMe$_2$ | | Na$^+$ | |
| 8-946 | 2,2-dimethyl-dioxolan-4-yl | F | F | =CHNMe$_2$ | | K$^+$ | |
| 8-947 | 2,2-dimethyl-dioxolan-4-yl | F | I | =CHNMe$_2$ | | Na$^+$ | |
| 8-948 | 2,2-dimethyl-dioxolan-4-yl | F | I | =CHNMe$_2$ | | K$^+$ | |
| 8-949 | 2,2-dimethyl-dioxolan-4-yl | F | CN | =CHNMe$_2$ | | Na$^+$ | |
| 8-950 | 2,2-dimethyl-dioxolan-4-yl | F | CN | =CHNMe$_2$ | | K$^+$ | |
| 8-951 | 2,2-dimethyl-dioxolan-4-yl | F | CF$_3$ | =CHNMe$_2$ | | Na$^+$ | |
| 8-952 | 2,2-dimethyl-dioxolan-4-yl | F | CF$_3$ | =CHNMe$_2$ | | K$^+$ | |

TABLE 9

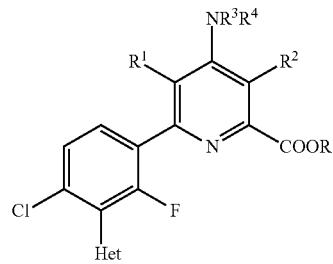

(I-ix)

| No. | Het | R¹ | R² | R³ | R⁴ | R | Physical data: ¹H-NMR: δ [CDCl₃] |
|---|---|---|---|---|---|---|---|
| 9-1 | 3-tert-butyl-1,2,4-oxadiazol-5-yl | H | Cl | H | H | H | |
| 9-2 | 3-tert-butyl-1,2,4-oxadiazol-5-yl | H | Cl | H | H | Me | |
| 9-3 | 3-tert-butyl-1,2,4-oxadiazol-5-yl | H | Cl | H | H | Et | |
| 9-4 | 3-tert-butyl-1,2,4-oxadiazol-5-yl | H | Br | H | H | H | |
| 9-5 | 3-tert-butyl-1,2,4-oxadiazol-5-yl | H | Br | H | H | Me | |
| 9-6 | 3-tert-butyl-1,2,4-oxadiazol-5-yl | H | Br | H | H | Et | |
| 9-7 | 3-tert-butyl-1,2,4-oxadiazol-5-yl | H | F | H | H | H | |
| 9-8 | 3-tert-butyl-1,2,4-oxadiazol-5-yl | H | F | H | H | Me | |
| 9-9 | 3-tert-butyl-1,2,4-oxadiazol-5-yl | H | I | H | H | H | |
| 9-10 | 3-tert-butyl-1,2,4-oxadiazol-5-yl | H | I | H | H | Me | |
| 9-11 | 3-tert-butyl-1,2,4-oxadiazol-5-yl | H | CN | H | H | H | |
| 9-12 | 3-tert-butyl-1,2,4-oxadiazol-5-yl | H | CN | H | H | Me | |
| 9-13 | 3-tert-butyl-1,2,4-oxadiazol-5-yl | H | CF₃ | H | H | H | |
| 9-14 | 3-tert-butyl-1,2,4-oxadiazol-5-yl | H | CF₃ | H | H | Me | |
| 9-15 | 3-tert-butyl-1,2,4-oxadiazol-5-yl | F | Cl | H | H | H | |
| 9-16 | 3-tert-butyl-1,2,4-oxadiazol-5-yl | F | Cl | H | H | Me | |
| 9-17 | 3-tert-butyl-1,2,4-oxadiazol-5-yl | F | Cl | H | H | Et | |
| 9-18 | 3-tert-butyl-1,2,4-oxadiazol-5-yl | F | Br | H | H | H | |
| 9-19 | 3-tert-butyl-1,2,4-oxadiazol-5-yl | F | Br | H | H | Me | |
| 9-20 | 3-tert-butyl-1,2,4-oxadiazol-5-yl | F | Br | H | H | Et | |
| 9-21 | 3-tert-butyl-1,2,4-oxadiazol-5-yl | F | F | H | H | H | |
| 9-22 | 3-tert-butyl-1,2,4-oxadiazol-5-yl | F | F | H | H | Me | |
| 9-23 | 3-tert-butyl-1,2,4-oxadiazol-5-yl | F | I | H | H | H | |
| 9-24 | 3-tert-butyl-1,2,4-oxadiazol-5-yl | F | I | H | H | Me | |
| 9-25 | 3-tert-butyl-1,2,4-oxadiazol-5-yl | F | CN | H | H | H | |
| 9-26 | 3-tert-butyl-1,2,4-oxadiazol-5-yl | F | CN | H | H | Me | |
| 9-27 | 3-tert-butyl-1,2,4-oxadiazol-5-yl | F | CF₃ | H | H | H | |
| 9-28 | 3-tert-butyl-1,2,4-oxadiazol-5-yl | F | CF₃ | H | H | Me | |
| 9-29 | 3-tert-butyl-1,2,4-oxadiazol-5-yl | Cl | Cl | H | H | H | |
| 9-30 | 3-tert-butyl-1,2,4-oxadiazol-5-yl | Cl | Cl | H | H | Me | |
| 9-31 | 3-tert-butyl-1,2,4-oxadiazol-5-yl | Cl | Cl | H | H | Et | |
| 9-32 | 3-tert-butyl-1,2,4-oxadiazol-5-yl | Cl | Br | H | H | H | |
| 9-33 | 3-tert-butyl-1,2,4-oxadiazol-5-yl | Cl | Br | H | H | Me | |
| 9-34 | 3-tert-butyl-1,2,4-oxadiazol-5-yl | Cl | Br | H | H | Et | |
| 9-35 | 3-tert-butyl-1,2,4-oxadiazol-5-yl | Cl | F | H | H | H | |
| 9-36 | 3-tert-butyl-1,2,4-oxadiazol-5-yl | Cl | F | H | H | Me | |
| 9-37 | 3-tert-butyl-1,2,4-oxadiazol-5-yl | Cl | I | H | H | H | |
| 9-38 | 3-tert-butyl-1,2,4-oxadiazol-5-yl | Cl | I | H | H | Me | |
| 9-39 | 3-tert-butyl-1,2,4-oxadiazol-5-yl | Cl | CN | H | H | H | |
| 9-40 | 3-tert-butyl-1,2,4-oxadiazol-5-yl | Cl | CN | H | H | Me | |
| 9-41 | 3-tert-butyl-1,2,4-oxadiazol-5-yl | Cl | CF₃ | H | H | H | |
| 9-42 | 3-tert-butyl-1,2,4-oxadiazol-5-yl | Cl | CF₃ | H | H | Me | |
| 9-43 | 3-tert-butyl-1,2,4-oxadiazol-5-yl | H | Cl | H | Me | H | |
| 9-44 | 3-tert-butyl-1,2,4-oxadiazol-5-yl | H | Cl | H | Me | Me | |
| 9-45 | 3-tert-butyl-1,2,4-oxadiazol-5-yl | H | Cl | H | Me | Et | |
| 9-46 | 3-tert-butyl-1,2,4-oxadiazol-5-yl | H | Br | H | Me | H | |
| 9-47 | 3-tert-butyl-1,2,4-oxadiazol-5-yl | H | Br | H | Me | Me | |
| 9-48 | 3-tert-butyl-1,2,4-oxadiazol-5-yl | H | Br | H | Me | Et | |
| 9-49 | 3-tert-butyl-1,2,4-oxadiazol-5-yl | H | F | H | Me | H | |
| 9-50 | 3-tert-butyl-1,2,4-oxadiazol-5-yl | H | F | H | Me | Me | |
| 9-51 | 3-tert-butyl-1,2,4-oxadiazol-5-yl | H | I | H | Me | H | |
| 9-52 | 3-tert-butyl-1,2,4-oxadiazol-5-yl | H | I | H | Me | Me | |
| 9-53 | 3-tert-butyl-1,2,4-oxadiazol-5-yl | H | CN | H | Me | H | |
| 9-54 | 3-tert-butyl-1,2,4-oxadiazol-5-yl | H | CN | H | Me | Me | |
| 9-55 | 3-tert-butyl-1,2,4-oxadiazol-5-yl | H | CF₃ | H | Me | H | |
| 9-56 | 3-tert-butyl-1,2,4-oxadiazol-5-yl | H | CF₃ | H | Me | Me | |
| 9-57 | 3-tert-butyl-1,2,4-oxadiazol-5-yl | F | Cl | H | Me | H | |
| 9-58 | 3-tert-butyl-1,2,4-oxadiazol-5-yl | F | Cl | H | Me | Me | |
| 9-59 | 3-tert-butyl-1,2,4-oxadiazol-5-yl | F | Cl | H | Me | Et | |
| 9-60 | 3-tert-butyl-1,2,4-oxadiazol-5-yl | F | Br | H | Me | H | |
| 9-61 | 3-tert-butyl-1,2,4-oxadiazol-5-yl | F | Br | H | Me | Me | |
| 9-62 | 3-tert-butyl-1,2,4-oxadiazol-5-yl | F | Br | H | Me | Et | |

TABLE 9-continued

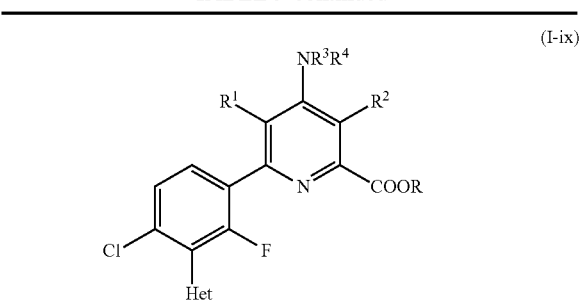

(I-ix)

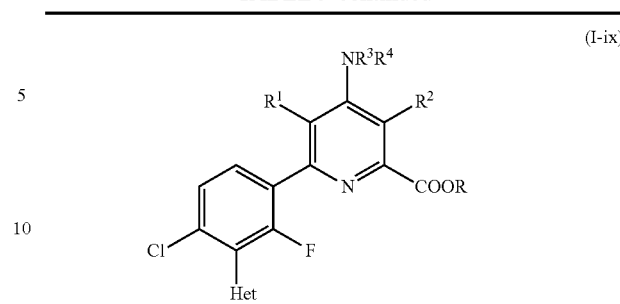

(I-ix)

| No. | Het | R¹ | R² | R³ | R⁴ | R | Physical data: $^1$H-NMR: δ [CDCl$_3$] |
|---|---|---|---|---|---|---|---|
| 9-63 | 3-tert-butyl-1,2,4-oxadiazol-5-yl | F | F | H | Me | H | |
| 9-64 | 3-tert-butyl-1,2,4-oxadiazol-5-yl | F | F | H | Me | Me | |
| 9-65 | 3-tert-butyl-1,2,4-oxadiazol-5-yl | F | I | H | Me | H | |
| 9-66 | 3-tert-butyl-1,2,4-oxadiazol-5-yl | F | I | H | Me | Me | |
| 9-67 | 3-tert-butyl-1,2,4-oxadiazol-5-yl | F | CN | H | Me | H | |
| 9-68 | 3-tert-butyl-1,2,4-oxadiazol-5-yl | F | CN | H | Me | Me | |
| 9-69 | 3-tert-butyl-1,2,4-oxadiazol-5-yl | F | CF$_3$ | H | Me | H | |
| 9-70 | 3-tert-butyl-1,2,4-oxadiazol-5-yl | F | CF$_3$ | H | Me | Me | |
| 9-71 | 3-tert-butyl-1,2,4-oxadiazol-5-yl | Cl | Cl | H | Me | H | |
| 9-72 | 3-tert-butyl-1,2,4-oxadiazol-5-yl | Cl | Cl | H | Me | Me | |
| 9-73 | 3-tert-butyl-1,2,4-oxadiazol-5-yl | Cl | Cl | H | Me | Et | |
| 9-74 | 3-tert-butyl-1,2,4-oxadiazol-5-yl | Cl | Br | H | Me | H | |
| 9-75 | 3-tert-butyl-1,2,4-oxadiazol-5-yl | Cl | Br | H | Me | Me | |
| 9-76 | 3-tert-butyl-1,2,4-oxadiazol-5-yl | Cl | Br | H | Me | Et | |
| 9-77 | 3-tert-butyl-1,2,4-oxadiazol-5-yl | Cl | F | H | Me | H | |
| 9-78 | 3-tert-butyl-1,2,4-oxadiazol-5-yl | Cl | F | H | Me | Me | |
| 9-79 | 3-tert-butyl-1,2,4-oxadiazol-5-yl | Cl | I | H | Me | H | |
| 9-80 | 3-tert-butyl-1,2,4-oxadiazol-5-yl | Cl | I | H | Me | Me | |
| 9-81 | 3-tert-butyl-1,2,4-oxadiazol-5-yl | Cl | CN | H | Me | H | |
| 9-82 | 3-tert-butyl-1,2,4-oxadiazol-5-yl | Cl | CN | H | Me | Me | |
| 9-83 | 3-tert-butyl-1,2,4-oxadiazol-5-yl | Cl | CF$_3$ | H | Me | H | |
| 9-84 | 3-tert-butyl-1,2,4-oxadiazol-5-yl | Cl | CF$_3$ | H | Me | Me | |
| 9-85 | 3-tert-butyl-1,2,4-oxadiazol-5-yl | H | Cl | Me | Me | H | |
| 9-86 | 3-tert-butyl-1,2,4-oxadiazol-5-yl | H | Cl | Me | Me | Me | |
| 9-87 | 3-tert-butyl-1,2,4-oxadiazol-5-yl | H | Cl | Me | Me | Et | |
| 9-88 | 3-tert-butyl-1,2,4-oxadiazol-5-yl | H | Br | Me | Me | H | |
| 9-89 | 3-tert-butyl-1,2,4-oxadiazol-5-yl | H | Br | Me | Me | Me | |
| 9-90 | 3-tert-butyl-1,2,4-oxadiazol-5-yl | H | Br | Me | Me | Et | |
| 9-91 | 3-tert-butyl-1,2,4-oxadiazol-5-yl | H | F | Me | Me | H | |
| 9-92 | 3-tert-butyl-1,2,4-oxadiazol-5-yl | H | F | Me | Me | Me | |
| 9-93 | 3-tert-butyl-1,2,4-oxadiazol-5-yl | H | I | Me | Me | H | |
| 9-94 | 3-tert-butyl-1,2,4-oxadiazol-5-yl | H | I | Me | Me | Me | |
| 9-95 | 3-tert-butyl-1,2,4-oxadiazol-5-yl | H | CN | Me | Me | H | |
| 9-96 | 3-tert-butyl-1,2,4-oxadiazol-5-yl | H | CN | Me | Me | Me | |
| 9-97 | 3-tert-butyl-1,2,4-oxadiazol-5-yl | H | CF$_3$ | Me | Me | H | |
| 9-98 | 3-tert-butyl-1,2,4-oxadiazol-5-yl | H | CF$_3$ | Me | Me | Me | |
| 9-99 | 3-tert-butyl-1,2,4-oxadiazol-5-yl | F | Cl | Me | Me | H | |
| 9-100 | 3-tert-butyl-1,2,4-oxadiazol-5-yl | F | Cl | Me | Me | Me | |
| 9-101 | 3-tert-butyl-1,2,4-oxadiazol-5-yl | F | Cl | Me | Me | Et | |
| 9-102 | 3-tert-butyl-1,2,4-oxadiazol-5-yl | F | Br | Me | Me | H | |
| 9-103 | 3-tert-butyl-1,2,4-oxadiazol-5-yl | F | Br | Me | Me | Me | |
| 9-104 | 3-tert-butyl-1,2,4-oxadiazol-5-yl | F | Br | Me | Me | Et | |
| 9-105 | 3-tert-butyl-1,2,4-oxadiazol-5-yl | F | F | Me | Me | H | |
| 9-106 | 3-tert-butyl-1,2,4-oxadiazol-5-yl | F | F | Me | Me | Me | |
| 9-107 | 3-tert-butyl-1,2,4-oxadiazol-5-yl | F | I | Me | Me | H | |
| 9-108 | 3-tert-butyl-1,2,4-oxadiazol-5-yl | F | I | Me | Me | Me | |
| 9-109 | 3-tert-butyl-1,2,4-oxadiazol-5-yl | F | CN | Me | Me | H | |
| 9-110 | 3-tert-butyl-1,2,4-oxadiazol-5-yl | F | CN | Me | Me | Me | |
| 9-111 | 3-tert-butyl-1,2,4-oxadiazol-5-yl | F | CF$_3$ | Me | Me | H | |
| 9-112 | 3-tert-butyl-1,2,4-oxadiazol-5-yl | F | CF$_3$ | Me | Me | Me | |
| 9-113 | 3-tert-butyl-1,2,4-oxadiazol-5-yl | Cl | Cl | Me | Me | H | |
| 9-114 | 3-tert-butyl-1,2,4-oxadiazol-5-yl | Cl | Cl | Me | Me | Me | |
| 9-115 | 3-tert-butyl-1,2,4-oxadiazol-5-yl | Cl | Cl | Me | Me | Et | |
| 9-116 | 3-tert-butyl-1,2,4-oxadiazol-5-yl | Cl | Br | Me | Me | H | |
| 9-117 | 3-tert-butyl-1,2,4-oxadiazol-5-yl | Cl | Br | Me | Me | Me | |
| 9-118 | 3-tert-butyl-1,2,4-oxadiazol-5-yl | Cl | Br | Me | Me | Et | |
| 9-119 | 3-tert-butyl-1,2,4-oxadiazol-5-yl | Cl | F | Me | Me | H | |
| 9-120 | 3-tert-butyl-1,2,4-oxadiazol-5-yl | Cl | F | Me | Me | Me | |
| 9-121 | 3-tert-butyl-1,2,4-oxadiazol-5-yl | Cl | I | Me | Me | H | |
| 9-122 | 3-tert-butyl-1,2,4-oxadiazol-5-yl | Cl | I | Me | Me | Me | |
| 9-123 | 3-tert-butyl-1,2,4-oxadiazol-5-yl | Cl | CN | Me | Me | H | |
| 9-124 | 3-tert-butyl-1,2,4-oxadiazol-5-yl | Cl | CN | Me | Me | Me | |

TABLE 9-continued

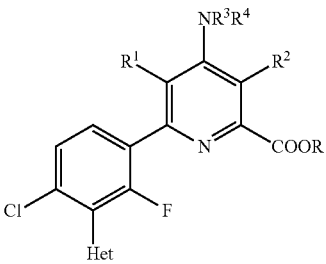

(I-ix)

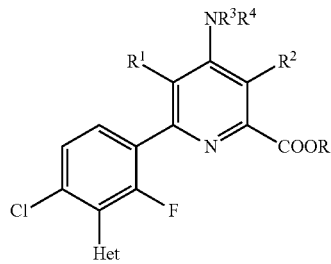

(I-ix)

| No. | Het | R¹ | R² | R³ | R⁴ | R | Physical data: ¹H-NMR: δ [CDCl₃] |
|---|---|---|---|---|---|---|---|
| 9-125 | 3-tert-butyl-1,2,4-oxadiazol-5-yl | Cl | CF₃ | Me | Me | H | |
| 9-126 | 3-tert-butyl-1,2,4-oxadiazol-5-yl | Cl | CF₃ | Me | Me | Me | |
| 9-127 | 3-tert-butyl-1,2,4-oxadiazol-5-yl | H | Cl | =CHNMe₂ | | H | |
| 9-128 | 3-tert-butyl-1,2,4-oxadiazol-5-yl | H | Cl | =CHNMe₂ | | Me | |
| 9-129 | 3-tert-butyl-1,2,4-oxadiazol-5-yl | H | Cl | =CHNMe₂ | | Et | |
| 9-130 | 3-tert-butyl-1,2,4-oxadiazol-5-yl | H | Br | =CHNMe₂ | | H | |
| 9-131 | 3-tert-butyl-1,2,4-oxadiazol-5-yl | H | Br | =CHNMe₂ | | Me | |
| 9-132 | 3-tert-butyl-1,2,4-oxadiazol-5-yl | H | Br | =CHNMe₂ | | Et | |
| 9-133 | 3-tert-butyl-1,2,4-oxadiazol-5-yl | H | F | =CHNMe₂ | | H | |
| 9-134 | 3-tert-butyl-1,2,4-oxadiazol-5-yl | H | F | =CHNMe₂ | | Me | |
| 9-135 | 3-tert-butyl-1,2,4-oxadiazol-5-yl | H | I | =CHNMe₂ | | H | |
| 9-136 | 3-tert-butyl-1,2,4-oxadiazol-5-yl | H | I | =CHNMe₂ | | Me | |
| 9-137 | 3-tert-butyl-1,2,4-oxadiazol-5-yl | H | CN | =CHNMe₂ | | H | |
| 9-138 | 3-tert-butyl-1,2,4-oxadiazol-5-yl | H | CN | =CHNMe₂ | | Me | |
| 9-139 | 3-tert-butyl-1,2,4-oxadiazol-5-yl | H | CF₃ | =CHNMe₂ | | H | |
| 9-140 | 3-tert-butyl-1,2,4-oxadiazol-5-yl | H | CF₃ | =CHNMe₂ | | Me | |
| 9-141 | 3-tert-butyl-1,2,4-oxadiazol-5-yl | F | Cl | =CHNMe₂ | | H | |
| 9-142 | 3-tert-butyl-1,2,4-oxadiazol-5-yl | F | Cl | =CHNMe₂ | | Me | |
| 9-143 | 3-tert-butyl-1,2,4-oxadiazol-5-yl | F | Cl | =CHNMe₂ | | Et | |
| 9-144 | 3-tert-butyl-1,2,4-oxadiazol-5-yl | F | Br | =CHNMe₂ | | H | |
| 9-145 | 3-tert-butyl-1,2,4-oxadiazol-5-yl | F | Br | =CHNMe₂ | | Me | |
| 9-146 | 3-tert-butyl-1,2,4-oxadiazol-5-yl | F | Br | =CHNMe₂ | | Et | |
| 9-147 | 3-tert-butyl-1,2,4-oxadiazol-5-yl | F | F | =CHNMe₂ | | H | |
| 9-148 | 3-tert-butyl-1,2,4-oxadiazol-5-yl | F | F | =CHNMe₂ | | Me | |
| 9-149 | 3-tert-butyl-1,2,4-oxadiazol-5-yl | F | I | =CHNMe₂ | | H | |
| 9-150 | 3-tert-butyl-1,2,4-oxadiazol-5-yl | F | I | =CHNMe₂ | | Me | |
| 9-151 | 3-tert-butyl-1,2,4-oxadiazol-5-yl | F | CN | =CHNMe₂ | | H | |
| 9-152 | 3-tert-butyl-1,2,4-oxadiazol-5-yl | F | CN | =CHNMe₂ | | Me | |
| 9-153 | 3-tert-butyl-1,2,4-oxadiazol-5-yl | F | CF₃ | =CHNMe₂ | | H | |
| 9-154 | 3-tert-butyl-1,2,4-oxadiazol-5-yl | F | CF₃ | =CHNMe₂ | | Me | |
| 9-155 | 3-tert-butyl-1,2,4-oxadiazol-5-yl | Cl | Cl | =CHNMe₂ | | H | |
| 9-156 | 3-tert-butyl-1,2,4-oxadiazol-5-yl | Cl | Cl | =CHNMe₂ | | Me | |
| 9-157 | 3-tert-butyl-1,2,4-oxadiazol-5-yl | Cl | Cl | =CHNMe₂ | | Et | |
| 9-158 | 3-tert-butyl-1,2,4-oxadiazol-5-yl | Cl | Br | =CHNMe₂ | | H | |
| 9-159 | 3-tert-butyl-1,2,4-oxadiazol-5-yl | Cl | Br | =CHNMe₂ | | Me | |
| 9-160 | 3-tert-butyl-1,2,4-oxadiazol-5-yl | Cl | Br | =CHNMe₂ | | Et | |
| 9-161 | 3-tert-butyl-1,2,4-oxadiazol-5-yl | Cl | F | =CHNMe₂ | | H | |
| 9-162 | 3-tert-butyl-1,2,4-oxadiazol-5-yl | Cl | F | =CHNMe₂ | | Me | |
| 9-163 | 3-tert-butyl-1,2,4-oxadiazol-5-yl | Cl | I | =CHNMe₂ | | H | |
| 9-164 | 3-tert-butyl-1,2,4-oxadiazol-5-yl | Cl | I | =CHNMe₂ | | Me | |
| 9-165 | 3-tert-butyl-1,2,4-oxadiazol-5-yl | Cl | CN | =CHNMe₂ | | H | |
| 9-166 | 3-tert-butyl-1,2,4-oxadiazol-5-yl | Cl | CN | =CHNMe₂ | | Me | |
| 9-167 | 3-tert-butyl-1,2,4-oxadiazol-5-yl | Cl | CF₃ | =CHNMe₂ | | H | |
| 9-168 | 3-tert-butyl-1,2,4-oxadiazol-5-yl | Cl | CF₃ | =CHNMe₂ | | Me | |
| 9-169 | thien-2-yl | H | Cl | H | H | H | |
| 9-170 | thien-2-yl | H | Cl | H | H | Me | |
| 9-171 | thien-2-yl | H | Cl | H | H | Et | |
| 9-172 | thien-2-yl | H | Br | H | H | H | |
| 9-173 | thien-2-yl | H | Br | H | H | Me | |
| 9-174 | thien-2-yl | H | Br | H | H | Et | |
| 9-175 | thien-2-yl | H | F | H | H | H | |
| 9-176 | thien-2-yl | H | F | H | H | Me | |
| 9-177 | thien-2-yl | H | I | H | H | H | |
| 9-178 | thien-2-yl | H | I | H | H | Me | |
| 9-179 | thien-2-yl | H | CN | H | H | H | |
| 9-180 | thien-2-yl | H | CN | H | H | Me | |
| 9-181 | thien-2-yl | H | CF₃ | H | H | H | |
| 9-182 | thien-2-yl | H | CF₃ | H | H | Me | |
| 9-183 | thien-2-yl | F | Cl | H | H | H | |
| 9-184 | thien-2-yl | F | Cl | H | H | Me | |
| 9-185 | thien-2-yl | F | Cl | H | H | Et | |
| 9-186 | thien-2-yl | F | Br | H | H | H | |
| 9-187 | thien-2-yl | F | Br | H | H | Me | |
| 9-188 | thien-2-yl | F | Br | H | H | Et | |
| 9-189 | thien-2-yl | F | F | H | H | H | |
| 9-190 | thien-2-yl | F | F | H | H | Me | |
| 9-191 | thien-2-yl | F | I | H | H | H | |
| 9-192 | thien-2-yl | F | I | H | H | Me | |
| 9-193 | thien-2-yl | F | CN | H | H | H | |
| 9-194 | thien-2-yl | F | CN | H | H | Me | |
| 9-195 | thien-2-yl | F | CF₃ | H | H | H | |
| 9-196 | thien-2-yl | F | CF₃ | H | H | Me | |
| 9-197 | thien-2-yl | H | Cl | H | Me | H | |
| 9-198 | thien-2-yl | H | Cl | H | Me | Me | |
| 9-199 | thien-2-yl | H | Cl | H | Me | Et | |
| 9-200 | then-2-yl | H | Br | H | Me | H | |
| 9-201 | thien-2-yl | H | Br | H | Me | Me | |
| 9-202 | thien-2-yl | H | Br | H | Me | Et | |
| 9-203 | thien-2-yl | H | F | H | Me | H | |
| 9-204 | thien-2-yl | H | F | H | Me | Me | |

TABLE 9-continued

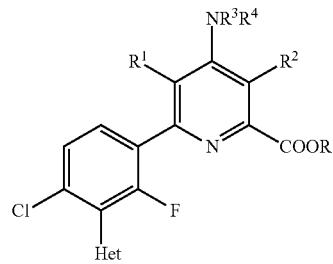

(I-ix)

| No. | Het | R¹ | R² | R³ | R⁴ | R | Physical data: ¹H-NMR: δ [CDCl₃] |
|---|---|---|---|---|---|---|---|
| 9-205 | thien-2-yl | H | I | H | Me | H | |
| 9-206 | thien-2-yl | H | I | H | Me | Me | |
| 9-207 | thien-2-yl | H | CN | H | Me | H | |
| 9-208 | thien-2-yl | H | CN | H | Me | Me | |
| 9-209 | thien-2-yl | H | CF₃ | H | Me | H | |
| 9-210 | thien-2-yl | H | CF₃ | H | Me | Me | |
| 9-211 | thien-2-yl | F | Cl | H | Me | H | |
| 9-212 | thien-2-yl | F | Cl | H | Me | Me | |
| 9-213 | thien-2-yl | F | Cl | H | Me | Et | |
| 9-214 | thien-2-yl | F | Br | H | Me | H | |
| 9-215 | thien-2-yl | F | Br | H | Me | Me | |
| 9-216 | thien-2-yl | F | Br | H | Me | Et | |
| 9-217 | thien-2-yl | F | F | H | Me | H | |
| 9-218 | thien-2-yl | F | F | H | Me | Me | |
| 9-219 | thien-2-yl | F | I | H | Me | H | |
| 9-220 | thien-2-yl | F | I | H | Me | Me | |
| 9-221 | thien-2-yl | F | CN | H | Me | H | |
| 9-222 | thien-2-yl | F | CN | H | Me | Me | |
| 9-223 | thien-2-yl | F | CF₃ | H | Me | H | |
| 9-224 | thien-2-yl | F | CF₃ | H | Me | Me | |
| 9-225 | thien-2-yl | H | Cl | Me | Me | H | |
| 9-226 | thien-2-yl | H | Cl | Me | Me | Me | |
| 9-227 | thien-2-yl | H | Cl | Me | Me | Et | |
| 9-228 | thien-2-yl | H | Br | Me | Me | H | |
| 9-229 | thien-2-yl | H | Br | Me | Me | Me | |
| 9-230 | thien-2-yl | H | Br | Me | Me | Et | |
| 9-231 | thien-2-yl | H | F | Me | Me | H | |
| 9-232 | thien-2-yl | H | F | Me | Me | Me | |
| 9-233 | thien-2-yl | H | I | Me | Me | H | |
| 9-234 | thien-2-yl | H | I | Me | Me | Me | |
| 9-235 | thien-2-yl | H | CN | Me | Me | H | |
| 9-236 | thien-2-yl | H | CN | Me | Me | Me | |
| 9-237 | thien-2-yl | H | CF₃ | Me | Me | H | |
| 9-238 | thien-2-yl | H | CF₃ | Me | Me | Me | |
| 9-239 | thien-2-yl | F | Cl | Me | Me | H | |
| 9-240 | thien-2-yl | F | Cl | Me | Me | Me | |
| 9-241 | thien-2-yl | F | Cl | Me | Me | Et | |
| 9-242 | thien-2-yl | F | Br | Me | Me | H | |
| 9-243 | thien-2-yl | F | Br | Me | Me | Me | |
| 9-244 | thien-2-yl | F | Br | Me | Me | Et | |
| 9-245 | thien-2-yl | F | F | Me | Me | H | |
| 9-246 | thien-2-yl | F | F | Me | Me | Me | |
| 9-247 | thien-2-yl | F | I | Me | Me | H | |
| 9-248 | thien-2-yl | F | I | Me | Me | Me | |
| 9-249 | thien-2-yl | F | CN | Me | Me | H | |
| 9-250 | thien-2-yl | F | CN | Me | Me | Me | |
| 9-251 | thien-2-yl | F | CF₃ | Me | Me | H | |
| 9-252 | thien-2-yl | F | CF₃ | Me | Me | Me | |
| 9-253 | thien-2-yl | H | Cl | =CHNMe₂ | | H | |
| 9-254 | thien-2-yl | H | Cl | =CHNMe₂ | | Me | |
| 9-255 | thien-2-yl | H | Cl | =CHNMe₂ | | Et | |
| 9-256 | thien-2-yl | H | Br | =CHNMe₂ | | H | |
| 9-257 | thien-2-yl | H | Br | =CHNMe₂ | | Me | |
| 9-258 | thien-2-yl | H | Br | =CHNMe₂ | | Et | |
| 9-259 | thien-2-yl | H | F | =CHNMe₂ | | H | |
| 9-260 | thien-2-yl | H | F | =CHNMe₂ | | Me | |
| 9-261 | thien-2-yl | H | I | =CHNMe₂ | | H | |
| 9-262 | thien-2-yl | H | I | =CHNMe₂ | | Me | |
| 9-263 | thien-2-yl | H | CN | =CHNMe₂ | | H | |
| 9-264 | thien-2-yl | H | CN | =CHNMe₂ | | Me | |
| 9-265 | thien-2-yl | H | CF₃ | =CHNMe₂ | | H | |
| 9-266 | thien-2-yl | H | CF₃ | =CHNMe₂ | | Me | |

TABLE 9-continued

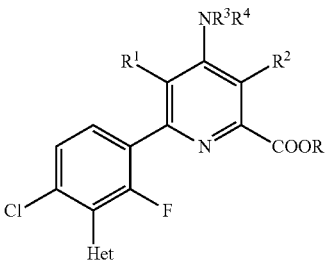

(I-ix)

| No. | Het | R¹ | R² | R³ | R⁴ | R | Physical data: ¹H-NMR: δ [CDCl₃] |
|---|---|---|---|---|---|---|---|
| 9-267 | thien-2-yl | F | Cl | =CHNMe₂ | | H | |
| 9-268 | thien-2-yl | F | Cl | =CHNMe₂ | | Me | |
| 9-269 | thien-2-yl | F | Cl | =CHNMe₂ | | Et | |
| 9-270 | thien-2-yl | F | Br | =CHNMe₂ | | H | |
| 9-271 | thien-2-yl | F | Br | =CHNMe₂ | | Me | |
| 9-272 | thien-2-yl | F | Br | =CHNMe₂ | | Et | |
| 9-273 | thien-2-yl | F | F | =CHNMe₂ | | H | |
| 9-274 | thien-2-yl | F | F | =CHNMe₂ | | Me | |
| 9-275 | thien-2-yl | F | I | =CHNMe₂ | | H | |
| 9-276 | thien-2-yl | F | I | =CHNMe₂ | | Me | |
| 9-277 | thien-2-yl | F | CN | =CHNMe₂ | | H | |
| 9-278 | thien-2-yl | F | CN | =CHNMe₂ | | Me | |
| 9-279 | thien-2-yl | F | CF₃ | =CHNMe₂ | | H | |
| 9-280 | thien-2-yl | F | CF₃ | =CHNMe₂ | | Me | |
| 9-281 | pyrrol-1-yl | H | Cl | H | H | H | |
| 9-282 | pyrrol-1-yl | H | Cl | H | H | Me | |
| 9-283 | pyrrol-1-yl | H | Cl | H | H | Et | |
| 9-284 | pyrrol-1-yl | H | Br | H | H | H | |
| 9-285 | pyrrol-1-yl | H | Br | H | H | Me | |
| 9-286 | pyrrol-1-yl | H | Br | H | H | Et | |
| 9-287 | pyrrol-1-yl | H | F | H | H | H | |
| 9-288 | pyrrol-1-yl | H | F | H | H | Me | |
| 9-289 | pyrrol-1-yl | H | I | H | H | H | |
| 9-290 | pyrrol-1-yl | H | I | H | H | Me | |
| 9-291 | pyrrol-1-yl | H | CN | H | H | H | |
| 9-292 | pyrrol-1-yl | H | CN | H | H | Me | |
| 9-293 | pyrrol-1-yl | H | CF₃ | H | H | H | |
| 9-294 | pyrrol-1-yl | H | CF₃ | H | H | Me | |
| 9-295 | pyrrol-1-yl | F | Cl | H | H | H | |
| 9-296 | pyrrol-1-yl | F | Cl | H | H | Me | |
| 9-297 | pyrrol-1-yl | F | Cl | H | H | Et | |
| 9-298 | pyrrol-1-yl | F | Br | H | H | H | |
| 9-299 | pyrrol-1-yl | F | Br | H | H | Me | |
| 9-300 | pyrrol-1-yl | F | Br | H | H | Et | |
| 9-301 | pyrrol-1-yl | F | F | H | H | H | |
| 9-302 | pyrrol-1-yl | F | F | H | H | Me | |
| 9-303 | pyrrol-1-yl | F | I | H | H | H | |
| 9-304 | pyrrol-1-yl | F | I | H | H | Me | |
| 9-305 | pyrrol-1-yl | F | CN | H | H | H | |
| 9-306 | pyrrol-1-yl | F | CN | H | H | Me | |
| 9-307 | pyrrol-1-yl | F | CF₃ | H | H | H | |
| 9-308 | pyrrol-1-yl | F | CF₃ | H | H | Me | |
| 9-309 | pyrrol-1-yl | H | Cl | H | Me | H | |
| 9-310 | pyrrol-1-yl | H | Cl | H | Me | Me | |
| 9-311 | pyrrol-1-yl | H | Cl | H | Me | Et | |
| 9-312 | pyrrol-1-yl | H | Br | H | Me | H | |
| 9-313 | pyrrol-1-yl | H | Br | H | Me | Me | |
| 9-314 | pyrrol-1-yl | H | Br | H | Me | Et | |
| 9-315 | pyrrol-1-yl | H | F | H | Me | H | |
| 9-316 | pyrrol-1-yl | H | F | H | Me | Me | |
| 9-317 | pyrrol-1-yl | H | I | H | Me | H | |
| 9-318 | pyrrol-1-yl | H | I | H | Me | Me | |
| 9-319 | pyrrol-1-yl | H | CN | H | Me | H | |
| 9-320 | pyrrol-1-yl | H | CN | H | Me | Me | |
| 9-321 | pyrrol-1-yl | H | CF₃ | H | Me | H | |
| 9-322 | pyrrol-1-yl | H | CF₃ | H | Me | Me | |
| 9-323 | pyrrol-1-yl | F | Cl | H | Me | H | |
| 9-324 | pyrrol-1-yl | F | Cl | H | Me | Me | |
| 9-325 | pyrrol-1-yl | F | Cl | H | Me | Et | |
| 9-326 | pyrrol-1-yl | F | Br | H | Me | H | |
| 9-327 | pyrrol-1-yl | F | Br | H | Me | Me | |
| 9-328 | pyrrol-1-yl | F | Br | H | Me | Et | |

TABLE 9-continued

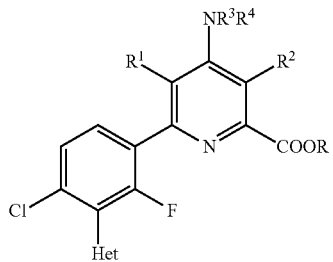

(I-ix)

| No. | Het | R¹ | R² | R³ | R⁴ | R | Physical data: ¹H-NMR: δ [CDCl₃] |
|---|---|---|---|---|---|---|---|
| 9-329 | pyrrol-1-yl | F | F | H | Me | H | |
| 9-330 | pyrrol-1-yl | F | F | H | Me | Me | |
| 9-331 | pyrrol-1-yl | F | I | H | Me | H | |
| 9-332 | pyrrol-1-yl | F | I | H | Me | Me | |
| 9-333 | pyrrol-1-yl | F | CN | H | Me | H | |
| 9-334 | pyrrol-1-yl | F | CN | H | Me | Me | |
| 9-335 | pyrrol-1-yl | F | CF₃ | H | Me | H | |
| 9-336 | pyrrol-1-yl | F | CF₃ | H | Me | Me | |
| 9-337 | pyrrol-1-yl | H | Cl | Me | Me | H | |
| 9-338 | pyrrol-1-yl | H | Cl | Me | Me | Me | |
| 9-339 | pyrrol-1-yl | H | Cl | Me | Me | Et | |
| 9-340 | pyrrol-1-yl | H | Br | Me | Me | H | |
| 9-341 | pyrrol-1-yl | H | Br | Me | Me | Me | |
| 9-342 | pyrrol-1-yl | H | Br | Me | Me | Et | |
| 9-343 | pyrrol-1-yl | H | F | Me | Me | H | |
| 9-344 | pyrrol-1-yl | H | F | Me | Me | Me | |
| 9-345 | pyrrol-1-yl | H | I | Me | Me | H | |
| 9-346 | pyrrol-1-yl | H | I | Me | Me | Me | |
| 9-347 | pyrrol-1-yl | H | CN | Me | Me | H | |
| 9-348 | pyrrol-1-yl | H | CN | Me | Me | Me | |
| 9-349 | pyrrol-1-yl | H | CF₃ | Me | Me | H | |
| 9-350 | pyrrol-1-yl | H | CF₃ | Me | Me | Me | |
| 9-351 | pyrrol-1-yl | F | Cl | Me | Me | H | |
| 9-352 | pyrrol-1-yl | F | Cl | Me | Me | Me | |
| 9-353 | pyrrol-1-yl | F | Cl | Me | Me | Et | |
| 9-354 | pyrrol-1-yl | F | Br | Me | Me | H | |
| 9-355 | pyrrol-1-yl | F | Br | Me | Me | Me | |
| 9-356 | pyrrol-1-yl | F | Br | Me | Me | Et | |
| 9-357 | pyrrol-1-yl | F | F | Me | Me | H | |
| 9-358 | pyrrol-1-yl | F | F | Me | Me | Me | |
| 9-359 | pyrrol-1-yl | F | I | Me | Me | H | |
| 9-360 | pyrrol-1-yl | F | I | Me | Me | Me | |
| 9-361 | pyrrol-1-yl | F | CN | Me | Me | H | |
| 9-362 | pyrrol-1-yl | F | CN | Me | Me | Me | |
| 9-363 | pyrrol-1-yl | F | CF₃ | Me | Me | H | |
| 9-364 | pyrrol-1-yl | F | CF₃ | Me | Me | Me | |
| 9-365 | pyrrol-1-yl | H | Cl | =CHNMe₂ | | H | |
| 9-366 | pyrrol-1-yl | H | Cl | =CHNMe₂ | | Me | |
| 9-367 | pyrrol-1-yl | H | Cl | =CHNMe₂ | | Et | |
| 9-368 | pyrrol-1-yl | H | Br | =CHNMe₂ | | H | |
| 9-369 | pyrrol-1-yl | H | Br | =CHNMe₂ | | Me | |
| 9-370 | pyrrol-1-yl | H | Br | =CHNMe₂ | | Et | |
| 9-371 | pyrrol-1-yl | H | F | =CHNMe₂ | | H | |
| 9-372 | pyrrol-1-yl | H | F | =CHNMe₂ | | Me | |
| 9-373 | pyrrol-1-yl | H | I | =CHNMe₂ | | H | |
| 9-374 | pyrrol-1-yl | H | I | =CHNMe₂ | | Me | |
| 9-375 | pyrrol-1-yl | H | CN | =CHNMe₂ | | H | |
| 9-376 | pyrrol-1-yl | H | CN | =CHNMe₂ | | Me | |
| 9-377 | pyrrol-1-yl | H | CF₃ | =CHNMe₂ | | H | |
| 9-378 | pyrrol-1-yl | H | CF₃ | =CHNMe₂ | | Me | |
| 9-379 | pyrrol-1-yl | F | Cl | =CHNMe₂ | | H | |
| 9-380 | pyrrol-1-yl | F | Cl | =CHNMe₂ | | Me | |
| 9-381 | pyrrol-1-yl | F | Cl | =CHNMe₂ | | Et | |
| 9-382 | pyrrol-1-yl | F | Br | =CHNMe₂ | | H | |
| 9-383 | pyrrol-1-yl | F | Br | =CHNMe₂ | | Me | |
| 9-384 | pyrrol-1-yl | F | Br | =CHNMe₂ | | Et | |
| 9-385 | pyrrol-1-yl | F | F | =CHNMe₂ | | H | |
| 9-386 | pyrrol-1-yl | F | F | =CHNMe₂ | | Me | |
| 9-387 | pyrrol-1-yl | F | I | =CHNMe₂ | | H | |
| 9-388 | pyrrol-1-yl | F | I | =CHNMe₂ | | Me | |
| 9-389 | pyrrol-1-yl | F | CN | =CHNMe₂ | | H | |
| 9-390 | pyrrol-1-yl | F | CN | =CHNMe₂ | | Me | |

TABLE 9-continued

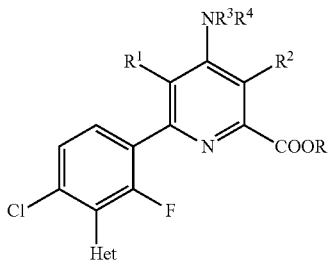

(I-ix)

| No. | Het | R¹ | R² | R³ | R⁴ | R | Physical data: ¹H-NMR: δ [CDCl₃] |
|---|---|---|---|---|---|---|---|
| 9-391 | pyrrol-1-yl | F | CF₃ | =CHNMe₂ | | H | |
| 9-392 | pyrrol-1-yl | F | CF₃ | =CHNMe₂ | | Me | |
| 9-393 | pyrazol-1-yl | H | Cl | H | H | H | |
| 9-394 | pyrazol-1-yl | H | Cl | H | H | Me | |
| 9-395 | pyrazol-1-yl | H | Cl | H | H | Et | |
| 9-396 | pyrazol-1-yl | H | Br | H | H | H | |
| 9-397 | pyrazol-1-yl | H | Br | H | H | Me | |
| 9-398 | pyrazol-1-yl | H | Br | H | H | Et | |
| 9-399 | pyrazol-1-yl | H | F | H | H | H | |
| 9-400 | pyrazol-1-yl | H | F | H | H | Me | |
| 9-401 | pyrazol-1-yl | H | I | H | H | H | |
| 9-402 | pyrazol-1-yl | H | I | H | H | Me | |
| 9-403 | pyrazol-1-yl | H | CN | H | H | H | |
| 9-404 | pyrazol-1-yl | H | CN | H | H | Me | |
| 9-405 | pyrazol-1-yl | H | CF₃ | H | H | H | |
| 9-406 | pyrazol-1-yl | H | CF₃ | H | H | Me | |
| 9-407 | pyrazol-1-yl | F | Cl | H | H | H | |
| 9-408 | pyrazol-1-yl | F | Cl | H | H | Me | |
| 9-409 | pyrazol-1-yl | F | Cl | H | H | Et | |
| 9-410 | pyrazol-1-yl | F | Br | H | H | H | |
| 9-411 | pyrazol-1-yl | F | Br | H | H | Me | |
| 9-412 | pyrazol-1-yl | F | Br | H | H | Et | |
| 9-413 | pyrazol-1-yl | F | F | H | H | H | |
| 9-414 | pyrazol-1-yl | F | F | H | H | Me | |
| 9-415 | pyrazol-1-yl | F | I | H | H | H | |
| 9-416 | pyrazol-1-yl | F | I | H | H | Me | |
| 9-417 | pyrazol-1-yl | F | CN | H | H | H | |
| 9-418 | pyrazol-1-yl | F | CN | H | H | Me | |
| 9-419 | pyrazol-1-yl | F | CF₃ | H | H | H | |
| 9-420 | pyrazol-1-yl | F | CF₃ | H | H | Me | |
| 9-421 | pyrazol-1-yl | H | Cl | H | Me | H | |
| 9-422 | pyrazol-1-yl | H | Cl | H | Me | Me | |
| 9-423 | pyrazol-1-yl | H | Cl | H | Me | Et | |
| 9-424 | pyrazol-1-yl | H | Br | H | Me | H | |
| 9-425 | pyrazol-1-yl | H | Br | H | Me | Me | |
| 9-426 | pyrazol-1-yl | H | Br | H | Me | Et | |
| 9-427 | pyrazol-1-yl | H | F | H | Me | H | |
| 9-428 | pyrazol-1-yl | H | F | H | Me | Me | |
| 9-429 | pyrazol-1-yl | H | I | H | Me | H | |
| 9-430 | pyrazol-1-yl | H | I | H | Me | Me | |
| 9-431 | pyrazol-1-yl | H | CN | H | Me | H | |
| 9-432 | pyrazol-1-yl | H | CN | H | Me | Me | |
| 9-433 | pyrazol-1-yl | H | CF₃ | H | Me | H | |
| 9-434 | pyrazol-1-yl | H | CF₃ | H | Me | Me | |
| 9-435 | pyrazol-1-yl | F | Cl | H | Me | H | |
| 9-436 | pyrazol-1-yl | F | Cl | H | Me | Me | |
| 9-437 | pyrazol-1-yl | F | Cl | H | Me | Et | |
| 9-438 | pyrazol-1-yl | F | Br | H | Me | H | |
| 9-439 | pyrazol-1-yl | F | Br | H | Me | Me | |
| 9-440 | pyrazol-1-yl | F | Br | H | Me | Et | |
| 9-441 | pyrazol-1-yl | F | F | H | Me | H | |
| 9-442 | pyrazol-1-yl | F | F | H | Me | Me | |
| 9-443 | pyrazol-1-yl | F | I | H | Me | H | |
| 9-444 | pyrazol-1-yl | F | I | H | Me | Me | |
| 9-445 | pyrazol-1-yl | F | CN | H | Me | H | |
| 9-446 | pyrazol-1-yl | F | CN | H | Me | Me | |
| 9-447 | pyrazol-1-yl | F | CF₃ | H | Me | H | |
| 9-448 | pyrazol-1-yl | F | CF₃ | H | Me | Me | |
| 9-449 | pyrazol-1-yl | H | Cl | Me | Me | H | |
| 9-450 | pyrazol-1-yl | H | Cl | Me | Me | Me | |
| 9-451 | pyrazol-1-yl | H | Cl | Me | Me | Et | |
| 9-452 | pyrazol-1-yl | H | Br | Me | Me | H | |

TABLE 9-continued

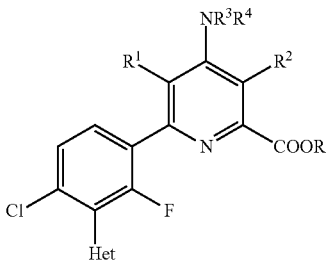

(I-ix)

| No. | Het | R¹ | R² | R³ | R⁴ | R | Physical data: ¹H-NMR: δ [CDCl₃] |
|---|---|---|---|---|---|---|---|
| 9-453 | pyrazol-1-yl | H | Br | Me | Me | Me | |
| 9-454 | pyrazol-1-yl | H | Br | Me | Me | Et | |
| 9-455 | pyrazol-1-yl | H | F | Me | Me | H | |
| 9-456 | pyrazol-1-yl | H | F | Me | Me | Me | |
| 9-457 | pyrazol-1-yl | H | I | Me | Me | H | |
| 9-458 | pyrazol-1-yl | H | I | Me | Me | Me | |
| 9-459 | pyrazol-1-yl | H | CN | Me | Me | H | |
| 9-460 | pyrazol-1-yl | H | CN | Me | Me | Me | |
| 9-461 | pyrazol-1-yl | H | CF₃ | Me | Me | H | |
| 9-462 | pyrazol-1-yl | H | CF₃ | Me | Me | Me | |
| 9-463 | pyrazol-1-yl | F | Cl | Me | Me | H | |
| 9-464 | pyrazol-1-yl | F | Cl | Me | Me | Me | |
| 9-465 | pyrazol-1-yl | F | Cl | Me | Me | Et | |
| 9-466 | pyrazol-1-yl | F | Br | Me | Me | H | |
| 9-467 | pyrazol-1-yl | F | Br | Me | Me | Me | |
| 9-468 | pyrazol-1-yl | F | Br | Me | Me | Et | |
| 9-469 | pyrazol-1-yl | F | F | Me | Me | H | |
| 9-470 | pyrazol-1-yl | F | F | Me | Me | Me | |
| 9-471 | pyrazol-1-yl | F | I | Me | Me | H | |
| 9-472 | pyrazol-1-yl | F | I | Me | Me | Me | |
| 9-473 | pyrazol-1-yl | F | CN | Me | Me | H | |
| 9-474 | pyrazol-1-yl | F | CN | Me | Me | Me | |
| 9-475 | pyrazol-1-yl | F | CF₃ | Me | Me | H | |
| 9-476 | pyrazol-1-yl | F | CF₃ | Me | Me | Me | |
| 9-477 | pyrazol-1-yl | H | Cl | =CHNMe₂ | | H | |
| 9-478 | pyrazol-1-yl | H | Cl | =CHNMe₂ | | Me | |
| 9-479 | pyrazol-1-yl | H | Cl | =CHNMe₂ | | Et | |
| 9-480 | pyrazol-1-yl | H | Br | =CHNMe₂ | | H | |
| 9-481 | pyrazol-1-yl | H | Br | =CHNMe₂ | | Me | |
| 9-482 | pyrazol-1-yl | H | Br | =CHNMe₂ | | Et | |
| 9-483 | pyrazol-1-yl | H | F | =CHNMe₂ | | H | |
| 9-484 | pyrazol-1-yl | H | F | =CHNMe₂ | | Me | |
| 9-485 | pyrazol-1-yl | H | I | =CHNMe₂ | | H | |
| 9-486 | pyrazol-1-yl | H | I | =CHNMe₂ | | Me | |
| 9-487 | pyrazol-1-yl | H | CN | =CHNMe₂ | | H | |
| 9-488 | pyrazol-1-yl | H | CN | =CHNMe₂ | | Me | |
| 9-489 | pyrazol-1-yl | H | CF₃ | =CHNMe₂ | | H | |
| 9-490 | pyrazol-1-yl | H | CF₃ | =CHNMe₂ | | Me | |
| 9-491 | pyrazol-1-yl | F | Cl | =CHNMe₂ | | H | |
| 9-492 | pyrazol-1-yl | F | Cl | =CHNMe₂ | | Me | |
| 9-493 | pyrazol-1-yl | F | Cl | =CHNMe₂ | | Et | |
| 9-494 | pyrazol-1-yl | F | Br | =CHNMe₂ | | H | |
| 9-495 | pyrazol-1-yl | F | Br | =CHNMe₂ | | Me | |
| 9-496 | pyrazol-1-yl | F | Br | =CHNMe₂ | | Et | |
| 9-497 | pyrazol-1-yl | F | F | =CHNMe₂ | | H | |
| 9-498 | pyrazol-1-yl | F | F | =CHNMe₂ | | Me | |
| 9-499 | pyrazol-1-yl | F | I | =CHNMe₂ | | H | |
| 9-500 | pyrazol-1-yl | F | I | =CHNMe₂ | | Me | |
| 9-501 | pyrazol-1-yl | F | CN | =CHNMe₂ | | H | |
| 9-502 | pyrazol-1-yl | F | CN | =CHNMe₂ | | Me | |
| 9-503 | pyrazol-1-yl | F | CF₃ | =CHNMe₂ | | H | |
| 9-504 | pyrazol-1-yl | F | CF₃ | =CHNMe₂ | | Me | |
| 9-505 | pyridin-3-yl | H | Cl | H | H | H | |
| 9-506 | pyridin-3-yl | H | Cl | H | H | Me | |
| 9-507 | pyridin-3-yl | H | Cl | H | H | Et | |
| 9-508 | pyridin-3-yl | H | Br | H | H | H | |
| 9-509 | pyridin-3-yl | H | Br | H | H | Me | |
| 9-510 | pyridin-3-yl | H | Br | H | H | Et | |
| 9-511 | pyridin-3-yl | H | F | H | H | H | |
| 9-512 | pyridin-3-yl | H | F | H | H | Me | |
| 9-513 | pyridin-3-yl | H | I | H | H | H | |
| 9-514 | pyridin-3-yl | H | I | H | H | Me | |
| 9-515 | pyridin-3-yl | H | CN | H | H | H | |
| 9-516 | pyridin-3-yl | H | CN | H | H | Me | |
| 9-517 | pyridin-3-yl | H | CF₃ | H | H | H | |
| 9-518 | pyridin-3-yl | H | CF₃ | H | H | Me | |
| 9-519 | pyridin-3-yl | F | Cl | H | H | H | |
| 9-520 | pyridin-3-yl | F | Cl | H | H | Me | |
| 9-521 | pyridin-3-yl | F | Cl | H | H | Et | |
| 9-522 | pyridin-3-yl | F | Br | H | H | H | |
| 9-523 | pyridin-3-yl | F | Br | H | H | Me | |
| 9-524 | pyridin-3-yl | F | Br | H | H | Et | |
| 9-525 | pyridin-3-yl | F | F | H | H | H | |
| 9-526 | pyridin-3-yl | F | F | H | H | Me | |
| 9-527 | pyridin-3-yl | F | I | H | H | H | |
| 9-528 | pyridin-3-yl | F | I | H | H | Me | |
| 9-529 | pyridin-3-yl | F | CN | H | H | H | |
| 9-530 | pyridin-3-yl | F | CN | H | H | Me | |
| 9-531 | pyridin-3-yl | F | CF₃ | H | H | H | |
| 9-532 | pyridin-3-yl | F | CF₃ | H | H | Me | |
| 9-533 | pyridin-3-yl | H | Cl | H | Me | H | |
| 9-534 | pyridin-3-yl | H | Cl | H | Me | Me | |
| 9-535 | pyridin-3-yl | H | Cl | H | Me | Et | |
| 9-536 | pyridin-3-yl | H | Br | H | Me | H | |
| 9-537 | pyridin-3-yl | H | Br | H | Me | Me | |
| 9-538 | pyridin-3-yl | H | Br | H | Me | Et | |
| 9-539 | pyridin-3-yl | H | F | H | Me | H | |
| 9-540 | pyridin-3-yl | H | F | H | Me | Me | |
| 9-541 | pyridin-3-yl | H | I | H | Me | H | |
| 9-542 | pyridin-3-yl | H | I | H | Me | Me | |
| 9-543 | pyridin-3-yl | H | CN | H | Me | H | |
| 9-544 | pyridin-3-yl | H | CN | H | Me | Me | |
| 9-545 | pyridin-3-yl | H | CF₃ | H | Me | H | |
| 9-546 | pyridin-3-yl | H | CF₃ | H | Me | Me | |
| 9-547 | pyridin-3-yl | F | Cl | H | Me | H | |
| 9-548 | pyridin-3-yl | F | Cl | H | Me | Me | |
| 9-549 | pyridin-3-yl | F | Cl | H | Me | Et | |
| 9-550 | pyridin-3-yl | F | Br | H | Me | H | |
| 9-551 | pyridin-3-yl | F | Br | H | Me | Me | |
| 9-552 | pyridin-3-yl | F | Br | H | Me | Et | |
| 9-553 | pyridin-3-yl | F | F | H | Me | H | |
| 9-554 | pyridin-3-yl | F | F | H | Me | Me | |
| 9-555 | pyridin-3-yl | F | I | H | Me | H | |
| 9-556 | pyridin-3-yl | F | I | H | Me | Me | |
| 9-557 | pyridin-3-yl | F | CN | H | Me | H | |
| 9-558 | pyridin-3-yl | F | CN | H | Me | Me | |
| 9-559 | pyridin-3-yl | F | CF₃ | H | Me | H | |
| 9-560 | pyridin-3-yl | F | CF₃ | H | Me | Me | |
| 9-561 | pyridin-3-yl | H | Cl | Me | Me | H | |
| 9-562 | pyridin-3-yl | H | Cl | Me | Me | Me | |
| 9-563 | pyridin-3-yl | H | Cl | Me | Me | Et | |
| 9-564 | pyridin-3-yl | H | Br | Me | Me | H | |
| 9-565 | pyridin-3-yl | H | Br | Me | Me | Me | |
| 9-566 | pyridin-3-yl | H | Br | Me | Me | Et | |
| 9-567 | pyridin-3-yl | H | F | Me | Me | H | |
| 9-568 | pyridin-3-yl | H | F | Me | Me | Me | |
| 9-569 | pyridin-3-yl | H | I | Me | Me | H | |
| 9-570 | pyridin-3-yl | H | I | Me | Me | Me | |
| 9-571 | pyridin-3-yl | H | CN | Me | Me | H | |
| 9-572 | pyridin-3-yl | H | CN | Me | Me | Me | |
| 9-573 | pyridin-3-yl | H | CF₃ | Me | Me | H | |
| 9-574 | pyridin-3-yl | H | CF₃ | Me | Me | Me | |
| 9-575 | pyridin-3-yl | F | Cl | Me | Me | H | |
| 9-576 | pyridin-3-yl | F | Cl | Me | Me | Me | |

TABLE 9-continued

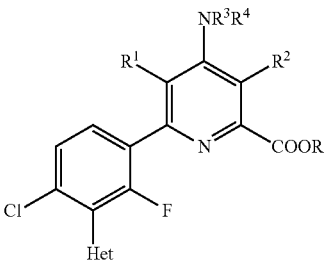

(I-ix)

| No. | Het | R¹ | R² | R³ | R⁴ | R | Physical data: ¹H-NMR: δ [CDCl₃] |
|---|---|---|---|---|---|---|---|
| 9-577 | pyridin-3-yl | F | Cl | Me | Me | Et | |
| 9-578 | pyridin-3-yl | F | Br | Me | Me | H | |
| 9-579 | pyridin-3-yl | F | Br | Me | Me | Me | |
| 9-580 | pyridin-3-yl | F | Br | Me | Me | Et | |
| 9-581 | pyridin-3-yl | F | F | Me | Me | H | |
| 9-582 | pyridin-3-yl | F | F | Me | Me | Me | |
| 9-583 | pyridin-3-yl | F | I | Me | Me | H | |
| 9-584 | pyridin-3-yl | F | I | Me | Me | Me | |
| 9-585 | pyridin-3-yl | F | CN | Me | Me | H | |
| 9-586 | pyridin-3-yl | F | CN | Me | Me | Me | |
| 9-587 | pyridin-3-yl | F | CF₃ | Me | Me | H | |
| 9-588 | pyridin-3-yl | F | CF₃ | Me | Me | Me | |
| 9-589 | pyridin-3-yl | H | Cl | =CHNMe₂ | H | | |
| 9-590 | pyridin-3-yl | H | Cl | =CHNMe₂ | Me | | |
| 9-591 | pyridin-3-yl | H | Cl | =CHNMe₂ | Et | | |
| 9-592 | pyridin-3-yl | H | Br | =CHNMe₂ | H | | |
| 9-593 | pyridin-3-yl | H | Br | =CHNMe₂ | Me | | |
| 9-594 | pyridin-3-yl | H | Br | =CHNMe₂ | Et | | |
| 9-595 | pyridin-3-yl | H | F | =CHNMe₂ | H | | |
| 9-596 | pyridin-3-yl | H | F | =CHNMe₂ | Me | | |
| 9-597 | pyridin-3-yl | H | I | =CHNMe₂ | H | | |
| 9-598 | pyridin-3-yl | H | I | =CHNMe₂ | Me | | |
| 9-599 | pyridin-3-yl | H | CN | =CHNMe₂ | H | | |
| 9-600 | pyridin-3-yl | H | CN | =CHNMe₂ | Me | | |
| 9-601 | pyridin-3-yl | H | CF₃ | =CHNMe₂ | H | | |
| 9-602 | pyridin-3-yl | H | CF₃ | =CHNMe₂ | Me | | |
| 9-603 | pyridin-3-yl | F | Cl | =CHNMe₂ | H | | |
| 9-604 | pyridin-3-yl | F | Cl | =CHNMe₂ | Me | | |
| 9-605 | pyridin-3-yl | F | Cl | =CHNMe₂ | Et | | |
| 9-606 | pyridin-3-yl | F | Br | =CHNMe₂ | H | | |
| 9-607 | pyridin-3-yl | F | Br | =CHNMe₂ | Me | | |
| 9-608 | pyridin-3-yl | F | Br | =CHNMe₂ | Et | | |
| 9-609 | pyridin-3-yl | F | F | =CHNMe₂ | H | | |
| 9-610 | pyridin-3-yl | F | F | =CHNMe₂ | Me | | |
| 9-611 | pyridin-3-yl | F | I | =CHNMe₂ | H | | |
| 9-612 | pyridin-3-yl | F | I | =CHNMe₂ | Me | | |
| 9-613 | pyridin-3-yl | F | CN | =CHNMe₂ | H | | |
| 9-614 | pyridin-3-yl | F | CN | =CHNMe₂ | Me | | |
| 9-615 | pyridin-3-yl | F | CF₃ | =CHNMe₂ | H | | |
| 9-616 | pyridin-3-yl | F | CF₃ | =CHNMe₂ | Me | | |
| 9-617 | oxiranyl | H | Cl | H | H | H | |
| 9-618 | oxiranyl | H | Cl | H | H | Me | 7.92 (dd, 1H), 7.27 (d, 1H), 7.19 (s, 1H), 4.86 (bs, 2H), 4.06 (m, 1H), 3.99 (s, 3H), 3.23 (t, 1H), 3.12 (m, 1H) |
| 9-619 | oxiranyl | H | Cl | H | H | Et | |
| 9-620 | oxiranyl | H | Br | H | H | H | |
| 9-621 | oxiranyl | H | Br | H | H | Me | |
| 9-622 | oxiranyl | H | Br | H | H | Et | |
| 9-623 | oxiranyl | H | F | H | H | H | |
| 9-624 | oxiranyl | H | F | H | H | Me | |
| 9-625 | oxiranyl | H | I | H | H | H | |
| 9-626 | oxiranyl | H | I | H | H | Me | |
| 9-627 | oxiranyl | H | CN | H | H | H | |
| 9-628 | oxiranyl | H | CN | H | H | Me | |
| 9-629 | oxiranyl | H | CF₃ | H | H | H | |
| 9-630 | oxiranyl | H | CF₃ | H | H | Me | |
| 9-631 | oxiranyl | F | Cl | H | H | H | |

TABLE 9-continued

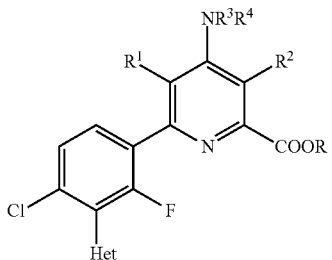

(I-ix)

| No. | Het | R¹ | R² | R³ | R⁴ | R | Physical data: ¹H-NMR: δ [CDCl₃] |
|---|---|---|---|---|---|---|---|
| 9-632 | oxiranyl | F | Cl | H | H | Me | |
| 9-633 | oxiranyl | F | Cl | H | H | Et | |
| 9-634 | oxiranyl | F | Br | H | H | H | |
| 9-635 | oxiranyl | F | Br | H | H | Me | |
| 9-636 | oxiranyl | F | Br | H | H | Et | |
| 9-637 | oxiranyl | F | F | H | H | H | |
| 9-638 | oxiranyl | F | F | H | H | Me | |
| 9-639 | oxiranyl | F | I | H | H | H | |
| 9-640 | oxiranyl | F | I | H | H | Me | |
| 9-641 | oxiranyl | F | CN | H | H | H | |
| 9-642 | oxiranyl | F | CN | H | H | Me | |
| 9-643 | oxiranyl | F | CF₃ | H | H | H | |
| 9-644 | oxiranyl | F | CF₃ | H | H | Me | |
| 9-645 | oxiranyl | H | Cl | H | Me | H | |
| 9-646 | oxiranyl | H | Cl | H | Me | Me | |
| 9-647 | oxiranyl | H | Cl | H | Me | Et | |
| 9-648 | oxiranyl | H | Br | H | Me | H | |
| 9-649 | oxiranyl | H | Br | H | Me | Me | |
| 9-650 | oxiranyl | H | Br | H | Me | Et | |
| 9-651 | oxiranyl | H | F | H | Me | H | |
| 9-652 | oxiranyl | H | F | H | Me | Me | |
| 9-653 | oxiranyl | H | I | H | Me | H | |
| 9-654 | oxiranyl | H | I | H | Me | Me | |
| 9-655 | oxiranyl | H | CN | H | Me | H | |
| 9-656 | oxiranyl | H | CN | H | Me | Me | |
| 9-657 | oxiranyl | H | CF₃ | H | Me | H | |
| 9-658 | oxiranyl | H | CF₃ | H | Me | Me | |
| 9-659 | oxiranyl | F | Cl | H | Me | H | |
| 9-660 | oxiranyl | F | Cl | H | Me | Me | |
| 9-661 | oxiranyl | F | Cl | H | Me | Et | |
| 9-662 | oxiranyl | F | Br | H | Me | H | |
| 9-663 | oxiranyl | F | Br | H | Me | Me | |
| 9-664 | oxiranyl | F | Br | H | Me | Et | |
| 9-665 | oxiranyl | F | F | H | Me | H | |
| 9-666 | oxiranyl | F | F | H | Me | Me | |
| 9-667 | oxiranyl | F | I | H | Me | H | |
| 9-668 | oxiranyl | F | I | H | Me | Me | |
| 9-669 | oxiranyl | F | CN | H | Me | H | |
| 9-670 | oxiranyl | F | CN | H | Me | Me | |
| 9-671 | oxiranyl | F | CF₃ | H | Me | H | |
| 9-672 | oxiranyl | F | CF₃ | H | Me | Me | |
| 9-673 | oxiranyl | H | Cl | Me | Me | H | |
| 9-674 | oxiranyl | H | Cl | Me | Me | Me | |
| 9-675 | oxiranyl | H | Cl | Me | Me | Et | |
| 9-676 | oxiranyl | H | Br | Me | Me | H | |
| 9-677 | oxiranyl | H | Br | Me | Me | Me | |
| 9-678 | oxiranyl | H | Br | Me | Me | Et | |
| 9-679 | oxiranyl | H | F | Me | Me | H | |
| 9-680 | oxiranyl | H | F | Me | Me | Me | |
| 9-681 | oxiranyl | H | I | Me | Me | H | |
| 9-682 | oxiranyl | H | I | Me | Me | Me | |
| 9-683 | oxiranyl | H | CN | Me | Me | H | |
| 9-684 | oxiranyl | H | CN | Me | Me | Me | |
| 9-685 | oxiranyl | H | CF₃ | Me | Me | H | |
| 9-686 | oxiranyl | H | CF₃ | Me | Me | Me | |
| 9-687 | oxiranyl | F | Cl | Me | Me | H | |
| 9-688 | oxiranyl | F | Cl | Me | Me | Me | |
| 9-689 | oxiranyl | F | Cl | Me | Me | Et | |
| 9-690 | oxiranyl | F | Br | Me | Me | H | |
| 9-691 | oxiranyl | F | Br | Me | Me | Me | |
| 9-692 | oxiranyl | F | Br | Me | Me | Et | |
| 9-693 | oxiranyl | F | F | Me | Me | H | |

TABLE 9-continued

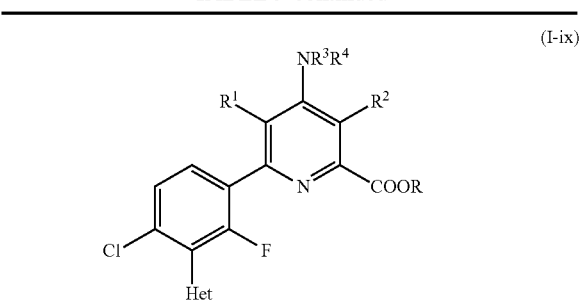

(I-ix)

| No. | Het | R¹ | R² | R³ | R⁴ | R | Physical data: ¹H-NMR: δ [CDCl₃] |
|---|---|---|---|---|---|---|---|
| 9-694 | oxiranyl | F | F | Me | Me | Me | |
| 9-695 | oxiranyl | F | I | Me | Me | H | |
| 9-696 | oxiranyl | F | I | Me | Me | Me | |
| 9-697 | oxiranyl | F | CN | Me | Me | H | |
| 9-698 | oxiranyl | F | CN | Me | Me | Me | |
| 9-699 | oxiranyl | F | CF₃ | Me | Me | H | |
| 9-700 | oxiranyl | F | CF₃ | Me | Me | Me | |
| 9-701 | oxiranyl | H | Cl | =CHNMe₂ | H | | |
| 9-702 | oxiranyl | H | Cl | =CHNMe₂ | Me | | |
| 9-703 | oxiranyl | H | Cl | =CHNMe₂ | Et | | |
| 9-704 | oxiranyl | H | Br | =CHNMe₂ | H | | |
| 9-705 | oxiranyl | H | Br | =CHNMe₂ | Me | | |
| 9-706 | oxiranyl | H | Br | =CHNMe₂ | Et | | |
| 9-707 | oxiranyl | H | F | =CHNMe₂ | H | | |
| 9-708 | oxiranyl | H | F | =CHNMe₂ | Me | | |
| 9-709 | oxiranyl | H | I | =CHNMe₂ | H | | |
| 9-710 | oxiranyl | H | I | =CHNMe₂ | Me | | |
| 9-711 | oxiranyl | H | CN | =CHNMe₂ | H | | |
| 9-712 | oxiranyl | H | CN | =CHNMe₂ | Me | | |
| 9-713 | oxiranyl | H | CF₃ | =CHNMe₂ | H | | |
| 9-714 | oxiranyl | H | CF₃ | =CHNMe₂ | Me | | |
| 9-715 | oxiranyl | F | Cl | =CHNMe₂ | H | | |
| 9-716 | oxiranyl | F | Cl | =CHNMe₂ | Me | | |
| 9-717 | oxiranyl | F | Cl | =CHNMe₂ | Et | | |
| 9-718 | oxiranyl | F | Br | =CHNMe₂ | H | | |
| 9-719 | oxiranyl | F | Br | =CHNMe₂ | Me | | |
| 9-720 | oxiranyl | F | Br | =CHNMe₂ | Et | | |
| 9-721 | oxiranyl | F | F | =CHNMe₂ | H | | |
| 9-722 | oxiranyl | F | F | =CHNMe₂ | Me | | |
| 9-723 | oxiranyl | F | I | =CHNMe₂ | H | | |
| 9-724 | oxiranyl | F | I | =CHNMe₂ | Me | | |
| 9-725 | oxiranyl | F | CN | =CHNMe₂ | H | | |
| 9-726 | oxiranyl | F | CN | =CHNMe₂ | Me | | |
| 9-727 | oxiranyl | F | CF₃ | =CHNMe₂ | H | | |
| 9-728 | oxiranyl | F | CF₃ | =CHNMe₂ | Me | | |
| 9-729 | 3,3-dimethyl-oxetan-2-yl | H | Cl | H | H | H | |
| 9-730 | 3,3-dimethyl-oxetan-2-yl | H | Cl | H | H | Me | 7.83 (dd, 1H), 7.25 (m, 2H), 6.06 (s, 1H), 4.98 (bs, 2H), 4.57 (d, 1H), 4.49 (d, 1H), 4.01 (s, 3H), 1.54 (s, 3H), 0.98 (s, 3H) |
| 9-731 | 3,3-dimethyl-oxetan-2-yl | H | Cl | H | H | Et | |
| 9-732 | 3,3-dimethyl-oxetan-2-yl | H | Br | H | H | H | |
| 9-733 | 3,3-dimethyl-oxetan-2-yl | H | Br | H | H | Me | |
| 9-734 | 3,3-dimethyl-oxetan-2-yl | H | Br | H | H | Et | |
| 9-735 | 3,3-dimethyl-oxetan-2-yl | H | F | H | H | H | |
| 9-736 | 3,3-dimethyl-oxetan-2-yl | H | F | H | H | Me | |
| 9-737 | 3,3-dimethyl-oxetan-2-yl | H | I | H | H | H | |
| 9-738 | 3,3-dimethyl-oxetan-2-yl | H | I | H | H | Me | |
| 9-739 | 3,3-dimethyl-oxetan-2-yl | H | CN | H | H | H | |
| 9-740 | 3,3-dimethyl-oxetan-2-yl | H | CN | H | H | Me | |
| 9-741 | 3,3-dimethyl-oxetan-2-yl | H | CF₃ | H | H | H | |
| 9-742 | 3,3-dimethyl-oxetan-2-yl | H | CF₃ | H | H | Me | |
| 9-743 | 3,3-dimethyl-oxetan-2-yl | F | Cl | H | H | H | |
| 9-744 | 3,3-dimethyl-oxetan-2-yl | F | Cl | H | H | Me | |
| 9-745 | 3,3-dimethyl-oxetan-2-yl | F | Cl | H | H | Et | |
| 9-746 | 3,3-dimethyl-oxetan-2-yl | F | Br | H | H | H | |
| 9-747 | 3,3-dimethyl-oxetan-2-yl | F | Br | H | H | Me | |
| 9-748 | 3,3-dimethyl-oxetan-2-yl | F | Br | H | H | Et | |
| 9-749 | 3,3-dimethyl-oxetan-2-yl | F | F | H | H | H | |
| 9-750 | 3,3-dimethyl-oxetan-2-yl | F | F | H | H | Me | |
| 9-751 | 3,3-dimethyl-oxetan-2-yl | F | I | H | H | H | |
| 9-752 | 3,3-dimethyl-oxetan-2-yl | F | I | H | H | Me | |
| 9-753 | 3,3-dimethyl-oxetan-2-yl | F | CN | H | H | H | |
| 9-754 | 3,3-dimethyl-oxetan-2-yl | F | CN | H | H | Me | |
| 9-755 | 3,3-dimethyl-oxetan-2-yl | F | CF₃ | H | H | H | |
| 9-756 | 3,3-dimethyl-oxetan-2-yl | F | CF₃ | H | H | Me | |
| 9-757 | 3,3-dimethyl-oxetan-2-yl | H | Cl | H | Me | H | |
| 9-758 | 3,3-dimethyl-oxetan-2-yl | H | Cl | H | Me | Me | |
| 9-759 | 3,3-dimethyl-oxetan-2-yl | H | Cl | H | Me | Et | |
| 9-760 | 3,3-dimethyl-oxetan-2-yl | H | Br | H | Me | H | |
| 9-761 | 3,3-dimethyl-oxetan-2-yl | H | Br | H | Me | Me | |
| 9-762 | 3,3-dimethyl-oxetan-2-yl | H | Br | H | Me | Et | |
| 9-763 | 3,3-dimethyl-oxetan-2-yl | H | F | H | Me | H | |
| 9-764 | 3,3-dimethyl-oxetan-2-yl | H | F | H | Me | Me | |
| 9-765 | 3,3-dimethyl-oxetan-2-yl | H | I | H | Me | H | |
| 9-766 | 3,3-dimethyl-oxetan-2-yl | H | I | H | Me | Me | |
| 9-767 | 3,3-dimethyl-oxetan-2-yl | H | CN | H | Me | H | |
| 9-768 | 3,3-dimethyl-oxetan-2-yl | H | CN | H | Me | Me | |
| 9-769 | 3,3-dimethyl-oxetan-2-yl | H | CF₃ | H | Me | H | |

TABLE 9-continued

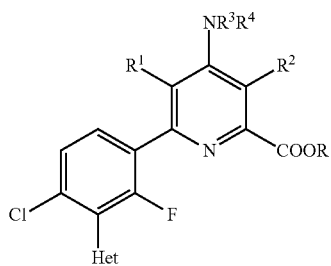

(I-ix)

| No. | Het | R¹ | R² | R³ | R⁴ | R | Physical data: ¹H-NMR: δ [CDCl₃] |
|---|---|---|---|---|---|---|---|
| 9-770 | 3,3-dimethyl-oxetan-2-yl | H | CF₃ | H | Me | Me | |
| 9-771 | 3,3-dimethyl-oxetan-2-yl | F | Cl | H | Me | H | |
| 9-772 | 3,3-dimethyl-oxetan-2-yl | F | Cl | H | Me | Me | |
| 9-773 | 3,3-dimethyl-oxetan-2-yl | F | Cl | H | Me | Et | |
| 9-774 | 3,3-dimethyl-oxetan-2-yl | F | Br | H | Me | H | |
| 9-775 | 3,3-dimethyl-oxetan-2-yl | F | Br | H | Me | Me | |
| 9-776 | 3,3-dimethyl-oxetan-2-yl | F | Br | H | Me | Et | |
| 9-777 | 3,3-dimethyl-oxetan-2-yl | F | F | H | Me | H | |
| 9-778 | 3,3-dimethyl-oxetan-2-yl | F | F | H | Me | Me | |
| 9-779 | 3,3-dimethyl-oxetan-2-yl | F | I | H | Me | H | |
| 9-780 | 3,3-dimethyl-oxetan-2-yl | F | I | H | Me | Me | |
| 9-781 | 3,3-dimethyl-oxetan-2-yl | F | CN | H | Me | H | |
| 9-782 | 3,3-dimethyl-oxetan-2-yl | F | CN | H | Me | Me | |
| 9-783 | 3,3-dimethyl-oxetan-2-yl | F | CF₃ | H | Me | H | |
| 9-784 | 3,3-dimethyl-oxetan-2-yl | F | CF₃ | H | Me | Me | |
| 9-785 | 3,3-dimethyl-oxetan-2-yl | H | Cl | Me | Me | H | |
| 9-786 | 3,3-dimethyl-oxetan-2-yl | H | Cl | Me | Me | Me | |
| 9-787 | 3,3-dimethyl-oxetan-2-yl | H | Cl | Me | Me | Et | |
| 9-788 | 3,3-dimethyl-oxetan-2-yl | H | Br | Me | Me | H | |
| 9-789 | 3,3-dimethyl-oxetan-2-yl | H | Br | Me | Me | Me | |
| 9-790 | 3,3-dimethyl-oxetan-2-yl | H | Br | Me | Me | Et | |
| 9-791 | 3,3-dimethyl-oxetan-2-yl | H | F | Me | Me | H | |
| 9-792 | 3,3-dimethyl-oxetan-2-yl | H | F | Me | Me | Me | |
| 9-793 | 3,3-dimethyl-oxetan-2-yl | H | I | Me | Me | H | |
| 9-794 | 3,3-dimethyl-oxetan-2-yl | H | I | Me | Me | Me | |
| 9-795 | 3,3-dimethyl-oxetan-2-yl | H | CN | Me | Me | H | |
| 9-796 | 3,3-dimethyl-oxetan-2-yl | H | CN | Me | Me | Me | |
| 9-797 | 3,3-dimethyl-oxetan-2-yl | H | CF₃ | Me | Me | H | |
| 9-798 | 3,3-dimethyl-oxetan-2-yl | H | CF₃ | Me | Me | Me | |
| 9-799 | 3,3-dimethyl-oxetan-2-yl | F | Cl | Me | Me | H | |
| 9-800 | 3,3-dimethyl-oxetan-2-yl | F | Cl | Me | Me | Me | |
| 9-801 | 3,3-dimethyl-oxetan-2-yl | F | Cl | Me | Me | Et | |
| 9-802 | 3,3-dimethyl-oxetan-2-yl | F | Br | Me | Me | H | |
| 9-803 | 3,3-dimethyl-oxetan-2-yl | F | Br | Me | Me | Me | |
| 9-804 | 3,3-dimethyl-oxetan-2-yl | F | Br | Me | Me | Et | |
| 9-805 | 3,3-dimethyl-oxetan-2-yl | F | F | Me | Me | H | |
| 9-806 | 3,3-dimethyl-oxetan-2-yl | F | F | Me | Me | Me | |
| 9-807 | 3,3-dimethyl-oxetan-2-yl | F | I | Me | Me | H | |
| 9-808 | 3,3-dimethyl-oxetan-2-yl | F | I | Me | Me | Me | |
| 9-809 | 3,3-dimethyl-oxetan-2-yl | F | CN | Me | Me | H | |
| 9-810 | 3,3-dimethyl-oxetan-2-yl | F | CN | Me | Me | Me | |
| 9-811 | 3,3-dimethyl-oxetan-2-yl | F | CF₃ | Me | Me | H | |
| 9-812 | 3,3-dimethyl-oxetan-2-yl | F | CF₃ | Me | Me | Me | |
| 9-813 | 3,3-dimethyl-oxetan-2-yl | H | Cl | =CHNMe₂ | | H | |
| 9-814 | 3,3-dimethyl-oxetan-2-yl | H | Cl | =CHNMe₂ | | Me | |
| 9-815 | 3,3-dimethyl-oxetan-2-yl | H | Cl | =CHNMe₂ | | Et | |
| 9-816 | 3,3-dimethyl-oxetan-2-yl | H | Br | =CHNMe₂ | | H | |
| 9-817 | 3,3-dimethyl-oxetan-2-yl | H | Br | =CHNMe₂ | | Me | |
| 9-818 | 3,3-dimethyl-oxetan-2-yl | H | Br | =CHNMe₂ | | Et | |
| 9-819 | 3,3-dimethyl-oxetan-2-yl | H | F | =CHNMe₂ | | H | |
| 9-820 | 3,3-dimethyl-oxetan-2-yl | H | F | =CHNMe₂ | | Me | |
| 9-821 | 3,3-dimethyl-oxetan-2-yl | H | I | =CHNMe₂ | | H | |
| 9-822 | 3,3-dimethyl-oxetan-2-yl | H | I | =CHNMe₂ | | Me | |
| 9-823 | 3,3-dimethyl-oxetan-2-yl | H | CN | =CHNMe₂ | | H | |
| 9-824 | 3,3-dimethyl-oxetan-2-yl | H | CN | =CHNMe₂ | | Me | |
| 9-825 | 3,3-dimethyl-oxetan-2-yl | H | CF₃ | =CHNMe₂ | | H | |
| 9-826 | 3,3-dimethyl-oxetan-2-yl | H | CF₃ | =CHNMe₂ | | Me | |
| 9-827 | 3,3-dimethyl-oxetan-2-yl | F | Cl | =CHNMe₂ | | H | |
| 9-828 | 3,3-dimethyl-oxetan-2-yl | F | Cl | =CHNMe₂ | | Me | |
| 9-829 | 3,3-dimethyl-oxetan-2-yl | F | Cl | =CHNMe₂ | | Et | |
| 9-830 | 3,3-dimethyl-oxetan-2-yl | F | Br | =CHNMe₂ | | H | |
| 9-831 | 3,3-dimethyl-oxetan-2-yl | F | Br | =CHNMe₂ | | Me | |

TABLE 9-continued

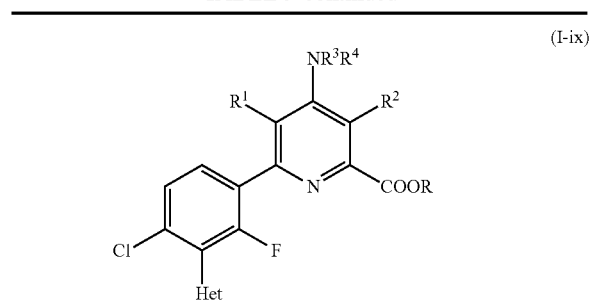

(I-ix)

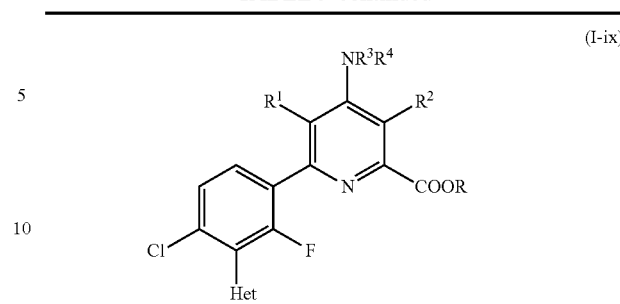

(I-ix)

| No. | Het | R¹ | R² | R³ | R⁴ | R | Physical data: ¹H-NMR: δ [CDCl₃] |
|---|---|---|---|---|---|---|---|
| 9-832 | 3,3-dimethyl-oxetan-2-yl | F | Br | =CHNMe₂ | | Et | |
| 9-833 | 3,3-dimethyl-oxetan-2-yl | F | F | =CHNMe₂ | | H | |
| 9-834 | 3,3-dimethyl-oxetan-2-yl | F | F | =CHNMe₂ | | Me | |
| 9-835 | 3,3-dimethyl-oxetan-2-yl | F | I | =CHNMe₂ | | H | |
| 9-836 | 3,3-dimethyl-oxetan-2-yl | F | I | =CHNMe₂ | | Me | |
| 9-837 | 3,3-dimethyl-oxetan-2-yl | F | CN | =CHNMe₂ | | H | |
| 9-838 | 3,3-dimethyl-oxetan-2-yl | F | CN | =CHNMe₂ | | Me | |
| 9-839 | 3,3-dimethyl-oxetan-2-yl | F | CF₃ | =CHNMe₂ | | H | |
| 9-840 | 3,3-dimethyl-oxetan-2-yl | F | CF₃ | =CHNMe₂ | | Me | |
| 9-841 | 2,2-dimethyl-dioxolan-4-yl | H | Cl | H | H | H | |
| 9-842 | 2,2-dimethyl-dioxolan-4-yl | H | Cl | H | H | Me | 7.90 (dd, 1H), 7.26 (m, 1H), 7.21 (d, 1H), 5.70 (dd, 1H), 4.83 (bs, 2H), 4.28 (dd, 1H), 4.11 (dd, 1H), 3.99 (s, 3H), 1.59 (s, 3H), 1.48 (s, 1H) |
| 9-843 | 2,2-dimethyl-dioxolan-4-yl | H | Cl | H | H | Et | |
| 9-844 | 2,2-dimethyl-dioxolan-4-yl | H | Br | H | H | H | |
| 9-845 | 2,2-dimethyl-dioxolan-4-yl | H | Br | H | H | Me | |
| 9-846 | 2,2-dimethyl-dioxolan-4-yl | H | Br | H | H | Et | |
| 9-847 | 2,2-dimethyl-dioxolan-4-yl | H | F | H | H | H | |
| 9-848 | 2,2-dimethyl-dioxolan-4-yl | H | F | H | H | Me | |
| 9-849 | 2,2-dimethyl-dioxolan-4-yl | H | I | H | H | H | |
| 9-850 | 2,2-dimethyl-dioxolan-4-yl | H | I | H | H | Me | |
| 9-851 | 2,2-dimethyl-dioxolan-4-yl | H | CN | H | H | H | |
| 9-852 | 2,2-dimethyl-dioxolan-4-yl | H | CN | H | H | Me | |
| 9-853 | 2,2-dimethyl-dioxolan-4-yl | H | CF₃ | H | H | H | |
| 9-854 | 2,2-dimethyl-dioxolan-4-yl | H | CF₃ | H | H | Me | |
| 9-855 | 2,2-dimethyl-dioxolan-4-yl | F | Cl | H | H | H | |
| 9-856 | 2,2-dimethyl-dioxolan-4-yl | F | Cl | H | H | Me | |
| 9-857 | 2,2-dimethyl-dioxolan-4-yl | F | Cl | H | H | Et | |
| 9-858 | 2,2-dimethyl-dioxolan-4-yl | F | Br | H | H | H | |
| 9-859 | 2,2-dimethyl-dioxolan-4-yl | F | Br | H | H | Me | |
| 9-860 | 2,2-dimethyl-dioxolan-4-yl | F | Br | H | H | Et | |
| 9-861 | 2,2-dimethyl-dioxolan-4-yl | F | F | H | H | H | |
| 9-862 | 2,2-dimethyl-dioxolan-4-yl | F | F | H | H | Me | |
| 9-863 | 2,2-dimethyl-dioxolan-4-yl | F | I | H | H | H | |
| 9-864 | 2,2-dimethyl-dioxolan-4-yl | F | I | H | H | Me | |
| 9-865 | 2,2-dimethyl-dioxolan-4-yl | F | CN | H | H | H | |
| 9-866 | 2,2-dimethyl-dioxolan-4-yl | F | CN | H | H | Me | |
| 9-867 | 2,2-dimethyl-dioxolan-4-yl | F | CF₃ | H | H | H | |
| 9-868 | 2,2-dimethyl-dioxolan-4-yl | F | CF₃ | H | H | Me | |
| 9-869 | 2,2-dimethyl-dioxolan-4-yl | H | Cl | H | Me | H | |
| 9-870 | 2,2-dimethyl-dioxolan-4-yl | H | Cl | H | Me | Me | |
| 9-871 | 2,2-dimethyl-dioxolan-4-yl | H | Cl | H | Me | Et | |
| 9-872 | 2,2-dimethyl-dioxolan-4-yl | H | Br | H | Me | H | |
| 9-873 | 2,2-dimethyl-dioxolan-4-yl | H | Br | H | Me | Me | |
| 9-874 | 2,2-dimethyl-dioxolan-4-yl | H | Br | H | Me | Et | |
| 9-875 | 2,2-dimethyl-dioxolan-4-yl | H | F | H | Me | H | |
| 9-876 | 2,2-dimethyl-dioxolan-4-yl | H | F | H | Me | Me | |
| 9-877 | 2,2-dimethyl-dioxolan-4-yl | H | I | H | Me | H | |
| 9-878 | 2,2-dimethyl-dioxolan-4-yl | H | I | H | Me | Me | |
| 9-879 | 2,2-dimethyl-dioxolan-4-yl | H | CN | H | Me | H | |
| 9-880 | 2,2-dimethyl-dioxolan-4-yl | H | CN | H | Me | Me | |
| 9-881 | 2,2-dimethyl-dioxolan-4-yl | H | CF₃ | H | Me | H | |
| 9-882 | 2,2-dimethyl-dioxolan-4-yl | H | CF₃ | H | Me | Me | |
| 9-883 | 2,2-dimethyl-dioxolan-4-yl | F | Cl | H | Me | H | |
| 9-884 | 2,2-dimethyl-dioxolan-4-yl | F | Cl | H | Me | Me | |
| 9-885 | 2,2-dimethyl-dioxolan-4-yl | F | Cl | H | Me | Et | |
| 9-886 | 2,2-dimethyl-dioxolan-4-yl | F | Br | H | Me | H | |
| 9-887 | 2,2-dimethyl-dioxolan-4-yl | F | Br | H | Me | Me | |
| 9-888 | 2,2-dimethyl-dioxolan-4-yl | F | Br | H | Me | Et | |
| 9-889 | 2,2-dimethyl-dioxolan-4-yl | F | F | H | Me | H | |

TABLE 9-continued

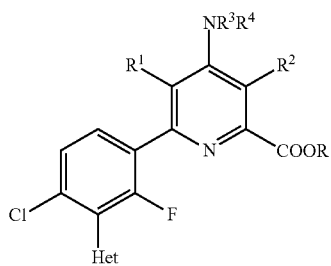

(I-ix)

| No. | Het | R¹ | R² | R³ | R⁴ | R | Physical data: $^1$H-NMR: δ [CDCl$_3$] |
|---|---|---|---|---|---|---|---|
| 9-890 | 2,2-dimethyl-dioxolan-4-yl | F | F | H | Me | Me | |
| 9-891 | 2,2-dimethyl-dioxolan-4-yl | F | I | H | Me | H | |
| 9-892 | 2,2-dimethyl-dioxolan-4-yl | F | I | H | Me | Me | |
| 9-893 | 2,2-dimethyl-dioxolan-4-yl | F | CN | H | Me | H | |
| 9-894 | 2,2-dimethyl-dioxolan-4-yl | F | CN | H | Me | Me | |
| 9-895 | 2,2-dimethyl-dioxolan-4-yl | F | CF$_3$ | H | Me | H | |
| 9-896 | 2,2-dimethyl-dioxolan-4-yl | F | CF$_3$ | H | Me | Me | |
| 9-897 | 2,2-dimethyl-dioxolan-4-yl | H | Cl | Me | Me | H | |
| 9-898 | 2,2-dimethyl-dioxolan-4-yl | H | Cl | Me | Me | Me | |
| 9-899 | 2,2-dimethyl-dioxolan-4-yl | H | Cl | Me | Me | Et | |
| 9-900 | 2,2-dimethyl-dioxolan-4-yl | H | Br | Me | Me | H | |
| 9-901 | 2,2-dimethyl-dioxolan-4-yl | H | Br | Me | Me | Me | |
| 9-902 | 2,2-dimethyl-dioxolan-4-yl | H | Br | Me | Me | Et | |
| 9-903 | 2,2-dimethyl-dioxolan-4-yl | H | F | Me | Me | H | |
| 9-904 | 2,2-dimethyl-dioxolan-4-yl | H | F | Me | Me | Me | |
| 9-905 | 2,2-dimethyl-dioxolan-4-yl | H | I | Me | Me | H | |
| 9-906 | 2,2-dimethyl-dioxolan-4-yl | H | I | Me | Me | Me | |
| 9-907 | 2,2-dimethyl-dioxolan-4-yl | H | CN | Me | Me | H | |
| 9-908 | 2,2-dimethyl-dioxolan-4-yl | H | CN | Me | Me | Me | |
| 9-909 | 2,2-dimethyl-dioxolan-4-yl | H | CF$_3$ | Me | Me | H | |
| 9-910 | 2,2-dimethyl-dioxolan-4-yl | H | CF$_3$ | Me | Me | Me | |
| 9-911 | 2,2-dimethyl-dioxolan-4-yl | F | Cl | Me | Me | H | |
| 9-912 | 2,2-dimethyl-dioxolan-4-yl | F | Cl | Me | Me | Me | |
| 9-913 | 2,2-dimethyl-dioxolan-4-yl | F | Cl | Me | Me | Et | |
| 9-914 | 2,2-dimethyl-dioxolan-4-yl | F | Br | Me | Me | H | |
| 9-915 | 2,2-dimethyl-dioxolan-4-yl | F | Br | Me | Me | Me | |
| 9-916 | 2,2-dimethyl-dioxolan-4-yl | F | Br | Me | Me | Et | |
| 9-917 | 2,2-dimethyl-dioxolan-4-yl | F | F | Me | Me | H | |
| 9-918 | 2,2-dimethyl-dioxolan-4-yl | F | F | Me | Me | Me | |
| 9-919 | 2,2-dimethyl-dioxolan-4-yl | F | I | Me | Me | H | |
| 9-920 | 2,2-dimethyl-dioxolan-4-yl | F | I | Me | Me | Me | |
| 9-921 | 2,2-dimethyl-dioxolan-4-yl | F | CN | Me | Me | H | |
| 9-922 | 2,2-dimethyl-dioxolan-4-yl | F | CN | Me | Me | Me | |
| 9-923 | 2,2-dimethyl-dioxolan-4-yl | F | CF$_3$ | Me | Me | H | |
| 9-924 | 2,2-dimethyl-dioxolan-4-yl | F | CF$_3$ | Me | Me | Me | |
| 9-925 | 2,2-dimethyl-dioxolan-4-yl | H | Cl | =CHNMe$_2$ | | H | |
| 9-926 | 2,2-dimethyl-dioxolan-4-yl | H | Cl | =CHNMe$_2$ | | Me | |
| 9-927 | 2,2-dimethyl-dioxolan-4-yl | H | Cl | =CHNMe$_2$ | | Et | |
| 9-928 | 2,2-dimethyl-dioxolan-4-yl | H | Br | =CHNMe$_2$ | | H | |
| 9-929 | 2,2-dimethyl-dioxolan-4-yl | H | Br | =CHNMe$_2$ | | Me | |
| 9-930 | 2,2-dimethyl-dioxolan-4-yl | H | Br | =CHNMe$_2$ | | Et | |
| 9-931 | 2,2-dimethyl-dioxolan-4-yl | H | F | =CHNMe$_2$ | | H | |
| 9-932 | 2,2-dimethyl-dioxolan-4-yl | H | F | =CHNMe$_2$ | | Me | |
| 9-933 | 2,2-dimethyl-dioxolan-4-yl | H | I | =CHNMe$_2$ | | H | |
| 9-934 | 2,2-dimethyl-dioxolan-4-yl | H | I | =CHNMe$_2$ | | Me | |
| 9-935 | 2,2-dimethyl-dioxolan-4-yl | H | CN | =CHNMe$_2$ | | H | |
| 9-936 | 2,2-dimethyl-dioxolan-4-yl | H | CN | =CHNMe$_2$ | | Me | |
| 9-937 | 2,2-dimethyl-dioxolan-4-yl | H | CF$_3$ | =CHNMe$_2$ | | H | |
| 9-938 | 2,2-dimethyl-dioxolan-4-yl | H | CF$_3$ | =CHNMe$_2$ | | Me | |
| 9-939 | 2,2-dimethyl-dioxolan-4-yl | F | Cl | =CHNMe$_2$ | | H | |
| 9-940 | 2,2-dimethyl-dioxolan-4-yl | F | Cl | =CHNMe$_2$ | | Me | |
| 9-941 | 2,2-dimethyl-dioxolan-4-yl | F | Cl | =CHNMe$_2$ | | Et | |
| 9-942 | 2,2-dimethyl-dioxolan-4-yl | F | Br | =CHNMe$_2$ | | H | |
| 9-943 | 2,2-dimethyl-dioxolan-4-yl | F | Br | =CHNMe$_2$ | | Me | |

TABLE 9-continued

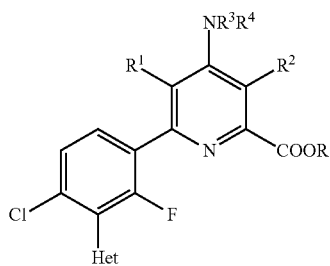

(I-ix)

| No. | Het | R¹ | R² | R³ | R⁴ | R | Physical data: ¹H-NMR: δ [CDCl₃] |
|---|---|---|---|---|---|---|---|
| 9-944 | 2,2-dimethyl-dioxolan-4-yl | F | Br | =CHNMe₂ | | Et | |
| 9-945 | 2,2-dimethyl-dioxolan-4-yl | F | F | =CHNMe₂ | | H | |
| 9-946 | 2,2-dimethyl-dioxolan-4-yl | F | F | =CHNMe₂ | | Me | |
| 9-947 | 2,2-dimethyl-dioxolan-4-yl | F | I | =CHNMe₂ | | H | |
| 9-948 | 2,2-dimethyl-dioxolan-4-yl | F | I | =CHNMe₂ | | Me | |

TABLE 9-continued

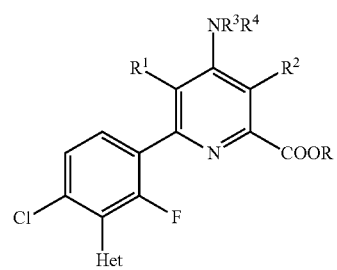

(I-ix)

| No. | Het | R¹ | R² | R³ | R⁴ | R | Physical data: ¹H-NMR: δ [CDCl₃] |
|---|---|---|---|---|---|---|---|
| 9-949 | 2,2-dimethyl-dioxolan-4-yl | F | CN | =CHNMe₂ | | H | |
| 9-950 | 2,2-dimethyl-dioxolan-4-yl | F | CN | =CHNMe₂ | | Me | |
| 9-951 | 2,2-dimethyl-dioxolan-4-yl | F | CF₃ | =CHNMe₂ | | H | |
| 9-952 | 2,2-dimethyl-dioxolan-4-yl | F | CF₃ | =CHNMe₂ | | Me | |

TABLE 10

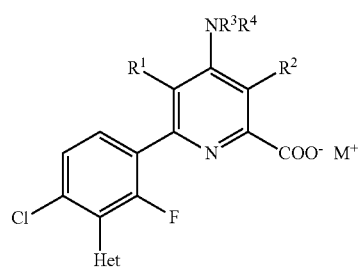

(I-x)

| No. | Het | R¹ | R² | R³ | R⁴ | M⁺ | Physical data: ¹H-NMR: δ [CDCl₃] |
|---|---|---|---|---|---|---|---|
| 10-1 | 3-tert-butyl-1,2,4-oxadiazol-5-yl | H | Cl | H | H | Na⁺ | |
| 10-2 | 3-tert-butyl-1,2,4-oxadiazol-5-yl | H | Cl | H | H | K⁺ | |
| 10-3 | 3-tert-butyl-1,2,4-oxadiazol-5-yl | H | Cl | H | H | NH₄⁺ | |
| 10-4 | 3-tert-butyl-1,2,4-oxadiazol-5-yl | H | Br | H | H | Na⁺ | |
| 10-5 | 3-tert-butyl-1,2,4-oxadiazol-5-yl | H | Br | H | H | K⁺ | |
| 10-6 | 3-tert-butyl-1,2,4-oxadiazol-5-yl | H | Br | H | H | NH₄⁺ | |
| 10-7 | 3-tert-butyl-1,2,4-oxadiazol-5-yl | H | F | H | H | Na⁺ | |
| 10-8 | 3-tert-butyl-1,2,4-oxadiazol-5-yl | H | F | H | H | K⁺ | |
| 10-9 | 3-tert-butyl-1,2,4-oxadiazol-5-yl | H | I | H | H | Na⁺ | |
| 10-10 | 3-tert-butyl-1,2,4-oxadiazol-5-yl | H | I | H | H | K⁺ | |
| 10-11 | 3-tert-butyl-1,2,4-oxadiazol-5-yl | H | CN | H | H | Na⁺ | |
| 10-12 | 3-tert-butyl-1,2,4-oxadiazol-5-yl | H | CN | H | H | K⁺ | |
| 10-13 | 3-tert-butyl-1,2,4-oxadiazol-5-yl | H | CF₃ | H | H | Na⁺ | |
| 10-14 | 3-tert-butyl-1,2,4-oxadiazol-5-yl | H | CF₃ | H | H | K⁺ | |
| 10-15 | 3-tert-butyl-1,2,4-oxadiazol-5-yl | F | Cl | H | H | Na⁺ | |
| 10-16 | 3-tert-butyl-1,2,4-oxadiazol-5-yl | F | Cl | H | H | K⁺ | |
| 10-17 | 3-tert-butyl-1,2,4-oxadiazol-5-yl | F | Cl | H | H | NH₄⁺ | |
| 10-18 | 3-tert-butyl-1,2,4-oxadiazol-5-yl | F | Br | H | H | Na⁺ | |
| 10-19 | 3-tert-butyl-1,2,4-oxadiazol-5-yl | F | Br | H | H | K⁺ | |
| 10-20 | 3-tert-butyl-1,2,4-oxadiazol-5-yl | F | Br | H | H | NH₄⁺ | |
| 10-21 | 3-tert-butyl-1,2,4-oxadiazol-5-yl | F | F | H | H | Na⁺ | |
| 10-22 | 3-tert-butyl-1,2,4-oxadiazol-5-yl | F | F | H | H | K⁺ | |
| 10-23 | 3-tert-butyl-1,2,4-oxadiazol-5-yl | F | I | H | H | Na⁺ | |
| 10-24 | 3-tert-butyl-1,2,4-oxadiazol-5-yl | F | I | H | H | K⁺ | |
| 10-25 | 3-tert-butyl-1,2,4-oxadiazol-5-yl | F | CN | H | H | Na⁺ | |
| 10-26 | 3-tert-butyl-1,2,4-oxadiazol-5-yl | F | CN | H | H | K⁺ | |
| 10-27 | 3-tert-butyl-1,2,4-oxadiazol-5-yl | F | CF₃ | H | H | Na⁺ | |
| 10-28 | 3-tert-butyl-1,2,4-oxadiazol-5-yl | F | CF₃ | H | H | K⁺ | |
| 10-29 | 3-tert-butyl-1,2,4-oxadiazol-5-yl | Cl | Cl | H | H | Na⁺ | |
| 10-30 | 3-tert-butyl-1,2,4-oxadiazol-5-yl | Cl | Cl | H | H | K⁺ | |

TABLE 10-continued

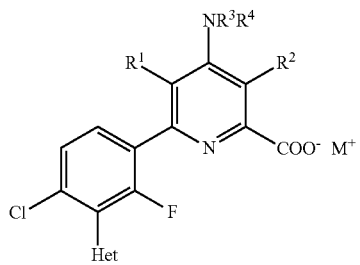

(I-x)

| No. | Het | R¹ | R² | R³ | R⁴ | M⁺ | Physical data: $^1$H-NMR: δ [CDCl$_3$] |
|---|---|---|---|---|---|---|---|
| 10-31 | 3-tert-butyl-1,2,4-oxadiazol-5-yl | Cl | Cl | H | H | NH$_4^+$ | |
| 10-32 | 3-tert-butyl-1,2,4-oxadiazol-5-yl | Cl | Br | H | H | Na$^+$ | |
| 10-33 | 3-tert-butyl-1,2,4-oxadiazol-5-yl | Cl | Br | H | H | K$^+$ | |
| 10-34 | 3-tert-butyl-1,2,4-oxadiazol-5-yl | Cl | Br | H | H | NH$_4^+$ | |
| 10-35 | 3-tert-butyl-1,2,4-oxadiazol-5-yl | Cl | F | H | H | Na$^+$ | |
| 10-36 | 3-tert-butyl-1,2,4-oxadiazol-5-yl | Cl | F | H | H | K$^+$ | |
| 10-37 | 3-tert-butyl-1,2,4-oxadiazol-5-yl | Cl | I | H | H | Na$^+$ | |
| 10-38 | 3-tert-butyl-1,2,4-oxadiazol-5-yl | Cl | I | H | H | K$^+$ | |
| 10-39 | 3-tert-butyl-1,2,4-oxadiazol-5-yl | Cl | CN | H | H | Na$^+$ | |
| 10-40 | 3-tert-butyl-1,2,4-oxadiazol-5-yl | Cl | CN | H | H | K$^+$ | |
| 10-41 | 3-tert-butyl-1,2,4-oxadiazol-5-yl | Cl | CF$_3$ | H | H | Na$^+$ | |
| 10-42 | 3-tert-butyl-1,2,4-oxadiazol-5-yl | Cl | CF$_3$ | H | H | K$^+$ | |
| 10-43 | 3-tert-butyl-1,2,4-oxadiazol-5-yl | H | Cl | H | Me | Na$^+$ | |
| 10-44 | 3-tert-butyl-1,2,4-oxadiazol-5-yl | H | Cl | H | Me | K$^+$ | |
| 10-45 | 3-tert-butyl-1,2,4-oxadiazol-5-yl | H | Cl | H | Me | NH$_4^+$ | |
| 10-46 | 3-tert-butyl-1,2,4-oxadiazol-5-yl | H | Br | H | Me | Na$^+$ | |
| 10-47 | 3-tert-butyl-1,2,4-oxadiazol-5-yl | H | Br | H | Me | K$^+$ | |
| 10-48 | 3-tert-butyl-1,2,4-oxadiazol-5-yl | H | Br | H | Me | NH$_4^+$ | |
| 10-49 | 3-tert-butyl-1,2,4-oxadiazol-5-yl | H | F | H | Me | Na$^+$ | |
| 10-50 | 3-tert-butyl-1,2,4-oxadiazol-5-yl | H | F | H | Me | K$^+$ | |
| 10-51 | 3-tert-butyl-1,2,4-oxadiazol-5-yl | H | I | H | Me | Na$^+$ | |
| 10-52 | 3-tert-butyl-1,2,4-oxadiazol-5-yl | H | I | H | Me | K$^+$ | |
| 10-53 | 3-tert-butyl-1,2,4-oxadiazol-5-yl | H | CN | H | Me | Na$^+$ | |
| 10-54 | 3-tert-butyl-1,2,4-oxadiazol-5-yl | H | CN | H | Me | K$^+$ | |
| 10-55 | 3-tert-butyl-1,2,4-oxadiazol-5-yl | H | CF$_3$ | H | Me | Na$^+$ | |
| 10-56 | 3-tert-butyl-1,2,4-oxadiazol-5-yl | H | CF$_3$ | H | Me | K$^+$ | |
| 10-57 | 3-tert-butyl-1,2,4-oxadiazol-5-yl | F | Cl | H | Me | Na$^+$ | |
| 10-58 | 3-tert-butyl-1,2,4-oxadiazol-5-yl | F | Cl | H | Me | K$^+$ | |
| 10-59 | 3-tert-butyl-1,2,4-oxadiazol-5-yl | F | Cl | H | Me | NH$_4^+$ | |
| 10-60 | 3-tert-butyl-1,2,4-oxadiazol-5-yl | F | Br | H | Me | Na$^+$ | |
| 10-61 | 3-tert-butyl-1,2,4-oxadiazol-5-yl | F | Br | H | Me | K$^+$ | |
| 10-62 | 3-tert-butyl-1,2,4-oxadiazol-5-yl | F | Br | H | Me | NH$_4^+$ | |
| 10-63 | 3-tert-butyl-1,2,4-oxadiazol-5-yl | F | F | H | Me | Na$^+$ | |
| 10-64 | 3-tert-butyl-1,2,4-oxadiazol-5-yl | F | F | H | Me | K$^+$ | |
| 10-65 | 3-tert-butyl-1,2,4-oxadiazol-5-yl | F | I | H | Me | Na$^+$ | |
| 10-66 | 3-tert-butyl-1,2,4-oxadiazol-5-yl | F | I | H | Me | K$^+$ | |
| 10-67 | 3-tert-butyl-1,2,4-oxadiazol-5-yl | F | CN | H | Me | Na$^+$ | |
| 10-68 | 3-tert-butyl-1,2,4-oxadiazol-5-yl | F | CN | H | Me | K$^+$ | |
| 10-69 | 3-tert-butyl-1,2,4-oxadiazol-5-yl | F | CF$_3$ | H | Me | Na$^+$ | |
| 10-70 | 3-tert-butyl-1,2,4-oxadiazol-5-yl | F | CF$_3$ | H | Me | K$^+$ | |
| 10-71 | 3-tert-butyl-1,2,4-oxadiazol-5-yl | Cl | Cl | H | Me | Na$^+$ | |
| 10-72 | 3-tert-butyl-1,2,4-oxadiazol-5-yl | Cl | Cl | H | Me | K$^+$ | |
| 10-73 | 3-tert-butyl-1,2,4-oxadiazol-5-yl | Cl | Cl | H | Me | NH$_4^+$ | |
| 10-74 | 3-tert-butyl-1,2,4-oxadiazol-5-yl | Cl | Br | H | Me | Na$^+$ | |
| 10-75 | 3-tert-butyl-1,2,4-oxadiazol-5-yl | Cl | Br | H | Me | K$^+$ | |
| 10-76 | 3-tert-butyl-1,2,4-oxadiazol-5-yl | Cl | Br | H | Me | NH$_4^+$ | |
| 10-77 | 3-tert-butyl-1,2,4-oxadiazol-5-yl | Cl | F | H | Me | Na$^+$ | |
| 10-78 | 3-tert-butyl-1,2,4-oxadiazol-5-yl | Cl | F | H | Me | K$^+$ | |
| 10-79 | 3-tert-butyl-1,2,4-oxadiazol-5-yl | Cl | I | H | Me | Na$^+$ | |
| 10-80 | 3-tert-butyl-1,2,4-oxadiazol-5-yl | Cl | I | H | Me | K$^+$ | |
| 10-81 | 3-tert-butyl-1,2,4-oxadiazol-5-yl | Cl | CN | H | Me | Na$^+$ | |
| 10-82 | 3-tert-butyl-1,2,4-oxadiazol-5-yl | Cl | CN | H | Me | K$^+$ | |
| 10-83 | 3-tert-butyl-1,2,4-oxadiazol-5-yl | Cl | CF$_3$ | H | Me | Na$^+$ | |
| 10-84 | 3-tert-butyl-1,2,4-oxadiazol-5-yl | Cl | CF$_3$ | H | Me | K$^+$ | |
| 10-85 | 3-tert-butyl-1,2,4-oxadiazol-5-yl | H | Cl | Me | Me | Na$^+$ | |
| 10-86 | 3-tert-butyl-1,2,4-oxadiazol-5-yl | H | Cl | Me | Me | K$^+$ | |
| 10-87 | 3-tert-butyl-1,2,4-oxadiazol-5-yl | H | Cl | Me | Me | NH$_4^+$ | |
| 10-88 | 3-tert-butyl-1,2,4-oxadiazol-5-yl | H | Br | Me | Me | Na$^+$ | |
| 10-89 | 3-tert-butyl-1,2,4-oxadiazol-5-yl | H | Br | Me | Me | K$^+$ | |
| 10-90 | 3-tert-butyl-1,2,4-oxadiazol-5-yl | H | Br | Me | Me | NH$_4^+$ | |
| 10-91 | 3-tert-butyl-1,2,4-oxadiazol-5-yl | H | F | Me | Me | Na$^+$ | |
| 10-92 | 3-tert-butyl-1,2,4-oxadiazol-5-yl | H | F | Me | Me | K$^+$ | |

TABLE 10-continued

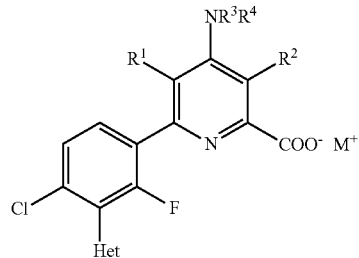

(I-x)

| No. | Het | $R^1$ | $R^2$ | $R^3$ | $R^4$ | $M^+$ | Physical data: $^1$H-NMR: δ [CDCl$_3$] |
|---|---|---|---|---|---|---|---|
| 10-93 | 3-tert-butyl-1,2,4-oxadiazol-5-yl | H | I | Me | Me | Na$^+$ | |
| 10-94 | 3-tert-butyl-1,2,4-oxadiazol-5-yl | H | I | Me | Me | K$^+$ | |
| 10-95 | 3-tert-butyl-1,2,4-oxadiazol-5-yl | H | CN | Me | Me | Na$^+$ | |
| 10-96 | 3-tert-butyl-1,2,4-oxadiazol-5-yl | H | CN | Me | Me | K$^+$ | |
| 10-97 | 3-tert-butyl-1,2,4-oxadiazol-5-yl | H | CF$_3$ | Me | Me | Na$^+$ | |
| 10-98 | 3-tert-butyl-1,2,4-oxadiazol-5-yl | H | CF$_3$ | Me | Me | K$^+$ | |
| 10-99 | 3-tert-butyl-1,2,4-oxadiazol-5-yl | F | Cl | Me | Me | Na$^+$ | |
| 10-100 | 3-tert-butyl-1,2,4-oxadiazol-5-yl | F | Cl | Me | Me | K$^+$ | |
| 10-101 | 3-tert-butyl-1,2,4-oxadiazol-5-yl | F | Cl | Me | Me | NH$_4^+$ | |
| 10-102 | 3-tert-butyl-1,2,4-oxadiazol-5-yl | F | Br | Me | Me | Na$^+$ | |
| 10-103 | 3-tert-butyl-1,2,4-oxadiazol-5-yl | F | Br | Me | Me | K$^+$ | |
| 10-104 | 3-tert-butyl-1,2,4-oxadiazol-5-yl | F | Br | Me | Me | NH$_4^+$ | |
| 10-105 | 3-tert-butyl-1,2,4-oxadiazol-5-yl | F | F | Me | Me | Na$^+$ | |
| 10-106 | 3-tert-butyl-1,2,4-oxadiazol-5-yl | F | F | Me | Me | K$^+$ | |
| 10-107 | 3-tert-butyl-1,2,4-oxadiazol-5-yl | F | I | Me | Me | Na$^+$ | |
| 10-108 | 3-tert-butyl-1,2,4-oxadiazol-5-yl | F | I | Me | Me | K$^+$ | |
| 10-109 | 3-tert-butyl-1,2,4-oxadiazol-5-yl | F | CN | Me | Me | Na$^+$ | |
| 10-110 | 3-tert-butyl-1,2,4-oxadiazol-5-yl | F | CN | Me | Me | K$^+$ | |
| 10-111 | 3-tert-butyl-1,2,4-oxadiazol-5-yl | F | CF$_3$ | Me | Me | Na$^+$ | |
| 10-112 | 3-tert-butyl-1,2,4-oxadiazol-5-yl | F | CF$_3$ | Me | Me | K$^+$ | |
| 10-113 | 3-tert-butyl-1,2,4-oxadiazol-5-yl | Cl | Cl | Me | Me | Na$^+$ | |
| 10-114 | 3-tert-butyl-1,2,4-oxadiazol-5-yl | Cl | Cl | Me | Me | K$^+$ | |
| 10-115 | 3-tert-butyl-1,2,4-oxadiazol-5-yl | Cl | Cl | Me | Me | NH$_4^+$ | |
| 10-116 | 3-tert-butyl-1,2,4-oxadiazol-5-yl | Cl | Br | Me | Me | Na$^+$ | |
| 10-117 | 3-tert-butyl-1,2,4-oxadiazol-5-yl | Cl | Br | Me | Me | K$^+$ | |
| 10-118 | 3-tert-butyl-1,2,4-oxadiazol-5-yl | Cl | Br | Me | Me | NH$_4^+$ | |
| 10-119 | 3-tert-butyl-1,2,4-oxadiazol-5-yl | Cl | F | Me | Me | Na$^+$ | |
| 10-120 | 3-tert-butyl-1,2,4-oxadiazol-5-yl | Cl | F | Me | Me | K$^+$ | |
| 10-121 | 3-tert-butyl-1,2,4-oxadiazol-5-yl | Cl | I | Me | Me | Na$^+$ | |
| 10-122 | 3-tert-butyl-1,2,4-oxadiazol-5-yl | Cl | I | Me | Me | K$^+$ | |
| 10-123 | 3-tert-butyl-1,2,4-oxadiazol-5-yl | Cl | CN | Me | Me | Na$^+$ | |
| 10-124 | 3-tert-butyl-1,2,4-oxadiazol-5-yl | Cl | CN | Me | Me | K$^+$ | |
| 10-125 | 3-tert-butyl-1,2,4-oxadiazol-5-yl | Cl | CF$_3$ | Me | Me | Na$^+$ | |
| 10-126 | 3-tert-butyl-1,2,4-oxadiazol-5-yl | Cl | CF$_3$ | Me | Me | K$^+$ | |
| 10-127 | 3-tert-butyl-1,2,4-oxadiazol-5-yl | H | Cl | =CHNMe$_2$ | | Na$^+$ | |
| 10-128 | 3-tert-butyl-1,2,4-oxadiazol-5-yl | H | Cl | =CHNMe$_2$ | | K$^+$ | |
| 10-129 | 3-tert-butyl-1,2,4-oxadiazol-5-yl | H | Cl | =CHNMe$_2$ | | NH$_4^+$ | |
| 10-130 | 3-tert-butyl-1,2,4-oxadiazol-5-yl | H | Br | =CHNMe$_2$ | | Na$^+$ | |
| 10-131 | 3-tert-butyl-1,2,4-oxadiazol-5-yl | H | Br | =CHNMe$_2$ | | K$^+$ | |
| 10-132 | 3-tert-butyl-1,2,4-oxadiazol-5-yl | H | Br | =CHNMe$_2$ | | NH$_4^+$ | |
| 10-133 | 3-tert-butyl-1,2,4-oxadiazol-5-yl | H | F | =CHNMe$_2$ | | Na$^+$ | |
| 10-134 | 3-tert-butyl-1,2,4-oxadiazol-5-yl | H | F | =CHNMe$_2$ | | K$^+$ | |
| 10-135 | 3-tert-butyl-1,2,4-oxadiazol-5-yl | H | I | =CHNMe$_2$ | | Na$^+$ | |
| 10-136 | 3-tert-butyl-1,2,4-oxadiazol-5-yl | H | I | =CHNMe$_2$ | | K$^+$ | |
| 10-137 | 3-tert-butyl-1,2,4-oxadiazol-5-yl | H | CN | =CHNMe$_2$ | | Na$^+$ | |
| 10-138 | 3-tert-butyl-1,2,4-oxadiazol-5-yl | H | CN | =CHNMe$_2$ | | K$^+$ | |
| 10-139 | 3-tert-butyl-1,2,4-oxadiazol-5-yl | H | CF$_3$ | =CHNMe$_2$ | | Na$^+$ | |
| 10-140 | 3-tert-butyl-1,2,4-oxadiazol-5-yl | H | CF$_3$ | =CHNMe$_2$ | | K$^+$ | |
| 10-141 | 3-tert-butyl-1,2,4-oxadiazol-5-yl | F | Cl | =CHNMe$_2$ | | Na$^+$ | |
| 10-142 | 3-tert-butyl-1,2,4-oxadiazol-5-yl | F | Cl | =CHNMe$_2$ | | K$^+$ | |
| 10-143 | 3-tert-butyl-1,2,4-oxadiazol-5-yl | F | Cl | =CHNMe$_2$ | | NH$_4^+$ | |
| 10-144 | 3-tert-butyl-1,2,4-oxadiazol-5-yl | F | Br | =CHNMe$_2$ | | Na$^+$ | |
| 10-145 | 3-tert-butyl-1,2,4-oxadiazol-5-yl | F | Br | =CHNMe$_2$ | | K$^+$ | |
| 10-146 | 3-tert-butyl-1,2,4-oxadiazol-5-yl | F | Br | =CHNMe$_2$ | | NH$_4^+$ | |
| 10-147 | 3-tert-butyl-1,2,4-oxadiazol-5-yl | F | F | =CHNMe$_2$ | | Na$^+$ | |
| 10-148 | 3-tert-butyl-1,2,4-oxadiazol-5-yl | F | F | =CHNMe$_2$ | | K$^+$ | |
| 10-149 | 3-tert-butyl-1,2,4-oxadiazol-5-yl | F | I | =CHNMe$_2$ | | Na$^+$ | |
| 10-150 | 3-tert-butyl-1,2,4-oxadiazol-5-yl | F | I | =CHNMe$_2$ | | K$^+$ | |
| 10-151 | 3-tert-butyl-1,2,4-oxadiazol-5-yl | F | CN | =CHNMe$_2$ | | Na$^+$ | |
| 10-152 | 3-tert-butyl-1,2,4-oxadiazol-5-yl | F | CN | =CHNMe$_2$ | | K$^+$ | |
| 10-153 | 3-tert-butyl-1,2,4-oxadiazol-5-yl | F | CF$_3$ | =CHNMe$_2$ | | Na$^+$ | |
| 10-154 | 3-tert-butyl-1,2,4-oxadiazol-5-yl | F | CF$_3$ | =CHNMe$_2$ | | K$^+$ | |

TABLE 10-continued

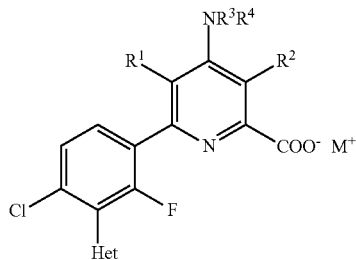

(I-x)

| No. | Het | $R^1$ | $R^2$ | $R^3$ | $R^4$ | $M^+$ | Physical data: $^1$H-NMR: δ [CDCl$_3$] |
|---|---|---|---|---|---|---|---|
| 10-155 | 3-tert-butyl-1,2,4-oxadiazol-5-yl | Cl | Cl | =CHNMe$_2$ | | Na$^+$ | |
| 10-156 | 3-tert-butyl-1,2,4-oxadiazol-5-yl | Cl | Cl | =CHNMe$_2$ | | K$^+$ | |
| 10-157 | 3-tert-butyl-1,2,4-oxadiazol-5-yl | Cl | Cl | =CHNMe$_2$ | | NH$_4^+$ | |
| 10-158 | 3-tert-butyl-1,2,4-oxadiazol-5-yl | Cl | Br | =CHNMe$_2$ | | Na$^+$ | |
| 10-159 | 3-tert-butyl-1,2,4-oxadiazol-5-yl | Cl | Br | =CHNMe$_2$ | | K$^+$ | |
| 10-160 | 3-tert-butyl-1,2,4-oxadiazol-5-yl | Cl | Br | =CHNMe$_2$ | | NH$_4^+$ | |
| 10-161 | 3-tert-butyl-1,2,4-oxadiazol-5-yl | Cl | F | =CHNMe$_2$ | | Na$^+$ | |
| 10-162 | 3-tert-butyl-1,2,4-oxadiazol-5-yl | Cl | F | =CHNMe$_2$ | | K$^+$ | |
| 10-163 | 3-tert-butyl-1,2,4-oxadiazol-5-yl | Cl | I | =CHNMe$_2$ | | Na$^+$ | |
| 10-164 | 3-tert-butyl-1,2,4-oxadiazol-5-yl | Cl | I | =CHNMe$_2$ | | K$^+$ | |
| 10-165 | 3-tert-butyl-1,2,4-oxadiazol-5-yl | Cl | CN | =CHNMe$_2$ | | Na$^+$ | |
| 10-166 | 3-tert-butyl-1,2,4-oxadiazol-5-yl | Cl | CN | =CHNMe$_2$ | | K$^+$ | |
| 10-167 | 3-tert-butyl-1,2,4-oxadiazol-5-yl | Cl | CF$_3$ | =CHNMe$_2$ | | Na$^+$ | |
| 10-168 | 3-tert-butyl-1,2,4-oxadiazol-5-yl | Cl | CF$_3$ | =CHNMe$_2$ | | K$^+$ | |
| 10-169 | thien-2-yl | H | Cl | H | H | Na$^+$ | |
| 10-170 | thien-2-yl | H | Cl | H | H | K$^+$ | |
| 10-171 | thien-2-yl | H | Cl | H | H | NH$_4^+$ | |
| 10-172 | thien-2-yl | H | Br | H | H | Na$^+$ | |
| 10-173 | thien-2-yl | H | Br | H | H | K$^+$ | |
| 10-174 | thien-2-yl | H | Br | H | H | NH$_4^+$ | |
| 10-175 | thien-2-yl | H | F | H | H | Na$^+$ | |
| 10-176 | thien-2-yl | H | F | H | H | K$^+$ | |
| 10-177 | thien-2-yl | H | I | H | H | Na$^+$ | |
| 10-178 | thien-2-yl | H | I | H | H | K$^+$ | |
| 10-179 | thien-2-yl | H | CN | H | H | Na$^+$ | |
| 10-180 | thien-2-yl | H | CN | H | H | K$^+$ | |
| 10-181 | thien-2-yl | H | CF$_3$ | H | H | Na$^+$ | |
| 10-182 | thien-2-yl | H | CF$_3$ | H | H | K$^+$ | |
| 10-183 | thien-2-yl | F | Cl | H | H | Na$^+$ | |
| 10-184 | thien-2-yl | F | Cl | H | H | K$^+$ | |
| 10-185 | thien-2-yl | F | Cl | H | H | NH$_4^+$ | |
| 10-186 | thien-2-yl | F | Br | H | H | Na$^+$ | |
| 10-187 | thien-2-yl | F | Br | H | H | K$^+$ | |
| 10-188 | thien-2-yl | F | Br | H | H | NH$_4^+$ | |
| 10-189 | thien-2-yl | F | F | H | H | Na$^+$ | |
| 10-190 | thien-2-yl | F | F | H | H | K$^+$ | |
| 10-191 | thien-2-yl | F | I | H | H | Na$^+$ | |
| 10-192 | thien-2-yl | F | I | H | H | K$^+$ | |
| 10-193 | thien-2-yl | F | CN | H | H | Na$^+$ | |
| 10-194 | thien-2-yl | F | CN | H | H | K$^+$ | |
| 10-195 | thien-2-yl | F | CF$_3$ | H | H | Na$^+$ | |
| 10-196 | thien-2-yl | F | CF$_3$ | H | H | K$^+$ | |
| 10-197 | thien-2-yl | H | Cl | H | Me | Na$^+$ | |
| 10-198 | thien-2-yl | H | Cl | H | Me | K$^+$ | |
| 10-199 | thien-2-yl | H | Cl | H | Me | NH$_4^+$ | |
| 10-200 | thien-2-yl | H | Br | H | Me | Na$^+$ | |
| 10-201 | thien-2-yl | H | Br | H | Me | K$^+$ | |
| 10-202 | thien-2-yl | H | Br | H | Me | NH$_4^+$ | |
| 10-203 | thien-2-yl | H | F | H | Me | Na$^+$ | |
| 10-204 | thien-2-yl | H | F | H | Me | K$^+$ | |
| 10-205 | thien-2-yl | H | I | H | Me | Na$^+$ | |
| 10-206 | thien-2-yl | H | I | H | Me | K$^+$ | |
| 10-207 | thien-2-yl | H | CN | H | Me | Na$^+$ | |
| 10-208 | thien-2-yl | H | CN | H | Me | K$^+$ | |
| 10-209 | thien-2-yl | H | CF$_3$ | H | Me | Na$^+$ | |
| 10-210 | thien-2-yl | H | CF$_3$ | H | Me | K$^+$ | |
| 10-211 | thien-2-yl | F | Cl | H | Me | Na$^+$ | |
| 10-212 | thien-2-yl | F | Cl | H | Me | K$^+$ | |
| 10-213 | thien-2-yl | F | Cl | H | Me | NH$_4^+$ | |
| 10-214 | thien-2-yl | F | Br | H | Me | Na$^+$ | |
| 10-215 | thien-2-yl | F | Br | H | Me | K$^+$ | |
| 10-216 | thien-2-yl | F | Br | H | Me | NH$_4^+$ | |

TABLE 10-continued

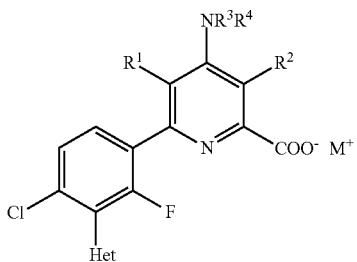

(I-x)

| No. | Het | $R^1$ | $R^2$ | $R^3$ | $R^4$ | $M^+$ | Physical data: $^1$H-NMR: δ [CDCl$_3$] |
|---|---|---|---|---|---|---|---|
| 10-217 | thien-2-yl | F | F | H | Me | Na$^+$ | |
| 10-218 | thien-2-yl | F | F | H | Me | K$^+$ | |
| 10-219 | thien-2-yl | F | I | H | Me | Na$^+$ | |
| 10-220 | thien-2-yl | F | I | H | Me | K$^+$ | |
| 10-221 | thien-2-yl | F | CN | H | Me | Na$^+$ | |
| 10-222 | thien-2-yl | F | CN | H | Me | K$^+$ | |
| 10-223 | thien-2-yl | F | CF$_3$ | H | Me | Na$^+$ | |
| 10-224 | thien-2-yl | F | CF$_3$ | H | Me | K$^+$ | |
| 10-225 | thien-2-yl | H | Cl | Me | Me | Na$^+$ | |
| 10-226 | thien-2-yl | H | Cl | Me | Me | K$^+$ | |
| 10-227 | thien-2-yl | H | Cl | Me | Me | NH$_4^+$ | |
| 10-228 | thien-2-yl | H | Br | Me | Me | Na$^+$ | |
| 10-229 | thien-2-yl | H | Br | Me | Me | K$^+$ | |
| 10-230 | thien-2-yl | H | Br | Me | Me | NH$_4^+$ | |
| 10-231 | thien-2-yl | H | F | Me | Me | Na$^+$ | |
| 10-232 | thien-2-yl | H | F | Me | Me | K$^+$ | |
| 10-233 | thien-2-yl | H | I | Me | Me | Na$^+$ | |
| 10-234 | thien-2-yl | H | I | Me | Me | K$^+$ | |
| 10-235 | thien-2-yl | H | CN | Me | Me | Na$^+$ | |
| 10-236 | thien-2-yl | H | CN | Me | Me | K$^+$ | |
| 10-237 | thien-2-yl | H | CF$_3$ | Me | Me | Na$^+$ | |
| 10-238 | thien-2-yl | H | CF$_3$ | Me | Me | K$^+$ | |
| 10-239 | thien-2-yl | F | Cl | Me | Me | Na$^+$ | |
| 10-240 | thien-2-yl | F | Cl | Me | Me | K$^+$ | |
| 10-241 | thien-2-yl | F | Cl | Me | Me | NH$_4^+$ | |
| 10-242 | thien-2-yl | F | Br | Me | Me | Na$^+$ | |
| 10-243 | thien-2-yl | F | Br | Me | Me | K$^+$ | |
| 10-244 | thien-2-yl | F | Br | Me | Me | NH$_4^+$ | |
| 10-245 | thien-2-yl | F | F | Me | Me | Na$^+$ | |
| 10-246 | thien-2-yl | F | F | Me | Me | K$^+$ | |
| 10-247 | thien-2-yl | F | I | Me | Me | Na$^+$ | |
| 10-248 | thien-2-yl | F | I | Me | Me | K$^+$ | |
| 10-249 | thien-2-yl | F | CN | Me | Me | Na$^+$ | |
| 10-250 | thien-2-yl | F | CN | Me | Me | K$^+$ | |
| 10-251 | thien-2-yl | F | CF$_3$ | Me | Me | Na$^+$ | |
| 10-252 | thien-2-yl | F | CF$_3$ | Me | Me | K$^+$ | |
| 10-253 | thien-2-yl | H | Cl | =CHNMe$_2$ | | Na$^+$ | |
| 10-254 | thien-2-yl | H | Cl | =CHNMe$_2$ | | K$^+$ | |
| 10-255 | thien-2-yl | H | Cl | =CHNMe$_2$ | | NH$_4^+$ | |
| 10-256 | thien-2-yl | H | Br | =CHNMe$_2$ | | Na$^+$ | |
| 10-257 | thien-2-yl | H | Br | =CHNMe$_2$ | | K$^+$ | |
| 10-258 | thien-2-yl | H | Br | =CHNMe$_2$ | | NH$_4^+$ | |
| 10-259 | thien-2-yl | H | F | =CHNMe$_2$ | | Na$^+$ | |
| 10-260 | thien-2-yl | H | F | =CHNMe$_2$ | | K$^+$ | |
| 10-261 | thien-2-yl | H | I | =CHNMe$_2$ | | Na$^+$ | |
| 10-262 | thien-2-yl | H | I | =CHNMe$_2$ | | K$^+$ | |
| 10-263 | thien-2-yl | H | CN | =CHNMe$_2$ | | Na$^+$ | |
| 10-264 | thien-2-yl | H | CN | =CHNMe$_2$ | | K$^+$ | |
| 10-265 | thien-2-yl | H | CF$_3$ | =CHNMe$_2$ | | Na$^+$ | |
| 10-266 | thien-2-yl | H | CF$_3$ | =CHNMe$_2$ | | K$^+$ | |
| 10-267 | thien-2-yl | F | Cl | =CHNMe$_2$ | | Na$^+$ | |
| 10-268 | thien-2-yl | F | Cl | =CHNMe$_2$ | | K$^+$ | |
| 10-269 | thien-2-yl | F | Cl | =CHNMe$_2$ | | NH$_4^+$ | |
| 10-270 | thien-2-yl | F | Br | =CHNMe$_2$ | | Na$^+$ | |
| 10-271 | thien-2-yl | F | Br | =CHNMe$_2$ | | K$^+$ | |
| 10-272 | thien-2-yl | F | Br | =CHNMe$_2$ | | NH$_4^+$ | |
| 10-273 | thien-2-yl | F | F | =CHNMe$_2$ | | Na$^+$ | |
| 10-274 | thien-2-yl | F | F | =CHNMe$_2$ | | K$^+$ | |
| 10-275 | thien-2-yl | F | I | =CHNMe$_2$ | | Na$^+$ | |
| 10-276 | thien-2-yl | F | I | =CHNMe$_2$ | | K$^+$ | |
| 10-277 | thien-2-yl | F | CN | =CHNMe$_2$ | | Na$^+$ | |
| 10-278 | thien-2-yl | F | CN | =CHNMe$_2$ | | K$^+$ | |

TABLE 10-continued

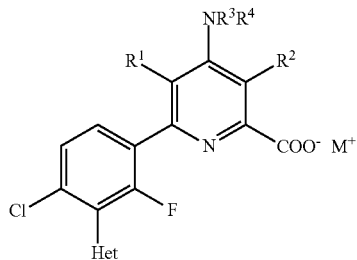

(I-x)

| No. | Het | R¹ | R² | R³ | R⁴ | M⁺ | Physical data: $^1$H-NMR: δ [CDCl$_3$] |
|---|---|---|---|---|---|---|---|
| 10-279 | thien-2-yl | F | CF$_3$ | =CHNMe$_2$ | | Na⁺ | |
| 10-280 | thien-2-yl | F | CF$_3$ | =CHNMe$_2$ | | K⁺ | |
| 10-281 | pyrrol-1-yl | H | Cl | H | H | Na⁺ | |
| 10-282 | pyrrol-1-yl | H | Cl | H | H | K⁺ | |
| 10-283 | pyrrol-1-yl | H | Cl | H | H | NH$_4^+$ | |
| 10-284 | pyrrol-1-yl | H | Br | H | H | Na⁺ | |
| 10-285 | pyrrol-1-yl | H | Br | H | H | K⁺ | |
| 10-286 | pyrrol-1-yl | H | Br | H | H | NH$_4^+$ | |
| 10-287 | pyrrol-1-yl | H | F | H | H | Na⁺ | |
| 10-288 | pyrrol-1-yl | H | F | H | H | K⁺ | |
| 10-289 | pyrrol-1-yl | H | I | H | H | Na⁺ | |
| 10-290 | pyrrol-1-yl | H | I | H | H | K⁺ | |
| 10-291 | pyrrol-1-yl | H | CN | H | H | Na⁺ | |
| 10-292 | pyrrol-1-yl | H | CN | H | H | K⁺ | |
| 10-293 | pyrrol-1-yl | H | CF$_3$ | H | H | Na⁺ | |
| 10-294 | pyrrol-1-yl | H | CF$_3$ | H | H | K⁺ | |
| 10-295 | pyrrol-1-yl | F | Cl | H | H | Na⁺ | |
| 10-296 | pyrrol-1-yl | F | Cl | H | H | K⁺ | |
| 10-297 | pyrrol-1-yl | F | Cl | H | H | NH$_4^+$ | |
| 10-298 | pyrrol-1-yl | F | Br | H | H | Na⁺ | |
| 10-299 | pyrrol-1-yl | F | Br | H | H | K⁺ | |
| 10-300 | pyrrol-1-yl | F | Br | H | H | NH$_4^+$ | |
| 10-301 | pyrrol-1-yl | F | F | H | H | Na⁺ | |
| 10-302 | pyrrol-1-yl | F | F | H | H | K⁺ | |
| 10-303 | pyrrol-1-yl | F | I | H | H | Na⁺ | |
| 10-304 | pyrrol-1-yl | F | I | H | H | K⁺ | |
| 10-305 | pyrrol-1-yl | F | CN | H | H | Na⁺ | |
| 10-306 | pyrrol-1-yl | F | CN | H | H | K⁺ | |
| 10-307 | pyrrol-1-yl | F | CF$_3$ | H | H | Na⁺ | |
| 10-308 | pyrrol-1-yl | F | CF$_3$ | H | H | K⁺ | |
| 10-309 | pyrrol-1-yl | H | Cl | H | Me | Na⁺ | |
| 10-310 | pyrrol-1-yl | H | Cl | H | Me | K⁺ | |
| 10-311 | pyrrol-1-yl | H | Cl | H | Me | NH$_4^+$ | |
| 10-312 | pyrrol-1-yl | H | Br | H | Me | Na⁺ | |
| 10-313 | pyrrol-1-yl | H | Br | H | Me | K⁺ | |
| 10-314 | pyrrol-1-yl | H | Br | H | Me | NH$_4^+$ | |
| 10-315 | pyrrol-1-yl | H | F | H | Me | Na⁺ | |
| 10-316 | pyrrol-1-yl | H | F | H | Me | K⁺ | |
| 10-317 | pyrrol-1-yl | H | I | H | Me | Na⁺ | |
| 10-318 | pyrrol-1-yl | H | I | H | Me | K⁺ | |
| 10-319 | pyrrol-1-yl | H | CN | H | Me | Na⁺ | |
| 10-320 | pyrrol-1-yl | H | CN | H | Me | K⁺ | |
| 10-321 | pyrrol-1-yl | H | CF$_3$ | H | Me | Na⁺ | |
| 10-322 | pyrrol-1-yl | H | CF$_3$ | H | Me | K⁺ | |
| 10-323 | pyrrol-1-yl | F | Cl | H | Me | Na⁺ | |
| 10-324 | pyrrol-1-yl | F | Cl | H | Me | K⁺ | |
| 10-325 | pyrrol-1-yl | F | Cl | H | Me | NH$_4^+$ | |
| 10-326 | pyrrol-1-yl | F | Br | H | Me | Na⁺ | |
| 10-327 | pyrrol-1-yl | F | Br | H | Me | K⁺ | |
| 10-328 | pyrrol-1-yl | F | Br | H | Me | NH$_4^+$ | |
| 10-329 | pyrrol-1-yl | F | F | H | Me | Na⁺ | |
| 10-330 | pyrrol-1-yl | F | F | H | Me | K⁺ | |
| 10-331 | pyrrol-1-yl | F | I | H | Me | Na⁺ | |
| 10-332 | pyrrol-1-yl | F | I | H | Me | K⁺ | |
| 10-333 | pyrrol-1-yl | F | CN | H | Me | Na⁺ | |
| 10-334 | pyrrol-1-yl | F | CN | H | Me | K⁺ | |
| 10-335 | pyrrol-1-yl | F | CF$_3$ | H | Me | Na⁺ | |
| 10-336 | pyrrol-1-yl | F | CF$_3$ | H | Me | K⁺ | |
| 10-337 | pyrrol-1-yl | H | Cl | Me | Me | Na⁺ | |
| 10-338 | pyrrol-1-yl | H | Cl | Me | Me | K⁺ | |
| 10-339 | pyrrol-1-yl | H | Cl | Me | Me | NH$_4^+$ | |
| 10-340 | pyrrol-1-yl | H | Br | Me | Me | Na⁺ | |

TABLE 10-continued (I-x)

| No. | Het | R¹ | R² | R³ | R⁴ | M⁺ | Physical data: $^1$H-NMR: δ [CDCl$_3$] |
|---|---|---|---|---|---|---|---|
| 10-341 | pyrrol-1-yl | H | Br | Me | Me | K⁺ | |
| 10-342 | pyrrol-1-yl | H | Br | Me | Me | NH$_4^+$ | |
| 10-343 | pyrrol-1-yl | H | F | Me | Me | Na⁺ | |
| 10-344 | pyrrol-1-yl | H | F | Me | Me | K⁺ | |
| 10-345 | pyrrol-1-yl | H | I | Me | Me | Na⁺ | |
| 10-346 | pyrrol-1-yl | H | I | Me | Me | K⁺ | |
| 10-347 | pyrrol-1-yl | H | CN | Me | Me | Na⁺ | |
| 10-348 | pyrrol-1-yl | H | CN | Me | Me | K⁺ | |
| 10-349 | pyrrol-1-yl | H | CF$_3$ | Me | Me | Na⁺ | |
| 10-350 | pyrrol-1-yl | H | CF$_3$ | Me | Me | K⁺ | |
| 10-351 | pyrrol-1-yl | F | Cl | Me | Me | Na⁺ | |
| 10-352 | pyrrol-1-yl | F | Cl | Me | Me | K⁺ | |
| 10-353 | pyrrol-1-yl | F | Cl | Me | Me | NH$_4^+$ | |
| 10-354 | pyrrol-1-yl | F | Br | Me | Me | Na⁺ | |
| 10-355 | pyrrol-1-yl | F | Br | Me | Me | K⁺ | |
| 10-356 | pyrrol-1-yl | F | Br | Me | Me | NH$_4^+$ | |
| 10-357 | pyrrol-1-yl | F | F | Me | Me | Na⁺ | |
| 10-358 | pyrrol-1-yl | F | F | Me | Me | K⁺ | |
| 10-359 | pyrrol-1-yl | F | I | Me | Me | Na⁺ | |
| 10-360 | pyrrol-1-yl | F | I | Me | Me | K⁺ | |
| 10-361 | pyrrol-1-yl | F | CN | Me | Me | Na⁺ | |
| 10-362 | pyrrol-1-yl | F | CN | Me | Me | K⁺ | |
| 10-363 | pyrrol-1-yl | F | CF$_3$ | Me | Me | Na⁺ | |
| 10-364 | pyrrol-1-yl | F | CF$_3$ | Me | Me | K⁺ | |
| 10-365 | pyrrol-1-yl | H | Cl | =CHNMe$_2$ | | Na⁺ | |
| 10-366 | pyrrol-1-yl | H | Cl | =CHNMe$_2$ | | K⁺ | |
| 10-367 | pyrrol-1-yl | H | Cl | =CHNMe$_2$ | | NH$_4^+$ | |
| 10-368 | pyrrol-1-yl | H | Br | =CHNMe$_2$ | | Na⁺ | |
| 10-369 | pyrrol-1-yl | H | Br | =CHNMe$_2$ | | K⁺ | |
| 10-370 | pyrrol-1-yl | H | Br | =CHNMe$_2$ | | NH$_4^+$ | |
| 10-371 | pyrrol-1-yl | H | F | =CHNMe$_2$ | | Na⁺ | |
| 10-372 | pyrrol-1-yl | H | F | =CHNMe$_2$ | | K⁺ | |
| 10-373 | pyrrol-1-yl | H | I | =CHNMe$_2$ | | Na⁺ | |
| 10-374 | pyrrol-1-yl | H | I | =CHNMe$_2$ | | K⁺ | |
| 10-375 | pyrrol-1-yl | H | CN | =CHNMe$_2$ | | Na⁺ | |
| 10-376 | pyrrol-1-yl | H | CN | =CHNMe$_2$ | | K⁺ | |
| 10-377 | pyrrol-1-yl | H | CF$_3$ | =CHNMe$_2$ | | Na⁺ | |
| 10-378 | pyrrol-1-yl | H | CF$_3$ | =CHNMe$_2$ | | K⁺ | |
| 10-379 | pyrrol-1-yl | F | Cl | =CHNMe$_2$ | | Na⁺ | |
| 10-380 | pyrrol-1-yl | F | Cl | =CHNMe$_2$ | | K⁺ | |
| 10-381 | pyrrol-1-yl | F | Cl | =CHNMe$_2$ | | NH$_4^+$ | |
| 10-382 | pyrrol-1-yl | F | Br | =CHNMe$_2$ | | Na⁺ | |
| 10-383 | pyrrol-1-yl | F | Br | =CHNMe$_2$ | | K⁺ | |
| 10-384 | pyrrol-1-yl | F | Br | =CHNMe$_2$ | | NH$_4^+$ | |
| 10-385 | pyrrol-1-yl | F | F | =CHNMe$_2$ | | Na⁺ | |
| 10-386 | pyrrol-1-yl | F | F | =CHNMe$_2$ | | K⁺ | |
| 10-387 | pyrrol-1-yl | F | I | =CHNMe$_2$ | | Na⁺ | |
| 10-388 | pyrrol-1-yl | F | I | =CHNMe$_2$ | | K⁺ | |
| 10-389 | pyrrol-1-yl | F | CN | =CHNMe$_2$ | | Na⁺ | |
| 10-390 | pyrrol-1-yl | F | CN | =CHNMe$_2$ | | K⁺ | |
| 10-391 | pyrrol-1-yl | F | CF$_3$ | =CHNMe$_2$ | | Na⁺ | |
| 10-392 | pyrrol-1-yl | F | CF$_3$ | =CHNMe$_2$ | | K⁺ | |
| 10-393 | pyrazol-1-yl | H | Cl | H | H | Na⁺ | |
| 10-394 | pyrazol-1-yl | H | Cl | H | H | K⁺ | |
| 10-395 | pyrazol-1-yl | H | Cl | H | H | NH$_4^+$ | |
| 10-396 | pyrazol-1-yl | H | Br | H | H | Na⁺ | |
| 10-397 | pyrazol-1-yl | H | Br | H | H | K⁺ | |
| 10-398 | pyrazol-1-yl | H | Br | H | H | NH$_4^+$ | |
| 10-399 | pyrazol-1-yl | H | F | H | H | Na⁺ | |
| 10-400 | pyrazol-1-yl | H | F | H | H | K⁺ | |
| 10-401 | pyrazol-1-yl | H | I | H | H | Na⁺ | |
| 10-402 | pyrazol-1-yl | H | I | H | H | K⁺ | |

TABLE 10-continued

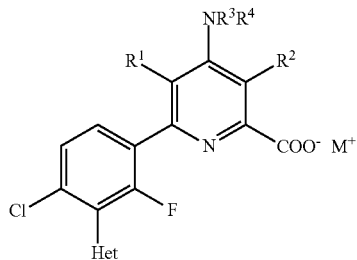

(I-x)

| No. | Het | R$^1$ | R$^2$ | R$^3$ | R$^4$ | M$^+$ | Physical data: $^1$H-NMR: δ [CDCl$_3$] |
|---|---|---|---|---|---|---|---|
| 10-403 | pyrazol-1-yl | H | CN | H | H | Na$^+$ | |
| 10-404 | pyrazol-1-yl | H | CN | H | H | K$^+$ | |
| 10-405 | pyrazol-1-yl | H | CF$_3$ | H | H | Na$^+$ | |
| 10-406 | pyrazol-1-yl | H | CF$_3$ | H | H | K$^+$ | |
| 10-407 | pyrazol-1-yl | F | Cl | H | H | Na$^+$ | |
| 10-408 | pyrazol-1-yl | F | Cl | H | H | K$^+$ | |
| 10-409 | pyrazol-1-yl | F | Cl | H | H | NH$_4$$^+$ | |
| 10-410 | pyrazol-1-yl | F | Br | H | H | Na$^+$ | |
| 10-411 | pyrazol-1-yl | F | Br | H | H | K$^+$ | |
| 10-412 | pyrazol-1-yl | F | Br | H | H | NH$_4$$^+$ | |
| 10-413 | pyrazol-1-yl | F | F | H | H | Na$^+$ | |
| 10-414 | pyrazol-1-yl | F | F | H | H | K$^+$ | |
| 10-415 | pyrazol-1-yl | F | I | H | H | Na$^+$ | |
| 10-416 | pyrazol-1-yl | F | I | H | H | K$^+$ | |
| 10-417 | pyrazol-1-yl | F | CN | H | H | Na$^+$ | |
| 10-418 | pyrazol-1-yl | F | CN | H | H | K$^+$ | |
| 10-419 | pyrazol-1-yl | F | CF$_3$ | H | H | Na$^+$ | |
| 10-420 | pyrazol-1-yl | F | CF$_3$ | H | H | K$^+$ | |
| 10-421 | pyrazol-1-yl | H | Cl | H | Me | Na$^+$ | |
| 10-422 | pyrazol-1-yl | H | Cl | H | Me | K$^+$ | |
| 10-423 | pyrazol-1-yl | H | Cl | H | Me | NH$_4$$^+$ | |
| 10-424 | pyrazol-1-yl | H | Br | H | Me | Na$^+$ | |
| 10-425 | pyrazol-1-yl | H | Br | H | Me | K$^+$ | |
| 10-426 | pyrazol-1-yl | H | Br | H | Me | NH$_4$$^+$ | |
| 10-427 | pyrazol-1-yl | H | F | H | Me | Na$^+$ | |
| 10-428 | pyrazol-1-yl | H | F | H | Me | K$^+$ | |
| 10-429 | pyrazol-1-yl | H | I | H | Me | Na$^+$ | |
| 10-430 | pyrazol-1-yl | H | I | H | Me | K$^+$ | |
| 10-431 | pyrazol-1-yl | H | CN | H | Me | Na$^+$ | |
| 10-432 | pyrazol-1-yl | H | CN | H | Me | K$^+$ | |
| 10-433 | pyrazol-1-yl | H | CF$_3$ | H | Me | Na$^+$ | |
| 10-434 | pyrazol-1-yl | H | CF$_3$ | H | Me | K$^+$ | |
| 10-435 | pyrazol-1-yl | F | Cl | H | Me | Na$^+$ | |
| 10-436 | pyrazol-1-yl | F | Cl | H | Me | K$^+$ | |
| 10-437 | pyrazol-1-yl | F | Cl | H | Me | NH$_4$$^+$ | |
| 10-438 | pyrazol-1-yl | F | Br | H | Me | Na$^+$ | |
| 10-439 | pyrazol-1-yl | F | Br | H | Me | K$^+$ | |
| 10-440 | pyrazol-1-yl | F | Br | H | Me | NH$_4$$^+$ | |
| 10-441 | pyrazol-1-yl | F | F | H | Me | Na$^+$ | |
| 10-442 | pyrazol-1-yl | F | F | H | Me | K$^+$ | |
| 10-443 | pyrazol-1-yl | F | I | H | Me | Na$^+$ | |
| 10-444 | pyrazol-1-yl | F | I | H | Me | K$^+$ | |
| 10-445 | pyrazol-1-yl | F | CN | H | Me | Na$^+$ | |
| 10-446 | pyrazol-1-yl | F | CN | H | Me | K$^+$ | |
| 10-447 | pyrazol-1-yl | F | CF$_3$ | H | Me | Na$^+$ | |
| 10-448 | pyrazol-1-yl | F | CF$_3$ | H | Me | K$^+$ | |
| 10-449 | pyrazol-1-yl | H | Cl | Me | Me | Na$^+$ | |
| 10-450 | pyrazol-1-yl | H | Cl | Me | Me | K$^+$ | |
| 10-451 | pyrazol-1-yl | H | Cl | Me | Me | NH$_4$$^+$ | |
| 10-452 | pyrazol-1-yl | H | Br | Me | Me | Na$^+$ | |
| 10-453 | pyrazol-1-yl | H | Br | Me | Me | K$^+$ | |
| 10-454 | pyrazol-1-yl | H | Br | Me | Me | NH$_4$$^+$ | |
| 10-455 | pyrazol-1-yl | H | F | Me | Me | Na$^+$ | |
| 10-456 | pyrazol-1-yl | H | F | Me | Me | K$^+$ | |
| 10-457 | pyrazol-1-yl | H | I | Me | Me | Na$^+$ | |
| 10-458 | pyrazol-1-yl | H | I | Me | Me | K$^+$ | |
| 10-459 | pyrazol-1-yl | H | CN | Me | Me | Na$^+$ | |
| 10-460 | pyrazol-1-yl | H | CN | Me | Me | K$^+$ | |
| 10-461 | pyrazol-1-yl | H | CF$_3$ | Me | Me | Na$^+$ | |
| 10-462 | pyrazol-1-yl | H | CF$_3$ | Me | Me | K$^+$ | |
| 10-463 | pyrazol-1-yl | F | Cl | Me | Me | Na$^+$ | |
| 10-464 | pyrazol-1-yl | F | Cl | Me | Me | K$^+$ | |

TABLE 10-continued

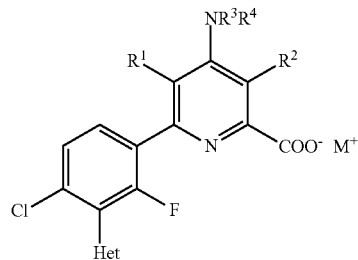

(I-x)

| No. | Het | $R^1$ | $R^2$ | $R^3$ | $R^4$ | $M^+$ | Physical data: $^1$H-NMR: δ [CDCl$_3$] |
|---|---|---|---|---|---|---|---|
| 10-465 | pyrazol-1-yl | F | Cl | Me | Me | $NH_4^+$ | |
| 10-466 | pyrazol-1-yl | F | Br | Me | Me | $Na^+$ | |
| 10-467 | pyrazol-1-yl | F | Br | Me | Me | $K^+$ | |
| 10-468 | pyrazol-1-yl | F | Br | Me | Me | $NH_4^+$ | |
| 10-469 | pyrazol-1-yl | F | F | Me | Me | $Na^+$ | |
| 10-470 | pyrazol-1-yl | F | F | Me | Me | $K^+$ | |
| 10-471 | pyrazol-1-yl | F | I | Me | Me | $Na^+$ | |
| 10-472 | pyrazol-1-yl | F | I | Me | Me | $K^+$ | |
| 10-473 | pyrazol-1-yl | F | CN | Me | Me | $Na^+$ | |
| 10-474 | pyrazol-1-yl | F | CN | Me | Me | $K^+$ | |
| 10-475 | pyrazol-1-yl | F | $CF_3$ | Me | Me | $Na^+$ | |
| 10-476 | pyrazol-1-yl | F | $CF_3$ | Me | Me | $K^+$ | |
| 10-477 | pyrazol-1-yl | H | Cl | =CHNMe$_2$ | | $Na^+$ | |
| 10-478 | pyrazol-1-yl | H | Cl | =CHNMe$_2$ | | $K^+$ | |
| 10-479 | pyrazol-1-yl | H | Cl | =CHNMe$_2$ | | $NH_4^+$ | |
| 10-480 | pyrazol-1-yl | H | Br | =CHNMe$_2$ | | $Na^+$ | |
| 10-481 | pyrazol-1-yl | H | Br | =CHNMe$_2$ | | $K^+$ | |
| 10-482 | pyrazol-1-yl | H | Br | =CHNMe$_2$ | | $NH_4^+$ | |
| 10-483 | pyrazol-1-yl | H | F | =CHNMe$_2$ | | $Na^+$ | |
| 10-484 | pyrazol-1-yl | H | F | =CHNMe$_2$ | | $K^+$ | |
| 10-485 | pyrazol-1-yl | H | I | =CHNMe$_2$ | | $Na^+$ | |
| 10-486 | pyrazol-1-yl | H | I | =CHNMe$_2$ | | $K^+$ | |
| 10-487 | pyrazol-1-yl | H | CN | =CHNMe$_2$ | | $Na^+$ | |
| 10-488 | pyrazol-1-yl | H | CN | =CHNMe$_2$ | | $K^+$ | |
| 10-489 | pyrazol-1-yl | H | $CF_3$ | =CHNMe$_2$ | | $Na^+$ | |
| 10-490 | pyrazol-1-yl | H | $CF_3$ | =CHNMe$_2$ | | $K^+$ | |
| 10-491 | pyrazol-1-yl | F | Cl | =CHNMe$_2$ | | $Na^+$ | |
| 10-492 | pyrazol-1-yl | F | Cl | =CHNMe$_2$ | | $K^+$ | |
| 10-493 | pyrazol-1-yl | F | Cl | =CHNMe$_2$ | | $NH_4^+$ | |
| 10-494 | pyrazol-1-yl | F | Br | =CHNMe$_2$ | | $Na^+$ | |
| 10-495 | pyrazol-1-yl | F | Br | =CHNMe$_2$ | | $K^+$ | |
| 10-496 | pyrazol-1-yl | F | Br | =CHNMe$_2$ | | $NH_4^+$ | |
| 10-497 | pyrazol-1-yl | F | F | =CHNMe$_2$ | | $Na^+$ | |
| 10-498 | pyrazol-1-yl | F | F | =CHNMe$_2$ | | $K^+$ | |
| 10-499 | pyrazol-1-yl | F | I | =CHNMe$_2$ | | $Na^+$ | |
| 10-500 | pyrazol-1-yl | F | I | =CHNMe$_2$ | | $K^+$ | |
| 10-501 | pyrazol-1-yl | F | CN | =CHNMe$_2$ | | $Na^+$ | |
| 10-502 | pyrazol-1-yl | F | CN | =CHNMe$_2$ | | $K^+$ | |
| 10-503 | pyrazol-1-yl | F | $CF_3$ | =CHNMe$_2$ | | $Na^+$ | |
| 10-504 | pyrazol-1-yl | F | $CF_3$ | =CHNMe$_2$ | | $K^+$ | |
| 10-505 | pyridin-3-yl | H | Cl | H | H | $Na^+$ | |
| 10-506 | pyridin-3-yl | H | Cl | H | H | $K^+$ | |
| 10-507 | pyridin-3-yl | H | Cl | H | H | $NH_4^+$ | |
| 10-508 | pyridin-3-yl | H | Br | H | H | $Na^+$ | |
| 10-509 | pyridin-3-yl | H | Br | H | H | $K^+$ | |
| 10-510 | pyridin-3-yl | H | Br | H | H | $NH_4^+$ | |
| 10-511 | pyridin-3-yl | H | F | H | H | $Na^+$ | |
| 10-512 | pyridin-3-yl | H | F | H | H | $K^+$ | |
| 10-513 | pyridin-3-yl | H | I | H | H | $Na^+$ | |
| 10-514 | pyridin-3-yl | H | I | H | H | $K^+$ | |
| 10-515 | pyridin-3-yl | H | CN | H | H | $Na^+$ | |
| 10-516 | pyridin-3-yl | H | CN | H | H | $K^+$ | |
| 10-517 | pyridin-3-yl | H | $CF_3$ | H | H | $Na^+$ | |
| 10-518 | pyridin-3-yl | H | $CF_3$ | H | H | $K^+$ | |
| 10-519 | pyridin-3-yl | F | Cl | H | H | $Na^+$ | |
| 10-520 | pyridin-3-yl | F | Cl | H | H | $K^+$ | |
| 10-521 | pyridin-3-yl | F | Cl | H | H | $NH_4^+$ | |
| 10-522 | pyridin-3-yl | F | Br | H | H | $Na^+$ | |
| 10-523 | pyridin-3-yl | F | Br | H | H | $K^+$ | |
| 10-524 | pyridin-3-yl | F | Br | H | H | $NH_4^+$ | |
| 10-525 | pyridin-3-yl | F | F | H | H | $Na^+$ | |
| 10-526 | pyridin-3-yl | F | F | H | H | $K^+$ | |

TABLE 10-continued

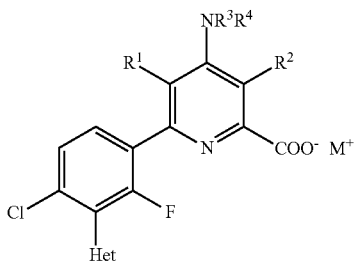

(I-x)

| No. | Het | R¹ | R² | R³ | R⁴ | M⁺ | Physical data: $^1$H-NMR: δ [CDCl$_3$] |
|---|---|---|---|---|---|---|---|
| 10-527 | pyridin-3-yl | F | I | H | H | Na⁺ | |
| 10-528 | pyridin-3-yl | F | I | H | H | K⁺ | |
| 10-529 | pyridin-3-yl | F | CN | H | H | Na⁺ | |
| 10-530 | pyridin-3-yl | F | CN | H | H | K⁺ | |
| 10-531 | pyridin-3-yl | F | CF$_3$ | H | H | Na⁺ | |
| 10-532 | pyridin-3-yl | F | CF$_3$ | H | H | K⁺ | |
| 10-533 | pyridin-3-yl | H | Cl | H | Me | Na⁺ | |
| 10-534 | pyridin-3-yl | H | Cl | H | Me | K⁺ | |
| 10-535 | pyridin-3-yl | H | Cl | H | Me | NH$_4$⁺ | |
| 10-536 | pyridin-3-yl | H | Br | H | Me | Na⁺ | |
| 10-537 | pyridin-3-yl | H | Br | H | Me | K⁺ | |
| 10-538 | pyridin-3-yl | H | Br | H | Me | NH$_4$⁺ | |
| 10-539 | pyridin-3-yl | H | F | H | Me | Na⁺ | |
| 10-540 | pyridin-3-yl | H | F | H | Me | K⁺ | |
| 10-541 | pyridin-3-yl | H | I | H | Me | Na⁺ | |
| 10-542 | pyridin-3-yl | H | I | H | Me | K⁺ | |
| 10-543 | pyridin-3-yl | H | CN | H | Me | Na⁺ | |
| 10-544 | pyridin-3-yl | H | CN | H | Me | K⁺ | |
| 10-545 | pyridin-3-yl | H | CF$_3$ | H | Me | Na⁺ | |
| 10-546 | pyridin-3-yl | H | CF$_3$ | H | Me | K⁺ | |
| 10-547 | pyridin-3-yl | F | Cl | H | Me | Na⁺ | |
| 10-548 | pyridin-3-yl | F | Cl | H | Me | K⁺ | |
| 10-549 | pyridin-3-yl | F | Cl | H | Me | NH$_4$⁺ | |
| 10-550 | pyridin-3-yl | F | Br | H | Me | Na⁺ | |
| 10-551 | pyridin-3-yl | F | Br | H | Me | K⁺ | |
| 10-552 | pyridin-3-yl | F | Br | H | Me | NH$_4$⁺ | |
| 10-553 | pyridin-3-yl | F | F | H | Me | Na⁺ | |
| 10-554 | pyridin-3-yl | F | F | H | Me | K⁺ | |
| 10-555 | pyridin-3-yl | F | I | H | Me | Na⁺ | |
| 10-556 | pyridin-3-yl | F | I | H | Me | K⁺ | |
| 10-557 | pyridin-3-yl | F | CN | H | Me | Na⁺ | |
| 10-558 | pyridin-3-yl | F | CN | H | Me | K⁺ | |
| 10-559 | pyridin-3-yl | F | CF$_3$ | H | Me | Na⁺ | |
| 10-560 | pyridin-3-yl | F | CF$_3$ | H | Me | K⁺ | |
| 10-561 | pyridin-3-yl | H | Cl | Me | Me | Na⁺ | |
| 10-562 | pyridin-3-yl | H | Cl | Me | Me | K⁺ | |
| 10-563 | pyridin-3-yl | H | Cl | Me | Me | NH$_4$⁺ | |
| 10-564 | pyridin-3-yl | H | Br | Me | Me | Na⁺ | |
| 10-565 | pyridin-3-yl | H | Br | Me | Me | K⁺ | |
| 10-566 | pyridin-3-yl | H | Br | Me | Me | NH$_4$⁺ | |
| 10-567 | pyridin-3-yl | H | F | Me | Me | Na⁺ | |
| 10-568 | pyridin-3-yl | H | F | Me | Me | K⁺ | |
| 10-569 | pyridin-3-yl | H | I | Me | Me | Na⁺ | |
| 10-570 | pyridin-3-yl | H | I | Me | Me | K⁺ | |
| 10-571 | pyridin-3-yl | H | CN | Me | Me | Na⁺ | |
| 10-572 | pyridin-3-yl | H | CN | Me | Me | K⁺ | |
| 10-573 | pyridin-3-yl | H | CF$_3$ | Me | Me | Na⁺ | |
| 10-574 | pyridin-3-yl | H | CF$_3$ | Me | Me | K⁺ | |
| 10-575 | pyridin-3-yl | F | Cl | Me | Me | Na⁺ | |
| 10-576 | pyridin-3-yl | F | Cl | Me | Me | K⁺ | |
| 10-577 | pyridin-3-yl | F | Cl | Me | Me | NH$_4$⁺ | |
| 10-578 | pyridin-3-yl | F | Br | Me | Me | Na⁺ | |
| 10-579 | pyridin-3-yl | F | Br | Me | Me | K⁺ | |
| 10-580 | pyridin-3-yl | F | Br | Me | Me | NH$_4$⁺ | |
| 10-581 | pyridin-3-yl | F | F | Me | Me | Na⁺ | |
| 10-582 | pyridin-3-yl | F | F | Me | Me | K⁺ | |
| 10-583 | pyridin-3-yl | F | I | Me | Me | Na⁺ | |
| 10-584 | pyridin-3-yl | F | I | Me | Me | K⁺ | |
| 10-585 | pyridin-3-yl | F | CN | Me | Me | Na⁺ | |
| 10-586 | pyridin-3-yl | F | CN | Me | Me | K⁺ | |
| 10-587 | pyridin-3-yl | F | CF$_3$ | Me | Me | Na⁺ | |
| 10-588 | pyridin-3-yl | F | CF$_3$ | Me | Me | K⁺ | |

TABLE 10-continued (I-x)

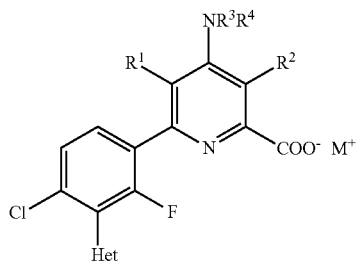

| No. | Het | R¹ | R² | R³ | R⁴ | M⁺ | Physical data: $^1$H-NMR: δ [CDCl$_3$] |
|---|---|---|---|---|---|---|---|
| 10-589 | pyridin-3-yl | H | Cl | =CHNMe$_2$ | | Na$^+$ | |
| 10-590 | pyridin-3-yl | H | Cl | =CHNMe$_2$ | | K$^+$ | |
| 10-591 | pyridin-3-yl | H | Cl | =CHNMe$_2$ | | NH$_4^+$ | |
| 10-592 | pyridin-3-yl | H | Br | =CHNMe$_2$ | | Na$^+$ | |
| 10-593 | pyridin-3-yl | H | Br | =CHNMe$_2$ | | K$^+$ | |
| 10-594 | pyridin-3-yl | H | Br | =CHNMe$_2$ | | NH$_4^+$ | |
| 10-595 | pyridin-3-yl | H | F | =CHNMe$_2$ | | Na$^+$ | |
| 10-596 | pyridin-3-yl | H | F | =CHNMe$_2$ | | K$^+$ | |
| 10-597 | pyridin-3-yl | H | I | =CHNMe$_2$ | | Na$^+$ | |
| 10-598 | pyridin-3-yl | H | I | =CHNMe$_2$ | | K$^+$ | |
| 10-599 | pyridin-3-yl | H | CN | =CHNMe$_2$ | | Na$^+$ | |
| 10-600 | pyridin-3-yl | H | CN | =CHNMe$_2$ | | K$^+$ | |
| 10-601 | pyridin-3-yl | H | CF$_3$ | =CHNMe$_2$ | | Na$^+$ | |
| 10-602 | pyridin-3-yl | H | CF$_3$ | =CHNMe$_2$ | | K$^+$ | |
| 10-603 | pyridin-3-yl | F | Cl | =CHNMe$_2$ | | Na$^+$ | |
| 10-604 | pyridin-3-yl | F | Cl | =CHNMe$_2$ | | K$^+$ | |
| 10-605 | pyridin-3-yl | F | Cl | =CHNMe$_2$ | | NH$_4^+$ | |
| 10-606 | pyridin-3-yl | F | Br | =CHNMe$_2$ | | Na$^+$ | |
| 10-607 | pyridin-3-yl | F | Br | =CHNMe$_2$ | | K$^+$ | |
| 10-608 | pyridin-3-yl | F | Br | =CHNMe$_2$ | | NH$_4^+$ | |
| 10-609 | pyridin-3-yl | F | F | =CHNMe$_2$ | | Na$^+$ | |
| 10-610 | pyridin-3-yl | F | F | =CHNMe$_2$ | | K$^+$ | |
| 10-611 | pyridin-3-yl | F | I | =CHNMe$_2$ | | Na$^+$ | |
| 10-612 | pyridin-3-yl | F | I | =CHNMe$_2$ | | K$^+$ | |
| 10-613 | pyridin-3-yl | F | CN | =CHNMe$_2$ | | Na$^+$ | |
| 10-614 | pyridin-3-yl | F | CN | =CHNMe$_2$ | | K$^+$ | |
| 10-615 | pyridin-3-yl | F | CF$_3$ | =CHNMe$_2$ | | Na$^+$ | |
| 10-616 | pyridin-3-yl | F | CF$_3$ | =CHNMe$_2$ | | K$^+$ | |
| 10-617 | oxiranyl | H | Cl | H | H | Na$^+$ | |
| 10-618 | oxiranyl | H | Cl | H | H | K$^+$ | |
| 10-619 | oxiranyl | H | Cl | H | H | NH$_4^+$ | |
| 10-620 | oxiranyl | H | Br | H | H | Na$^+$ | |
| 10-621 | oxiranyl | H | Br | H | H | K$^+$ | |
| 10-622 | oxiranyl | H | Br | H | H | NH$_4^+$ | |
| 10-623 | oxiranyl | H | F | H | H | Na$^+$ | |
| 10-624 | oxiranyl | H | F | H | H | K$^+$ | |
| 10-625 | oxiranyl | H | I | H | H | Na$^+$ | |
| 10-626 | oxiranyl | H | I | H | H | K$^+$ | |
| 10-627 | oxiranyl | H | CN | H | H | Na$^+$ | |
| 10-628 | oxiranyl | H | CN | H | H | K$^+$ | |
| 10-629 | oxiranyl | H | CF$_3$ | H | H | Na$^+$ | |
| 10-630 | oxiranyl | H | CF$_3$ | H | H | K$^+$ | |
| 10-631 | oxiranyl | F | Cl | H | H | Na$^+$ | |
| 10-632 | oxiranyl | F | Cl | H | H | K$^+$ | |
| 10-633 | oxiranyl | F | Cl | H | H | NH$_4^+$ | |
| 10-634 | oxiranyl | F | Br | H | H | Na$^+$ | |
| 10-635 | oxiranyl | F | Br | H | H | K$^+$ | |
| 10-636 | oxiranyl | F | Br | H | H | NH$_4^+$ | |
| 10-637 | oxiranyl | F | F | H | H | Na$^+$ | |
| 10-638 | oxiranyl | F | F | H | H | K$^+$ | |
| 10-639 | oxiranyl | F | I | H | H | Na$^+$ | |
| 10-640 | oxiranyl | F | I | H | H | K$^+$ | |
| 10-641 | oxiranyl | F | CN | H | H | Na$^+$ | |
| 10-642 | oxiranyl | F | CN | H | H | K$^+$ | |
| 10-643 | oxiranyl | F | CF$_3$ | H | H | Na$^+$ | |
| 10-644 | oxiranyl | F | CF$_3$ | H | H | K$^+$ | |
| 10-645 | oxiranyl | H | Cl | H | Me | Na$^+$ | |
| 10-646 | oxiranyl | H | Cl | H | Me | K$^+$ | |
| 10-647 | oxiranyl | H | Cl | H | Me | NH$_4^+$ | |
| 10-648 | oxiranyl | H | Br | H | Me | Na$^+$ | |
| 10-649 | oxiranyl | H | Br | H | Me | K$^+$ | |
| 10-650 | oxiranyl | H | Br | H | Me | NH$_4^+$ | |

TABLE 10-continued

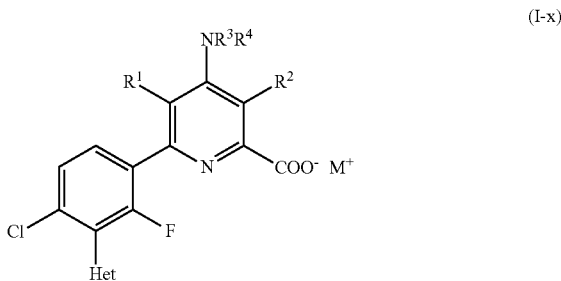

(I-x)

| No. | Het | $R^1$ | $R^2$ | $R^3$ | $R^4$ | $M^+$ | Physical data: $^1$H-NMR: δ [CDCl$_3$] |
|---|---|---|---|---|---|---|---|
| 10-651 | oxiranyl | H | F | H | Me | Na$^+$ | |
| 10-652 | oxiranyl | H | F | H | Me | K$^+$ | |
| 10-653 | oxiranyl | H | I | H | Me | Na$^+$ | |
| 10-654 | oxiranyl | H | I | H | Me | K$^+$ | |
| 10-655 | oxiranyl | H | CN | H | Me | Na$^+$ | |
| 10-656 | oxiranyl | H | CN | H | Me | K$^+$ | |
| 10-657 | oxiranyl | H | CF$_3$ | H | Me | Na$^+$ | |
| 10-658 | oxiranyl | H | CF$_3$ | H | Me | K$^+$ | |
| 10-659 | oxiranyl | F | Cl | H | Me | Na$^+$ | |
| 10-660 | oxiranyl | F | Cl | H | Me | K$^+$ | |
| 10-661 | oxiranyl | F | Cl | H | Me | NH$_4^+$ | |
| 10-662 | oxiranyl | F | Br | H | Me | Na$^+$ | |
| 10-663 | oxiranyl | F | Br | H | Me | K$^+$ | |
| 10-664 | oxiranyl | F | Br | H | Me | NH$_4^+$ | |
| 10-665 | oxiranyl | F | F | H | Me | Na$^+$ | |
| 10-666 | oxiranyl | F | F | H | Me | K$^+$ | |
| 10-667 | oxiranyl | F | I | H | Me | Na$^+$ | |
| 10-668 | oxiranyl | F | I | H | Me | K$^+$ | |
| 10-669 | oxiranyl | F | CN | H | Me | Na$^+$ | |
| 10-670 | oxiranyl | F | CN | H | Me | K$^+$ | |
| 10-671 | oxiranyl | F | CF$_3$ | H | Me | Na$^+$ | |
| 10-672 | oxiranyl | F | CF$_3$ | H | Me | K$^+$ | |
| 10-673 | oxiranyl | H | Cl | Me | Me | Na$^+$ | |
| 10-674 | oxiranyl | H | Cl | Me | Me | K$^+$ | |
| 10-675 | oxiranyl | H | Cl | Me | Me | NH$_4^+$ | |
| 10-676 | oxiranyl | H | Br | Me | Me | Na$^+$ | |
| 10-677 | oxiranyl | H | Br | Me | Me | K$^+$ | |
| 10-678 | oxiranyl | H | Br | Me | Me | NH$_4^+$ | |
| 10-679 | oxiranyl | H | F | Me | Me | Na$^+$ | |
| 10-680 | oxiranyl | H | F | Me | Me | K$^+$ | |
| 10-681 | oxiranyl | H | I | Me | Me | Na$^+$ | |
| 10-682 | oxiranyl | H | I | Me | Me | K$^+$ | |
| 10-683 | oxiranyl | H | CN | Me | Me | Na$^+$ | |
| 10-684 | oxiranyl | H | CN | Me | Me | K$^+$ | |
| 10-685 | oxiranyl | H | CF$_3$ | Me | Me | Na$^+$ | |
| 10-686 | oxiranyl | H | CF$_3$ | Me | Me | K$^+$ | |
| 10-687 | oxiranyl | F | Cl | Me | Me | Na$^+$ | |
| 10-688 | oxiranyl | F | Cl | Me | Me | K$^+$ | |
| 10-689 | oxiranyl | F | Cl | Me | Me | NH$_4^+$ | |
| 10-690 | oxiranyl | F | Br | Me | Me | Na$^+$ | |
| 10-691 | oxiranyl | F | Br | Me | Me | K$^+$ | |
| 10-692 | oxiranyl | F | Br | Me | Me | NH$_4^+$ | |
| 10-693 | oxiranyl | F | F | Me | Me | Na$^+$ | |
| 10-694 | oxiranyl | F | F | Me | Me | K$^+$ | |
| 10-695 | oxiranyl | F | I | Me | Me | Na$^+$ | |
| 10-696 | oxiranyl | F | I | Me | Me | K$^+$ | |
| 10-697 | oxiranyl | F | CN | Me | Me | Na$^+$ | |
| 10-698 | oxiranyl | F | CN | Me | Me | K$^+$ | |
| 10-699 | oxiranyl | F | CF$_3$ | Me | Me | Na$^+$ | |
| 10-700 | oxiranyl | F | CF$_3$ | Me | Me | K$^+$ | |
| 10-701 | oxiranyl | H | Cl | =CHNMe$_2$ | | Na$^+$ | |
| 10-702 | oxiranyl | H | Cl | =CHNMe$_2$ | | K$^+$ | |
| 10-703 | oxiranyl | H | Cl | =CHNMe$_2$ | | NH$_4^+$ | |
| 10-704 | oxiranyl | H | Br | =CHNMe$_2$ | | Na$^+$ | |
| 10-705 | oxiranyl | H | Br | =CHNMe$_2$ | | K$^+$ | |
| 10-706 | oxiranyl | H | Br | =CHNMe$_2$ | | NH$_4^+$ | |
| 10-707 | oxiranyl | H | F | =CHNMe$_2$ | | Na$^+$ | |
| 10-708 | oxiranyl | H | F | =CHNMe$_2$ | | K$^+$ | |
| 10-709 | oxiranyl | H | I | =CHNMe$_2$ | | Na$^+$ | |
| 10-710 | oxiranyl | H | I | =CHNMe$_2$ | | K$^+$ | |
| 10-711 | oxiranyl | H | CN | =CHNMe$_2$ | | Na$^+$ | |
| 10-712 | oxiranyl | H | CN | =CHNMe$_2$ | | K$^+$ | |

TABLE 10-continued

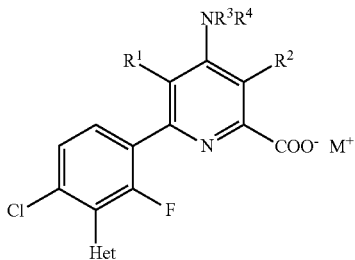

(I-x)

| No. | Het | R¹ | R² | R³ | R⁴ | M⁺ | Physical data: $^1$H-NMR: δ [CDCl$_3$] |
|---|---|---|---|---|---|---|---|
| 10-713 | oxiranyl | H | CF$_3$ | =CHNMe$_2$ | | Na⁺ | |
| 10-714 | oxiranyl | H | CF$_3$ | =CHNMe$_2$ | | K⁺ | |
| 10-715 | oxiranyl | F | Cl | =CHNMe$_2$ | | Na⁺ | |
| 10-716 | oxiranyl | F | Cl | =CHNMe$_2$ | | K⁺ | |
| 10-717 | oxiranyl | F | Cl | =CHNMe$_2$ | | NH$_4$⁺ | |
| 10-718 | oxiranyl | F | Br | =CHNMe$_2$ | | Na⁺ | |
| 10-719 | oxiranyl | F | Br | =CHNMe$_2$ | | K⁺ | |
| 10-720 | oxiranyl | F | Br | =CHNMe$_2$ | | NH$_4$⁺ | |
| 10-721 | oxiranyl | F | F | =CHNMe$_2$ | | Na⁺ | |
| 10-722 | oxiranyl | F | F | =CHNMe$_2$ | | K⁺ | |
| 10-723 | oxiranyl | F | I | =CHNMe$_2$ | | Na⁺ | |
| 10-724 | oxiranyl | F | I | =CHNMe$_2$ | | K⁺ | |
| 10-725 | oxiranyl | F | CN | =CHNMe$_2$ | | Na⁺ | |
| 10-726 | oxiranyl | F | CN | =CHNMe$_2$ | | K⁺ | |
| 10-727 | oxiranyl | F | CF$_3$ | =CHNMe$_2$ | | Na⁺ | |
| 10-728 | oxiranyl | F | CF$_3$ | =CHNMe$_2$ | | K⁺ | |
| 10-729 | 3,3-dimethyl-oxetan-2-yl | H | Cl | H | H | Na⁺ | |
| 10-730 | 3,3-dimethyl-oxetan-2-yl | H | Cl | H | H | K⁺ | |
| 10-731 | 3,3-dimethyl-oxetan-2-yl | H | Cl | H | H | NH$_4$⁺ | |
| 10-732 | 3,3-dimethyl-oxetan-2-yl | H | Br | H | H | Na⁺ | |
| 10-733 | 3,3-dimethyl-oxetan-2-yl | H | Br | H | H | K⁺ | |
| 10-734 | 3,3-dimethyl-oxetan-2-yl | H | Br | H | H | NH$_4$⁺ | |
| 10-735 | 3,3-dimethyl-oxetan-2-yl | H | F | H | H | Na⁺ | |
| 10-736 | 3,3-dimethyl-oxetan-2-yl | H | F | H | H | K⁺ | |
| 10-737 | 3,3-dimethyl-oxetan-2-yl | H | I | H | H | Na⁺ | |
| 10-738 | 3,3-dimethyl-oxetan-2-yl | H | I | H | H | K⁺ | |
| 10-739 | 3,3-dimethyl-oxetan-2-yl | H | CN | H | H | Na⁺ | |
| 10-740 | 3,3-dimethyl-oxetan-2-yl | H | CN | H | H | K⁺ | |
| 10-741 | 3,3-dimethyl-oxetan-2-yl | H | CF$_3$ | H | H | Na⁺ | |
| 10-742 | 3,3-dimethyl-oxetan-2-yl | H | CF$_3$ | H | H | K⁺ | |
| 10-743 | 3,3-dimethyl-oxetan-2-yl | F | Cl | H | H | Na⁺ | |
| 10-744 | 3,3-dimethyl-oxetan-2-yl | F | Cl | H | H | K⁺ | |
| 10-745 | 3,3-dimethyl-oxetan-2-yl | F | Cl | H | H | NH$_4$⁺ | |
| 10-746 | 3,3-dimethyl-oxetan-2-yl | F | Br | H | H | Na⁺ | |
| 10-747 | 3,3-dimethyl-oxetan-2-yl | F | Br | H | H | K⁺ | |
| 10-748 | 3,3-dimethyl-oxetan-2-yl | F | Br | H | H | NH$_4$⁺ | |
| 10-749 | 3,3-dimethyl-oxetan-2-yl | F | F | H | H | Na⁺ | |
| 10-750 | 3,3-dimethyl-oxetan-2-yl | F | F | H | H | K⁺ | |
| 10-751 | 3,3-dimethyl-oxetan-2-yl | F | I | H | H | Na⁺ | |
| 10-752 | 3,3-dimethyl-oxetan-2-yl | F | I | H | H | K⁺ | |
| 10-753 | 3,3-dimethyl-oxetan-2-yl | F | CN | H | H | Na⁺ | |
| 10-754 | 3,3-dimethyl-oxetan-2-yl | F | CN | H | H | K⁺ | |
| 10-755 | 3,3-dimethyl-oxetan-2-yl | F | CF$_3$ | H | H | Na⁺ | |
| 10-756 | 3,3-dimethyl-oxetan-2-yl | F | CF$_3$ | H | H | K⁺ | |
| 10-757 | 3,3-dimethyl-oxetan-2-yl | H | Cl | H | Me | Na⁺ | |
| 10-758 | 3,3-dimethyl-oxetan-2-yl | H | Cl | H | Me | K⁺ | |
| 10-759 | 3,3-dimethyl-oxetan-2-yl | H | Cl | H | Me | NH$_4$⁺ | |
| 10-760 | 3,3-dimethyl-oxetan-2-yl | H | Br | H | Me | Na⁺ | |
| 10-761 | 3,3-dimethyl-oxetan-2-yl | H | Br | H | Me | K⁺ | |
| 10-762 | 3,3-dimethyl-oxetan-2-yl | H | Br | H | Me | NH$_4$⁺ | |
| 10-763 | 3,3-dimethyl-oxetan-2-yl | H | F | H | Me | Na⁺ | |
| 10-764 | 3,3-dimethyl-oxetan-2-yl | H | F | H | Me | K⁺ | |
| 10-765 | 3,3-dimethyl-oxetan-2-yl | H | I | H | Me | Na⁺ | |
| 10-766 | 3,3-dimethyl-oxetan-2-yl | H | I | H | Me | K⁺ | |
| 10-767 | 3,3-dimethyl-oxetan-2-yl | H | CN | H | Me | Na⁺ | |
| 10-768 | 3,3-dimethyl-oxetan-2-yl | H | CN | H | Me | K⁺ | |
| 10-769 | 3,3-dimethyl-oxetan-2-yl | H | CF$_3$ | H | Me | Na⁺ | |
| 10-770 | 3,3-dimethyl-oxetan-2-yl | H | CF$_3$ | H | Me | K⁺ | |
| 10-771 | 3,3-dimethyl-oxetan-2-yl | F | Cl | H | Me | Na⁺ | |
| 10-772 | 3,3-dimethyl-oxetan-2-yl | F | Cl | H | Me | K⁺ | |
| 10-773 | 3,3-dimethyl-oxetan-2-yl | F | Cl | H | Me | NH$_4$⁺ | |
| 10-774 | 3,3-dimethyl-oxetan-2-yl | F | Br | H | Me | Na⁺ | |

TABLE 10-continued

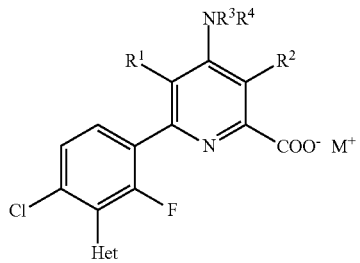

(I-x)

| No. | Het | R¹ | R² | R³ | R⁴ | M⁺ | Physical data: ¹H-NMR: δ [CDCl₃] |
|---|---|---|---|---|---|---|---|
| 10-775 | 3,3-dimethyl-oxetan-2-yl | F | Br | H | Me | K⁺ | |
| 10-776 | 3,3-dimethyl-oxetan-2-yl | F | Br | H | Me | NH₄⁺ | |
| 10-777 | 3,3-dimethyl-oxetan-2-yl | F | F | H | Me | Na⁺ | |
| 10-778 | 3,3-dimethyl-oxetan-2-yl | F | F | H | Me | K⁺ | |
| 10-779 | 3,3-dimethyl-oxetan-2-yl | F | I | H | Me | Na⁺ | |
| 10-780 | 3,3-dimethyl-oxetan-2-yl | F | I | H | Me | K⁺ | |
| 10-781 | 3,3-dimethyl-oxetan-2-yl | F | CN | H | Me | Na⁺ | |
| 10-782 | 3,3-dimethyl-oxetan-2-yl | F | CN | H | Me | K⁺ | |
| 10-783 | 3,3-dimethyl-oxetan-2-yl | F | CF₃ | H | Me | Na⁺ | |
| 10-784 | 3,3-dimethyl-oxetan-2-yl | F | CF₃ | H | Me | K⁺ | |
| 10-785 | 3,3-dimethyl-oxetan-2-yl | H | Cl | Me | Me | Na⁺ | |
| 10-786 | 3,3-dimethyl-oxetan-2-yl | H | Cl | Me | Me | K⁺ | |
| 10-787 | 3,3-dimethyl-oxetan-2-yl | H | Cl | Me | Me | NH₄⁺ | |
| 10-788 | 3,3-dimethyl-oxetan-2-yl | H | Br | Me | Me | Na⁺ | |
| 10-789 | 3,3-dimethyl-oxetan-2-yl | H | Br | Me | Me | K⁺ | |
| 10-790 | 3,3-dimethyl-oxetan-2-yl | H | Br | Me | Me | NH₄⁺ | |
| 10-791 | 3,3-dimethyl-oxetan-2-yl | H | F | Me | Me | Na⁺ | |
| 10-792 | 3,3-dimethyl-oxetan-2-yl | H | F | Me | Me | K⁺ | |
| 10-793 | 3,3-dimethyl-oxetan-2-yl | H | I | Me | Me | Na⁺ | |
| 10-794 | 3,3-dimethyl-oxetan-2-yl | H | I | Me | Me | K⁺ | |
| 10-795 | 3,3-dimethyl-oxetan-2-yl | H | CN | Me | Me | Na⁺ | |
| 10-796 | 3,3-dimethyl-oxetan-2-yl | H | CN | Me | Me | K⁺ | |
| 10-797 | 3,3-dimethyl-oxetan-2-yl | H | CF₃ | Me | Me | Na⁺ | |
| 10-798 | 3,3-dimethyl-oxetan-2-yl | H | CF₃ | Me | Me | K⁺ | |
| 10-799 | 3,3-dimethyl-oxetan-2-yl | F | Cl | Me | Me | Na⁺ | |
| 10-800 | 3,3-dimethyl-oxetan-2-yl | F | Cl | Me | Me | K⁺ | |
| 10-801 | 3,3-dimethyl-oxetan-2-yl | F | Cl | Me | Me | NH₄⁺ | |
| 10-802 | 3,3-dimethyl-oxetan-2-yl | F | Br | Me | Me | Na⁺ | |
| 10-803 | 3,3-dimethyl-oxetan-2-yl | F | Br | Me | Me | K⁺ | |
| 10-804 | 3,3-dimethyl-oxetan-2-yl | F | Br | Me | Me | NH₄⁺ | |
| 10-805 | 3,3-dimethyl-oxetan-2-yl | F | F | Me | Me | Na⁺ | |
| 10-806 | 3,3-dimethyl-oxetan-2-yl | F | F | Me | Me | K⁺ | |
| 10-807 | 3,3-dimethyl-oxetan-2-yl | F | I | Me | Me | Na⁺ | |
| 10-808 | 3,3-dimethyl-oxetan-2-yl | F | I | Me | Me | K⁺ | |
| 10-809 | 3,3-dimethyl-oxetan-2-yl | F | CN | Me | Me | Na⁺ | |
| 10-810 | 3,3-dimethyl-oxetan-2-yl | F | CN | Me | Me | K⁺ | |
| 10-811 | 3,3-dimethyl-oxetan-2-yl | F | CF₃ | Me | Me | Na⁺ | |
| 10-812 | 3,3-dimethyl-oxetan-2-yl | F | CF₃ | Me | Me | K⁺ | |
| 10-813 | 3,3-dimethyl-oxetan-2-yl | H | Cl | =CHNMe₂ | | Na⁺ | |
| 10-814 | 3,3-dimethyl-oxetan-2-yl | H | Cl | =CHNMe₂ | | K⁺ | |
| 10-815 | 3,3-dimethyl-oxetan-2-yl | H | Cl | =CHNMe₂ | | NH₄⁺ | |
| 10-816 | 3,3-dimethyl-oxetan-2-yl | H | Br | =CHNMe₂ | | Na⁺ | |
| 10-817 | 3,3-dimethyl-oxetan-2-yl | H | Br | =CHNMe₂ | | K⁺ | |
| 10-818 | 3,3-dimethyl-oxetan-2-yl | H | Br | =CHNMe₂ | | NH₄⁺ | |
| 10-819 | 3,3-dimethyl-oxetan-2-yl | H | F | =CHNMe₂ | | Na⁺ | |
| 10-820 | 3,3-dimethyl-oxetan-2-yl | H | F | =CHNMe₂ | | K⁺ | |
| 10-821 | 3,3-dimethyl-oxetan-2-yl | H | I | =CHNMe₂ | | Na⁺ | |
| 10-822 | 3,3-dimethyl-oxetan-2-yl | H | I | =CHNMe₂ | | K⁺ | |
| 10-823 | 3,3-dimethyl-oxetan-2-yl | H | CN | =CHNMe₂ | | Na⁺ | |
| 10-824 | 3,3-dimethyl-oxetan-2-yl | H | CN | =CHNMe₂ | | K⁺ | |
| 10-825 | 3,3-dimethyl-oxetan-2-yl | H | CF₃ | =CHNMe₂ | | Na⁺ | |
| 10-826 | 3,3-dimethyl-oxetan-2-yl | H | CF₃ | =CHNMe₂ | | K⁺ | |
| 10-827 | 3,3-dimethyl-oxetan-2-yl | F | Cl | =CHNMe₂ | | Na⁺ | |
| 10-828 | 3,3-dimethyl-oxetan-2-yl | F | Cl | =CHNMe₂ | | K⁺ | |
| 10-829 | 3,3-dimethyl-oxetan-2-yl | F | Cl | =CHNMe₂ | | NH₄⁺ | |
| 10-830 | 3,3-dimethyl-oxetan-2-yl | F | Br | =CHNMe₂ | | Na⁺ | |
| 10-831 | 3,3-dimethyl-oxetan-2-yl | F | Br | =CHNMe₂ | | K⁺ | |
| 10-832 | 3,3-dimethyl-oxetan-2-yl | F | Br | =CHNMe₂ | | NH₄⁺ | |
| 10-833 | 3,3-dimethyl-oxetan-2-yl | F | F | =CHNMe₂ | | Na⁺ | |
| 10-834 | 3,3-dimethyl-oxetan-2-yl | F | F | =CHNMe₂ | | K⁺ | |
| 10-835 | 3,3-dimethyl-oxetan-2-yl | F | I | =CHNMe₂ | | Na⁺ | |
| 10-836 | 3,3-dimethyl-oxetan-2-yl | F | I | =CHNMe₂ | | K⁺ | |

TABLE 10-continued

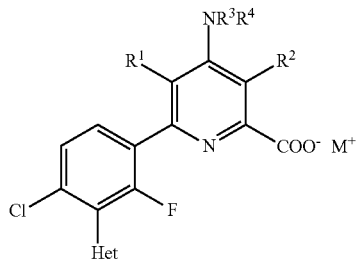

(I-x)

| No. | Het | R¹ | R² | R³ | R⁴ | M⁺ | Physical data: $^1$H-NMR: δ [CDCl$_3$] |
|---|---|---|---|---|---|---|---|
| 10-837 | 3,3-dimethyl-oxetan-2-yl | F | CN | =CHNMe$_2$ | | Na⁺ | |
| 10-838 | 3,3-dimethyl-oxetan-2-yl | F | CN | =CHNMe$_2$ | | K⁺ | |
| 10-839 | 3,3-dimethyl-oxetan-2-yl | F | CF$_3$ | =CHNMe$_2$ | | Na⁺ | |
| 10-840 | 3,3-dimethyl-oxetan-2-yl | F | CF$_3$ | =CHNMe$_2$ | | K⁺ | |
| 10-841 | 2,2-dimethyl-dioxolan-4-yl | H | Cl | H | H | Na⁺ | |
| 10-842 | 2,2-dimethyl-dioxolan-4-yl | H | Cl | H | H | K⁺ | |
| 10-843 | 2,2-dimethyl-dioxolan-4-yl | H | Cl | H | H | NH$_4$⁺ | |
| 10-844 | 2,2-dimethyl-dioxolan-4-yl | H | Br | H | H | Na⁺ | |
| 10-845 | 2,2-dimethyl-dioxolan-4-yl | H | Br | H | H | K⁺ | |
| 10-846 | 2,2-dimethyl-dioxolan-4-yl | H | Br | H | H | NH$_4$⁺ | |
| 10-847 | 2,2-dimethyl-dioxolan-4-yl | H | F | H | H | Na⁺ | |
| 10-848 | 2,2-dimethyl-dioxolan-4-yl | H | F | H | H | K⁺ | |
| 10-849 | 2,2-dimethyl-dioxolan-4-yl | H | I | H | H | Na⁺ | |
| 10-850 | 2,2-dimethyl-dioxolan-4-yl | H | I | H | H | K⁺ | |
| 10-851 | 2,2-dimethyl-dioxolan-4-yl | H | CN | H | H | Na⁺ | |
| 10-852 | 2,2-dimethyl-dioxolan-4-yl | H | CN | H | H | K⁺ | |
| 10-853 | 2,2-dimethyl-dioxolan-4-yl | H | CF$_3$ | H | H | Na⁺ | |
| 10-854 | 2,2-dimethyl-dioxolan-4-yl | H | CF$_3$ | H | H | K⁺ | |
| 10-855 | 2,2-dimethyl-dioxolan-4-yl | F | Cl | H | H | Na⁺ | |
| 10-856 | 2,2-dimethyl-dioxolan-4-yl | F | Cl | H | H | K⁺ | |
| 10-857 | 2,2-dimethyl-dioxolan-4-yl | F | Cl | H | H | NH$_4$⁺ | |
| 10-858 | 2,2-dimethyl-dioxolan-4-yl | F | Br | H | H | Na⁺ | |
| 10-859 | 2,2-dimethyl-dioxolan-4-yl | F | Br | H | H | K⁺ | |
| 10-860 | 2,2-dimethyl-dioxolan-4-yl | F | Br | H | H | NH$_4$⁺ | |
| 10-861 | 2,2-dimethyl-dioxolan-4-yl | F | F | H | H | Na⁺ | |
| 10-862 | 2,2-dimethyl-dioxolan-4-yl | F | F | H | H | K⁺ | |
| 10-863 | 2,2-dimethyl-dioxolan-4-yl | F | I | H | H | Na⁺ | |
| 10-864 | 2,2-dimethyl-dioxolan-4-yl | F | I | H | H | K⁺ | |
| 10-865 | 2,2-dimethyl-dioxolan-4-yl | F | CN | H | H | Na⁺ | |
| 10-866 | 2,2-dimethyl-dioxolan-4-yl | F | CN | H | H | K⁺ | |
| 10-867 | 2,2-dimethyl-dioxolan-4-yl | F | CF$_3$ | H | H | Na⁺ | |
| 10-868 | 2,2-dimethyl-dioxolan-4-yl | F | CF$_3$ | H | H | K⁺ | |
| 10-869 | 2,2-dimethyl-dioxolan-4-yl | H | Cl | H | Me | Na⁺ | |
| 10-870 | 2,2-dimethyl-dioxolan-4-yl | H | Cl | H | Me | K⁺ | |
| 10-871 | 2,2-dimethyl-dioxolan-4-yl | H | Cl | H | Me | NH$_4$⁺ | |
| 10-872 | 2,2-dimethyl-dioxolan-4-yl | H | Br | H | Me | Na⁺ | |
| 10-873 | 2,2-dimethyl-dioxolan-4-yl | H | Br | H | Me | K⁺ | |
| 10-874 | 2,2-dimethyl-dioxolan-4-yl | H | Br | H | Me | NH$_4$⁺ | |
| 10-875 | 2,2-dimethyl-dioxolan-4-yl | H | F | H | Me | Na⁺ | |
| 10-876 | 2,2-dimethyl-dioxolan-4-yl | H | F | H | Me | K⁺ | |
| 10-877 | 2,2-dimethyl-dioxolan-4-yl | H | I | H | Me | Na⁺ | |
| 10-878 | 2,2-dimethyl-dioxolan-4-yl | H | I | H | Me | K⁺ | |
| 10-879 | 2,2-dimethyl-dioxolan-4-yl | H | CN | H | Me | Na⁺ | |
| 10-880 | 2,2-dimethyl-dioxolan-4-yl | H | CN | H | Me | K⁺ | |
| 10-881 | 2,2-dimethyl-dioxolan-4-yl | H | CF$_3$ | H | Me | Na⁺ | |
| 10-882 | 2,2-dimethyl-dioxolan-4-yl | H | CF$_3$ | H | Me | K⁺ | |
| 10-883 | 2,2-dimethyl-dioxolan-4-yl | F | Cl | H | Me | Na⁺ | |
| 10-884 | 2,2-dimethyl-dioxolan-4-yl | F | Cl | H | Me | K⁺ | |
| 10-885 | 2,2-dimethyl-dioxolan-4-yl | F | Cl | H | Me | NH$_4$⁺ | |
| 10-886 | 2,2-dimethyl-dioxolan-4-yl | F | Br | H | Me | Na⁺ | |
| 10-887 | 2,2-dimethyl-dioxolan-4-yl | F | Br | H | Me | K⁺ | |
| 10-888 | 2,2-dimethyl-dioxolan-4-yl | F | Br | H | Me | NH$_4$⁺ | |
| 10-889 | 2,2-dimethyl-dioxolan-4-yl | F | F | H | Me | Na⁺ | |
| 10-890 | 2,2-dimethyl-dioxolan-4-yl | F | F | H | Me | K⁺ | |
| 10-891 | 2,2-dimethyl-dioxolan-4-yl | F | I | H | Me | Na⁺ | |
| 10-892 | 2,2-dimethyl-dioxolan-4-yl | F | I | H | Me | K⁺ | |
| 10-893 | 2,2-dimethyl-dioxolan-4-yl | F | CN | H | Me | Na⁺ | |
| 10-894 | 2,2-dimethyl-dioxolan-4-yl | F | CN | H | Me | K⁺ | |
| 10-895 | 2,2-dimethyl-dioxolan-4-yl | F | CF$_3$ | H | Me | Na⁺ | |
| 10-896 | 2,2-dimethyl-dioxolan-4-yl | F | CF$_3$ | H | Me | K⁺ | |
| 10-897 | 2,2-dimethyl-dioxolan-4-yl | H | Cl | Me | Me | Na⁺ | |
| 10-898 | 2,2-dimethyl-dioxolan-4-yl | H | Cl | Me | Me | K⁺ | |

TABLE 10-continued

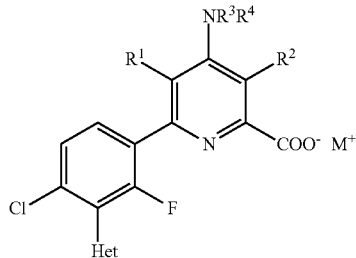

(I-x)

| No. | Het | R¹ | R² | R³ | R⁴ | M⁺ | Physical data: $^1$H-NMR: δ [CDCl$_3$] |
|---|---|---|---|---|---|---|---|
| 10-899 | 2,2-dimethyl-dioxolan-4-yl | H | Cl | Me | Me | NH$_4^+$ | |
| 10-900 | 2,2-dimethyl-dioxolan-4-yl | H | Br | Me | Me | Na$^+$ | |
| 10-901 | 2,2-dimethyl-dioxolan-4-yl | H | Br | Me | Me | K$^+$ | |
| 10-902 | 2,2-dimethyl-dioxolan-4-yl | H | Br | Me | Me | NH$_4^+$ | |
| 10-903 | 2,2-dimethyl-dioxolan-4-yl | H | F | Me | Me | Na$^+$ | |
| 10-904 | 2,2-dimethyl-dioxolan-4-yl | H | F | Me | Me | K$^+$ | |
| 10-905 | 2,2-dimethyl-dioxolan-4-yl | H | I | Me | Me | Na$^+$ | |
| 10-906 | 2,2-dimethyl-dioxolan-4-yl | H | I | Me | Me | K$^+$ | |
| 10-907 | 2,2-dimethyl-dioxolan-4-yl | H | CN | Me | Me | Na$^+$ | |
| 10-908 | 2,2-dimethyl-dioxolan-4-yl | H | CN | Me | Me | K$^+$ | |
| 10-909 | 2,2-dimethyl-dioxolan-4-yl | H | CF$_3$ | Me | Me | Na$^+$ | |
| 10-910 | 2,2-dimethyl-dioxolan-4-yl | H | CF$_3$ | Me | Me | K$^+$ | |
| 10-911 | 2,2-dimethyl-dioxolan-4-yl | F | Cl | Me | Me | Na$^+$ | |
| 10-912 | 2,2-dimethyl-dioxolan-4-yl | F | Cl | Me | Me | K$^+$ | |
| 10-913 | 2,2-dimethyl-dioxolan-4-yl | F | Cl | Me | Me | NH$_4^+$ | |
| 10-914 | 2,2-dimethyl-dioxolan-4-yl | F | Br | Me | Me | Na$^+$ | |
| 10-915 | 2,2-dimethyl-dioxolan-4-yl | F | Br | Me | Me | K$^+$ | |
| 10-916 | 2,2-dimethyl-dioxolan-4-yl | F | Br | Me | Me | NH$_4^+$ | |
| 10-917 | 2,2-dimethyl-dioxolan-4-yl | F | F | Me | Me | Na$^+$ | |
| 10-918 | 2,2-dimethyl-dioxolan-4-yl | F | F | Me | Me | K$^+$ | |
| 10-919 | 2,2-dimethyl-dioxolan-4-yl | F | I | Me | Me | Na$^+$ | |
| 10-920 | 2,2-dimethyl-dioxolan-4-yl | F | I | Me | Me | K$^+$ | |
| 10-921 | 2,2-dimethyl-dioxolan-4-yl | F | CN | Me | Me | Na$^+$ | |
| 10-922 | 2,2-dimethyl-dioxolan-4-yl | F | CN | Me | Me | K$^+$ | |
| 10-923 | 2,2-dimethyl-dioxolan-4-yl | F | CF$_3$ | Me | Me | Na$^+$ | |
| 10-924 | 2,2-dimethyl-dioxolan-4-yl | F | CF$_3$ | Me | Me | K$^+$ | |
| 10-925 | 2,2-dimethyl-dioxolan-4-yl | H | Cl | =CHNMe$_2$ | | Na$^+$ | |
| 10-926 | 2,2-dimethyl-dioxolan-4-yl | H | Cl | =CHNMe$_2$ | | K$^+$ | |
| 10-927 | 2,2-dimethyl-dioxolan-4-yl | H | Cl | =CHNMe$_2$ | | NH$_4^+$ | |
| 10-928 | 2,2-dimethyl-dioxolan-4-yl | H | Br | =CHNMe$_2$ | | Na$^+$ | |
| 10-929 | 2,2-dimethyl-dioxolan-4-yl | H | Br | =CHNMe$_2$ | | K$^+$ | |
| 10-930 | 2,2-dimethyl-dioxolan-4-yl | H | Br | =CHNMe$_2$ | | NH$_4^+$ | |
| 10-931 | 2,2-dimethyl-dioxolan-4-yl | H | F | =CHNMe$_2$ | | Na$^+$ | |
| 10-932 | 2,2-dimethyl-dioxolan-4-yl | H | F | =CHNMe$_2$ | | K$^+$ | |
| 10-933 | 2,2-dimethyl-dioxolan-4-yl | H | I | =CHNMe$_2$ | | Na$^+$ | |
| 10-934 | 2,2-dimethyl-dioxolan-4-yl | H | I | =CHNMe$_2$ | | K$^+$ | |
| 10-935 | 2,2-dimethyl-dioxolan-4-yl | H | CN | =CHNMe$_2$ | | Na$^+$ | |
| 10-936 | 2,2-dimethyl-dioxolan-4-yl | H | CN | =CHNMe$_2$ | | K$^+$ | |
| 10-937 | 2,2-dimethyl-dioxolan-4-yl | H | CF$_3$ | =CHNMe$_2$ | | Na$^+$ | |
| 10-938 | 2,2-dimethyl-dioxolan-4-yl | H | CF$_3$ | =CHNMe$_2$ | | K$^+$ | |
| 10-939 | 2,2-dimethyl-dioxolan-4-yl | F | Cl | =CHNMe$_2$ | | Na$^+$ | |
| 10-940 | 2,2-dimethyl-dioxolan-4-yl | F | Cl | =CHNMe$_2$ | | K$^+$ | |
| 10-941 | 2,2-dimethyl-dioxolan-4-yl | F | Cl | =CHNMe$_2$ | | NH$_4^+$ | |
| 10-942 | 2,2-dimethyl-dioxolan-4-yl | F | Br | =CHNMe$_2$ | | Na$^+$ | |
| 10-943 | 2,2-dimethyl-dioxolan-4-yl | F | Br | =CHNMe$_2$ | | K$^+$ | |
| 10-944 | 2,2-dimethyl-dioxolan-4-yl | F | Br | =CHNMe$_2$ | | NH$_4^+$ | |
| 10-945 | 2,2-dimethyl-dioxolan-4-yl | F | F | =CHNMe$_2$ | | Na$^+$ | |
| 10-946 | 2,2-dimethyl-dioxolan-4-yl | F | F | =CHNMe$_2$ | | K$^+$ | |
| 10-947 | 2,2-dimethyl-dioxolan-4-yl | F | I | =CHNMe$_2$ | | Na$^+$ | |
| 10-948 | 2,2-dimethyl-dioxolan-4-yl | F | I | =CHNMe$_2$ | | K$^+$ | |
| 10-949 | 2,2-dimethyl-dioxolan-4-yl | F | CN | =CHNMe$_2$ | | Na$^+$ | |
| 10-950 | 2,2-dimethyl-dioxolan-4-yl | F | CN | =CHNMe$_2$ | | K$^+$ | |
| 10-951 | 2,2-dimethyl-dioxolan-4-yl | F | CF$_3$ | =CHNMe$_2$ | | Na$^+$ | |
| 10-952 | 2,2-dimethyl-dioxolan-4-yl | F | CF$_3$ | =CHNMe$_2$ | | K$^+$ | |

B. Formulation Examples a) A dust is obtained by mixing 10 parts by weight of an active compound combination according to the invention and 90 parts by weight of talc as inert material and comminuting the mixture in a hammer mill.

b) A wettable powder which is readily dispersible in water is obtained by mixing 25 parts by weight of an active compound combination according to the invention, 64 parts by weight of kaolin-containing quartz as inert material, 10 parts by weight of potassium lignosulfonate and 1 part by weight of sodium oleoylmethyltaurinate as wetter and dispersant, and grinding the mixture in a pinned-disk mill.

c) A dispersion concentrate which is readily dispersible in water is obtained by mixing 20 parts by weight of an active compound combination according to the invention with 6 parts by weight of alkylphenol polyglycol ether (®Triton X 207), 3 parts by weight of isotridecanol polyglycol ether (8 EO) and 71 parts by weight of paraffinic mineral oil (boiling range for example approx. 255 to more than 277° C.), and grinding the mixture in a ball mill to a fineness of below 5 microns.

d) An emulsifiable concentrate is obtained from 15 parts by weight of an active compound combination according to the invention, 75 parts by weight of cyclohexanone as solvent and 10 parts by weight of oxethylated nonylphenol as emulsifier.

e) Water-dispersible granules are obtained by mixing 75 parts by weight of an active compound combination according to the invention,
   10 parts by weight of calcium lignosulfonate,
   5 parts by weight of sodium lauryl sulfate,
   3 parts by weight of polyvinyl alcohol and
   7 parts by weight of kaolin
   grinding the mixture on a pinned-disk mill and granulating the powder in a fluidized bed by spraying on water as granulation liquid.

f) Water-dispersible granules are also obtained by homogenizing and precomminuting, on a colloid mill
   25 parts by weight of an active compound combination according to the invention
   5 parts by weight of sodium 2,2'-dinaphthylmethane-6,6'-disulfonate
   2 parts by weight of sodium oleoylmethyltaurinate,
   1 part by weight of polyvinyl alcohol,
   17 parts by weight of calcium carbonate and
   50 parts by weight of water
   subsequently grinding the mixture on a bead mill and atomizing and drying the resulting suspension in a spray tower by means of a single-substance nozzle.

C. Biological Examples

Pre-Emergence Herbicidal Action Against Weed Plants

Seeds of mono- and dicotyledonous weed and crop plants are set out in wood fiber pots in sandy loam soil and covered with soil. The inventive compounds formulated in the form of wettable powders (WP) or as emulsion concentrates (EC) are then applied to the surface of the covering earth as an aqueous suspension or emulsion at a water application rate of 600 to 800 l/ha (converted) with addition of 0.2% wetting agent. After the treatment, the pots are placed in a greenhouse and kept under good growth conditions for the test plants. The damage to the test plants is scored visually after an experiment time of 3 weeks in comparison to untreated controls (herbicidal action in percent (%): 100% action=plants have died, 0% action=like control plants). For example, compounds No. 9-842 and 9-618 at an application rate of 320 g/ha each exhibit the action shown in table 11 against *Amaranthus retroflexus* and *Veronica persica*.

TABLE 11

| Structure | Example No. | Application rate g/ha | AMARE | VERPE |
|---|---|---|---|---|
| (structure) | 9-842 | 320 | 90 | 100 |
| (structure) | 9-618 | 320 |  | 100 |

Post-Emergence Herbicidal Action Against Weed Plants

Seeds of mono- and dicotyledonous weed and crop plants are set out in wood fiber pots in sandy loam soil, covered with soil and cultivated in a greenhouse under good growth conditions. 2 to 3 weeks after sowing, the trial plants are treated at the one-leaf stage. The inventive compounds formulated in the form of wettable powders (WP) or as emulsion concentrates (EC) are then sprayed onto the green plant parts as an aqueous suspension or emulsion with a water application rate of 600 to 800 l/ha (converted) with addition of 0.2% wetting agent. After the trial plants have stood in the greenhouse under optimal growth conditions for about 3 weeks, the action of the preparations is scored visually in comparison to untreated controls (herbicidal action in percent (%): 100% action=plants have died, 0% action=like control plants). For example, compounds No. 9-842 and 9-618 each exhibit, at an application rate of 320 g/ha, the effect shown in table 12 against *Veronica persica*, *Gossypium hirsutum* and *Ipomoea purpurea*.

TABLE 12

| Structure | Example No. | Application rate g/ha | ABUTH | PHBPU | VERPE |
|---|---|---|---|---|---|
| 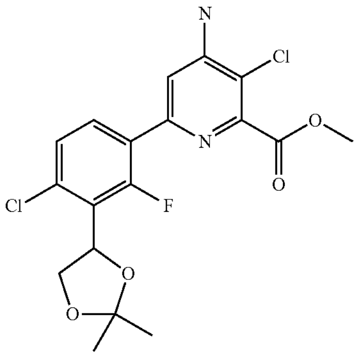 [SMILES: COC(=O)c1nc(-c2ccc(Cl)c(C3COC(C)(C)O3)c2F)cc(N)c1Cl] | 9-842 | 320 | 80 | 90 | 100 |
| 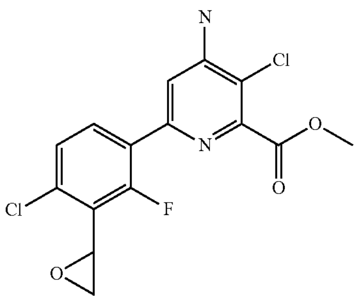 [SMILES: COC(=O)c1nc(-c2ccc(Cl)c(C3CO3)c2F)cc(N)c1Cl] | 9-618 | 320 | 80 | | 90 |

The invention claimed is:

1. A compound comprising at least one of the formulae (I-a) or (I-c) and/or an N-oxide thereof (I-a)

(I-c)

wherein
in formula (I-a) the radicals are each defined as follows:
X is O;
m is 1;
Y is O;
n is 1;
p is 1;
R' is selected from hydrogen, $(C_1-C_4)$alkyl, $(C_1-C_4)$haloalkyl, $(C_2-C_4)$-alkoxyalkyl, $(C_2-C_4)$alkylthioalkyl, $(C_2-C_4)$alkenyl, oxiranyl, $(C_1-C_4)$-alkyloxiranyl, oxiranyl-$(C_1-C_4)$alkyl, $(C_2-C_4)$haloalkenyl, 2-halooxiranyl, 3-halooxiranyl, 2,3-dihalooxiranyl, $(C_3-C_6)$alkoxyalkenyl, $(C_3-C_6)$alkylthioalkenyl, $(C_2-C_4)$alkynyl, and $(C_2-C_4)$haloalkynyl;
and where the other radicals are each as defined below;
in formula (I-c) M$^+$ is defined as a cation;
and where the other radicals are each as defined below;
R$^1$ is selected from hydrogen, fluorine and chlorine;
R$^2$ is selected from fluorine, chlorine, bromine, iodine;
R$^3$ is hydrogen;
R$^4$ is hydrogen;
Ar is a phenyl group, where the phenyl group is optionally substituted by 1-3 R$^{21}$ radicals, and where the phenyl group bears, as substituents, at least one heterocyclyl radical selected from 1,2,4-oxadiazol-5-yl, thien-2-yl, pyrrol-1-yl, pyrazol-1-yl, pyridin-2-yl, pyridin-3-yl, pyridin-4-yl, 1,3-oxazol-2-yl, isoxazol-3-yl, oxiranyl, 1-methyloxiran-1-yl, 2-methyloxiran-1-yl, 1,2-dimethyloxiran-1-yl, 2,2-dimethyloxiran-1-yl, trimethyloxiran-1-yl, dioxolanyl, and 2,2-dimethyl-dioxolan-4-yl, where the heterocyclyl radical is optionally substituted by 1 to 3 R$^{26}$ radicals;
R$^{21}$ is selected from fluorine, chlorine, trifluoromethyl, methyl and methoxy, and
R$^{26}$ is selected from methyl, tert-butyl, fluorine, chlorine, trifluoromethyl and methoxy.

2. A compound as claimed in claim 1, in which Ar is a phenyl radical substituted in the 4 position by a heterocyclyl group selected from 1,2,4-oxadiazol-5-yl, thien-2-yl, pyrrol-1-yl, pyrazol-1-yl and pyridin-3-yl which in turn are optionally substituted by 1, 2 or 3 radicals selected from methyl, tert-butyl, fluorine, chlorine, trifluoromethyl and methoxy and the phenyl radical is optionally additionally substituted in the 2 position by a halogen atom and in the 3 position by an alkoxy group.

3. A compound as claimed in claim 1, in which Ar is a phenyl radical substituted in the 3 position by a heterocyclyl group selected from 1,2,4-oxadiazol-5-yl, thien-2-yl, pyrrol-1-yl, pyrazol-1-yl and pyridin-3-yl which in turn are optionally substituted by 1, 2 or 3 radicals selected from methyl, tert-butyl, fluorine, chlorine, trifluoromethyl and methoxy and the phenyl radical is optionally additionally substituted in the 2 and in the 4 position by a halogen atom.

4. An agrochemical composition comprising
   (a) at least one compound as defined in claim 1, and
   (b) one or more assistants and additives customary in crop protection.

5. A method for controlling unwanted plants or for regulating growth of plants, comprising applying an effective amount of at least one compound of as defined in claim 1, to plants, seed and/or an area on which plants grow.

6. A compound as claimed in claim 1, wherein Ar is a phenyl group.

7. A compound as claimed in claim 1, wherein Ar bears as a substituent a 1,2,4-oxadiazol-5-yl group which may be substituted by 1 to 3 $R^{26}$ radicals.

8. A compound according to claim 1 wherein Ar is a phenyl group substituted in the 3 position by 1,2,4-oxadiazol-5-yl.

\* \* \* \* \*